(12) United States Patent
Liu et al.

(10) Patent No.: US 11,859,170 B2
(45) Date of Patent: Jan. 2, 2024

(54) POLYPEPTIDES HAVING LYSOZYME ACTIVITY, POLYNUCLEOTIDES ENCODING SAME AND USES AND COMPOSITIONS THEREOF

(71) Applicant: Novozymes A/S, Bagsvaerd (DK)

(72) Inventors: Ye Liu, Beijing (CN); Ming Li, Beijing (CN); Kirk Matthew Schnorr, Holte (DK); Peter Bjarke Olsen, Copenhagen (DK)

(73) Assignee: Novozymes A/S, Bagsvaerd (DK)

( * ) Notice: Subject to any disclaimer, the term of this patent is extended or adjusted under 35 U.S.C. 154(b) by 721 days.

(21) Appl. No.: 16/607,404

(22) PCT Filed: May 11, 2018

(86) PCT No.: PCT/CN2018/086528
§ 371 (c)(1),
(2) Date: Oct. 23, 2019

(87) PCT Pub. No.: WO2018/206001
PCT Pub. Date: Nov. 15, 2018

(65) Prior Publication Data
US 2020/0131492 A1    Apr. 30, 2020

(30) Foreign Application Priority Data

May 12, 2017   (WO) ................ PCT/CN2017/084074

(51) Int. Cl.
| | | |
|---|---|---|
| A23K 20/189 | (2016.01) | |
| A23K 40/10 | (2016.01) | |
| C12N 9/36 | (2006.01) | |
| A23K 40/30 | (2016.01) | |
| A23K 50/30 | (2016.01) | |
| A23K 50/75 | (2016.01) | |
| A23K 50/80 | (2016.01) | |
| A23K 10/30 | (2016.01) | |

(52) U.S. Cl.
CPC ............ *C12N 9/2462* (2013.01); *A23K 10/30* (2016.05); *A23K 20/189* (2016.05); *A23K 40/10* (2016.05); *A23K 40/30* (2016.05); *A23K 50/30* (2016.05); *A23K 50/75* (2016.05); *A23K 50/80* (2016.05); *C12Y 302/01017* (2013.01)

(58) Field of Classification Search
CPC ...... A23K 20/189; A23K 40/10; A23K 40/30; C12N 9/2462
See application file for complete search history.

(56) References Cited

U.S. PATENT DOCUMENTS

| | | | |
|---|---|---|---|
| 4,335,022 A | 10/1982 | Rabussay | |
| 5,041,236 A | 8/1991 | Carpenter | |
| 9,663,775 B2 | 5/2017 | Schnorr | |
| 2012/0288490 A1 | 11/2012 | De Maria | |
| 2014/0325711 A1* | 10/2014 | Schnorr ............. | C12N 15/1003 435/252.31 |

FOREIGN PATENT DOCUMENTS

| | | |
|---|---|---|
| CN | 102858968 A | 1/2013 |
| EP | 0425016 A2 | 5/1991 |
| WO | 00/21381 A1 | 4/2000 |
| WO | 2004/017988 A1 | 3/2004 |
| WO | 2004/026334 A1 | 4/2004 |
| WO | 2005/080559 A1 | 9/2005 |
| WO | 2008/124764 A1 | 10/2008 |
| WO | 2013/076253 A1 | 5/2013 |
| WO | 2017/000922 A1 | 1/2017 |
| WO | 2017/001701 A1 | 1/2017 |
| WO | 2017/001703 A1 | 1/2017 |
| WO | 2017/064092 A1 | 4/2017 |

OTHER PUBLICATIONS

"What is the true definition of 'Plant-Based' and why does it matter?", https://rootthefuture.com/definition-of-plant-based/, Nov. 2020 (Year: 2020).*
Hughey et al., Applied and Environmental Microbiology, vol. 53, pp. 2165-2170 (1987).
Masschalck et al., Journal of Food Protection, vol. 65, No. 12, pp. 1916-1923 (2002).
Vries et al, 2017, Uniprot No. A0A1Q5TMG8.
Zhu et al, 2017, Uniprot No. A0AOF7TVL0.

* cited by examiner

*Primary Examiner* — Ruth A Davis
(74) *Attorney, Agent, or Firm* — Adam Rucker

(57) ABSTRACT

Animal feed or animal feed additives comprising one or more polypeptides having lysozyme activity. Polypeptides having lysozyme activity, polynucleotides encoding the polypeptides nucleic acid constructs, vectors, and host cells comprising the polynucleotides as well as methods of producing and using the polypeptides.

Figure 1:
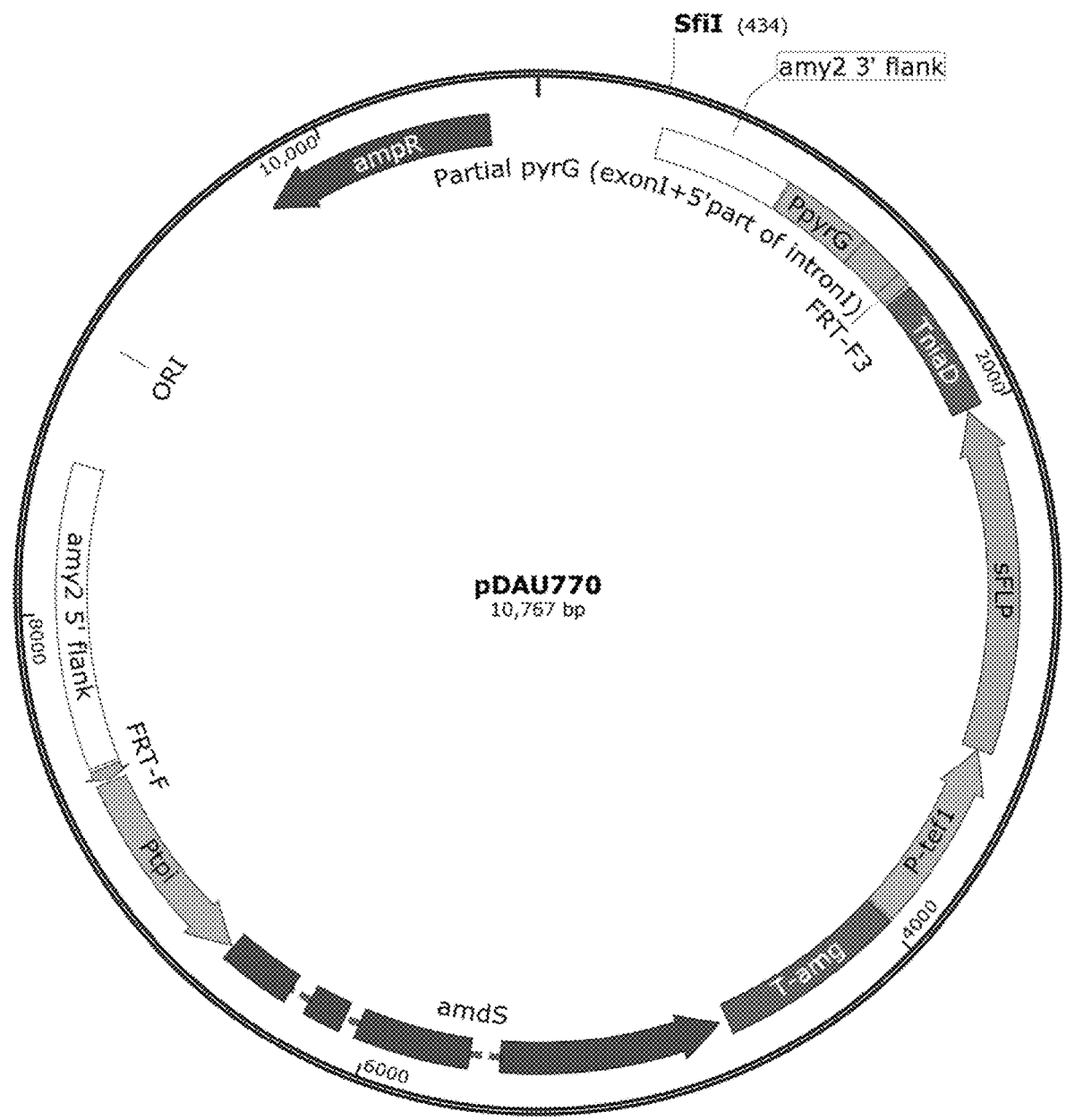

20 Claims, 2 Drawing Sheets
Specification includes a Sequence Listing.

POLYPEPTIDES HAVING LYSOZYME ACTIVITY, POLYNUCLEOTIDES ENCODING SAME AND USES AND COMPOSITIONS THEREOF

CROSS-REFERENCE TO RELATED APPLICATIONS

This application is a 35 U.S.C. 371 national application of international application no. PCT/CN2018/086528 filed May 11, 2018, which claims priority or the benefit under 35 U.S.C. 119 of International application no. PCT/CN2017/084074 filed May 12, 2017. The content of each application is fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to novel LYS polypeptides having lysozyme activity, polynucleotides encoding the polypeptides, nucleic acid constructs, vectors, and host cells comprising the polynucleotides as well as methods of producing the polypeptides. The present invention also relates to compositions, specifically animal feed, comprising LYS polypeptides and the use of the LYS polypeptide in animal feed.

Description of the Related Art

Lysozyme is an O-glycosyl hydrolase produced as a defensive mechanism against bacteria by many organisms. The enzyme causes the hydrolysis of bacterial cell walls by cleaving the glycosidic bonds of peptidoglycan; an important structural molecule in bacteria. After having their cell walls weakened by lysozyme action, bacterial cells lyse as a result of unbalanced osmotic pressure.

Lysozyme naturally occurs in many organisms such as viruses, plants, insects, birds, reptiles and mammals. In mammals, Lysozyme has been isolated from nasal secretions, saliva, tears, intestinal content, urine and milk. The enzyme cleaves the glycosidic bond between carbon number 1 of N-acetylmuramic acid and carbon number 4 of N-acetyl-D-glucosamine. In vivo, these two carbohydrates are polymerized to form the cell wall polysaccharide of many microorganisms.

Lysozyme has until now been classified into seven different glycoside hydrolase (GH) families (CAZy, www.cazy.org): GH18, GH19, hen egg-white lysozyme (GH22), goose egg-white lysozyme (GH23), bacteriophage T4 lysozyme (GH24), *Sphingomonas* flagellar protein (GH73) and *Chalaropsis* lysozymes (GH25).

Lysozyme extracted from hen egg white is the primary product available on the commercial market, but does not cleave N,6-O-diacetylmuramic acid in e.g. *Staphylococcus aureus* cell walls and is thus unable to lyse this important human pathogen among others (Masschalck B, Deckers D, Michiels CW (2002), "Lytic and nonlytic mechanism of inactivation of gram-positive bacteria by lysozyme under atmospheric and high hydrostatic pressure", *J Food Prot.* 65(12):1916-23).

Use of lysozyme has been suggested in animal feed (see for example WO 00/21381 and WO 04/026334), in cheese production (see for example WO 05/080559), food preservation (Hughey and Johnson (1987) *Appl Environ Microbiol* 53:2165), detergents (see for example U.S. Pat. No. 5,041,236 and EP 0425016), in oral care (see for example U.S. Pat. No. 4,355,022, WO 04/017988 and WO 08/124764), cosmetology and dermatology, contraception, urology, and gynecology (see for example WO 08/124764).

Antimicrobial growth promoters (AGP's) have traditionally been used for growth promotion in animals, and probably work by preventing low level infections by pathogens such as *Clostridium perfringens*. However, AGP's are increasingly being banned worldwide and therefore new solutions to promote animal growth but which are not AGP's are of interest.

SUMMARY OF THE INVENTION

The inventors have discovered a completely novel class of polypeptides having lysozyme activity. As such, the invention relates to a composition comprising at least 0.01 mg of LYS polypeptide per kilogram of composition, wherein the polypeptide (a) has lysozyme activity and (b) comprises one or more LAD catalytic domains; wherein the LAD catalytic domain gives a domT score of at least 180 when queried using a Profile Hidden Markov Model (HMM) prepared using SEQ ID NOs: 46 to 187 and hmmbuild software program. Typically, the query is carried out using hmmscan software program by the Method of Determining the LAD Catalytic Domain by HMM.

The invention further relates to an isolated polypeptide having lysozyme activity, selected from the group consisting of:
   (a) a polypeptide having at least 95% sequence identity to the polypeptide of SEQ ID NO: 3;
   (b) a polypeptide having at least 94% sequence identity to the polypeptide of SEQ ID NO: 6;
   (c) a polypeptide having at least 80% sequence identity to the polypeptide of SEQ ID NO: 9;
   (d) a polypeptide having at least 80% sequence identity to the polypeptide of SEQ ID NO: 12;
   (e) a polypeptide having at least 87% sequence identity to the polypeptide of SEQ ID NO: 15;
   (f) a polypeptide having at least 81% sequence identity to the polypeptide of SEQ ID NO: 18;
   (g) a polypeptide having at least 80% sequence identity to the polypeptide of SEQ ID NO: 21;
   (h) a polypeptide having at least 80% sequence identity to the polypeptide of SEQ ID NO: 24;
   (i) a polypeptide having at least 87% sequence identity to the polypeptide of SEQ ID NO: 27;
   (j) a polypeptide having at least 96.2% sequence identity to the polypeptide of SEQ ID NO: 30;
   (k) a polypeptide having at least 80% sequence identity to the polypeptide of SEQ ID NO: 33;
   (l) a polypeptide having at least 80% sequence identity to the polypeptide of SEQ ID NO: 36;
   (m) a polypeptide having at least 81% sequence identity to the polypeptide of SEQ ID NO: 39;
   (n) a polypeptide having at least 80% sequence identity to the polypeptide of SEQ ID NO: 42;
   (o) a variant of the polypeptide of SEQ ID NO: 3, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10 or 11 positions;

(p) a variant of the polypeptide of SEQ ID NO: 6, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12 or 13 positions;

(q) a variant of the polypeptide selected from the group consisting of SEQ ID NO: 9 and SEQ ID NO: 36, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43 or 44 positions;

(r) a variant of the polypeptide selected from the group consisting of SEQ ID NO: 12, SEQ ID NO: 21, SEQ ID NO: 24, SEQ ID NO: 33 and SEQ ID NO: 42, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 positions;

(s) a variant of the polypeptide selected from the group consisting of SEQ ID NO: 15 and SEQ ID NO: 27, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28 or 29 positions;

(t) a variant of the polypeptide selected from the group consisting of SEQ ID NO: 18 and SEQ ID NO: 39, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41 or 42 positions;

(u) a variant of the polypeptide of SEQ ID NO: 30, wherein the variant has lysozyme activity and comprises one or more amino acid substitutions, and/or one or more amino acid deletions, and/or one or more amino acid insertions or any combination thereof in 1, 2, 3, 4, 5, 6, 7 or 8 positions;

(v) a polypeptide comprising the polypeptide of (a), (b), (c), (d), (e), (f), (g), (h), (i), (j), (k), (l), (m), (n), (o), (p), (q), (r), (s), (t) or (u) and a N-terminal and/or C-terminal His-tag and/or HQ-tag;

(w) a polypeptide comprising the polypeptide of (a), (b), (c), (d), (e), (f), (g), (h), (i), (j), (k), (l), (m), (n), (o), (p), (q), (r), (s), (t) or (u) and a N-terminal and/or C-terminal extension of up to 10 amino acids, e.g. 1, 2, 3, 4, 5, 6, 7, 8, 9 or 10 amino acids; and (x) a fragment of the polypeptide of (a), (b), (c), (d), (e), (f), (g), (h), (i), (j), (k), (l), (m), (n), (o), (p), (q), (r), (s), (t) or (u) having lysozyme activity and having at least 90% of the length of the mature polypeptide.

The invention also relates to animal feed additives or animal feed comprising the LYS polypeptide of the invention; use of the lysozyme of the LYS polypeptide in animal feed, in animal feed additives, in the preparation of a composition for use in animal feed, and for improving one or more performance parameters in an animal. The invention further relates to methods of improving performance parameters of an animal and for preparing an animal feed; isolated polynucleotides encoding the polypeptides of the invention, nucleic acid constructs, recombinant expression vectors, recombinant host cells and method of producing the LYS polypeptide of the invention. The invention is further directed to the use of composition of the invention in animal feed; in animal feed additives; in the preparation of a composition for use in animal feed; for improving the nutritional value of an animal feed; for increasing digestibility of the animal feed; and/or for improving one or more performance parameters in an animal.

Overview of Sequence Listing

SEQ ID NO: 1 is the cDNA sequence of a LYS polypeptide as isolated from *Penicillium simplicissimum*.

SEQ ID NO: 2 is the amino acid sequence as deduced from SEQ ID NO: 1.

SEQ ID NO: 3 is the amino acid sequence of the mature LYS polypeptide from *Penicillium simplicissimum*.

SEQ ID NO: 4 is the cDNA sequence of a LYS polypeptide as isolated from *Penicillium vasconiae*.

SEQ ID NO: 5 is the amino acid sequence as deduced from SEQ ID NO: 4.

SEQ ID NO: 6 is the amino acid sequence of the mature LYS polypeptide from *Penicillium vasconiae*.

SEQ ID NO: 7 is the cDNA sequence of a LYS polypeptide as isolated from *Talaromyces proteolyticus*.

SEQ ID NO: 8 is the amino acid sequence as deduced from SEQ ID NO: 7.

SEQ ID NO: 9 is the amino acid sequence of the mature LYS polypeptide from *Talaromyces proteolyticus*.

SEQ ID NO: 10 is the cDNA sequence of a LYS polypeptide as isolated from *Aspergillus* sp. XZ2668.

SEQ ID NO: 11 is the amino acid sequence as deduced from SEQ ID NO: 10.

SEQ ID NO: 12 is the amino acid sequence of the mature LYS polypeptide from *Aspergillus* sp. XZ2668.

SEQ ID NO: 13 is the cDNA sequence of a LYS polypeptide as isolated from *Penicillium antarcticum*.

SEQ ID NO: 14 is the amino acid sequence as deduced from SEQ ID NO: 13.

SEQ ID NO: 15 is the amino acid sequence of the mature LYS polypeptide from *Penicillium antarcticum*.

SEQ ID NO: 16 is the cDNA sequence of a LYS polypeptide as isolated from *Ovatospora brasiliensis*.

SEQ ID NO: 17 is the amino acid sequence as deduced from SEQ ID NO: 16.

SEQ ID NO: 18 is the amino acid sequence of the mature LYS polypeptide from *Ovatospora brasiliensis*.

SEQ ID NO: 19 is the cDNA sequence of a LYS polypeptide as isolated from *Penicillium wellingtonense*.

SEQ ID NO: 20 is the amino acid sequence as deduced from SEQ ID NO: 19.

SEQ ID NO: 21 is the amino acid sequence of the mature LYS polypeptide from *Penicillium wellingtonense*.

SEQ ID NO: 22 is the cDNA sequence of a LYS polypeptide as isolated from *Penicillium roseopurpureum*.

SEQ ID NO: 23 is the amino acid sequence as deduced from SEQ ID NO: 22.

SEQ ID NO: 24 is the amino acid sequence of the mature LYS polypeptide from *Penicillium roseopurpureum*.

SEQ ID NO: 25 is the cDNA sequence of a LYS polypeptide as isolated from *Penicillium virgatum*.

SEQ ID NO: 26 is the amino acid sequence as deduced from SEQ ID NO: 25.

SEQ ID NO: 27 is the amino acid sequence of the mature LYS polypeptide from *Penicillium virgatum*.

SEQ ID NO: 28 is the cDNA sequence of a LYS polypeptide as isolated from *Aspergillus niveus*.

SEQ ID NO: 29 is the amino acid sequence as deduced from SEQ ID NO: 28.

SEQ ID NO: 30 is the amino acid sequence of the mature LYS polypeptide from *Aspergillus niveus*.

SEQ ID NO: 31 is the cDNA sequence of a LYS polypeptide as isolated from *Chaetomium* sp. ZY369.

SEQ ID NO: 32 is the amino acid sequence as deduced from SEQ ID NO: 31.

SEQ ID NO: 33 is the amino acid sequence of the mature LYS polypeptide from *Chaetomium* sp. ZY369.

SEQ ID NO: 34 is the cDNA sequence of a LYS polypeptide as isolated from *Talaromyces atricola*.

SEQ ID NO: 35 is the amino acid sequence as deduced from SEQ ID NO: 34.

SEQ ID NO: 36 is the amino acid sequence of the mature LYS polypeptide from *Talaromyces atricola*.

SEQ ID NO: 37 is the cDNA sequence of a LYS polypeptide as isolated from *Trichocladium asperum*.

SEQ ID NO: 38 is the amino acid sequence as deduced from SEQ ID NO: 37.

SEQ ID NO: 39 is the amino acid sequence of the mature LYS polypeptide from *Trichocladium asperum*.

SEQ ID NO: 40 is the cDNA sequence of a LYS polypeptide as isolated from *Metarhizium carneum*.

SEQ ID NO: 41 is the amino acid sequence as deduced from SEQ ID NO: 40.

SEQ ID NO: 42 is the amino acid sequence of the mature LYS polypeptide from *Metarhizium carneum*.

SEQ ID NO: 43 is the cDNA sequence of a LYS polypeptide as isolated from *Thielavia terrestris*.

SEQ ID NO: 44 is the amino acid sequence as deduced from SEQ ID NO: 43.

SEQ ID NO: 45 is the amino acid sequence of the mature LYS polypeptide from *Thielavia terrestris*.

SEQ ID NO: 46 is the amino acid sequence of the LAD domain of SWISSPROT:A1C4L9 from *Aspergillus clavatus*.

SEQ ID NO: 47 is the amino acid sequence of the LAD domain of SWISSPROT:A4X6S9 from *Salinispora tropica*.

SEQ ID NO: 48 is the amino acid sequence of the LAD domain of SWISSPROT:A8M1H3 from *Salinispora arenicola*.

SEQ ID NO: 49 is the amino acid sequence of the LAD domain of SWISSPROT:Q3L9Z6 from *Rhodococcus erythropolis*.

SEQ ID NO: 50 is the amino acid sequence of the LAD domain of SWISSPROT:B5U576 from *Mycobacterium phage* Pacc40.

SEQ ID NO: 51 is the amino acid sequence of the LAD domain of SWISSPROT:B6GZX8 from *Penicillium rubens*.

SEQ ID NO: 52 is the amino acid sequence of the LAD domain of SWISSPROT:D1S6X5 from *Micromonospora aurantiaca*.

SEQ ID NO: 53 is the amino acid sequence of the LAD domain of SWISSPROT:D1S8J3 from *Micromonospora aurantiaca*.

SEQ ID NO: 54 is the amino acid sequence of the LAD domain of SWISSPROT:D1SH66 from *Micromonospora aurantiaca*.

SEQ ID NO: 55 is the amino acid sequence of the LAD domain of SWISSPROT:D5GBH0 from *Tuber melanosporum*.

SEQ ID NO: 56 is the amino acid sequence of the LAD domain of SWISSPROT:G9P583 from *Hypocrea atroviridis*.

SEQ ID NO: 57 is the amino acid sequence of the LAD domain of SWISSPROT:E9ED38 from *Metarhizium acridum*.

SEQ ID NO: 58 is the amino acid sequence of the LAD domain of SWISSPROT:E9FAK9 from *Metarhizium robertsii*.

SEQ ID NO: 59 is the amino acid sequence of the LAD domain of SWISSPROT:F4F8N8 from *Verrucosispora maris*.

SEQ ID NO: 60 is the amino acid sequence of the LAD domain of SWISSPROT:F4F159 from *Verrucosispora maris*.

SEQ ID NO: 61 is the amino acid sequence of the LAD domain of SWISSPROT:J4USU4 from *Beauveria bassiana*.

SEQ ID NO: 62 is the amino acid sequence of the LAD domain of SWISSPROT:G2QV10 from *Thielavia terrestris*.

SEQ ID NO: 63 is the amino acid sequence of the LAD domain of SWISSPROT:A0A1C6W456 from *Micromonospora peucetia*.

SEQ ID NO: 64 is the amino acid sequence of the LAD domain of SWISSPROT:H8E7T0 from *Microbacterium laevaniformans*.

SEQ ID NO: 65 is the amino acid sequence of the LAD domain of SWISSPROT:I0PF45 from *Mycobacterium abscessus*.

SEQ ID NO: 66 is the amino acid sequence of the LAD domain of SWISSPROT:I0L0M9 from *Micromonospora lupini* str Lupac.

SEQ ID NO: 67 is the amino acid sequence of the LAD domain of SWISSPROT:I0L3A4 from *Micromonospora lupini* str Lupac.

SEQ ID NO: 68 is the amino acid sequence of the LAD domain of SWISSPROT:A0A0B2X541 from *Metarhizium album*.

SEQ ID NO: 69 is the amino acid sequence of the LAD domain of SWISSPROT:A0A168BML7 from *Aschersonia aleyrodis*.

SEQ ID NO: 70 is the amino acid sequence of the LAD domain of SWISSPROT:A0A0B2WV75 from *Metarhizium album*.

SEQ ID NO: 71 is the amino acid sequence of the LAD domain of SWISSPROT:A0A167BWW4 from *Cordyceps brongniartii*.

SEQ ID NO: 72 is the amino acid sequence of the LAD domain of SWISSPROT:A0A167ECQ5 from *Metarhizium rileyi*.

SEQ ID NO: 73 is the amino acid sequence of the LAD domain of SWISSPROT:A0A162JZ16 from *Cordyceps confragosa*.

SEQ ID NO: 74 is the amino acid sequence of the LAD domain of SWISSPROT:A0A168DNP6 from *Cordyceps confragosa*.

SEQ ID NO: 75 is the amino acid sequence of the LAD domain of SWISSPROT:A0A168DOL5 from *Cordyceps confragosa*.

SEQ ID NO: 76 is the amino acid sequence of the LAD domain of SWISSPROT:A0A168BQC6 from *Isaria fumosorosea*.

SEQ ID NO: 77 is the amino acid sequence of the LAD domain of SWISSPROT:A0A167X055 from *Isaria fumosorosea*.

SEQ ID NO: 78 is the amino acid sequence of the LAD domain of SWISSPROT:A0A167NNI6 from *Isaria fumosorosea*.

SEQ ID NO: 79 is the amino acid sequence of the LAD domain of SWISSPROT:A0A179H6H8 from *Purpureocillium lilacinum*.

SEQ ID NO: 80 is the amino acid sequence of the LAD domain of SWISSPROT:A0A179FH10 from *Pochonia chlamydosporia*.

SEQ ID NO: 81 is the amino acid sequence of the LAD domain of SWISSPROT:A0A179F665 from *Pochonia chlamydosporia*.

SEQ ID NO: 82 is the amino acid sequence of the LAD domain of SWISSPROT:A0A179F1Q1 from *Pochonia chlamydosporia*.

SEQ ID NO: 83 is the amino acid sequence of the LAD domain of SWISSPROT:S7ZNE7 from *Penicillium oxalicum*.

SEQ ID NO: 84 is the amino acid sequence of the LAD domain of SWISSPROT:A0A0D9PBV5 from *Metarhizium anisopliae*.

SEQ ID NO: 85 is the amino acid sequence of the LAD domain of SWISSPROT:A0A0D9NPP1 from *Metarhizium anisopliae*.

SEQ ID NO: 86 is the amino acid sequence of the LAD domain of SWISSPROT:W6QNL2 from *Penicillium roqueforti*.

SEQ ID NO: 87 is the amino acid sequence of the LAD domain of SWISSPROT:A0A0U1M0W5 from *Talaromyces islandicus*.

SEQ ID NO: 88 is the amino acid sequence of the LAD domain of SWISSPROT:A0A0A219P6 from *Penicillium expansum*.

SEQ ID NO: 89 is the amino acid sequence of the LAD domain of SWISSPROT:A0A086T4C8 from *Acremonium chrysogenum*.

SEQ ID NO: 90 is the amino acid sequence of the LAD domain of SWISSPROT:X8ERY9 from *Mycobacterium chelonae*.

SEQ ID NO: 91 is the amino acid sequence of the LAD domain of SWISSPROT:A0A081HTU5 from *Mycobacterium* sp TKK.

SEQ ID NO: 92 is the amino acid sequence of the LAD domain of SWISSPROT:A0A0A1TMJ0 from *Torrubiella hemipterigena*.

SEQ ID NO: 93 is the amino acid sequence of the LAD domain of SWISSPROT:A0A0A1TNZ8 from *Torrubiella hemipterigena*.

SEQ ID NO: 94 is the amino acid sequence of the LAD domain of SWISSPROT:A0A0A1D149 from *Arthrobacter* sp PAMC.

SEQ ID NO: 95 is the amino acid sequence of the LAD domain of SWISSPROT:A0A0A6UNI9 from *Actinoplanes utahensis*.

SEQ ID NO: 96 is the amino acid sequence of the LAD domain of SWISSPROT:A0A0B4I0X1 from *Metarhizium majus*.

SEQ ID NO: 97 is the amino acid sequence of the LAD domain of SWISSPROT:A0A0D0WU99 from *Micromonospora carbonacea*.

SEQ ID NO: 98 is the amino acid sequence of the LAD domain of SWISSPROT:A0A0D1LTE6 from *Mycobacterium immunogenum*.

SEQ ID NO: 99 is the amino acid sequence of the LAD domain of SWISSPROT:A0A0F8A5E8 from *Hirsutella minnesotensis*.

SEQ ID NO: 100 is the amino acid sequence of the LAD domain of SWISSPROT:A0A0F8A617 from *Hirsutella minnesotensis*.

SEQ ID NO: 101 is the amino acid sequence of the LAD domain of SWISSPROT:A0A0F7TVL0 from *Penicillium brasilianum*.

SEQ ID NO: 102 is the amino acid sequence of the LAD domain of SWISSPROT:A0A0L0N1U6 from *Tolypocladium ophioglossoides*.

SEQ ID NO: 103 is the amino acid sequence of the LAD domain of SWISSPROT:A0A0M0UGY1 from *Madurella mycetomatis*.

SEQ ID NO: 104 is the amino acid sequence of the LAD domain of SWISSPROT:A0A0K8L1J1 from *Aspergillus udagawae*.

SEQ ID NO: 105 is the amino acid sequence of the LAD domain of SWISSPROT:A0A0H5NX60 from *Nocardia farcinica*.

SEQ ID NO: 106 is the amino acid sequence of the LAD domain of SWISSPROT:A0A0M2RBW0 from *Micromonospora* sp HK10.

SEQ ID NO: 107 is the amino acid sequence of the LAD domain of SWISSPROT:A0A0M2RKI6 from *Micromonospora* sp HK10.

SEQ ID NO: 108 is the amino acid sequence of the LAD domain of SWISSPROT:A0A1F5LVD8 from *Penicillium murcianum*.

SEQ ID NO: 109 is the amino acid sequence of the LAD domain of SWISSPROT:A0A0M8XNG9 from *Micromonospora* sp.

SEQ ID NO: 110 is the amino acid sequence of the LAD domain of SWISSPROT:A0A0W7W0M4 from *Trichoderma gamsii*.

SEQ ID NO: 111 is the amino acid sequence of the LAD domain of SWISSPROT:A0A0Q9MHJ4 from *Arthrobacter* sp Soil761.

SEQ ID NO: 112 is the amino acid sequence of the LAD domain of SWISSPROT:A0A0Q9MU26 from *Arthrobacter* sp Soil736.

SEQ ID NO: 113 is the amino acid sequence of the LAD domain of SWISSPROT:A0A0P0DUT5 from *Microbacterium* sp No 7.

SEQ ID NO: 114 is the amino acid sequence of the LAD domain of SWISSPROT:A0A0Q9N9Z1 from *Arthrobacter* sp Soil762.

SEQ ID NO: 115 is the amino acid sequence of the LAD domain of SWISSPROT:A0A1C6RVB7 from *Micromonospora halophytica*.

SEQ ID NO: 116 is the amino acid sequence of the LAD domain of SWISSPROT:A0A1C6SUA9 from *Micromonospora nigra*.

SEQ ID NO: 117 is the amino acid sequence of the LAD domain of SWISSPROT:A0A135LMU8 from *Penicillium patulum*.

SEQ ID NO: 118 is the amino acid sequence of the LAD domain of SWISSPROT:A0A0S9BYR1 from *Arthrobacter* sp Leaf69.

SEQ ID NO: 119 is the amino acid sequence of the LAD domain of SWISSPROT:A0A0U0ZSQ6 from *Mycobacterium abscessus*.

SEQ ID NO: 120 is the amino acid sequence of the LAD domain of SWISSPROT:A0A100WIQ1 from *Mycobacterium canariasense*.

SEQ ID NO: 121 is the amino acid sequence of the LAD domain of SWISSPROT:A0A1091P50 from *Micromonospora rifamycinica*.

SEQ ID NO: 122 is the amino acid sequence of the LAD domain of SWISSPROT:A0A109IHN3 from *Micromonospora rifamycinica*.

SEQ ID NO: 123 is the amino acid sequence of the LAD domain of SWISSPROT:A0A0S2M353 from *Arthrobacter alpinus*.

SEQ ID NO: 124 is the amino acid sequence of the LAD domain of SWISSPROT:A0A134DEL4 from *Microbacterium hominis*.

SEQ ID NO: 125 is the amino acid sequence of the LAD domain of SWISSPROT:A0A142KAG2 from *Gordonia phage* Obliviate.

SEQ ID NO: 126 is the amino acid sequence of the LAD domain of SWISSPROT:A0A136PN50 from *Micromonospora rosaria*.

SEQ ID NO: 127 is the amino acid sequence of the LAD domain of SWISSPROT:A0A138A7X6 from *Tsukamurella pseudospumae*.

SEQ ID NO: 128 is the amino acid sequence of the LAD domain of SWISSPROT:A0A136PTZ6 from *Micromonospora rosaria*.

SEQ ID NO: 129 is the amino acid sequence of the LAD domain of SWISSPROT:A0A177U5Z0 from *Tilletia walkeri*.

SEQ ID NO: 130 is the amino acid sequence of the LAD domain of SWISSPROT:A0A177VGU0 from *Tilletia controversa*.

SEQ ID NO: 131 is the amino acid sequence of the LAD domain of SWISSPROT:A0A179G202 from *Pochonia chlamydosporia* 170.

SEQ ID NO: 132 is the amino acid sequence of the LAD domain of SWISSPROT:A0A179G1N9 from *Pochonia chlamydosporia* 170.

SEQ ID NO: 133 is the amino acid sequence of the LAD domain of SWISSPROT:A0A179FEB3 from *Pochonia chlamydosporia* 170.

SEQ ID NO: 134 is the amino acid sequence of the LAD domain of SWISSPROT:A0A179HTK7 from *Purpureocillium lilacinum*.

SEQ ID NO: 135 is the amino acid sequence of the LAD domain of SWISSPROT:A0A1770655 from *Paraphaeosphaeria sporulosa*.

SEQ ID NO: 136 is the amino acid sequence of the LAD domain of SWISSPROT:A0A167GE76 from *Cordyceps brongniartii* RCEF 3172.

SEQ ID NO: 137 is the amino acid sequence of the LAD domain of SWISSPROT:A0A160DID3 from *Gordonia phage* Utz.

SEQ ID NO: 138 is the amino acid sequence of the LAD domain of SWISSPROT:A0A175J866 from *Arthrobacter nicotinovorans*.

SEQ ID NO: 139 is the amino acid sequence of the LAD domain of SWISSPROT:A0A1A1X5E5 from *Mycobacterium conceptionense*.

SEQ ID NO: 140 is the amino acid sequence of the LAD domain of SWISSPROT:A0A1A8ZCI7 from *Micromonospora narathiwatensis*.

SEQ ID NO: 141 is the amino acid sequence of the LAD domain of SWISSPROT:A0A1A8Z6H4 from *Micromonospora narathiwatensis*.

SEQ ID NO: 142 is the amino acid sequence of the LAD domain of SWISSPROT:A0A1A8Z6S5 from *Micromonospora auratinigra*.

SEQ ID NO: 143 is the amino acid sequence of the LAD domain of SWISSPROT:A0A1A2MHG1 from *Mycobacterium* sp E1747.

SEQ ID NO: 144 is the amino acid sequence of the LAD domain of SWISSPROT:A0A1A9BD29 from *Micromonospora sediminicola*.

SEQ ID NO: 145 is the amino acid sequence of the LAD domain of SWISSPROT:A0A196L8B1 from *Microbacterium* sp H83.

SEQ ID NO: 146 is the amino acid sequence of the LAD domain of SWISSPROT:A0A1C4X8A3 from *Micromonospora coriariae*.

SEQ ID NO: 147 is the amino acid sequence of the LAD domain of SWISSPROT:A0A1C6U2J5 from *Micromonospora citrea*.

SEQ ID NO: 148 is the amino acid sequence of the LAD domain of SWISSPROT:A0A1C6V2H5 from *Micromonospora peucetia*.

SEQ ID NO: 149 is the amino acid sequence of the LAD domain of SWISSPROT:A0A1C6VFJ6 from *Micromonospora yangpuensis*.

SEQ ID NO: 150 is the amino acid sequence of the LAD domain of SWISSPROT:A0A1C6S481 from *Micromonospora rhizosphaerae*.

SEQ ID NO: 151 is the amino acid sequence of the LAD domain of SWISSPROT:A0A1C5K5N0 from *Micromonospora echinaurantiaca*.

SEQ ID NO: 152 is the amino acid sequence of the LAD domain of SWISSPROT:A0A1C5K0N2 from *Micromonospora inositola*.

SEQ ID NO: 153 is the amino acid sequence of the LAD domain of SWISSPROT:A0A1C5JUR0 from *Micromonospora inositola*.

SEQ ID NO: 154 is the amino acid sequence of the LAD domain of SWISSPROT:A0A1C5JX99 from *Micromonospora coxensis*.

SEQ ID NO: 155 is the amino acid sequence of the LAD domain of SWISSPROT:A0A1C4ZAM5 from *Micromonospora mirobrigensis*.

SEQ ID NO: 156 is the amino acid sequence of the LAD domain of SWISSPROT:A0A1C4Z5B4 from *Micromonospora viridifaciens*.

SEQ ID NO: 157 is the amino acid sequence of the LAD domain of SWISSPROT:A0A1C4YQ99 from *Micromonospora haikouensis*.

SEQ ID NO: 158 is the amino acid sequence of the LAD domain of SWISSPROT:A0A1C6W5T7 from *Micromonospora peucetia*.

SEQ ID NO: 159 is the amino acid sequence of the LAD domain of SWISSPROT:A0A1C6W1B9 from *Micromonospora citrea*.

SEQ ID NO: 160 is the amino acid sequence of the LAD domain of SWISSPROT:A0A1C5A7S5 from *Micromonospora saelicesensis*.

SEQ ID NO: 161 is the amino acid sequence of the LAD domain of SWISSPROT:A0A1C5A2Q7 from *Micromonospora echinospora*.

SEQ ID NO: 162 is the amino acid sequence of the LAD domain of SWISSPROT:A0A1C4ZJ35 from *Micromonospora purpureochromogenes*.

SEQ ID NO: 163 is the amino acid sequence of the LAD domain of SWISSPROT:A0A1C5G758 from *Micromonospora echinofusca*.

SEQ ID NO: 164 is the amino acid sequence of the LAD domain of SWISSPROT:A0A1C5H5B2 from *Micromonospora echinaurantiaca*.

SEQ ID NO: 165 is the amino acid sequence of the LAD domain of SWISSPROT:A0A1C6TPW2 from *Micromonospora citrea*.

SEQ ID NO: 166 is the amino acid sequence of the LAD domain of SWISSPROT:A0A1C5IVI4 from *Micromonospora echinaurantiaca*.

SEQ ID NO: 167 is the amino acid sequence of the LAD domain of SWISSPROT:A0A1C6SEC0 from *Micromonospora pallida*.

SEQ ID NO: 168 is the amino acid sequence of the LAD domain of SWISSPROT:A0A1C6SF84 from *Micromonospora rhizosphaerae*.

SEQ ID NO: 169 is the amino acid sequence of the LAD domain of SWISSPROT:A0A1C6SQT8 from *Micromonospora pallida*.

SEQ ID NO: 170 is the amino acid sequence of the LAD domain of SWISSPROT:A0A1C3N2H1 from *Micromonospora krabiensis*.

SEQ ID NO: 171 is the amino acid sequence of the LAD domain of SWISSPROT:A0A1C3N0X1 from *Micromonospora krabiensis*.

SEQ ID NO: 172 is the amino acid sequence of the LAD domain of SWISSPROT:A0A1C9EHM2 from *Mycobacterium phage* Tonenili.

SEQ ID NO: 173 is the amino acid sequence of the LAD domain of SWISSPROT:A0A1C9EHF6 from *Mycobacterium phage* Tonenili.

SEQ ID NO: 174 is the amino acid sequence of the LAD domain of SWISSPROT:A0A1E41B54 from *Pseudonocardia* sp SCN 72-86.

SEQ ID NO: 175 is the amino acid sequence of the LAD domain of SWISSPROT:A0A1G8AK84 from *Microbacterium pygmaeum*.

SEQ ID NO: 176 is the amino acid sequence of the LAD domain of SWISSPROT:A0A1E4NTZ4 from *Pseudonocardia* sp SCN 73-27.

SEQ ID NO: 177 is the amino acid sequence of the LAD domain of SWISSPROT:A0A1J0MA43 from *Mycobacterium phage* Lukilu.

SEQ ID NO: 178 is the amino acid sequence of the LAD domain of SWISSPROT:A0A1N6R3C0 from *Micromonospora avicenniae*.

SEQ ID NO: 179 is the amino acid sequence of the LAD domain of SWISSPROT:A0A1N0VNN7 from *Mycobacterium abscessus* subsp *abscessus*.

SEQ ID NO: 180 is the amino acid sequence of the LAD domain of SWISSPROT:A0A1N4DHL3 from *Mycobacterium abscessus* subsp *abscessus*.

SEQ ID NO: 181 is the amino acid sequence of the LAD domain of SWISSPROT:A0A1N4RVY0 from *Mycobacterium abscessus* subsp *abscessus*.

SEQ ID NO: 182 is the amino acid sequence of the LAD domain of SWISSPROT:A0A1N6X5P6 from *Micromonospora avicenniae*.

SEQ ID NO: 183 is the amino acid sequence of the LAD domain of SWISSPROT:A0A1N2VK68 from *Mycobacterium abscessus* subsp *abscessus*.

SEQ ID NO: 184 is the amino acid sequence of the LAD domain of SWISSPROT:A0A1N1GK82 from *Mycobacterium abscessus* subsp *abscessus*.

SEQ ID NO: 185 is the amino acid sequence of the LAD domain of SWISSPROT:A0A1N1EP78 from *Mycobacterium abscessus* subsp *abscessus*.

SEQ ID NO: 186 is the amino acid sequence of the LAD domain of SWISSPROT:A0A1N1G9F3 from *Mycobacterium abscessus* subsp *abscessus*.

SEQ ID NO: 187 is the amino acid sequence of the LAD domain of SWISSPROT:A0A1Q8LJS1 from *Pseudonocardia* sp Ae717_Ps2.

SEQ ID NO: 188 is the amino acid sequence of the lysozyme enhancing domain of SWISSPROT:B2ASY2 from *Podospora anserina*.

SEQ ID NO: 189 is the amino acid sequence of the lysozyme enhancing domain of SWISSPROT:B6GZX8 from *Penicillium chrysogenum*.

SEQ ID NO: 190 is the amino acid sequence of the lysozyme enhancing domain of SWISSPROT:C7ZQ22 from *Nectria haematococca*.

SEQ ID NO: 191 is the amino acid sequence of the lysozyme enhancing domain of SWISSPROT:E9DSA6 from *Metarhizium acridum*.

SEQ ID NO: 192 is the amino acid sequence of the lysozyme enhancing domain of SWISSPROT:E9F1Z9 from *Metarhizium robertsii*.

SEQ ID NO: 193 is the amino acid sequence of the lysozyme enhancing domain of SWISSPROT:E9FC42 from *Metarhizium robertsii*.

SEQ ID NO: 194 is the amino acid sequence of the lysozyme enhancing domain of SWISSPROT:F9F2K5 from *Fusarium oxysporum*.

SEQ ID NO: 195 is the amino acid sequence of the lysozyme enhancing domain of SWISSPROT:F9GF09 from *Fusarium oxysporum*.

SEQ ID NO: 196 is the amino acid sequence of the lysozyme enhancing domain of SWISSPROT:G2QV10 from *Thielavia terrestris*.

SEQ ID NO: 197 is the amino acid sequence of the lysozyme enhancing domain of SWISSPROT:G2QV26 from *Thielavia terrestris*.

SEQ ID NO: 198 is the amino acid sequence of the lysozyme enhancing domain of SWISSPROT:J5TH48 from *Trichosporon asahii* var. *Asahii*.

SEQ ID NO: 199 is the amino acid sequence of the lysozyme enhancing domain of SWISSPROT:J4UH35 from *Trichosporon asahii* var. *Asahii*.

SEQ ID NO: 200 is the amino acid sequence of the lysozyme enhancing domain of SWISSPROT:J9NQ28 from *Fusarium oxysporum* f. sp. *Lycopersici*.

SEQ ID NO: 201 is the amino acid sequence of the lysozyme enhancing domain of SWISSPROT:J9NQW0 from *Fusarium oxysporum* f. sp. *Lycopersici*.

SEQ ID NO: 202 is the amino acid sequence of the lysozyme enhancing domain of SWISSPROT:K1VMN5 from *Trichosporon asahii* var. *Asahii*.

SEQ ID NO: 203 is the amino acid sequence of the lysozyme enhancing domain of SWISSPROT:K1WL46 from *Trichosporon asahii* var. *Asahii*.

SEQ ID NO: 204 is the amino acid sequence of the lysozyme enhancing domain of SWISSPROT:W9Z045 from *Fusarium oxysporum* f. sp. *Melonis*.

SEQ ID NO: 205 is the amino acid sequence of the lysozyme enhancing domain of SWISSPROT:XOA5V9 from *Fusarium oxysporum* f. sp. *Melonis*.

SEQ ID NO: 206 is the amino acid sequence of the lysozyme enhancing domain of SWISSPROT:N1S551 from *Fusarium oxysporum* f. sp. *Cubense*.

SEQ ID NO: 207 is the amino acid sequence of the lysozyme enhancing domain of SWISSPROT:N4UD22 from *Fusarium oxysporum* f. sp. *Cubense*.

SEQ ID NO: 208 is the amino acid sequence of the lysozyme enhancing domain of SWISSPROT:N4UT47 from *Fusarium oxysporum* f. sp. *Cubense*.

SEQ ID NO: 209 is the amino acid sequence of the lysozyme enhancing domain of SWISSPROT:W9KVWV4 from *Fusarium oxysporum*.

SEQ ID NO: 210 is the amino acid sequence of the lysozyme enhancing domain of SWISSPROT:X0MM97 from *Fusarium oxysporum* f. sp. *Vasinfectum*.

SEQ ID NO: 211 is the amino acid sequence of the lysozyme enhancing domain of SWISSPROT:W7N5Q6 from *Gibberella moniliformis*.

SEQ ID NO: 212 is the amino acid sequence of the lysozyme enhancing domain of SWISSPROT:X0BE07 from *Fusarium oxysporum* f. sp. *Raphani*.

SEQ ID NO: 213 is the amino acid sequence of the lysozyme enhancing domain of SWISSPROT:X0B118 from *Fusarium oxysporum*.

SEQ ID NO: 214 is the amino acid sequence of the lysozyme enhancing domain of SWISSPROT:W9NW59 from *Fusarium oxysporum* f. sp. *Pisi*.

SEQ ID NO: 215 is the amino acid sequence of the lysozyme enhancing domain of SWISSPROT:W9NXR4 from *Fusarium oxysporum* f. sp. *Pisi*.

SEQ ID NO: 216 is the amino acid sequence of the lysozyme enhancing domain of SWISSPROT:S7ZNE7 from *Penicillium oxalicum*.

SEQ ID NO: 217 is the amino acid sequence of the lysozyme enhancing domain of SWISSPROT:S7Z5Z6 from *Penicillium oxalicum*.

SEQ ID NO: 218 is the amino acid sequence of the lysozyme enhancing domain of SWISSPROT:W9LDD0 from *Fusarium oxysporum* f. sp. *Lycopersici*.

SEQ ID NO: 219 is the amino acid sequence of the lysozyme enhancing domain of SWISSPROT:W9HEM8 from *Fusarium oxysporum*.

SEQ ID NO: 220 is the amino acid sequence of the lysozyme enhancing domain of SWISSPROT:W9JDH4 from *Fusarium oxysporum*.

SEQ ID NO: 221 is the amino acid sequence of the lysozyme enhancing domain of SWISSPROT:S0EPI6 from *Gibberella fujikuroi*.

SEQ ID NO: 222 is the amino acid sequence of the lysozyme enhancing domain of SWISSPROT:W6QNL2 from *Penicillium roqueforti*.

SEQ ID NO: 223 is the amino acid sequence of the lysozyme enhancing domain of SWISSPROT: U4LJD9 from *Pyronema omphalodes*.

SEQ ID NO: 224 is the amino acid sequence of the lysozyme enhancing domain of SWISSPROT:U4LG64 from *Pyronema omphalodes*.

SEQ ID NO: 225 is the amino acid sequence of the lysozyme enhancing domain of SWISSPROT: A0A094AK50 from *Pseudogymnoascus pannorum*.

SEQ ID NO: 226 is the amino acid sequence of the lysozyme enhancing domain of SWISSPROT:W9JIH2 from *Fusarium oxysporum*.

SEQ ID NO: 227 is the amino acid sequence of the lysozyme enhancing domain of SWISSPROT:X0FW82 from *Fusarium oxysporum* f. sp. *radicis-lycopersici*.

SEQ ID NO: 228 is the amino acid sequence of the lysozyme enhancing domain of SWISSPROT: A0A086TBY7 from *Acremonium chrysogenum*.

SEQ ID NO: 229 is the amino acid sequence of the lysozyme enhancing domain of SWISSPROT:A0A086T755 from *Acremonium chrysogenum*.

SEQ ID NO: 230 is the amino acid sequence of the lysozyme enhancing domain of SWISSPROT: A0A086T4C8 from *Acremonium chrysogenum*.

SEQ ID NO: 231 is the amino acid sequence of the lysozyme enhancing domain of SWISSPROT: A0A086NNR4 from *Metarhizium anisopliae*.

SEQ ID NO: 232 is the amino acid sequence of the lysozyme enhancing domain of SWISSPROT: A0A086NFK5 from *Metarhizium anisopliae*.

SEQ ID NO: 233 is the amino acid sequence of the lysozyme enhancing domain of SWISSPROT: A0A094FY19 from *Pseudogymnoascus pannorum*.

SEQ ID NO: 234 is the amino acid sequence of the lysozyme enhancing domain of SWISSPROT: A0A094G1N0 from *Pseudogymnoascus pannorum*.

SEQ ID NO: 235 is the amino acid sequence of the lysozyme enhancing domain of SWISSPROT: A0A094GEA0 from *Pseudogymnoascus pannorum*.

SEQ ID NO: 236 is the amino acid sequence of the lysozyme enhancing domain of SWISSPROT: A0A094GJR5 from *Pseudogymnoascus pannorum*.

SEQ ID NO: 237 is the amino acid sequence of the lysozyme enhancing domain of SWISSPROT:A0A094G660 from *Pseudogymnoascus pannorum*.

SEQ ID NO: 238 is the amino acid sequence of the lysozyme enhancing domain of SWISSPROT: A0A093YBN4 from *Pseudogymnoascus pannorum*.

SEQ ID NO: 239 is the amino acid sequence of the lysozyme enhancing domain of SWISSPROT:A0A094FSZ5 from *Pseudogymnoascus pannorum*.

SEQ ID NO: 240 is the amino acid sequence of the lysozyme enhancing domain of SWISSPROT: A0A094FBW1 from *Pseudogymnoascus pannorum*.

SEQ ID NO: 241 is the amino acid sequence of the lysozyme enhancing domain of SWISSPROT: A0A094H0G2 from *Pseudogymnoascus pannorum*.

SEQ ID NO: 242 is the amino acid sequence of the lysozyme enhancing domain of SWISSPROT: A0A094H7M1 from *Pseudogymnoascus pannorum*.

SEQ ID NO: 243 is the amino acid sequence of the lysozyme enhancing domain of SWISSPROT: A0A093Y8W3 from *Pseudogymnoascus pannorum*.

SEQ ID NO: 244 is the amino acid sequence of the lysozyme enhancing domain of SWISSPROT: A0A094GYN9 from *Pseudogymnoascus pannorum*.

SEQ ID NO: 245 is the amino acid sequence of the lysozyme enhancing domain of SWISSPROT: A0A093XAD4 from *Pseudogymnoascus pannorum*.

SEQ ID NO: 246 is the amino acid sequence of the lysozyme enhancing domain of SWISSPROT:A0A094H7J6 from *Pseudogymnoascus pannorum*.

SEQ ID NO: 247 is the amino acid sequence of the lysozyme enhancing domain of SWISSPROT:A0A094E0I1 from *Pseudogymnoascus pannorum*.

SEQ ID NO: 248 is the amino acid sequence of the lysozyme enhancing domain of SWISSPROT: A0A094CC50 from *Pseudogymnoascus pannorum*.

SEQ ID NO: 249 is the amino acid sequence of the lysozyme enhancing domain of SWISSPROT:A0A094II95 from *Pseudogymnoascus pannorum*.

SEQ ID NO: 250 is the amino acid sequence of the lysozyme enhancing domain of SWISSPROT: A0A094IAA0 from *Pseudogymnoascus pannorum*.

SEQ ID NO: 251 is the amino acid sequence of the lysozyme enhancing domain of SWISSPROT:A0A094IBC0 from *Pseudogymnoascus pannorum*.

SEQ ID NO: 252 is the amino acid sequence of the lysozyme enhancing domain of SWISSPROT:A0A094E946 from *Pseudogymnoascus pannorum*.

SEQ ID NO: 253 is the amino acid sequence of the lysozyme enhancing domain of SWISSPROT: A0A094A3A0 from *Pseudogymnoascus pannorum*.

SEQ ID NO: 254 is the amino acid sequence of the lysozyme enhancing domain of SWISSPROT:A1C4L9 from *Aspergillus clavatus*.

SEQ ID NO: 255 is the amino acid sequence of the lysozyme enhancing domain of SWISSPROT:A1CBV9 from *Aspergillus clavatus*.

SEQ ID NO: 256 is the amino acid sequence of the lysozyme enhancing domain of SWISSPROT:A1DA80 from *Neosartorya fischeri*.

SEQ ID NO: 257 is the amino acid sequence of the lysozyme enhancing domain of SWISSPROT:A1DBW2 from *Neosartorya fischeri*.

SEQ ID NO: 258 is the amino acid sequence of the lysozyme enhancing domain of SWISSPROT:A1DDF2 from *Neosartorya fischeri*.

SEQ ID NO: 259 is the amino acid sequence of the lysozyme enhancing domain of SWISSPROT:Q0CED1 from *Aspergillus terreus*.

SEQ ID NO: 260 is the amino acid sequence of the lysozyme enhancing domain of SWISSPROT:Q0CED2 from *Aspergillus terreus*.

SEQ ID NO: 261 is the amino acid sequence of the lysozyme enhancing domain of SWISSPROT:Q0CV85 from *Aspergillus terreus*.

SEQ ID NO: 262 is the amino acid sequence of the lysozyme enhancing domain of SWISSPROT:Q2GND8 from *Chaetomium globosum*.

SEQ ID NO: 263 is the amino acid sequence of the lysozyme enhancing domain of SWISSPROT:Q2GND9 from *Chaetomium globosum*.

SEQ ID NO: 264 is the amino acid sequence of the lysozyme enhancing domain of SWISSPROT:Q2H6W7 from *Chaetomium globosum*.

SEQ ID NO: 265 is the amino acid sequence of the lysozyme enhancing domain of SWISSPROT:Q4WAY2 from *Neosartorya fumigata*.

SEQ ID NO: 266 is the amino acid sequence of the lysozyme enhancing domain of SWISSPROT:Q4WBR4 from *Neosartorya fumigata*.

SEQ ID NO: 267 is the amino acid sequence of the lysozyme enhancing domain of SWISSPROT:Q4WVY3 from *Neosartorya fumigata*.

SEQ ID NO: 268 is the amino acid sequence of the lysozyme enhancing domain of SWISSPROT:B6H9X5 from *Penicillium* chrysogenum.

SEQ ID NO: 269 is the amino acid sequence of the lysozyme enhancing domain of SWISSPROT:B6HR38 from *Penicillium* chrysogenum.

SEQ ID NO: 270 is the amino acid sequence of the lysozyme enhancing domain of SWISSPROT:C7Z8W0 from *Nectria haematococca*.

SEQ ID NO: 271 is the amino acid sequence of the lysozyme enhancing domain of SWISSPROT:C7ZQ20 from *Nectria haematococca*.

SEQ ID NO: 272 is the amino acid sequence of the lysozyme enhancing domain of SWISSPROT:G0RP87 from *Hypocrea jecorina*.

SEQ ID NO: 273 is the amino acid sequence of the lysozyme enhancing domain of SWISSPROT:G2RG69 from *Thielavia terrestris*.

SEQ ID NO: 274 is the amino acid sequence of the lysozyme enhancing domain of SWISSPROT:G2QNE9 from *Thielavia heterothallica*.

SEQ ID NO: 275 is the amino acid sequence of the lysozyme enhancing domain of SWISSPROT:G0RM22 from *Hypocrea jecorina*.

SEQ ID NO: 276 is the amino acid sequence of the lysozyme enhancing domain of SWISSPROT:G0SG36 from *Chaetomium thermophilum* var. *Thermophilum*.

SEQ ID NO: 277 is the amino acid sequence of the lysozyme enhancing domain of SWISSPROT:G0RZV3 from *Chaetomium thermophilum* var. *Thermophilum*.

SEQ ID NO: 278 is the amino acid sequence of the lysozyme enhancing domain of SWISSPROT:J9NQV9 from *Fusarium oxysporum* f. sp. *Lycopersici*.

SEQ ID NO: 279 is the amino acid sequence of the lysozyme enhancing domain of SWISSPROT:G2QD02 from *Thielavia heterothallica*.

SEQ ID NO: 280 is the amino acid sequence of the lysozyme enhancing domain of SWISSPROT:G2QNF0 from *Thielavia heterothallica*.

SEQ ID NO: 281 is the amino acid sequence of the lysozyme enhancing domain of SWISSPROT:G9MHR1 from *Hypocrea virens*.

SEQ ID NO: 282 is the amino acid sequence of the lysozyme enhancing domain of SWISSPROT:E9ELX9 from *Metarhizium robertsii*.

SEQ ID NO: 283 is the amino acid sequence of the lysozyme enhancing domain of SWISSPROT:F9F2K4 from *Fusarium oxysporum*.

SEQ ID NO: 284 is the amino acid sequence of the lysozyme enhancing domain of SWISSPROT:G0RZV2 from *Chaetomium thermophilum* var. *Thermophilum*.

SEQ ID NO: 285 is the amino acid sequence of the lysozyme enhancing domain of SWISSPROT:G2RG70 from *Thielavia terrestris*.

SEQ ID NO: 286 is the amino acid sequence of the lysozyme enhancing domain of SWISSPROT:W9Z992 from *Fusarium oxysporum* f. sp. *Melonis*.

SEQ ID NO: 287 is the amino acid sequence of the lysozyme enhancing domain of SWISSPROT:W9ZZW9 from *Fusarium oxysporum* f. sp. *Melonis*.

SEQ ID NO: 288 is the amino acid sequence of the lysozyme enhancing domain of SWISSPROT:W9ZAE8 from *Fusarium oxysporum* f. sp. *Melonis*.

SEQ ID NO: 289 is the amino acid sequence of the lysozyme enhancing domain of SWISSPROT:N1RWA4 from *Fusarium oxysporum* f. sp. *Cubense*.

SEQ ID NO: 290 is the amino acid sequence of the lysozyme enhancing domain of SWISSPROT:N4UKT7 from *Fusarium oxysporum* f. sp. *Cubense*.

SEQ ID NO: 291 is the amino acid sequence of the lysozyme enhancing domain of SWISSPROT:W9KX02 from *Fusarium oxysporum*.

SEQ ID NO: 292 is the amino acid sequence of the lysozyme enhancing domain of SWISSPROT:X0B4J3 from *Fusarium oxysporum* f. sp. *Raphani*.

SEQ ID NO: 293 is the amino acid sequence of the lysozyme enhancing domain of SWISSPROT:W6QE02 from *Penicillium roqueforti*.

SEQ ID NO: 294 is the amino acid sequence of the lysozyme enhancing domain of SWISSPROT:W6R4X8 from *Penicillium roqueforti*.

SEQ ID NO: 295 is the amino acid sequence of the lysozyme enhancing domain of SWISSPROT:A0A024S9B8 from *Trichoderma reesei*.

SEQ ID NO: 296 is the amino acid sequence of the lysozyme enhancing domain of SWISSPROT: A0A086NN36 from *Metarhizium anisopliae*.

SEQ ID NO: 297 is the amino acid sequence of the lysozyme enhancing domain of SWISSPROT: A0A094GA03 from *Pseudogymnoascus pannorum*.

SEQ ID NO: 298 is the amino acid sequence of the lysozyme enhancing domain of SWISSPROT: A0A094C8U1 from *Pseudogymnoascus pannorum*.

SEQ ID NO: 299 is the amino acid sequence of the lysozyme enhancing domain of SWISSPROT:A0A093Z6Z8 from *Pseudogymnoascus pannorum*.

SEQ ID NO: 300 is the amino acid sequence of the lysozyme enhancing domain of SWISSPROT: A0A094IML3 from *Pseudogymnoascus pannorum*.

SEQ ID NO: 301 is the amino acid sequence of the lysozyme enhancing domain of SWISSPROT: A0A094GY79 from *Pseudogymnoascus pannorum*.

SEQ ID NO: 302 is the amino acid sequence of the lysozyme enhancing domain of SWISSPROT: A0A093XPZ7 from *Pseudogymnoascus pannorum*.

SEQ ID NO: 303 is the amino acid sequence of the lysozyme enhancing domain of SWISSPROT: A0A093XAS9 from *Pseudogymnoascus pannorum*.

SEQ ID NO: 304 is the amino acid sequence of the lysozyme enhancing domain of SWISSPROT:A0A09418J6 from *Pseudogymnoascus pannorum*.

SEQ ID NO: 305 is the amino acid sequence of the lysozyme enhancing domain of SWISSPROT: A0A094FTL0 from *Pseudogymnoascus pannorum*.

SEQ ID NO: 306 is the amino acid sequence of the lysozyme enhancing domain of SWISSPROT:A0A094AT39 from *Pseudogymnoascus pannorum*.

SEQ ID NO: 307 is the amino acid sequence of the lysozyme enhancing domain of SWISSPROT: A0A093XSP5 from *Pseudogymnoascus pannorum*.

SEQ ID NO: 308 is the amino acid sequence of the lysozyme enhancing domain of SWISSPROT: A0A094BAE6 from *Pseudogymnoascus pannorum*.

SEQ ID NO: 309 is the amino acid sequence of the lysozyme enhancing domain of SWISSPROT:A0A0941E25 from *Pseudogymnoascus pannorum*.

SEQ ID NO: 310 is the amino acid sequence of the lysozyme enhancing domain of SWISSPROT: A0A094HNM8 from *Pseudogymnoascus pannorum*.

SEQ ID NO: 311 is the amino acid sequence of the lysozyme enhancing domain of SWISSPROT:A0A094ETJ5 from *Pseudogymnoascus pannorum*.

SEQ ID NO: 312 is the amino acid sequence of the lysozyme enhancing domain of SWISSPROT:A0A094EPJ7 from *Pseudogymnoascus pannorum*.

SEQ ID NO: 313 is the amino acid sequence of the lysozyme enhancing domain of SWISSPROT: A0A094E9W0 from *Pseudogymnoascus pannorum*.

SEQ ID NO: 314 is the amino acid sequence of the lysozyme enhancing domain of SWISSPROT: A0A094BWD6 from *Pseudogymnoascus pannorum*.

SEQ ID NO: 315 is the amino acid sequence of the lysozyme enhancing domain of SWISSPROT: A0A094BTS1 from *Pseudogymnoascus pannorum*.

SEQ ID NO: 316 is the amino acid sequence of the lysozyme enhancing domain of SWISSPROT: A0A093ZTZ8 from *Pseudogymnoascus pannorum*.

SEQ ID NO: 317 is conserved motif I AG[I/L]AT[A/G][I/L][T/V]ES.

SEQ ID NO: 318 is conserved motif II V[G/A]XLCQXVQXSAYP.

SEQ ID NO: 319 is conserved motif III [CGY][YF][VIL][ASTP][DG]X[YF][VIT]X[TS][GAN].

SEQ ID NO: 320 is the synthetic DNA construct of plasmid pDAu770.

SEQ ID NO: 321 is the forward primer KKSC0972-F.

SEQ ID NO: 322 is the reverse primer KKSC0972-R.

SEQ ID NO: 323 is forward primer F1.

SEQ ID NO: 324 is reverse primer F1.

SEQ ID NO: 325 is forward primer F3.

SEQ ID NO: 326 is reverse primer F3.

SEQ ID NO: 327 Primer bind forward.

SEQ ID NO: 328 Primer bind reverse.

SEQ ID NO: 329 is the amino acid sequence of the truncated LYA polypeptide from *Ovatospora brasiliensis*.

FIGURES

FIG. 1 represents the map of the different DNA features included on the plasmid pDAu770. The amy2 locus flanking regions (3' and 5') are indicated by white boxes. Promoter regions are indicated by green boxes for the promoter region of the pyrG, tef1 and tpi gene. The purple boxes indicate the selection cassette (ampR for ampicillin resistance and amdS for acetamide selection). The terminator regions are indicated by blue boxes for the terminator region of the niaD and amg genes. The coding region of the FLPase (sFLP) and the first exon of the pyrG gene are indicated in orange. The 5' region of the pyrG intron is indicated in grey. The origin of replication of the plasmid is indicated by ORI.

Figure 2:
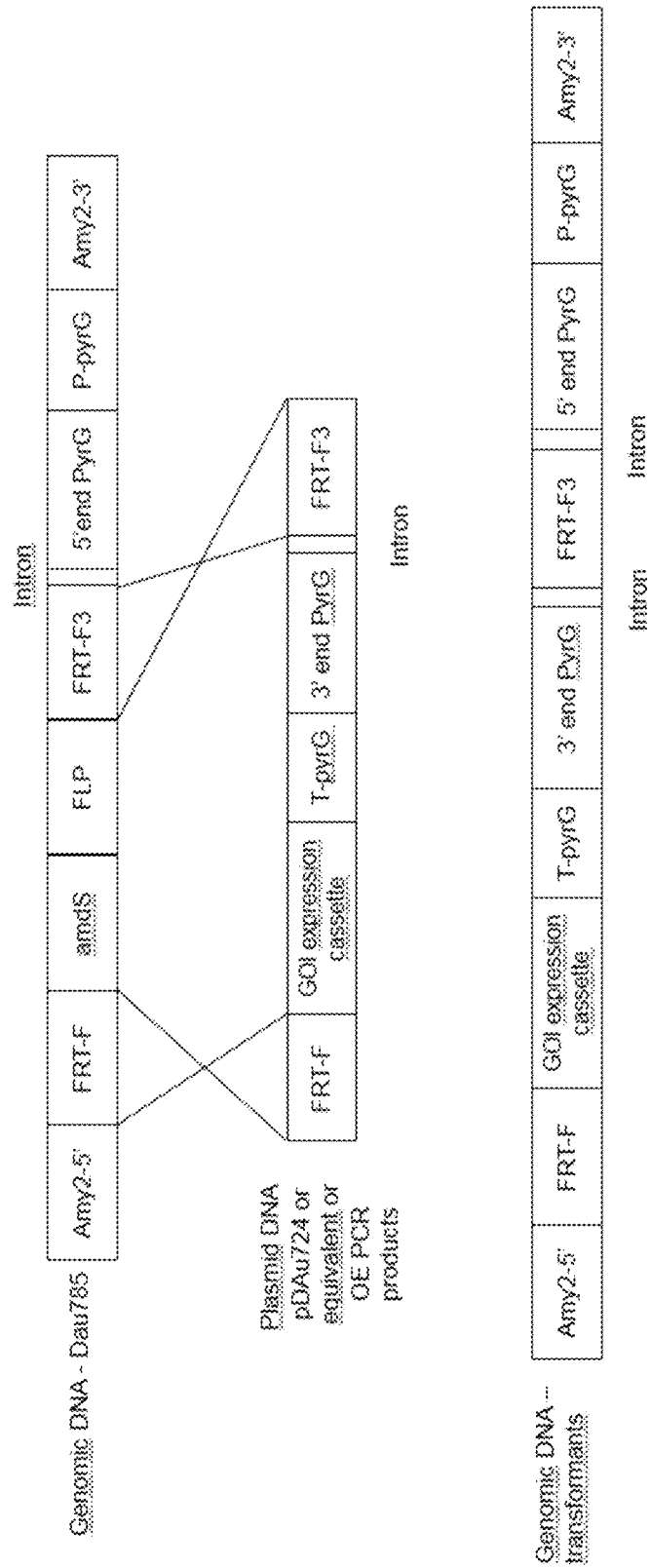

FIG. 2 is the schematic representation of transformation of the host strain DAu785 by the transforming DNA (either plasmid pDAu724 or derivatives or OverlapExtension PCR products.

Top panel represents the locus amy2 with the integration of the FLP landing pad composed of FRT-F and FRT-F3 the FLPase recognition site, as well as the amdS (acetamide) selection marker and the FLPase expression cassette. A split PyrG marker has been used and at the amy2 locus the 5' end of the pyrG marker is inserted.

Middle panel represents the transforming DNA, in particular the region that is integrated at the FLP landing pad by site specific recombination mediated by FLPase. The plasmid or PCR product must contain FRT-F and F3 sites as well as the remaining 3' part of the pyrG marker.

Bottom panel represents the resulting amy2 locus after site specific integration of the transforming DNA between the FRT sites. The amdS and FLP cassettes have been exchanged with the GOI expression cassette and the 3' part of the pyrG marker reconstituting a fully functional selection marker.

Definitions

Animal: The term "animal" refers to any animal except humans. Examples of animals are monogastric animals, including but not limited to pigs or swine (including, but not limited to, piglets, growing pigs, and sows); poultry such as turkeys, ducks, quail, guinea fowl, geese, pigeons (including squabs) and chicken (including but not limited to broiler chickens (referred to herein as broiles), chicks, layer hens (referred to herein as layers)); horses (including but not limited to hotbloods, coldbloods and warm bloods) crustaceans (including but not limited to shrimps and prawns) and fish (including but not limited to amberjack, arapaima, barb, bass, bluefish, bocachico, bream, bullhead, cachama, carp, catfish, catla, chanos, char, cichlid, cobia, cod, crappie, dorada, drum, eel, goby, goldfish, gourami, grouper, guapote, halibut, java, labeo, lai, loach, mackerel, milkfish, mojarra, mudfish, mullet, paco, pearlspot, pejerrey, perch, pike, pompano, roach, salmon, sampa, sauger, sea bass, seabream, shiner, sleeper, snakehead, snapper, snook, sole, spinefoot, sturgeon, sunfish, sweetfish, tench, terror, tilapia, trout, tuna, turbot, vendace, walleye and whitefish).

Animal feed: The term "animal feed" refers to any compound, preparation, or mixture suitable for, or intended for intake by a monogastric animal. Animal feed for a monogastric animal typically comprises concentrates as well as vitamins, minerals, enzymes, direct fed microbial, amino acids and/or other feed ingredients (such as in a premix).

Antimicrobial activity: The term "antimicrobial activity" is defined herein as an activity that kills or inhibits the growth of microorganisms, such as, algae, archea, bacteria, fungi and/or protozoans. The antimicrobial activity can, for example, be bactericidal meaning the killing of bacteria or bacteriostatic meaning the prevention of bacterial growth. The antimicrobial activity can include catalyzing the hydrolysis of 1,4-beta-linkages between N-acetylmuramic acid and N-acetyl-D-glucosamine residues in a peptidoglycan and between N-acetyl-D-glucosamine residues in chitodextrins. Antimicrobial activity can also include the LYS polypeptide binding to the surface of the microorganism and inhibiting its growth. The antimicrobial effect can also include the use of the LYS polypeptides of the present invention for activation of bacterial autolysins, as an immunostimulator, by inhibiting or reducing bacterial toxins and by an opsonin effect.

Body Weight Gain: The term "body weight gain" means an increase in live weight of an animal during a given period of time e.g. the increase in weight from day 1 to day 21.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Concentrates: The term "concentrates" means feed with high protein and energy concentrations, such as fish meal, molasses, oligosaccharides, sorghum, seeds and grains (either whole or prepared by crushing, milling, etc. from e.g. corn, oats, rye, barley, wheat), oilseed press cake (e.g. from cottonseed, safflower, sunflower, soybean (such as soybean meal), rapeseed/canola, peanut or groundnut), palm kernel cake, yeast derived material and distillers grains (such as wet distillers grains (WDS) and dried distillers grains with solubles (DDGS)).

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

European Production Efficacy Factor (EPEF): The "European Production Efficacy Factor" is a way of comparing the performance of animals. This single-figure facilitates comparison of performance within and among farms and can be used to assess environmental, climatic and managemental variables. The EPEF is calculated as [(liveability (%)×Liveweight (kg))/(Age at depletion (days)×FCR)]×100, wherein livability is the percentage of animals alive at slaughter, Liveweight is the average weight of the animals at slaughter, age of depletion is the age of the animals at slaughter and FCR is the feed conversion ratio at slaughter.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Feed Conversion Ratio (FCR): FCR is a measure of an animal's efficiency in converting feed mass into increases of the desired output. Animals raised for meat—such as swine, poultry and fish—the output is the mass gained by the animal. Specifically, FCR is calculated as feed intake divided by weight gain, all over a specified period. Improvement in FCR means reduction of the FCR value. A FCR improvement of 2% means that the FCR was reduced by 2%.

Feed efficiency: The term "feed efficiency" means the amount of weight gain per unit of feed when the animal is fed ad-libitum or a specified amount of food during a period of time. By "increased feed efficiency" it is meant that the use of a feed additive composition according the present invention in feed results in an increased weight gain per unit of feed intake compared with an animal fed without said feed additive composition being present.

Forage: The term "forage" as defined herein also includes roughage. Forage is fresh plant material such as hay and silage from forage plants, grass and other forage plants, seaweed, sprouted grains and legumes, or any combination thereof. Examples of forage plants are Alfalfa (lucerne), birdsfoot trefoil, brassica (e.g. kale, rapeseed (canola), rutabaga (swede), turnip), clover (e.g. alsike clover, red clover, subterranean clover, white clover), grass (e.g. Bermuda grass, brome, false oat grass, fescue, heath grass, meadow grasses, orchard grass, ryegrass, Timothy-grass), corn (maize), millet, barley, oats, rye, sorghum, soybeans and wheat and vegetables such as beets. Forage further includes crop residues from grain production (such as corn stover; straw from wheat, barley, oat, rye and other grains); residues from vegetables like beet tops; residues from oilseed production like stems and leaves form soy beans, rapeseed and other legumes; and fractions from the refining of grains for animal or human consumption or from fuel production or other industries.

Fragment: The term "fragment" means a LYS polypeptide having one or more (e.g., several) amino acids absent from the amino and/or carboxyl terminus of a mature polypeptide or domain; wherein the fragment has lysozyme activity.

In one aspect, the fragment comprises at least 90% of the length of the mature polypeptide, such as at least 203 amino acids of SEQ ID NO: 2, at least 203 amino acids of SEQ ID NO: 3, at least 203 amino acids of SEQ ID NO: 5, at least 203 amino acids of SEQ ID NO: 6, at least 200 amino acids of SEQ ID NO: 8, at least 200 amino acids of SEQ ID NO: 9, at least 273 amino acids of SEQ ID NO: 11, at least 273 amino acids of SEQ ID NO: 12, at least 205 amino acids of SEQ ID NO: 14, at least 205 amino acids of SEQ ID NO: 15, at least 207 amino acids of SEQ ID NO: 17, at least 207 amino acids of SEQ ID NO: 18, at least 207 amino acids of SEQ ID NO: 20, at least 207 amino acids of SEQ ID NO: 21, at least 208 amino acids of SEQ ID NO: 23, at least 208 amino acids of SEQ ID NO: 24, at least 205 amino acids of SEQ ID NO: 26, at least 205 amino acids of SEQ ID NO: 27, at least 205 amino acids of SEQ ID NO: 29, at least 205 amino acids of SEQ ID NO: 30, at least 203 amino acids of SEQ ID NO: 32, at least 203 amino acids of SEQ ID NO: 33, at least 202 amino acids of SEQ ID NO: 35, at least 202 amino acids of SEQ ID NO: 36, at least 202 amino acids of SEQ ID NO: 38, at least 202 amino acids of SEQ ID NO: 39, at least 273 amino acids of SEQ ID NO: 41, at least 273 amino acids of SEQ ID NO: 42, at least 204 amino acids of SEQ ID NO: 44, or at least 204 amino acids of SEQ ID NO: 45.

In one aspect, the fragment comprises at least 92% of the length of the mature polypeptide, such as at least 207 amino acids of SEQ ID NO: 2, at least 207 amino acids of SEQ ID NO: 3, at least 207 amino acids of SEQ ID NO: 5, at least 207 amino acids of SEQ ID NO: 6, at least 205 amino acids of SEQ ID NO: 8, at least 205 amino acids of SEQ ID NO: 9, at least 279 amino acids of SEQ ID NO: 11, at least 279 amino acids of SEQ ID NO: 12, at least 209 amino acids of SEQ ID NO: 14, at least 209 amino acids of SEQ ID NO: 15, at least 211 amino acids of SEQ ID NO: 17, at least 211 amino acids of SEQ ID NO: 18, at least 211 amino acids of SEQ ID NO: 20, at least 211 amino acids of SEQ ID NO: 21, at least 213 amino acids of SEQ ID NO: 23, at least 213 amino acids of SEQ ID NO: 24, at least 209 amino acids of SEQ ID NO: 26, at least 209 amino acids of SEQ ID NO: 27, at least 209 amino acids of SEQ ID NO: 29, at least 209 amino acids of SEQ ID NO: 30, at least 207 amino acids of SEQ ID NO: 32, at least 207 amino acids of SEQ ID NO: 33, at least 207 amino acids of SEQ ID NO: 35, at least 207 amino acids of SEQ ID NO: 36, at least 207 amino acids of SEQ ID NO: 38, at least 207 amino acids of SEQ ID NO: 39, at least 279 amino acids of SEQ ID NO: 41, at least 279 amino acids of SEQ ID NO: 42, at least 208 amino acids of SEQ ID NO: 44, or at least 208 amino acids of SEQ ID NO: 45.

In one aspect, the fragment comprises at least 94% of the length of the mature polypeptide, such as at least 212 amino acids of SEQ ID NO: 2, at least 212 amino acids of SEQ ID NO: 3, at least 212 amino acids of SEQ ID NO: 5, at least 212 amino acids of SEQ ID NO: 6, at least 209 amino acids of SEQ ID NO: 8, at least 209 amino acids of SEQ ID NO: 9, at least 285 amino acids of SEQ ID NO: 11, at least 285 amino acids of SEQ ID NO: 12, at least 214 amino acids of SEQ ID NO: 14, at least 214 amino acids of SEQ ID NO: 15, at least 216 amino acids of SEQ ID NO: 17, at least 216 amino acids of SEQ ID NO: 18, at least 216 amino acids of SEQ ID NO: 20, at least 216 amino acids of SEQ ID NO: 21, at least 218 amino acids of SEQ ID NO: 23, at least 218 amino acids of SEQ ID NO: 24, at least 214 amino acids of SEQ ID NO: 26, at least 214 amino acids of SEQ ID NO: 27, at least 214 amino acids of SEQ ID NO: 29, at least 214 amino acids of SEQ ID NO: 30, at least 212 amino acids of SEQ ID NO: 32, at least 212 amino acids of SEQ ID NO: 33, at least 211 amino acids of SEQ ID NO: 35, at least 211 amino acids of SEQ ID NO: 36, at least 211 amino acids of SEQ ID NO: 38, at least 211 amino acids of SEQ ID NO: 39, at least 285 amino acids of SEQ ID NO: 41, at least 285 amino acids of SEQ ID NO: 42, at least 213 amino acids of SEQ ID NO: 44, or at least 213 amino acids of SEQ ID NO: 45.

In one aspect, the fragment comprises at least 96% of the length of the mature polypeptide, such as at least 216 amino acids of SEQ ID NO: 2, at least 216 amino acids of SEQ ID NO: 3, at least 216 amino acids of SEQ ID NO: 5, at least 216 amino acids of SEQ ID NO: 6, at least 214 amino acids of SEQ ID NO: 8, at least 214 amino acids of SEQ ID NO: 9, at least 291 amino acids of SEQ ID NO: 11, at least 291 amino acids of SEQ ID NO: 12, at least 218 amino acids of SEQ ID NO: 14, at least 218 amino acids of SEQ ID NO: 15, at least 220 amino acids of SEQ ID NO: 17, at least 220 amino acids of SEQ ID NO: 18, at least 220 amino acids of SEQ ID NO: 20, at least 220 amino acids of SEQ ID NO: 21, at least 222 amino acids of SEQ ID NO: 23, at least 222 amino acids of SEQ ID NO: 24, at least 218 amino acids of SEQ ID NO: 26, at least 218 amino acids of SEQ ID NO: 27, at least 218 amino acids of SEQ ID NO: 29, at least 218 amino acids of SEQ ID NO: 30, at least 216 amino acids of SEQ ID NO: 32, at least 216 amino acids of SEQ ID NO: 33, at least 216 amino acids of SEQ ID NO: 35, at least 216 amino acids of SEQ ID NO: 36, at least 216 amino acids of SEQ ID NO: 38, at least 216 amino acids of SEQ ID NO: 39, at least 291 amino acids of SEQ ID NO: 41, at least 291 amino acids of SEQ ID NO: 42, at least 217 amino acids of SEQ ID NO: 44, or at least 217 amino acids of SEQ ID NO: 45.

In one aspect, the fragment comprises at least 98% of the length of the mature polypeptide, such as at least 221 amino acids of SEQ ID NO: 2, at least 221 amino acids of SEQ ID NO: 3, at least 221 amino acids of SEQ ID NO: 5, at least 221 amino acids of SEQ ID NO: 6, at least 218 amino acids of SEQ ID NO: 8, at least 218 amino acids of SEQ ID NO: 9, at least 297 amino acids of SEQ ID NO: 11, at least 297 amino acids of SEQ ID NO: 12, at least 223 amino acids of SEQ ID NO: 14, at least 223 amino acids of SEQ ID NO: 15, at least 225 amino acids of SEQ ID NO: 17, at least 225 amino acids of SEQ ID NO: 18, at least 225 amino acids of SEQ ID NO: 20, at least 225 amino acids of SEQ ID NO: 21, at least 227 amino acids of SEQ ID NO: 23, at least 227 amino acids of SEQ ID NO: 24, at least 223 amino acids of SEQ ID NO: 26, at least 223 amino acids of SEQ ID NO: 27, at least 223 amino acids of SEQ ID NO: 29, at least 223 amino acids of SEQ ID NO: 30, at least 221 amino acids of SEQ ID NO: 32, at least 221 amino acids of SEQ ID NO: 33, at least 220 amino acids of SEQ ID NO: 35, at least 220 amino acids of SEQ ID NO: 36, at least 220 amino acids of SEQ ID NO: 38, at least 220 amino acids of SEQ ID NO: 39, at least 297 amino acids of SEQ ID NO: 41, at least 297 amino acids of SEQ ID NO: 42, at least 222 amino acids of SEQ ID NO: 44, or at least 222 amino acids of SEQ ID NO: 45.

In one aspect, the fragment comprises at least 99% of the length of the mature polypeptide, such as at least 223 amino acids of SEQ ID NO: 2, at least 223 amino acids of SEQ ID NO: 3, at least 223 amino acids of SEQ ID NO: 5, at least 223 amino acids of SEQ ID NO: 6, at least 220 amino acids of SEQ ID NO: 8, at least 220 amino acids of SEQ ID NO: 9, at least 300 amino acids of SEQ ID NO: 11, at least 300 amino acids of SEQ ID NO: 12, at least 225 amino acids of SEQ ID NO: 14, at least 225 amino acids of SEQ ID NO: 15, at least 227 amino acids of SEQ ID NO: 17, at least 227 amino acids of SEQ ID NO: 18, at least 227 amino acids of SEQ ID NO: 20, at least 227 amino acids of SEQ ID NO: 21, at least 229 amino acids of SEQ ID NO: 23, at least 229 amino acids of SEQ ID NO: 24, at least 225 amino acids of SEQ ID NO: 26, at least 225 amino acids of SEQ ID NO: 27, at least 225 amino acids of SEQ ID NO: 29, at least 225 amino acids of SEQ ID NO: 30, at least 223 amino acids of SEQ ID NO: 32, at least 223 amino acids of SEQ ID NO: 33, at least 222 amino acids of SEQ ID NO: 35, at least 222 amino acids of SEQ ID NO: 36, at least 222 amino acids of SEQ ID NO: 38, at least 222 amino acids of SEQ ID NO: 39, at least 300 amino acids of SEQ ID NO: 41, at least 300 amino acids of SEQ ID NO: 42, at least 224 amino acids of SEQ ID NO: 44, or at least 224 amino acids of SEQ ID NO: 45.

Fusion polypeptide: The term "fusion polypeptide" is a polypeptide in which one polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779). A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Hybrid polypeptide: The term "hybrid polypeptide" means a polypeptide comprising domains from two or more polypeptides, e.g., a binding domain from one polypeptide and a catalytic domain from another polypeptide. The domains may be fused at the N-terminus or the C-terminus.

Isolated: The term "isolated" means a substance in a form that does not occur in nature or in an environment in which the substance does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Lysozyme activity: The term "lysozyme activity" means the hydrolysis of the 1,4-beta-linkages between N-acetylmuramic acid and N-acetyl-D-glucosamine residues in a peptidoglycan, resulting in bacteriolysis. Lysozyme belongs to the enzyme class EC 3.2.1.17. Lysozyme activity is typically measured by the lytic action of the lysozyme on *Micrococcus luteus* ATCC 4698. In appropriate experimental conditions these changes are proportional to the amount of lysozyme in the medium (c.f. INS 1105 of the Combined Compendium of Food Additive Specifications of the Food and Agriculture Organisation of the UN (www.fao.org)). For the purpose of the present invention, lysozyme activity is determined according to the reducing-ends assay described in Example 1 ("Determination of Lysozyme Activity using reducing ends assay"). The polypeptide has lysozyme activity if it shows activity against *Micrococcus luteus* ATCC 4698.

In one aspect, the polypeptides of the present invention have at least 50%, e.g., preferably at least 60%, preferably at least 70%, more preferably at least 80%, more preferably at least 90%, even more preferably at least 95% or most preferably at least 100% of the lysozyme activity of SEQ ID NO: 12, preferably wherein lysozyme activity is determined as described in Example 1. In one aspect, the polypeptides of the present invention have at least 50%, e.g., preferably at least 60%, preferably at least 70%, more preferably at least 80%, more preferably at least 90%, even more preferably at least 95% or most preferably at least 100% of the lysozyme activity of SEQ ID NO: 12 wherein lysozyme activity is determined as follows: LYS polypeptide (50 μL of 0.7 μg/mL LYS polypeptide in phosphate buffer (5 mM citrate, 5 mM $K_2HPO_4$, 0.01% TritonX-100, pH 5.0)) is mixed with *Micrococcus lysodeikticus* solution (450 μL of 1% lyophilized *Micrococcus lysodeikticus* ATCC No. 4698 in milli-Q water) and incubated at 40° C. with shaking (500 rpm) for 45 min; the sample is centrifuged (4000 g, 5 min); supernatant (100 μL) is mixed with HCl (50 μL 3.2M) and incubated at 95° C. for 80 min; NaOH (50 μL, 3.5 M) is added and 150 μL of the sample is added to 4-hydroxybenzhydrazide in K—Na tartrate/NaOH buffer (75 μL of 50 g/L K—Na tartrate+20 g/L NaOH); the mixture is incubated at 95° C. for 10 min; and the optical density is measured at 405 nm.

Mature polypeptide: The term "mature polypeptide" means a polypeptide in its final form following translation and any post-translational modifications, such as N-terminal processing, C-terminal truncation, glycosylation, phosphorylation, etc.

In one aspect, the mature polypeptide is amino acids 1 to 226 of SEQ ID NO: 2 and amino acids −19 to −1 of SEQ ID NO: 2 are a signal peptide. In another aspect, the mature polypeptide is amino acids 1 to 226 of SEQ ID NO: 3. In one aspect, the mature polypeptide is amino acids 1 to 226 of SEQ ID NO: 5 and amino acids −19 to −1 of SEQ ID NO: 5 are a signal peptide. In another aspect, the mature polypeptide is amino acids 1 to 226 of SEQ ID NO: 6. In one aspect, the mature polypeptide is amino acids 1 to 223 of SEQ ID NO: 8 and amino acids −20 to −1 of SEQ ID NO: 8 are a signal peptide. In another aspect, the mature polypeptide is amino acids 1 to 223 of SEQ ID NO: 9. In one aspect, the mature polypeptide is amino acids 1 to 304 of SEQ ID NO: 11 and amino acids −20 to −1 of SEQ ID NO: 11 are a signal peptide. In another aspect, the mature polypeptide is amino acids 1 to 304 of SEQ ID NO: 12. In one aspect, the mature polypeptide is amino acids 1 to 228 of SEQ ID NO: 14 and amino acids −19 to −1 of SEQ ID NO: 14 are a signal peptide. In another aspect, the mature polypeptide is amino acids 1 to 228 of SEQ ID NO: 15. In one aspect, the mature polypeptide is amino acids 1 to 230 of SEQ ID NO: 17 and amino acids −20 to −1 of SEQ ID NO: 17 are a signal peptide. In another aspect, the mature polypeptide is amino acids 1 to 230 of SEQ ID NO: 18. In one aspect, the mature polypeptide is amino acids 1 to 230 of SEQ ID NO: 20 and amino acids −21 to −1 of SEQ ID NO: 20 are a signal peptide. In another aspect, the mature polypeptide is amino acids 1 to 230 of SEQ ID NO: 21. In one aspect, the mature polypeptide is amino acids 1 to 232 of SEQ ID NO: 23 and amino acids −22 to −1 of SEQ ID NO: 23 are a signal peptide. In another aspect, the mature polypeptide is amino acids 1 to 232 of SEQ ID NO: 24. In one aspect, the mature polypeptide is amino acids 1 to 228 of SEQ ID NO: 26 and amino acids −20 to −1 of SEQ ID NO: 26 are a signal peptide. In another aspect, the mature polypeptide is amino acids 1 to 228 of SEQ ID NO: 27. In one aspect, the mature polypeptide is amino acids 1 to 228 of SEQ ID NO: 29 and amino acids −20 to −1 of SEQ ID NO: 29 are a signal peptide. In another aspect, the mature polypeptide is amino acids 1 to 228 of SEQ ID NO: 30. In one aspect, the mature polypeptide is amino acids 1 to 226 of SEQ ID NO: 32 and amino acids −19 to −1 of SEQ ID NO: 32 are a signal peptide. In another aspect, the mature polypeptide is amino acids 1 to 226 of SEQ ID NO: 33. In one aspect, the mature polypeptide is amino acids 1 to 225 of SEQ ID NO: 35 and amino acids −20 to −1 of SEQ ID NO: 35 are a signal peptide. In another aspect, the mature polypeptide is amino acids 1 to 225 of SEQ ID NO: 36. In one aspect, the mature polypeptide is amino acids 1 to 225 of SEQ ID NO: 38 and amino acids −19 to −1 of SEQ ID NO: 38 are a signal peptide. In another aspect, the mature polypeptide is amino acids 1 to 225 of SEQ ID NO: 39. In one aspect, the mature polypeptide is amino acids 1 to 304 of SEQ ID NO: 41 and amino acids −19 to −1 of SEQ ID NO: 41 are a signal peptide. In another aspect, the mature polypeptide is amino acids 1 to 304 of SEQ ID NO: 42. In one aspect, the mature polypeptide is amino acids 1 to 227 of SEQ ID NO: 44 and amino acids −19 to −1 of SEQ ID NO: 44 are a signal peptide. In another aspect, the mature polypeptide is amino acids 1 to 227 of SEQ ID NO: 45.

It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide having lysozyme activity.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Obtained or obtainable from: The term "obtained or obtainable from" means that the polypeptide may be found in an organism from a specific taxonomic rank. In one embodiment, the polypeptide is obtained or obtainable from the kingdom Fungi, wherein the term kingdom is the taxonomic rank. In a preferred embodiment, the polypeptide is obtained or obtainable from the phylum Ascomycota, wherein the term phylum is the taxonomic rank. In another preferred embodiment, the polypeptide is obtained or obtainable from the subphylum Pezizomycotina, wherein the term subphylum is the taxonomic rank.

If the taxonomic rank of a polypeptide is not known, it can easily be determined by a person skilled in the art by performing a BLASTP search of the polypeptide (using e.g. the National Center for Biotechnology Information (NCIB) website http://www.ncbi.nlm.nih.gov/) and comparing it to the closest homologues. An unknown polypeptide which is a fragment of a known polypeptide is considered to be of the same taxonomic species. An unknown natural polypeptide or artificial variant which comprises a substitution, deletion and/or insertion in up to 10 positions is considered to be from the same taxonomic species as the known polypeptide.

Operably linked: The term "operably linked" means a configuration in which a control sequence is placed at an appropriate position relative to the coding sequence of a polynucleotide such that the control sequence directs expression of the coding sequence.

Roughage: The term "roughage" means dry plant material with high levels of fiber, such as fiber, bran, husks from seeds and grains and crop residues (such as stover, copra, straw, chaff, sugar beet waste).

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labelled "longest identity" (obtained using the -nobrief option) is used as the percent identity and is calculated as follows:

$$(\text{Identical Residues} \times 100)/(\text{Length of Alignment} - \text{Total Number of Gaps in Alignment})$$

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labelled "longest identity" (obtained using the -nobrief option) is used as the percent identity and is calculated as follows:

$$(\text{Identical Deoxyribonucleotides} \times 100)/(\text{Length of Alignment} - \text{Total Number of Gaps in Alignment})$$

Subsequence: The term "subsequence" means a polynucleotide having one or more (e.g., several) nucleotides absent from the 5' and/or 3' end of a mature polypeptide coding sequence; wherein the subsequence encodes a fragment having lysozyme activity.

Substantially pure polypeptide: The term "substantially pure polypeptide" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the polypeptide is at least 92% pure, e.g., at least 94% pure, at least 95% pure, at least 96% pure, at least 97% pure, at least 98% pure, at least 99%, at least 99.5% pure, and 100% pure by weight of the total polypeptide material present in the preparation. The polypeptides of the present invention are preferably in a substantially pure form. This can be accomplished, for example, by preparing the polypeptide by well known recombinant methods or by classical purification methods.

Variant: The term "variant" means a polypeptide having lysozyme activity comprising an alteration, i.e., a substitution, insertion, and/or deletion, of one or more (several) amino acid residues at one or more (e.g., several) positions. A substitution means replacement of the amino acid occupying a position with a different amino acid; a deletion means removal of the amino acid occupying a position; and an insertion means adding 1, 2, or 3 amino acids adjacent to and immediately following the amino acid occupying the position.

In one aspect, the variant according to the invention may comprise from 1 to 5; from 1 to 10; from 1 to 15; from 1 to 20; from 1 to 25; from 1 to 30; from 1 to 35; from 1 to 40; from 1 to 45; or from 1-50, i.e. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 alterations.

In one aspect, the variant of the present invention has at least 50%, e.g., preferably at least 60%, preferably at least 70%, more preferably at least 80%, more preferably at least 90%, even more preferably at least 95% or most preferably at least 100% of the lysozyme activity of SEQ ID NO: 12, preferably wherein lysozyme activity is determined as described in Example 1. In one aspect, the variant of the present invention has at least 50%, e.g., preferably at least 60%, preferably at least 70%, more preferably at least 80%, more preferably at least 90%, even more preferably at least 95% or most preferably at least 100% of the lysozyme activity of SEQ ID NO: 12 wherein lysozyme activity is determined as follows: LYS polypeptide (50 µL of 0.7 µg/mL LYS polypeptide in phosphate buffer (5 mM citrate, 5 mM $K_2HPO_4$, 0.01% TritonX-100, pH 5.0)) is mixed with *Micrococcus lysodeikticus* solution (450 µL of 1% lyophilized *Micrococcus lysodeikticus* ATCC No. 4698 in milli-Q water) and incubated at 40° C. with shaking (500 rpm) for 45 min; the sample is centrifuged (4000 g, 5 min); supernatant (100 µL) is mixed with HCl (50 µL 3.2M) and incubated at 95° C. for 80 min; NaOH (50 µL, 3.5 M) is added and 150 µL of the sample is added to 4-hydroxybenzhydrazide in K—Na tartrate/NaOH buffer (75 µL of 50 g/L K—Na tartrate+20 g/L NaOH); the mixture is incubated at 95° C. for 10 min; and the optical density is measured at 405 nm.

In one aspect, the variant according to the invention may comprise from 1 to 5; from 1 to 10; from 1 to 15; from 1 to 20; from 1 to 25; from 1 to 30; from 1 to 35; from 1 to 40; from 1 to 45; or from 1-50, i.e. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 alterations and has at least 50%, e.g., preferably at least 60%, preferably at least 70%, more preferably at least 80%, more preferably at least 90%, even more preferably at least 95% or most preferably at least 100% of the lysozyme activity of SEQ ID NO: 12, preferably wherein lysozyme activity is determined as described in Example 1.

Nomenclature

For purposes of the present invention, the nomenclature [E/Q] means that the amino acid at this position may be a glutamic acid (Glu, E) or a glutamine (Gln, Q). Likewise the nomenclature [V/G/A/I] means that the amino acid at this position may be a valine (Val, V), glycine (Gly, G), alanine (Ala, A) or isoleucine (Ile, I), and so forth for other combinations as described herein. Unless otherwise limited further, the amino acid X is defined such that it may be any of the 20 natural amino acids.

DETAILED DESCRIPTION OF THE INVENTION

The inventors have discovered a completely novel class of polypeptides having lysozyme activity. Said polypeptides are structurally quite different from known lysozymes. As shown in the sequence identity matrix below, the polypeptides of the present invention all have a sequence identity less than 45% to the prior art sequences disclosed in WO2013/076259, suggesting that these novel polypeptides may have a different folding pattern to known lysozymes.

| | GH class | SEQ3 | SEQ2 | SEQ4 | SEQ6 | SEQ8 | HEWL |
|---|---|---|---|---|---|---|---|
| SEQ ID NO: 3 of present invention | Not defined | 100 | 27 | 33.3 | 43.8 | 23.3 | 30.93 |
| SEQ ID NO: 2 of WO2013/076259 | GH23 | 27 | 100 | 27 | 33.3 | 32 | 21.3 |
| SEQ ID NO: 4 of WO2013/076259 | GH24 | 33.3 | 27 | 100 | 79 | 32.7 | 33.33 |
| SEQ ID NO: 6 of WO2013/076259 | GH25 | 43.8 | 33.3 | 79 | 100 | 34.1 | 44.78 |
| SEQ ID NO: 8 of WO2013/076259 | GH25 | 23.3 | 32 | 32.7 | 34.1 | 100 | 28.97 |
| Hen Egg White (Swissprot P00698) | GH22 | 30.9 | 21.3 | 33.3 | 44.8 | 29 | 100 |

The polypeptides of the present invention demonstrate typical lysozyme activity such as activity in the traditional OD drop assay against *Micrococcus lysodeikticus* (see example 14) or a reducing ends assay using *Micrococcus lysodeikticus* as substrate (see example 13).

The polypeptides of the invention having lysozyme activity are herein named LYS polypeptides and comprise one or more LAD (Lysozyme Active Domain) catalytic domains and optionally one or more lysozyme enhancing domains (LED).

Compositions Comprising Polypeptides Having Lysozyme Activity

In the first aspect, the invention relates to a composition comprising at least 0.01 mg of LYS polypeptide per kilogram of composition, wherein the polypeptide (a) has lysozyme activity and (b) comprises one or more LAD catalytic domains; wherein the LAD catalytic domain gives a domT score of at least 180 when queried using a Profile Hidden Markov Model (HMM) prepared using SEQ ID NOs: 46 to 187 and hmmbuild software program, and wherein the query is carried out using hmmscan software program by the Method of Determining the LAD Catalytic Domain by HMM.

In an embodiment, the polypeptide further comprises one or more lysozyme enhancing domains (LED). Thus, the invention further relates to a composition comprising at least 0.01 mg of LYS polypeptide per kilogram of composition, wherein:
(a) the LYS polypeptide has lysozyme activity;
(b) the LYS polypeptide comprises one or more LAD catalytic domains; wherein the LAD catalytic domain gives a domT score of at least 180 when queried using a Profile Hidden Markov Model (HMM) prepared using SEQ ID NOs: 46 to 187 and hmmbuild software program, and wherein the query is carried out using hmmscan software program by the Method of Determining the LAD Catalytic Domain by HMM;

(c) the polypeptide comprises one or more LED domains, wherein the LED gives a domT score of at least 100 when queried using a Profile Hidden Markov Model prepared using SEQ ID NOs: 188 to 316 and hmmbuild software program, and wherein the query is carried out using the hmmscan software program.

The theory behind Profile HMMs as described in Durbin et al. (Biological sequence analysis: probabilistic models of proteins and nucleic acids, Cambridge University Press, 1998) and Krogh et al. (1994 *J. Mol. Biol.* 235:1501-1531), both incorporated herein by reference, is characterization of a set of proteins based on the probability of each amino acid occurring at each position in the alignment of the proteins of the set.

Specifically, profile HMMs are statistical models of multiple sequence alignments, or even of single sequences. They capture position-specific information about how conserved each column of the alignment is, and which residues are likely. All profile methods are more or less statistical descriptions of the consensus of a multiple sequence alignment. They use position-specific scores for amino acids or nucleotides (residues) and position specific penalties for opening and extending an insertion or deletion. Traditional pairwise alignment (for example, BLAST, FASTA or the Smith/Waterman algorithm) uses position-independent scoring parameters. This property of profiles captures important information about the degree of conservation at various positions in the multiple alignment, and the varying degree to which gaps and insertions are permitted.

The advantage of using HMMs is that HMMs have a formal probabilistic basis. Probability theory is used to guide how all the scoring parameters should be set. One of the most important aspect is that HMMs have a consistent theory for setting position-specific gap and insertion scores. The methods are consistent and therefore highly automatable, allowing hundreds of profile HMMs to be applied to e.g. whole genome analysis. An example of a protein domain model database is Pfam (Sonnhammer et al., 1997, 'A comprehensive database of protein families based on seed alignments', Proteins, 28:405-420; Finn et al., 2010, 'The Pfam protein families database', Nucl. Acids Res., 38:D211-D222), which is a significant part of the Interpro protein domain annotation system. The construction and use of Pfam is tightly tied to the HMM ER software package (see https://en.wikipedia.org/wiki/HMMER).

The LAD catalytic domain is defined in the following manner. SEQ ID NOs: 46 to 187, which are partial sequences of the Uniprot entries as explained in the 'overview of sequence listing' section herein, are aligned using the software program MUSCLE v3.8.31 with the default settings. Using this alignment, a hidden Markov model (HMM) is built for the LAD catalytic domain. The HMM is constructed using the software program 'hmmbuild' from the package HMMER 3.0 (March 2010) (http://hmmer.org/) and the software is invoked using the default settings.

A LAD catalytic domain is defined to match the above mentioned HMM using the software program 'hmmscan' from the package HMMER 3.0 (March 2010) (http://hmmer.org/) using the default settings if the domT score is at least 170. In a preferred embodiment, the domT score is at least 175, preferably at least 180, more preferably at least 185, even more preferably at least 190, even more preferably at least 195, or most preferably at least 200.

The HMM profile of the LAD catalytic domain as generated using SEQ ID NOs: 46 to 187 according to the procedure above is given in example 10. The HMM profile can be copied into a text file which is subsequently loaded into the software program 'hmmscan' so that other polypeptides can be tested to see whether said polypeptide comprises one or more LAD catalytic domains.

The Lysozyme Enhancing Domain (LED) is defined in the following manner. SEQ ID NOs: 188 to 316, which are partial sequences of the Uniprot entries as explained in the 'overview of sequence listing' section herein, are aligned using the software program MUSCLE v3.8.31 with the default settings. Using this alignment, a hidden Markov model (HMM) is built for the LED. The HMM is constructed using the software program 'hmmbuild' from the package HMMER 3.0 (March 2010) (http://hmmer.org/) and the software is invoked using the default settings.

A LED is defined to match the above mentioned HMM using the software program 'hmmscan' from the package HMMER 3.0 (March 2010) (http://hmmer.org/) using the default settings if the domT score is at least 100. In a preferred embodiment, the domT score is at least 103, preferably at least 106, more preferably at least 109, more preferably at least 112, more preferably at least 115, more preferably at least 118, even more preferably at least 121, or most preferably at least 124.

The HMM profile of the LED as generated using SEQ ID NOs: 188 to 316 according to the procedure above is given in example 11. The HMM profile can be copied into a text file which is subsequently loaded into the software program 'hmmscan' so that other polypeptides can be tested to see whether said polypeptide comprises one or more LED.

In an embodiment, the LAD catalytic domain gives a domT score of at least 175 and the LED gives a domT score of at least 100. In an embodiment, the LAD catalytic domain gives a domT score of at least 180 and the LED gives a domT score of at least 100. In an embodiment, the LAD catalytic domain gives a domT score of at least 185 and the LED gives a domT score of at least 100. In an embodiment, the LAD catalytic domain gives a domT score of at least 190 and the LED gives a domT score of at least 100. In an embodiment, the LAD catalytic domain gives a domT score of at least 195 and the LED gives a domT score of at least 100. In an embodiment, the LAD catalytic domain gives a domT score of at least 200 and the LED gives a domT score of at least 100.

In an embodiment, the LAD catalytic domain gives a domT score of at least 175 and the LED gives a domT score of at least 103. In an embodiment, the LAD catalytic domain gives a domT score of at least 180 and the LED gives a domT score of at least 103. In an embodiment, the LAD catalytic domain gives a domT score of at least 185 and the LED gives a domT score of at least 103. In an embodiment, the LAD catalytic domain gives a domT score of at least 190 and the LED gives a domT score of at least 103. In an embodiment, the LAD catalytic domain gives a domT score of at least 195 and the LED gives a domT score of at least 103. In an embodiment, the LAD catalytic domain gives a domT score of at least 200 and the LED gives a domT score of at least 103.

In an embodiment, the LAD catalytic domain gives a domT score of at least 175 and the LED gives a domT score of at least 106. In an embodiment, the LAD catalytic domain gives a domT score of at least 180 and the LED gives a domT score of at least 106. In an embodiment, the LAD catalytic domain gives a domT score of at least 185 and the LED gives a domT score of at least 106. In an embodiment, the LAD catalytic domain gives a domT score of at least 190 and the LED gives a domT score of at least 106. In an embodiment, the LAD catalytic domain gives a domT score of at least 195 and the LED gives a domT score of at least 106. In an embodiment, the LAD catalytic domain gives a domT score of at least 200 and the LED gives a domT score of at least 106.

In an embodiment, the LAD catalytic domain gives a domT score of at least 175 and the LED gives a domT score of at least 109. In an embodiment, the LAD catalytic domain gives a domT score of at least 180 and the LED gives a domT score of at least 109. In an embodiment, the LAD catalytic domain gives a domT score of at least 185 and the LED gives a domT score of at least 109. In an embodiment, the LAD catalytic domain gives a domT score of at least 190 and the LED gives a domT score of at least 109. In an embodiment, the LAD catalytic domain gives a domT score of at least 195 and the LED gives a domT score of at least 109. In an embodiment, the LAD catalytic domain gives a domT score of at least 200 and the LED gives a domT score of at least 109.

In an embodiment, the LAD catalytic domain gives a domT score of at least 175 and the LED gives a domT score of at least 112. In an embodiment, the LAD catalytic domain gives a domT score of at least 180 and the LED gives a domT score of at least 112. In an embodiment, the LAD catalytic domain gives a domT score of at least 185 and the LED gives a domT score of at least 112. In an embodiment, the LAD catalytic domain gives a domT score of at least 190 and the LED gives a domT score of at least 112. In an embodiment, the LAD catalytic domain gives a domT score of at least 195 and the LED gives a domT score of at least 112. In an embodiment, the LAD catalytic domain gives a domT score of at least 200 and the LED gives a domT score of at least 112.

In an embodiment, the LAD catalytic domain gives a domT score of at least 175 and the LED gives a domT score of at least 115. In an embodiment, the LAD catalytic domain gives a domT score of at least 180 and the LED gives a domT score of at least 115. In an embodiment, the LAD catalytic domain gives a domT score of at least 185 and the LED gives a domT score of at least 115. In an embodiment, the LAD catalytic domain gives a domT score of at least 190 and the LED gives a domT score of at least 115. In an embodiment, the LAD catalytic domain gives a domT score of at least 195 and the LED gives a domT score of at least 115. In an embodiment, the LAD catalytic domain gives a domT score of at least 200 and the LED gives a domT score of at least 115.

In an embodiment, the LAD catalytic domain gives a domT score of at least 175 and the LED gives a domT score of at least 118. In an embodiment, the LAD catalytic domain gives a domT score of at least 180 and the LED gives a domT score of at least 118. In an embodiment, the LAD catalytic domain gives a domT score of at least 185 and the LED gives a domT score of at least 118. In an embodiment, the LAD catalytic domain gives a domT score of at least 190 and the LED gives a domT score of at least 118. In an embodiment, the LAD catalytic domain gives a domT score of at least 195 and the LED gives a domT score of at least 118. In an embodiment, the LAD catalytic domain gives a domT score of at least 200 and the LED gives a domT score of at least 118.

In an embodiment, the LAD catalytic domain comprises one or more motif I: AG[I/L]AT[A/G][I/L][T/V]ES (SEQ ID NO: 317). In an embodiment, the LAD catalytic domain comprises one or more motif II V[G/A]XLCQXVQXSAYP (SEQ ID NO: 318). In an embodiment, the LED comprises one or more motif III: [CGY][YF][VIL][ASTP][DG]X[YF][VIT]X[TS][GAN] (SEQ ID NO: 319). In an embodiment, the LAD catalytic domain comprises one or more motif I: AG[I/L]AT[A/G][I/L][T/V]ES (SEQ ID NO: 317) and one or more motif II V[G/A]XLCQXVQXSAYP (SEQ ID NO: 318). In an embodiment, the LAD catalytic domain comprises one or more motif I: AG[I/L]AT[A/G][I/L][T/V]ES (SEQ ID NO: 317) and the LED comprises one or more motif III: [CGY][YF][VIL][ASTP][DG]X[YF][VIT]X[TS][GAN] (SEQ ID NO: 319). In an embodiment, the LAD catalytic domain comprises one or more motif II V[G/A]XLCQXVQXSAYP (SEQ ID NO: 318) and the LED comprises one or more motif III: [CGY][YF][VIL][ASTP][DG]X[YF][VIT]X[TS][GAN] (SEQ ID NO: 319). In an embodiment, the LAD catalytic domain comprises one or more motif I: AG[I/L]AT[A/G][I/L][T/V]ES (SEQ ID NO: 317) and one or more motif II V[G/A]XLCQXVQXSAYP (SEQ ID NO: 318) and the LED comprises one or more motif III: [CGY][YF][VIL][ASTP][DG]X[YF][VIT]X[TS][GAN] (SEQ ID NO: 319).

In one embodiment of the first aspect, the invention relates to a composition comprising one or more LYS polypeptides having lysozyme activity, wherein the polypeptide is dosed at least 0.01 mg of polypeptide per kilogram of composition and is selected from the group consisting of:
- (a) a polypeptide having at least 80%, e.g., at least 85%, at least 90% or at least 95% sequence identity to the polypeptide of SEQ ID NO: 3;
- (b) a polypeptide having at least 80%, e.g., at least 85%, at least 90% or at least 95% sequence identity to the polypeptide of SEQ ID NO: 6;
- (c) a polypeptide having at least 80%, e.g., at least 85%, at least 90% or at least 95% sequence identity to the polypeptide of SEQ ID NO: 9;
- (d) a polypeptide having at least 80%, e.g., at least 85%, at least 90% or at least 95% sequence identity to the polypeptide of SEQ ID NO: 12;
- (e) a polypeptide having at least 80%, e.g., at least 85%, at least 90% or at least 95% sequence identity to the polypeptide of SEQ ID NO: 15;
- (f) a polypeptide having at least 80%, e.g., at least 85%, at least 90% or at least 95% sequence identity to the polypeptide of SEQ ID NO: 18;
- (g) a polypeptide having at least 80%, e.g., at least 85%, at least 90% or at least 95% sequence identity to the polypeptide of SEQ ID NO: 21;
- (h) a polypeptide having at least 80%, e.g., at least 85%, at least 90% or at least 95% sequence identity to the polypeptide of SEQ ID NO: 24;
- (i) a polypeptide having at least 80%, e.g., at least 85%, at least 90% or at least 95% sequence identity to the polypeptide of SEQ ID NO: 27;
- (j) a polypeptide having at least 80%, e.g., at least 85%, at least 90% or at least 95% sequence identity to the polypeptide of SEQ ID NO: 30;
- (k) a polypeptide having at least 80%, e.g., at least 85%, at least 90% or at least 95% sequence identity to the polypeptide of SEQ ID NO: 33;
- (l) a polypeptide having at least 80%, e.g., at least 85%, at least 90% or at least 95% sequence identity to the polypeptide of SEQ ID NO: 36;
- (m) a polypeptide having at least 80%, e.g., at least 85%, at least 90% or at least 95% sequence identity to the polypeptide of SEQ ID NO: 39;

(n) a polypeptide having at least 80%, e.g., at least 85%, at least 90% or at least 95% sequence identity to the polypeptide of SEQ ID NO: 42;

(o) a polypeptide having at least 80%, e.g., at least 85%, at least 90% or at least 95% sequence identity to the polypeptide of SEQ ID NO: 45;

(p) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42 and SEQ ID NO: 45, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 positions;

(q) a polypeptide comprising the polypeptide of (a), (b), (c), (d), (e), (f), (g), (h), (i), (j), (k), (l), (m), (n), (o) or (p) and a N-terminal and/or C-terminal His-tag and/or HQ-tag;

(r) a polypeptide comprising the polypeptide of (a), (b), (c), (d), (e), (f), (g), (h), (i), (j), (k), (l), (m), (n), (o) or (p) and a N-terminal and/or C-terminal extension of up to 10 amino acids, e.g. 1, 2, 3, 4, 5, 6, 7, 8, 9 or 10 amino acids; and (s) a fragment of the polypeptide of (a), (b), (c), (d), (e), (f), (g), (h), (i), (j), (k), (l), (m), (n), (o) or (p) having lysozyme activity and having at least 90% of the length of the mature polypeptide.

In one embodiment of the first aspect, the invention relates to a composition comprising one or more LYS polypeptides having lysozyme activity, wherein the LYS polypeptide is dosed at least 0.01 mg of polypeptide per kilogram of composition and comprises a LAD catalytic domain that is selected from the group consisting of:

(a) a polypeptide having at least 80%, e.g., at least 85%, at least 90% or at least 95% sequence identity to amino acids 84 to 226 of SEQ ID NO: 3;

(b) a polypeptide having at least 80%, e.g., at least 85%, at least 90% or at least 95% sequence identity to amino acids 84 to 226 of SEQ ID NO: 6;

(c) a polypeptide having at least 80%, e.g., at least 85%, at least 90% or at least 95% sequence identity to amino acids 81 to 220 of SEQ ID NO: 9;

(d) a polypeptide having at least 80%, e.g., at least 85%, at least 90% or at least 95% sequence identity to amino acids 161 to 304 of SEQ ID NO: 12;

(e) a polypeptide having at least 80%, e.g., at least 85%, at least 90% or at least 95% sequence identity to amino acids 85 to 228 of SEQ ID NO: 15;

(f) a polypeptide having at least 80%, e.g., at least 85%, at least 90% or at least 95% sequence identity to amino acids 88 to 230 of SEQ ID NO: 18;

(g) a polypeptide having at least 80%, e.g., at least 85%, at least 90% or at least 95% sequence identity to amino acids 87 to 230 of SEQ ID NO: 21;

(h) a polypeptide having at least 80%, e.g., at least 85%, at least 90% or at least 95% sequence identity to amino acids 90 to 232 of SEQ ID NO: 24;

(i) a polypeptide having at least 80%, e.g., at least 85%, at least 90% or at least 95% sequence identity to amino acids 85 to 228 of SEQ ID NO: 27;

(j) a polypeptide having at least 80%, e.g., at least 85%, at least 90% or at least 95% sequence identity to amino acids 85 to 228 of SEQ ID NO: 30;

(k) a polypeptide having at least 80%, e.g., at least 85%, at least 90% or at least 95% sequence identity to amino acids 84 to 226 of SEQ ID NO: 33;

(l) a polypeptide having at least 80%, e.g., at least 85%, at least 90% or at least 95% sequence identity to amino acids 83 to 222 of SEQ ID NO: 36;

(m) a polypeptide having at least 80%, e.g., at least 85%, at least 90% or at least 95% sequence identity to amino acids 82 to 225 of SEQ ID NO: 39;

(n) a polypeptide having at least 80%, e.g., at least 85%, at least 90% or at least 95% sequence identity to amino acids 161 to 303 of SEQ ID NO: 42; and (o) a polypeptide having at least 80%, e.g., at least 85%, at least 90% or at least 95% sequence identity to amino acids 85 to 227 of SEQ ID NO: 45.

In one embodiment of the first aspect, the invention relates to a composition comprising one or more LYS polypeptides having lysozyme activity, wherein the LYS polypeptide is dosed at least 0.01 mg of polypeptide per kilogram of composition and comprises a LAD catalytic domain that is selected from the group consisting of:

(a) a polypeptide having at least 80%, e.g., at least 85%, at least 90% or at least 95% sequence identity to amino acids 84 to 226 of SEQ ID NO: 3;

(b) a polypeptide having at least 80%, e.g., at least 85%, at least 90% or at least 95% sequence identity to amino acids 84 to 226 of SEQ ID NO: 6;

(c) a polypeptide having at least 80%, e.g., at least 85%, at least 90% or at least 95% sequence identity to amino acids 81 to 220 of SEQ ID NO: 9;

(d) a polypeptide having at least 80%, e.g., at least 85%, at least 90% or at least 95% sequence identity to amino acids 161 to 304 of SEQ ID NO: 12;

(e) a polypeptide having at least 80%, e.g., at least 85%, at least 90% or at least 95% sequence identity to amino acids 85 to 228 of SEQ ID NO: 15;

(f) a polypeptide having at least 80%, e.g., at least 85%, at least 90% or at least 95% sequence identity to amino acids 88 to 230 of SEQ ID NO: 18;

(g) a polypeptide having at least 80%, e.g., at least 85%, at least 90% or at least 95% sequence identity to amino acids 87 to 230 of SEQ ID NO: 21;

(h) a polypeptide having at least 80%, e.g., at least 85%, at least 90% or at least 95% sequence identity to amino acids 90 to 232 of SEQ ID NO: 24;

(i) a polypeptide having at least 80%, e.g., at least 85%, at least 90% or at least 95% sequence identity to amino acids 85 to 228 of SEQ ID NO: 27;

(j) a polypeptide having at least 80%, e.g., at least 85%, at least 90% or at least 95% sequence identity to amino acids 85 to 228 of SEQ ID NO: 30;

(k) a polypeptide having at least 80%, e.g., at least 85%, at least 90% or at least 95% sequence identity to amino acids 84 to 226 of SEQ ID NO: 33;

(l) a polypeptide having at least 80%, e.g., at least 85%, at least 90% or at least 95% sequence identity to amino acids 83 to 222 of SEQ ID NO: 36;

(m) a polypeptide having at least 80%, e.g., at least 85%, at least 90% or at least 95% sequence identity to amino acids 82 to 225 of SEQ ID NO: 39;

(n) a polypeptide having at least 80%, e.g., at least 85%, at least 90% or at least 95% sequence identity to amino acids 161 to 303 of SEQ ID NO: 42; and (o) a polypeptide having at least 80%, e.g., at least 85%, at least 90% or at least 95% sequence identity to amino acids 85 to 227 of SEQ ID NO: 45;
and wherein the LYS polypeptide comprises a LED domain that is selected from the group consisting of:
(a) a polypeptide having at least 80%, e.g., at least 85%, at least 90% or at least 95% sequence identity to amino acids 1 to 73 of SEQ ID NO: 3;
(b) a polypeptide having at least 80%, e.g., at least 85%, at least 90% or at least 95% sequence identity to amino acids 1 to 73 of SEQ ID NO: 6;
(c) a polypeptide having at least 80%, e.g., at least 85%, at least 90% or at least 95% sequence identity to amino acids 1 to 73 of SEQ ID NO: 9;
(d) a polypeptide having at least 80%, e.g., at least 85%, at least 90% or at least 95% sequence identity to amino acids 1 to 72 of SEQ ID NO: 12;
(e) a polypeptide having at least 80%, e.g., at least 85%, at least 90% or at least 95% sequence identity to amino acids 1 to 73 of SEQ ID NO: 15;
(f) a polypeptide having at least 80%, e.g., at least 85%, at least 90% or at least 95% sequence identity to amino acids 1 to 73 of SEQ ID NO: 18;
(g) a polypeptide having at least 80%, e.g., at least 85%, at least 90% or at least 95% sequence identity to amino acids 1 to 73 of SEQ ID NO: 21;
(h) a polypeptide having at least 80%, e.g., at least 85%, at least 90% or at least 95% sequence identity to amino acids 1 to 73 of SEQ ID NO: 24;
(i) a polypeptide having at least 80%, e.g., at least 85%, at least 90% or at least 95% sequence identity to amino acids 1 to 73 of SEQ ID NO: 27;
(j) a polypeptide having at least 80%, e.g., at least 85%, at least 90% or at least 95% sequence identity to amino acids 1 to 73 of SEQ ID NO: 30;
(k) a polypeptide having at least 80%, e.g., at least 85%, at least 90% or at least 95% sequence identity to amino acids 1 to 73 of SEQ ID NO: 33;
(l) a polypeptide having at least 80%, e.g., at least 85%, at least 90% or at least 95% sequence identity to amino acids 1 to 73 of SEQ ID NO: 36;
(m) a polypeptide having at least 80%, e.g., at least 85%, at least 90% or at least 95% sequence identity to amino acids 1 to 72 of SEQ ID NO: 39;
(n) a polypeptide having at least 80%, e.g., at least 85%, at least 90% or at least 95% sequence identity to amino acids 1 to 73 of SEQ ID NO: 42;
(o) a polypeptide having at least 80%, e.g., at least 85%, at least 90% or at least 95% sequence identity to amino acids 1 to 73 of SEQ ID NO: 45;
(d) a polypeptide having at least 80%, e.g., at least 85%, at least 90% or at least 95% sequence identity to amino acids 96 to 167 of SEQ ID NO: 12; and
(n) a polypeptide having at least 80%, e.g., at least 85%, at least 90% or at least 95% sequence identity to amino acids 96 to 168 of SEQ ID NO: 42.

In one embodiment to any part of the first aspect, the LAD catalytic domain comprises one or more motif I: AG[I/L]AT[A/G][I/L][T/V]ES (SEQ ID NO: 317). In an embodiment, the LAD catalytic domain comprises one or more motif II V[G/A]XLCQXVQXSAYP (SEQ ID NO: 318). In an embodiment, the LED comprises one or more motif III: [CGY][YF][VIL][ASTP][DG]X[YF][VIT]X[TS][GAN] (SEQ ID NO: 319). In an embodiment, the LAD catalytic domain comprises one or more motif I: AG[I/L]AT[A/G][I/L][T/V]ES (SEQ ID NO: 317) and one or more motif II V[G/A]XLCQXVQXSAYP (SEQ ID NO: 318). In an embodiment, the LAD catalytic domain comprises one or more motif I: AG[I/L]AT[A/G][I/L][T/V]ES (SEQ ID NO: 317) and the LED comprises one or more motif III: [CGY][YF][VIL][ASTP][DG]X[YF][VIT]X[TS][GAN] (SEQ ID NO: 319). In an embodiment, the LAD catalytic domain comprises one or more motif II V[G/A]XLCQXVQXSAYP (SEQ ID NO: 318) and the LED comprises one or more motif III: [CGY][YF][VIL][ASTP][DG]X[YF][VIT]X[TS][GAN] (SEQ ID NO: 319). In an embodiment, the LAD catalytic domain comprises one or more motif I: AG[I/L]AT[A/G][I/L][T/V]ES (SEQ ID NO: 317) and one or more motif II V[G/A]XLCQXVQXSAYP (SEQ ID NO: 318) and the LED comprises one or more motif III: [CGY][YF][VIL][ASTP][DG]X[YF][VIT]X[TS][GAN] (SEQ ID NO: 319).

In one embodiment to any part of the first aspect, the polypeptide is of fungal origin. In an embodiment, the polypeptide is obtained or obtainable from the taxonomic phylum Ascomycota, preferably the taxonomic subphylum Pezizomycotina.

In one embodiment to any part of the first aspect, the composition comprises at least 0.01 mg of polypeptide (enzyme protein) per kilogram of composition, such as at least 0.02 mg, 0.05 mg, 0.10 mg, 0.2 mg, 0.5 mg, 1.0 mg, 2 mg, 5 mg, 10 mg, 20 mg, 50 mg, 100 mg, 200 mg, 500 mg, 1.0 g, 2.5 g, 5 g, 7.5 g, 10 g, 25 g, 50 g, 75 g or 100 g per kilogram of composition. In one embodiment, the composition comprises at most 250 g of polypeptide per kilogram of composition, such as at most 150 g, 100 g, 50 g, 40 g, 30 g, 20 g, 10 g, 7.5 g, 5 g, 2.5 g, 1.0 g, 750 mg, 500 mg, 250 mg, 100 mg, 50 mg, 25 mg, 10 mg, 5 mg, 2.5 mg or 1 mg per kilogram of composition. In one embodiment, the composition comprises between 0.01 mg and 250 g of polypeptide (enzyme protein) per kilogram of composition, such as between 0.02 mg, 0.05 mg, 0.10 mg, 0.2 mg, 0.5 mg, 1.0 mg, 2 mg, 5 mg, 10 mg, 20 mg, 50 mg, 100 mg, 200 mg, 500 mg, 1.0 g, 2.5 g, 5 g, 7.5 g, 10 g, 25 g, 50 g, 75 g or 100 g per kilogram of composition and 150 g, 100 g, 50 g, 40 g, 30 g, 20 g, 10 g, 7.5 g, 5 g, 2.5 g, 1.0 g, 750 mg, 500 mg, 250 mg, 100 mg, 50 mg, 25 mg, 10 mg, 5 mg, 2.5 mg or 1 mg per kilogram of composition, or any combination thereof.

In one embodiment to any part of the first aspect, the composition comprises one or more formulating agents (such as those described herein), preferably a formulating agent selected from the list consisting of glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, kaolin, maltodextrin, cyclodextrin, wheat, PVA, acetate, phosphate and cellulose, preferably selected from the list consisting of 1, 2-propylene glycol, 1, 3-propylene glycol, sodium sulfate, dextrin, cellulose, sodium thiosulfate, kaolin and calcium carbonate.

In one embodiment to any part of the first aspect, the composition comprises one or more additional enzymes. The one or more additional enzymes is preferably selected from the group consisting of acetyl xylan esterase, alpha-amylase, beta-amylase, arabinofuranosidase, cellobiohydrolases, cellulase, feruloyl esterase, galactanase, alpha-galactosidase, beta-galactosidase, beta-glucanase, beta-glucosidase, lipase, lysophospholipase, lysozyme, mannanase, alpha-mannosidase, beta-mannosidase, phytase, phospholipase A1, phospholipase A2, phospholipase C, phospholipase D, protease, pullulanase, pectinase, pectin lyase, xylanase, beta-xylosidase or any combination thereof.

In one embodiment to any part of the first aspect, the composition comprises one or more probiotics. The one or more probiotics is preferably selected from the group consisting of *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Bifidobacterium bifidum, Bifidobacterium animalis, Bifidobacterium* sp., *Carnobacterium* sp., *Clostridium butyricum, Clostridium* sp., *Enterococcus faecium, Enterococcus* sp., *Lactobacillus* sp., *Lactobacillus acidophilus, Lactobacillus farciminus, Lactobacillus rhamnosus, Lactobacillus reuteri, Lactobacillus salivarius, Lactococcus lactis, Lactococcus* sp., *Leuconostoc* sp., *Megasphaera elsdenii, Megasphaera* sp., *Pediococcus acidilactici, Pediococcus* sp., *Propionibacterium thoenii, Propionibacterium* sp. and *Streptococcus* sp. or any combination thereof.

Granules Comprising Polypeptides Having Lysozyme Activity

In a second aspect, the invention relates to a granule comprising a LYS polypeptide, wherein the polypeptide (a) has lysozyme activity and (b) comprises one or more LAD catalytic domains; wherein the LAD catalytic domain gives a domT score of at least 180 when queried using a Profile Hidden Markov Model (HMM) prepared using SEQ ID NOs: 46 to 187 and hmmbuild software program, and wherein the query is carried out using hmmscan software program by the Method of Determining the LAD Catalytic Domain by HMM. In one embodiment, the granule comprises a core particle and one or more coatings. In a preferred embodiment, the coating comprises salt and/or wax and/or flour. Preferred formulations are disclosed in the formulation section below.

In an embodiment, the polypeptide further comprises one or more lysozyme enhancing domains (LED). Thus, the invention further relates to a granule comprising a LYS polypeptide, wherein:
  (a) the LYS polypeptide has lysozyme activity;
  (b) the LYS polypeptide comprises one or more LAD catalytic domains, wherein the LAD catalytic domain gives a domT score of at least 170 when queried using a Profile Hidden Markov Model prepared using SEQ ID NOs: 46 to 187 and hmmbuild software program, and wherein the query is carried out using hmmscan software program by the Method of Determining the LAD Catalytic Domain by HMM;
  (c) the polypeptide comprises one or more LED domains, wherein the LED gives a domT score of at least 100 when queried using a Profile Hidden Markov Model prepared using SEQ ID NOs: 188 to 316 and hmmbuild software program, and typically wherein the query is carried out using the hmmscan software program by the Method of Determining the Lysozyme Enhancing Domain by HMM.

In one embodiment, the granule comprises a core particle and one or more coatings. In a preferred embodiment, the coating comprises salt and/or wax and/or flour. Preferred formulations are disclosed in the formulation section below.

In an embodiment, the domT score of the LAD catalytic domain is at least 175, preferably at least 180, more preferably at least 185, even more preferably at least 190, even more preferably at least 195, or most preferably at least 200. In an embodiment, the domT score of the LED is at least 103, preferably at least 106, more preferably at least 109, more preferably at least 112, more preferably at least 115, more preferably at least 118, even more preferably at least 121, or most preferably at least 124. Preferred combinations of domT scores are as disclosed in the first aspect of the invention.

In an embodiment, the LAD catalytic domain comprises one or more motif I: AG[I/L]AT[A/G][I/L][T/V]ES (SEQ ID NO: 317). In an embodiment, the LAD catalytic domain comprises one or more motif II V[G/A]XLCQXVQXSAYP (SEQ ID NO: 318). In an embodiment, the LED comprises one or more motif III: [CGY][YF][VIL][ASTP][DG]X[YF][VIT]X[TS][GAN] (SEQ ID NO: 319). In an embodiment, the LAD catalytic domain comprises one or more motif I: AG[I/L]AT[A/G][I/L][T/V]ES (SEQ ID NO: 317) and one or more motif II V[G/A]XLCQXVQXSAYP (SEQ ID NO: 318). In an embodiment, the LAD catalytic domain comprises one or more motif I: AG[I/L]AT[A/G][I/L][T/V]ES (SEQ ID NO: 317) and the LED comprises one or more motif III: [CGY][YF][VIL][ASTP][DG]X[YF][VIT]X[TS][GAN] (SEQ ID NO: 319). In an embodiment, the LAD catalytic domain comprises one or more motif II V[G/A]XLCQXVQXSAYP (SEQ ID NO: 318) and the LED comprises one or more motif III: [CGY][YF][VIL][ASTP][DG]X[YF][VIT]X[TS][GAN] (SEQ ID NO: 319). In an embodiment, the LAD catalytic domain comprises one or more motif I: AG[I/L]AT[A/G][I/L][T/V]ES (SEQ ID NO: 317) and one or more motif II V[G/A]XLCQXVQXSAYP (SEQ ID NO: 318) and the LED comprises one or more motif III: [CGY][YF][VIL][ASTP][DG]X[YF][VIT]X[TS][GAN] (SEQ ID NO: 319).

In one embodiment of the second aspect, the invention relates to a granule comprising one or more LYS polypeptides having lysozyme activity, wherein the LYS polypeptide is selected from the group consisting of:
  (a) a polypeptide having at least 80%, e.g., at least 85%, at least 90% or at least 95% sequence identity to the polypeptide of SEQ ID NO: 3;
  (b) a polypeptide having at least 80%, e.g., at least 85%, at least 90% or at least 95% sequence identity to the polypeptide of SEQ ID NO: 6;
  (c) a polypeptide having at least 80%, e.g., at least 85%, at least 90% or at least 95% sequence identity to the polypeptide of SEQ ID NO: 9;
  (d) a polypeptide having at least 80%, e.g., at least 85%, at least 90% or at least 95% sequence identity to the polypeptide of SEQ ID NO: 12;
  (e) a polypeptide having at least 80%, e.g., at least 85%, at least 90% or at least 95% sequence identity to the polypeptide of SEQ ID NO: 15;
  (f) a polypeptide having at least 80%, e.g., at least 85%, at least 90% or at least 95% sequence identity to the polypeptide of SEQ ID NO: 18;
  (g) a polypeptide having at least 80%, e.g., at least 85%, at least 90% or at least 95% sequence identity to the polypeptide of SEQ ID NO: 21;
  (h) a polypeptide having at least 80%, e.g., at least 85%, at least 90% or at least 95% sequence identity to the polypeptide of SEQ ID NO: 24;
  (i) a polypeptide having at least 80%, e.g., at least 85%, at least 90% or at least 95% sequence identity to the polypeptide of SEQ ID NO: 27;
  (j) a polypeptide having at least 80%, e.g., at least 85%, at least 90% or at least 95% sequence identity to the polypeptide of SEQ ID NO: 30;
  (k) a polypeptide having at least 80%, e.g., at least 85%, at least 90% or at least 95% sequence identity to the polypeptide of SEQ ID NO: 33;

(l) a polypeptide having at least 80%, e.g., at least 85%, at least 90% or at least 95% sequence identity to the polypeptide of SEQ ID NO: 36;

(m) a polypeptide having at least 80%, e.g., at least 85%, at least 90% or at least 95% sequence identity to the polypeptide of SEQ ID NO: 39;

(n) a polypeptide having at least 80%, e.g., at least 85%, at least 90% or at least 95% sequence identity to the polypeptide of SEQ ID NO: 42;

(o) a polypeptide having at least 80%, e.g., at least 85%, at least 90% or at least 95% sequence identity to the polypeptide of SEQ ID NO: 45;

(p) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42 and SEQ ID NO: 45, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 positions;

(q) a polypeptide comprising the polypeptide of (a), (b), (c), (d), (e), (f), (g), (h), (i), (j), (k), (l), (m), (n), (o) or (p) and a N-terminal and/or C-terminal His-tag and/or HQ-tag;

(r) a polypeptide comprising the polypeptide of (a), (b), (c), (d), (e), (f), (g), (h), (i), (j), (k), (l), (m), (n), (o) or (p) and a N-terminal and/or C-terminal extension of up to 10 amino acids, e.g. 1, 2, 3, 4, 5, 6, 7, 8, 9 or 10 amino acids; and (s) a fragment of the polypeptide of (a), (b), (c), (d), (e), (f), (g), (h), (i), (j), (k), (l), (m), (n), (o) or (p) having lysozyme activity and having at least 90% of the length of the mature polypeptide.

In one embodiment, the granule comprises a core particle and one or more coatings. In a preferred embodiment, the coating comprises salt and/or wax and/or flour. Preferred formulations are disclosed in the formulation section below.

In one embodiment of the second aspect, the invention relates to a granule comprising one or more LYS polypeptides having lysozyme activity, wherein the LYS polypeptide comprises a LAD catalytic domain that is selected from the group consisting of:

(a) a polypeptide having at least 80%, e.g., at least 85%, at least 90% or at least 95% sequence identity to amino acids 84 to 226 of SEQ ID NO: 3;

(b) a polypeptide having at least 80%, e.g., at least 85%, at least 90% or at least 95% sequence identity to amino acids 84 to 226 of SEQ ID NO: 6;

(c) a polypeptide having at least 80%, e.g., at least 85%, at least 90% or at least 95% sequence identity to amino acids 81 to 220 of SEQ ID NO: 9;

(d) a polypeptide having at least 80%, e.g., at least 85%, at least 90% or at least 95% sequence identity to amino acids 161 to 304 of SEQ ID NO: 12;

(e) a polypeptide having at least 80%, e.g., at least 85%, at least 90% or at least 95% sequence identity to amino acids 85 to 228 of SEQ ID NO: 15;

(f) a polypeptide having at least 80%, e.g., at least 85%, at least 90% or at least 95% sequence identity to amino acids 88 to 230 of SEQ ID NO: 18;

(g) a polypeptide having at least 80%, e.g., at least 85%, at least 90% or at least 95% sequence identity to amino acids 87 to 230 of SEQ ID NO: 21;

(h) a polypeptide having at least 80%, e.g., at least 85%, at least 90% or at least 95% sequence identity to amino acids 90 to 232 of SEQ ID NO: 24;

(i) a polypeptide having at least 80%, e.g., at least 85%, at least 90% or at least 95% sequence identity to amino acids 85 to 228 of SEQ ID NO: 27;

(j) a polypeptide having at least 80%, e.g., at least 85%, at least 90% or at least 95% sequence identity to amino acids 85 to 228 of SEQ ID NO: 30;

(k) a polypeptide having at least 80%, e.g., at least 85%, at least 90% or at least 95% sequence identity to amino acids 84 to 226 of SEQ ID NO: 33;

(l) a polypeptide having at least 80%, e.g., at least 85%, at least 90% or at least 95% sequence identity to amino acids 83 to 222 of SEQ ID NO: 36;

(m) a polypeptide having at least 80%, e.g., at least 85%, at least 90% or at least 95% sequence identity to amino acids 82 to 225 of SEQ ID NO: 39;

(n) a polypeptide having at least 80%, e.g., at least 85%, at least 90% or at least 95% sequence identity to amino acids 161 to 303 of SEQ ID NO: 42; and (o) a polypeptide having at least 80%, e.g., at least 85%, at least 90% or at least 95% sequence identity to amino acids 85 to 227 of SEQ ID NO: 45.

In one embodiment of the second aspect, the invention relates to a granule comprising one or more LYS polypeptides having lysozyme activity, wherein the LYS polypeptide comprises a LAD catalytic domain that is selected from the group consisting of:

(a) a polypeptide having at least 80%, e.g., at least 85%, at least 90% or at least 95% sequence identity to amino acids 84 to 226 of SEQ ID NO: 3;

(b) a polypeptide having at least 80%, e.g., at least 85%, at least 90% or at least 95% sequence identity to amino acids 84 to 226 of SEQ ID NO: 6;

(c) a polypeptide having at least 80%, e.g., at least 85%, at least 90% or at least 95% sequence identity to amino acids 81 to 220 of SEQ ID NO: 9;

(d) a polypeptide having at least 80%, e.g., at least 85%, at least 90% or at least 95% sequence identity to amino acids 161 to 304 of SEQ ID NO: 12;

(e) a polypeptide having at least 80%, e.g., at least 85%, at least 90% or at least 95% sequence identity to amino acids 85 to 228 of SEQ ID NO: 15;

(f) a polypeptide having at least 80%, e.g., at least 85%, at least 90% or at least 95% sequence identity to amino acids 88 to 230 of SEQ ID NO: 18;

(g) a polypeptide having at least 80%, e.g., at least 85%, at least 90% or at least 95% sequence identity to amino acids 87 to 230 of SEQ ID NO: 21;

(h) a polypeptide having at least 80%, e.g., at least 85%, at least 90% or at least 95% sequence identity to amino acids 90 to 232 of SEQ ID NO: 24;

(i) a polypeptide having at least 80%, e.g., at least 85%, at least 90% or at least 95% sequence identity to amino acids 85 to 228 of SEQ ID NO: 27;

(j) a polypeptide having at least 80%, e.g., at least 85%, at least 90% or at least 95% sequence identity to amino acids 85 to 228 of SEQ ID NO: 30;

(k) a polypeptide having at least 80%, e.g., at least 85%, at least 90% or at least 95% sequence identity to amino acids 84 to 226 of SEQ ID NO: 33;

(l) a polypeptide having at least 80%, e.g., at least 85%, at least 90% or at least 95% sequence identity to amino acids 83 to 222 of SEQ ID NO: 36;
(m) a polypeptide having at least 80%, e.g., at least 85%, at least 90% or at least 95% sequence identity to amino acids 82 to 225 of SEQ ID NO: 39;
(n) a polypeptide having at least 80%, e.g., at least 85%, at least 90% or at least 95% sequence identity to amino acids 161 to 303 of SEQ ID NO: 42; and
(o) a polypeptide having at least 80%, e.g., at least 85%, at least 90% or at least 95% sequence identity to amino acids 85 to 227 of SEQ ID NO: 45;

and wherein the LYS polypeptide comprises a LED domain that is selected from the group consisting of:
(a) a polypeptide having at least 80%, e.g., at least 85%, at least 90% or at least 95% sequence identity to amino acids 1 to 73 of SEQ ID NO: 3;
(b) a polypeptide having at least 80%, e.g., at least 85%, at least 90% or at least 95% sequence identity to amino acids 1 to 73 of SEQ ID NO: 6;
(c) a polypeptide having at least 80%, e.g., at least 85%, at least 90% or at least 95% sequence identity to amino acids 1 to 73 of SEQ ID NO: 9;
(d) a polypeptide having at least 80%, e.g., at least 85%, at least 90% or at least 95% sequence identity to amino acids 1 to 72 of SEQ ID NO: 12;
(e) a polypeptide having at least 80%, e.g., at least 85%, at least 90% or at least 95% sequence identity to amino acids 1 to 73 of SEQ ID NO: 15;
(f) a polypeptide having at least 80%, e.g., at least 85%, at least 90% or at least 95% sequence identity to amino acids 1 to 73 of SEQ ID NO: 18;
(g) a polypeptide having at least 80%, e.g., at least 85%, at least 90% or at least 95% sequence identity to amino acids 1 to 73 of SEQ ID NO: 21;
(h) a polypeptide having at least 80%, e.g., at least 85%, at least 90% or at least 95% sequence identity to amino acids 1 to 73 of SEQ ID NO: 24;
(i) a polypeptide having at least 80%, e.g., at least 85%, at least 90% or at least 95% sequence identity to amino acids 1 to 73 of SEQ ID NO: 27;
(j) a polypeptide having at least 80%, e.g., at least 85%, at least 90% or at least 95% sequence identity to amino acids 1 to 73 of SEQ ID NO: 30;
(k) a polypeptide having at least 80%, e.g., at least 85%, at least 90% or at least 95% sequence identity to amino acids 1 to 73 of SEQ ID NO: 33;
(l) a polypeptide having at least 80%, e.g., at least 85%, at least 90% or at least 95% sequence identity to amino acids 1 to 73 of SEQ ID NO: 36;
(m) a polypeptide having at least 80%, e.g., at least 85%, at least 90% or at least 95% sequence identity to amino acids 1 to 72 of SEQ ID NO: 39;
(n) a polypeptide having at least 80%, e.g., at least 85%, at least 90% or at least 95% sequence identity to amino acids 1 to 73 of SEQ ID NO: 42;
(o) a polypeptide having at least 80%, e.g., at least 85%, at least 90% or at least 95% sequence identity to amino acids 1 to 73 of SEQ ID NO: 45;
(d) a polypeptide having at least 80%, e.g., at least 85%, at least 90% or at least 95% sequence identity to amino acids 96 to 167 of SEQ ID NO: 12; and
(n) a polypeptide having at least 80%, e.g., at least 85%, at least 90% or at least 95% sequence identity to amino acids 96 to 168 of SEQ ID NO: 42.

In one embodiment, the granule comprises a core particle and one or more coatings. In a preferred embodiment, the coating comprises salt and/or wax and/or flour. Preferred formulations are disclosed in the formulation section below.

In one embodiment to any part of the second aspect, the LAD catalytic domain comprises one or more motif I: AG[I/L]AT[A/G][I/L][T/V]ES (SEQ ID NO: 317). In an embodiment, the LAD catalytic domain comprises one or more motif II V[G/A]XLCQXVQXSAYP (SEQ ID NO: 318). In an embodiment, the LED comprises one or more motif III: [CGY][YF][VIL][ASTP][DG]X[YF][VIT]X[TS][GAN] (SEQ ID NO: 319). In an embodiment, the LAD catalytic domain comprises one or more motif I: AG[I/L]AT[A/G][I/L][T/V]ES (SEQ ID NO: 317) and one or more motif II V[G/A]XLCQXVQXSAYP (SEQ ID NO: 318). In an embodiment, the LAD catalytic domain comprises one or more motif I: AG[I/L]AT[A/G][I/L][T/V]ES (SEQ ID NO: 317) and the LED comprises one or more motif III: [CGY][YF][VIL][ASTP][DG]X[YF][VIT]X[TS][GAN] (SEQ ID NO: 319). In an embodiment, the LAD catalytic domain comprises one or more motif II V[G/A]XLCQXVQXSAYP (SEQ ID NO: 318) and the LED comprises one or more motif III: [CGY][YF][VIL][ASTP][DG]X[YF][VIT]X[TS][GAN] (SEQ ID NO: 319). In an embodiment, the LAD catalytic domain comprises one or more motif I: AG[I/L] AT[A/G][I/L][T/V]ES (SEQ ID NO: 317) and one or more motif II V[G/A]XLCQXVQXSAYP (SEQ ID NO: 318) and the LED comprises one or more motif III: [CGY][YF][VIL] [ASTP][DG]X[YF][VIT]X[TS][GAN] (SEQ ID NO: 319).

In one embodiment to any part of the second aspect, the polypeptide is of fungal origin. In an embodiment, the polypeptide is obtained or obtainable from the taxonomic phylum Ascomycota, preferably the taxonomic subphylum Pezizomycotina.

In one embodiment to any part of the first aspect, the composition comprises at least 0.01 mg of polypeptide (enzyme protein) per kilogram of composition, such as at least 0.02 mg, 0.05 mg, 0.10 mg, 0.2 mg, 0.5 mg, 1.0 mg, 2 mg, 5 mg, 10 mg, 20 mg, 50 mg, 100 mg, 200 mg, 500 mg, 1.0 g, 2.5 g, 5 g, 7.5 g, 10 g, 25 g, 50 g, 75 g or 100 g per kilogram of composition. In one embodiment, the composition comprises at most 250 g of polypeptide per kilogram of composition, such as at most 150 g, 100 g, 50 g, 40 g, 30 g, 20 g, 10 g, 7.5 g, 5 g, 2.5 g, 1.0 g, 750 mg, 500 mg, 250 mg, 100 mg, 50 mg, 25 mg, 10 mg, 5 mg, 2.5 mg or 1 mg per kilogram of composition. In one embodiment, the composition comprises between 0.01 mg and 250 g of polypeptide (enzyme protein) per kilogram of composition, such as between 0.02 mg, 0.05 mg, 0.10 mg, 0.2 mg, 0.5 mg, 1.0 mg, 2 mg, 5 mg, 10 mg, 20 mg, 50 mg, 100 mg, 200 mg, 500 mg, 1.0 g, 2.5 g, 5 g, 7.5 g, 10 g, 25 g, 50 g, 75 g or 100 g per kilogram of composition and 150 g, 100 g, 50 g, 40 g, 30 g, 20 g, 10 g, 7.5 g, 5 g, 2.5 g, 1.0 g, 750 mg, 500 mg, 250 mg, 100 mg, 50 mg, 25 mg, 10 mg, 5 mg, 2.5 mg or 1 mg per kilogram of composition, or any combination thereof.

In one embodiment to any part of the second aspect, the granule comprises one or more formulating agents (such as those described herein), preferably a formulating agent selected from the list consisting of glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, kaolin, maltodextrin, cyclodextrin, wheat, PVA, acetate, phosphate and cellulose, preferably selected from the list consisting of 1, 2-propylene glycol, 1, 3-propylene glycol, sodium sulfate, dextrin, cellulose, sodium thiosulfate, kaolin and calcium carbonate.

In one embodiment to any part of the second aspect, the granule comprises a core particle and one or more coatings. In a preferred embodiment, the coating comprises salt and/or wax and/or flour. Preferred formulations are disclosed in the formulation section below.

In one embodiment to any part of the second aspect, the granule comprises one or more additional enzymes. The one or more additional enzymes is preferably selected from the group consisting of acetyl xylan esterase, alpha-amylase, beta-amylase, arabinofuranosidase, cellobiohydrolases, cellulase, feruloyl esterase, galactanase, alpha-galactosidase, beta-galactosidase, beta-glucanase, beta-glucosidase, lipase, lysophospholipase, lysozyme, mannanase, alpha-mannosidase, beta-mannosidase, phytase, phospholipase A1, phospholipase A2, phospholipase C, phospholipase D, protease, pullulanase, pectinase, pectin lyase, xylanase, beta-xylosidase or any combination thereof.

In one embodiment to any part of the second aspect, the granule comprises one or more probiotics. The one or more probiotics is preferably selected from the group consisting of *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Bifidobacterium bifidum, Bifidobacterium animalis, Bifidobacterium* sp., *Carnobacterium* sp., *Clostridium butyricum, Clostridium* sp., *Enterococcus faecium, Enterococcus* sp., *Lactobacillus* sp., *Lactobacillus acidophilus, Lactobacillus farciminus, Lactobacillus rhamnosus, Lactobacillus reuteri, Lactobacillus salivarius, Lactococcus lactis, Lactococcus* sp., *Leuconostoc* sp., *Megasphaera elsdenii, Megasphaera* sp., *Pediococcus acidilactici, Pediococcus* sp., *Propionibacterium thoenii, Propionibacterium* sp. and *Streptococcus* sp. or any combination thereof.

Liquid Formulations Comprising Polypeptides Having Lysozyme Activity

In a third aspect, the invention relates to liquid formulations, wherein the liquid formulation comprises:
  (a) 0.01% to 25% w/w of LYS polypeptide wherein:
    (i) the LYS polypeptide has lysozyme activity;
    (ii) the LYS polypeptide comprises one or more LAD catalytic domains, wherein the LAD catalytic domain gives a domT score of at least 170 when queried using a Profile Hidden Markov Model prepared using SEQ ID NOs: 46 to 187 and hmmbuild software program, and wherein the query is carried out using hmmscan software program by the Method of Determining the LAD Catalytic Domain by HMM;
  (b) 20% to 80% w/w of polyol;
  (c) 0.01% to 2.0% w/w preservative; and
  (d) water.

In an embodiment, the domT score of the LAD catalytic domain is at least 175, preferably at least 180, more preferably at least 185, even more preferably at least 190, even more preferably at least 195, or most preferably at least 200. In an embodiment, the domT score of the LED is at least 103, preferably at least 106, more preferably at least 109, more preferably at least 112, more preferably at least 115, more preferably at least 118, even more preferably at least 121, or most preferably at least 124. Preferred combinations of domT scores are as disclosed in the first aspect of the invention.

In an embodiment, the polypeptide further comprises one or more lysozyme enhancing domains (LED). Thus, the invention further relates to a liquid formulation, wherein the liquid formulation comprises:
  (a) 0.01% to 25% w/w of LYS polypeptide wherein:
    (i) the LYS polypeptide has lysozyme activity;
    (ii) the LYS polypeptide comprises one or more LAD catalytic domains, wherein the LAD catalytic domain gives a domT score of at least 170 when queried using a Profile Hidden Markov Model prepared using SEQ ID NOs: 46 to 187 and hmmbuild software program, and wherein the query is carried out using hmmscan software program by the Method of Determining the LAD Catalytic Domain by HMM;
    (iii) the LYS polypeptide comprises one or more LED domains, wherein the LED gives a domT score of at least 100 when queried using a Profile Hidden Markov Model prepared using SEQ ID NOs: 188 to 316 and hmmbuild software program, and wherein the query is carried out using the hmmscan software program by the Method of Determining the Lysozyme Enhancing Domain by HMM;
  (b) 20% to 80% w/w of polyol;
  (c) 0.01% to 2.0% w/w preservative; and
  (d) water.

In an embodiment, the domT score of the LAD catalytic domain is at least 175, preferably at least 180, more preferably at least 185, even more preferably at least 190, even more preferably at least 195, or most preferably at least 200. In an embodiment, the domT score of the LED is at least 103, preferably at least 106, more preferably at least 109, more preferably at least 112, more preferably at least 115, more preferably at least 118, even more preferably at least 121, or most preferably at least 124. Preferred combinations of domT scores are as disclosed in the first aspect of the invention.

In one embodiment of the third aspect, the invention relates to a liquid formulation comprising one or more LYS polypeptides having lysozyme activity, wherein the liquid formulation comprises:
  (A) 0.01% to 25% w/w of LYS polypeptide wherein the LYS polypeptide is selected from the group consisting of:
    (a) a polypeptide having at least 80%, e.g., at least 85%, at least 90% or at least 95% sequence identity to the polypeptide of SEQ ID NO: 3;
    (b) a polypeptide having at least 80%, e.g., at least 85%, at least 90% or at least 95% sequence identity to the polypeptide of SEQ ID NO: 6;
    (c) a polypeptide having at least 80%, e.g., at least 85%, at least 90% or at least 95% sequence identity to the polypeptide of SEQ ID NO: 9;
    (d) a polypeptide having at least 80%, e.g., at least 85%, at least 90% or at least 95% sequence identity to the polypeptide of SEQ ID NO: 12;
    (e) a polypeptide having at least 80%, e.g., at least 85%, at least 90% or at least 95% sequence identity to the polypeptide of SEQ ID NO: 15;
    (f) a polypeptide having at least 80%, e.g., at least 85%, at least 90% or at least 95% sequence identity to the polypeptide of SEQ ID NO: 18;
    (g) a polypeptide having at least 80%, e.g., at least 85%, at least 90% or at least 95% sequence identity to the polypeptide of SEQ ID NO: 21;
    (h) a polypeptide having at least 80%, e.g., at least 85%, at least 90% or at least 95% sequence identity to the polypeptide of SEQ ID NO: 24;
    (i) a polypeptide having at least 80%, e.g., at least 85%, at least 90% or at least 95% sequence identity to the polypeptide of SEQ ID NO: 27;
    (j) a polypeptide having at least 80%, e.g., at least 85%, at least 90% or at least 95% sequence identity to the polypeptide of SEQ ID NO: 30;

(k) a polypeptide having at least 80%, e.g., at least 85%, at least 90% or at least 95% sequence identity to the polypeptide of SEQ ID NO: 33;
(l) a polypeptide having at least 80%, e.g., at least 85%, at least 90% or at least 95% sequence identity to the polypeptide of SEQ ID NO: 36;
(m) a polypeptide having at least 80%, e.g., at least 85%, at least 90% or at least 95% sequence identity to the polypeptide of SEQ ID NO: 39;
(n) a polypeptide having at least 80%, e.g., at least 85%, at least 90% or at least 95% sequence identity to the polypeptide of SEQ ID NO: 42;
(o) a polypeptide having at least 80%, e.g., at least 85%, at least 90% or at least 95% sequence identity to the polypeptide of SEQ ID NO: 45;
(p) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42 and SEQ ID NO: 45, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 positions;
(q) a polypeptide comprising the polypeptide of (a), (b), (c), (d), (e), (f), (g), (h), (i), (j), (k), (l), (m), (n), (o) or (p) and a N-terminal and/or C-terminal His-tag and/or HQ-tag;
(r) a polypeptide comprising the polypeptide of (a), (b), (c), (d), (e), (f), (g), (h), (i), (j), (k), (l), (m), (n), (o) or (p) and a N-terminal and/or C-terminal extension of up to 10 amino acids, e.g. 1, 2, 3, 4, 5, 6, 7, 8, 9 or 10 amino acids; and
(s) a fragment of the polypeptide of (a), (b), (c), (d), (e), (f), (g), (h), (i), (j), (k), (l), (m), (n), (o) or (p) having lysozyme activity and having at least 90% of the length of the mature polypeptide;
(B) 20% to 80% w/w of polyol;
(D) 0.01% to 2.0% w/w preservative; and
(D) water.

In one embodiment of the third aspect, the invention relates to a liquid formulation comprising one or more LYS polypeptides having lysozyme activity, wherein the liquid formulation comprises:
(A) 0.01% to 25% w/w of LYS polypeptide wherein the LYS polypeptide comprises a LAD catalytic domain that is selected from the group consisting of:
(a) a polypeptide having at least 80%, e.g., at least 85%, at least 90% or at least 95% sequence identity to amino acids 84 to 226 of SEQ ID NO: 3;
(b) a polypeptide having at least 80%, e.g., at least 85%, at least 90% or at least 95% sequence identity to amino acids 84 to 226 of SEQ ID NO: 6;
(c) a polypeptide having at least 80%, e.g., at least 85%, at least 90% or at least 95% sequence identity to amino acids 81 to 220 of SEQ ID NO: 9;
(d) a polypeptide having at least 80%, e.g., at least 85%, at least 90% or at least 95% sequence identity to amino acids 161 to 304 of SEQ ID NO: 12;
(e) a polypeptide having at least 80%, e.g., at least 85%, at least 90% or at least 95% sequence identity to amino acids 85 to 228 of SEQ ID NO: 15;
(f) a polypeptide having at least 80%, e.g., at least 85%, at least 90% or at least 95% sequence identity to amino acids 88 to 230 of SEQ ID NO: 18;
(g) a polypeptide having at least 80%, e.g., at least 85%, at least 90% or at least 95% sequence identity to amino acids 87 to 230 of SEQ ID NO: 21;
(h) a polypeptide having at least 80%, e.g., at least 85%, at least 90% or at least 95% sequence identity to amino acids 90 to 232 of SEQ ID NO: 24;
(i) a polypeptide having at least 80%, e.g., at least 85%, at least 90% or at least 95% sequence identity to amino acids 85 to 228 of SEQ ID NO: 27;
(j) a polypeptide having at least 80%, e.g., at least 85%, at least 90% or at least 95% sequence identity to amino acids 85 to 228 of SEQ ID NO: 30;
(k) a polypeptide having at least 80%, e.g., at least 85%, at least 90% or at least 95% sequence identity to amino acids 84 to 226 of SEQ ID NO: 33;
(l) a polypeptide having at least 80%, e.g., at least 85%, at least 90% or at least 95% sequence identity to amino acids 83 to 222 of SEQ ID NO: 36;
(m) a polypeptide having at least 80%, e.g., at least 85%, at least 90% or at least 95% sequence identity to amino acids 82 to 225 of SEQ ID NO: 39;
(n) a polypeptide having at least 80%, e.g., at least 85%, at least 90% or at least 95% sequence identity to amino acids 161 to 303 of SEQ ID NO: 42; and
(o) a polypeptide having at least 80%, e.g., at least 85%, at least 90% or at least 95% sequence identity to amino acids 85 to 227 of SEQ ID NO: 45;
(B) 20% to 80% w/w of polyol;
(C) 0.01% to 2.0% w/w preservative; and
(D) water.

In one embodiment of the third aspect, the invention relates to a liquid formulation comprising one or more LYS polypeptides having lysozyme activity, wherein the liquid formulation comprises:
(A) 0.01% to 25% w/w of LYS polypeptide wherein the LYS polypeptide comprises a LAD catalytic domain that is selected from the group consisting of:
(a) a polypeptide having at least 80%, e.g., at least 85%, at least 90% or at least 95% sequence identity to amino acids 84 to 226 of SEQ ID NO: 3;
(b) a polypeptide having at least 80%, e.g., at least 85%, at least 90% or at least 95% sequence identity to amino acids 84 to 226 of SEQ ID NO: 6;
(c) a polypeptide having at least 80%, e.g., at least 85%, at least 90% or at least 95% sequence identity to amino acids 81 to 220 of SEQ ID NO: 9;
(d) a polypeptide having at least 80%, e.g., at least 85%, at least 90% or at least 95% sequence identity to amino acids 161 to 304 of SEQ ID NO: 12;
(e) a polypeptide having at least 80%, e.g., at least 85%, at least 90% or at least 95% sequence identity to amino acids 85 to 228 of SEQ ID NO: 15;
(f) a polypeptide having at least 80%, e.g., at least 85%, at least 90% or at least 95% sequence identity to amino acids 88 to 230 of SEQ ID NO: 18;
(g) a polypeptide having at least 80%, e.g., at least 85%, at least 90% or at least 95% sequence identity to amino acids 87 to 230 of SEQ ID NO: 21;
(h) a polypeptide having at least 80%, e.g., at least 85%, at least 90% or at least 95% sequence identity to amino acids 90 to 232 of SEQ ID NO: 24;
(i) a polypeptide having at least 80%, e.g., at least 85%, at least 90% or at least 95% sequence identity to amino acids 85 to 228 of SEQ ID NO: 27;

(j) a polypeptide having at least 80%, e.g., at least 85%, at least 90% or at least 95% sequence identity to amino acids 85 to 228 of SEQ ID NO: 30;
(k) a polypeptide having at least 80%, e.g., at least 85%, at least 90% or at least 95% sequence identity to amino acids 84 to 226 of SEQ ID NO: 33;
(l) a polypeptide having at least 80%, e.g., at least 85%, at least 90% or at least 95% sequence identity to amino acids 83 to 222 of SEQ ID NO: 36;
(m) a polypeptide having at least 80%, e.g., at least 85%, at least 90% or at least 95% sequence identity to amino acids 82 to 225 of SEQ ID NO: 39;
(n) a polypeptide having at least 80%, e.g., at least 85%, at least 90% or at least 95% sequence identity to amino acids 161 to 303 of SEQ ID NO: 42; and
(o) a polypeptide having at least 80%, e.g., at least 85%, at least 90% or at least 95% sequence identity to amino acids 85 to 227 of SEQ ID NO: 45;
(B) the LYS polypeptide comprises a LED domain selected from the group consisting of:
(a) a polypeptide having at least 80%, e.g., at least 85%, at least 90% or at least 95% sequence identity to amino acids 1 to 73 of SEQ ID NO: 3;
(b) a polypeptide having at least 80%, e.g., at least 85%, at least 90% or at least 95% sequence identity to amino acids 1 to 73 of SEQ ID NO: 6;
(c) a polypeptide having at least 80%, e.g., at least 85%, at least 90% or at least 95% sequence identity to amino acids 1 to 73 of SEQ ID NO: 9;
(d) a polypeptide having at least 80%, e.g., at least 85%, at least 90% or at least 95% sequence identity to amino acids 1 to 72 of SEQ ID NO: 12;
(e) a polypeptide having at least 80%, e.g., at least 85%, at least 90% or at least 95% sequence identity to amino acids 1 to 73 of SEQ ID NO: 15;
(f) a polypeptide having at least 80%, e.g., at least 85%, at least 90% or at least 95% sequence identity to amino acids 1 to 73 of SEQ ID NO: 18;
(g) a polypeptide having at least 80%, e.g., at least 85%, at least 90% or at least 95% sequence identity to amino acids 1 to 73 of SEQ ID NO: 21;
(h) a polypeptide having at least 80%, e.g., at least 85%, at least 90% or at least 95% sequence identity to amino acids 1 to 73 of SEQ ID NO: 24;
(i) a polypeptide having at least 80%, e.g., at least 85%, at least 90% or at least 95% sequence identity to amino acids 1 to 73 of SEQ ID NO: 27;
(j) a polypeptide having at least 80%, e.g., at least 85%, at least 90% or at least 95% sequence identity to amino acids 1 to 73 of SEQ ID NO: 30;
(k) a polypeptide having at least 80%, e.g., at least 85%, at least 90% or at least 95% sequence identity to amino acids 1 to 73 of SEQ ID NO: 33;
(l) a polypeptide having at least 80%, e.g., at least 85%, at least 90% or at least 95% sequence identity to amino acids 1 to 73 of SEQ ID NO: 36;
(m) a polypeptide having at least 80%, e.g., at least 85%, at least 90% or at least 95% sequence identity to amino acids 1 to 72 of SEQ ID NO: 39;
(n) a polypeptide having at least 80%, e.g., at least 85%, at least 90% or at least 95% sequence identity to amino acids 1 to 73 of SEQ ID NO: 42;
(o) a polypeptide having at least 80%, e.g., at least 85%, at least 90% or at least 95% sequence identity to amino acids 1 to 73 of SEQ ID NO: 45;

(d) a polypeptide having at least 80%, e.g., at least 85%, at least 90% or at least 95% sequence identity to amino acids 96 to 167 of SEQ ID NO: 12; and
(n) a polypeptide having at least 80%, e.g., at least 85%, at least 90% or at least 95% sequence identity to amino acids 96 to 168 of SEQ ID NO: 42;
(C) 20% to 80% w/w of polyol;
(D) 0.01% to 2.0% w/w preservative; and
(E) water.

In one embodiment to any part of the third aspect, the LAD catalytic domain comprises one or more motif I: AG[I/L]AT[A/G][I/L][T/V]ES (SEQ ID NO: 317). In an embodiment, the LAD catalytic domain comprises one or more motif II V[G/A]XLCQXVQXSAYP (SEQ ID NO: 318). In an embodiment, the LED comprises one or more motif III: [CGY][YF][VIL][ASTP][DG]X[YF][VIT]X[TS][GAN] (SEQ ID NO: 319). In an embodiment, the LAD catalytic domain comprises one or more motif I: AG[I/L]AT[A/G][I/L][T/V]ES (SEQ ID NO: 317) and one or more motif II V[G/A]XLCQXVQXSAYP (SEQ ID NO: 318). In an embodiment, the LAD catalytic domain comprises one or more motif I: AG[I/L]AT[A/G][I/L][T/V]ES (SEQ ID NO: 317) and the LED comprises one or more motif III: [CGY][YF][VIL][ASTP][DG]X[YF][VIT]X[TS][GAN] (SEQ ID NO: 319). In an embodiment, the LAD catalytic domain comprises one or more motif II V[G/A]XLCQXVQXSAYP (SEQ ID NO: 318) and the LED comprises one or more motif III: [CGY][YF][VIL][ASTP][DG]X[YF][VIT]X[TS][GAN] (SEQ ID NO: 319). In an embodiment, the LAD catalytic domain comprises one or more motif I: AG[I/L]AT[A/G][I/L][T/V]ES (SEQ ID NO: 317) and one or more motif II V[G/A]XLCQXVQXSAYP (SEQ ID NO: 318) and the LED comprises one or more motif III: [CGY][YF][VIL][ASTP][DG]X[YF][VIT]X[TS][GAN] (SEQ ID NO: 319).

In one embodiment to any part of the third aspect, the polypeptide is of fungal origin. In an embodiment, the polypeptide is obtained or obtainable from the taxonomic phylum Ascomycota, preferably the taxonomic subphylum Pezizomycotina.

In one embodiment to any part of the third aspect, the liquid formulation comprises one or more formulating agents (such as those described herein), preferably a formulating agent selected from the list consisting of glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, PVA, acetate and phosphate, preferably selected from the list consisting of 1, 2-propylene glycol, 1, 3-propylene glycol, sodium sulfate, dextrin, cellulose, sodium thiosulfate, kaolin and calcium carbonate.

In one embodiment to any part of the third aspect, the liquid formulation comprises one or more polyols, preferably a polyol selected from the group consisting of glycerol, sorbitol, propylene glycol (MPG), ethylene glycol, diethylene glycol, triethylene glycol, 1, 2-propylene glycol or 1, 3-propylene glycol, dipropylene glycol, polyethylene glycol (PEG) having an average molecular weight below about 600 and polypropylene glycol (PPG) having an average molecular weight below about 600, more preferably selected from the group consisting of glycerol, sorbitol and propylene glycol (MPG) or any combination thereof.

In one embodiment to any part of the third aspect, the liquid formulation comprises 20%-80% polyol (i.e. total amount of polyol), preferably 25%-75% polyol, more preferably 30%-70% polyol, more preferably 35%-65% polyol or most preferably 40%-60% polyol. In one embodiment to any part of the third aspect, the liquid formulation comprises 20%-80% polyol, preferably 25%-75% polyol, more preferably 30%-70% polyol, more preferably 35%-65% polyol or most preferably 40%-60% polyol wherein the polyol is selected from the group consisting of glycerol, sorbitol, propylene glycol (MPG), ethylene glycol, diethylene glycol, triethylene glycol, 1, 2-propylene glycol or 1, 3-propylene glycol, dipropylene glycol, polyethylene glycol (PEG) having an average molecular weight below about 600 and polypropylene glycol (PPG) having an average molecular weight below about 600. In one embodiment to any part of the third aspect, the liquid formulation comprises 20%-80% polyol (i.e. total amount of polyol), preferably 25%-75% polyol, more preferably 30%-70% polyol, more preferably 35%-65% polyol or most preferably 40%-60% polyol wherein the polyol is selected from the group consisting of glycerol, sorbitol and propylene glycol (MPG).

In one embodiment to any part of the third aspect, the preservative is selected from the group consisting of sodium sorbate, potassium sorbate, sodium benzoate and potassium benzoate or any combination thereof. In one embodiment, the liquid formulation comprises 0.02% to 1.5% w/w preservative, more preferably 0.05% to 1.0% w/w preservative or most preferably 0.1% to 0.5% w/w preservative. In one embodiment, the liquid formulation comprises 0.01% to 2.0% w/w preservative (i.e. total amount of preservative), preferably 0.02% to 1.5% w/w preservative, more preferably 0.05% to 1.0% w/w preservative or most preferably 0.1% to 0.5% w/w preservative wherein the preservative is selected from the group consisting of sodium sorbate, potassium sorbate, sodium benzoate and potassium benzoate or any combination thereof.

In one embodiment to any part of the third aspect, the liquid formulation comprises 0.05% to 20% w/w LYS polypeptide, more preferably 0.2% to 15% w/w LYS polypeptide, more preferably 0.5% to 15% w/w LYS polypeptide or most preferably 1.0% to 10% w/w LYS polypeptide.

In one embodiment to any part of the third aspect, the liquid formulation comprises one or more additional enzymes. The one or more additional enzymes is preferably selected from the group consisting of acetyl xylan esterase, alpha-amylase, beta-amylase, arabinofuranosidase, cellobiohydrolase, cellulase, feruloyl esterase, galactanase, alpha-galactosidase, beta-galactosidase, beta-glucanase, beta-glucosidase, lipase, lysophospholipase, lysozyme, mannanase, alpha-mannosidase, beta-mannosidase, phytase, phospholipase A1, phospholipase A2, phospholipase C, phospholipase D, protease, pullulanase, pectinase, pectin lyase, xylanase, beta-xylosidase or any combination thereof.

In one embodiment to any part of the third aspect, the liquid formulation comprises one or more probiotics. The one or more probiotics is preferably selected from the group consisting of *Bacillus subtilis*, *Bacillus licheniformis*, *Bacillus amyloliquefaciens*, *Bacillus cereus*, *Bacillus pumilus*, *Bacillus polymyxa*, *Bacillus megaterium*, *Bacillus coagulans*, *Bacillus circulans*, *Bifidobacterium bifidum*, *Bifidobacterium animalis*, *Bifidobacterium* sp., *Carnobacterium* sp., *Clostridium butyricum*, *Clostridium* sp., *Enterococcus faecium*, *Enterococcus* sp., *Lactobacillus* sp., *Lactobacillus acidophilus*, *Lactobacillus farciminus*, *Lactobacillus rhamnosus*, *Lactobacillus reuteri*, *Lactobacillus salivarius*, *Lactococcus lactis*, *Lactococcus* sp., *Leuconostoc* sp., *Megasphaera elsdenii*, *Megasphaera* sp., *Pediococcus acidilactici*, *Pediococcus* sp., *Propionibacterium thoenii*, *Propionibacterium* sp. and *Streptococcus* sp. or any combination thereof.

Polypeptides Having Lysozyme Activity

In a fourth aspect, the invention relates to polypeptides having lysozyme activity having at least 95%, e.g., at least 96%, at least 97%, at least 98%, at least 99%, or 100% sequence identity to the mature polypeptide of SEQ ID NO: 2. In one embodiment, the polypeptides differ by up to 11 amino acids, e.g., 1, 2, 3, 4, 5, 6, 7, 8, 9, 10, or 11 amino acids from the mature polypeptide of SEQ ID NO: 2.

In a continuation of the fourth aspect, the invention relates to polypeptides having lysozyme activity having at least 95%, e.g., at least 96%, at least 97%, at least 98%, at least 99%, or 100% sequence identity to SEQ ID NO: 3. In one embodiment, the polypeptides differ by up to 11 amino acids, e.g., 1, 2, 3, 4, 5, 6, 7, 8, 9, 10, or 11 amino acids from SEQ ID NO: 3.

In one embodiment, the invention relates to polypeptides having lysozyme activity and having a sequence identity to SEQ ID NO: 3 of at least 95% and wherein the polypeptide has at least 50%, such as at least 75%, at least 90%, at least 95% or at least 100% of the lysozyme activity of SEQ ID NO: 3. In one embodiment, lysozyme activity is determined as described in example 1.

In one embodiment, the polypeptide comprises or consists of the mature polypeptide of SEQ ID NO: 2. In one embodiment, the polypeptide preferably comprises or consists of the amino acid sequence of SEQ ID NO: 3; comprises the amino acid sequence of SEQ ID NO: 3 and a N-terminal and/or C-terminal His-tag and/or HQ-tag; comprises the amino acid sequence of SEQ ID NO: 3 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 3. In one embodiment, the polypeptide comprises or consists of amino acids 1 to 226 of SEQ ID NO: 3. In one embodiment, the polypeptide has been isolated.

In a continuation of the fourth aspect, the invention relates to polypeptides having lysozyme activity encoded by a polynucleotide having a sequence identity to the mature polypeptide coding sequence of SEQ ID NO: 1 of at least 95%, e.g., at least 96%, at least 97%, at least 98%, at least 99%, or 100%. In a further embodiment, the polypeptide has been isolated.

In a continuation of the fourth aspect, the invention relates to variants of SEQ ID NO: 3 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 3 is not more than 11, e.g. 1, 2, 3, 4, 5, 6, 7, 8, 9, 10, or 11. In an embodiment, the number of positions comprising one or more amino acid substitutions, and/or one or more amino acid deletions, and/or one or more amino acid insertions or any combination thereof in SEQ ID NO: 3 is not more than 10, e.g., 1, 2, 3, 4, 5, 6, 7, 8, 9 or 10. In one embodiment, the number of substitutions and/or deletions and/or insertions in SEQ ID NO: 3 is not more than 10, e.g. 1, 2, 3, 4, 5, 6, 7, 8, 9, or 10. In a further embodiment, the number of substitutions, preferably conservative substitutions, in SEQ ID NO: 3 is not more than 10, e.g. 1, 2, 3, 4, 5, 6, 7, 8, 9, or 10.

In an embodiment of the fourth aspect, the variant has at least 50%, such as at least 75%, at least 90%, at least 95% or at least 100% of the lysozyme activity of SEQ ID NO: 3. In one embodiment, lysozyme activity is determined as described in example 1.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly. Other examples of conservative substitutions are G to A; A to G, S; V to I, L, A, T, S; I to V, L, M; L to I, M, V; M to L, I, V; P to A, S, N; F to Y, W, H; Y to F, W, H; W to Y, F, H; R to K, E, D; K to R, E, D; H to Q, N, S; D to N, E, K, R, Q; E to Q, D, K, R, N; S to T, A; T to S, V, A; C to S, T, A; N to D, Q, H, S; Q to E, N, H, K, R.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for lysozyme activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labelling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, *phage* display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide or a fusion polypeptide.

In a fifth aspect, the invention relates to polypeptides having lysozyme activity having at least 94%, e.g., at least 95%, at least 96%, at least 97%, at least 98%, at least 99%, or 100% sequence identity to the mature polypeptide of SEQ ID NO: 5. In one embodiment, the polypeptides differ by up to 13 amino acids, e.g., 1, 2, 3, 4, 5, 6, 7, 8, 9, 10, 11, 12, or 13 amino acids from the mature polypeptide of SEQ ID NO: 5.

In a continuation of the fifth aspect, the invention relates to polypeptides having lysozyme activity having at least 94%, e.g., at least 95%, at least 96%, at least 97%, at least 98%, at least 99%, or 100% sequence identity to SEQ ID NO: 6. In one embodiment, the polypeptides differ by up to 13 amino acids, e.g., 1, 2, 3, 4, 5, 6, 7, 8, 9, 10, 11, 12, or 13 amino acids from SEQ ID NO: 6.

In one embodiment, the invention relates to polypeptides having lysozyme activity and having a sequence identity to SEQ ID NO: 6 of at least 94% and wherein the polypeptide has at least 50%, such as at least 75%, at least 90%, at least 95% or at least 100% of the lysozyme activity of SEQ ID NO: 6. In one embodiment, the invention relates to polypeptides having lysozyme activity and having a sequence identity to SEQ ID NO: 6 of at least 95% and wherein the polypeptide has at least 50%, such as at least 75%, at least 90%, at least 95% or at least 100% of the lysozyme activity of SEQ ID NO: 6. In one embodiment, lysozyme activity is determined as described in example 1.

In one embodiment, the polypeptide comprises or consists of the mature polypeptide of SEQ ID NO: 5. In one embodiment, the polypeptide preferably comprises or consists of the amino acid sequence of SEQ ID NO: 6; comprises the amino acid sequence of SEQ ID NO: 6 and a N-terminal and/or C-terminal His-tag and/or HQ-tag; comprises the amino acid sequence of SEQ ID NO: 6 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 6. In one embodiment, the polypeptide comprises or consists of amino acids 1 to 226 of SEQ ID NO: 6. In one embodiment, the polypeptide has been isolated.

In a continuation of the fifth aspect, the invention relates to polypeptides having lysozyme activity encoded by a polynucleotide having a sequence identity to the mature polypeptide coding sequence of SEQ ID NO: 4 of at least 94%, e.g., at least 95%, at least 96%, at least 97%, at least 98%, at least 99%, or 100%. In a further embodiment, the polypeptide has been isolated.

In a continuation of the fifth aspect, the invention relates to variants of SEQ ID NO: 6 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 6 is not more than 13, e.g. 1, 2, 3, 4, 5, 6, 7, 8, 9, 10, 11, 12, or 13. In an embodiment, the number of positions comprising one or more amino acid substitutions, and/or one or more amino acid deletions, and/or one or more amino acid insertions or any combination thereof in SEQ ID NO: 6 is not more than 10, e.g., 1, 2, 3, 4, 5, 6, 7, 8, 9 or 10. In one embodiment, the number of substitutions and/or deletions and/or insertions in SEQ ID NO: 6 is not more than 10, e.g. 1, 2, 3, 4, 5, 6, 7, 8, 9, or 10. In a further embodiment, the number of substitutions, preferably conservative substitutions, in SEQ ID NO: 6 is not more than 10, e.g. 1, 2, 3, 4, 5, 6, 7, 8, 9, or 10. Examples of amino acid changes and conservative substitutions are described in the fourth aspect of the invention.

In an embodiment of the fifth aspect, the variant has at least 50%, such as at least 75%, at least 90%, at least 95% or at least 100% of the lysozyme activity of SEQ ID NO: 6. In one embodiment, lysozyme activity is determined as described in example 1.

In a sixth aspect, the invention relates to polypeptides having lysozyme activity having at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 8. In one embodiment, the polypeptides differ by up to 44 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or 44 amino acids from the mature polypeptide of SEQ ID NO: 8.

In a continuation of the sixth aspect, the invention relates to polypeptides having lysozyme activity having at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 9. In one embodiment, the polypeptides differ by up to 44 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or 44 amino acids from SEQ ID NO: 9.

In one embodiment, the invention relates to polypeptides having lysozyme activity and having a sequence identity to SEQ ID NO: 9 of at least 80% and wherein the polypeptide has at least 50%, such as at least 75%, at least 90%, at least 95% or at least 100% of the lysozyme activity of SEQ ID NO: 9. In one embodiment, the invention relates to polypeptides having lysozyme activity and having a sequence identity to SEQ ID NO: 9 of at least 85% and wherein the polypeptide has at least 50%, such as at least 75%, at least 90%, at least 95% or at least 100% of the lysozyme activity of SEQ ID NO: 9. In one embodiment, the invention relates to polypeptides having lysozyme activity and having a sequence identity to SEQ ID NO: 9 of at least 90% and wherein the polypeptide has at least 50%, such as at least 75%, at least 90%, at least 95% or at least 100% of the lysozyme activity of SEQ ID NO: 9. In one embodiment, the invention relates to polypeptides having lysozyme activity and having a sequence identity to SEQ ID NO: 9 of at least 95% and wherein the polypeptide has at least 50%, such as at least 75%, at least 90%, at least 95% or at least 100% of the lysozyme activity of SEQ ID NO: 9. In one embodiment, lysozyme activity is determined as described in example 1.

In one embodiment, the polypeptide comprises or consists of the mature polypeptide of SEQ ID NO: 8. In one embodiment, the polypeptide preferably comprises or consists of the amino acid sequence of SEQ ID NO: 9; comprises the amino acid sequence of SEQ ID NO: 9 and a N-terminal and/or C-terminal His-tag and/or HQ-tag; comprises the amino acid sequence of SEQ ID NO: 9 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 9. In one embodiment, the polypeptide comprises or consists of amino acids 1 to 223 of SEQ ID NO: 9. In one embodiment, the polypeptide has been isolated.

In a continuation of the sixth aspect, the invention relates to polypeptides having lysozyme activity encoded by a polynucleotide having a sequence identity to the mature polypeptide coding sequence of SEQ ID NO: 7 of at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the sixth aspect, the invention relates to variants of SEQ ID NO: 9 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 9 is not more than 44, e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or 44. In an embodiment, the number of positions comprising one or more amino acid substitutions, and/or one or more amino acid deletions, and/or one or more amino acid insertions or any combination thereof in SEQ ID NO: 9 is not more than 10, e.g., 1, 2, 3, 4, 5, 6, 7, 8, 9 or 10. In one embodiment, the number of substitutions and/or deletions and/or insertions in SEQ ID NO: 9 is not more than 10, e.g. 1, 2, 3, 4, 5, 6, 7, 8, 9, or 10. In a further embodiment, the number of substitutions, preferably conservative substitutions, in SEQ ID NO: 9 is not more than 10, e.g. 1, 2, 3, 4, 5, 6, 7, 8, 9, or 10. Examples of amino acid changes and conservative substitutions are described in the fourth aspect of the invention.

In an embodiment of the sixth aspect, the variant has at least 50%, such as at least 75%, at least 90%, at least 95% or at least 100% of the lysozyme activity of SEQ ID NO: 9. In one embodiment, lysozyme activity is determined as described in example 1.

In a seventh aspect, the invention relates to polypeptides having lysozyme activity having at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 11. In one embodiment, the polypeptides differ by up to 50 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids from the mature polypeptide of SEQ ID NO: 11.

In a continuation of the seventh aspect, the invention relates to polypeptides having lysozyme activity having at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 12. In one embodiment, the polypeptides differ by up to 50 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids from SEQ ID NO: 12.

In one embodiment, the invention relates to polypeptides having lysozyme activity and having a sequence identity to SEQ ID NO: 12 of at least 80% and wherein the polypeptide has at least 50%, such as at least 75%, at least 90%, at least 95% or at least 100% of the lysozyme activity of SEQ ID NO: 12. In one embodiment, the invention relates to polypeptides having lysozyme activity and having a sequence identity to SEQ ID NO: 12 of at least 85% and wherein the polypeptide has at least 50%, such as at least 75%, at least 90%, at least 95% or at least 100% of the lysozyme activity of SEQ ID NO: 12. In one embodiment, the invention relates to polypeptides having lysozyme activity and having a sequence identity to SEQ ID NO: 12 of at least 90% and wherein the polypeptide has at least 50%, such as at least 75%, at least 90%, at least 95% or at least 100% of the lysozyme activity of SEQ ID NO: 12. In one embodiment, the invention relates to polypeptides having lysozyme activity and having a sequence identity to SEQ ID NO: 12 of at least 95% and wherein the polypeptide has at least 50%, such as at least 75%, at least 90%, at least 95% or at least 100% of the lysozyme activity of SEQ ID NO: 12. In one embodiment, lysozyme activity is determined as described in example 1.

In one embodiment, the polypeptide comprises or consists of the mature polypeptide of SEQ ID NO: 11. In one embodiment, the polypeptide preferably comprises or consists of the amino acid sequence of SEQ ID NO: 12; comprises the amino acid sequence of SEQ ID NO: 12 and a N-terminal and/or C-terminal His-tag and/or HQ-tag; comprises the amino acid sequence of SEQ ID NO: 12 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 12. In one embodiment, the polypeptide comprises or consists of amino acids 1 to 304 of SEQ ID NO: 12. In one embodiment, the polypeptide has been isolated.

In a continuation of the seventh aspect, the invention relates to polypeptides having lysozyme activity encoded by a polynucleotide having a sequence identity to the mature polypeptide coding sequence of SEQ ID NO: 10 of at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the seventh aspect, the invention relates to variants of SEQ ID NO: 12 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 12 is not more than 50, e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. In an embodiment, the number of positions comprising one or more amino acid substitutions, and/or one or more amino acid deletions, and/or one or more amino acid insertions or any combination thereof in SEQ ID NO: 12 is not more than 10, e.g., 1, 2, 3, 4, 5, 6, 7, 8, 9 or 10. In one embodiment, the number of substitutions and/or deletions and/or insertions in SEQ ID NO: 12 is not more than 10, e.g. 1, 2, 3, 4, 5, 6, 7, 8, 9, or 10. In a further embodiment, the number of substitutions, preferably conservative substitutions, in SEQ ID NO: 12 is not more than 10, e.g. 1, 2, 3, 4, 5, 6, 7, 8, 9, or 10. Examples of amino acid changes and conservative substitutions are described in the fourth aspect of the invention.

In an embodiment of the seventh aspect, the variant has at least 50%, such as at least 75%, at least 90%, at least 95% or at least 100% of the lysozyme activity of SEQ ID NO: 12. In one embodiment, lysozyme activity is determined as described in example 1.

In a eighth aspect, the invention relates to polypeptides having lysozyme activity having at least 87%, e.g., at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 14. In one embodiment, the polypeptides differ by up to 29 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, or 29 amino acids from the mature polypeptide of SEQ ID NO: 14.

In a continuation of the eighth aspect, the invention relates to polypeptides having lysozyme activity having at least 87%, e.g., at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 15. In one embodiment, the polypeptides differ by up to 29 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, or 29 amino acids from SEQ ID NO: 15.

In one embodiment, the invention relates to polypeptides having lysozyme activity and having a sequence identity to SEQ ID NO: 15 of at least 87% and wherein the polypeptide has at least 50%, such as at least 75%, at least 90%, at least 95% or at least 100% of the lysozyme activity of SEQ ID NO: 15. In one embodiment, the invention relates to polypeptides having lysozyme activity and having a sequence identity to SEQ ID NO: 15 of at least 90% and wherein the polypeptide has at least 50%, such as at least 75%, at least 90%, at least 95% or at least 100% of the lysozyme activity of SEQ ID NO: 15. In one embodiment, the invention relates to polypeptides having lysozyme activity and having a sequence identity to SEQ ID NO: 15 of at least 95% and wherein the polypeptide has at least 50%, such as at least 75%, at least 90%, at least 95% or at least 100% of the lysozyme activity of SEQ ID NO: 15. In one embodiment, lysozyme activity is determined as described in example 1.

In one embodiment, the polypeptide comprises or consists of the mature polypeptide of SEQ ID NO: 14. In one embodiment, the polypeptide preferably comprises or consists of the amino acid sequence of SEQ ID NO: 15; comprises the amino acid sequence of SEQ ID NO: 15 and a N-terminal and/or C-terminal His-tag and/or HQ-tag; comprises the amino acid sequence of SEQ ID NO: 15 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 15. In one embodiment, the polypeptide comprises or consists of amino acids 1 to 228 of SEQ ID NO: 15. In one embodiment, the polypeptide has been isolated.

In a continuation of the eighth aspect, the invention relates to polypeptides having lysozyme activity encoded by a polynucleotide having a sequence identity to the mature polypeptide coding sequence of SEQ ID NO: 13 of at least 87%, e.g., at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the eighth aspect, the invention relates to variants of SEQ ID NO: 15 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 15 is not more than 29, e.g. 1, 2, 3, 4, 5, 6, 7, 8, 9, 10, 11, 12, 13, 14, 15, 16, 17, 18, 19, 20, 21, 22, 23, 24, 25, 26, 27, 28, or 29. In an embodiment, the number of positions comprising one or more amino acid substitutions, and/or one or more amino acid deletions, and/or one or more amino acid insertions or any combination thereof in SEQ ID NO: 15 is not more than 10, e.g., 1, 2, 3, 4, 5, 6, 7, 8, 9 or 10. In one embodiment, the number of substitutions and/or deletions and/or insertions in SEQ ID NO: 15 is not more than 10, e.g. 1, 2, 3, 4, 5, 6, 7, 8, 9, or 10. In a further embodiment, the number of substitutions, preferably conservative substitutions, in SEQ ID NO: 15 is not more than 10, e.g. 1, 2, 3, 4, 5, 6, 7, 8, 9, or 10. Examples of amino acid changes and conservative substitutions are described in the fourth aspect of the invention.

In an embodiment of the eighth aspect, the variant has at least 50%, such as at least 75%, at least 90%, at least 95% or at least 100% of the lysozyme activity of SEQ ID NO: 15. In one embodiment, lysozyme activity is determined as described in example 1.

In a ninth aspect, the invention relates to polypeptides having lysozyme activity having at least 81%, e.g., at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 17. In one embodiment, the polypeptides differ by up to 43 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, or 43 amino acids from the mature polypeptide of SEQ ID NO: 17.

In a continuation of the ninth aspect, the invention relates to polypeptides having lysozyme activity having at least 81%, e.g., at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 18. In one embodiment, the polypeptides differ by up to 43 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, or 43 amino acids from SEQ ID NO: 18.

In a continuation of the ninth aspect, the invention relates to polypeptides having lysozyme activity having at least 81%, e.g., at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 18. In one embodiment, the polypeptides differ by up to 28 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27 or 28 amino acids from SEQ ID NO: 239.

In one embodiment, the invention relates to polypeptides having lysozyme activity and having a sequence identity to SEQ ID NO: 18 of at least 81% and wherein the polypeptide has at least 50%, such as at least 75%, at least 90%, at least 95% or at least 100% of the lysozyme activity of SEQ ID NO: 18. In one embodiment, the invention relates to polypeptides having lysozyme activity and having a sequence identity to SEQ ID NO: 18 of at least 85% and wherein the polypeptide has at least 50%, such as at least 75%, at least 90%, at least 95% or at least 100% of the lysozyme activity of SEQ ID NO: 18. In one embodiment, the invention relates to polypeptides having lysozyme activity and having a sequence identity to SEQ ID NO: 18 of at least 90% and wherein the polypeptide has at least 50%, such as at least 75%, at least 90%, at least 95% or at least 100% of the lysozyme activity of SEQ ID NO: 18. In one embodiment, the invention relates to polypeptides having lysozyme activity and having a sequence identity to SEQ ID NO: 18 of at least 95% and wherein the polypeptide has at least 50%, such as at least 75%, at least 90%, at least 95% or at least 100% of the lysozyme activity of SEQ ID NO: 18. In one embodiment, lysozyme activity is determined as described in example 1.

In one embodiment, the polypeptide comprises or consists of the mature polypeptide of SEQ ID NO: 17. In one embodiment, the polypeptide comprises or consists of the mature polypeptide of SEQ ID NO: 239. In one embodiment, the polypeptide preferably comprises or consists of the amino acid sequence of SEQ ID NO: 18; comprises the amino acid sequence of SEQ ID NO: 18 and a N-terminal and/or C-terminal His-tag and/or HQ-tag; comprises the amino acid sequence of SEQ ID NO: 18 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 18. In one embodiment, the polypeptide comprises or consists of amino acids 1 to 230 of SEQ ID NO: 18. In one embodiment, the polypeptide comprises or consists of amino acids 1 to 146 of SEQ ID NO: 18. In one embodiment, the polypeptide has been isolated.

In a continuation of the ninth aspect, the invention relates to polypeptides having lysozyme activity encoded by a polynucleotide having a sequence identity to the mature polypeptide coding sequence of SEQ ID NO: 16 of at least 81%, e.g., at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the ninth aspect, the invention relates to variants of SEQ ID NO: 18 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 18 is not more than 43, e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, or 43. In an embodiment, the number of positions comprising one or more amino acid substitutions, and/or one or more amino acid deletions, and/or one or more amino acid insertions or any combination thereof in SEQ ID NO: 18 is not more than 10, e.g., 1, 2, 3, 4, 5, 6, 7, 8, 9 or 10. In one embodiment, the number of substitutions and/or deletions and/or insertions in SEQ ID NO: 18 is not more than 10, e.g. 1, 2, 3, 4, 5, 6, 7, 8, 9, or 10. In a further embodiment, the number of substitutions, preferably conservative substitutions, in SEQ ID NO: 18 is not more than 10, e.g. 1, 2, 3, 4, 5, 6, 7, 8, 9, or 10. Examples of amino acid changes and conservative substitutions are described in the fourth aspect of the invention.

In an embodiment of the ninth aspect, the variant has at least 50%, such as at least 75%, at least 90%, at least 95% or at least 100% of the lysozyme activity of SEQ ID NO: 18. In one embodiment, lysozyme activity is determined as described in example 1.

In a tenth aspect, the invention relates to polypeptides having lysozyme activity having at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 20. In one embodiment, the polypeptides differ by up to 45 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 amino acids from the mature polypeptide of SEQ ID NO: 20.

In a continuation of the tenth aspect, the invention relates to polypeptides having lysozyme activity having at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 21. In one embodiment, the polypeptides differ by up to 45 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 amino acids from SEQ ID NO: 21.

In one embodiment, the invention relates to polypeptides having lysozyme activity and having a sequence identity to SEQ ID NO: 21 of at least 80% and wherein the polypeptide has at least 50%, such as at least 75%, at least 90%, at least 95% or at least 100% of the lysozyme activity of SEQ ID NO: 21. In one embodiment, the invention relates to polypeptides having lysozyme activity and having a sequence identity to SEQ ID NO: 21 of at least 85% and wherein the polypeptide has at least 50%, such as at least 75%, at least 90%, at least 95% or at least 100% of the lysozyme activity of SEQ ID NO: 21. In one embodiment, the invention relates to polypeptides having lysozyme activity and having a sequence identity to SEQ ID NO: 21 of at least 90% and wherein the polypeptide has at least 50%, such as at least 75%, at least 90%, at least 95% or at least 100% of the lysozyme activity of SEQ ID NO: 21. In one embodiment, the invention relates to polypeptides having lysozyme activity and having a sequence identity to SEQ ID NO: 21 of at least 95% and wherein the polypeptide has at least 50%, such as at least 75%, at least 90%, at least 95% or at least 100% of the lysozyme activity of SEQ ID NO: 21. In one embodiment, lysozyme activity is determined as described in example 1.

In one embodiment, the polypeptide comprises or consists of the mature polypeptide of SEQ ID NO: 20. In one embodiment, the polypeptide preferably comprises or consists of the amino acid sequence of SEQ ID NO: 21; comprises the amino acid sequence of SEQ ID NO: 21 and a N-terminal and/or C-terminal His-tag and/or HQ-tag; comprises the amino acid sequence of SEQ ID NO: 21 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 21. In one embodiment, the polypeptide comprises or consists of amino acids 1 to 230 of SEQ ID NO: 21. In one embodiment, the polypeptide has been isolated.

In a continuation of the tenth aspect, the invention relates to polypeptides having lysozyme activity encoded by a polynucleotide having a sequence identity to the mature polypeptide coding sequence of SEQ ID NO: 19 of at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the tenth aspect, the invention relates to variants of SEQ ID NO: 21 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 21 is not more than 45, e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45. In an embodiment, the number of positions comprising one or more amino acid substitutions, and/or one or more amino acid deletions, and/or one or more amino acid insertions or any combination thereof in SEQ ID NO: 21 is not more than 10, e.g., 1, 2, 3, 4, 5, 6, 7, 8, 9 or 10. In one embodiment, the number of substitutions and/or deletions and/or insertions in SEQ ID NO: 21 is not more than 10, e.g. 1, 2, 3, 4, 5, 6, 7, 8, 9, or 10. In a further embodiment, the number of substitutions, preferably conservative substitutions, in SEQ ID NO: 21 is not more than 10, e.g. 1, 2, 3, 4, 5, 6, 7, 8, 9, or 10. Examples of amino acid changes and conservative substitutions are described in the fourth aspect of the invention.

In an embodiment of the tenth aspect, the variant has at least 50%, such as at least 75%, at least 90%, at least 95% or at least 100% of the lysozyme activity of SEQ ID NO: 21. In one embodiment, lysozyme activity is determined as described in example 1.

In a eleventh aspect, the invention relates to polypeptides having lysozyme activity having at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 23. In one embodiment, the polypeptides differ by up to 46 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or 46 amino acids from the mature polypeptide of SEQ ID NO: 23.

In a continuation of the eleventh aspect, the invention relates to polypeptides having lysozyme activity having at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 24. In one embodiment, the polypeptides differ by up to 46 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or 46 amino acids from SEQ ID NO: 24.

In one embodiment, the invention relates to polypeptides having lysozyme activity and having a sequence identity to SEQ ID NO: 24 of at least 80% and wherein the polypeptide has at least 50%, such as at least 75%, at least 90%, at least 95% or at least 100% of the lysozyme activity of SEQ ID NO: 24. In one embodiment, the invention relates to polypeptides having lysozyme activity and having a sequence identity to SEQ ID NO: 24 of at least 85% and wherein the polypeptide has at least 50%, such as at least 75%, at least 90%, at least 95% or at least 100% of the lysozyme activity of SEQ ID NO: 24. In one embodiment, the invention relates to polypeptides having lysozyme activity and having a sequence identity to SEQ ID NO: 24 of at least 90% and wherein the polypeptide has at least 50%, such as at least 75%, at least 90%, at least 95% or at least 100% of the lysozyme activity of SEQ ID NO: 24. In one embodiment, the invention relates to polypeptides having lysozyme activity and having a sequence identity to SEQ ID NO: 24 of at least 95% and wherein the polypeptide has at least 50%, such as at least 75%, at least 90%, at least 95% or at least 100% of the lysozyme activity of SEQ ID NO: 24. In one embodiment, lysozyme activity is determined as described in example 1.

In one embodiment, the polypeptide comprises or consists of the mature polypeptide of SEQ ID NO: 23. In one embodiment, the polypeptide preferably comprises or consists of the amino acid sequence of SEQ ID NO: 24; comprises the amino acid sequence of SEQ ID NO: 24 and a N-terminal and/or C-terminal His-tag and/or HQ-tag; comprises the amino acid sequence of SEQ ID NO: 24 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 24. In one embodiment, the polypeptide comprises or consists of amino acids 1 to 232 of SEQ ID NO: 24. In one embodiment, the polypeptide has been isolated.

In a continuation of the eleventh aspect, the invention relates to polypeptides having lysozyme activity encoded by a polynucleotide having a sequence identity to the mature polypeptide coding sequence of SEQ ID NO: 22 of at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the eleventh aspect, the invention relates to variants of SEQ ID NO: 24 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 24 is not more than 46, e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or 46. In an embodiment, the number of positions comprising one or more amino acid substitutions, and/or one or more amino acid deletions, and/or one or more amino acid insertions or any combination thereof in SEQ ID NO: 24 is not more than 10, e.g., 1, 2, 3, 4, 5, 6, 7, 8, 9 or 10. In one embodiment, the number of substitutions and/or deletions and/or insertions in SEQ ID NO: 24 is not more than 10, e.g. 1, 2, 3, 4, 5, 6, 7, 8, 9, or 10. In a further embodiment, the number of substitutions, preferably conservative substitutions, in SEQ ID NO: 24 is not more than 10, e.g. 1, 2, 3, 4, 5, 6, 7, 8, 9, or 10. Examples of amino acid changes and conservative substitutions are described in the fourth aspect of the invention.

In an embodiment of the eleventh aspect, the variant has at least 50%, such as at least 75%, at least 90%, at least 95% or at least 100% of the lysozyme activity of SEQ ID NO: 24. In one embodiment, lysozyme activity is determined as described in example 1.

In a twelfth aspect, the invention relates to polypeptides having lysozyme activity having at least 87%, e.g., at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 26. In one embodiment, the polypeptides differ by up to 29 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, or 29 amino acids from the mature polypeptide of SEQ ID NO: 26.

In a continuation of the twelfth aspect, the invention relates to polypeptides having lysozyme activity having at least 87%, e.g., at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 27. In one embodiment, the polypeptides differ by up to 29 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, or 29 amino acids from SEQ ID NO: 27.

In one embodiment, the invention relates to polypeptides having lysozyme activity and having a sequence identity to SEQ ID NO: 27 of at least 87% and wherein the polypeptide has at least 50%, such as at least 75%, at least 90%, at least 95% or at least 100% of the lysozyme activity of SEQ ID NO: 27. In one embodiment, the invention relates to polypeptides having lysozyme activity and having a sequence identity to SEQ ID NO: 27 of at least 90% and wherein the polypeptide has at least 50%, such as at least 75%, at least 90%, at least 95% or at least 100% of the lysozyme activity of SEQ ID NO: 27. In one embodiment, the invention relates to polypeptides having lysozyme activity and having a sequence identity to SEQ ID NO: 27 of at least 95% and wherein the polypeptide has at least 50%, such as at least 75%, at least 90%, at least 95% or at least 100% of the lysozyme activity of SEQ ID NO: 27. In one embodiment, lysozyme activity is determined as described in example 1.

In one embodiment, the polypeptide comprises or consists of the mature polypeptide of SEQ ID NO: 26. In one embodiment, the polypeptide preferably comprises or consists of the amino acid sequence of SEQ ID NO: 27; comprises the amino acid sequence of SEQ ID NO: 27 and a N-terminal and/or C-terminal His-tag and/or HQ-tag; comprises the amino acid sequence of SEQ ID NO: 27 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 27. In one embodiment, the polypeptide comprises or consists of amino acids 1 to 228 of SEQ ID NO: 27. In one embodiment, the polypeptide has been isolated.

In a continuation of the twelfth aspect, the invention relates to polypeptides having lysozyme activity encoded by a polynucleotide having a sequence identity to the mature polypeptide coding sequence of SEQ ID NO: 25 of at least 87%, e.g., at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the twelfth aspect, the invention relates to variants of SEQ ID NO: 27 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 27 is not more than 29, e.g. 1, 2, 3, 4, 5, 6, 7, 8, 9, 10, 11, 12, 13, 14, 15, 16, 17, 18, 19, 20, 21, 22, 23, 24, 25, 26, 27, 28, or 29. In an embodiment, the number of positions comprising one or more amino acid substitutions, and/or one or more amino acid deletions, and/or one or more amino acid insertions or any combination thereof in SEQ ID NO: 27 is not more than 10, e.g., 1, 2, 3, 4, 5, 6, 7, 8, 9 or 10. In one embodiment, the number of substitutions and/or deletions and/or insertions in SEQ ID NO: 27 is not more than 10, e.g. 1, 2, 3, 4, 5, 6, 7, 8, 9, or 10. In a further embodiment, the number of substitutions, preferably conservative substitutions, in SEQ ID NO: 27 is not more than 10, e.g. 1, 2, 3, 4, 5, 6, 7, 8, 9, or 10. Examples of amino acid changes and conservative substitutions are described in the fourth aspect of the invention.

In an embodiment of the twelfth aspect, the variant has at least 50%, such as at least 75%, at least 90%, at least 95% or at least 100% of the lysozyme activity of SEQ ID NO: 27. In one embodiment, lysozyme activity is determined as described in example 1.

In a thirteenth aspect, the invention relates to polypeptides having lysozyme activity having at least 96%, e.g., at least 97%, at least 98%, at least 99%, or 100% sequence identity to the mature polypeptide of SEQ ID NO: 29. In one embodiment, the polypeptides differ by up to 8 amino acids, e.g., 1, 2, 3, 4, 5, 6, 7, or 8 amino acids from the mature polypeptide of SEQ ID NO: 29.

In a continuation of the thirteenth aspect, the invention relates to polypeptides having lysozyme activity having at least 96%, e.g., at least 97%, at least 98%, at least 99%, or 100% sequence identity to SEQ ID NO: 30. In one embodiment, the polypeptides differ by up to 8 amino acids, e.g., 1, 2, 3, 4, 5, 6, 7, or 8 amino acids from SEQ ID NO: 30.

In one embodiment, the invention relates to polypeptides having lysozyme activity and having a sequence identity to SEQ ID NO: 30 of at least 96% and wherein the polypeptide has at least 50%, such as at least 75%, at least 90%, at least 95% or at least 100% of the lysozyme activity of SEQ ID NO: 30. In one embodiment, lysozyme activity is determined as described in example 1.

In one embodiment, the polypeptide comprises or consists of the mature polypeptide of SEQ ID NO: 29. In one embodiment, the polypeptide preferably comprises or consists of the amino acid sequence of SEQ ID NO: 30; comprises the amino acid sequence of SEQ ID NO: 30 and a N-terminal and/or C-terminal His-tag and/or HQ-tag; comprises the amino acid sequence of SEQ ID NO: 30 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 30. In one embodiment, the polypeptide comprises or consists of amino acids 1 to 228 of SEQ ID NO: 30. In one embodiment, the polypeptide has been isolated.

In a continuation of the thirteenth aspect, the invention relates to polypeptides having lysozyme activity encoded by a polynucleotide having a sequence identity to the mature polypeptide coding sequence of SEQ ID NO: 28 of at least 96%, e.g., at least 97%, at least 98%, at least 99%, or 100%. In a further embodiment, the polypeptide has been isolated.

In a continuation of the thirteenth aspect, the invention relates to variants of SEQ ID NO: 30 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 30 is not more than 8, e.g. 1, 2, 3, 4, 5, 6, 7, or 8. In one embodiment, the number of substitutions and/or deletions and/or insertions in SEQ ID NO: 30 is not more than 8, e.g. 1, 2, 3, 4, 5, 6, 7, or 8. In a further embodiment, the number of substitutions, preferably conservative substitutions, in SEQ ID NO: 30 is not more than 8, e.g. 1, 2, 3, 4, 5, 6, 7, or 8. Examples of amino acid changes and conservative substitutions are described in the fourth aspect of the invention.

In an embodiment of the thirteenth aspect, the variant has at least 50%, such as at least 75%, at least 90%, at least 95% or at least 100% of the lysozyme activity of SEQ ID NO: 30. In one embodiment, lysozyme activity is determined as described in example 1.

In a fourteenth aspect, the invention relates to polypeptides having lysozyme activity having at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 32. In one embodiment, the polypeptides differ by up to 45 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 amino acids from the mature polypeptide of SEQ ID NO: 32.

In a continuation of the fourteenth aspect, the invention relates to polypeptides having lysozyme activity having at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 33. In one embodiment, the polypeptides differ by up to 45 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 amino acids from SEQ ID NO: 33.

In one embodiment, the invention relates to polypeptides having lysozyme activity and having a sequence identity to SEQ ID NO: 33 of at least 80% and wherein the polypeptide has at least 50%, such as at least 75%, at least 90%, at least 95% or at least 100% of the lysozyme activity of SEQ ID NO: 33. In one embodiment, the invention relates to polypeptides having lysozyme activity and having a sequence identity to SEQ ID NO: 33 of at least 85% and wherein the polypeptide has at least 50%, such as at least 75%, at least 90%, at least 95% or at least 100% of the lysozyme activity of SEQ ID NO: 33. In one embodiment, the invention relates to polypeptides having lysozyme activity and having a sequence identity to SEQ ID NO: 33 of at least 90% and wherein the polypeptide has at least 50%, such as at least 75%, at least 90%, at least 95% or at least 100% of the lysozyme activity of SEQ ID NO: 33. In one embodiment, the invention relates to polypeptides having lysozyme activity and having a sequence identity to SEQ ID NO: 33 of at least 95% and wherein the polypeptide has at least 50%, such as at least 75%, at least 90%, at least 95% or at least 100% of the lysozyme activity of SEQ ID NO: 33. In one embodiment, lysozyme activity is determined as described in example 1.

In one embodiment, the polypeptide comprises or consists of the mature polypeptide of SEQ ID NO: 32. In one embodiment, the polypeptide preferably comprises or consists of the amino acid sequence of SEQ ID NO: 33; comprises the amino acid sequence of SEQ ID NO: 33 and a N-terminal and/or C-terminal His-tag and/or HQ-tag; comprises the amino acid sequence of SEQ ID NO: 33 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 33. In one embodiment, the polypeptide comprises or consists of amino acids 1 to 226 of SEQ ID NO: 33. In one embodiment, the polypeptide has been isolated.

In a continuation of the fourteenth aspect, the invention relates to polypeptides having lysozyme activity encoded by a polynucleotide having a sequence identity to the mature polypeptide coding sequence of SEQ ID NO: 31 of at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the fourteenth aspect, the invention relates to variants of SEQ ID NO: 33 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 33 is not more than 45, e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45. In an embodiment, the number of positions comprising one or more amino acid substitutions, and/or one or more amino acid deletions, and/or one or more amino acid insertions or any combination thereof in SEQ ID NO: 33 is not more than 10, e.g., 1, 2, 3, 4, 5, 6, 7, 8, 9 or 10. In one embodiment, the number of substitutions and/or deletions and/or insertions in SEQ ID NO: 33 is not more than 10, e.g. 1, 2, 3, 4, 5, 6, 7, 8, 9, or 10. In a further embodiment, the number of substitutions, preferably conservative substitutions, in SEQ ID NO: 33 is not more than 10, e.g. 1, 2, 3, 4, 5, 6, 7, 8, 9, or 10. Examples of amino acid changes and conservative substitutions are described in the fourth aspect of the invention.

In an embodiment of the fourteenth aspect, the variant has at least 50%, such as at least 75%, at least 90%, at least 95% or at least 100% of the lysozyme activity of SEQ ID NO: 33. In one embodiment, lysozyme activity is determined as described in example 1.

In a fifteenth aspect, the invention relates to polypeptides having lysozyme activity having at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 35. In one embodiment, the polypeptides differ by up to 44 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or 44 amino acids from the mature polypeptide of SEQ ID NO: 35.

In a continuation of the fifteenth aspect, the invention relates to polypeptides having lysozyme activity having at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 36. In one embodiment, the polypeptides differ by up to 44 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or 44 amino acids from SEQ ID NO: 36.

In one embodiment, the invention relates to polypeptides having lysozyme activity and having a sequence identity to SEQ ID NO: 36 of at least 80% and wherein the polypeptide has at least 50%, such as at least 75%, at least 90%, at least 95% or at least 100% of the lysozyme activity of SEQ ID NO: 36. In one embodiment, the invention relates to polypeptides having lysozyme activity and having a sequence identity to SEQ ID NO: 36 of at least 85% and wherein the polypeptide has at least 50%, such as at least 75%, at least 90%, at least 95% or at least 100% of the lysozyme activity of SEQ ID NO: 36. In one embodiment, the invention relates to polypeptides having lysozyme activity and having a sequence identity to SEQ ID NO: 36 of at least 90% and wherein the polypeptide has at least 50%, such as at least 75%, at least 90%, at least 95% or at least 100% of the lysozyme activity of SEQ ID NO: 36. In one embodiment, the invention relates to polypeptides having lysozyme activity and having a sequence identity to SEQ ID NO: 36 of at least 95% and wherein the polypeptide has at least 50%, such as at least 75%, at least 90%, at least 95% or at least 100% of the lysozyme activity of SEQ ID NO: 36. In one embodiment, lysozyme activity is determined as described in example 1.

In one embodiment, the polypeptide comprises or consists of the mature polypeptide of SEQ ID NO: 35. In one embodiment, the polypeptide preferably comprises or consists of the amino acid sequence of SEQ ID NO: 36; comprises the amino acid sequence of SEQ ID NO: 36 and a N-terminal and/or C-terminal His-tag and/or HQ-tag; comprises the amino acid sequence of SEQ ID NO: 36 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 36. In one embodiment, the polypeptide comprises or consists of amino acids 1 to 225 of SEQ ID NO: 36. In one embodiment, the polypeptide has been isolated.

In a continuation of the fifteenth aspect, the invention relates to polypeptides having lysozyme activity encoded by a polynucleotide having a sequence identity to the mature polypeptide coding sequence of SEQ ID NO: 34 of at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the fifteenth aspect, the invention relates to variants of SEQ ID NO: 36 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 36 is not more than 44, e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or 44. In an embodiment, the number of positions comprising one or more amino acid substitutions, and/or one or more amino acid deletions, and/or one or more amino acid insertions or any combination thereof in SEQ ID NO: 36 is not more than 10, e.g., 1, 2, 3, 4, 5, 6, 7, 8, 9 or 10. In one embodiment, the number of substitutions and/or deletions and/or insertions in SEQ ID NO: 36 is not more than 10, e.g. 1, 2, 3, 4, 5, 6, 7, 8, 9, or 10. In a further embodiment, the number of substitutions, preferably conservative substitutions, in SEQ ID NO: 36 is not more than 10, e.g. 1, 2, 3, 4, 5, 6, 7, 8, 9, or 10. Examples of amino acid changes and conservative substitutions are described in the fourth aspect of the invention.

In an embodiment of the fifteenth aspect, the variant has at least 50%, such as at least 75%, at least 90%, at least 95% or at least 100% of the lysozyme activity of SEQ ID NO: 36. In one embodiment, lysozyme activity is determined as described in example 1.

In a sixteenth aspect, the invention relates to polypeptides having lysozyme activity having at least 81%, e.g., at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 38. In one embodiment, the polypeptides differ by up to 42 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, or 42 amino acids from the mature polypeptide of SEQ ID NO: 38.

In a continuation of the sixteenth aspect, the invention relates to polypeptides having lysozyme activity having at least 81%, e.g., at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 39. In one embodiment, the polypeptides differ by up to 42 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, or 42 amino acids from SEQ ID NO: 39.

In one embodiment, the invention relates to polypeptides having lysozyme activity and having a sequence identity to SEQ ID NO: 39 of at least 81% and wherein the polypeptide has at least 50%, such as at least 75%, at least 90%, at least 95% or at least 100% of the lysozyme activity of SEQ ID NO: 39. In one embodiment, the invention relates to polypeptides having lysozyme activity and having a sequence identity to SEQ ID NO: 39 of at least 85% and wherein the polypeptide has at least 50%, such as at least 75%, at least 90%, at least 95% or at least 100% of the lysozyme activity of SEQ ID NO: 39. In one embodiment, the invention relates to polypeptides having lysozyme activity and having a sequence identity to SEQ ID NO: 39 of at least 90% and wherein the polypeptide has at least 50%, such as at least 75%, at least 90%, at least 95% or at least 100% of the lysozyme activity of SEQ ID NO: 39. In one embodiment, the invention relates to polypeptides having lysozyme activity and having a sequence identity to SEQ ID NO: 39 of at least 95% and wherein the polypeptide has at least 50%, such as at least 75%, at least 90%, at least 95% or at least 100% of the lysozyme activity of SEQ ID NO: 39. In one embodiment, lysozyme activity is determined as described in example 1.

In one embodiment, the polypeptide comprises or consists of the mature polypeptide of SEQ ID NO: 38. In one embodiment, the polypeptide preferably comprises or consists of the amino acid sequence of SEQ ID NO: 39; comprises the amino acid sequence of SEQ ID NO: 39 and a N-terminal and/or C-terminal His-tag and/or HQ-tag; comprises the amino acid sequence of SEQ ID NO: 39 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 39. In one embodiment, the polypeptide comprises or consists of amino acids 1 to 225 of SEQ ID NO: 39. In one embodiment, the polypeptide has been isolated.

In a continuation of the sixteenth aspect, the invention relates to polypeptides having lysozyme activity encoded by a polynucleotide having a sequence identity to the mature polypeptide coding sequence of SEQ ID NO: 37 of at least 81%, e.g., at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the sixteenth aspect, the invention relates to variants of SEQ ID NO: 39 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 39 is not more than 42, e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, or 42. In an embodiment, the number of positions comprising one or more amino acid substitutions, and/or one or more amino acid deletions, and/or one or more amino acid insertions or any combination thereof in SEQ ID NO: 39 is not more than 10, e.g., 1, 2, 3, 4, 5, 6, 7, 8, 9 or 10. In one embodiment, the number of substitutions and/or deletions and/or insertions in SEQ ID NO: 39 is not more than 10, e.g. 1, 2, 3, 4, 5, 6, 7, 8, 9, or 10. In a further embodiment, the number of substitutions, preferably conservative substitutions, in SEQ ID NO: 39 is not more than 10, e.g. 1, 2, 3, 4, 5, 6, 7, 8, 9, or 10. Examples of amino acid changes and conservative substitutions are described in the fourth aspect of the invention.

In an embodiment of the sixteenth aspect, the variant has at least 50%, such as at least 75%, at least 90%, at least 95% or at least 100% of the lysozyme activity of SEQ ID NO: 39. In one embodiment, lysozyme activity is determined as described in example 1.

In a seventeenth aspect, the invention relates to polypeptides having lysozyme activity having at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 41. In one embodiment, the polypeptides differ by up to 50 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids from the mature polypeptide of SEQ ID NO: 41.

In a continuation of the seventeenth aspect, the invention relates to polypeptides having lysozyme activity having at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 42. In one embodiment, the polypeptides differ by up to 50 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids from SEQ ID NO: 42.

In one embodiment, the invention relates to polypeptides having lysozyme activity and having a sequence identity to SEQ ID NO: 42 of at least 80% and wherein the polypeptide has at least 50%, such as at least 75%, at least 90%, at least 95% or at least 100% of the lysozyme activity of SEQ ID NO: 42. In one embodiment, the invention relates to polypeptides having lysozyme activity and having a sequence identity to SEQ ID NO: 42 of at least 85% and wherein the polypeptide has at least 50%, such as at least 75%, at least 90%, at least 95% or at least 100% of the lysozyme activity of SEQ ID NO: 42. In one embodiment, the invention relates to polypeptides having lysozyme activity and having a sequence identity to SEQ ID NO: 42 of at least 90% and wherein the polypeptide has at least 50%, such as at least 75%, at least 90%, at least 95% or at least 100% of the lysozyme activity of SEQ ID NO: 42. In one embodiment, the invention relates to polypeptides having lysozyme activity and having a sequence identity to SEQ ID NO: 42 of at least 95% and wherein the polypeptide has at least 50%, such as at least 75%, at least 90%, at least 95% or at least 100% of the lysozyme activity of SEQ ID NO: 42. In one embodiment, lysozyme activity is determined as described in example 1.

In one embodiment, the polypeptide comprises or consists of the mature polypeptide of SEQ ID NO: 41. In one embodiment, the polypeptide preferably comprises or consists of the amino acid sequence of SEQ ID NO: 42; comprises the amino acid sequence of SEQ ID NO: 42 and a N-terminal and/or C-terminal His-tag and/or HQ-tag; comprises the amino acid sequence of SEQ ID NO: 42 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 42. In one embodiment, the polypeptide comprises or consists of amino acids 1 to 304 of SEQ ID NO: 42. In one embodiment, the polypeptide has been isolated.

In a continuation of the seventeenth aspect, the invention relates to polypeptides having lysozyme activity encoded by a polynucleotide having a sequence identity to the mature polypeptide coding sequence of SEQ ID NO: 40 of at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the seventeenth aspect, the invention relates to variants of SEQ ID NO: 42 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 42 is not more than 50, e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. In an embodiment, the number of positions comprising one or more amino acid substitutions, and/or one or more amino acid deletions, and/or one or more amino acid insertions or any combination thereof in SEQ ID NO: 42 is not more than 10, e.g., 1, 2, 3, 4, 5, 6, 7, 8, 9 or 10. In one embodiment, the number of substitutions and/or deletions and/or insertions in SEQ ID NO: 42 is not more than 10, e.g. 1, 2, 3, 4, 5, 6, 7, 8, 9, or 10. In a further embodiment, the number of substitutions, preferably conservative substitutions, in SEQ ID NO: 42 is not more than 10, e.g. 1, 2, 3, 4, 5, 6, 7, 8, 9, or 10. Examples of amino acid changes and conservative substitutions are described in the fourth aspect of the invention.

In an embodiment of the seventeenth aspect, the variant has at least 50%, such as at least 75%, at least 90%, at least 95% or at least 100% of the lysozyme activity of SEQ ID NO: 42. In one embodiment, lysozyme activity is determined as described in example 1.

In a eighteenth aspect, the invention relates to polypeptides having lysozyme activity having at least 100%, e.g., or 100% sequence identity to the mature polypeptide of SEQ ID NO: 44. In one embodiment, the polypeptides differ by up to 0 amino acids, e.g., or 1 amino acids from the mature polypeptide of SEQ ID NO: 44.

In a continuation of the eighteenth aspect, the invention relates to polypeptides having lysozyme activity having at least 100%, e.g., or 100% sequence identity to SEQ ID NO: 45. In one embodiment, the polypeptides differ by up to 0 amino acids, e.g., or 1 amino acids from SEQ ID NO: 45.

In one embodiment, the invention relates to polypeptides having lysozyme activity and having a sequence identity to SEQ ID NO: 45 of at least 100% and wherein the polypeptide has at least 50%, such as at least 75%, at least 90%, at least 95% or at least 100% of the lysozyme activity of SEQ ID NO: 45. In one embodiment, lysozyme activity is determined as described in example 1.

In one embodiment, the polypeptide comprises or consists of the mature polypeptide of SEQ ID NO: 44. In one embodiment, the polypeptide preferably comprises or consists of the amino acid sequence of SEQ ID NO: 45; comprises the amino acid sequence of SEQ ID NO: 45 and a N-terminal and/or C-terminal His-tag and/or HQ-tag; comprises the amino acid sequence of SEQ ID NO: 45 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 45. In one embodiment, the polypeptide comprises or consists of amino acids 1 to 227 of SEQ ID NO: 45. In one embodiment, the polypeptide has been isolated.

In a continuation of the eighteenth aspect, the invention relates to polypeptides having lysozyme activity encoded by a polynucleotide having a sequence identity to the mature polypeptide coding sequence of SEQ ID NO: 43 of at least 100%, e.g., or 100%. In a further embodiment, the polypeptide has been isolated.

In a continuation of the eighteenth aspect, the invention relates to variants of SEQ ID NO: 45 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 45 is not more than 0, e.g. or 1. In one embodiment, the number of substitutions and/or deletions and/or insertions in SEQ ID NO: 45 is not more than 0, e.g. or 1. In a further embodiment, the number of substitutions, preferably conservative substitutions, in SEQ ID NO: 45 is not more than 0, e.g. or 1. Examples of amino acid changes and conservative substitutions are described in the fourth aspect of the invention.

In an embodiment of the eighteenth aspect, the variant has at least 50%, such as at least 75%, at least 90%, at least 95% or at least 100% of the lysozyme activity of SEQ ID NO: 45. In one embodiment, lysozyme activity is determined as described in example 1.

Taxonomic and Structural Families

In an embodiment, the LAD catalytic domain comprises one or more motif I: AG[I/L]AT[A/G][I/L][T/V]ES (SEQ ID NO: 317). In an embodiment, the LAD catalytic domain comprises one or more motif II V[G/A]XLCQXVQXSAYP (SEQ ID NO: 318). In an embodiment, the LED comprises one or more motif III: [CGY][YF][VIL][ASTP][DG]X[YF][VIT]X[TS][GAN] (SEQ ID NO: 319). In an embodiment, the LAD catalytic domain comprises one or more motif I: AG[I/L]AT[A/G][I/L][T/V]ES (SEQ ID NO: 317) and one or more motif II V[G/A]XLCQXVQXSAYP (SEQ ID NO: 318). In an embodiment, the LAD catalytic domain comprises one or more motif I: AG[I/L]AT[A/G][I/L][T/V]ES (SEQ ID NO: 317) and the LED comprises one or more motif III: [CGY][YF][VIL][ASTP][DG]X[YF][VIT]X[TS][GAN] (SEQ ID NO: 319). In an embodiment, the LAD catalytic domain comprises one or more motif II V[G/A]XLCQXVQXSAYP (SEQ ID NO: 318) and the LED comprises one or more motif III: [CGY][YF][VIL][ASTP][DG]X[YF][VIT]X[TS][GAN] (SEQ ID NO: 319). In an embodiment, the LAD catalytic domain comprises one or more motif I: AG[I/L]AT[A/G][I/L][T/V]ES (SEQ ID NO: 317) and one or more motif II V[G/A]XLCQXVQXSAYP (SEQ ID NO: 318) and the LED comprises one or more motif III: [CGY][YF][VIL][ASTP][DG]X[YF][VIT]X[TS][GAN] (SEQ ID NO: 319).

In one embodiment, the polypeptide having lysozyme activity is obtained or is obtainable from the taxonomic phylum Ascomycota, preferably the taxonomic subphylum Pezizomycotina and is preferably is selected from the group selected from SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42 and SEQ ID NO: 45.

In one embodiment, the polypeptide having lysozyme activity is obtained or is obtainable from the taxonomic class Eurotiomycetes, preferably the taxonomic order Eurotiales and is more preferably selected from the group consisting of SEQ ID NO: 3, SEQ ID NO: 6, SEQ ID NO:9, SEQ ID NO: 12, SEQ ID NO: 15, SEQ ID NO: 21, SEQ ID NO: 24, SEQ ID NO: 27, SEQ ID NO: 30 and SEQ ID NO: 36.

In one embodiment, the polypeptide having lysozyme activity is obtained or is obtainable from the taxonomic order Eurotiales, preferably the taxonomic family Aspergillaceae and is more preferably selected from the group consisting of SEQ ID NO: 3, SEQ ID NO: 6, SEQ ID NO: 12, SEQ ID NO: 15, SEQ ID NO: 21, SEQ ID NO: 24, SEQ ID NO: 27 and SEQ ID NO: 30.

In one embodiment, the polypeptide having lysozyme activity is obtained or is obtainable from the taxonomic order Eurotiales, preferably the taxonomic family Trichocomaceae and is more preferably selected from the group consisting of SEQ ID NO: 9 and SEQ ID NO: 36.

In one embodiment, the polypeptide having lysozyme activity is obtained or is obtainable from the taxonomic class Sordariomycetes and is preferably selected from the group selected from SEQ ID NO: 18, SEQ ID NO: 33, SEQ ID NO: 39, SEQ ID NO: 42 and SEQ ID NO: 45.

In one embodiment, the polypeptide having lysozyme activity is obtained or is obtainable from the taxonomic order Sordariales, preferably the taxonomic family Chaetomiaceae and is more preferably selected from the group consisting of SEQ ID NO: 18, SEQ ID NO: 33, SEQ ID NO: 39 and SEQ ID NO: 45.

In one embodiment, the polypeptide having lysozyme activity is obtained or is obtainable from the taxonomic order Hypocreales, preferably the taxonomic family Clavicipitaceae and is more preferably selected from the group consisting of SEQ ID NO: 42.

Sources of Polypeptides Having Lysozyme Activity

A polypeptide having lysozyme activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a fungal polypeptide. In one aspect, the polypeptide is a polypeptide having lysozyme activity from a fungus of the class Eurotiomycetes, such as from the order Eurotiales, or from the family Aspergillaceae, or from the genus *Penicillium*, or from the species *Penicillium simplicissimum, Penicillium vasconiae, Penicillium antarcticum, Penicillium wellingtonense, Penicillium roseopurpureum* or *Penicillium virgatum*.

The polypeptide may be a fungal polypeptide. In one aspect, the polypeptide is a polypeptide having lysozyme activity from a fungus of the class Eurotiomycetes, such as from the order Eurotiales, or from the family Aspergillaceae, or from the genus *Aspergillus*, or from the species *Aspergillus* sp. XZ2668 or *Aspergillus niveus*.

The polypeptide may be a fungal polypeptide. In one aspect, the polypeptide is a polypeptide having lysozyme activity from a fungus of the class Eurotiomycetes, such as from the order Eurotiales, or from the family Trichocomaceae, or from the genus *Talaromyces*, or from the species *Talaromyces proteolyticus* or *Talaromyces atricola*.

The polypeptide may be a fungal polypeptide. In one aspect, the polypeptide is a polypeptide having lysozyme activity from a fungus of the class Sordariomycetes, such as from the order Hypocreales, or from the family Clavicipitaceae, or from the genus *Metarhizium*, or from the species *Metarhizium carneum*.

The polypeptide may be a fungal polypeptide. In one aspect, the polypeptide is a polypeptide having lysozyme activity from a fungus of the class Sordariomycetes, such as from the order Sordariales, or from the family Chaetomiaceae, or from the genus *Ovatospora*, or from the species *Ovatospora brasiliensis*.

The polypeptide may be a fungal polypeptide. In one aspect, the polypeptide is a polypeptide having lysozyme activity from a fungus of the class Sordariomycetes, such as from the order Sordariales, or from the family Chaetomiaceae, or from the genus *Chaetomium*, or from the species *Chaetomium* sp. ZY369.

The polypeptide may be a fungal polypeptide. In one aspect, the polypeptide is a polypeptide having lysozyme activity from a fungus of the class Sordariomycetes, such as from the order Sordariales, or from the family Chaetomiaceae, or from the genus *Trichocladium*, or from the species *Trichocladium asperum*.

The polypeptide may be a fungal polypeptide. In one aspect, the polypeptide is a polypeptide having lysozyme activity from a fungus of the class Sordariomycetes, such as from the order Sordariales, or from the family Chaetomiaceae, or from the genus *Thielavia*, or from the species *Thielavia terrestris*.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polynucleotides

The present invention also relates to polynucleotides encoding a polypeptide of the present invention, as described herein. In an embodiment, the polynucleotide encoding the polypeptide of the present invention has been isolated.

The techniques used to isolate or clone a polynucleotide are known in the art and include isolation from genomic DNA or cDNA, or a combination thereof. The cloning of the polynucleotides from genomic DNA can be effected, e.g., by using the well-known polymerase chain reaction (PCR) or antibody screening of expression libraries to detect cloned DNA fragments with shared structural features. See, e.g., Innis et al., 1990, *PCR: A Guide to Methods and Application*, *Academic Press*, New York. Other nucleic acid amplification procedures such as ligase chain reaction (LCR), ligation activated transcription (LAT) and polynucleotide-based amplification (NASBA) may be used. The polynucleotides may be cloned from a strain of *Trichophaea* or a strain of *Trichoderma*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dania (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosylaminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMß1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

In some embodiments, the polypeptide is heterologous to the recombinant host cell.

In some embodiments, at least one of the one or more control sequences is heterologous to the polynucleotide encoding the polypeptide.

In some embodiments, the recombinant host cell comprises at least two copies, e.g., three, four, or five, of the polynucleotide of the present invention.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus,* and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella,* and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* and *Bacillus thuringiensis* cells.

The bacterial host cell may also be any *Streptococcus* cell including, but not limited to, *Streptococcus equisimilis, Streptococcus pyogenes, Streptococcus uberis,* and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus,* and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol. (Praha)* 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi,* 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces,* or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology,* Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and optionally, (b) recovering the polypeptide.

In one aspect, the cell is a *Penicillium simplicissimum* cell. In one aspect, the cell is a *Penicillium vasconiae* cell. In one aspect, the cell is a *Talaromyces proteolyticus* cell. In one aspect, the cell is an *Aspergillus* sp. XZ2668 cell. In one aspect, the cell is a *Penicillium antarcticum* cell. In one aspect, the cell is a *Ovatospora brasiliensis* cell. In one aspect, the cell is a *Penicillium wellingtonense* cell. In one aspect, the cell is a *Penicillium roseopurpureum* cell. In one aspect, the cell is a *Penicillium virgatum* cell. In one aspect, the cell is an *Aspergillus niveus* cell. In one aspect, the cell is a *Chaetomium* sp. ZY369 cell. In one aspect, the cell is a *Talaromyces atricola* cell. In one aspect, the cell is a *Trichocladium asperum* cell. In one aspect, the cell is a *Metarhizium carneum* cell. In one aspect, the cell is a *Thielavia terrestris* cell.

The present invention also relates to methods of producing a polypeptide of the present invention, comprising (a) cultivating a recombinant host cell of the present invention under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the fermentation medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

Plants

The present invention also relates to isolated plants, e.g., a transgenic plant, plant part, or plant cell, comprising a polynucleotide of the present invention so as to express and produce a polypeptide or domain in recoverable quantities. The polypeptide or domain may be recovered from the plant or plant part. Alternatively, the plant or plant part containing the polypeptide or domain may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyma, vascular tissues, meristems.

Plant cells and specific plant cell compartments, such as chloroplasts, apoplasts, mitochondria, vacuoles, peroxisomes and cytoplasm are also considered to be a plant part.

Also included within the scope of the present invention are the progeny of such plants, plant parts, and plant cells.

The transgenic plant or plant cell expressing the polypeptide or domain may be constructed in accordance with methods known in the art.

The present invention also relates to methods of producing a polypeptide or domain of the present invention comprising (a) cultivating a transgenic plant or a plant cell comprising a polynucleotide encoding the polypeptide or domain under conditions conducive for production of the polypeptide or domain; and (b) recovering the polypeptide or domain.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In some embodiments, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In some embodiments, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In some embodiments, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Enzyme Compositions

The present invention also relates to compositions comprising a polypeptide of the present invention. Preferably, the compositions are enriched in the polypeptide of the invention. The term "enriched" indicates that the lysozyme activity of the composition has been increased, e.g., with an enrichment factor of at least 1.1, such as at least 1.2, at least 1.3, at least 1.4, at least 1.5, at least 2.0, at least 3.0, at least 4.0, at least 5.0, at least 10.

In a preferred embodiment, the composition comprises one or more LYS polypeptides having lysozyme activity selected from the list consisting of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42 and SEQ ID NO: 45.

In an embodiment, the composition comprises the polypeptide of the invention and one or more formulating agents, as described below.

The compositions may further comprise multiple enzymatic activities, such as one or more (e.g., several) enzymes selected from the group consisting of phytase, xylanase, galactanase, alpha-galactosidase, beta-galactosidase, protease, phospholipase A1, phospholipase A2, lysophospholipase, phospholipase C, phospholipase D, amylase, lysozyme, arabinofuranosidase, beta-xylosidase, acetyl xylan esterase, feruloyl esterase, cellulase, cellobiohydrolases, beta-glucosidase, pullulanase, and beta-glucanase or any combination thereof.

The compositions may further comprise one or more probiotics. In an embodiment, the probiotic is selected from the group consisting of *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Bifidobacterium bifidum, Bifidobacterium animalis, Bifidobacterium* sp., *Carnobacterium* sp., *Clostridium butyricum, Clostridium* sp., *Enterococcus faecium, Enterococcus* sp., *Lactobacillus* sp., *Lactobacillus acidophilus, Lactobacillus farciminus, Lactobacillus rhamnosus, Lactobacillus reuteri, Lactobacillus salivarius, Lactococcus Lactis, Lactococcus* sp., *Leuconostoc* sp., *Megasphaera elsdenii, Megasphaera* sp., *Pediococsus acidilactici, Pediococcus* sp., *Propionibacterium thoenii, Propionibacterium* sp. and *Streptococcus* sp. or any combination thereof.

In an embodiment, the composition comprises one or more formulating agents as disclosed herein, preferably one or more of the compounds selected from the list consisting of glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, kaolin, maltodextrin, cyclodextrin, wheat, PVA, acetate, phosphate, kaolin and cellulose.

In an embodiment, the composition comprises one or more components selected from the list consisting of vitamins, minerals and amino acids.

Formulation

The enzyme of the invention may be formulated as a liquid or a solid. For a liquid formulation, the formulating agent may comprise a polyol (such as e.g. glycerol, ethylene glycol or propylene glycol), a salt (such as e.g. sodium chloride, sodium benzoate, potassium sorbate) or a sugar or sugar derivative (such as e.g. dextrin, glucose, sucrose, and sorbitol). Thus in one embodiment, the composition is a liquid composition comprising the polypeptide of the invention and one or more formulating agents selected from the list consisting of glycerol, ethylene glycol, 1,2-propylene glycol, 1,3-propylene glycol, sodium chloride, sodium benzoate, potassium sorbate, dextrin, glucose, sucrose, and sorbitol. The liquid formulation may be sprayed onto the feed after it has been pelleted or may be added to drinking water given to the animals.

For a solid formulation, the formulation may be for example as a granule, spray dried powder or agglomerate (e.g. as disclosed in WO2000/70034). The formulating agent may comprise a salt (organic or inorganic zinc, sodium, potassium or calcium salts such as e.g. such as calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, potassium sulfate, sodium acetate, sodium benzoate, sodium carbonate, sodium chloride, sodium citrate, sodium sulfate, zinc acetate, zinc benzoate, zinc carbonate, zinc chloride, zinc citrate, zinc sorbate, zinc sulfate), starch or a sugar or sugar derivative (such as e.g. sucrose, dextrin, glucose, lactose, sorbitol).

In one embodiment, the composition is a solid composition, such as a spray dried composition, comprising the LYS polypeptide of the invention and one or more formulating agents selected from the list consisting of sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, kaolin, maltodextrin, cyclodextrin, wheat, PVA, acetate, phosphate and cellulose. In a preferred embodiment, the formulating agent is selected from one or more of the following compounds: sodium sulfate, dextrin, cellulose, sodium thiosulfate, magnesium sulfate and calcium carbonate.

The present invention also relates to enzyme granules/particles comprising the LYS polypeptide of the invention optionally combined with one or more additional enzymes. The granule is composed of a core, and optionally one or more coatings (outer layers) surrounding the core.

Typically the granule/particle size, measured as equivalent spherical diameter (volume based average particle size), of the granule is 20-2000 µm, particularly 50-1500 µm, 100-1500 µm or 250-1200 µm.

The core can be prepared by granulating a blend of the ingredients, e.g., by a method comprising granulation techniques such as crystallization, precipitation, pan-coating, fluid bed coating, fluid bed agglomeration, rotary atomization, extrusion, prilling, spheronization, size reduction methods, drum granulation, and/or high shear granulation.

Methods for preparing the core can be found in Handbook of Powder Technology; Particle size enlargement by C. E. Capes; Volume 1; 1980; Elsevier. Preparation methods include known feed and granule formulation technologies, e.g.:

a) spray dried products, wherein a liquid enzyme-containing solution is atomized in a spray drying tower to form small droplets which during their way down the drying tower dry to form an enzyme-containing particulate material;

b) layered products, wherein the enzyme is coated as a layer around a pre-formed inert core particle, wherein an enzyme-containing solution is atomized, typically in a fluid bed apparatus wherein the pre-formed core particles are fluidized, and the enzyme-containing solution adheres to the core particles and dries up to leave a layer of dry enzyme on the surface of the core particle. Particles of a desired size can be obtained this way if a useful core particle of the desired size can be found. This type of product is described in, e.g., WO 97/23606;

c) absorbed core particles, wherein rather than coating the enzyme as a layer around the core, the enzyme is absorbed onto and/or into the surface of the core. Such a process is described in WO 97/39116.

d) extrusion or pelletized products, wherein an enzyme-containing paste is pressed to pellets or under pressure is extruded through a small opening and cut into particles which are subsequently dried. Such particles usually have a considerable size because of the material in which the extrusion opening is made (usually a plate with bore holes) sets a limit on the allowable pressure drop over the extrusion opening. Also, very high extrusion pressures when using a small opening increase heat generation in the enzyme paste, which is harmful to the enzyme;

e) prilled products, wherein an enzyme-containing powder is suspended in molten wax and the suspension is sprayed, e.g., through a rotating disk atomiser, into a cooling chamber where the droplets quickly solidify (Michael S. Showell (editor); *Powdered detergents*; Surfactant Science Series; 1998; vol. 71; page 140-142; Marcel Dekker). The product obtained is one wherein the enzyme is uniformly distributed throughout an inert material instead of being concentrated on its surface. Also U.S. Pat. Nos. 4,016,040 and 4,713,245 are documents relating to this technique;

f) mixer granulation products, wherein a liquid is added to a dry powder composition of, e.g., conventional granulating components, the enzyme being introduced either via the liquid or the powder or both. The liquid and the powder are mixed and as the moisture of the liquid is absorbed in the dry powder, the components of the dry powder will start to adhere and agglomerate and particles will build up, forming granulates comprising the enzyme. Such a process is described in U.S. Pat. No. 4,106,991 and related documents EP 170360, EP 304332, EP 304331, WO 90/09440 and WO 90/09428. In a particular product of this process wherein various high-shear mixers can be used as granulators, granulates consisting of enzyme as enzyme, fillers and binders etc. are mixed with cellulose fibres to reinforce the particles to give the so-called T-granulate. Reinforced particles, being more robust, release less enzymatic dust.

g) size reduction, wherein the cores are produced by milling or crushing of larger particles, pellets, tablets, briquettes etc. containing the enzyme. The wanted core particle fraction is obtained by sieving the milled or crushed product. Over and undersized particles can be recycled. Size reduction is described in (Martin Rhodes (editor); Principles of Powder Technology; 1990; Chapter 10; John Wiley & Sons);

h) fluid bed granulation, which involves suspending particulates in an air stream and spraying a liquid onto the fluidized particles via nozzles. Particles hit by spray droplets get wetted and become tacky. The tacky particles collide with other particles and adhere to them and form a granule;

i) the cores may be subjected to drying, such as in a fluid bed drier. Other known methods for drying granules in the feed or detergent industry can be used by the skilled person. The drying preferably takes place at a product temperature of from 25 to 90° C. For some enzymes it is important the cores comprising the enzyme contain a low amount of water before coating. If water sensitive enzymes are coated before excessive water is removed, it will be trapped within the core and it may affect the activity of the enzyme negatively. After drying, the cores preferably contain 0.1-10% w/w water.

The core may include additional materials such as fillers, fibre materials (cellulose or synthetic fibres), stabilizing agents, solubilizing agents, suspension agents, viscosity regulating agents, light spheres, plasticizers, salts, lubricants and fragrances.

The core may include a binder, such as synthetic polymer, wax, fat, or carbohydrate.

The core may include a salt of a multivalent cation, a reducing agent, an antioxidant, a peroxide decomposing catalyst and/or an acidic buffer component, typically as a homogenous blend.

In one embodiment, the core comprises a material selected from the group consisting of salts (such as calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, potassium sulfate, sodium acetate, sodium benzoate, sodium carbonate, sodium chloride, sodium citrate, sodium sulfate, zinc acetate, zinc benzoate, zinc carbonate, zinc chloride, zinc citrate, zinc sorbate, zinc sulfate), starch or a sugar or sugar derivative (such as e.g. sucrose, dextrin, glucose, lactose, sorbitol), sugar or sugar derivative (such as e.g. sucrose, dextrin, glucose, lactose, sorbitol), small organic molecules, starch, flour, cellulose and minerals and clay minerals (also known as hydrous aluminium phyllosilicates). In one embodiment, the core comprises a clay mineral such as kaolinite or kaolin.

The core may include an inert particle with the enzyme absorbed into it, or applied onto the surface, e.g., by fluid bed coating.

The core may have a diameter of 20-2000 µm, particularly 50-1500 µm, 100-1500 µm or 250-1200 µm.

The core may be surrounded by at least one coating, e.g., to improve the storage stability, to reduce dust formation during handling, or for coloring the granule. The optional coating(s) may include a salt and/or wax and/or flour coating, or other suitable coating materials.

The coating may be applied in an amount of at least 0.1% by weight of the core, e.g., at least 0.5%, 1% or 5%. The amount may be at most 100%, 70%, 50%, 40% or 30%.

The coating is preferably at least 0.1 µm thick, particularly at least 0.5 µm, at least 1 µm or at least 5 µm. In some embodiments the thickness of the coating is below 100 µm, such as below 60 µm, or below 40 µm.

The coating should encapsulate the core unit by forming a substantially continuous layer. A substantially continuous layer is to be understood as a coating having few or no holes, so that the core unit is encapsulated or enclosed with few or no uncoated areas. The layer or coating should in particular be homogeneous in thickness.

The coating can further contain other materials as known in the art, e.g., fillers, antisticking agents, pigments, dyes, plasticizers and/or binders, such as titanium dioxide, kaolin, calcium carbonate or talc.

A salt coating may comprise at least 60% by weight of a salt, e.g., at least 65%, at least 70%, at least 75%, at least 80%, at least 85%, at least 90%, at least 95% or at least 99% by weight.

The salt may be added from a salt solution where the salt is completely dissolved or from a salt suspension wherein the fine particles are less than 50 µm, such as less than 10 µm or less than 5 µm.

The salt coating may comprise a single salt or a mixture of two or more salts. The salt may be water soluble, in particular having a solubility at least 0.1 g in 100 g of water at 20° C., preferably at least 0.5 g per 100 g water, e.g., at least 1 g per 100 g water, e.g., at least 5 g per 100 g water.

The salt may be an inorganic salt, e.g., salts of sulfate, sulfite, phosphate, phosphonate, nitrate, chloride or carbonate or salts of simple organic acids (less than 10 carbon atoms, e.g., 6 or less carbon atoms) such as citrate, malonate or acetate. Examples of cations in these salts are alkali or earth alkali metal ions, the ammonium ion or metal ions of the first transition series, such as sodium, potassium, magnesium, calcium, zinc or aluminium. Examples of anions include chloride, bromide, iodide, sulfate, sulfite, bisulfite, thiosulfate, phosphate, monobasic phosphate, dibasic phosphate, hypophosphite, dihydrogen pyrophosphate, tetraborate, borate, carbonate, bicarbonate, metasilicate, citrate, malate, maleate, malonate, succinate, sorbate, lactate, formate, acetate, butyrate, propionate, benzoate, tartrate, ascorbate or gluconate. In particular alkali- or earth alkali metal salts of sulfate, sulfite, phosphate, phosphonate, nitrate, chloride or carbonate or salts of simple organic acids such as citrate, malonate or acetate may be used.

The salt in the coating may have a constant humidity at 20° C. above 60%, particularly above 70%, above 80% or above 85%, or it may be another hydrate form of such a salt (e.g., anhydrate). The salt coating may be as described in WO1997/05245, WO1998/54980, WO1998/55599, WO2000/70034, WO2006/034710, WO2008/017661, WO2008/017659, WO2000/020569, WO2001/004279, WO1997/05245, WO2000/01793, WO2003/059086, WO2003/059087, WO2007/031483, WO2007/031485, WO2007/044968, WO2013/192043, WO2014/014647 and WO2015/197719 or polymer coating such as described in WO 2001/00042.

Specific examples of suitable salts are NaCl (CH20° C.=76%), Na2CO3 (CH20° C.=92%), NaNO3 (CH20° C.=73%), Na2HPO4 (CH20° C.=95%), Na3PO4 (CH25° C.=92%), NH4Cl (CH20° C.=79.5%), (NH4)2HPO4 (CH20° C.=93.0%), NH4H2PO4 (CH20° C.=93.1%), (NH4)2SO4 (CH20° C.=81.1%), KCl (CH20° C.=85%), K2HPO4 (CH20° C.=92%), KH2PO4 (CH20° C.=96.5%), KNO3 (CH20° C.=93.5%), Na2SO4 (CH20° C.=93%), K2SO4 (CH20° C.=98%), KHSO4 (CH20° C.=86%), MgSO4 (CH20° C.=90%), ZnSO4 (CH20° C.=90%) and sodium citrate (CH25° C.=86%). Other examples include NaH2PO4, (NH4)H2PO4, CuSO4, Mg(NO3)2, magnesium acetate, calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, sodium acetate, sodium benzoate, sodium citrate, sodium sulfate, zinc acetate, zinc benzoate, zinc carbonate, zinc chloride, zinc citrate and zinc sorbate.

The salt may be in anhydrous form, or it may be a hydrated salt, i.e. a crystalline salt hydrate with bound water(s) of crystallization, such as described in WO 99/32595. Specific examples include anhydrous sodium sulfate (Na2SO4), anhydrous magnesium sulfate (MgSO4), magnesium sulfate heptahydrate (MgSO4.7H2O), zinc sulfate heptahydrate (ZnSO4.7H2O), sodium phosphate dibasic heptahydrate (Na2HPO4.7H2O), magnesium nitrate hexahydrate (Mg(NO3)2(6H2O)), sodium citrate dihydrate and magnesium acetate tetrahydrate.

Preferably the salt is applied as a solution of the salt, e.g., using a fluid bed.

A wax coating may comprise at least 60% by weight of a wax, e.g., at least 65%, at least 70%, at least 75%, at least 80%, at least 85%, at least 90%, at least 95% or at least 99% by weight.

Specific examples of waxes are polyethylene glycols; polypropylenes; Carnauba wax; Candelilla wax; bees wax; hydrogenated plant oil or animal tallow such as polyethylene glycol (PEG), methyl hydroxy-propyl cellulose (MHPC), polyvinyl alcohol (PVA), hydrogenated ox tallow, hydrogenated palm oil, hydrogenated cotton seeds and/or hydrogenated soy bean oil; fatty acid alcohols; mono-glycerides and/or di-glycerides, such as glyceryl stearate, wherein stearate is a mixture of stearic and palmitic acid; microcrystalline wax; paraffin's; and fatty acids, such as hydrogenated linear long chained fatty acids and derivatives thereof. A preferred wax is palm oil or hydrogenated palm oil.

The granule may comprise a core comprising the LYS polypeptide of the invention, one or more salt coatings and one or more wax coatings. Examples of enzyme granules with multiple coatings are shown in WO1993/07263, WO1997/23606 and WO2016/149636.

Non-dusting granulates may be produced, e.g., as disclosed in U.S. Pat. Nos. 4,106,991 and 4,661,452 and may optionally be coated by methods known in the art. The coating materials can be waxy coating materials and film-forming coating materials. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591.

The granulate may further comprise one or more additional enzymes. Each enzyme will then be present in more granules securing a more uniform distribution of the enzymes, and also reduces the physical segregation of different enzymes due to different particle sizes. Methods for producing multi-enzyme co-granulates is disclosed in the ip.com disclosure IPCOM000200739D.

Another example of formulation of enzymes by the use of co-granulates is disclosed in WO 2013/188331.

The present invention also relates to protected enzymes prepared according to the method disclosed in EP 238,216.

Thus, in a further aspect, the present invention provides a granule, which comprises:
 (a) a core comprising a LYS polypeptide having lysozyme activity according to the invention, and
 (b) a coating consisting of one or more layer(s) surrounding the core.

In one embodiment, the coating comprises a salt coating as described herein. In one embodiment, the coating comprises a wax coating as described herein. In one embodiment, the coating comprises a salt coating followed by a wax coating as described herein.

Animal Feed Additives

The present invention also relates to animal feed additives comprising one or more LYS polypeptides having lysozyme activity. Thus, in one embodiment, the invention relates to an animal feed additive comprising a LYS polypeptide, wherein:
 (a) the polypeptide has lysozyme activity;
 (b) the polypeptide comprises one or more LAD catalytic domains; and
 (c) the LAD catalytic domain gives a domT score of at least 170 when queried using a Profile Hidden Markov Model prepared using SEQ ID NOs: 46 to 187 and hmmbuild software program, and wherein the query is carried out using hmmscan software program by the Method of Determining the Lysozyme Enhancing Domain by HMM.

In an embodiment, the polypeptide further comprises one or more lysozyme enhancing domains, wherein the lysozyme enhancing domain gives a domT score of at least 100 when queried using a Profile Hidden Markov Model prepared using SEQ ID NOs: 188 to 316 and hmmbuild software program, and wherein the query is carried out using the hmmscan software program.

In an embodiment, the domT score of the LAD catalytic domain is at least 175, preferably at least 180, more preferably at least 185, even more preferably at least 190, even more preferably at least 195, or most preferably at least 200. In an embodiment, the domT score of the LED is at least 103, preferably at least 106, more preferably at least 109, more preferably at least 112, more preferably at least 115, more preferably at least 118, even more preferably at least 121, or most preferably at least 124. Preferred combinations of domT scores are as disclosed in the first aspect of the invention.

In an embodiment, the LAD catalytic domain comprises one or more motif I: AG[I/L]AT[A/G][I/L][T/V]ES (SEQ ID NO: 317). In an embodiment, the LAD catalytic domain comprises one or more motif II V[G/A]XLCQXVQXSAYP (SEQ ID NO: 318). In an embodiment, the LED comprises one or more motif III: [CGY][YF][VIL][ASTP][DG]X[YF][VIT]X[TS][GAN] (SEQ ID NO: 319). In an embodiment, the LAD catalytic domain comprises one or more motif I: AG[I/L]AT[A/G][I/L][T/V]ES (SEQ ID NO: 317) and one or more motif II V[G/A]XLCQXVQXSAYP (SEQ ID NO: 318). In an embodiment, the LAD catalytic domain comprises one or more motif I: AG[I/L]AT[A/G][I/L][T/V]ES (SEQ ID NO: 317) and the LED comprises one or more motif III: [CGY][YF][VIL][ASTP][DG]X[YF][VIT]X[TS][GAN] (SEQ ID NO: 319). In an embodiment, the LAD catalytic domain comprises one or more motif II V[G/A]XLCQXVQXSAYP (SEQ ID NO: 318) and the LED comprises one or more motif III: [CGY][YF][VIL][ASTP][DG]X[YF][VIT]X[TS][GAN] (SEQ ID NO: 319). In an embodiment, the LAD catalytic domain comprises one or more motif I: AG[I/L]AT[A/G][I/L][T/V]ES (SEQ ID NO: 317) and one or more motif II V[G/A]XLCQXVQXSAYP (SEQ ID NO: 318) and the LED comprises one or more motif III: [CGY][YF][VIL][ASTP][DG]X[YF][VIT]X[TS][GAN] (SEQ ID NO: 319).

In another aspect, the invention relates to animal feed additives comprising one or more LYS polypeptides having lysozyme activity, wherein the polypeptide is selected from the group consisting of:
 (a) a polypeptide having at least 80%, such as at least 85%, at least 90% or at least 95% sequence identity to the polypeptide of SEQ ID NO: 3;
 (b) a polypeptide having at least 84%, such as at least 85%, at least 90% or at least 95% sequence identity to the polypeptide of SEQ ID NO: 6;
 (c) a polypeptide having at least 80%, such as at least 85%, at least 90% or at least 95% sequence identity to the polypeptide of SEQ ID NO: 9;
 (d) a polypeptide having at least 80%, such as at least 85%, at least 90% or at least 95% sequence identity to the polypeptide of SEQ ID NO: 12;
 (e) a polypeptide having at least 80%, such as at least 85%, at least 90% or at least 95% sequence identity to the polypeptide of SEQ ID NO: 15;
 (f) a polypeptide having at least 80%, such as at least 85%, at least 90% or at least 95% sequence identity to the polypeptide of SEQ ID NO: 18;
 (g) a polypeptide having at least 80%, such as at least 85%, at least 90% or at least 95% sequence identity to the polypeptide of SEQ ID NO: 21;
 (h) a polypeptide having at least 80%, such as at least 85%, at least 90% or at least 95% sequence identity to the polypeptide of SEQ ID NO: 24;
 (i) a polypeptide having at least 80%, such as at least 85%, at least 90% or at least 95% sequence identity to the polypeptide of SEQ ID NO: 27;
 (j) a polypeptide having at least 84%, such as at least 85%, at least 90% or at least 95% sequence identity to the polypeptide of SEQ ID NO: 30;
 (k) a polypeptide having at least 80%, such as at least 85%, at least 90% or at least 95% sequence identity to the polypeptide of SEQ ID NO: 33;
 (l) a polypeptide having at least 80%, such as at least 85%, at least 90% or at least 95% sequence identity to the polypeptide of SEQ ID NO: 36;
 (m) a polypeptide having at least 84%, such as at least 85%, at least 90% or at least 95% sequence identity to the polypeptide of SEQ ID NO: 39;
 (n) a polypeptide having at least 80%, such as at least 85%, at least 90% or at least 95% sequence identity to the polypeptide of SEQ ID NO: 42;
 (o) a polypeptide having at least 80%, such as at least 85%, at least 90% or at least 95% sequence identity to the polypeptide of SEQ ID NO: 45;

(p) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42 and SEQ ID NO: 45, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 positions;

(q) a polypeptide comprising the polypeptide of (a), (b), (c), (d), (e), (f), (g), (h), (i), (j), (k), (l), (m), (n), (o) or (p) and a N-terminal and/or C-terminal His-tag and/or HQ-tag;

(r) a polypeptide comprising the polypeptide of (a), (b), (c), (d), (e), (f), (g), (h), (i), (j), (k), (l), (m), (n), (o) or (p) and a N-terminal and/or C-terminal extension of up to 10 amino acids, e.g. 1, 2, 3, 4, 5, 6, 7, 8, 9 or 10 amino acids; and (s) a fragment of the polypeptide of (a), (b), (c), (d), (e), (f), (g), (h), (i), (j), (k), (l), (m), (n), (o) or (p) having lysozyme activity and having at least 90% of the length of the mature polypeptide.

In an embodiment, the LAD catalytic domain comprises one or more motif I: AG[I/L]AT[A/G][I/L][T/V]ES (SEQ ID NO: 317). In an embodiment, the LAD catalytic domain comprises one or more motif II V[G/A]XLCQXVQXSAYP (SEQ ID NO: 318). In an embodiment, the LED comprises one or more motif III: [CGY][YF][VIL][ASTP][DG]X[YF][VIT]X[TS][GAN] (SEQ ID NO: 319). In an embodiment, the LAD catalytic domain comprises one or more motif I: AG[I/L]AT[A/G][I/L][T/V]ES (SEQ ID NO: 317) and one or more motif II V[G/A]XLCQXVQXSAYP (SEQ ID NO: 318). In an embodiment, the LAD catalytic domain comprises one or more motif I: AG[I/L]AT[A/G][I/L][T/V]ES (SEQ ID NO: 317) and the LED comprises one or more motif III: [CGY][YF][VIL][ASTP][DG]X[YF][VIT]X[TS][GAN] (SEQ ID NO: 319). In an embodiment, the LAD catalytic domain comprises one or more motif II V[G/A]XLCQXVQXSAYP (SEQ ID NO: 318) and the LED comprises one or more motif III: [CGY][YF][VIL][ASTP][DG]X[YF][VIT]X[TS][GAN] (SEQ ID NO: 319). In an embodiment, the LAD catalytic domain comprises one or more motif I: AG[I/L]AT[A/G][I/L][T/V]ES (SEQ ID NO: 317) and one or more motif II V[G/A]XLCQXVQXSAYP (SEQ ID NO: 318) and the LED comprises one or more motif III: [CGY][YF][VIL][ASTP][DG]X[YF][VIT]X[TS][GAN] (SEQ ID NO: 319).

In one embodiment, the polypeptide is of fungal origin. In an embodiment, the polypeptide is obtained or obtainable from the taxonomic phylum Ascomycota, preferably the taxonomic subphylum Pezizomycotina.

In an embodiment, the amount of enzyme in the animal feed additive is between 0.001% and 10% by weight of the composition.

In an embodiment, the animal feed additive comprises one or more formulating agents, preferably as described herein above.

In an embodiment, the animal feed additive comprises one or more additional enzymes, preferably as described herein below.

In an embodiment, the animal feed additive comprises one or more probiotics, preferably as described herein below.

In an embodiment, the animal feed additive comprises one or more vitamins, preferably as described herein below.

In an embodiment, the animal feed additive comprises one or more minerals, preferably as described herein below.

In an embodiment, the animal feed additive comprises one or more amino acids, preferably as described herein below.

In an embodiment, the animal feed additive comprises one or more prebiotics, preferably as described herein below.

In an embodiment, the animal feed additive comprises one or more organic acids, preferably as described herein below.

In an embodiment, the animal feed additive comprises one or more phytogenics, preferably as described herein below.

Animal Feed

The present invention also relates to animal feed compositions comprising one or more lysozymes of the invention. In one embodiment, the invention relates to an animal feed comprising the granule as described herein and plant based material. In one embodiment, the invention relates to an animal feed comprising the animal feed additive as described herein and plant based material.

Animal feed compositions or diets have a relatively high content of protein. Poultry and pig diets can be characterised as indicated in Table B of WO 01/58275, columns 2-3. Fish diets can be characterised as indicated in column 4 of this Table B. Furthermore such fish diets usually have a crude fat content of 200-310 g/kg.

An animal feed composition according to the invention has a crude protein content of 50-800 g/kg, and furthermore comprises at least one polypeptide having lysozyme activity as claimed herein.

Furthermore, or in the alternative (to the crude protein content indicated above), the animal feed composition of the invention has a content of metabolisable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In particular embodiments, the content of metabolisable energy, crude protein, calcium, phosphorus, methionine, methionine plus cysteine, and/or lysine is within any one of ranges 2, 3, 4 or 5 in Table B of WO 01/58275 (R. 2-5).

Crude protein is calculated as nitrogen (N) multiplied by a factor 6.25, i.e. Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington DC).

Metabolisable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 DA Beekbergen, The Netherlands. Grafisch bedrijf Ponsen & looijen by, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In a particular embodiment, the animal feed composition of the invention contains at least one vegetable protein as defined above.

The animal feed composition of the invention may also contain animal protein, such as Meat and Bone Meal, Feather meal, and/or Fish Meal, typically in an amount of 0-25%. The animal feed composition of the invention may also comprise Dried Distillers Grains with Solubles (DDGS), typically in amounts of 0-30%.

In still further particular embodiments, the animal feed composition of the invention contains 0-80% maize; and/or 0-80% sorghum; and/or 0-70% wheat; and/or 0-70% Barley; and/or 0-30% oats; and/or 0-40% soybean meal; and/or 0-25% fish meal; and/or 0-25% meat and bone meal; and/or 0-20% whey.

The animal feed may comprise vegetable proteins. In particular embodiments, the protein content of the vegetable proteins is at least 10, 20, 30, 40, 50, 60, 70, 80, or 90% (w/w). Vegetable proteins may be derived from vegetable protein sources, such as legumes and cereals, for example, materials from plants of the families Fabaceae (Leguminosae), Cruciferaceae, Chenopodiaceae, and Poaceae, such as soy bean meal, lupin meal, rapeseed meal, and combinations thereof.

In a particular embodiment, the vegetable protein source is material from one or more plants of the family Fabaceae, e.g., soybean, lupine, pea, or bean. In another particular embodiment, the vegetable protein source is material from one or more plants of the family Chenopodiaceae, e.g. beet, sugar beet, spinach or quinoa. Other examples of vegetable protein sources are rapeseed, and cabbage. In another particular embodiment, soybean is a preferred vegetable protein source. Other examples of vegetable protein sources are cereals such as barley, wheat, rye, oat, maize (corn), rice, and sorghum.

Animal diets can e.g. be manufactured as mash feed (non-pelleted) or pelleted feed. Typically, the milled feedstuffs are mixed and sufficient amounts of essential vitamins and minerals are added according to the specifications for the species in question. Enzymes can be added as solid or liquid enzyme formulations. For example, for mash feed a solid or liquid enzyme formulation may be added before or during the ingredient mixing step. For pelleted feed the (liquid or solid) lysozyme/enzyme preparation may also be added before or during the feed ingredient step. Typically a liquid lysozyme/enzyme preparation comprises the polypeptide having lysozyme activity of the invention optionally with a polyol, such as glycerol, ethylene glycol or propylene glycol, and is added after the pelleting step, such as by spraying the liquid formulation onto the pellets. The enzyme may also be incorporated in a feed additive or premix.

Alternatively, the polypeptide having lysozyme activity can be prepared by freezing a mixture of liquid enzyme solution with a bulking agent such as ground soybean meal, and then lyophilizing the mixture.

The final enzyme concentration in the diet is within the range of 0.01-200 mg enzyme protein per kg diet, preferably between 0.05-100 mg/kg diet, more preferably 0.1-50 mg, even more preferably 0.2-20 mg enzyme protein per kg animal diet.

It is at present contemplated that the enzyme is administered in one or more of the following amounts (dosage ranges): 0.01-200; 0.05-100; 0.1-50; 0.2-20; 0.1-1; 0.2-2; 0.5-5; or 1-10; —all these ranges being in mg LYS polypeptide protein per kg feed (ppm).

For determining mg LYS polypeptide protein per kg feed, the LYS polypeptide is purified from the feed composition, and the specific activity of the purified LYS polypeptide is determined using a relevant assay (see under lysozyme activity). The lysozyme activity of the feed composition as such is also determined using the same assay, and on the basis of these two determinations, the dosage in mg lysozyme protein per kg feed is calculated.

In a particular embodiment, the animal feed additive of the invention is intended for being included (or prescribed as having to be included) in animal diets or feed at levels of 0.01 to 10.0%; more particularly 0.05 to 5.0%; or 0.2 to 1.0% (% meaning g additive per 100 g feed). This is so in particular for premixes.

The same principles apply for determining mg LYS polypeptide protein in feed additives. Of course, if a sample is available of the LYS polypeptide used for preparing the feed additive or the feed, the specific activity is determined from this sample (no need to purify the LYS polypeptide from the feed composition or the additive).

Thus in a further aspect, the present invention also relates to an animal feed comprising one or more LYS polypeptides having lysozyme activity and plant based material. In another aspect, the present invention also relates to an animal feed comprising the animal feed additive of the invention (as described herein above) and plant based material.

In one embodiment, the invention relates to an animal feed comprising plant based material and a LYS polypeptide, wherein the polypeptide (a) has lysozyme activity and (b) comprises one or more LAD catalytic domains; wherein the LAD catalytic domain gives a domT score of at least 180 when queried using a Profile Hidden Markov Model (HMM) prepared using SEQ ID NOs: 46 to 187 and hmmbuild software program, and wherein the query is carried out using hmmscan software program by the Method of Determining the LAD Catalytic Domain by HMM.

In an embodiment, the polypeptide further comprises one or more lysozyme enhancing domains, wherein the lysozyme enhancing domain gives a domT score of at least 100 when queried using a Profile Hidden Markov Model prepared using SEQ ID NOs: 188 to 316 and hmmbuild software program, and wherein the query is carried out using the hmmscan software program by the Method of Determining the Lysozyme.

In an embodiment, the domT score of the LAD catalytic domain is at least 175, preferably at least 180, more preferably at least 185, even more preferably at least 190, even more preferably at least 195, or most preferably at least 200. In an embodiment, the domT score of the LED is at least 103, preferably at least 106, more preferably at least 109, more preferably at least 112, more preferably at least 115, more preferably at least 118, even more preferably at least 121, or most preferably at least 124. Preferred combinations of domT scores are as disclosed in the first aspect of the invention.

In an embodiment, the LAD catalytic domain comprises one or more motif I: AG[I/L]AT[A/G][I/L][T/V]ES (SEQ ID NO: 317). In an embodiment, the LAD catalytic domain comprises one or more motif II V[G/A]XLCQXVQXSAYP (SEQ ID NO: 318). In an embodiment, the LED comprises one or more motif III: [CGY][YF][VIL][ASTP][DG]X[YF][VIT]X[TS][GAN] (SEQ ID NO: 319). In an embodiment, the LAD catalytic domain comprises one or more motif I: AG[I/L]AT[A/G][I/L][T/V]ES (SEQ ID NO: 317) and one or more motif II V[G/A]XLCQXVQXSAYP (SEQ ID NO: 318). In an embodiment, the LAD catalytic domain comprises one or more motif I: AG[I/L]AT[A/G][I/L][T/V]ES (SEQ ID NO: 317) and the LED comprises one or more motif III: [CGY][YF][VIL][ASTP][DG]X[YF][VIT]X[TS][GAN] (SEQ ID NO: 319). In an embodiment, the LAD catalytic domain comprises one or more motif II V[G/A]XLCQXVQXSAYP (SEQ ID NO: 318) and the LED comprises one or more motif III: [CGY][YF][VIL][ASTP][DG]X[YF][VIT]X[TS][GAN] (SEQ ID NO: 319). In an embodiment, the LAD catalytic domain comprises one or more motif I: AG[I/L]AT[A/G][I/L][T/V]ES (SEQ ID NO: 317) and one or more motif II V[G/A]XLCQXVQXSAYP (SEQ ID NO: 318) and the LED comprises one or more motif III: [CGY][YF][VIL][ASTP][DG]X[YF][VIT]X[TS][GAN] (SEQ ID NO: 319).

In another aspect, the invention relates to an animal feed comprising plant based material and one or more LYS polypeptides having lysozyme activity, wherein the polypeptide is selected from the group consisting of:

(a) a polypeptide having at least 80%, such as at least 85%, at least 90% or at least 95% sequence identity to the polypeptide of SEQ ID NO: 3;

(b) a polypeptide having at least 84%, such as at least 85%, at least 90% or at least 95% sequence identity to the polypeptide of SEQ ID NO: 6;

(c) a polypeptide having at least 80%, such as at least 85%, at least 90% or at least 95% sequence identity to the polypeptide of SEQ ID NO: 9;

(d) a polypeptide having at least 80%, such as at least 85%, at least 90% or at least 95% sequence identity to the polypeptide of SEQ ID NO: 12;

(e) a polypeptide having at least 80%, such as at least 85%, at least 90% or at least 95% sequence identity to the polypeptide of SEQ ID NO: 15;

(f) a polypeptide having at least 80%, such as at least 85%, at least 90% or at least 95% sequence identity to the polypeptide of SEQ ID NO: 18;

(g) a polypeptide having at least 80%, such as at least 85%, at least 90% or at least 95% sequence identity to the polypeptide of SEQ ID NO: 21;

(h) a polypeptide having at least 80%, such as at least 85%, at least 90% or at least 95% sequence identity to the polypeptide of SEQ ID NO: 24;

(i) a polypeptide having at least 80%, such as at least 85%, at least 90% or at least 95% sequence identity to the polypeptide of SEQ ID NO: 27;

(j) a polypeptide having at least 84%, such as at least 85%, at least 90% or at least 95% sequence identity to the polypeptide of SEQ ID NO: 30;

(k) a polypeptide having at least 80%, such as at least 85%, at least 90% or at least 95% sequence identity to the polypeptide of SEQ ID NO: 33;

(l) a polypeptide having at least 80%, such as at least 85%, at least 90% or at least 95% sequence identity to the polypeptide of SEQ ID NO: 36;

(m) a polypeptide having at least 84%, such as at least 85%, at least 90% or at least 95% sequence identity to the polypeptide of SEQ ID NO: 39;

(n) a polypeptide having at least 80%, such as at least 85%, at least 90% or at least 95% sequence identity to the polypeptide of SEQ ID NO: 42;

(o) a polypeptide having at least 80%, such as at least 85%, at least 90% or at least 95% sequence identity to the polypeptide of SEQ ID NO: 45;

(p) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42 and SEQ ID NO: 45, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 positions;

(q) a polypeptide comprising the polypeptide of (a), (b), (c), (d), (e), (f), (g), (h), (i), (j), (k), (l), (m), (n), (o) or (p) and a N-terminal and/or C-terminal His-tag and/or HQ-tag;

(r) a polypeptide comprising the polypeptide of (a), (b), (c), (d), (e), (f), (g), (h), (i), (j), (k), (l), (m), (n), (o) or (p) and a N-terminal and/or C-terminal extension of up to 10 amino acids, e.g. 1, 2, 3, 4, 5, 6, 7, 8, 9 or 10 amino acids; and (s) a fragment of the polypeptide of (a), (b), (c), (d), (e), (f), (g), (h), (i), (j), (k), (l), (m), (n), (o) or (p) having lysozyme activity and having at least 90% of the length of the mature polypeptide.

In an embodiment, the LAD catalytic domain comprises one or more motif I: AG[I/L]AT[A/G][I/L][T/V]ES (SEQ ID NO: 317). In an embodiment, the LAD catalytic domain comprises one or more motif II V[G/A]XLCQXVQXSAYP (SEQ ID NO: 318). In an embodiment, the LED comprises one or more motif III: [CGY][YF][VIL][ASTP][DG]X[YF][VIT]X[TS][GAN] (SEQ ID NO: 319). In an embodiment, the LAD catalytic domain comprises one or more motif I: AG[I/L]AT[A/G][I/L][T/V]ES (SEQ ID NO: 317) and one or more motif II V[G/A]XLCQXVQXSAYP (SEQ ID NO: 318). In an embodiment, the LAD catalytic domain comprises one or more motif I: AG[I/L]AT[A/G][I/L][T/V]ES (SEQ ID NO: 317) and the LED comprises one or more motif III: [CGY][YF][VIL][ASTP][DG]X[YF][VIT]X[TS][GAN] (SEQ ID NO: 319). In an embodiment, the LAD catalytic domain comprises one or more motif II V[G/A]XLCQXVQXSAYP (SEQ ID NO: 318) and the LED comprises one or more motif III: [CGY][YF][VIL][ASTP][DG]X[YF][VIT]X[TS][GAN] (SEQ ID NO: 319). In an embodiment, the LAD catalytic domain comprises one or more motif I: AG[I/L]AT[A/G][I/L][T/V]ES (SEQ ID NO: 317) and one or more motif II V[G/A]XLCQXVQXSAYP (SEQ ID NO: 318) and the LED comprises one or more motif III: [CGY][YF][VIL][ASTP][DG]X[YF][VIT]X[TS][GAN] (SEQ ID NO: 319).

In one embodiment, the polypeptide is of fungal origin. In an embodiment, the polypeptide is obtained or obtainable from the taxonomic phylum Ascomycota, preferably the taxonomic subphylum Pezizomycotina.

In an embodiment, the plant based material is selected from the group consisting of legumes, cereals, oats, rye, barley, wheat, maize, corn, sorghum, switchgrass, millet, pearl millet, foxtail millet, soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape), rice, beet, cabbage, sugar beet, spinach, quinoa, or pea, in a processed form thereof (such as soybean meal, rapeseed meal) or any combination thereof.

In a further embodiment, the animal feed has been pelleted.

Additional Enzymes

In another embodiment, the compositions described herein optionally include one or more enzymes. Enzymes can be classified on the basis of the handbook Enzyme Nomenclature from NC-IUBMB, 1992), see also the ENZYME site at the internet: http://www.expasy.ch/enzyme/. ENZYME is a repository of information relative to the nomenclature of enzymes. It is primarily based on the recommendations of the Nomenclature Committee of the International Union of Biochemistry and Molecular Biology (IUB-MB), Academic Press, Inc., 1992, and it describes each type of characterized enzyme for which an EC (Enzyme Commission) number has been provided (Bairoch A. The ENZYME database, 2000, *Nucleic Acids Res* 28:304-305). This IUB-MB Enzyme nomenclature is based on their substrate specificity and occasionally on their molecular mechanism; such a classification does not reflect the structural features of these enzymes.

Another classification of certain glycoside hydrolase enzymes, such as endoglucanase, xylanase, galactanase, mannanase, dextranase, lysozyme and galactosidase is described in Henrissat et al, "The carbohydrate-active enzymes database (CAZy) in 2013", *Nucl. Acids Res.* (1 Jan. 2014) 42 (D1): D490-D495; see also www.cazy.org.

Thus the composition of the invention may also comprise at least one other enzyme selected from the group comprising of phytase (EC 3.1.3.8 or 3.1.3.26); xylanase (EC 3.2.1.8); galactanase (EC 3.2.1.89); alpha-galactosidase (EC 3.2.1.22); protease (EC 3.4); phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); amylase such as, for example, alpha-amylase (EC 3.2.1.1); arabinofuranosidase (EC 3.2.1.55); beta-xylosidase (EC 3.2.1.37); acetyl xylan esterase (EC 3.1.1.72); feruloyl esterase (EC 3.1.1.73); cellulase (EC 3.2.1.4); cellobiohydrolases (EC 3.2.1.91); beta-glucosidase (EC 3.2.1.21); pullulanase (EC 3.2.1.41); alpha-mannosidase (EC 3.2.1.24), mannanase (EC 3.2.1.25) and beta-glucanase (EC 3.2.1.4 or EC 3.2.1.6), or any mixture thereof.

In a particular embodiment, the composition of the invention comprises a phytase (EC 3.1.3.8 or 3.1.3.26). Examples of commercially available phytases include Bio-Feed™ Phytase (Novozymes), Ronozyme® P, Ronozyme® NP and Ronozyme® HiPhos (DSM Nutritional Products), Natuphos™ (BASF), Natuphos™ E (BASF), Finase® and Quantum® Blue (AB Enzymes), OptiPhos® (Huvepharma), AveMix® Phytase (Aveve Biochem), Phyzyme® XP (Verenium/DuPont) and Axtra® PHY (DuPont). Other preferred phytases include those described in e.g. WO 98/28408, WO 00/43503, and WO 03/066847.

In a particular embodiment, the composition of the invention comprises a xylanase (EC 3.2.1.8). Examples of commercially available xylanases include Ronozyme® WX (DSM Nutritional Products), Econase® XT and Barley (AB Vista), Xylathin® (Verenium), Hostazym® X (Huvepharma), Axtra® XB (Xylanase/beta-glucanase, DuPont) and Axtra® XAP (Xylanase/amylase/protease, DuPont), AveMix® XG 10 (xylanase/glucanase) and AveMix® 02 CS (xylanase/glucanase/pectinase, Aveve Biochem), and Naturgrain (BASF).

In a particular embodiment, the composition of the invention comprises a protease (EC 3.4). Examples of commercially available proteases include Ronozyme® ProAct (DSM Nutritional Products).

In a particular embodiment, the composition of the invention comprises an alpha-amylase (EC 3.2.1.1). Examples of commercially available alpha-amylases include Ronozyme® A and RONOZYME® RumiStar™ (DSM Nutritional Products).

In one embodiment, the composition of the invention comprises a multicomponent enzyme product, such as FRA® Octazyme (Framelco), Ronozyme® G2, Ronozyme® VP and Ronozyme® MultiGrain (DSM Nutritional Products), Rovabio® Excel or Rovabio® Advance (Adisseo).

Eubiotics

Eubiotics are compounds which are designed to give a healthy balance of the micro-flora in the gastrointestinal tract. Eubiotics cover a number of different feed additives, such as probiotics, prebiotics, phytogenics (essential oils) and organic acids which are described in more detail below.

Probiotics

In an embodiment, the animal feed composition further comprises one or more additional probiotic. In a particular embodiment, the animal feed composition further comprises a bacterium from one or more of the following genera: *Lactobacillus, Lactococcus, Streptococcus, Bacillus, Pediococcus, Enterococcus, Leuconostoc, Carnobacterium, Propionibacterium, Bifidobacterium, Clostridium* and *Megasphaera* or any combination thereof.

In a preferred embodiment, animal feed composition further comprises a bacterium from one or more of the following strains: *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Enterococcus faecium, Enterococcus* spp, and *Pediococcus* spp, *Lactobacillus* spp, *Bifidobacterium* spp, *Lactobacillus acidophilus, Pediococsus acidilactici, Lactococcus lactis, Bifidobacterium bifidum, Propionibacterium thoenii, Lactobacillus farciminus, Lactobacillus rhamnosus, Clostridium butyricum, Bifidobacterium animalis* ssp. *animalis, Lactobacillus reuteri, Lactobacillus salivarius* ssp. *salivarius, Megasphaera elsdenii, Propionibacteria* sp.

In a more preferred embodiment, composition, animal feed additive or animal feed further comprises a bacterium from one or more of the following strains of *Bacillus subtilis*: 3A-P4 (PTA-6506), 15A-P4 (PTA-6507), 22C-P1 (PTA-6508), 2084 (NRRL B-500130), LSSA01 (NRRL-B-50104), BS27 (NRRL B-501 05), BS 18 (NRRL B-50633), BS 278 (NRRL B-50634), DSM 29870, DSM 29871, DSM 32315, NRRL B-50136, NRRL B-50605, NRRL B-50606, NRRL B-50622 and PTA-7547.

In a more preferred embodiment, composition, animal feed additive or animal feed further comprises a bacterium from one or more of the following strains of *Bacillus pumilus*: NRRL B-50016, ATCC 700385, NRRL B-50885 or NRRL B-50886.

In a more preferred embodiment, composition, animal feed additive or animal feed further comprises a bacterium from one or more of the following strains of *Bacillus licheniformis*: NRRL B 50015, NRRL B-50621 or NRRL B-50623.

In a more preferred embodiment, composition, animal feed additive or animal feed further comprises a bacterium from one or more of the following strains of *Bacillus amyloliquefaciens*: DSM 29869, DSM 29869, NRRL B-50607, PTA-7543, PTA-7549, NRRL B-50349, NRRL B-50606, NRRL B-50013, NRRL B-50151, NRRL B-50141, NRRL B-50147 or NRRL B-50888.

The bacterial count of each of the bacterial strains in the animal feed composition is between $1 \times 10^4$ and $1 \times 10^{14}$ CFU/kg of dry matter, preferably between $1 \times 10^6$ and $1 \times 10^{12}$ CFU/kg of dry matter, and more preferably between $1 \times 10^7$ and $1 \times 10^{11}$ CFU/kg of dry matter. In a more preferred embodiment the bacterial count of each of the bacterial strains in the animal feed composition is between $1\times10^8$ and $1\times10^{10}$ CFU/kg of dry matter.

The bacterial count of each of the bacterial strains in the animal feed composition is between $1\times10^5$ and $1\times10^{15}$ CFU/animal/day, preferably between $1\times10^7$ and $1\times10^{13}$ CFU/animal/day, and more preferably between $1\times10^8$ and $1\times10^{12}$ CFU/animal/day. In a more preferred embodiment the bacterial count of each of the bacterial strains in the animal feed composition is between $1\times10^9$ and $1\times10^{11}$ CFU/animal/day. In one embodiment, the amount of probiotics is 0.001% to 10% by weight of the composition.

In another embodiment, the one or more bacterial strains are present in the form of a stable spore.

Examples of commercial products are Cylactin® (DSM Nutritional Products), Alterion (Adisseo), Enviva PRO (DuPont Animal Nutrition), Syncra® (mix enzyme+probiotic, DuPont Animal Nutrition), Ecobiol® and Fecinor0 (Norel/Evonik) and GutCare® PY1 (Evonik).

Prebiotics

Prebiotics are substances that induce the growth or activity of microorganisms (e.g., bacteria and fungi) that contribute to the well-being of their host. Prebiotics are typically non-digestible fiber compounds that pass undigested through the upper part of the gastrointestinal tract and stimulate the growth or activity of advantageous bacteria that colonize the large bowel by acting as substrate for them. Normally, prebiotics increase the number or activity of bifidobacteria and lactic acid bacteria in the GI tract.

Yeast derivatives (inactivated whole yeasts or yeast cell walls) can also be considered as prebiotics. They often comprise mannan-oligosaccharids, yeast beta-glucans or protein contents and are normally derived from the cell wall of the yeast, Saccharomyces cerevisiae.

In one embodiment, the amount of prebiotics is 0.001% to 10% by weight of the composition. Examples of yeast products are Yang® and Agrimos (Lallemand Animal Nutrition).

Phytogenics

Phytogenics are a group of natural growth promoters or non-antibiotic growth promoters used as feed additives, derived from herbs, spices or other plants. Phytogenics can be single substances prepared from essential oils/extracts, essential oils/extracts, single plants and mixture of plants (herbal products) or mixture of essential oils/extracts/plants (specialized products).

Examples of phytogenics are rosemary, sage, oregano, thyme, clove, and lemongrass. Examples of essential oils are thymol, eugenol, meta-cresol, vaniline, salicylate, resorcine, guajacol, gingerol, lavender oil, ionones, irone, eucalyptol, menthol, peppermint oil, alpha-pinene; limonene, anethol, linalool, methyl dihydrojasmonate, carvacrol, propionic acid/propionate, acetic acid/acetate, butyric acid/butyrate, rosemary oil, clove oil, geraniol, terpineol, citronellol, amyl and/or benzyl salicylate, cinnamaldehyde, plant polyphenol (tannin), turmeric and curcuma extract.

In one embodiment, the amount of phytogeneics is 0.001% to 10% by weight of the composition. Examples of commercial products are Crina® (DSM Nutritional Products); Cinergy™, Biacid™, ProHacid™ Classic and ProHacid™ Advance™ (all Promivi/Cargill) and Envivo EO (DuPont Animal Nutrition).

Organic Acids

Organic acids (C1-C7) are widely distributed in nature as normal constituents of plants or animal tissues. They are also formed through microbial fermentation of carbohydrates mainly in the large intestine. They are often used in swine and poultry production as a replacement of antibiotic growth promoters since they have a preventive effect on the intestinal problems like necrotic enteritis in chickens and Escherichia coli infection in young pigs. Organic acids can be sold as mono component or mixtures of typically 2 or 3 different organic acids. Examples of organic acids are propionic acid, formic acid, citric acid, lactic acid, sorbic acid, malic acid, acetic acid, fumaric acid, benzoic acid, butyric acid and tartaric acid or their salt (typically sodium or potassium salt such as potassium diformate or sodium butyrate).

In one embodiment, the amount of organic acid is 0.001% to 10% by weight of the composition. Examples of commercial products are VevoVitall® (DSM Nutritional Products), Amasil®, Luprisil®, Lupro-Grain®, Lupro-Cid®, Lupro-Mix® (BASF), n-Butyric Acid AF (OXEA) and Adimix Precision (Nutriad).

Premix

The incorporation of the composition of feed additives as exemplified herein above to animal feeds, for example poultry feeds, is in practice carried out using a concentrate or a premix. A premix designates a preferably uniform mixture of one or more microingredients with diluent and/or carrier. Premixes are used to facilitate uniform dispersion of micro-ingredients in a larger mix. A premix according to the invention can be added to feed ingredients or to the drinking water as solids (for example as water soluble powder) or liquids.

Amino Acids

The composition of the invention may further comprise one or more amino acids. Examples of amino acids which are used in animal feed are lysine, alanine, beta-alanine, threonine, methionine and tryptophan. In one embodiment, the amount of amino acid is 0.001% to 10% by weight of the composition.

Vitamins and Minerals

In another embodiment, the animal feed may include one or more vitamins, such as one or more fat-soluble vitamins and/or one or more water-soluble vitamins. In another embodiment, the animal feed may optionally include one or more minerals, such as one or more trace minerals and/or one or more macro minerals.

Usually fat- and water-soluble vitamins, as well as trace minerals form part of a so-called premix intended for addition to the feed, whereas macro minerals are usually separately added to the feed.

Non-limiting examples of fat-soluble vitamins include vitamin A, vitamin D3, vitamin E, and vitamin K, e.g., vitamin K3.

Non-limiting examples of water-soluble vitamins include vitamin C, vitamin B12, biotin and choline, vitamin B1, vitamin B2, vitamin B6, niacin, folic acid and panthothenate, e.g., Ca-D-panthothenate.

Non-limiting examples of trace minerals include boron, cobalt, chloride, chromium, copper, fluoride, iodine, iron, manganese, molybdenum, iodine, selenium and zinc.

Non-limiting examples of macro minerals include calcium, magnesium, phosphorus, potassium and sodium.

In one embodiment, the amount of vitamins is 0.001% to 10% by weight of the composition. In one embodiment, the amount of minerals is 0.001% to 10% by weight of the composition.

The nutritional requirements of these components (exemplified with poultry and piglets/pigs) are listed in Table A of WO 01/58275. Nutritional requirement means that these components should be provided in the diet in the concentrations indicated.

In the alternative, the animal feed additive of the invention comprises at least one of the individual components specified in Table A of WO 01/58275. At least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A.

In a still further embodiment, the animal feed additive of the invention comprises at least one of the below vitamins, preferably to provide an in-feed-concentration within the ranges specified in the below Table 1 (for piglet diets, and broiler diets, respectively).

TABLE 1

Typical vitamin recommendations

| Vitamin | Piglet diet | Broiler diet |
| --- | --- | --- |
| Vitamin A | 10,000-15,000 IU/kg feed | 8-12,500 IU/kg feed |
| Vitamin D3 | 1800-2000 IU/kg feed | 3000-5000 IU/kg feed |
| Vitamin E | 60-100 mg/kg feed | 150-240 mg/kg feed |
| Vitamin K3 | 2-4 mg/kg feed | 2-4 mg/kg feed |
| Vitamin B1 | 2-4 mg/kg feed | 2-3 mg/kg feed |
| Vitamin B2 | 6-10 mg/kg feed | 7-9 mg/kg feed |
| Vitamin B6 | 4-8 mg/kg feed | 3-6 mg/kg feed |
| Vitamin B12 | 0.03-0.05 mg/kg feed | 0.015-0.04 mg/kg feed |
| Niacin (Vitamin B3) | 30-50 mg/kg feed | 50-80 mg/kg feed |
| Pantothenic acid | 20-40 mg/kg feed | 10-18 mg/kg feed |
| Folic acid | 1-2 mg/kg feed | 1-2 mg/kg feed |
| Biotin | 0.15-0.4 mg/kg feed | 0.15-0.3 mg/kg feed |
| Choline chloride | 200-400 mg/kg feed | 300-600 mg/kg feed |

Other Feed Ingredients

The composition of the invention may further comprise colouring agents, stabilisers, growth improving additives and aroma compounds/flavourings, polyunsaturated fatty acids (PUFAs); reactive oxygen generating species, antioxidants, anti-microbial peptides, anti-fungal polypeptides and mycotoxin management compounds.

Examples of colouring agents are carotenoids such as beta-carotene, astaxanthin, and lutein.

Examples of aroma compounds/flavourings are creosol, anethol, deca-, undeca- and/or dodeca-lactones, ionones, irone, gingerol, piperidine, propylidene phatalide, butylidene phatalide, capsaicin and tannin.

Examples of antimicrobial peptides (AMP's) are CAP18, Leucocin A, Tritrpticin, Protegrin-1, Thanatin, Defensin, Lactoferrin, Lactoferricin, and Ovispirin such as Novispirin (Robert Lehrer, 2000), Plectasins, and Statins, including the compounds and polypeptides disclosed in WO 03/044049 and WO 03/048148, as well as variants or fragments of the above that retain antimicrobial activity.

Examples of antifungal polypeptides (AFP's) are the *Aspergillus giganteus*, and *Aspergillus niger* peptides, as well as variants and fragments thereof which retain antifungal activity, as disclosed in WO 94/01459 and WO 02/090384.

Examples of polyunsaturated fatty acids are C18, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and enzymes such as an oxidase, an oxygenase or a syntethase.

Antioxidants can be used to limit the number of reactive oxygen species which can be generated such that the level of reactive oxygen species is in balance with antioxidants.

Mycotoxins, such as deoxynivalenol, aflatoxin, zearalenone and fumonisin can be found in animal feed and can result in negative animal performance or illness. Compounds which can manage the levels of mycotoxin, such as via deactivation of the mycotoxin or via binding of the mycotoxin, can be added to the feed to ameliorate these negative effects. Examples of mycotoxin management compounds are Vitafix®, Vitafix Ultra (Nuscience), Mycofix®, Mycofix® Secure, FUMzyme®, Biomin® BBSH, Biomin® MTV (Biomin), Mold-Nil®, Toxy-Nil® and Unike® Plus (Nutriad).

Uses

Use in Animal Feed

A LYS polypeptide of the invention may also be used in animal feed, wherein the term "animal" refers to all animals except humans. Examples of animals are mono-gastric animals, e.g. pigs or swine (including, but not limited to, piglets, growing pigs, and sows); poultry (including but not limited to poultry, turkey, duck, quail, guinea fowl, goose, pigeon, squab, chicken, broiler, layer, pullet and chick); fish (including but not limited to amberjack, arapaima, barb, bass, bluefish, bocachico, bream, bullhead, cachama, carp, catfish, catla, chanos, char, cichlid, cobia, cod, crappie, dorada, drum, eel, goby, goldfish, gourami, grouper, guapote, halibut, java, labeo, lai, loach, mackerel, milkfish, mojarra, mudfish, mullet, paco, pearlspot, pejerrey, perch, pike, pompano, roach, salmon, sampa, sauger, sea bass, seabream, shiner, sleeper, snakehead, snapper, snook, sole, spinefoot, sturgeon, sunfish, sweetfish, tench, terror, tilapia, trout, tuna, turbot, vendace, walleye and whitefish); and crustaceans (including but not limited to shrimps and prawns).

In the use according to the invention the LYS polypeptide can be fed to the animal before, after, or simultaneously with the diet. The latter is preferred.

In a particular embodiment, the LYS polypeptide, in the form in which it is added to the feed, or when being included in a feed additive, is well-defined. Well-defined means that the LYS polypeptide preparation is at least 50% pure as determined by Size-exclusion chromatography (see Example 12 of WO 01/58275). In other particular embodiments the LYS polypeptide preparation is at least 60, 70, 80, 85, 88, 90, 92, 94, or at least 95% pure as determined by this method.

A well-defined LYS polypeptide preparation is advantageous. For instance, it is much easier to dose correctly to the feed a LYS polypeptide that is essentially free from interfering or contaminating other lysozymes. The term dose correctly refers in particular to the objective of obtaining consistent and constant results, and the capability of optimizing dosage based upon the desired effect.

For the use in animal feed, however, the LYS polypeptide need not be pure; it may e.g. include other enzymes, in which case it could be termed a LYS polypeptide preparation.

The LYS polypeptide preparation can be (a) added directly to the feed, or (b) it can be used in the production of one or more intermediate compositions such as feed additives or premixes that is subsequently added to the feed (or used in a treatment process). The degree of purity described above refers to the purity of the original LYS polypeptide preparation, whether used according to (a) or (b) above.

Methods of Improving Animal Performance

In an embodiment, the present invention also relates to a method of improving the performance of an animal comprising administering to the animal the animal feed or the animal feed additive of the invention.

In a preferred embodiment, the method of improving the performance of an animal comprises administering to the animal the animal feed or the animal feed additive comprising the LYS polypeptide of the invention. In one embodiment, the LYS polypeptide is selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 24, SEQ ID NO: 27, SEQ ID NO: 30, SEQ ID NO: 33, SEQ ID NO: 36, SEQ ID NO: 39, SEQ ID NO: 42 and SEQ ID NO: 45.

In an embodiment, the present invention also relates to the use of the animal feed or an animal feed additive of the invention for improving the performance of an animal. In another embodiment, the invention relates to the use of one or more lysozymes of the invention for improving the performance of an animal.

In one embodiment, 'improving the performance of an animal' means that there is an increase in body weight gain. In another embodiment, 'improving the performance of an animal' means that there is an improved feed conversion ratio. In a further embodiment, 'improving the performance of an animal' means that there is an increased feed efficiency. In a further embodiment, 'improving the performance of an animal' means that there is an increase in body weight gain and/or an improved feed conversion ratio and/or an increased feed efficiency.

In an embodiment, the animal feed comprises plant based material selected from the group consisting of legumes, cereals, oats, rye, barley, wheat, maize, corn, sorghum, switchgrass, millet, pearl millet, foxtail millet, soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape), rice, beet, cabbage, sugar beet, spinach, quinoa, or pea, in a processed form thereof (such as soybean meal, rapeseed meal) or any combination thereof.

Methods of Preparing an Animal Feed

In an embodiment, the present invention provides a method for preparing an animal feed comprising adding one or more LYS polypeptide of the invention to one or more animal feed ingredients. Animal feed ingredients include, but are not limited to concentrates (as defined herein), forage (as defined herein), enzymes, probiotic, vitamins, minerals and amino acids.

In a preferred embodiment, the method of preparing an animal feed comprises mixing plant based material with the LYS polypeptide of the invention. In one embodiment, the LYS polypeptide is selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 24, SEQ ID NO: 27, SEQ ID NO: 30, SEQ ID NO: 33, SEQ ID NO: 36, SEQ ID NO: 39, SEQ ID NO: 42 and SEQ ID NO: 45.

In an embodiment, the plant based material is selected from the group consisting of legumes, cereals, oats, rye, barley, wheat, maize, corn, sorghum, switchgrass, millet, pearl millet, foxtail millet, soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape), rice, beet, cabbage, sugar beet, spinach, quinoa, or pea, in a processed form thereof (such as soybean meal, rapeseed meal) or any combination thereof.

Preferred Embodiments

Herein follows a list of preferred embodiments of the invention.

1. A composition comprising at least 0.01 mg of LYS polypeptide per kilogram of composition, wherein the polypeptide (a) has lysozyme activity and (b) comprises one or more LAD catalytic domains; wherein the LAD catalytic domain gives a domT score of at least 180 when queried using a Profile Hidden Markov Model (HMM) prepared using SEQ ID NOs: 46 to 187 and hmmbuild software program, suitably wherein the query is carried out using hmmscan software program by the Method of Determining the LAD Catalytic Domain by HMM.

2. The composition of item 1, wherein the polypeptide further comprises one or more lysozyme enhancing domains, wherein the lysozyme enhancing domain gives a domT score of at least 100 when queried using a Profile Hidden Markov Model prepared using SEQ ID NOs: 188 to 316 and hmmbuild software program, and wherein the query is carried out using the hmmscan software program by the Method of Determining the Lysozyme Enhancing Domain.

3. The composition of any of items 1 to 2, wherein
   (a) the LAD catalytic domain comprises one or more motif I: AG[I/L]AT[A/G][I/L][T/V]ES (SEQ ID NO: 317) and/or one or more motif II V[G/A]XLCQXVQXSAYP (SEQ ID NO: 318); and/or
   (b) the lysozyme enhancing domain comprises one or more motif III: [CGY][YF][VIL][ASTP][DG]X[YF][VIT]X[TS][GAN] (SEQ ID NO: 319).

4. A composition comprising one or more LYS polypeptides having lysozyme activity, wherein the polypeptide is dosed at least 0.01 mg of polypeptide per kilogram of composition and is selected from the group consisting of:
   (a) a polypeptide having at least 80% sequence identity to the polypeptide of SEQ ID NO: 3;
   (b) a polypeptide having at least 80% sequence identity to the polypeptide of SEQ ID NO: 6;
   (c) a polypeptide having at least 80% sequence identity to the polypeptide of SEQ ID NO: 9;
   (d) a polypeptide having at least 80% sequence identity to the polypeptide of SEQ ID NO: 12;
   (e) a polypeptide having at least 80% sequence identity to the polypeptide of SEQ ID NO: 15;
   (f) a polypeptide having at least 80% sequence identity to the polypeptide of SEQ ID NO: 18;
   (g) a polypeptide having at least 80% sequence identity to the polypeptide of SEQ ID NO: 21;
   (h) a polypeptide having at least 80% sequence identity to the polypeptide of SEQ ID NO: 24;
   (i) a polypeptide having at least 80% sequence identity to the polypeptide of SEQ ID NO: 27;
   (j) a polypeptide having at least 80% sequence identity to the polypeptide of SEQ ID NO: 30;
   (k) a polypeptide having at least 80% sequence identity to the polypeptide of SEQ ID NO: 33;
   (l) a polypeptide having at least 80% sequence identity to the polypeptide of SEQ ID NO: 36;
   (m) a polypeptide having at least 80% sequence identity to the polypeptide of SEQ ID NO: 39;
   (n) a polypeptide having at least 80% sequence identity to the polypeptide of SEQ ID NO: 42;
   (o) a polypeptide having at least 80% sequence identity to the polypeptide of SEQ ID NO: 45;

(p) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42 and SEQ ID NO: 45, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 positions;

(q) a polypeptide comprising the polypeptide of (a), (b), (c), (d), (e), (f), (g), (h), (i), (j), (k), (l), (m), (n), (o) or (p) and a N-terminal and/or C-terminal His-tag and/or HQ-tag;

(r) a polypeptide comprising the polypeptide of (a), (b), (c), (d), (e), (f), (g), (h), (i), (j), (k), (l), (m), (n), (o) or (p) and a N-terminal and/or C-terminal extension of up to 10 amino acids, e.g. 1, 2, 3, 4, 5, 6, 7, 8, 9 or 10 amino acids; and (s) a fragment of the polypeptide of (a), (b), (c), (d), (e), (f), (g), (h), (i), (j), (k), (l), (m), (n), (o) or (p) having lysozyme activity and having at least 90% of the length of the mature polypeptide.

5. The composition of item 4, wherein the polypeptide is selected from the group consisting of:
   (a) a polypeptide having at least 85% sequence identity to the polypeptide of SEQ ID NO: 3;
   (b) a polypeptide having at least 85% sequence identity to the polypeptide of SEQ ID NO: 6;
   (c) a polypeptide having at least 85% sequence identity to the polypeptide of SEQ ID NO: 9;
   (d) a polypeptide having at least 85% sequence identity to the polypeptide of SEQ ID NO: 12;
   (e) a polypeptide having at least 85% sequence identity to the polypeptide of SEQ ID NO: 15;
   (f) a polypeptide having at least 85% sequence identity to the polypeptide of SEQ ID NO: 18;
   (g) a polypeptide having at least 85% sequence identity to the polypeptide of SEQ ID NO: 21;
   (h) a polypeptide having at least 85% sequence identity to the polypeptide of SEQ ID NO: 24;
   (i) a polypeptide having at least 85% sequence identity to the polypeptide of SEQ ID NO: 27;
   (j) a polypeptide having at least 85% sequence identity to the polypeptide of SEQ ID NO: 30;
   (k) a polypeptide having at least 85% sequence identity to the polypeptide of SEQ ID NO: 33;
   (l) a polypeptide having at least 85% sequence identity to the polypeptide of SEQ ID NO: 36;
   (m) a polypeptide having at least 85% sequence identity to the polypeptide of SEQ ID NO: 39;
   (n) a polypeptide having at least 85% sequence identity to the polypeptide of SEQ ID NO: 42;
   (o) a polypeptide having at least 85% sequence identity to the polypeptide of SEQ ID NO: 45; and
   (p) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42 and SEQ ID NO: 45, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 positions.

6. The composition of item 4, wherein the polypeptide is selected from the group consisting of:
   (a) a polypeptide having at least 90% sequence identity to the polypeptide of SEQ ID NO: 3;
   (b) a polypeptide having at least 90% sequence identity to the polypeptide of SEQ ID NO: 6;
   (c) a polypeptide having at least 90% sequence identity to the polypeptide of SEQ ID NO: 9;
   (d) a polypeptide having at least 90% sequence identity to the polypeptide of SEQ ID NO: 12;
   (e) a polypeptide having at least 90% sequence identity to the polypeptide of SEQ ID NO: 15;
   (f) a polypeptide having at least 90% sequence identity to the polypeptide of SEQ ID NO: 18;
   (g) a polypeptide having at least 90% sequence identity to the polypeptide of SEQ ID NO: 21;
   (h) a polypeptide having at least 90% sequence identity to the polypeptide of SEQ ID NO: 24;
   (i) a polypeptide having at least 90% sequence identity to the polypeptide of SEQ ID NO: 27;
   (j) a polypeptide having at least 90% sequence identity to the polypeptide of SEQ ID NO: 30;
   (k) a polypeptide having at least 90% sequence identity to the polypeptide of SEQ ID NO: 33;
   (l) a polypeptide having at least 90% sequence identity to the polypeptide of SEQ ID NO: 36;
   (m) a polypeptide having at least 90% sequence identity to the polypeptide of SEQ ID NO: 39;
   (n) a polypeptide having at least 90% sequence identity to the polypeptide of SEQ ID NO: 42;
   (o) a polypeptide having at least 90% sequence identity to the polypeptide of SEQ ID NO: 45; and
   (p) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42 and SEQ ID NO: 45, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21 or 22 positions.

7. The composition of item 4, wherein the polypeptide is selected from the group consisting of:
   (a) a polypeptide having at least 95% sequence identity to the polypeptide of SEQ ID NO: 3;
   (b) a polypeptide having at least 95% sequence identity to the polypeptide of SEQ ID NO: 6;
   (c) a polypeptide having at least 95% sequence identity to the polypeptide of SEQ ID NO: 9;
   (d) a polypeptide having at least 95% sequence identity to the polypeptide of SEQ ID NO: 12;
   (e) a polypeptide having at least 95% sequence identity to the polypeptide of SEQ ID NO: 15;
   (f) a polypeptide having at least 95% sequence identity to the polypeptide of SEQ ID NO: 18;
   (g) a polypeptide having at least 95% sequence identity to the polypeptide of SEQ ID NO: 21;
   (h) a polypeptide having at least 95% sequence identity to the polypeptide of SEQ ID NO: 24;

(i) a polypeptide having at least 95% sequence identity to the polypeptide of SEQ ID NO: 27;
(j) a polypeptide having at least 95% sequence identity to the polypeptide of SEQ ID NO: 30;
(k) a polypeptide having at least 95% sequence identity to the polypeptide of SEQ ID NO: 33;
(l) a polypeptide having at least 95% sequence identity to the polypeptide of SEQ ID NO: 36;
(m) a polypeptide having at least 95% sequence identity to the polypeptide of SEQ ID NO: 39;
(n) a polypeptide having at least 95% sequence identity to the polypeptide of SEQ ID NO: 42;
(o) a polypeptide having at least 95% sequence identity to the polypeptide of SEQ ID NO: 45; and
(p) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42 and SEQ ID NO: 45, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10 or 11 positions.

8. The composition of any of items 4 to 7, wherein the LYS polypeptide comprises one or more motifs selected from the group consisting of

```
(a) motif I:
                                   (SEQ ID NO: 317)
AG[I/L]AT[A/G][I/L][T/V]ES;

(b) motif II
                                   (SEQ ID NO: 318)
V[G/A]XLCQXVQXSAYP;
and (c) motif III:
                                   (SEQ ID NO: 319)
[CGY][YF][VIL][ASTP][DG]X[YF][VIT]X[TS][GAN].
```

9. The composition of any of items 1 to 8, wherein the polypeptide is of fungal origin.
10. The composition of any of items 1 to 9, wherein the polypeptide is obtained or obtainable from the taxonomic phylum Ascomycota, preferably the taxonomic subphylum Pezizomycotina.
11. The composition of any of items 1 to 10, wherein the polypeptide comprises or consists of amino acids1 to 226 of SEQ ID NO: 2, amino acids 1 to 226 of SEQ ID NO: 3, amino acids 1 to 226 of SEQ ID NO: 5, amino acids 1 to 226 of SEQ ID NO: 6, amino acids 1 to 223 of SEQ ID NO: 8, amino acids 1 to 223 of SEQ ID NO: 9, amino acids 1 to 304 of SEQ ID NO: 11, amino acids 1 to 304 of SEQ ID NO: 12, amino acids 1 to 228 of SEQ ID NO: 14, amino acids 1 to 228 of SEQ ID NO: 15, amino acids 1 to 230 of SEQ ID NO: 17, amino acids 1 to 230 of SEQ ID NO: 18, amino acids 1 to 230 of SEQ ID NO: 20, amino acids 1 to 230 of SEQ ID NO: 21, amino acids 1 to 232 of SEQ ID NO: 23, amino acids 1 to 232 of SEQ ID NO: 24, amino acids 1 to 228 of SEQ ID NO: 26, amino acids 1 to 228 of SEQ ID NO: 27, amino acids 1 to 228 of SEQ ID NO: 29, amino acids 1 to 228 of SEQ ID NO: 30, amino acids 1 to 226 of SEQ ID NO: 32, amino acids 1 to 226 of SEQ ID NO: 33, amino acids 1 to 225 of SEQ ID NO: 35, amino acids 1 to 225 of SEQ ID NO: 36, amino acids 1 to 225 of SEQ ID NO: 38, amino acids 1 to 225 of SEQ ID NO: 39, amino acids 1 to 304 of SEQ ID NO: 41, amino acids 1 to 304 of SEQ ID NO: 42, amino acids 1 to 227 of SEQ ID NO: 44, or amino acids 1 to 227 of SEQ ID NO: 45.
12. The composition of any of items 1 to 11 further comprising one or more formulating agents.
13. The composition of item 12, wherein the one or more formulating agent is selected from the group consisting of glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, kaolin, maltodextrin, cyclodextrin, wheat, PVA, acetate, phosphate and cellulose or any combination thereof.
14. The composition of any of items 1 to 13 further comprising one or more additional enzymes.
15. The composition of item 14 wherein the one or more additional enzymes is selected from the group consisting of acetyl xylan esterase, alpha-amylase, beta-amylase, arabinofuranosidase, cellobiohydrolases, cellulase, feruloyl esterase, galactanase, alpha-galactosidase, beta-galactosidase, beta-glucanase, beta-glucosidase, lipase, lysophospholipase, lysozyme, mannanase, alpha-mannosidase, beta-mannosidase, phytase, phospholipase A1, phospholipase A2, phospholipase C, phospholipase D, protease, pullulanase, pectinase, pectin lyase, xylanase, beta-xylosidase, or any combination thereof.
16. The composition of any of items 1 to 15 further comprising one or more microbes.
17. The composition of item 16, wherein the one or more microbes is selected from the group consisting of *Bacillus subtilis*, *Bacillus licheniformis*, *Bacillus amyloliquefaciens*, *Bacillus cereus*, *Bacillus pumilus*, *Bacillus polymyxa*, *Bacillus megaterium*, *Bacillus coagulans*, *Bacillus circulans*, *Bifidobacterium bifidum*, *Bifidobacterium animalis*, *Bifidobacterium* sp., *Carnobacterium* sp., *Clostridium butyricum*, *Clostridium* sp., *Enterococcus faecium*, *Enterococcus* sp., *Lactobacillus* sp., *Lactobacillus acidophilus*, *Lactobacillus farciminus*, *Lactobacillus rhamnosus*, *Lactobacillus reuteri*, *Lactobacillus salivarius*, *Lactococcus Lactis*, *Lactococcus* sp., *Leuconostoc* sp., *Megasphaera elsdenii*, *Megasphaera* sp., *Pediococsus acidilactici*, *Pediococcus* sp., *Propionibacterium thoenii*, *Propionibacterium* sp. and *Streptococcus* sp. or any combination thereof.
18. The composition of any of items 1 to 17 further comprising one or more components selected from the list consisting of:
one or more vitamins;
one or more minerals;
one or more amino acids;
one or more phytogenics;
one or more prebiotics;
one or more organic acids; and
one or more other feed ingredients.
19. A granule comprising the composition of any of items 1 to 18.
20. The granule of item 19 wherein the granule is coated.
21. The granule of item 20 wherein the coating comprises a salt and/or wax and/or a flour.

22. An animal feed additive comprising the composition of any of items 1 to 18 or the granule of any of items 19 to 21.
23. An animal feed comprising plant based material and the composition of any of items 1 to 18, the granule of any of items 19 to 21 or the animal feed additive of item 22.
24. The animal feed of item 23, wherein the plant based material is selected from the group consisting of legumes, cereals, oats, rye, barley, wheat, maize, corn, sorghum, switchgrass, millet, pearl millet, foxtail millet, soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape), rice, beet, cabbage, sugar beet, spinach, quinoa, or pea, in a processed form thereof (such as soybean meal, rapeseed meal) or any combination thereof.
25. A pelleted animal feed comprising plant based material and the composition of any of items 1 to 18, the granule of any of items 19 to 21 or the animal feed additive of item 22.
26. The pelleted animal feed of item 25, wherein the plant based material is selected from the group consisting of legumes, cereals, oats, rye, barley, wheat, maize, corn, sorghum, switchgrass, millet, pearl millet, foxtail millet, soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape), rice, beet, cabbage, sugar beet, spinach, quinoa, or pea, in a processed form thereof (such as soybean meal, rapeseed meal) or any combination thereof.
27. A liquid formulation comprising the composition of any of items 1 to 18.
28. The liquid formulation of item 27, wherein the LYS polypeptide is dosed between 0.01% to 25% w/w of liquid formulation, preferably 0.05% to 20% w/w LYS polypeptide, more preferably 0.2% to 15% w/w LYS polypeptide, more preferably 0.5% to 15% w/w LYS polypeptide or most preferably 1.0% to 10% w/w LYS polypeptide.
29. The liquid formulation of any of items 27 to 28, wherein the formulation further comprises 20% to 80% w/w of polyol.
30. The liquid formulation of item 29, wherein the polyol is selected from the group consisting of glycerol, sorbitol, propylene glycol (MPG), ethylene glycol, diethylene glycol, triethylene glycol, 1, 2-propylene glycol or 1, 3-propylene glycol, dipropylene glycol, polyethylene glycol (PEG) having an average molecular weight below about 600 and polypropylene glycol (PPG) having an average molecular weight below about 600 or any combination thereof.
31. The liquid formulation of any of items 27 to 30, wherein the formulation further comprises 0.01% to 2.0% w/w preservative.
32. The liquid formulation of item 31, wherein the preservative is selected from the group consisting of sodium sorbate, potassium sorbate, sodium benzoate and potassium benzoate or any combination thereof.
33. The liquid formulation of any of items 27 to 32 further comprising one or more components selected from the list consisting of:
one or more enzymes;
one or more microbes;
one or more vitamins;
one or more minerals;
one or more amino acids;
one or more phytogenics;
one or more prebiotics;
one or more organic acids; and
one or more other feed ingredients.
34. A method of preparing an animal feed comprising applying the liquid formulation of any of items 27 to 33 onto plant based material.
35. The method of item 34, wherein the liquid formulation is applied via a spray.
36. The method of any of items 34 to 35, wherein the plant based material is selected from the group consisting of legumes, cereals, oats, rye, barley, wheat, maize, corn, sorghum, switchgrass, millet, pearl millet, foxtail millet, soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape), rice, beet, cabbage, sugar beet, spinach, quinoa, or pea, in a processed form thereof (such as soybean meal, rapeseed meal) or any combination thereof.
37. The method of any of items 34 to 36, wherein the plant based material is in pelleted form.
38. A pelleted animal feed prepared using the method of any of items 34 to 37.
39. A method of improving one or more performance parameters of an animal comprising administering to one or more animals the composition of any of items 1 to 18, the granule of any of items 19 to 21, the animal feed additive of item 22, the animal feed of any of items 23 to 24, the pelleted animal feed of any of items 25 to 26 or 38 or the liquid formulation of any of items 27 to 33.
40. The method of item 39 wherein the performance parameter is selected from the list consisting of body weight gain (BWG), European Production Efficiency Factor (EPEF) and Feed Conversion Ratio (FCR) or any combination thereof.
41. A method of preparing an animal feed, comprising mixing the composition of any of items 1 to 18, the granule of any of items 19 to 21, the animal feed additive of item 22, the animal feed of any of items 23 to 24, the pelleted animal feed of any of items 25 to 26 or 38 or the liquid formulation of any of items 27 to 33 with plant based material.
42. The method of item 41, wherein the plant based material is selected from the group consisting of legumes, cereals, oats, rye, barley, wheat, maize, corn, sorghum, switchgrass, millet, pearl millet, foxtail millet, soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape), rice, beet, cabbage, sugar beet, spinach, quinoa, or pea, in a processed form thereof (such as soybean meal, rapeseed meal) or any combination thereof.
43. Use of composition of any of items 1 to 18, the granule of any of items 19 to 21, the animal feed additive of item 22, the animal feed of any of items 23 to 24, the pelleted animal feed of any of items 25 to 26 or 38 or the liquid formulation of any of items 27 to 33:
in animal feed;
in animal feed additives;
in the preparation of a composition for use in animal feed;
for improving the nutritional value of an animal feed;

for increasing digestibility of the animal feed; and/or for improving one or more performance parameters in an animal.

44. An isolated polypeptide having lysozyme activity, selected from the group consisting of:
   (a) a polypeptide having at least 95%, e.g., at least 96%, at least 97%, at least 98%, at least 99%, or 100% sequence identity to the polypeptide of SEQ ID NO: 3;
   (b) a polypeptide having at least 94%, e.g., at least 95%, at least 96%, at least 97%, at least 98%, at least 99%, or 100% sequence identity to the polypeptide of SEQ ID NO: 6;
   (C) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 9;
   (d) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 12;
   (e) a polypeptide having at least 87%, e.g., at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 15;
   (f) a polypeptide having at least 81%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 18;
   (g) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 21;
   (h) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 24;
   (i) a polypeptide having at least 87%, e.g., at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 27;
   (j) a polypeptide having at least 96.2%, e.g., at least 97%, at least 97.5%, at least 98%, at least 98.5%, at least 99%, or 100% sequence identity to the polypeptide of SEQ ID NO: 30;
   (k) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 33;
   (l) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 36;
   (m) a polypeptide having at least 81%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 39;
   (n) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 42;
   (o) a variant of the polypeptide of SEQ ID NO: 3, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10 or 11 positions;
   (p) a variant of the polypeptide of SEQ ID NO: 6, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12 or 13 positions;
   (q) a variant of the polypeptide selected from the group consisting of SEQ ID NO: 9 and SEQ ID NO: 36, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43 or 44 positions;
   (r) a variant of the polypeptide selected from the group consisting of SEQ ID NO: 12, SEQ ID NO: 21, SEQ ID NO: 24, SEQ ID NO: 33 and SEQ ID NO: 42, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 positions;
   (s) a variant of the polypeptide selected from the group consisting of SEQ ID NO: 15 and SEQ ID NO: 27, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28 or 29 positions;
   (t) a variant of the polypeptide selected from the group consisting of SEQ ID NO: 18 and SEQ ID NO: 39, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41 or 42 positions;
(u) a variant of the polypeptide of SEQ ID NO: 30, wherein the variant has lysozyme activity and comprises one or more amino acid substitutions, and/or one or more amino acid deletions, and/or one or more amino acid insertions or any combination thereof in 1, 2, 3, 4, 5, 6, 7 or 8 positions;
(v) a polypeptide comprising the polypeptide of (a), (b), (c), (d), (e), (f), (g), (h), (i), (j), (k), (l), (m), (n), (o), (p), (q), (r), (s), (t) or (u) and a N-terminal and/or C-terminal His-tag and/or HQ-tag;
(w) a polypeptide comprising the polypeptide of (a), (b), (c), (d), (e), (f), (g), (h), (i), (j), (k), (l), (m), (n), (o), (p), (q), (r), (s), (t) or (u) and a N-terminal and/or C-terminal extension of up to 10 amino acids, e.g. 1, 2, 3, 4, 5, 6, 7, 8, 9 or 10 amino acids; and
(x) a fragment of the polypeptide of (a), (b), (c), (d), (e), (f), (g), (h), (i), (j), (k), (l), (m), (n), (o), (p), (q), (r), (s), (t) or (u) having lysozyme activity and having at least 90% of the length of the mature polypeptide.

45. The polypeptide according to item 44, wherein the polypeptide comprises or consists of amino acids 1 to 316 of SEQ ID NO: 2, amino acids 1 to 316 of SEQ ID NO: 3, amino acids 1 to 322 of SEQ ID NO: 4, amino acids 1 to 318 of SEQ ID NO: 6, amino acids 1 to 318 of SEQ ID NO: 7, amino acids 1 to 326 of SEQ ID NO: 8, amino acids 1 to 316 of SEQ ID NO: 10, amino acids 1 to 316 of SEQ ID NO: 11, amino acids 1 to 324 of SEQ ID NO: 12, amino acids 1 to 316 of SEQ ID NO: 14, amino acids 1 to 316 of SEQ ID NO: 15, amino acids 1 to 324 of SEQ ID NO: 16, amino acids 1 to 316 of SEQ ID NO: 18, amino acids 1 to 316 of SEQ ID NO: 19, amino acids 1 to 324 of SEQ ID NO: 20, amino acids 1 to 316 of SEQ ID NO: 22, amino acids 1 to 316 of SEQ ID NO: 23, amino acids 1 to 324 of SEQ ID NO: 24, amino acids 1 to 516 of SEQ ID NO: 26, amino acids 1 to 516 of SEQ ID NO: 27, amino acids 1 to 524 of SEQ ID NO: 28, amino acids 1 to 317 of SEQ ID NO: 30, amino acids 1 to 317 of SEQ ID NO: 31, amino acids 1 to 325 of SEQ ID NO: 32, amino acids 1 to 316 of SEQ ID NO: 34, amino acids 1 to 316 of SEQ ID NO: 35, amino acids 1 to 324 of SEQ ID NO: 36, amino acids 1 to 316 of SEQ ID NO: 38, amino acids 1 to 316 of SEQ ID NO: 39 or amino acids 1 to 324 of SEQ ID NO: 40.
46. A polynucleotide encoding the polypeptide of any of items 44 to 45.
47. A nucleic acid construct or expression vector comprising the polynucleotide of item 46 operably linked to one or more control sequences that direct the production of the polypeptide in an expression host.
48. A recombinant host cell comprising the polynucleotide of item 46 operably linked to one or more control sequences that direct the production of the polypeptide.
49. The recombinant host cell of item 48, wherein the host is a filamentous fungus, such as *Aspergillus*, *Trichoderma* or *Fusarium*, or a yeast, such as *Pichia* or *Saccharomyces*.
50. The recombinant host cell of item 49, wherein the host is an *Aspergillus*, such as *Aspergillus awamori*, *Aspergillus foetidus*, *Aspergillus japonicus*, *Aspergillus nidulans*, *Aspergillus niger* or *Aspergillus oryzae*.
51. The recombinant host cell of item 49, wherein the host is a *Trichoderma*, such as *Trichoderma harzianum*, *Trichoderma koningii*, *Trichoderma longibrachiatum*, *Trichoderma reesei* or *Trichoderma viride*.
52. The recombinant host cell of item 48, wherein the host is a *Bacillus* such as *Bacillus alkalophilus*, *Bacillus amyloliquefaciens*, *Bacillus brevis*, *Bacillus circulans*, *Bacillus clausii*, *Bacillus coagulans*, *Bacillus firmus*, *Geobacillus stearothermophilus*, *Bacillus lautus*, *Bacillus lentus*, *Bacillus licheniformis*, *Bacillus megaterium*, *Bacillus pumilus*, *Bacillus stearothermophilus*, *Bacillus subtilis*, or *Bacillus thuringiensis*.
53. A method of producing the polypeptide of any of items 44 to 45, comprising:
   (a) cultivating a cell, which in its wild-type form produces the polypeptide, under conditions conductive for production of the polypeptide; and
   (b) recovering the polypeptide.
54. A method of producing the polypeptide of any of items 44 to 45, comprising:
   (a) cultivating the recombinant host cell of any of items 48 to 52 under conditions conducive for production of the polypeptide; and
   (b) recovering the polypeptide.
55. A transgenic plant, plant part or plant cell transformed with a polynucleotide encoding the polypeptide of any of items 44 to 45.
56. A whole broth formulation or cell culture composition comprising a polypeptide of any of items 44 to 45.

The present invention is further described by the following examples that should not be construed as limiting the scope of the invention.

Examples

Strains

*Escherichia coli* Top-10 strain purchased from Invitrogen (Life Technologies, Carlsbad, CA, USA) was used to propagate our expression vectors encoding for LYS polypeptides.

*Aspergillus oryzae* strain MT3568 was used for heterologous expression of the LYS polypeptide encoding sequences. *A. oryzae* MT3568 is an amdS (acetamidase) disrupted gene derivative of *Aspergillus oryzae* JaL355 (WO 2002/40694) in which pyrG auxotrophy was restored by disrupting the *A. oryzae* acetamidase (amdS) gene with the pyrG gene.

The fungal strain NN044175 was isolated from soil samples collected from China, in 1998 by the dilution plate method with PDA medium, pH7, 25 C. It was then purified by transferring a single conidium onto a PDA agar plate. The strain NN044175 was identified as *Penicillium simplicissimum*, based on both morphological characteristics and ITS rDNA sequence.

The fungal strain NN053742 was isolated from a soil sample collected from Hubei province, China, in 2011 by the dilution plate method with PDA medium, at pH3, 25 C. It was then purified by transferring a single conidium onto a PDA agar plate. The strain NN053742 was identified as *Penicillium vasconiae*, based on both morphological characteristics and ITS rDNA sequence.

The fungal strain NN058285 was isolated from soil samples collected from Guizhou Province, China, in 2014 by the dilution plate method with PDA medium pH3. It was then purified by transferring a single conidium onto a PDA agar plate. The strain NN058285 was identified as *Talaromyces proteolyticus*, based on both morphological characteristics and ITS rDNA sequence.

The fungal strain NN053333 was isolated from soil samples collected from Hunan province, China, in 2010 by the dilution plate method with PDA medium, pH7, 25 C. It was then purified by transferring a single conidium onto a PDA agar plate. The strain NN053333 was identified as *Aspergillus* sp. XZ2668, based on both morphological characteristics and ITS rDNA sequence.

The fungal strain NN058605 was from CBS with access number as CBS100492. The strain NN058605 was identified as *Penicillium antarcticum*, based on both morphological characteristics and ITS rDNA sequence.

The fungal strain NN047528 was isolated from soil samples collected from China, in 1998 by the dilution plate method with YG medium, pH7, 37C. It was then purified by transferring a single conidium onto a PDA agar plate. The strain NN047528 was identified as *Ovatospora brasiliensis*, based on both morphological characteristics and ITS rDNA sequence.

The fungal strain NN054749 was isolated from soil samples collected from Tibet, China, in 2012 by the dilution plate method with PDA medium, pH7, 10C. It was then purified by transferring a single conidium onto a PDA agar plate. The strain NN054749 was identified as *Penicillium wellingtonense*, based on both morphological characteristics and ITS rDNA sequence.

The fungal strain NN054129 was isolated from soil samples collected from Gotland, Sweden in 2011 by the dilution plate method with Water agar, 24C. It was then purified by transferring a single conidium onto a PDA agar plate. The strain NN054129 was identified as *Penicillium roseopurpureum*, based on both morphological characteristics and ITS rDNA sequence.

The fungal strain NN058650 was isolated from soil samples collected from Guizhou Province, China, in 2014 by the dilution plate method with PDA medium pH3. It was then purified by transferring a single conidium onto a PDA agar plate. The strain NN058650 was identified as *Penicillium virgatum*, based on both morphological characteristics and ITS rDNA sequence.

The fungal strain NN046949 was isolated from soil samples collected from China, in 1998 by the dilution plate method with YG medium, pH7, 37C. It was then purified by transferring a single conidium onto a PDA agar plate. The strain NN046949 was identified as *Aspergillus niveus*, based on both morphological characteristics and ITS rDNA sequence.

The fungal strain NN057921 was obtained through a collaboration with Professor Cai Lei in Institute of Microbiology, CAS, in 2014. The strain was collected from China. It was identified as *Chaetomium* sp. ZY369, based on both morphological characteristics and ITS rDNA sequence.

The fungal strain NN058427 was isolated from soil samples collected from Guizhou Province, China, in 2014 by the dilution plate method with PDA medium pH3, 25C. It was then purified by transferring a single conidium onto a PDA agar plate. The strain N NN058427 was identified as *Talaromyces atricola*, based on both morphological characteristics and ITS rDNA sequence.

The fungal strain NN053773 was obtained through a collaboration with Institute of Microbiology, CAS, in 2011. The strain was collected from China and isolated by the dilution plate method with PDA medium pH7, 10C. It was then purified by transferring a single conidium onto a PDA agar plate. The strain NN053773 was identified as *Trichocladium asperum*, based on both morphological characteristics and ITS rDNA sequence.

The fungal strain NN058086 was isolated from soil samples collected from Guizhou Province, China, in 2014 by the dilution plate method with PDA medium pH3, 25C. It was then purified by transferring a single conidium onto a PDA agar plate. The strain NN058086 was identified as *Metarhizium carneum*, based on both morphological characteristics and ITS rDNA sequence.

Strain *Thielavia terrestris* strain NRRL 8126 was purchased ATCC, and inoculated onto a PDA plate and incubated for 7 days at 37° C. in the darkness. Mycelia and spores from the plate were inoculated into 500 ml shake flasks containing 100 mls of YPG medium. The flasks were incubated for 6 days at 37° C. with shaking at 150 rpm.

Media and Solutions

DAP4C-1 medium was composed of 0.5 g yeast extract, 10 g maltose, 20 g dextrose, 11 g magnesium sulphate heptahydrate, 1 g dipotassium phosphate, 2 g citric acid monohydrate, 5.2 g potassium phosphate tribasic monohydrate, 1 mL Dowfax 63N10 (antifoaming agent), 2.5 g calcium carbonate, supplemented with 1 mL KU6 metal solution, and deionised water to 1000 mL.

KU6 metal solution was composed of 6.8 g $ZnCl_2$, 2.5 g $CuSO_4·5H_2O$, 0.13 g $NiCl_2$, 13.9 g $FeSO_4·7H_2O$, 8.45 g $MnSO_4·H_2O$, 3 g $C_6H_8O_7·H_2O$, and deionised water to 1000 mL.

YP 2% glucose medium was composed of 10 g yeast extract, 20 g Bacto-peptone, 20 g glucose, and deionised water to 1000 mL.

LB plates were composed of 10 g of Bacto-tryptone, 5 g of yeast extract, 10 g of sodium chloride, 15 g of Bacto-agar, and deionised water to 1000 mL.

LB medium was composed of 10 g of Bacto-tryptone, 5 g of yeast extract, and 10 g of sodium chloride, and deionised water to 1000 mL.

COVE-Sucrose-T plates were composed of 342 g of sucrose, 20 g of agar powder, 20 mL of COVE salt solution, and deionised water to 1000 mL. The medium was sterilized by autoclaving at 15 psi for 15 minutes (Bacteriological Analytical Manual, 8th Edition, Revision A, 1998). The medium was cooled to 60° C. and 10 mM acetamide, Triton X-100 (50 µL/500 mL) were added.

COVE-N-Agar tubes were composed of 218 g Sorbitol, 10 g Dextrose, 2.02 g $KNO_3$, 25 g agar, 50 mL Cove salt solution, and deionised water up to 1000 mL.

COVE salt solution was composed of 26 g of $MgSO_4·7H_2O$, 26 g of KCL, 26 g of $KH_2PO_4$, 50 mL of COVE trace metal solution, and deionised water to 1000 mL.

COVE trace metal solution was composed of 0.04 g of $Na_2B_4O_7·10H_2O$, 0.4 g of $CuSO_4·5H_2O$, 1.2 g of $FeSO_4·7H_2O$, 0.7 g of $MnSO_4·H_2O$, 0.8 g of $Na_2MoO_4·2H_2O$, 10 g of $ZnSO_4·7H_2O$, and deionised water to 1000 mL. YPM medium contained 1% of Yeast extract, 2% of Peptone and 2% of Maltose.

Example 1: Determination of Lysozyme Activity Using Reducing Ends Assay

The LYS polypeptide was diluted in phosphate buffer (5 mM citrate, 5 mM $K_2HPO_4$, 0.01% TritonX-100, pH 5.0) to 50 µg/mL in polypropylene tubes. The diluted LYS polypeptide was further diluted in a 96-well polypropylene microtiter plate to a concentration of 5.0 or 0.7 µg/mL in phosphate buffer (5 mM citrate, 5 mM $K_2HPO_4$, 0.01% TritonX-100, pH 5.0). In a polypropylene deepwell plate 50 µL of the LYS polypeptide dilution was mixed with 450 µL 1% *Micrococcus lysodeikticus* solution (lyophilized *Micrococcus lysodeikticus* ATCC No. 4698 (Sigma M3770) in milli-Q water) and incubated at 40° C. with shaking (500 rpm) for 45 min. After incubation the deepwell plate was centrifuged (4000 g, 5 min) to pellet insoluble material and 100 μL of the supernatant was mixed with 50 μL 3.2M HCl in a 96-well PCR plate and incubated at 95° C. for 80 min. 50 μL of 3.5 M NaOH was added to each well of the PCR plate, and 150 μL of each sample was transferred to a new PCR plate containing 75 μL/well 4-hydroxybenzhydrazide solution in K—Na tartrate/NaOH buffer (50 g/L K—Na tartrate+20 g/L NaOH). The plate was incubated at 95° C. for 10 min before 100 μL/sample was transferred to a clear flat-bottomed microtiter plate for optical density (OD) measurement at 405 nm. OD measurements were performed on three times diluted samples (50 μL sample diluted in 100 μL in Milli-Q water).

Example 2: Determination of Lysozyme Activity Using OD Drop Assay

Freeze-dried *Micrococcus lysodeikticus* ATCC No. 4698 (Sigma) was washed and suspended in 60 mM $KH_2PO_4$ buffer at pH6.0 with final concentration of 1% (w/v) as substrate stock. The concentration of the strain was adjusted by adding citric acid-$Na_2HPO_4$ buffer until OD450 reach approximately 1.

Citric acid-$Na_2HPO_4$ pH4 buffer were prepared by adding 61.45 ml 0.1M citric acid and 38.55 ml 0.2M $Na_2HPO_4$ for pH4. 20 μL enzyme at 50 μg/mL and 200 μL of diluted bacterial strain solution in citric acid-$Na_2HPO_4$ buffer at pH4 were added to a 96 well plate, mixed and the OD450 was read. Then the plate was incubated at 37° C., 300 rpm for 1 hour and the OD450 was read. The OD difference between the 1 hour time point to the initial read showed the OD drop activity for the LYS polypeptide. Blank was set by adding 20 ul MQ water or the corresponding buffer, and each sample was measured in triplicate.

Example 3: Genomic DNA Extraction

*Penicillium simplicissimum* strain NN044175 was inoculated onto a PDA plate and incubated for 7 days at 25° C. in the darkness. Several mycelia-PDA plugs were inoculated into 500 ml shake flasks containing 100 ml of YPG medium. The flasks were incubated for 9 days at 25° C. with shaking at 160 rpm.

*Penicillium vasconiae* strain NN053742 was inoculated onto a PDA plate and incubated for 7 days at 25° C. in the darkness. Several mycelia-PDA plugs were inoculated into 500 ml shake flasks containing 100 ml of YPG medium. The flasks were incubated for 3 days at 25° C. with shaking at 160 rpm.

*Talaromyces proteolyticus* strain NN058285 was inoculated onto a PDA plate and incubated for 7 days at 25° C. in the darkness. Several mycelia-PDA plugs were inoculated into 500 ml shake flasks containing 100 ml of YPG medium. The flasks were incubated for 4 days at 25° C. with shaking at 160 rpm.

*Aspergillus* sp. strain NN053333 was inoculated onto a PDA plate and incubated for 7 days at 25° C. in the darkness. Several mycelia-PDA plugs were inoculated into 500 ml shake flasks containing 100 ml of YPG medium. The flasks were incubated for 5 days at 25° C. with shaking at 160 rpm.

*Penicillium antarcticum* strain NN058605 was inoculated onto a PDA plate and incubated for 7 days at 25° C. in the darkness. Several mycelia-PDA plugs were inoculated into 500 ml shake flasks containing 100 ml of YPG medium. The flasks were incubated for 4 days at 25° C. with shaking at 160 rpm.

*Ovatospora brasiliensis* strain NN047528 was inoculated onto a PDA plate and incubated for 7 days at 37° C. in the darkness. Several mycelia-PDA plugs were inoculated into 500 ml shake flasks containing 100 ml of YPG medium. The flasks were incubated for 2 days at 37° C. with shaking at 160 rpm.

*Penicillium wellingtonense* strain NN054749 was inoculated onto a PDA plate and incubated for 7 days at 25° C. in the darkness. Several mycelia-PDA plugs were inoculated into 500 ml shake flasks containing 100 ml of YPG medium. The flasks were incubated for 11 days at 25° C. with shaking at 160 rpm.

*Penicillium roseopurpureum* strain NN054129 was inoculated onto a PDA plate and incubated for 7 days at 25° C. in the darkness. Several mycelia-PDA plugs were inoculated into 500 ml shake flasks containing 100 ml of YPG medium. The flasks were incubated for 4 days at 25° C. with shaking at 160 rpm.

*Penicillium virgatum* strain NN058650 was inoculated onto a PDA plate and incubated for 7 days at 25° C. in the darkness. Several mycelia-PDA plugs were inoculated into 500 ml shake flasks containing 100 ml of YPG medium. The flasks were incubated for 4 days at 25° C. with shaking at 160 rpm.

*Aspergillus niveus* strain NN046949 was inoculated onto a PDA plate and incubated for 7 days at 25° C. in the darkness. Several mycelia-PDA plugs were inoculated into 500 ml shake flasks containing 100 ml of YPG medium. The flasks were incubated for 3 days at 25° C. with shaking at 160 rpm.

*Chaetomium* sp. strain NN057921 were inoculated onto a PDA plate and incubated for 7 days at 37° C. in the darkness. Several mycelia-PDA plugs were inoculated into 500 ml shake flasks containing 100 ml of YPG medium. The flasks were incubated for 8 days at 37° C. with shaking at 160 rpm.

The mycelia of *Penicillium antarcticum* strain NN058605 were collected by filtration through MIRACLOTH® (Calbiochem, La Jolla, CA, USA) and frozen under liquid nitrogen. Frozen mycelia were ground, by a mortar and a pestle, to a fine powder, and genomic DNA was isolated using MP Fast DNA spin kit for soil (MP Biomedicals, Santa Ana, California, USA) following the manufacturer's instruction.

*Talaromyces atricola* strain NN058427 was inoculated onto a PDA plate and incubated for 7 days at 25° C. in the darkness. Several mycelia-PDA plugs were inoculated into 500 ml shake flasks containing 100 ml of YPG medium. The flasks were incubated for 3 days at 25° C. with shaking at 160 rpm.

*Trichocladium asperum* strain NN053773 was inoculated onto a PDA plate and incubated for 7 days at 15° C. in the darkness. Several mycelia-PDA plugs were inoculated into 500 ml shake flasks containing 100 ml of YPG medium. The flasks were incubated for 4 days at 15° C. with shaking at 160 rpm.

*Metarhizium carneum* strain NN058086 was inoculated onto a PDA plate and incubated for 7 days at 25° C. in the darkness. Several mycelia-PDA plugs were inoculated into 500 ml shake flasks containing 100 ml of YPG medium. The flasks were incubated for 4 days at 25° C. with shaking at 160 rpm.

The mycelia of *Thielavia terrestris* were collected by filtration through MIRACLOTH® (Calbiochem, La Jolla, CA, USA) and frozen under liquid nitrogen. Frozen mycelia were ground, by a mortar and a pestle, to a fine powder, and genomic DNA was isolated using DNeasy® Plant Maxi Kit (24) (QIAGEN GmbH, Hilden, Germany) following the manufacturer's instructions.

The mycelia of all the other strains were collected by filtration through MIRACLOTH® and frozen under liquid nitrogen. Frozen mycelia were ground, by a mortar and a pestle, to a fine powder, and genomic DNA was isolated using DNeasy® Plant Maxi Kit (24) (QIAGEN GmbH, Hilden, Germany) following the manufacturer's instruction.

Example 4: Genome Sequencing, Assembly and Annotation

The extracted genomic DNA samples of *Penicillium simplicissimum* strain NN044175 were delivered to Exiqon A/S (Denmark) for genome sequencing using an ILLUMINA® MiSeq System (Illumina, Inc., San Diego, CA, USA). The raw reads were assembled at Novozymes Denmark using program Idba (Peng, Yu et al., 2010, *Research in Computational Molecular Biology*, 6044:426-440. Springer Berlin Heidelberg).

The extracted genomic DNA samples of *Talaromyces proteolyticus* strain NN058285, *Penicillium antarcticum* strain NN058605, *Penicillium roseopurpureum* strain NN054129, *Penicillium virgatum* strain NN058650, *Aspergillus niveus* strain NN046949, *Metarhizium carneum* strain NN058086 were delivered to Exiqon A/S for genome sequencing using an ILLUMINA® MiSeq System. The raw reads were assembled at Novozymes Denmark using program Spades (Anton Bankevich et al., 2012, *Journal of Computational Biology*, 19(5): 455-477).

The extracted genomic DNA samples of *Penicillium vasconiae* strain NN053742, *Ovatospora brasiliensis* strain NN047528, *Trichocladium asperum* strain NN053773 were delivered to Fasteris (Switzerland) for genome sequencing using an ILLUMINA® HiSeq 2000 System (Illumina, Inc., San Diego, CA, USA). The raw reads were assembled at Novozymes Denmark using program Idba.

The extracted genomic DNA samples of *Aspergillus* sp. strain NN053333, *Chaetomium* sp. strain NN057921 and *Talaromyces atricola* strain NN058427 were delivered to Novozymes Davis (USA) for genome sequencing using an ILLUMINA® MiSeq System. The raw reads were assembled at Novozymes Denmark using program Spades.

The extracted genomic DNA samples of *Penicillium wellingtonense* strain NN054749 were delivered to Novozymes Davis for genome sequencing using an ILLUMINA® MiSeq System. The raw reads were assembled at Novozymes Denmark using program Idba.

The assembled sequences were analyzed using standard bioinformatics methods for gene identification and function prediction. GeneMark-ES fungal version (Ter-Hovhannisyan V et al., 2008, *Genome Research* 18(12): 1979-1990) was used for gene prediction. Blastall version 2.2.10 (Altschul et al., 1990, *Journal of Molecular Biology*. 215(3): 403-410, ftp://ftp.ncbi.nlm.nih.gov/blast/executables/release/2.2.10/) and HMMER version 2.1.1 (National Center for Biotechnology Information (NCBI), Bethesda, MD, USA) were used to predict function based on structural homology. The NZ5 family was identified directly by analysis of the Blast results. The Agene program (Munch and Krogh, 2006, *BMC Bioinformatics* 7: 263) and SignalP program (Nielsen et al., 1997, *Protein Engineering* 10: 1-6) were used to identify start codons. SignalP program was further used to predict signal peptides. Pepstats (Rice et al., 2000, *Trends in Genetics*. 16(6): 276-277) was used to predict isoelectric points and molecular weights.

Example 5: Cloning, Expression and Fermentation of Fungal NZ5 Genes (SEQ ID NO: 1, 4, 7, 10, 13, 16, 19, 22, 25, 28, 31, 34, 37 and 40)

Fourteen fungal LYS wild type genes, LYS_Pesi (SEQ ID NO:1), LYS_Pv (SEQ ID NO:4), LYS_Tapr (SEQ ID NO:7), LYS_Asp2668 (SEQ ID NO:10), LYS_Pean (SEQ ID NO:13), LYS_chbr (SEQ ID NO:16), LYS_Pewe (SEQ ID NO:19), LYS_Pr (SEQ ID NO:22), LYS_Pevir (SEQ ID NO:25), LYS_asni (SEQ ID NO:28), LYS_ch369 (SEQ ID NO: 31), LYS_Taat (SEQ ID NO:34), LYS_Tras (SEQ ID NO: 37), LYS_Meca2 (SEQ ID NO:40) were cloned from *Penicillium simplicissimum* strain NN044175, *Penicillium vasconiae* strain NN053742, *Talaromyces proteolyticus* strain NN058285, *Aspergillus* sp. strain NN053333, *Penicillium antarcticum* strain NN058605, *Ovatospora brasiliensis* strain NN047528, *Penicillium wellingtonense* strain NN054749, *Penicillium roseopurpureum* strain NN054129, *Penicillium virgatum* strain NN058650, *Aspergillus niveus* strain NN046949, *Chaetomium* sp. strain NN057921, *Talaromyces atricola* strain NN058427, *Trichocladium asperum* strain NN053773, *Metarhizium carneum* strain NN058086 respectively.

The fungal LYS genes were cloned into an *Aspergillus oryzae* expression vector pCaHj505 as described in WO2013029496. The transcription of the LYS coding sequence with the native secretion signal was under the control of an *Aspergillus oryzae* alpha-amylase gene promoter.

The final expression plasmids, p505-LYS_Pesi, p505-LYS_Pv, p505-LYS_Tapr, p505-LYS_Asp2668, p505-LYS_Pean, p505-LYS_chbr, p505-LYS_Pewe, p505-LYS_Pr, p505-LYS_Pevir, p505-LYS_asni, p505-LYS_ch369, p505-LYS_Taat, p505-LYS_Tras and p505-LYS_Meca2, were individually transformed into an *Aspergillus oryzae* expression host. The LYS genes were integrated by homologous recombination into the *Aspergillus oryzae* host genome upon transformation. Four transformants of each transformation were selected from the selective media agar plate and inoculated to 3 ml of YPM or Dap4C medium in 24-well plate and incubated at 30° C., 150 rpm. After 3 days incubation, 20 μl of supernatant from each transformant were analyzed on NuPAGE Novex 4-12% Bis-Tris Gel w/MES according to the manufacturer's instructions. The resulting gel was stained with Instant Blue. SDS-PAGE profiles of the cultures showed that all genes were expressed with 1 protein band detected at approximately 28 kDa, 25 kDa, 25 kDa, 35 kDa, 25 kDa, 25 kDa, 25 kDa, 25 kDa, 25 kDa, 25 kDa, 25 kDa, 25 kDa, 25 kDa, 30 kDa. The recombinant *Aspergillus oryzae* strains with the strongest protein band were selected for shaking flask culturing. The recombinant strains were inoculated on slant made of slant medium and incubated at 37C for 6-7 days. When strains were well grown to fully sporulated, they were inoculated to 2 L shaking flasks each containing 400 ml of YPM or DAP4C, 5-6 flasks for each strain. Flasks were shaking at 80 rpm, 30C. Cultures were harvested on day 3 or day 4 and filtered using a 0.22 μm DURAPORE Membrane and were purified as described in example 9.

Example 6: Construction of the Improved Split-Marker *Aspergillus oryzae* Host

An improved *Aspergillus oryzae* host/vector system comparable to the one described in example 5 disclosed in WO 2016026938A1 was constructed. The improvement was made to reduce the size of the transforming DNA by moving the FLPase expression cassette located on PART-11 of the plasmid pDAu724 (see page 34 in WO2016/026938, FIG. 7 and SEQ ID NO:30) to the integration locus amy2 in the genome of the host strain. The cloning of the FLPase expression cassette into pDAu703 (WO2016/026938 page 32 and FIG. 6 and SEQ ID:29) in done by amplification of the FLPase expression cassette from pDAu724 and cloning in between FRT-F3 and the amdS selection marker of pDAu703 to give the plasmid pDAu770 (FIG. 1, SEQ ID NO: 320). The same protocol as described in WO2016/026938 page 33 was used to transform the linearized plasmid pDAu770 into protoplasts of *A. oryzae* strain Jal1338 (disclosed in WO2012/160097). Transformants were selected on AmdS selection plates to obtain strain DAu785. The resulting recombinant host strain DAu785 has a modified amy2 locus comparable to the one in DAU716 (WO2016/026938) with the addition of the FLPase expression cassette (FIG. 2, top panel). The host strain DAu785 is now constitutively expressing the FLPase site specific recombinase allowing the integration at the FRT sites of the transforming DNA in this case the PCR fragments obtained by Overlap Extension PCR reaction (FIG. 2, middle and bottom panels) and described in Example 7.

Example 7: Overlap Extension PCR Cloning (SEQ ID NO: 43)

A PCR amplification of SEQ ID NO: 43 encoding the LYS polypeptide was carried out using Phusion High-Fidelity DNA polymerase (New England Biolabs, BioNordika Denmark A/S, Herlev, Denmark) in a 50 µL volume reaction and the primers disclosed in table 2.

TABLE 2

PCR primers

| Primer* | Primer SEQ ID NO: | Sequence |
|---|---|---|
| KKSC0972-F | 321 | 5'-CTATATACACAACTGGGGATCCACC ATGCAGCTCTCCCTCCTCGT |
| KKSC0972-R | 322 | 5'-TAGAGTCGACCCAGCCGCGCCGGCCA TTACAACCCACCAGCCTGGC |

*-F-forward primer; -R-reverse primer; Bold letters represent coding sequence.

The PCR reaction mix consisted of 10 µL Phusion reaction buffer HF (5×); 1 µL of PCR nucleotide Mix (10 mM); 2 µL forward cloning primers (2.5 mM); 2 µL reverse cloning primers (2.5 mM); 1 µL Phusion High-Fidelity DNA Polymerase #M0530L (2000U/mL); and PCR grade water up to 50 µL. PCR reaction was incubated on a thermocycler T100 (Biorad, Hercules, California, USA) using the following program: initial denaturation of 2 min at 98° C. followed by 30 cycles of 10 sec at 98° C., 2 min at 72° C. and ending up by a final elongation of 10 min at 72° C. The PCR amplicon was purified using AM Pure XP beads system kit (Agencourt, Beverly, Massachusetts, USA) adapted on a Biomek FXp Liquid handler (Beckman Coulter, Brea, California, USA).

pDAu724 plasmid was used as DNA template to amplify two PCR products (F1 and F3) in reactions composed of 10 µL of KAPA polymerase buffer 5×, 1 µL 10 mM KAPA PCR Nucleotide Mix, 1 µL of 10 µM of the appropriate forward primers (SEQ ID NO: 323 for F1 and SEQ ID NO: 325 for F3, table 3), 1 µL of 10 µM of the appropriate reverse primers (SEQ ID NO: 324 for F1 and SEQ ID NO: 326 for F3, table 3), 1 to 10 ng of pDAu724 plasmid, 1 µL of KAPA Biosystems polymerase KK2502 (1unit) and PCR-grade water up to 50 µL.

PCR amplification reactions were carried out on a DYAD® Dual-Block Thermal Cycler (MJ Research Inc., Waltham, MA, USA) programmed for 2 min. at 98° C. and followed by 35 cycles of 10 sec. at 98° C. and 2 min. at 72° C. and one final cycle of 10 min. at 72° C.

Five µl of the PCR reaction were analyzed by 1% agarose gel electrophoresis using TAE buffer where DNA bands of the appropriate size were observed. The remaining PCR reactions were purified using an ILLUSTRA™ GFX™ PCR DNA and Gel Band Purification Kit according to the manufacturer's instructions.

TABLE 3

PCR primers

| Primer | Primer SEQ ID NO: | Sequence |
|---|---|---|
| Forward primer F1 | 323 | GAATTCGAGCTCGGTACCTTGAAGTTC |
| Reverse primer F1 | 324 | GGTGGATCCCCAGTTGTGTATATAGAGGATT |
| Forward primer F3 | 325 | TGCGCGGCGCGGCTGGGTCGACTCTA |
| Reverse primer F3 | 326 | TTCACACAGGAAACAGCTATGACCATG |

Overlap Extension PCR reaction for cloning the LYS polypeptide gene amplified from *Thielavia terrestris* gDNA was composed of 10 µL KAPA polymerase buffer (5×), 1 µL 10 mM KAPA PCR Nucleotide Mix, 50 ng of PCR fragment F1 and equimolar amounts of PCR fragment F3 and LYS polypeptide gene encoding for SEQ ID NO: 45, 1 µl KAPA Biosystems polymerase KK2502 (1unit) and PCR-grade water up to 48 µL. Reaction was incubated on a DYAD® Dual-Block Thermal Cycler (MJ Research Inc., Waltham, MA, USA) using a program composed of 2 min. at 98° C.; followed by 5 cycles each composed of 10 sec. at 98° C., 30 sec. at 68° C., and 5 min. at 72° C. and completed by a final extension of 8 min. at 72° C.

During the OE PCR reaction, annealing between fragment F1 and the LYS polypeptide gene encoding for SEQ ID NO: 45 was ensured by the overlap in SEQ ID NO: 327 included in the forward cloning primer (KKSC0972-F) and annealing between fragment F3 and the LYS polypeptide gene encoding for SEQ ID NO: 45 was ensured by the overlapping SEQ ID NO: 328 included in the reverse cloning primer (KKSC0972-R).

One µL of 10 mM primer SEQ1 and 1 µL of 10 mM primer SEQ4 were added to the OE PCR reaction and the reaction was incubated a second time on a DYAD® Dual-Block Thermal Cycler (MJ Research Inc., Waltham, MA, USA) using a program composed of 2 min at 98° C.; followed by 25 cycles each composed of 10 sec. at 98° C., and 4 min. at 72° C. and completed by a final extension of 10 min. at 72° C.

Five µl of the PCR reaction was analysed by 1% agarose gel electrophoresis using TAE buffer where an DNA band of the appropriate size was observed. The remaining PCR reaction was up-concentrated to 20 μL by heating the tube at 60° C. 10 μL of this reaction was used for *Aspergillus oryzae* DAu785 protoplasts transformation.

```
Primer bind forward SEQ ID NO: 327:
CTATATACACAACTGGGGATCCACC

Primer bind reverse SEQ ID NO: 328:
TAGAGTCGACCCAGCCGCGCCGGCCA
```

Example 8: Preparation of *Aspergillus* protoplasts

Protoplasts of *Aspergillus oryzae* MT3568 were prepared according to WO 95/002043. One hundred μl of protoplasts were mixed with OE PCR fragment KKSC0972 and 250 μL of 60% PEG 4000 (Applichem, Darmstadt, Germany) (polyethylene glycol, molecular weight 4,000), 10 mM CaCl$_2$, and 10 mM Tris-HCl pH 7.5 and gently mixed. The mixtures were incubated at 37° C. for 30 minutes and the protoplasts were spread onto COVE plates for selection. After incubation for 4-7 days at 37° C. spores of four transformants were inoculated into 0.2 mL of YP+2% glucose or DAP4C-1 medium in 96 well microtiter plates. After 4 days cultivation at 30° C., the culture broths were analysed by SDS-PAGE to identify transformants producing the highest amounts of LYS polypeptide.

Spores of the best transformant from the transformation were spread onto COVE plates containing 0.01% TRITON® X-100 in order to isolate single colonies. The spreading was repeated twice in total on COVE plates containing 10 mM sodium nitrate. Spores were then inoculated into 500 mL shake flasks containing 100 mL of YP+2% glucose and incubated for 4 days at 30° C. with shaking at 100 rpm. Culture broths were harvested by filtration using a 0.2 μm filter device and purified as described in Example 9.

Example 9: Purification of LYS Polypeptides

Activity Detection for Purification Procedure

Freeze-dried bacterial strains *Micrococcus lysodeikticus* ATCC No. 4698 (Sigma) and *Exiguobacterium* sp. (isolated from soil) were separately washed and suspended in 60 mM KH$_2$PO$_4$ buffer at pH6.0 with final concentration of 1% (w/v) as substrate stock. Before activity detection, the concentration of substrate was diluted into 0.035% which correlates to OD450 about 0.7 by 60 mM KH2PO4 buffer at pH6.0 or pH 4.0. 10 ul of polypeptide sample (or 5 ul of sample with 5 ul of MQ water if containing high concentration of salt) and 190 ul of 0.035% substrate were added into 96-well plate, and then read OD450. The plate was incubated for 30 or 60 minutes, 300 rpm at room temperature or 37° C. in the thermomixer. The plate was shaked 10 seconds and read OD450 again. The OD drop showed lysozyme activity. Blank is added 10 μl of 60 mM KH$_2$PO$_4$ at pH 6.0 or pH4.0 buffer, and each sample was measured in duplicate if necessary.

Purification of SEQ ID NO: 3

The culture supernatant was firstly precipitated with ammonium sulfate (80% saturation), then dialyzed with 20 mM NaAc at pH4.5. The solution was filtered with 0.45 um filter and then loaded into SP Fast Flow column (GE Healthcare) equilibrated with 20 mM NaAc at pH4.5. A gradient increase of NaCl concentration was applied as elution buffer from zero to 1M, and then the elution fractions and flow-through fraction were collected to detect lysozyme activity. The fractions with lysozyme activity were analyzed by SDS-PAGE, and then concentrated for further evaluation. The protein concentration was determined by Qubit® Protein Assay Kit (Invitrogen, cat Q33212).

Purification of SEQ ID NO: 6

The culture supernatant was firstly precipitated with ammonium sulfate (80% saturation), then the precipitation was added water to adjust conductance to about 140 mS/cm. The solution was filtered with 0.45 um filter and then loaded into HIC High Performance column (GE Healthcare) equilibrated with 20 mM PBS at pH8.0 with 1.2M (NH$_4$)$_2$SO$_4$ added. A gradient decrease of (NH$_4$)$_2$SO$_4$ concentration was applied as elution buffer from 1.2M to zero, and then elution fractions and flow-through fraction were collected to detect lysozyme activity.

The flow-through and Fractions from 1 to 15 were collected and conductance was adjusted to 180 mS/cm, then reloaded into HIC column equilibrated with 20 mM PBS at pH8.0 with 1.8M (NH$_4$)$_2$SO$_4$ added. A gradient decrease of (NH$_4$)$_2$SO$_4$ concentration was applied as elution buffer from 1.8M to zero, and then elution fractions and flow-through fraction were collected to detect lysozyme activity. The fractions with lysozyme activity were analyzed by SDS-PAGE, pooled together, and diafiltrated with 20 mM PBS at pH6.0. The protein concentration was determined by Qubit® Protein Assay Kit (Invitrogen, cat Q33212).

Purification of SEQ ID NO: 9

The culture supernatant was firstly precipitated with ammonium sulfate (80% saturation), then the precipitation was added water to adjust conductance to about 170 mS/cm. The solution was filtered with 0.45 um filter and then loaded into HIC High Performance column (GE Healthcare) equilibrated with 20 mM PBS at pH7.0 with 1.5M (NH$_4$)$_2$SO$_4$ added. A gradient decrease of (NH$_4$)$_2$SO$_4$ concentration was applied as elution buffer from 1.5M to zero, and then elution fractions and flow-through fraction were collected to detect lysozyme activity. The fractions with lysozyme activity were analyzed by SDS-PAGE, pooled together, and diafiltrated with 20 mM PBS at pH6.0. The protein concentration was determined by Qubit® Protein Assay Kit (Invitrogen, cat Q33212).

Purification of SEQ ID NO: 12

The culture supernatant was firstly precipitated with ammonium sulfate (80% saturation), then the precipitation was added water to adjust conductance to about 185 mS/cm. The solution was filtered with 0.45 um filter and then loaded into HIC High Performance column (GE Healthcare) equilibrated with 20 mM PBS at pH6.0 with 1.8M (NH$_4$)$_2$SO$_4$ added. A gradient decrease of (NH$_4$)$_2$SO$_4$ concentration was applied as elution buffer from 1.8M to zero, and then elution fractions and flow-through fraction were collected to detect lysozyme activity. The fractions with lysozyme activity were analyzed by SDS-PAGE, pooled together, and diafiltrated with 20 mM Bis-Tris at pH6.0.

The sample was loaded into a Mono Q column (GE Healthcare) equilibrated with 20 mM Bis-Tris at pH6.0. A gradient increase of NaCl concentration was applied as elution buffer from zero to 1M, and then the elution fractions and flow-through fraction were collected to detect lysozyme activity. The fractions with lysozyme activity were analyzed by SDS-PAGE, and then concentrated for further evaluation. The protein concentration was determined by Qubit® Protein Assay Kit (Invitrogen, cat Q33212).

Purification of SEQ ID NO: 15

The culture supernatant was firstly precipitated with ammonium sulfate (80% saturation), then the precipitation was added water to adjust conductance to about 170 mS/cm. The solution was filtered with 0.45 um filter and then loaded into Phenyl Fast Flow column (GE Healthcare) equilibrated with 20 mM PBS at pH6.0 with 1.5M $(NH_4)_2SO_4$ added. A gradient decrease of $(NH_4)_2SO_4$ concentration was applied as elution buffer from 1.5M to zero, and then elution fractions and flow-through fraction were collected to detect lysozyme activity.

The flow-through and Fractions with lysozyme activity were collected and conductance was adjusted to 190 mS/cm, then reloaded into HIC column equilibrated with 20 mM PBS at pH6.0 with 1.5M $(NH_4)_2SO_4$ added again. A gradient decrease of $(NH_4)_2SO_4$ concentration was applied as elution buffer from 1.5M to zero, and then elution fractions and flow-through fraction were collected to detect lysozyme activity. The fractions with lysozyme activity were analyzed by SDS-PAGE, pooled together, and diafiltrated with 20 mM PBS at pH6.0. The protein concentration was determined by Qubit® Protein Assay Kit (Invitrogen, cat Q33212).

Purification of SEQ ID NO: 18

The culture supernatant from the expression of LYS_chbr (SEQ ID NO:16) was firstly precipitated with ammonium sulfate (80% saturation), then the precipitation was added water to adjust conductance to about 170 mS/cm. The solution was filtered with 0.45 um filter and then loaded into Phenyl Sepharose High Performance column (GE Healthcare) equilibrated with 20 mM PBS at pH6.0 with 1.8M $(NH_4)_2SO_4$ added. A gradient decrease of $(NH_4)_2SO_4$ concentration was applied as elution buffer from 1.8M to zero, and then elution fractions and flow-through fraction were collected to detect lysozyme activity. The fractions with lysozyme activity were analyzed by SDS-PAGE, and fractions were pooled together, and diafiltrated with 20 mM PBS at pH6.0. The protein concentration was determined by Qubit® Protein Assay Kit (Invitrogen, cat Q33212).

Analysis by intact molecular weight (MAXIS II electrospray mass spectrometer (Bruker Daltonik GmbH, Bremen, DE)) showed that the major product corresponded to amino acids 1 to 230 of SEQ ID NO: 18 (detected mass 24128.35 Da, predicted mass 24128.21 Da) with a minor product corresponded to amino acids 4 to 230 of SEQ ID NO: 18 (detected mass 23768.79 Da, predicted mass 23768.16 Da).

Purification of SEQ ID NO: 329

The culture supernatant from the expression of LYS_chbr (SEQ ID NO:16) was firstly precipitated with ammonium sulfate (80% saturation), then dialyzed with 20 mM PBS at pH6.5. The solution was filtered with 0.45 um filter and then loaded into Capto SP column (GE Healthcare) equilibrated with 20 mM PBS at pH6.5. A gradient increase of NaCl concentration was applied as elution buffer from zero to 1M, and then the elution fractions and flow-through fraction were collected to detect lysozyme activity. The fractions with lysozyme activity were analyzed by SDS-PAGE, and then concentrated for further evaluation. The protein concentration was determined by Qubit® Protein Assay Kit (Invitrogen, cat Q33212).

Analysis by N-terminal sequencing (Applied Biosystems Precise Amino Acid Sequencer Model 494) and intact molecular weight (MAXIS II electrospray mass spectrometer (Bruker Daltonik GmbH, Bremen, DE)) showed that the N-terminal LED domain had been cleaved off leaving the LAD catalytic domain and that the molecule had a heterogeneous N-terminal (see table 4). The major product corresponded to residues 85-230 which is disclosed as SEQ ID NO: 329.

TABLE 4

N-terminal and intact molecular weigh determination

| Applied Biosystems N-terminal sequence | Residues of SEQ ID NO: 18 | Intact Molecular Weight | | ID |
|---|---|---|---|---|
| | | M.Wt Calculated | M.Wt. Observed | |
| GNLPGLN | 88-230 | 15167.31 Da | 15167.92 Da | OK |
| GKGNLPG | 86-230 | 15352.54 Da | 15353.04 Da | OK |
| GGKGNLP | 85-230 | 15409.59 Da | 15410.06 Da | OK |

Purification of SEQ ID NO: 21

The culture supernatant was firstly precipitated with ammonium sulfate (80% saturation), then the precipitation was added water to adjust conductance to about 140 mS/cm. The solution was filtered with 0.45 um filter and then loaded into Phenyl Fast Flow column (GE Healthcare) equilibrated with 20 mM NaAc at pH4.5 with 2M NaCl added. A gradient decrease of NaCl concentration was applied as elution buffer from 2M to zero, and then elution fractions and flow-through fraction were collected to detect lysozyme activity.

The flow-through and Fractions with lysozyme activity were collected and conductance was adjusted to 180 mS/cm, then reloaded into HIC column equilibrated with 20 mM NaAc at pH4.5 with 4M NaCl added again. A gradient decrease of NaCl concentration was applied as elution buffer from 4M to zero, and then elution fractions and flow-through fraction were collected to detect lysozyme activity. The fractions with lysozyme activity and unbound sample were analyzed by SDS-PAGE, pooled together, and concentrated. The protein concentration was determined by Qubit® Protein Assay Kit (Invitrogen, cat Q33212).

Purification of SEQ ID NO: 24

The culture supernatant was firstly precipitated with ammonium sulfate (80% saturation), then the precipitation was added water to adjust conductance to about 170 mS/cm. The solution was filtered with 0.45 um filter and then loaded into HIC High Performance column (GE Healthcare) equilibrated with 20 mM PBS at pH6.0 with 4M NaCl added. A gradient decrease of NaCl concentration was applied as elution buffer from 4M to zero, and then elution fractions and flow-through fraction were collected to detect lysozyme activity.

The flow-through and unbound sample with lysozyme activity were collected and conductance was adjusted to 190 mS/cm, then reloaded into HIC column equilibrated with 20 mM PBS at pH6.0 with 1.8M $(NH_4)_2SO_4$ added again. A gradient decrease of $(NH_4)_2SO_4$ concentration was applied as elution buffer from 1.8M to zero, and then elution fractions and flow-through fraction were collected to detect lysozyme activity. The fractions with lysozyme activity were analyzed by SDS-PAGE, pooled together, and diafiltrated with 20 mM PBS at pH6.0. The protein concentration was determined by Qubit® Protein Assay Kit (Invitrogen, cat Q33212).

Purification of SEQ ID NO: 27

The culture supernatant was firstly precipitated with ammonium sulfate (80% saturation), then dialyzed with 20 mM NaAc at pH5.5. The solution was filtered with 0.45 um filter and then loaded into Capto SP column (GE Healthcare) equilibrated with 20 mM NaAc at pH5.5. A gradient increase of NaCl concentration was applied as elution buffer from zero to 1M, and then the elution fractions and flow-through fraction were collected to detect lysozyme activity. The fractions with lysozyme activity were analyzed by SDS-PAGE. The fractions with lysozyme activity were pooled and concentrated, but degradation of sample was found.

The conductance of sample was adjusted to 200 mS/cm, then reloaded into Phenyl High Performance column equilibrated with 20 mM PBS at pH6.0 with 2.0M $(NH_4)_2SO_4$ added again. A gradient decrease of $(NH_4)_2SO_4$ concentration was applied as elution buffer from 2.0M to zero, and then elution fractions and flow-through fraction were collected to detect lysozyme activity. The fractions with lysozyme activity were analyzed by SDS-PAGE, pooled together, and diafiltrated with 20 mM PBS at pH6.0. The protein concentration was determined by Qubit® Protein Assay Kit (Invitrogen, cat Q33212).

Purification of SEQ ID NO: 30

The culture supernatant was firstly precipitated with ammonium sulfate (80% saturation), then dialyzed with 20 mM NaAc at pH4.5. The solution was filtered with 0.45 um filter and then loaded into Capto SP column (GE Healthcare) equilibrated with 20 mM NaAc at pH4.5. A gradient increase of NaCl concentration was applied as elution buffer from zero to 1M, and then the elution fractions and flow-through fraction were collected to detect lysozyme activity. The fractions with lysozyme activity were analyzed by SDS-PAGE, and then concentrated for further evaluation. The protein concentration was determined by Qubit® Protein Assay Kit (Invitrogen, cat Q33212).

Purification of SEQ ID NO: 33

The culture supernatant of 033X73 was firstly precipitated with ammonium sulfate (80% saturation), then dialyzed with 20 mM NaAc at pH4.5. The solution was filtered with 0.45 um filter and then loaded into Capto SP column (GE Healthcare) equilibrated with 20 mM NaAc at pH4.5. A gradient increase of NaCl concentration was applied as elution buffer from zero to 1M, and then the elution fractions and flow-through fraction were collected to detect lysozyme activity. The fractions with lysozyme activity were analyzed by SDS-PAGE, and then concentrated for further evaluation. The protein concentration was determined by Qubit® Protein Assay Kit (Invitrogen, cat Q33212).

Purification of SEQ ID NO: 36

The culture supernatant was firstly precipitated with ammonium sulfate (80% saturation), then dialyzed with 20 mM PBS at pH7.0. The solution was filtered with 0.45 um filter and then loaded into Capto Q column (GE Healthcare) equilibrated with 20 mM PBS at pH7.0. A gradient increase of NaCl concentration was applied as elution buffer from zero to 1M, and then the elution fractions and flow-through fraction were collected to detect lysozyme activity. The fractions with lysozyme activity were analyzed by SDS-PAGE. The flow-through fraction with lysozyme activity was picked up for further purification.

The pH of flow-through fraction was adjusted to pH4.5, then reloaded into Capto SP column equilibrated with 20 mM NaAC at pH4.5. A gradient increase of NaCl concentration was applied as elution buffer from zero to 1M, and then the elution fractions and flow-through fraction were collected to detect lysozyme activity. The fractions with lysozyme activity were analyzed by SDS-PAGE, and pooled together. The protein concentration was determined by Qubit® Protein Assay Kit (Invitrogen, cat Q33212).

Purification of SEQ ID NO: 39

The culture supernatant was firstly precipitated with ammonium sulfate (80% saturation), then the precipitation was added water to adjust conductance to about 170 mS/cm. The solution was filtered with 0.45 um filter and then loaded into Phenyl Sepharose 6 Fast Flow column (GE Healthcare) equilibrated with 20 mM PBS at pH6.0 with 1.5M $(NH_4)_2SO_4$ added. A gradient decrease of $(NH_4)_2SO_4$ concentration was applied as elution buffer from 1.5M to zero, and then elution fractions and flow-through fraction were collected to detect lysozyme activity. The lysozyme activity still was found in flow-through fraction and fractions 1 to 12, and they were pooled together for further purification.

The conductance of samples with lysozyme activity was adjusted to 190 mS/cm, then reloaded into Phenyl Sepharose High Performance column equilibrated with 20 mM PBS at pH6.0 with 1.8M $(NH_4)_2SO_4$ added again. A gradient decrease of $(NH_4)_2SO_4$ concentration was applied as elution buffer from 1.8M to zero, and then elution fractions and flow-through fraction were collected to detect lysozyme activity. The fractions with lysozyme activity were analyzed by SDS-PAGE, pooled together, and diafiltrated with 20 mM PBS at pH6.0. The protein concentration was determined by Qubit® Protein Assay Kit (Invitrogen, cat Q33212).

Purification of SEQ ID NO: 42

The culture supernatant was firstly precipitated with ammonium sulfate (80% saturation), then the precipitation was added water to adjust conductance to about 170 mS/cm. The solution was filtered with 0.45 um filter and then loaded into Phenyl Sepharose High Performance column (GE Healthcare) equilibrated with 20 mM PBS at pH6.0 with 1.5M $(NH_4)_2SO_4$ added. A gradient decrease of $(NH_4)_2SO_4$ concentration was applied as elution buffer from 1.5M to zero, and then elution fractions and flow-through fraction were collected to detect lysozyme activity. The fractions with lysozyme activity were analyzed by SDS-PAGE, but with two bands found. The fractions with lysozyme activity were pooled together for further purification.

The conductance of the fractions was adjusted to 140 mS/cm, then reloaded into Phenyl Sepharose High Performance column equilibrated with 20 mM PBS at pH6.0 with 1.2M $(NH_4)_2SO_4$ added again. A gradient decrease of $(NH_4)_2SO_4$ concentration was applied as elution buffer from 1.2M to zero, and then elution fractions and flow-through fraction were collected to detect lysozyme activity. The fractions with lysozyme activity were analyzed by SDS-PAGE. Fractions 29 to 37 have lower molecular weight, were pooled together, and diafiltrated with 20 mM PBS at pH6.0. Fraction 43 to 45 have higher molecular weight, were pooled together, and diafiltrated with 20 mM PBS at pH6.0. The protein concentration was determined by Qubit® Protein Assay Kit (Invitrogen, cat Q33212).

Analysis by N-terminal sequencing (Applied Biosystems Precise Amino Acid Sequencer Model 494) showed that the product began with the N-terminal sequence YPIKDNN, corresponding to amino acids 1 to 7 of SEQ ID NO: 42.

Analysis by intact molecular weight (MAXIS II electrospray mass spectrometer (Bruker Daltonik GmbH, Bremen, DE)) showed that the major product corresponded to amino acids 1 to 304 of SEQ ID NO: 42 (detected mass 31755.59 Da, predicted mass 31754.97 Da). There was also a small amount of a secondary product corresponding to amino acids 76 to 304 of SEQ ID NO: 42 (detected mass 23617.23 Da, predicted mass 23617.15 Da) due to the first LED domain being cleaved off the N-terminal.

Purification of SEQ ID NO: 45

The fermentation supernatant with the lysozyme was filtered through a Fast PES Bottle top filter with a 0.22 μm cut-off. 250 ml filtered fermentation samples was diluted with 250 ml MilliQ water and pH was adjusted to 4.5. The lysozyme containing solution was purified by chromatography on Capto S, approximately 30 ml in a XK16 column, using as buffer A 50 mM Na-acetate pH 4.5, and as buffer B 50 mM Na-acetate+2 M NaCl pH 4.5 using a 0-100% gradient over ca. 10CV. The fractions from the column were pooled based on the chromatogram (absorption at 280 and 254 nm) and SDS-PAGE analysis.

The molecular weight was estimated to 25 kDa from SDS-PAGE and the purity was >90%.

Example 10: Method of Determining the LAD Catalytic Domain by HMM

SEQ ID NOs: 46 to 187 were aligned using the software program MUSCLE v3.8.31 with the default settings. Using this alignment, the HMM was constructed using the software program 'hmmbuild' from the package HMMER 3.0 (March 2010) (http://hmmer.org/) and the software was invoked using the default settings by the command: hmmscan3—tblout output.dat model.hmm sequences.fasta. The LAD catalytic domain HMM profile thereby generated for subsequent loading into the software program 'hmmscan' is given below.

```
HMMER3/b [3.0 | March 2010]
NAME LAD catalytic domain
LENG 136
ALPH amino
RF no
CS no
MAP yes
DATE Fri Apr 21 12:03:08 2017
NSEQ 142
EFFN 1.547058
CKSUM 201442427
STATS LOCAL MSV -10.1515 0.71110
STATS LOCAL VITERBI -10.6276 0.71110
STATS LOCAL FORWARD -4.1803 0.71110
HMM        A       C       D       E       F       G       H       I       K       L       M       N
           P       Q       R       S       T       V       W       Y
           m->m    m->i    m->d    i->m    i->i    d->m    d->d
  COMPO   2.28000 4.46955 2.96306 2.70047 3.44014 2.89264 3.73492 2.95902
          2.72837 2.64684 3.53697 3.08243 3.38858 2.79348 2.98339 2.54635 2.85094 2.67860
          4.50931 3.45344
          2.68610 4.42256 2.77533 2.73152 3.46377 2.40496 3.72526 3.29372
          2.67763 2.69331 4.24673 2.90332 2.73683 3.18173 2.89805 2.37875 2.77520 2.98532
          4.58508 3.61512
          0.86176 1.29948 1.18774 1.49367 0.25431 0.00000 *
      1   2.70450 4.96091 2.44483 2.25748 4.38595 1.70411 3.76708 3.83155
          2.65982 3.40989 4.23378 2.69810 3.83638 2.89968 3.15311 2.53822 2.77031 3.44613
          5.62694 4.24971 17 - -
          2.68618 4.42225 2.77519 2.73123 3.46354 2.40513 3.72494 3.29354
          2.67741 2.69355 4.24690 2.90347 2.73739 3.18146 2.89801 2.37887 2.77519 2.98518
          4.58477 3.61503
          0.02516 4.09093 4.81328 0.61958 0.77255 0.70021 0.68613
      2   2.95798 4.37838 4.41979 3.85216 2.84679 4.06442 4.15724 2.49260
          3.70306 1.06749 3.04032 4.02131 4.37743 3.87638 3.84752 3.36755 3.18313 2.46409
          3.85059 2.85522 18 - -
          2.68618 4.42225 2.77519 2.73123 3.46354 2.40513 3.72494 3.29354
          2.67741 2.69355 4.24690 2.90347 2.73739 3.18146 2.89801 2.37887 2.77519 2.98518
          4.58477 3.61503
          0.02269 4.19301 4.91535 0.61958 0.77255 0.78684 0.60749
      3   2.64712 5.07695 2.31050 2.33245 4.40298 2.91636 3.64509 3.86596
          2.37831 3.34917 4.16311 2.30868 3.81995 2.76486 2.86800 2.40011 2.43728 3.46575
          5.56134 4.16658 19 - -
          2.68618 4.42225 2.77519 2.73123 3.46354 2.40513 3.72494 3.29354
          2.67741 2.69355 4.24690 2.90347 2.73739 3.18146 2.89801 2.37887 2.77519 2.98518
          4.58477 3.61503
          0.02259 4.19722 4.91957 0.61958 0.77255 0.69335 0.69294
      4   2.14335 5.06169 2.79203 2.15230 4.37029 3.13800 3.41689 3.83159
          2.36004 3.35168 4.11530 2.86703 3.32033 2.51530 2.75969 2.34749 2.87496 3.40178
          5.51777 4.12854 20 - -
          2.68618 4.42225 2.77519 2.73123 3.46354 2.40513 3.72494 3.29354
          2.67741 2.69355 4.24690 2.90347 2.73739 3.18146 2.89801 2.37887 2.77519 2.98518
          4.58477 3.61503
          0.02150 4.24624 4.96858 0.61958 0.77255 0.57423 0.82813
      5   2.32752 4.64440 3.12310 2.59357 3.83630 3.40168 3.74641 3.18648
          2.50736 2.57706 3.73330 3.10307 3.85311 2.95065 2.73902 2.58368 2.21457 2.53579
          5.18615 3.89627 21 - -
          2.68618 4.42225 2.77519 2.73123 3.46354 2.40513 3.72494 3.29354
          2.67741 2.69355 4.24690 2.90347 2.73739 3.18146 2.89801 2.37887 2.77519 2.98518
          4.58477 3.61503
          0.01979 4.32837 5.05072 0.61958 0.77255 0.64493 0.74380
      6   2.80872 5.24372 2.92193 2.38964 4.59162 3.53977 3.72591 4.02013
```

2.14929 3.51532 4.32009 2.91909 3.77704 1.36571 2.64059 2.86001 3.11361 3.64412
5.64559 4.31503 22 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01973 4.33131 5.05366 0.61958 0.77255 0.64820 0.74021
7 2.62542 4.63457 2.55319 2.60028 3.82280 3.52902 3.75230 3.03815
2.62398 2.57975 2.90066 3.12772 3.91645 2.93691 3.05484 2.18187 2.58195 2.78875
5.17871 3.89049 23 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01973 4.33131 5.05366 0.61958 0.77255 0.62772 0.76315
8 2.35670 5.14104 2.59023 2.29666 4.47219 2.93010 3.62820 3.94710
2.04764 3.43912 4.18729 2.84545 3.83264 2.55019 2.41265 2.56554 2.74894 3.52457
5.58079 4.17986 24 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01956 4.34008 5.06243 0.61958 0.77255 0.52419 0.89657
9 2.70329 4.59946 3.33128 2.77671 3.58063 3.60472 2.72765 2.94006
2.73677 2.77463 3.69458 2.14343 3.98982 3.07351 3.13881 2.83571 2.93476 2.52531
5.01301 2.57944 25 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01861 4.38940 5.11175 0.61958 0.77255 0.57190 0.83115
10 0.58061 4.39851 3.89198 3.70803 4.66940 3.05741 4.71068 4.00280
3.76833 3.77981 4.64326 3.71756 3.68666 4.04155 4.00008 2.69179 3.01786 3.44176
6.02272 4.86740 26 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01861 4.38940 5.11175 0.61958 0.77255 0.57190 0.83115
11 2.28535 5.06565 2.88471 2.36748 4.19761 3.27471 3.62729 3.53322
2.10760 3.18026 4.11808 2.80247 3.71214 2.51474 2.31369 2.57926 2.86084 3.38794
5.52458 3.98224 27 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01861 4.38940 5.11175 0.61958 0.77255 0.55657 0.85138
12 1.95678 4.83280 2.92821 2.43631 4.06399 2.95241 3.71153 3.30570
2.47325 3.04114 3.90855 3.04375 3.89352 2.78279 2.87396 2.61802 2.53741 2.71961
5.34398 4.01659 28 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01849 4.39559 5.11794 0.61958 0.77255 0.56314 0.84262
13 2.65884 4.25606 4.53713 3.95931 3.05007 4.05376 4.40064 1.21113
3.82028 2.25497 3.31657 4.10649 4.40020 4.01626 3.95164 3.36535 2.97633 1.88140
4.97279 3.28929 29 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01849 4.39559 5.11794 0.61958 0.77255 0.56314 0.84262
14 3.09624 4.49244 5.08148 4.54556 3.69891 4.61127 5.10139 1.09511
4.43687 2.08328 3.22577 4.70341 4.88972 4.64468 4.57704 3.97183 3.20262 1.33503
5.56774 4.38580 30 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01849 4.39559 5.11794 0.61958 0.77255 0.56314 0.84262
15 1.87078 5.06861 2.67006 2.34424 4.37045 3.16553 3.65393 3.82623
2.28226 3.35531 4.12231 2.87229 3.85367 2.70349 2.62439 2.49490 2.76661 3.35529
5.19663 4.14646 31 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01849 4.39559 5.11794 0.61958 0.77255 0.44025 1.03248
16 2.43366 4.90407 3.07169 1.93881 4.14929 3.51322 3.71660 3.38468
2.44374 3.14212 3.97548 3.04089 3.90532 2.38664 2.91529 2.71114 2.76736 2.33204
5.40352 4.06677 32 - -

-continued

```
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01756 4.44649 5.16884 0.61958 0.77255 0.48576 0.95510
17 1.69111 4.40326 3.80425 3.41677 4.37951 1.19800 4.42086 3.72489
3.41793 3.46042 4.30219 3.40956 3.96367 3.70234 3.73859 2.67449 2.74965 2.61793
5.75300 4.54416 33 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01756 4.44649 5.16884 0.61958 0.77255 0.48576 0.95510
18 2.67801 5.17603 3.05013 2.31240 4.51586 3.49631 3.67694 3.96645
1.74435 3.22387 4.22607 2.91297 3.91428 2.52932 2.01448 2.64975 2.92944 3.35475
5.59394 4.23259 34 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01756 4.44649 5.16884 0.61958 0.77255 0.48576 0.95510
19 2.48895 5.18440 2.65300 2.21077 4.52329 3.29253 3.65271 4.00175
1.95386 3.48470 4.12914 2.89759 3.86079 2.50491 2.18622 2.57065 2.85720 3.57201
5.61837 4.21554 35 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01756 4.44649 5.16884 0.61958 0.77255 0.48576 0.95510
20 2.43351 4.88117 2.77074 2.22081 4.11935 3.46932 3.71513 3.38326
2.42344 2.62406 2.69401 3.04226 3.90131 2.82540 2.62123 2.56251 2.91163 3.14773
5.38359 3.90443 36 - -
2.68618 4.42225 2.77517 2.73121 3.46348 2.40513 3.72495 3.29354
2.67741 2.69355 4.24690 2.90347 2.73740 3.18147 2.89801 2.37887 2.77520 2.98519
4.58477 3.61503
0.04246 3.32766 5.16884 0.48651 0.95390 0.48576 0.95510
21 2.69712 5.18519 2.72756 2.39570 4.51082 1.98188 3.08098 3.97672
2.20957 3.47648 4.23700 2.82477 3.89080 2.76334 2.37850 2.67797 2.96922 3.56665
5.62338 4.23301 38 - -
2.68633 4.42243 2.77509 2.73132 3.46372 2.40492 3.72439 3.29372
2.67759 2.69347 4.24708 2.90365 2.73730 3.18093 2.89819 2.37883 2.77537 2.98501
4.58495 3.61521
0.10524 2.36234 5.16884 1.78389 0.18390 0.48576 0.95510
22 3.08450 4.42239 4.90061 4.32017 3.36955 4.33853 4.69926 1.58167
4.16773 1.61994 2.77727 4.43627 4.63435 4.05013 4.24780 3.66605 3.31710 1.41643
5.15040 3.90088 49 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01756 4.44649 5.16884 0.61958 0.77255 0.48576 0.95510
23 2.59988 4.75855 3.17066 2.72521 4.40766 2.14059 3.94805 3.84514
2.77802 3.44012 4.23907 3.03326 2.07393 2.98757 3.22451 2.01551 2.47915 3.41576
5.65635 4.33552 50 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01756 4.44649 5.16884 0.61958 0.77255 0.48576 0.95510
24 2.39242 5.12137 2.88795 2.13091 4.33191 3.46970 3.57957 3.90215
2.31739 3.35239 4.03851 2.90526 2.72477 2.72379 2.19066 2.50080 2.91724 3.45054
5.57111 4.18029 51 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01756 4.44649 5.16884 0.61958 0.77255 0.48576 0.95510
25 2.71674 5.18303 2.94981 2.39383 4.38247 3.46358 3.04209 3.88509
1.96661 3.38118 4.23031 2.98468 3.89750 2.14189 2.03986 2.68912 2.96595 3.57326
5.60356 4.22936 52 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01756 4.44649 5.16884 0.61958 0.77255 0.48576 0.95510
26 1.71921 4.45728 3.85035 3.71589 4.87129 0.76439 4.79418 4.28684
3.88233 4.01035 4.83765 3.73888 4.01975 4.11397 4.12696 2.72115 3.06866 3.62581
6.18704 5.04378 53 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01756 4.44649 5.16884 0.61958 0.77255 0.48576 0.95510
27 2.59152 2.48781 4.45380 3.85081 3.15329 3.82710 4.15011 1.84112
3.67495 1.97419 3.00019 3.92506 4.19158 3.38567 3.69697 3.13011 2.91063 2.23021
3.68826 3.44124 54 - -
```

-continued 2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01756 4.44649 5.16884 0.61958 0.77255 0.48576 0.95510
28 2.65209 3.96839 3.84226 3.11334 3.36636 3.72249 4.00157 2.32334
3.11605 2.17547 3.29883 3.58242 4.09639 2.77690 3.22956 2.96075 2.67088 1.76667
4.85107 3.53972 55 - -
2.68619 4.42226 2.77521 2.73124 3.46355 2.40514 3.72495 3.29355
2.67742 2.69356 4.24691 2.90341 2.73735 3.18147 2.89802 2.37888 2.77521 2.98519
4.58478 3.61490
0.03420 3.57804 5.16884 0.73477 0.65319 0.48576 0.95510
29 2.07224 4.45423 4.82417 4.28807 3.72902 4.39122 4.89895 1.15537
4.18214 2.34671 3.58878 4.46949 4.73704 4.42219 4.36253 3.74086 3.24252 1.52460
5.49002 4.28913 59 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01756 4.44649 5.16884 0.61958 0.77255 0.48576 0.95510
30 1.15453 3.74267 3.77490 3.26721 3.89912 2.36201 4.18636 3.24727
3.21520 2.97973 3.85757 3.52789 3.99672 3.50932 3.54238 2.73423 2.92343 2.74165
5.32643 3.69760 60 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01756 4.44649 5.16884 0.61958 0.77255 0.48576 0.95510
31 2.84534 4.33315 4.79654 4.21517 3.00397 4.21925 4.58222 1.49254
4.06138 1.49784 3.23805 4.07937 4.54078 4.22140 4.14680 3.54186 3.21703 1.75514
5.07561 3.90804 61 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01756 4.44649 5.16884 0.61958 0.77255 0.48576 0.95510
32 1.19836 4.20261 3.80733 3.28440 3.79916 3.46684 4.16982 3.08236
3.21815 2.85747 2.79726 3.55364 4.02738 3.51320 3.53422 2.61082 2.45216 2.77505
5.24805 4.03169 62 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01756 4.44649 5.16884 0.61958 0.77255 0.48576 0.95510
33 2.67861 4.43286 3.96982 3.42894 3.65753 3.77789 4.27411 2.58096
3.33280 2.44008 3.15099 3.73934 4.23535 3.64118 3.63033 3.09698 1.23658 2.16899
5.22762 4.01619 63 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
34 1.44620 4.53665 3.43775 2.81280 3.93249 2.34265 3.97126 3.24629
2.88857 2.99055 3.71572 3.31646 3.97140 3.21318 3.28442 2.63939 2.78238 2.66627
5.31139 4.05101 64 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
35 3.04606 4.42292 4.75886 4.16570 2.88260 4.22029 4.49891 2.34117
4.00836 1.03933 2.20271 4.29137 4.51739 4.12726 4.08499 3.42153 3.27084 2.49510
4.93841 3.26659 65 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
36 2.71461 4.59963 3.37734 2.81076 3.81249 3.60715 3.88255 3.10147
2.75570 2.84474 3.60963 3.28475 4.01656 1.92884 3.13739 2.77826 2.55554 1.85209
5.20271 3.93973 66 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
37 3.23633 5.68513 2.52859 0.74729 4.98392 3.53491 4.03390 4.51339
2.90426 4.00099 4.88649 3.02799 4.14144 2.82546 3.36929 3.14048 3.51910 4.11671
6.12487 4.69016 67 - -
2.68619 4.42226 2.77521 2.73122 3.46355 2.40510 3.72496 3.29355
2.67742 2.69356 4.24691 2.90348 2.73741 3.18143 2.89802 2.37884 2.77521 2.98516
4.58478 3.61504
0.03910 3.42113 5.17311 0.68213 0.70429 0.48576 0.95510
38 2.39513 4.11214 3.35820 3.20332 4.42695 3.26670 4.28663 3.82011
3.21286 3.50054 4.32164 3.46375 3.94681 3.51782 3.58241 0.93820 2.31575 3.34233
5.75692 4.51511 71 - -

-continued 2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
39 2.58578 5.14774 2.75533 2.34338 4.46814 2.68238 3.67933 3.93571
2.37780 3.44618 4.20504 2.13940 3.68658 2.77456 2.84780 2.37578 2.39625 3.52717
5.60429 4.20804 72 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
40 3.20020 4.54721 4.96249 4.36943 2.96426 4.39636 4.64583 2.10604
4.20651 0.83885 2.83629 4.48315 4.65449 4.27813 4.25147 3.71872 3.42034 2.57150
3.89377 3.67606 73 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
41 2.69560 4.72458 3.22090 2.63257 3.92297 3.56535 3.56009 2.72958
2.13988 2.63336 3.74365 3.14689 3.95072 2.89799 2.30477 2.78249 2.47712 3.01102
5.25331 3.23392 74 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
42 2.72660 4.33347 3.80539 3.20123 3.45879 3.75585 4.04605 2.31867
3.16049 2.48505 1.91296 2.34384 4.13604 3.45213 3.45614 2.98531 2.96321 2.24154
4.95867 3.74251 75 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
43 3.27737 4.67049 4.55145 4.06069 2.47355 4.24815 3.04419 3.15657
3.89846 1.64280 3.78329 4.07582 4.58700 4.03579 4.02494 3.55869 3.50219 2.88245
3.33803 1.24804 76 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
44 0.51810 4.44568 4.02569 3.87596 4.67377 3.25002 4.83448 3.91947
3.91283 3.77914 4.70430 3.82610 4.05779 4.19265 4.11231 2.69966 3.08739 3.40908
6.08181 4.89612 77 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
45 2.82915 4.93329 2.91029 2.80758 4.72631 3.36731 4.23890 4.33583
3.16837 3.93241 4.78070 0.84802 4.06265 3.45665 3.58212 2.30119 3.25191 3.81189
6.00977 4.62640 78 - -
2.68627 4.42234 2.77499 2.73132 3.46363 2.40491 3.72503 3.29363
2.67750 2.69350 4.24699 2.90356 2.73748 3.18111 2.89793 2.37896 2.77514 2.98527
4.58486 3.61512
0.05713 2.99842 5.17311 1.58281 0.22991 0.48576 0.95510
46 2.44557 5.15547 2.81273 2.27429 4.48469 3.15265 3.59265 3.95947
2.21519 3.45385 3.88587 2.75206 3.27069 2.59201 2.49640 2.15937 2.87349 3.48110
5.59762 4.05507 89 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
47 2.13454 5.00394 2.91686 2.45903 4.28160 2.96306 3.68619 3.67500
2.15235 3.28140 3.87376 2.63736 3.88029 2.80019 2.83287 2.41440 2.70755 2.87275
5.48352 4.11976 90 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
48 2.72141 4.35240 2.87142 3.17074 3.46488 3.73995 3.73692 2.49287
3.11195 2.30200 3.45239 3.53638 4.11660 3.40062 3.42677 3.00245 2.95465 1.43634
4.95481 3.60798 91 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
49 2.12915 4.48324 3.64290 3.40938 4.58739 3.18867 4.50853 3.96004
3.46395 3.53103 4.54098 3.58182 0.86537 3.78586 3.75910 2.64147 3.03200 3.44121
5.94006 4.71598 92 - -

-continued 2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
50 2.01164 5.32733 2.29923 1.57851 4.64741 3.27623 3.76224 4.13187
2.55344 3.62677 4.39593 2.92867 3.92919 2.69728 3.09144 2.54063 3.07699 3.70865
5.77773 4.35069 93 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
51 2.71221 4.62091 3.84225 3.72618 4.73636 3.34639 4.79405 4.36144
3.84443 4.04592 4.94233 3.81925 4.13886 4.14747 4.08008 0.47186 3.24139 3.75589
6.06282 4.83690 94 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
52 2.66443 4.20422 4.02877 3.41213 2.99738 3.77235 4.00427 2.62502
3.33273 1.34843 2.95964 3.64909 4.14137 3.15046 3.37243 3.05142 2.90210 2.37881
4.80399 3.44902 95 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
53 2.47713 5.18116 2.61739 2.34620 4.51729 3.13019 3.65365 3.99682
2.04882 3.48212 4.16874 2.22347 3.85828 2.41978 2.72356 2.58280 2.82696 3.48795
5.61851 4.21297 96 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
54 2.73893 4.19220 4.24842 3.53966 2.57306 3.84157 3.74088 2.33976
3.46086 1.99185 3.21748 3.83249 4.20652 3.73421 3.63828 3.13341 2.97029 2.44433
4.64684 1.75323 97 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
55 2.71240 5.13365 2.69940 2.43599 4.41459 3.50972 3.49117 3.85066
2.43114 3.37180 4.22210 3.01430 1.47487 2.86242 2.98711 2.79453 3.04627 3.49615
5.61591 4.25331 98 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
56 3.01695 4.95117 3.34848 2.93690 2.87628 3.79607 1.23282 3.57422
2.90391 3.12848 4.07095 2.86681 4.20183 3.25586 3.28583 3.07855 3.25131 3.31857
4.61908 2.76108 99 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
57 3.18894 5.84895 1.02997 1.80049 5.12950 3.38073 3.98591 4.67160
3.00026 4.12922 4.96533 2.84549 4.07391 2.43811 3.61066 3.05626 3.47306 4.21602
6.27452 4.73944 100 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
58 1.87056 5.02650 2.84164 2.46171 4.33046 2.29263 3.72123 3.76686
2.39089 3.23960 4.11787 3.01321 3.90717 2.85149 2.40724 2.72437 2.95880 3.40262
5.52546 4.16743 101 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
59 2.87296 4.29463 4.42304 3.69558 3.46367 4.04793 4.40439 2.07618
3.67094 2.05941 3.34949 4.05306 4.40386 3.95876 3.89843 3.10391 3.01800 1.11333
5.06040 3.86470 102 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
60 2.52335 4.51129 3.62019 3.55772 4.90051 0.60958 4.75107 4.41575
3.82700 4.10403 4.93001 3.66459 4.02959 4.06543 4.08722 2.50971 3.10678 3.71678
6.21996 5.01896 103 - -

-continued 2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
61 2.56709 4.93698 2.98607 2.45383 4.19080 3.24189 3.51161 3.61622
2.39299 3.20196 4.00362 2.98136 3.89479 2.84277 2.59044 1.74729 2.79854 3.27778
4.06346 3.72954 104 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
62 3.38324 5.87953 0.59437 2.43450 5.16499 3.51089 4.19299 4.82683
3.33417 4.31592 5.25707 3.02299 4.19831 3.13634 3.96628 3.25372 3.71690 4.38903
6.38048 4.86658 105 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
63 2.28041 4.89681 3.06750 2.53375 4.06796 2.85605 1.87529 3.55546
2.53845 3.16132 3.98206 3.01976 3.93000 2.75092 2.95635 2.75641 2.95343 3.23664
5.39946 3.72687 106 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
64 2.73536 5.16994 1.55165 2.40682 4.24291 3.11994 3.71533 3.93310
2.40910 3.28038 4.23100 2.48568 3.90074 2.83461 2.94504 2.72540 2.98937 3.53862
5.62732 3.93150 107 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
65 2.62666 4.61256 3.39176 3.21148 4.63783 3.28182 4.41739 4.20282
3.32467 3.84412 4.67922 3.16840 4.02180 3.67404 3.51687 0.68426 3.10405 3.63275
5.95670 4.66134 108 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
66 3.28127 4.55225 5.16566 4.64383 3.79600 4.71020 5.24685 1.56503
4.54047 1.99718 3.60026 4.80975 4.98633 4.76535 4.69380 4.08383 3.11988 0.89374
5.70699 4.51592 109 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
67 2.83680 4.79292 3.36129 3.31483 4.92387 0.56396 4.64949 4.54776
3.68201 4.17787 5.03927 2.99221 4.16071 3.94307 4.00415 2.97866 3.33903 3.92368
6.16418 4.94755 110 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
68 2.70449 4.13848 4.32502 3.73159 3.13755 3.83631 4.15179 2.03453
3.58574 1.52919 3.00530 3.87723 3.62487 3.66752 3.71454 2.91360 2.87147 2.05586
4.75960 3.51144 111 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
69 2.73703 4.50887 4.57967 4.02838 1.13149 4.19889 4.29405 2.61213
3.88343 1.97359 2.83383 4.17612 4.52379 4.04901 4.01988 3.51275 3.32702 2.56914
4.71360 3.20993 112 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
70 3.52506 5.43753 3.46574 3.27167 4.68799 3.87734 4.41883 4.45892
3.05955 3.89409 4.94547 3.72159 4.46342 0.47963 3.31382 3.56707 3.84071 4.16117
5.86192 4.62247 113 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
71 3.02299 5.04929 3.40906 2.92277 4.01409 3.75171 3.94381 3.49511
2.54678 2.80533 3.66251 3.37318 4.18320 1.04133 2.83982 3.09078 3.26561 3.31350
5.42159 4.07886 114 - -

-continued 2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
72 3.23277 5.37526 3.60226 2.97446 4.85343 3.84765 3.82756 4.21956
2.11769 3.65014 4.51048 3.38477 4.13356 2.19382 0.97246 3.05467 3.41202 3.88371
5.68623 4.50401 115 - -
2.68625 4.42237 2.77523 2.73135 3.46365 2.40496 3.72506 3.29355
2.67750 2.69364 4.24690 2.90336 2.73708 3.18158 2.89804 2.37895 2.77531 2.98487
4.58431 3.61515
0.36967 1.63266 2.17482 0.89983 0.52195 0.48576 0.95510
73 1.76091 4.60585 3.22695 2.66138 3.81873 3.21041 3.77958 3.20393
2.63580 2.87005 3.72561 3.15358 3.75753 2.86242 3.08379 2.38691 2.78816 2.67495
5.18090 3.39722 123 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01963 4.33652 5.05887 0.61958 0.77255 0.39638 1.11703
74 2.36188 4.66636 3.23919 2.64903 3.85241 3.48742 3.78659 3.17689
2.61741 2.87246 3.42621 3.16440 2.54039 2.70411 3.07610 2.15587 2.83967 2.88009
3.85405 3.79583 124 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
75 2.61045 4.23100 3.89390 3.31670 3.10119 2.37718 3.92350 2.41741
3.11684 2.43089 3.34271 3.57347 4.03101 3.48884 3.48808 2.78635 2.90801 2.39128
2.56930 3.00068 125 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
76 4.23911 5.35111 5.11059 4.88905 2.16141 4.82451 3.72509 3.97319
4.62130 3.22244 4.51964 4.46153 5.12779 4.55830 4.58510 4.24512 4.45234 3.88962
0.95146 1.31009 126 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
77 2.54730 4.84000 3.12323 2.67492 4.36810 1.48789 3.89014 3.79317
2.30863 3.38625 4.19529 3.14795 3.09597 3.04853 3.05662 2.71985 2.63434 3.40162
5.60425 4.28424 127 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
78 2.66228 5.17663 2.18695 2.38019 4.51071 3.46112 3.72860 3.97811
2.49394 3.49608 4.26544 2.46913 3.53684 2.84670 3.01297 2.30433 1.95746 3.57076
5.66185 4.26183 128 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
79 2.62597 3.72459 4.74145 4.16976 3.49514 4.17644 4.57946 1.53523
4.02504 2.06669 3.43633 4.27639 4.52278 4.21862 4.13372 3.37728 2.96630 1.32915
5.12648 3.93497 129 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
80 1.71018 5.09500 2.91003 2.28837 4.39860 3.20819 3.68055 3.85185
2.18117 3.38129 4.15199 2.97202 3.82904 2.59376 2.69863 2.63050 2.91871 3.35040
5.55436 4.17589 130 - -
2.68618 4.42225 2.77520 2.73123 3.46354 2.40513 3.72495 3.29354
2.67741 2.69355 4.24690 2.90347 2.73740 3.18146 2.89797 2.37887 2.77520 2.98518
4.58477 3.61503
0.02663 3.88177 5.17311 0.56218 0.84389 0.48576 0.95510
81 2.48394 3.10163 2.25908 2.04705 4.39152 3.47485 3.67962 3.84650
2.44021 3.37821 4.14764 2.96397 3.87525 2.41597 2.88073 2.68095 2.61892 3.42222
5.55416 4.17129 132 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
82 2.68177 3.55032 2.55328 2.65458 3.90044 3.55585 3.77777 3.23585
2.63297 2.14245 3.79147 3.07691 3.94510 2.97547 2.27756 2.59681 2.81043 2.92572
5.24224 3.94809 133 - -

-continued 2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
83 3.55146 5.02464 4.74999 4.42776 3.62483 4.31991 5.02933 2.86859
4.15961 2.16114 0.58493 4.62225 4.81483 4.51696 4.28820 3.94221 3.88517 2.93677
5.51590 4.31836 134 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
84 2.78950 5.27104 1.60171 2.36299 4.59227 3.42284 3.72878 4.07088
2.40039 3.56687 4.33046 2.53375 3.91054 2.77186 2.80759 2.59881 2.49679 3.65129
5.71587 4.30134 135 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
85 1.77249 4.42802 3.73213 3.25700 4.00890 3.41128 4.22625 3.23512
3.21280 2.95449 3.94696 3.53063 1.56755 3.52335 3.54799 2.70627 2.96075 2.25370
5.43619 4.20828 136 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
86 1.87784 5.02782 2.72866 2.33198 4.31028 3.19386 3.53042 3.75421
2.37531 3.26556 3.94889 2.98159 3.87619 2.75751 2.76120 2.54384 2.55560 3.23490
5.50000 3.78285 137 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
87 2.67637 2.87529 3.70049 3.09589 3.25828 3.44585 3.90857 2.60314
2.80465 2.33125 3.42306 3.49082 4.06803 3.27375 2.53060 2.91907 2.80152 2.55072
4.90754 2.46622 138 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
88 1.79992 4.78437 3.03555 2.72524 4.41183 3.38379 3.98195 3.84389
2.83464 3.45092 4.26320 2.85725 3.94926 2.98839 3.27815 1.35854 2.96383 3.42785
5.67722 4.35764 139 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
89 0.80355 4.37389 3.94778 3.56894 4.36811 3.25124 4.50693 3.63938
3.52971 3.44162 4.30193 3.48702 3.98332 3.81712 3.81331 2.60473 2.39172 2.87424
5.76557 4.57199 140 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
90 2.25481 5.11116 2.94963 2.41107 4.42260 2.57292 3.24732 3.87706
2.30147 3.39764 4.16527 2.97537 3.88387 2.61155 2.07107 2.60293 2.93976 3.41342
5.56165 4.18457 141 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
91 2.25875 4.65512 3.27561 2.71191 3.71913 3.58308 3.80002 3.21470
2.22262 2.23688 2.92970 3.19070 3.96792 2.32664 3.05287 2.79258 2.92381 2.93018
5.19763 3.91802 142 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
92 4.10061 5.33819 5.05020 4.90417 0.39707 4.58135 4.27801 3.59955
4.80953 2.84635 4.25771 4.72981 5.04948 4.82350 4.78408 4.31507 4.41322 3.62708
4.41534 2.73487 143 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
93 3.73347 4.97315 5.03984 4.66909 1.28357 4.63286 3.84974 3.24734
4.49074 2.00016 3.89704 4.40634 4.92154 4.43197 4.47846 3.98159 3.95025 3.15737
3.99370 1.21085 144 - -

-continued 2.68638 4.42247 2.77536 2.73135 3.46369 2.40447 3.72497 3.29375
2.67759 2.69372 4.24711 2.90334 2.73680 3.18155 2.89812 2.37878 2.77536 2.98540
4.58498 3.61517
0.11081 2.31033 5.17311 1.90953 0.16035 0.48576 0.95510
94 2.36046 5.18606 2.46437 2.08364 4.52401 3.06141 3.65211 4.00557
2.21277 3.47210 4.22927 2.71281 3.71770 2.67965 2.50031 2.53113 2.72851 3.53705
5.62257 4.21483 156 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
95 2.02461 5.10851 2.83785 2.25064 4.41932 2.69662 3.66732 3.77266
2.22782 3.39937 4.16115 2.95643 3.86815 2.74425 2.55833 2.39296 2.92164 3.37408
5.56407 4.17669 157 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
96 3.77195 5.02078 5.51168 4.93411 3.22586 5.09901 5.36604 2.28434
4.77671 0.68399 1.90625 5.18303 5.15259 4.73558 4.79347 4.47651 3.97588 2.64824
5.44208 4.46890 158 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
97 2.27665 4.54429 3.31069 2.67276 3.77380 3.58986 3.81443 3.12693
2.13922 2.16378 3.62025 3.19158 3.97401 3.01825 2.81563 2.81424 2.79037 2.51297
5.15297 3.55805 159 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
98 2.49488 5.19607 2.45038 2.24856 4.53529 3.23631 3.65787 4.01546
1.90310 3.49690 4.24001 2.83925 3.86393 2.61300 2.31130 2.64491 2.75545 3.58392
5.62980 4.22437 160 - -
2.68620 4.42244 2.77520 2.73124 3.46373 2.40506 3.72514 3.29342
2.67743 2.69374 4.24709 2.90323 2.73741 3.18123 2.89767 2.37906 2.77520 2.98503
4.58496 3.61522
0.09568 2.45835 5.17311 1.90622 0.16092 0.48576 0.95510
99 2.64610 4.19287 4.51782 3.92763 2.77711 3.97094 4.30822 1.78813
3.57005 2.08485 3.28244 4.04333 4.32451 3.95582 3.66707 3.27791 3.03016 1.43763
4.87494 3.69158 175 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.02184 4.45077 4.61181 0.61958 0.77255 0.48576 0.95510
100 2.57644 5.19801 2.27538 2.38818 4.52814 3.35083 3.68719 4.00392
2.23129 3.50058 4.25504 2.58839 2.30709 2.79494 2.80539 2.41521 2.96353 3.58321
5.64771 4.24193 176 - -
2.68622 4.42229 2.77523 2.73127 3.46358 2.40516 3.72498 3.29358
2.67744 2.69359 4.24693 2.90350 2.73743 3.18150 2.89804 2.37890 2.77523 2.98522
4.58481 3.61363
0.19911 1.74384 5.16884 0.21958 1.62384 0.48146 0.96202
101 2.99688 5.49109 2.31693 2.31426 4.82026 1.50085 3.89510 4.31373
2.80362 3.81760 4.62442 1.94387 4.01089 2.75286 3.34734 2.82386 3.26700 3.89190
5.98283 4.52864 178 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
102 2.70284 4.52919 3.24032 2.96189 3.71775 3.56073 3.97139 3.17965
2.94172 2.87349 3.75897 3.21460 4.03711 3.27740 3.29933 2.53512 2.46622 2.91647
1.54333 3.85468 179 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.02978 4.45077 4.03581 0.61958 0.77255 0.48576 0.95510
103 2.61665 5.23073 2.48892 1.93564 4.56747 3.45738 3.61649 4.05178
2.24240 3.53134 4.27684 2.80050 3.64002 1.94619 2.84919 2.64239 2.89577 3.61752
5.66449 4.25113 180 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01770 4.43869 5.16104 0.61958 0.77255 0.50512 0.92491
104 2.50715 5.12699 2.77810 2.33590 4.44582 3.30582 3.61595 3.91337
2.30426 3.35320 4.17496 2.61050 3.85772 2.65896 2.39675 2.29108 2.36063 3.50352
5.57542 3.76373 181 - -

```
2.68618 4.42225 2.77515 2.73124 3.46354 2.40513 3.72495 3.29354
2.67741 2.69355 4.24690 2.90347 2.73740 3.18147 2.89801 2.37884 2.77520 2.98519
4.58477 3.61503
0.03088 3.70193 5.16104 0.63198 0.75831 0.47385 0.97446
105 2.60454 4.24739 3.87526 3.29633 3.36055 3.57144 3.72308 2.65342
3.19345 2.14470 1.84807 3.60313 4.10632 3.35860 3.01033 3.00275 2.85663 2.18919
4.84814 3.64240 184 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
106 2.39134 5.15060 2.35146 2.27357 4.47362 3.41528 3.68003 3.94208
2.43822 3.37742 4.20939 2.86965 2.78407 2.78921 2.79582 2.01297 2.86585 3.53191
5.60823 4.21105 185 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
107 2.62098 4.25013 3.87151 3.29482 3.36602 3.73620 3.93542 2.37557
2.91952 2.03620 3.23025 3.60470 2.54484 3.47456 3.42600 3.00516 2.82863 1.90641
4.85591 3.64926 186 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
108 2.06052 4.40686 3.81765 3.48760 4.63190 1.17260 4.52999 4.05972
3.52970 3.73232 4.53659 3.59957 3.80588 3.79688 3.84625 2.40774 1.76640 3.46864
5.96429 4.76728 187 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
109 2.30528 5.00504 2.79584 2.32132 4.28012 3.35093 3.68460 3.71938
2.30210 3.20302 4.06501 2.97029 3.87976 2.52168 2.83814 2.53315 2.26799 2.84934
4.56909 4.11805 188 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
110 1.74241 4.18228 4.15006 3.56681 3.06887 3.80169 3.83739 2.56132
3.44556 1.80992 3.28778 3.77234 4.16953 3.66514 3.62758 3.08801 2.93731 2.40159
3.19051 3.11867 189 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
111 1.15417 2.40052 3.43268 3.31342 3.94825 3.05617 4.23524 3.29134
3.27802 2.88728 3.90490 3.55144 3.99881 3.56368 3.59756 2.72050 2.93186 2.96489
5.37506 4.15892 190 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
112 3.26861 5.44238 2.97663 2.64398 4.75892 3.69012 4.06288 4.30148
2.66362 3.78982 4.71915 3.28643 4.23921 0.76296 2.96287 3.24618 3.53605 3.96409
5.86880 4.56259 191 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
113 1.91522 4.95047 2.97467 2.39757 4.20895 3.50202 3.70112 3.61309
2.14870 3.19155 3.18272 3.01748 3.89338 2.73359 2.84536 2.53242 2.55518 3.29391
5.43928 4.09037 192 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
114 3.29634 4.59962 5.14480 4.67781 3.93848 4.66858 5.40358 1.71382
4.56710 2.45181 3.72266 4.84032 5.02031 4.85191 4.75526 4.08284 3.33697 0.67655
5.91411 4.69288 193 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
115 3.15567 5.44348 2.80271 2.49407 4.78415 3.60247 3.94943 4.28979
2.58206 3.78846 4.65575 2.96667 4.14360 0.91366 2.91447 3.11238 3.41462 3.91870
5.87574 4.52658 194 - -
```

-continued

```
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
116 2.71563 4.90409 3.12545 2.55928 4.14921 2.85289 3.44680 3.05862
2.22913 3.15932 3.97583 3.07155 3.92680 2.53911 2.16870 2.75050 2.94327 2.44686
5.39558 4.07226 195 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
117 2.19207 4.40484 3.86126 3.64147 4.76639 3.17370 4.68117 4.15367
3.70231 3.88127 4.70113 3.67352 3.97014 3.97418 3.96685 0.66193 2.77617 3.52234
6.10860 4.92572 196 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
118 1.23716 4.99590 2.82777 2.30137 4.34451 3.20483 3.85483 3.76823
2.68928 3.36557 4.18982 3.06501 3.97138 2.91804 3.03321 2.75915 3.06515 3.41893
5.59981 4.25545 197 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
119 2.63152 4.27604 4.03648 3.47068 1.69703 3.81555 3.85315 2.68413
3.36748 2.44928 3.39118 3.31828 4.18646 3.53607 3.59165 3.09668 2.86423 2.46901
4.64999 2.19303 198 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
120 3.10050 4.93865 3.89438 3.80685 5.08138 2.93213 4.95457 4.68524
3.99850 4.30514 5.22080 4.02495 0.41952 4.31180 4.23729 3.27299 3.60547 4.11129
6.18106 5.18331 199 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
121 2.63821 5.16765 1.71131 2.06185 4.48005 3.20764 3.58490 3.94854
2.45253 3.45931 4.22038 2.80491 3.88069 2.79852 2.94579 2.60137 2.82264 3.54145
4.92801 3.93756 200 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
122 1.86376 4.90237 3.28241 2.68163 4.15144 3.62338 3.62925 3.54290
2.36576 2.72221 3.98901 3.18063 4.00712 2.90768 1.74335 2.86644 3.03069 3.24561
5.38278 4.04754 201 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
123 4.19177 5.36263 4.97401 4.78151 2.11394 4.76326 3.76878 3.89368
4.60093 3.15403 4.48829 4.44462 5.10497 4.55202 4.59461 4.21077 4.43309 3.83039
3.88657 0.47676 202 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01749 4.45077 5.17311 0.61958 0.77255 0.48576 0.95510
124 1.79635 5.14532 2.26839 2.39026 4.45744 3.24099 3.34630 3.84057
2.35322 3.43625 4.19753 2.81236 3.87618 2.60394 2.87095 2.67589 2.92156 3.51869
5.59711 4.13300 203 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.02128 4.45077 4.66879 0.61958 0.77255 0.48576 0.95510
125 2.49141 5.20122 2.74864 2.18402 4.54180 3.39680 3.60493 4.01898
1.78979 3.49991 4.24589 2.89607 3.84714 2.16259 2.63607 2.67773 2.87195 3.59004
5.63139 4.23074 204 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.02321 4.44704 4.48894 0.61958 0.77255 0.49180 0.94553
126 2.70259 4.78288 3.10316 2.62084 3.23014 3.55717 2.77689 3.39328
2.58605 3.02278 3.86371 3.04868 3.94378 2.53415 2.11061 2.76991 2.93283 3.10180
3.35180 3.35576 205 - -
```

-continued

```
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01765 4.44148 5.16383 0.61958 0.77255 0.50070 0.93168
127 2.64699 4.39217 3.56865 2.05763 3.29481 3.66295 3.91739 2.60538
2.95345 2.50897 2.59486 3.40402 4.04141 3.00636 3.30409 2.90867 2.78869 2.22561
4.97634 3.56924 206 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01765 4.44148 5.16383 0.61958 0.77255 0.50070 0.93168
128 2.15651 5.08647 2.66218 2.31635 4.38993 2.79836 3.66501 3.84743
2.38128 3.37411 4.13923 2.89371 2.92678 2.67029 2.83170 2.46722 2.70744 3.45474
4.50984 4.16121 207 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01765 4.44148 5.16383 0.61958 0.77255 0.50070 0.93168
129 2.47139 5.13557 2.73837 1.94974 4.45770 3.46490 3.60456 3.85623
2.21863 2.88369 4.18268 2.94198 3.82238 2.40411 2.53877 2.63956 2.79959 3.31420
5.58153 4.18624 208 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.01765 4.44148 5.16383 0.61958 0.77255 0.50070 0.93168
130 0.54170 4.41455 3.99487 3.83758 4.67181 3.21702 4.80217 3.94160
3.87765 3.78720 4.68767 3.78860 4.02574 4.15301 4.08310 2.61480 3.04914 3.40878
6.07441 4.88693 209 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.04858 4.44148 3.33421 0.61958 0.77255 0.50070 0.93168
131 2.47060 5.10222 2.92302 2.23845 4.41518 3.31163 3.65256 3.83300
2.30764 3.39268 4.15289 2.86002 3.85601 2.39911 2.32759 2.51827 2.29611 3.30596
5.55412 4.16668 210 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.03356 4.41110 3.86983 0.61958 0.77255 0.54715 0.86416
132 2.26873 5.14785 2.83342 2.18702 4.47827 3.38243 3.63990 3.95273
2.07133 3.41537 4.19342 2.78217 3.84499 2.33511 2.64759 2.45499 2.67363 3.49865
5.58841 4.18815 211 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.03225 4.39603 3.94192 0.61958 0.77255 0.56894 0.83500
133 3.29475 4.59909 5.27958 4.75843 3.67853 4.82300 5.34776 1.05587
4.65842 1.73667 3.38036 4.93089 5.04836 4.83561 4.78636 4.20753 3.60004 1.39603
5.69975 4.55067 212 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.19685 4.38251 1.79460 0.61958 0.77255 0.58780 0.81091
134 2.59525 2.26255 4.26037 3.68225 3.24006 3.81148 4.16702 2.18927
3.54565 2.25647 3.24248 3.85052 4.18879 3.76123 3.70265 3.11792 2.92528 1.72461
4.80046 2.95881 213 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.04263 4.20800 3.61724 0.61958 0.77255 0.77092 0.62099
135 2.12293 5.06795 2.53477 2.27785 4.37789 3.30834 3.61326 3.84072
2.22403 3.35911 4.12421 2.69439 3.80736 2.57158 2.81142 2.37052 2.76704 3.41396
5.52424 4.13208 214 - -
2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
0.05033 4.19589 3.38058 0.61958 0.77255 0.78725 0.60714
136 1.41298 4.54007 3.16784 2.67479 3.96764 3.28514 3.85979 3.32496
2.60972 2.92660 3.87024 3.16231 3.88002 3.04176 3.09126 2.66015 2.58267 3.00986
5.31055 4.04058 215 - -
2.68596 4.42247 2.77539 2.73143 3.46365 2.40403 3.72516 3.29358
2.67762 2.69335 4.24680 2.90368 2.73761 3.18168 2.89806 2.37907 2.77541 2.98531
4.58498 3.61491
0.51189 0.91469 * 1.07030 0.41993 0.00000 *
//
```

Example 11: Method of Determining the Lysozyme Enhancing Domain by HMM

SEQ ID NOs: 188 to 316 were aligned using the software program MUSCLE v3.8.31 with the default settings. Using this alignment, the HMM was constructed using the software program 'hmmbuild' from the package HMMER 3.0 (March 2010) (http://hmmer.org/) and the software was invoked using the default settings by the command: hmmscan3—tblout output.dat model.hmm sequences.fasta. The lysozyme enhancing domain HMM profile thereby generated for subsequent loading into the software program 'hmmscan' is given below.

```
HMMER3/b [3.0 | March 2010]
NAME lysozyme_enhancing_domain
LENG 73
ALPH amino
RF no
CS no
MAP yes
DATE Tue Feb 3 15:29:15 2015
NSEQ 129
EFFN 1.263702
CKSUM 3302514446
STATS LOCAL MSV -9.1036 0.71868
STATS LOCAL VITERBI -9.7357 0.71868
STATS LOCAL FORWARD -3.7686 0.71868
HMM      A      C      D      E      F      G      H      I      K      L      M      N
         P      Q      R      S      T      V      W      Y
         m->m   m->i   m->d   i->m   i->i   d->m   d->d
COMPO   2.64236 3.16005 2.87141 2.79417 3.60706 2.63596 3.86157 2.94229
        2.65279 2.95816 3.97690 3.11757 3.46392 3.12498 3.11011 2.56828 2.58627 2.58086
        4.17029 3.04296
        2.68618 4.42225 2.77519 2.73123 3.46354 2.40513 3.72494 3.29354 2.67741
        2.69355 4.24690 2.90347 2.73739 3.18146 2.89801 2.37887 2.77519 2.98518 4.58477
        3.61503
        0.17958 4.32413 1.88959 0.61958 0.77255 0.00000 *
    1   3.80107 5.04040 4.67499 4.39045 1.81828 4.48873 3.56285 3.50991
        4.23379 2.82560 4.11380 4.16131 4.81340 4.22617 4.28030 3.87997 4.03091 3.43577
        3.70270 0.73371 1 - -
        2.68618 4.42225 2.77519 2.73123 3.46354 2.40513 3.72494 3.29354 2.67741
        2.69355 4.24690 2.90347 2.73739 3.18146 2.89801 2.37887 2.77519 2.98518 4.58477
        3.61503
        0.02327 4.16783 4.89017 0.61958 0.77255 0.67437 0.71228
    2   2.33952 4.44593 3.23890 3.02979 4.35083 3.16321 4.20776 3.67603
        3.02584 3.40031 4.31198 3.32021 1.10553 3.46227 3.39562 2.64660 2.86963 3.24503
        5.70138 4.44714 2--
        2.68618 4.42225 2.77519 2.73123 3.46354 2.40513 3.72494 3.29354 2.67741
        2.69355 4.24690 2.90347 2.73739 3.18146 2.89801 2.37887 2.77519 2.98518 4.58477
        3.61503
        0.02327 4.16783 4.89017 0.61958 0.77255 0.58149 0.81886
    3   2.99224 4.47028 5.00531 4.50059 3.72470 4.59877 5.18674 1.10701
        4.40105 2.19903 3.51509 4.69439 4.89181 4.65354 4.58483 3.98375 3.44715 1.21838
        5.67709 4.47722 3--
        2.68618 4.42225 2.77519 2.73123 3.46354 2.40513 3.72494 3.29354 2.67741
        2.69355 4.24690 2.90347 2.73739 3.18146 2.89801 2.37887 2.77519 2.98518 4.58477
        3.61503
        0.02218 4.21548 4.93783 0.61958 0.77255 0.62351 0.76800
    4   2.67119 4.76820 3.04982 2.54195 4.12069 3.43519 3.75916 3.51149
        2.19874 3.13703 3.97428 2.96845 3.89558 2.93360 2.89915 2.57877 1.61288 3.10281
        5.38435 4.08520 4--
        2.68618 4.42225 2.77519 2.73123 3.46354 2.40513 3.72494 3.29354 2.67741
        2.69355 4.24690 2.90347 2.73739 3.18146 2.89801 2.37887 2.77519 2.98518 4.58477
        3.61503
        0.02491 4.21548 4.62159 0.61958 0.77255 0.52151 0.90048
    5   2.37234 5.08464 2.49824 2.21575 4.41120 1.99198 3.58111 3.86677
        2.52882 3.41126 4.20120 2.81325 3.86140 2.84200 3.02691 2.42476 2.83819 3.48001
        5.60144 4.21122 5--
        2.68618 4.42225 2.77519 2.73123 3.46354 2.40513 3.72494 3.29354 2.67741
        2.69355 4.24690 2.90347 2.73739 3.18146 2.89801 2.37887 2.77519 2.98518 4.58477
        3.61503
        0.02114 4.26301 4.98536 0.61958 0.77255 0.56183 0.84436
    6   2.63301 5.17310 2.09015 2.17272 4.49463 3.27178 3.65545 3.97097
        2.38584 3.47241 4.23433 2.52660 3.34330 2.76874 2.94084 2.41690 2.44683 3.55393
        5.62559 4.21427 6--
        2.68618 4.42225 2.77519 2.73123 3.46354 2.40513 3.72494 3.29354 2.67741
        2.69355 4.24690 2.90347 2.73739 3.18146 2.89801 2.37887 2.77519 2.98518 4.58477
        3.61503
        0.07099 4.26555 2.90975 0.61958 0.77255 0.56422 0.84119
    7   2.61111 4.85146 2.70126 2.41033 4.02944 2.66646 3.65077 3.52514
        2.43178 3.11934 3.92649 2.77281 3.83428 2.77300 2.91547 2.42718 2.41739 2.79685
        5.35415 3.75427 7--
```

-continued 2.68619 4.42226 2.77521 2.73124 3.46355 2.40511 3.72496 3.29355 2.67742
2.69356 4.24691 2.90348 2.73741 3.18147 2.89802 2.37888 2.77504 2.98519 4.58478
3.61504
0.09494 2.48394 4.93906 0.38374 1.14353 0.52245 0.89910
8 3.16563 4.52406 5.00410 4.47860 3.59477 4.61318 5.11093 1.75130
4.36399 1.66390 3.39589 4.68330 4.88103 4.58179 4.52924 3.98371 3.48258 0.98654
5.56065 4.39116 9 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02108 4.26555 4.98790 0.61958 0.77255 0.56422 0.84119
9 2.74568 5.18103 2.62071 2.37499 4.50785 3.44148 3.43386 3.97009
2.14487 3.46738 4.24084 1.77122 3.86903 2.77625 2.44752 2.65464 2.97757 3.56615
5.60976 4.22640 10 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02108 4.26555 4.98790 0.61958 0.77255 0.43965 1.03356
10 3.21633 0.35479 4.79708 4.65548 4.57914 3.72194 5.20787 3.82938
4.49870 3.70850 4.85167 4.53077 4.45916 4.82584 4.53365 3.48556 3.72159 3.53505
5.86530 4.85631 11 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
11 3.30119 5.31389 3.73668 3.09114 4.51121 3.86969 3.13217 4.16018
2.10415 3.58751 4.49408 3.45992 4.26052 2.99924 0.83233 3.31264 3.47550 3.85705
5.50391 4.26079 12 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
12 2.24421 4.51545 3.30473 2.81428 4.39051 3.23670 4.14928 3.77491
3.04692 3.44962 4.27960 3.30747 3.89875 3.36729 3.42822 1.05895 2.51437 3.31859
5.70279 4.43964 13 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
13 2.69468 4.75034 2.89429 2.56341 4.66767 0.94912 4.20148 4.12822
3.15097 3.75743 4.60332 3.20872 3.96757 3.42394 3.55601 2.47312 3.12631 3.62410
5.94365 4.63448 14 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
14 2.67424 4.69741 3.65691 3.53445 4.63811 3.40395 4.65858 4.09486
3.63150 3.77181 4.76683 3.75211 0.59051 3.99224 3.88152 2.99980 3.31792 3.64480
5.92609 4.77080 15 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
15 2.26323 4.51933 3.21961 2.94036 4.47411 1.38422 4.14822 3.91245
3.06085 3.54037 4.34588 2.97288 3.87499 3.35219 3.46854 1.96711 2.52323 3.40350
5.76384 4.49002 16 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
16 2.20668 4.36145 3.82003 3.56662 4.41076 3.20360 4.55272 3.51597
3.53768 3.41304 4.35967 3.64187 3.96341 3.86648 3.78744 2.68079 0.81042 3.10831
5.83931 4.64399 17 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
17 2.61570 5.10849 2.62653 2.38205 4.43252 2.78078 3.60811 3.89018
2.47426 3.42628 4.20945 2.71231 3.87390 2.61734 2.99949 1.64993 2.94705 3.49936
5.60799 4.21799 18 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
18 2.58292 4.58689 3.02231 2.68583 3.00245 3.32285 2.97170 3.14564
2.67302 2.81683 3.67939 2.99852 3.79428 3.00246 3.09283 2.65865 2.82740 2.88473
5.11794 2.25478 19 - -

-continued 2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
19 2.02971 5.05961 2.68453 2.36019 4.37471 3.26819 3.65420 3.83090
2.10672 3.36092 4.13132 2.92980 3.45060 2.77060 2.82369 2.16905 2.88648 3.43886
5.53518 4.15201 20 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
20 3.16684 4.47509 4.98151 4.48359 3.78153 4.52597 5.13073 1.23357
4.37208 2.38350 3.60515 4.64947 4.86068 4.63385 4.54770 3.62858 3.43521 1.03896
5.65865 4.43929 21 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
21 2.67985 4.50015 3.40866 2.83947 3.66095 3.60615 3.61051 2.50038
2.12953 2.71143 3.59755 3.27678 3.98763 2.81347 3.06211 2.85030 2.83675 1.92294
5.06195 3.81377 22 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
22 2.57540 5.16214 3.25351 2.63376 4.54584 3.62294 3.69980 3.93939
1.30635 3.43432 4.24813 3.13299 4.00544 2.78831 2.11440 2.89381 2.74985 3.58326
5.55169 4.27942 23 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
23 2.54455 4.73655 3.02733 2.59505 4.05985 3.44683 3.70095 3.46466
2.60056 3.09418 3.92399 3.08417 3.89235 2.67009 3.04116 2.11836 1.78482 2.95974
5.35882 4.04770 24 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
24 3.40982 4.75103 4.67192 4.22624 1.97308 4.35966 3.81417 3.04888
4.07862 2.38151 3.72579 4.16721 4.67838 4.14717 4.17038 3.68839 3.63576 2.47365
4.02768 0.99393 25 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
25 2.33607 5.05721 2.94517 2.24042 4.36369 3.44673 3.55543 3.81754
1.82729 3.31948 4.11325 2.80831 3.17764 2.75227 2.78214 2.58400 2.65726 3.32087
5.51479 4.13659 26 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
26 2.36555 5.04925 3.04993 2.35049 4.35720 3.51989 3.68369 3.71551
1.45376 3.06828 4.12214 3.00561 3.91721 2.74243 2.72409 2.73518 2.95391 3.42066
5.49677 4.16815 27 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
27 2.61202 4.80098 2.75023 2.62858 4.42906 1.32629 3.93435 3.86483
2.78346 3.46292 4.27988 3.09911 3.91159 3.10786 2.85440 2.43819 2.91018 3.44468
5.68001 4.35178 28 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
28 2.39518 5.06692 2.42469 2.35324 4.15968 3.22653 3.04826 3.83188
2.39351 3.35617 4.12096 2.82671 3.83411 2.52507 2.87979 2.43622 2.35726 3.41027
5.52582 4.13893 29 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
29 2.56098 5.10975 1.84700 2.22610 4.41970 3.43432 3.64564 3.82090
2.31577 3.39892 4.16246 2.88269 3.84241 2.68525 2.69153 2.62766 2.81515 3.48193
5.56120 3.47482 30 - -

-continued 2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
30 2.71289 4.20867 4.05384 3.08944 3.32534 3.70711 4.11635 2.10460
3.37170 2.31376 3.31881 3.74286 4.18005 3.62760 3.59433 3.09939 2.94743 1.40821
4.85949 3.10435 31 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
31 2.56066 3.98356 2.83917 2.26935 4.26245 3.45019 3.65582 3.70207
1.96206 3.26063 4.04582 2.95679 3.84786 2.75603 2.89654 2.30158 2.29348 3.33728
5.46026 4.09624 32 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
32 2.98261 4.34033 4.74407 4.16222 2.74015 4.19374 4.48870 1.33722
4.00888 1.70186 3.16247 4.27271 4.50036 4.14592 4.09048 3.51345 3.21313 1.97755
4.93581 3.15765 33 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
33 2.50714 4.52249 3.32761 2.73441 3.99413 2.87824 3.93263 3.37611
2.83014 3.05077 3.89907 3.20556 3.90546 3.15647 3.23473 2.09891 1.66153 2.58887
5.34950 4.08041 34 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
34 2.73372 0.86170 4.21080 3.82223 3.72250 3.51687 4.43487 3.14732
3.50989 2.93675 3.97687 3.88251 4.17078 3.93344 3.44432 2.99564 3.14856 2.89652
5.25169 3.70577 35 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
35 2.78221 4.93521 3.15849 2.72873 3.66991 3.61431 3.78500 3.57206
2.57323 3.13265 4.05241 3.20038 4.05162 1.36867 2.92156 2.93601 3.12692 3.29834
5.09768 2.57435 36 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
36 2.39232 4.68655 3.16574 2.46000 3.89951 3.51768 3.74742 2.86223
2.34831 2.93724 3.78511 3.11031 3.91433 2.90991 3.00803 2.69966 1.85059 2.95170
5.23226 3.93826 37 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
37 2.38712 4.95526 2.95139 2.14292 4.22581 3.30071 3.48757 3.66208
2.41922 3.22834 4.01725 2.96015 3.42523 2.64575 2.85382 2.40915 2.33462 3.08668
5.43599 3.59495 38 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
38 3.32493 5.03100 4.08842 4.05521 5.14287 0.28143 5.12256 4.87721
4.29611 4.46333 5.45951 4.25516 4.43330 4.58529 4.45932 3.51325 3.84001 4.31766
6.09414 5.26815 39 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
39 2.77845 5.16916 2.50798 1.90461 4.47239 3.42576 3.73520 3.92893
2.55535 3.46812 4.26082 2.91770 3.47218 2.74953 3.05304 2.74879 1.68968 3.54385
5.65411 4.25701 40 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
40 2.55637 3.36322 2.86419 2.49420 4.07854 3.43147 3.53651 3.49427
2.36324 3.10007 3.91410 2.51497 3.86778 2.83786 2.95074 2.24490 2.43049 3.00556
5.34651 3.93774 41 - -

```
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
41 3.32262 4.56891 5.24679 4.77118 3.84175 4.81012 5.48421 1.14831
4.68143 2.30177 3.60891 4.94823 5.08094 4.93596 4.85577 4.22682 3.58792 0.99460
5.88795 4.67682 42 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
42 2.65825 5.10541 2.72992 2.15627 3.98363 3.31023 3.53625 3.89170
2.18852 3.23731 4.15424 2.23857 3.82936 2.65748 2.86654 2.25743 2.79796 3.48165
5.55380 4.15800 43 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
43 2.61182 4.52680 3.60621 3.51889 4.78008 0.61583 4.68006 4.23876
3.72062 3.95294 4.83622 3.66170 4.02536 4.00392 3.97409 2.79132 2.85714 3.64017
6.05621 4.90618 44 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
44 2.79049 5.22667 2.25221 2.33027 4.53369 3.27947 3.53614 4.00930
2.56097 3.52971 4.31450 1.59788 3.89352 2.86397 3.06987 2.39242 3.03945 3.49407
5.69864 4.13140 45 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
45 2.49378 3.36932 2.74714 2.42229 4.10830 3.46961 3.68039 3.52770
2.44255 3.12654 3.93602 2.51463 3.86384 2.82770 2.94369 2.19290 2.51568 3.13211
5.36588 3.76024 46 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
46 2.69732 4.16858 4.15640 3.57668 3.28068 3.80998 4.13366 1.64485
3.45403 1.84904 3.26899 3.79253 3.96991 3.68559 3.64246 2.81777 2.62992 2.15853
4.82146 3.52063 47 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
47 4.19233 5.38393 4.84605 4.67977 3.27817 4.29458 4.57157 4.26819
4.41284 3.57367 4.87507 4.74845 4.85287 4.77414 4.45256 4.39169 4.52083 4.16862
0.32020 3.26075 48 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
48 3.20149 5.67973 0.78816 2.34486 4.76934 3.43076 3.17601 4.55895
3.07436 4.04716 4.94146 2.92732 4.07402 3.21129 3.65781 3.08955 3.50632 4.14006
6.03658 4.51417 49 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
49 2.76346 4.98544 3.15831 2.56957 4.01057 3.55403 3.68400 3.67589
1.47331 2.89158 4.05158 3.07047 3.93382 2.56322 2.45400 2.78078 2.98070 3.34485
5.41794 3.49426 50 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
50 2.64257 4.43619 3.56736 3.08202 3.77537 3.52079 4.05811 2.42620
3.00927 2.79176 3.72810 2.99222 4.03030 3.35753 3.34645 2.85418 1.35329 2.62966
5.23131 3.98292 51 - -
2.68619 4.42226 2.77521 2.73124 3.46340 2.40514 3.72496 3.29355 2.67742
2.69356 4.24691 2.90348 2.73741 3.18148 2.89802 2.37888 2.77521 2.98520 4.58478
3.61472
0.08832 2.54971 5.04648 0.37639 1.15942 0.48576 0.95510
51 2.52068 4.47414 3.35565 2.74391 3.33968 3.48613 3.81115 3.00228
2.76056 2.69538 3.20591 3.24034 3.68619 2.82417 3.12828 2.08694 2.32290 2.59916
4.31681 3.78415 53 - -
```

-continued 2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
52 2.77860 4.87789 1.42239 2.56155 3.13731 3.54366 3.74371 3.49507
2.67769 3.09585 3.97167 3.06454 3.97169 2.99708 3.12924 2.82286 3.01884 3.20614
4.04928 3.59798 54 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
53 2.94931 5.28328 2.08563 2.39481 4.84632 1.16425 4.00151 4.36230
3.01231 3.90219 4.74326 2.45548 3.99074 3.18038 3.56729 2.91382 3.29175 3.89959
6.06470 4.62009 55 - -
2.68621 4.42228 2.77522 2.73126 3.46357 2.40509 3.72497 3.29357 2.67727
2.69358 4.24693 2.90346 2.73742 3.18149 2.89804 2.37878 2.77522 2.98521 4.58480
3.61506
0.08509 2.58845 5.04648 0.73284 0.65497 0.48576 0.95510
54 3.21633 0.35479 4.79708 4.65548 4.57914 3.72194 5.20787 3.82938
4.49870 3.70850 4.85167 4.53077 4.45916 4.82584 4.53365 3.48556 3.72159 3.53505
5.86530 4.85631 59 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
55 4.07603 5.22780 4.94333 4.71701 1.81696 4.70604 3.64405 3.73694
4.54415 3.00155 4.31962 4.34626 5.01267 4.44587 4.52415 4.10863 4.29875 3.67538
3.75731 0.60600 60 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
56 3.29932 4.57114 5.13914 4.65306 3.79025 4.73170 5.36042 1.62171
4.54191 2.21256 3.57888 4.84627 5.01963 4.80796 4.72647 4.13701 3.56571 0.76183
5.80720 4.58938 61 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
57 1.40302 4.31490 3.77731 3.44350 4.52474 3.10962 4.46137 3.90675
3.45708 3.61908 4.43729 3.53676 3.86941 3.73557 3.76041 1.18441 2.55005 3.34107
5.86901 4.67381 62 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
58 3.16638 5.52729 0.80512 2.42994 5.07620 2.30005 4.12607 4.65042
3.22647 4.16769 5.05164 2.99972 4.08759 3.32219 3.82773 3.09290 3.51563 4.17606
6.23444 4.80691 63 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
59 3.11990 4.36544 4.32127 3.81191 2.17745 4.09367 3.78203 3.04592
3.23806 2.64903 3.67717 3.91110 4.44159 3.85035 3.84946 3.39383 3.34718 2.77912
3.74216 1.06936 64 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
60 3.51146 4.91649 4.45325 4.08004 2.02567 4.31163 3.69403 3.46524
3.96389 2.92976 4.07889 4.05659 4.68281 4.07537 4.10672 2.99801 3.75887 3.31559
3.91189 0.78971 65 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01987 4.32413 5.04648 0.61958 0.77255 0.48576 0.95510
61 2.72553 4.31253 4.16671 3.66674 3.67680 3.72642 4.41126 2.29394
3.56150 2.58708 3.60951 3.86666 4.24179 3.84789 3.80334 2.76599 2.38224 1.10833
5.25833 4.04936 66 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02985 4.32413 4.12501 0.61958 0.77255 0.48576 0.95510
62 2.51216 5.16569 2.33791 2.35923 4.49437 3.19374 3.66109 3.96480
1.64210 3.46558 4.22781 2.83561 3.85394 2.71011 2.84192 2.54559 2.88860 3.55105
5.61534 4.21583 67 - -

2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02007 4.31435 5.03670 0.61958 0.77255 0.49963 0.93333
63 2.49188 4.38955 3.59551 3.16295 4.09719 3.28177 4.17679 3.38911
3.04040 3.15453 4.02841 3.43067 3.92288 3.44894 3.44644 2.11805 1.20176 2.68117
5.48692 4.25411 68 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02007 4.31435 5.03670 0.61958 0.77255 0.49963 0.93333
64 1.89508 4.31720 3.70048 3.48388 4.63634 0.95179 4.55159 4.00807
3.58485 3.73760 4.55934 3.55250 3.87506 3.84242 3.86415 2.56592 2.50453 3.40204
5.97883 4.79808 69 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.03953 4.31435 3.67355 0.61958 0.77255 0.49963 0.93333
65 2.63597 3.39258 3.14566 2.45530 3.91792 3.49097 3.54341 3.31288
2.40023 2.95698 3.79792 3.08785 3.89316 2.92081 3.00148 1.97899 2.29007 2.96915
5.24220 3.94276 70 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02046 4.29528 5.01763 0.61958 0.77255 0.52575 0.89432
66 2.59137 4.97540 2.68695 2.29850 4.05453 3.34590 3.64946 3.59380
2.42308 3.26160 4.04572 2.57932 3.83844 2.77492 2.90216 1.98570 2.44689 3.22530
5.46068 4.09334 71 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02046 4.29528 5.01763 0.61958 0.77255 0.52575 0.89432
67 2.36239 3.82492 3.07537 2.52645 4.05085 1.94430 3.77137 3.45853
2.53920 3.08721 3.91418 2.86394 3.87403 2.94691 3.05153 2.46988 2.65768 3.12923
5.35184 4.04208 72 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02046 4.29528 5.01763 0.61958 0.77255 0.52575 0.89432
68 2.51473 4.23017 3.73065 3.15738 2.96324 3.66009 3.93184 2.62617
3.08387 2.43082 2.74387 3.49391 3.33993 3.35931 3.14679 2.64784 2.86016 2.49302
4.81896 2.22311 73 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02046 4.29528 5.01763 0.61958 0.77255 0.52575 0.89432
69 2.33893 4.26290 4.21737 3.66773 3.27773 3.87203 4.32579 2.12233
3.56960 2.41061 3.43058 3.89614 4.28394 3.82133 3.79298 2.87144 3.03565 1.21453
5.06701 3.86005 74 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02293 4.29528 4.70670 0.61958 0.77255 0.52575 0.89432
70 2.49593 4.60476 3.23381 2.52485 3.79749 3.53767 3.76569 3.14297
2.26081 2.40764 3.70182 3.15412 3.92810 2.98301 3.03430 2.76728 2.09050 2.55846
5.16115 3.88294 75 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02051 4.29287 5.01521 0.61958 0.77255 0.52898 0.88967
71 2.60687 5.12624 2.52016 2.23382 4.44833 2.55208 3.64005 3.91884
2.12896 3.37075 4.18386 2.86694 3.03933 2.74997 2.89501 2.33562 2.83629 3.50672
5.58015 4.17955 76 - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02051 4.29287 5.01521 0.61958 0.77255 0.52898 0.88967
72 2.57816 5.12677 2.87095 2.24649 4.45454 3.41210 3.40077 3.91086
1.59193 3.41242 4.17909 2.90547 3.85681 2.60853 2.68264 2.65653 2.67555 3.50960
5.55782 4.18309 77 - -
2.68618 4.42225 2.77520 2.73117 3.46354 2.40513 3.72495 3.29354 2.67741
2.69355 4.24690 2.90347 2.73740 3.18147 2.89801 2.37887 2.77520 2.98519 4.58477
3.61503
0.09497 3.41028 2.85473 0.52137 0.90068 0.52898 0.88967
73 3.08258 0.42515 4.66004 4.49479 4.42412 3.61311 5.06351 3.64868
4.33208 3.53771 4.67608 4.38809 4.34603 4.66309 4.38494 3.35266 3.58099 3.36315
5.74041 4.70439 79 - -

```
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.01461 4.23357 * 0.61958 0.77255 0.00000 *
//
```

Example 12: Determination of DomT Scores

The DomT scores for the LAD domain and the LED domain of the LYS polypeptides of the invention were determined using the LAD Catalytic Domain HMM from Example 10 and the Lysozyme Enhancing Domain HMM from Example 11 as described herein are presented in table 5 below.

TABLE 5

DomT scores for LAD and LED domains

| Sequence | LAD domain Amino acid numbers | LAD domain DomT score | LED domain Amino acid numbers | LED domain DomT score |
|---|---|---|---|---|
| SEQ ID NO: 3 | 84 to 226 | 202.5 | 1 to 73 | 118.3 |
| SEQ ID NO: 6 | 84 to 226 | 195.4 | 1 to 73 | 118.5 |
| SEQ ID NO: 9 | 81 to 220 | 199.2 | 1 to 73 | 116.7 |
| SEQ ID NO: 12 | 161 to 304 | 193.4 | 1 to 72 | 108.7 |
| | | | 76 to 147 | 104.6 |
| SEQ ID NO: 15 | 85 to 228 | 200.1 | 1 to 73 | 125.2 |
| SEQ ID NO: 18 | 88 to 230 | 205.3 | 1 to 73 | 119.7 |
| SEQ ID NO: 21 | 87 to 230 | 201.4 | 1 to 73 | 116.9 |
| SEQ ID NO: 24 | 90 to 232 | 201.5 | 1 to 73 | 119.1 |
| SEQ ID NO: 27 | 85 to 228 | 199.8 | 1 to 73 | 123 |
| SEQ ID NO: 30 | 85 to 228 | 202.8 | 1 to 73 | 122.6 |
| SEQ ID NO: 33 | 84 to 226 | 198.2 | 1 to 73 | 115.2 |
| SEQ ID NO: 36 | 83 to 222 | 194.9 | 1 to 73 | 113.1 |
| SEQ ID NO: 39 | 82 to 225 | 203.0 | 1 to 72 | 117.4 |
| SEQ ID NO: 42 | 161 to 303 | 192.6 | 1 to 73 | 115.8 |
| | | | 77 to 149 | 111.2 |
| SEQ ID NO: 45 | 85 to 227 | 208.3 | 1 to 73 | 124.9 |
| SEQ ID NO: 329 | 4 to 146 | 205.3 | — | — |

All of the claimed LYS polypeptides have a LAD DomT score of at least 170, indicating good homology to the LAD HMM model. Likewise all claimed LYS polypeptides have a LED, had a LED DomT score of at least 100, indicating good homology to the LED HMM model.

Example 13: Activity of LYS Polypeptides as Determined Using Reducing Ends Assay The LYS polypeptides of the invention were tested according to Example 1 at two enzyme concentrations and the results are shown in tables 6 to 8 below.

TABLE 6

OD Drop of SEQ ID NO: 3

| LYS polypeptide | OD Drop (5.0 μg/ml)[1] | OD Drop (0.7 μg/ml)[1] |
|---|---|---|
| SEQ ID NO: 3 | 5.4 | 2.4 |

[1] enzyme concentration

TABLE 7

OD Drop of SEQ ID NO: 6 to 45

| LYS polypeptide | OD Drop (5.0 μg/ml)[1] | OD Drop (0.7 μg/ml)[1] |
|---|---|---|
| SEQ ID NO: 6 | 4.4 | 2.0 |
| SEQ ID NO: 9 | 5.2 | 2.7 |
| SEQ ID NO: 12 | 2.4 | 1.4 |
| SEQ ID NO: 15 | 6.7 | 3.2 |
| SEQ ID NO: 21 | 3.9 | 2.2 |
| SEQ ID NO: 24 | 3.1 | 1.8 |
| SEQ ID NO: 27 | 7.8 | 4.6 |
| SEQ ID NO: 30 | 8.7 | 6.0 |
| SEQ ID NO: 33 | 8.6 | 5.7 |
| SEQ ID NO: 36 | 5.4 | 2.9 |
| SEQ ID NO: 39 | 7.8 | 4.8 |
| SEQ ID NO: 42 | 5.1 | 3.1 |
| SEQ ID NO: 45 | 8.5 | 3.9 |
| SEQ ID NO: 329 | 5.0 | 2.3 |

[1] enzyme concentration

As can be seen, the LYS polypeptides of the invention display lysozyme activity as determined using the reducing ends assay.

Example 14: Activity of LYS Polypeptides as Determined Using OD Drop Assay

The LYA polypeptides of the invention were tested according to Example 2 at pH4 and the results are shown in tables 8 and 9 below.

TABLE 8

OD Drop against *M. luteus*

| LYS polypeptide | OD Drop *M. luteus* 1 h, pH 4 |
|---|---|
| SEQ ID NO: 3 | 0.116 |
| SEQ ID NO: 6 | 0.151 |
| SEQ ID NO: 9 | 0.121 |
| SEQ ID NO: 12 | 0.177 |
| SEQ ID NO: 15 | 0.125 |
| SEQ ID NO: 21 | 0.113 |
| SEQ ID NO: 24 | 0.121 |
| SEQ ID NO: 27 | 0.071 |
| SEQ ID NO: 30 | 0.081 |
| SEQ ID NO: 33 | 0.052 |
| SEQ ID NO: 36 | 0.171 |
| SEQ ID NO: 39 | 0.154 |
| SEQ ID NO: 42 | 0.162 |

TABLE 9

OD Drop against *M. luteus*

| LYS polypeptide | OD Drop *M. luteus* 1 h, pH 4 |
|---|---|
| SEQ ID NO: 18 | 0.078 |
| SEQ ID NO: 329 | 0.063 |

As can be seen, the LYS polypeptides of the invention display lysozyme activity as determined using the traditional OD drop assay against *M luteus*.

Example 19: Animal Feed and Animal Feed Additives Comprising a LYS Polypeptide

Animal Feed Additive

A formulation comprising the LYS polypeptide of the invention (e.g. SEQ ID NO: 3, 6, 9, 12, 15, 18, 21, 24, 27, 30, 33, 36, 39, 42, 45 or 239) containing 0.01 g to 10 g enzyme protein is added to the following premix (per kilo of premix):

| | | |
|---|---|---|
| 5000000 | IE | Vitamin A |
| 1000000 | IE | Vitamin D3 |
| 13333 | mg | Vitamin E |
| 1000 | mg | Vitamin K3 |
| 750 | mg | Vitamin B1 |
| 2500 | mg | Vitamin B2 |
| 1500 | mg | Vitamin B6 |
| 7666 | mcg | Vitamin B12 |
| 12333 | mg | Niacin |
| 33333 | mcg | Biotin |
| 300 | mg | Folic Acid |
| 3000 | mg | Ca-D-Panthothenate |
| 1666 | mg | Cu |
| 16666 | mg | Fe |
| 16666 | mg | Zn |
| 23333 | mg | Mn |
| 133 | mg | Co |
| 66 | mg | I |
| 66 | mg | Se |
| 5.8 | % | Calcium |
| 25 | % | Sodium |

Animal Feed

This is an example of an animal feed (broiler feed) comprising the animal feed additive as described above:

62.55% Maize
33.8% Soybean meal (50% crude protein)
1.0% Soybean oil
0.2% DL-Methionine
0.22% DCP (dicalcium phosphate)
0.76% $CaCO_3$ (calcium carbonate)
0.32% Sand
0.15% NaCl (sodium chloride)
1% of the above Premix The ingredients are mixed, and the feed is pelleted at the desired temperature, e.g. 60, 65, 75, 80, 85, 90 or even 95° C.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. An animal feed comprising a plant material and at least 0.01 mg of a polypeptide per kilogram of animal feed, wherein the polypeptide has lysozyme activity and at least 80% sequence identity to the polypeptide of SEQ ID NO: 3.

2. The animal feed of claim 1, wherein the polypeptide has at least 85% sequence identity to the polypeptide of SEQ ID NO: 3.

3. The animal feed of claim 1, wherein the polypeptide has at least 90% sequence identity to the polypeptide of SEQ ID NO: 3.

4. The animal feed of claim 1, wherein the polypeptide has at least 95% sequence identity to the polypeptide of SEQ ID NO: 3.

5. The animal feed of claim 1, wherein the polypeptide comprises SEQ ID NO: 3.

6. The animal feed of claim 1, wherein the polypeptide is a variant of the polypeptide of SEQ ID NO: 3, wherein the variant has lysozyme activity and comprises one or more amino acid substitutions, one or more amino acid deletions, one or more amino acid insertions or any combination thereof.

7. The animal feed of claim 1, wherein the polypeptide comprises an N-terminal and/or C-terminal His-tag and/or HQ-tag.

8. The animal feed of claim 1, wherein the polypeptide is a fragment of the polypeptide of SEQ ID NO: 3 and has at least 90% of the length of the polypeptide of SEQ ID NO: 3.

9. The animal feed of claim 1, wherein the plant material is selected from the group consisting of legumes, cereals, oats, rye, barley, wheat, maize, corn, sorghum, switchgrass, millet, pearl millet, foxtail millet, soybean, wild soybean, beans, lupin, tepary bean, scarlet runner bean, slimjim bean, lima bean, French bean, fava bean, chickpea, lentil, peanut, Spanish peanut, canola, oilseed rape, rice, beet, cabbage, sugar beet, spinach, quinoa, and pea, and any combination thereof.

10. The animal feed of claim 1, wherein the plant material is soybean meal and/or rapeseed meal.

11. The animal feed of claim 1, further comprising whey.

12. The animal feed of claim 1, further comprising an animal protein.

13. The animal feed of claim 12, wherein the animal protein is meat and bone meal, feather meal, and/or fish meal.

14. The animal feed of claim 1, further comprising a vegetable protein.

15. The animal feed of claim 1, further comprising a formulating agent selected from the group consisting of glycerol, ethylene glycol, 1,2-propylene glycol, 1,3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, kaolin, maltodextrin, cyclodextrin, wheat, PVA, acetate, phosphate and cellulose.

16. The animal feed of claim 1, further comprising one or more additional enzymes . . . selected from the group consisting of acetyl xylan esterase, alpha-amylase, beta-amylase, arabinofuranosidase, cellobiohydrolases, cellulase, feruloyl esterase, galactanase, alpha-galactosidase, beta-galactosidase, beta-glucanase, beta-glucosidase, lipase, lysophospholipase, lysozyme, mannanase, alpha-mannosidase, beta-mannosidase, phytase, phospholipase A1, phospholipase A2, phospholipase C, phospholipase D, protease, pullulanase, pectinase, pectin lyase, xylanase, beta-xylosidase and any combination thereof.

17. The animal feed of claim 1, which is in the form of a granule.

18. The animal feed of claim 1, further comprising one or more vitamins, one or more minerals, one or more amino acids, one or more prebiotics, one or more organic acids, and/or one or more phytogenics.

19. The animal feed of claim 1, wherein said plant material comprises barley, wheat, rye, oat, maize, rice, and/or sorghum.

20. A method of improving one or more performance parameters of an animal comprising administering to the animal the animal feed of claim 1.

* * * * *

SEQUENCE LISTING

```
<160> NUMBER OF SEQ ID NOS: 329

<210> SEQ ID NO 1
<211> LENGTH: 809
<212> TYPE: DNA
<213> ORGANISM: Penicillium simplicissimum
<220> FEATURE:
<221> NAME/KEY: CDS
<222> LOCATION: (1)..(429)
<220> FEATURE:
<221> NAME/KEY: sig_peptide
<222> LOCATION: (1)..(57)
<220> FEATURE:
<221> NAME/KEY: mat_peptide
<222> LOCATION: (58)..(806)
<220> FEATURE:
<221> NAME/KEY: CDS
<222> LOCATION: (501)..(806)

<400> SEQUENCE: 1 atg cac ttc tcg ctc ctc gcc atc tcc gca gcc att gcc ttg ccc ctg      48
Met His Phe Ser Leu Leu Ala Ile Ser Ala Ala Ile Ala Leu Pro Leu
                -15                 -10                  -5 gcc agt gcc tat ccc gtc aac gcg gac gat ctc cac tgc cgc tct ggt      96
Ala Ser Ala Tyr Pro Val Asn Ala Asp Asp Leu His Cys Arg Ser Gly
     -1   1                   5                  10 cct ggc acc aac tat ggc atc gtg aag tcc tac aag cgc gga acc gac     144
Pro Gly Thr Asn Tyr Gly Ile Val Lys Ser Tyr Lys Arg Gly Thr Asp
 15                  20                  25 ctc agc atc acc tgc cag gcc acc ggc acc gac gtc aac ggt gac gag     192
Leu Ser Ile Thr Cys Gln Ala Thr Gly Thr Asp Val Asn Gly Asp Glu
 30                  35                  40                  45
```

| | | | | | | | | | | | | | | | | |
|---|---|---|---|---|---|---|---|---|---|---|---|---|---|---|---|---|
| ctc | tgg | gac | aag | acc | tcc | gac | ggc | tgc | tac | gtg | agc | gac | tac | tat | gtc | 240 |
| Leu | Trp | Asp | Lys 50 | Thr | Ser | Asp | Gly | Cys 55 | Tyr | Val | Ser | Asp | Tyr 60 | Tyr | Val | |
| aag | acc | ggc | tcc | agc | agc | tac | gtt | acc | aag | cac | tgc | gac | ggc | agc | tcc | 288 |
| Lys | Thr | Gly | Ser 65 | Ser | Ser | Tyr | Val | Thr 70 | Lys | His | Cys | Asp | Gly 75 | Ser | Ser | |
| ggc | ggc | ggc | agc | agc | ggt | ggc | aac | ctg | ccc | ggc | ctg | act | gct | act | cag | 336 |
| Gly | Gly | Gly | Ser 80 | Ser | Gly | Gly | Asn | Leu 85 | Pro | Gly | Leu | Thr | Ala 90 | Thr | Gln | |
| tcc | aag | cac | gcc | aag | gaa | atc | atc | gcc | gag | gcc | aag | cgt | gag | gat | ctg | 384 |
| Ser | Lys | His | Ala 95 | Lys | Glu | Ile | Ile | Ala 100 | Glu | Ala | Lys | Arg | Glu 105 | Asp | Leu | |
| ggt | ctg | cac | ggc | tgc | tct | gcc | ggt | att | gcg | act | gcc | ctt | gtt | gag | | 429 |
| Gly | Leu | His | Gly | Cys 115 | Ser | Ala | Gly | Ile | Ala 120 | Thr | Ala | Leu | Val | Glu | | |
| 110 | | | | | | | | | | | | | | | | |
| gtatgaacat tgacattccg cccttgata gcaatctccc tcgaaatacg atcgactaac | | | | | | | | | | | | | | | | 489 |
| aattcctcta g tcg aac atc ttg atc tat gcc aac aag gct gtc ccc tct | | | | | | | | | | | | | | | | 539 |
| | | | Ser | Asn | Ile | Leu | Ile 125 | Tyr | Ala | Asn | Lys | Ala 130 | Val | Pro | Ser 135 | |
| tcc | ctc | aac | tac | ccc | cac | gac | gcc | gtt | ggc | tcg | gac | cac | gac | agt | gtt | 587 |
| Ser | Leu | Asn | Tyr 140 | Pro | His | Asp | Ala | Val 145 | Gly | Ser | Asp | His | Asp 150 | Ser | Val | |
| ggt | atc | ttc | cag | cag | cgc | gct | atg | tat | tac | ccc | aac | att | gcc | gct | gat | 635 |
| Gly | Ile | Phe | Gln 155 | Gln | Arg | Ala | Met | Tyr 160 | Tyr | Pro | Asn | Ile | Ala 165 | Ala | Asp | |
| atg | gat | gcc | gcc | aag | tct | gct | gcc | cag | ttc | ttt | gag | aag | atg | aag | aac | 683 |
| Met | Asp | Ala | Ala | Lys 175 | Ser | Ala | Ala | Gln | Phe 180 | Phe | Glu | Lys | Met | Lys 185 | Asn | |
| 170 | | | | | | | | | | | | | | | | |
| gtt | agt | ggc | tgg | aag | tca | atg | gct | gtt | gga | agc | ctc | tgc | cag | aag | gtc | 731 |
| Val | Ser | Gly | Trp 190 | Lys | Ser | Met | Ala | Val 195 | Gly | Ser | Leu | Cys | Gln 200 | Lys | Val | |
| cag | ggc | tcc | gct | tat | cct | act | cgc | tat | gct | gag | cgt | gtt | tct | gag | gct | 779 |
| Gln | Gly | Ser | Ala 205 | Tyr | Pro | Thr | Arg | Tyr 210 | Ala | Glu | Arg | Val | Ser 215 | Glu | Ala | |
| gag | aag | atc | tgc | aaa | gct | ggt | ggc | atc | taa | | | | | | | 809 |
| Glu | Lys | Ile | Cys 220 | Lys | Ala | Gly | Gly | Ile 225 | | | | | | | | |

<210> SEQ ID NO 2
<211> LENGTH: 245
<212> TYPE: PRT
<213> ORGANISM: Penicillium simplicissimum

<400> SEQUENCE: 2

Met His Phe Ser Leu Leu Ala Ile Ser Ala Ala Ile Ala Leu Pro Leu
            -15                 -10                 -5

Ala Ser Ala Tyr Pro Val Asn Ala Asp Asp Leu His Cys Arg Ser Gly
        -1  1                   5                   10

Pro Gly Thr Asn Tyr Gly Ile Val Lys Ser Tyr Lys Arg Gly Thr Asp
            15                  20                  25

Leu Ser Ile Thr Cys Gln Ala Thr Gly Thr Asp Val Asn Gly Asp Glu
30                  35                  40                  45

Leu Trp Asp Lys Thr Ser Asp Gly Cys Tyr Val Ser Asp Tyr Tyr Val
                50                  55                  60

Lys Thr Gly Ser Ser Ser Tyr Val Thr Lys His Cys Asp Gly Ser Ser
                65                  70                  75

Gly Gly Gly Ser Ser Gly Gly Asn Leu Pro Gly Leu Thr Ala Thr Gln
            80                  85                  90

```
Ser Lys His Ala Lys Glu Ile Ile Ala Glu Ala Lys Arg Glu Asp Leu
    95                 100                 105

Gly Leu His Gly Cys Ser Ala Gly Ile Ala Thr Ala Leu Val Glu Ser
110                 115                 120                 125

Asn Ile Leu Ile Tyr Ala Asn Lys Ala Val Pro Ser Ser Leu Asn Tyr
                130                 135                 140

Pro His Asp Ala Val Gly Ser Asp His Asp Ser Val Gly Ile Phe Gln
                145                 150                 155

Gln Arg Ala Met Tyr Tyr Pro Asn Ile Ala Ala Asp Met Asp Ala Ala
                160                 165                 170

Lys Ser Ala Ala Gln Phe Phe Glu Lys Met Lys Asn Val Ser Gly Trp
175                 180                 185

Lys Ser Met Ala Val Gly Ser Leu Cys Gln Lys Val Gln Gly Ser Ala
190                 195                 200                 205

Tyr Pro Thr Arg Tyr Ala Glu Arg Val Ser Glu Ala Glu Lys Ile Cys
                210                 215                 220

Lys Ala Gly Gly Ile
                225

<210> SEQ ID NO 3
<211> LENGTH: 226
<212> TYPE: PRT
<213> ORGANISM: Penicillium simplicissimum
<220> FEATURE:
<221> NAME/KEY: mat_peptide
<222> LOCATION: (1)..(226)

<400> SEQUENCE: 3

Tyr Pro Val Asn Ala Asp Asp Leu His Cys Arg Ser Gly Pro Gly Thr
1               5                   10                  15

Asn Tyr Gly Ile Val Lys Ser Tyr Lys Arg Gly Thr Asp Leu Ser Ile
                20                  25                  30

Thr Cys Gln Ala Thr Gly Thr Asp Val Asn Gly Asp Glu Leu Trp Asp
            35                  40                  45

Lys Thr Ser Asp Gly Cys Tyr Val Ser Asp Tyr Val Lys Thr Gly
        50                  55                  60

Ser Ser Ser Tyr Val Thr Lys His Cys Asp Gly Ser Ser Gly Gly Gly
65                  70                  75                  80

Ser Ser Gly Gly Asn Leu Pro Gly Leu Thr Ala Thr Gln Ser Lys His
                85                  90                  95

Ala Lys Glu Ile Ile Ala Glu Ala Lys Arg Glu Asp Leu Gly Leu His
                100                 105                 110

Gly Cys Ser Ala Gly Ile Ala Thr Ala Leu Val Glu Ser Asn Ile Leu
            115                 120                 125

Ile Tyr Ala Asn Lys Ala Val Pro Ser Ser Leu Asn Tyr Pro His Asp
        130                 135                 140

Ala Val Gly Ser Asp His Asp Ser Val Gly Ile Phe Gln Gln Arg Ala
145                 150                 155                 160

Met Tyr Tyr Pro Asn Ile Ala Ala Asp Met Asp Ala Ala Lys Ser Ala
                165                 170                 175

Ala Gln Phe Phe Glu Lys Met Lys Asn Val Ser Gly Trp Lys Ser Met
            180                 185                 190

Ala Val Gly Ser Leu Cys Gln Lys Val Gln Gly Ser Ala Tyr Pro Thr
        195                 200                 205
```

Arg Tyr Ala Glu Arg Val Ser Glu Ala Glu Lys Ile Cys Lys Ala Gly
    210             215                 220

Gly Ile
225

<210> SEQ ID NO 4
<211> LENGTH: 808
<212> TYPE: DNA
<213> ORGANISM: Penicillium vasconiae
<220> FEATURE:
<221> NAME/KEY: CDS
<222> LOCATION: (1)..(429)
<220> FEATURE:
<221> NAME/KEY: sig_peptide
<222> LOCATION: (1)..(57)
<220> FEATURE:
<221> NAME/KEY: mat_peptide
<222> LOCATION: (58)..(805)
<220> FEATURE:
<221> NAME/KEY: CDS
<222> LOCATION: (500)..(805)

<400> SEQUENCE: 4

```
atg cac ttc tcg ctc ctc gcc atc tcc gca gcc att gcc ctg ccc ctg      48
Met His Phe Ser Leu Leu Ala Ile Ser Ala Ala Ile Ala Leu Pro Leu
                -15                 -10                  -5 gcc agc gcc tat ccc gtc aac gct gac gat ctc cac tgc cgc tct ggt      96
Ala Ser Ala Tyr Pro Val Asn Ala Asp Asp Leu His Cys Arg Ser Gly
        -1   1               5                  10 cct ggc acc agc tac ggc att gtc aag tcc tac aag cgc gga act gac     144
Pro Gly Thr Ser Tyr Gly Ile Val Lys Ser Tyr Lys Arg Gly Thr Asp
     15                  20                  25 ctc acc atc acc tgc cag gcc gcc ggc acc gat gtc aac ggt gat gag     192
Leu Thr Ile Thr Cys Gln Ala Ala Gly Thr Asp Val Asn Gly Asp Glu
30                  35                  40                  45 ctc tgg gac aag acc tcc gac ggc tgc tat gtg agc gac tac tac gtc     240
Leu Trp Asp Lys Thr Ser Asp Gly Cys Tyr Val Ser Asp Tyr Tyr Val
                50                  55                  60 aag acc ggc tcc agc agc tac gtt gcc aag cac tgt gac ggc ggc tct     288
Lys Thr Gly Ser Ser Ser Tyr Val Ala Lys His Cys Asp Gly Gly Ser
            65                  70                  75 agc ggt ggc agc agc ggc ggt gac ttg cct ggt ctg agt gct act cag     336
Ser Gly Gly Ser Ser Gly Gly Asp Leu Pro Gly Leu Ser Ala Thr Gln
        80                  85                  90 tcc aag cac gcc agg gct atc atc gcc gag gcg aag agt gag gat ctg     384
Ser Lys His Ala Arg Ala Ile Ile Ala Glu Ala Lys Ser Glu Asp Leu
    95                 100                 105 ggt ctg cac ggc tgc tcg gct ggt att gcg act gcc ctt gtg gag         429
Gly Leu His Gly Cys Ser Ala Gly Ile Ala Thr Ala Leu Val Glu
110                 115                 120 gtaagaacac tccttaatca caattcctcc ttataagatc aatagtatca tcaactaaca   489
acctctatag tcg agc atc ctg atc tat gcc aac cgg gat gtc ccc act      538
               Ser Ser Ile Leu Ile Tyr Ala Asn Arg Asp Val Pro Thr
                       125                 130                 135 tcc ctg aac tac ccc cat gac gct att ggc tcg gac aac gac agt gtc     586
Ser Leu Asn Tyr Pro His Asp Ala Ile Gly Ser Asp Asn Asp Ser Val
            140                 145                 150 ggc atc ttc cag cag cgc gcc att tac tac ccc gac att gcg gct gat     634
Gly Ile Phe Gln Gln Arg Ala Ile Tyr Tyr Pro Asp Ile Ala Ala Asp
        155                 160                 165 atg gat gcc gcc aag tct gct gcc cag ttc ttc aag aag atg aag aac     682
Met Asp Ala Ala Lys Ser Ala Ala Gln Phe Phe Lys Lys Met Lys Asn
170                 175                 180                 185
```

```
att agc ggc tgg aag tct atg gct gtt gga acc ctt tgc cag aag gtc       730
Ile Ser Gly Trp Lys Ser Met Ala Val Gly Thr Leu Cys Gln Lys Val
            190                 195                 200 cag ggc tct gct tat cct act cgc tat gct gag cgt gtt gct gag gcg       778
Gln Gly Ser Ala Tyr Pro Thr Arg Tyr Ala Glu Arg Val Ala Glu Ala
                205                 210                 215 gag aag att tgc aat gct ggt ggt att taa                               808
Glu Lys Ile Cys Asn Ala Gly Gly Ile
            220                 225
```

<210> SEQ ID NO 5
<211> LENGTH: 245
<212> TYPE: PRT
<213> ORGANISM: Penicillium vasconiae

<400> SEQUENCE: 5

```
Met His Phe Ser Leu Leu Ala Ile Ser Ala Ala Ile Ala Leu Pro Leu
                -15                 -10                  -5

Ala Ser Ala Tyr Pro Val Asn Ala Asp Asp Leu His Cys Arg Ser Gly
        -1   1               5                  10

Pro Gly Thr Ser Tyr Gly Ile Val Lys Ser Tyr Lys Arg Gly Thr Asp
             15                  20                  25

Leu Thr Ile Thr Cys Gln Ala Ala Gly Thr Asp Val Asn Gly Asp Glu
 30                  35                  40                  45

Leu Trp Asp Lys Thr Ser Asp Gly Cys Tyr Val Ser Asp Tyr Tyr Val
                 50                  55                  60

Lys Thr Gly Ser Ser Tyr Val Ala Lys His Cys Asp Gly Ser
                 65                  70                  75

Ser Gly Gly Ser Ser Gly Gly Asp Leu Pro Gly Leu Ser Ala Thr Gln
             80                  85                  90

Ser Lys His Ala Arg Ala Ile Ile Ala Glu Ala Lys Ser Glu Asp Leu
             95                 100                 105

Gly Leu His Gly Cys Ser Ala Gly Ile Ala Thr Ala Leu Val Glu Ser
110                 115                 120                 125

Ser Ile Leu Ile Tyr Ala Asn Arg Asp Val Pro Thr Ser Leu Asn Tyr
                130                 135                 140

Pro His Asp Ala Ile Gly Ser Asp Asn Asp Ser Val Gly Ile Phe Gln
                145                 150                 155

Gln Arg Ala Ile Tyr Tyr Pro Asp Ile Ala Ala Asp Met Asp Ala Ala
            160                 165                 170

Lys Ser Ala Ala Gln Phe Phe Lys Lys Met Lys Asn Ile Ser Gly Trp
175                 180                 185

Lys Ser Met Ala Val Gly Thr Leu Cys Gln Lys Val Gln Gly Ser Ala
190                 195                 200                 205

Tyr Pro Thr Arg Tyr Ala Glu Arg Val Ala Glu Ala Glu Lys Ile Cys
                210                 215                 220

Asn Ala Gly Gly Ile
            225
```

<210> SEQ ID NO 6
<211> LENGTH: 226
<212> TYPE: PRT
<213> ORGANISM: Penicillium vasconiae
<220> FEATURE:
<221> NAME/KEY: mat_peptide
<222> LOCATION: (1)..(226)

```
<400> SEQUENCE: 6

Tyr Pro Val Asn Ala Asp Asp Leu His Cys Arg Ser Gly Pro Gly Thr
1               5                   10                  15

Ser Tyr Gly Ile Val Lys Ser Tyr Lys Arg Gly Thr Asp Leu Thr Ile
            20                  25                  30

Thr Cys Gln Ala Ala Gly Thr Asp Val Asn Gly Asp Glu Leu Trp Asp
        35                  40                  45

Lys Thr Ser Asp Gly Cys Tyr Val Ser Asp Tyr Val Lys Thr Gly
    50                  55                  60

Ser Ser Ser Tyr Val Ala Lys His Cys Asp Gly Ser Ser Gly Gly
65                  70                  75                  80

Ser Ser Gly Gly Asp Leu Pro Gly Leu Ser Ala Thr Gln Ser Lys His
            85                  90                  95

Ala Arg Ala Ile Ile Ala Glu Ala Lys Ser Glu Asp Leu Gly Leu His
                100                 105                 110

Gly Cys Ser Ala Gly Ile Ala Thr Ala Leu Val Glu Ser Ser Ile Leu
            115                 120                 125

Ile Tyr Ala Asn Arg Asp Val Pro Thr Ser Leu Asn Tyr Pro His Asp
    130                 135                 140

Ala Ile Gly Ser Asp Asn Asp Ser Val Gly Ile Phe Gln Gln Arg Ala
145                 150                 155                 160

Ile Tyr Tyr Pro Asp Ile Ala Ala Asp Met Asp Ala Ala Lys Ser Ala
                165                 170                 175

Ala Gln Phe Phe Lys Lys Met Lys Asn Ile Ser Gly Trp Lys Ser Met
            180                 185                 190

Ala Val Gly Thr Leu Cys Gln Lys Val Gln Gly Ser Ala Tyr Pro Thr
        195                 200                 205

Arg Tyr Ala Glu Arg Val Ala Glu Ala Glu Lys Ile Cys Asn Ala Gly
    210                 215                 220

Gly Ile
225

<210> SEQ ID NO 7
<211> LENGTH: 802
<212> TYPE: DNA
<213> ORGANISM: Talaromyces proteolyticus
<220> FEATURE:
<221> NAME/KEY: CDS
<222> LOCATION: (1)..(423)
<220> FEATURE:
<221> NAME/KEY: sig_peptide
<222> LOCATION: (1)..(60)
<220> FEATURE:
<221> NAME/KEY: mat_peptide
<222> LOCATION: (61)..(799)
<220> FEATURE:
<221> NAME/KEY: CDS
<222> LOCATION: (494)..(799)

<400> SEQUENCE: 7 atg ttt gct act tcg ctc att gca ctg tcc ctc gtg aca atc ctc ccc    48
Met Phe Ala Thr Ser Leu Ile Ala Leu Ser Leu Val Thr Ile Leu Pro
-20             -15                 -10                 -5 atc tcc aac gcc tat ccc atc aaa acc gat ggt ctt cac tgc cgt tcc    96
Ile Ser Asn Ala Tyr Pro Ile Lys Thr Asp Gly Leu His Cys Arg Ser
            -1  1               5                   10 gga ccg gga acg ggt tat tcg atc gtg aag acc tac aac aag ggc gaa   144
Gly Pro Gly Thr Gly Tyr Ser Ile Val Lys Thr Tyr Asn Lys Gly Glu
        15                  20                  25
```

```
gag gtc tcg atc act tgc cag gcc cct gga act gat gtt aat gga gac      192
Glu Val Ser Ile Thr Cys Gln Ala Pro Gly Thr Asp Val Asn Gly Asp
 30                  35                  40 tcc ctt tgg gat aag act tct gat ggc tgc tat gtc act gat tac tac      240
Ser Leu Trp Asp Lys Thr Ser Asp Gly Cys Tyr Val Thr Asp Tyr Tyr
 45                  50                  55                  60 gtt agc aca ggc act agt ggc tac gtc act ggt gag tgt ggt agt acc      288
Val Ser Thr Gly Thr Ser Gly Tyr Val Thr Gly Glu Cys Gly Ser Thr
                     65                  70                  75 ggt ggc agt ggt gga aaa ctt ccg ggt ctt gac tct aca caa tcg tcc      336
Gly Gly Ser Gly Gly Lys Leu Pro Gly Leu Asp Ser Thr Gln Ser Ser
             80                  85                  90 cat gcc cga gcc att atc gca gag gcc aaa aag gag agt cta ggt cgt      384
His Ala Arg Ala Ile Ile Ala Glu Ala Lys Lys Glu Ser Leu Gly Arg
         95                 100                 105 cag ggc tgc ctt gcc ggc att gca act gct ttg act gag gtatggctta      433
Gln Gly Cys Leu Ala Gly Ile Ala Thr Ala Leu Thr Glu
    110                 115                 120 accctactca taaattcccc ttacattgtt tttttaccaa tcatgtctaa ctgagcgcag    493 tcg agc att ctg gtc tac gca aac gag gcc gtt cca gaa tcg atg aaa      541
Ser Ser Ile Leu Val Tyr Ala Asn Glu Ala Val Pro Glu Ser Met Lys
             125                 130                 135 tac aag cac gat gcc gtt ggc agc gac cac gat agc att ggc atc ttc      589
Tyr Lys His Asp Ala Val Gly Ser Asp His Asp Ser Ile Gly Ile Phe
         140                 145                 150 cag cag cgc gca atg tac tat ccc aat atc gcc gca gac atg gat cca      637
Gln Gln Arg Ala Met Tyr Tyr Pro Asn Ile Ala Ala Asp Met Asp Pro
     155                 160                 165 gca aag tcg gct gca cag ttc ttt gct aaa atg aag gag gtt agt gga      685
Ala Lys Ser Ala Ala Gln Phe Phe Ala Lys Met Lys Glu Val Ser Gly
170                 175                 180                 185 tgg cga agc atg aac gtt ggt gaa ctc tgc cag aag gtt caa gga tct      733
Trp Arg Ser Met Asn Val Gly Glu Leu Cys Gln Lys Val Gln Gly Ser
                 190                 195                 200 gcc tat cct act cga tat gaa cag cat ctg tct gct gct gaa gcg atc      781
Ala Tyr Pro Thr Arg Tyr Glu Gln His Leu Ser Ala Ala Glu Ala Ile
             205                 210                 215 tgc tct gct gac agt gat tga                                          802
Cys Ser Ala Asp Ser Asp
         220

<210> SEQ ID NO 8
<211> LENGTH: 243
<212> TYPE: PRT
<213> ORGANISM: Talaromyces proteolyticus

<400> SEQUENCE: 8

Met Phe Ala Thr Ser Leu Ile Ala Leu Ser Leu Val Thr Ile Leu Pro
-20                 -15                 -10                  -5

Ile Ser Asn Ala Tyr Pro Ile Lys Thr Asp Gly Leu His Cys Arg Ser
             -1  1                   5                  10

Gly Pro Gly Thr Gly Tyr Ser Ile Val Lys Thr Tyr Asn Lys Gly Glu
         15                  20                  25

Glu Val Ser Ile Thr Cys Gln Ala Pro Gly Thr Asp Val Asn Gly Asp
     30                  35                  40

Ser Leu Trp Asp Lys Thr Ser Asp Gly Cys Tyr Val Thr Asp Tyr Tyr
45                  50                  55                  60

Val Ser Thr Gly Thr Ser Gly Tyr Val Thr Gly Glu Cys Gly Ser Thr
                 65                  70                  75
```

```
Gly Gly Ser Gly Gly Lys Leu Pro Gly Leu Asp Ser Thr Gln Ser Ser
            80                  85                  90

His Ala Arg Ala Ile Ile Ala Glu Ala Lys Lys Glu Ser Leu Gly Arg
        95                 100                 105

Gln Gly Cys Leu Ala Gly Ile Ala Thr Ala Leu Thr Glu Ser Ser Ile
    110                 115                 120

Leu Val Tyr Ala Asn Glu Ala Val Pro Glu Ser Met Lys Tyr Lys His
125                 130                 135                 140

Asp Ala Val Gly Ser Asp His Asp Ser Ile Gly Ile Phe Gln Gln Arg
                145                 150                 155

Ala Met Tyr Tyr Pro Asn Ile Ala Ala Asp Met Asp Pro Ala Lys Ser
        160                 165                 170

Ala Ala Gln Phe Phe Ala Lys Met Lys Glu Val Ser Gly Trp Arg Ser
    175                 180                 185

Met Asn Val Gly Glu Leu Cys Gln Lys Val Gln Gly Ser Ala Tyr Pro
        190                 195                 200

Thr Arg Tyr Glu Gln His Leu Ser Ala Ala Glu Ala Ile Cys Ser Ala
205                 210                 215                 220

Asp Ser Asp

<210> SEQ ID NO 9
<211> LENGTH: 223
<212> TYPE: PRT
<213> ORGANISM: Talaromyces proteolyticus
<220> FEATURE:
<221> NAME/KEY: mat_peptide
<222> LOCATION: (1)..(223)

<400> SEQUENCE: 9

Tyr Pro Ile Lys Thr Asp Gly Leu His Cys Arg Ser Gly Pro Gly Thr
1               5                  10                  15

Gly Tyr Ser Ile Val Lys Thr Tyr Asn Lys Gly Glu Glu Val Ser Ile
            20                  25                  30

Thr Cys Gln Ala Pro Gly Thr Asp Val Asn Gly Asp Ser Leu Trp Asp
        35                  40                  45

Lys Thr Ser Asp Gly Cys Tyr Val Thr Asp Tyr Tyr Val Ser Thr Gly
    50                  55                  60

Thr Ser Gly Tyr Val Thr Gly Glu Cys Gly Ser Thr Gly Gly Ser Gly
65                  70                  75                  80

Gly Lys Leu Pro Gly Leu Asp Ser Thr Gln Ser Ser His Ala Arg Ala
                85                  90                  95

Ile Ile Ala Glu Ala Lys Lys Glu Ser Leu Gly Arg Gln Gly Cys Leu
            100                 105                 110

Ala Gly Ile Ala Thr Ala Leu Thr Glu Ser Ser Ile Leu Val Tyr Ala
        115                 120                 125

Asn Glu Ala Val Pro Glu Ser Met Lys Tyr Lys His Asp Ala Val Gly
    130                 135                 140

Ser Asp His Asp Ser Ile Gly Ile Phe Gln Gln Arg Ala Met Tyr Tyr
145                 150                 155                 160

Pro Asn Ile Ala Ala Asp Met Asp Pro Ala Lys Ser Ala Ala Gln Phe
                165                 170                 175

Phe Ala Lys Met Lys Glu Val Ser Gly Trp Arg Ser Met Asn Val Gly
            180                 185                 190
```

```
Glu Leu Cys Gln Lys Val Gln Gly Ser Ala Tyr Pro Thr Arg Tyr Glu
        195                 200                 205

Gln His Leu Ser Ala Ala Glu Ala Ile Cys Ser Ala Asp Ser Asp
    210                 215                 220

<210> SEQ ID NO 10
<211> LENGTH: 1043
<212> TYPE: DNA
<213> ORGANISM: Aspergillus sp. XZ2668
<220> FEATURE:
<221> NAME/KEY: CDS
<222> LOCATION: (1)..(666)
<220> FEATURE:
<221> NAME/KEY: sig_peptide
<222> LOCATION: (1)..(60)
<220> FEATURE:
<221> NAME/KEY: mat_peptide
<222> LOCATION: (61)..(1040)
<220> FEATURE:
<221> NAME/KEY: CDS
<222> LOCATION: (735)..(1040)

<400> SEQUENCE: 10
```

| | | | | | | | | | | | | | | | | |
|---|---|---|---|---|---|---|---|---|---|---|---|---|---|---|---|---|
| atg | atg | ttc | att | cca | ctc | gtc | act | ctt | tgc | ttt | gca | gct | gct | atc | ccc | 48 |
| Met | Met | Phe | Ile | Pro | Leu | Val | Thr | Leu | Cys | Phe | Ala | Ala | Ala | Ile | Pro | |
| -20 | | | | -15 | | | | -10 | | | | | | -5 | | |
| gtt | gtc | cga | gca | tac | cca | gtc | aaa | gct | gat | gtc | cat | tgc | cgt | tcg | ggc | 96 |
| Val | Val | Arg | Ala | Tyr | Pro | Val | Lys | Ala | Asp | Val | His | Cys | Arg | Ser | Gly | |
| | | -1 | 1 | | | | 5 | | | | | 10 | | | | |
| cct | gga | acc | agc | tat | tcc | att | gtc | aag | aca | tac | agc | acg | ggg | act | cag | 144 |
| Pro | Gly | Thr | Ser | Tyr | Ser | Ile | Val | Lys | Thr | Tyr | Ser | Thr | Gly | Thr | Gln | |
| | | | 15 | | | | | 20 | | | | | 25 | | | |
| atc | tcg | gtt | agc | tgc | cag | gct | gct | ggt | aca | gat | gtt | gat | ggt | gac | cag | 192 |
| Ile | Ser | Val | Ser | Cys | Gln | Ala | Ala | Gly | Thr | Asp | Val | Asp | Gly | Asp | Gln | |
| | | 30 | | | | | 35 | | | | | 40 | | | | |
| ctg | tgg | gac | aag | acc | tct | gat | ggc | tgc | tat | gtc | tcc | gac | tat | tat | gtg | 240 |
| Leu | Trp | Asp | Lys | Thr | Ser | Asp | Gly | Cys | Tyr | Val | Ser | Asp | Tyr | Tyr | Val | |
| 45 | | | | | 50 | | | | | 55 | | | | | 60 | |
| tcc | aca | ggc | agc | agc | aac | tat | gtt | acc | agc | cac | tgc | cct | acc | gag | tac | 288 |
| Ser | Thr | Gly | Ser | Ser | Asn | Tyr | Val | Thr | Ser | His | Cys | Pro | Thr | Glu | Tyr | |
| | | | | 65 | | | | | 70 | | | | | 75 | | |
| gcc | att | aaa | act | gat | gtc | aac | tgt | cgt | tcc | ggt | ccc | gga | acc | aat | tat | 336 |
| Ala | Ile | Lys | Thr | Asp | Val | Asn | Cys | Arg | Ser | Gly | Pro | Gly | Thr | Asn | Tyr | |
| | | | 80 | | | | | 85 | | | | | 90 | | | |
| ggt | att | gtc | aag | aca | tac | aat | cag | gga | gtg | atg | gtt | tct | ctc | aac | tgc | 384 |
| Gly | Ile | Val | Lys | Thr | Tyr | Asn | Gln | Gly | Val | Met | Val | Ser | Leu | Asn | Cys | |
| | | 95 | | | | | 100 | | | | | 105 | | | | |
| cag | gct | tcc | ggc | acc | gat | gtc | gat | ggc | gat | tct | ctc | tgg | gac | aag | aca | 432 |
| Gln | Ala | Ser | Gly | Thr | Asp | Val | Asp | Gly | Asp | Ser | Leu | Trp | Asp | Lys | Thr | |
| | 110 | | | | | 115 | | | | | 120 | | | | | |
| tcc | gat | ggc | tgc | tat | gtc | tct | gac | tac | tac | gtg | gcc | acc | ggc | agc | agc | 480 |
| Ser | Asp | Gly | Cys | Tyr | Val | Ser | Asp | Tyr | Tyr | Val | Ala | Thr | Gly | Ser | Ser | |
| 125 | | | | | 130 | | | | | 135 | | | | | 140 | |
| agt | tat | gtg | aca | agc | gct | tgc | agc | ggc | agc | agc | agt | ggc | ggt | ggt | | 528 |
| Ser | Tyr | Val | Thr | Ser | Ala | Cys | Ser | Gly | Ser | Ser | Ser | Gly | Gly | Gly | | |
| | | | | 145 | | | | | 150 | | | | | 155 | | |
| gga | agc | agc | agc | agc | ggc | aac | ctg | ccc | agt | ctc | gat | tcc | acc | cag | tcg | 576 |
| Gly | Ser | Ser | Ser | Ser | Gly | Asn | Leu | Pro | Ser | Leu | Asp | Ser | Thr | Gln | Ser | |
| | | | 160 | | | | | 165 | | | | | 170 | | | |
| gcc | cac | gcc | cgc | gcc | att | atc | gga | gaa | gcc | aag | agc | caa | aat | gtt | ggt | 624 |
| Ala | His | Ala | Arg | Ala | Ile | Ile | Gly | Glu | Ala | Lys | Ser | Gln | Asn | Val | Gly | |
| | 175 | | | | | 180 | | | | | 185 | | | | | |

```
cgt caa ggc tgc ctt gct ggc att gca act gcc ctg gtt gag         666
Arg Gln Gly Cys Leu Ala Gly Ile Ala Thr Ala Leu Val Glu
    190             195             200 gtaagaggtt ccccatatct caaggtacca tttttactgg atgaatgatt gctaactgtg  726 tacaccag tcg agc atg ctt atg tat gct aac agc aat gtc gcc gca tcg   776
         Ser Ser Met Leu Met Tyr Ala Asn Ser Asn Val Ala Ala Ser
                 205             210             215 ctc agc tat cct cat gat gct gtc ggc tcg gac tac gat agc gtc ggc    824
Leu Ser Tyr Pro His Asp Ala Val Gly Ser Asp Tyr Asp Ser Val Gly
            220             225             230 ctc ttc cag cag cgt gtg tcg att tat acc aac ctc gct gct gat atg    872
Leu Phe Gln Gln Arg Val Ser Ile Tyr Thr Asn Leu Ala Ala Asp Met
        235             240             245 gat gct gca caa tct gcc ggc cag ttt ttt gat gag atg aag aaa gtc    920
Asp Ala Ala Gln Ser Ala Gly Gln Phe Phe Asp Glu Met Lys Lys Val
    250             255             260 agt ggc tgg gag act atg aac gtt ggt gat ctt tgc cag gag gtg cag    968
Ser Gly Trp Glu Thr Met Asn Val Gly Asp Leu Cys Gln Glu Val Gln
265             270             275             280 agg tca gcc tat cca gac cga tat gcg ggg gaa gtt tcg act gct gag   1016
Arg Ser Ala Tyr Pro Asp Arg Tyr Ala Gly Glu Val Ser Thr Ala Glu
            285             290             295 tca atc tgc tct gct ggt ggt ttg taa                                1043
Ser Ile Cys Ser Ala Gly Gly Leu
            300

<210> SEQ ID NO 11
<211> LENGTH: 324
<212> TYPE: PRT
<213> ORGANISM: Aspergillus sp. XZ2668

<400> SEQUENCE: 11

Met Met Phe Ile Pro Leu Val Thr Leu Cys Phe Ala Ala Ala Ile Pro
-20             -15             -10                 -5

Val Val Arg Ala Tyr Pro Val Lys Ala Asp Val His Cys Arg Ser Gly
         -1  1             5                   10

Pro Gly Thr Ser Tyr Ser Ile Val Lys Thr Tyr Ser Thr Gly Thr Gln
            15              20                  25

Ile Ser Val Ser Cys Gln Ala Ala Gly Thr Asp Val Asp Gly Asp Gln
        30              35              40

Leu Trp Asp Lys Thr Ser Asp Gly Cys Tyr Val Ser Tyr Tyr Val
45              50              55              60

Ser Thr Gly Ser Ser Asn Tyr Val Thr Ser His Cys Pro Thr Glu Tyr
            65              70              75

Ala Ile Lys Thr Asp Val Asn Cys Arg Ser Gly Pro Gly Thr Asn Tyr
            80              85              90

Gly Ile Val Lys Thr Tyr Asn Gln Gly Val Met Val Ser Leu Asn Cys
            95              100             105

Gln Ala Ser Gly Thr Asp Val Asp Gly Asp Ser Leu Trp Asp Lys Thr
        110             115             120

Ser Asp Gly Cys Tyr Val Ser Tyr Tyr Val Ala Thr Gly Ser Ser
125             130             135             140

Ser Tyr Val Thr Ser Ala Cys Ser Gly Ser Ser Ser Gly Gly Gly
            145             150             155

Gly Ser Ser Ser Ser Gly Asn Leu Pro Ser Leu Asp Ser Thr Gln Ser
            160             165             170
```

```
Ala His Ala Arg Ala Ile Ile Gly Glu Ala Lys Ser Gln Asn Val Gly
            175                 180                 185

Arg Gln Gly Cys Leu Ala Gly Ile Ala Thr Ala Leu Val Glu Ser Ser
    190                 195                 200

Met Leu Met Tyr Ala Asn Ser Asn Val Ala Ala Ser Leu Ser Tyr Pro
205                 210                 215                 220

His Asp Ala Val Gly Ser Asp Tyr Asp Ser Val Gly Leu Phe Gln Gln
                225                 230                 235

Arg Val Ser Ile Tyr Thr Asn Leu Ala Ala Asp Met Asp Ala Ala Gln
                240                 245                 250

Ser Ala Gly Gln Phe Phe Asp Glu Met Lys Lys Val Ser Gly Trp Glu
                255                 260                 265

Thr Met Asn Val Gly Asp Leu Cys Gln Glu Val Gln Arg Ser Ala Tyr
    270                 275                 280

Pro Asp Arg Tyr Ala Gly Glu Val Ser Thr Ala Glu Ser Ile Cys Ser
285                 290                 295                 300

Ala Gly Gly Leu

<210> SEQ ID NO 12
<211> LENGTH: 304
<212> TYPE: PRT
<213> ORGANISM: Aspergillus sp. XZ2668
<220> FEATURE:
<221> NAME/KEY: mat_peptide
<222> LOCATION: (1)..(304)

<400> SEQUENCE: 12

Tyr Pro Val Lys Ala Asp Val His Cys Arg Ser Gly Pro Gly Thr Ser
1               5                   10                  15

Tyr Ser Ile Val Lys Thr Tyr Ser Thr Gly Thr Gln Ile Ser Val Ser
            20                  25                  30

Cys Gln Ala Ala Gly Thr Asp Val Asp Gly Asp Gln Leu Trp Asp Lys
        35                  40                  45

Thr Ser Asp Gly Cys Tyr Val Ser Asp Tyr Tyr Val Ser Thr Gly Ser
    50                  55                  60

Ser Asn Tyr Val Thr Ser His Cys Pro Thr Glu Tyr Ala Ile Lys Thr
65                  70                  75                  80

Asp Val Asn Cys Arg Ser Gly Pro Gly Thr Asn Tyr Gly Ile Val Lys
                85                  90                  95

Thr Tyr Asn Gln Gly Val Met Val Ser Leu Asn Cys Gln Ala Ser Gly
            100                 105                 110

Thr Asp Val Asp Gly Asp Ser Leu Trp Asp Lys Thr Ser Asp Gly Cys
        115                 120                 125

Tyr Val Ser Asp Tyr Tyr Val Ala Thr Gly Ser Ser Ser Tyr Val Thr
    130                 135                 140

Ser Ala Cys Ser Gly Ser Ser Ser Gly Gly Gly Ser Ser Ser
145                 150                 155                 160

Ser Gly Asn Leu Pro Ser Leu Asp Ser Thr Gln Ser Ala His Ala Arg
                165                 170                 175

Ala Ile Ile Gly Glu Ala Lys Ser Gln Asn Val Gly Arg Gln Gly Cys
            180                 185                 190

Leu Ala Gly Ile Ala Thr Ala Leu Val Glu Ser Ser Met Leu Met Tyr
        195                 200                 205

Ala Asn Ser Asn Val Ala Ala Ser Leu Ser Tyr Pro His Asp Ala Val
    210                 215                 220
```

```
Gly Ser Asp Tyr Asp Ser Val Gly Leu Phe Gln Gln Arg Val Ser Ile
225                 230                 235                 240

Tyr Thr Asn Leu Ala Ala Asp Met Asp Ala Gln Ser Ala Gly Gln
                245                 250                 255

Phe Phe Asp Glu Met Lys Lys Val Ser Gly Trp Glu Thr Met Asn Val
            260                 265                 270

Gly Asp Leu Cys Gln Glu Val Gln Arg Ser Ala Tyr Pro Asp Arg Tyr
                275                 280                 285

Ala Gly Glu Val Ser Thr Ala Glu Ser Ile Cys Ser Ala Gly Gly Leu
            290                 295                 300
```

<210> SEQ ID NO 13
<211> LENGTH: 797
<212> TYPE: DNA
<213> ORGANISM: Penicillium antarcticum
<220> FEATURE:
<221> NAME/KEY: CDS
<222> LOCATION: (1)..(435)
<220> FEATURE:
<221> NAME/KEY: sig_peptide
<222> LOCATION: (1)..(57)
<220> FEATURE:
<221> NAME/KEY: mat_peptide
<222> LOCATION: (58)..(794)
<220> FEATURE:
<221> NAME/KEY: CDS
<222> LOCATION: (489)..(794)

<400> SEQUENCE: 13

```
atg cat ttc caa ctc gtg act ctc tcc gtt gcc ttg ctc tcc ccg ttt         48
Met His Phe Gln Leu Val Thr Leu Ser Val Ala Leu Leu Ser Pro Phe
            -15                 -10                 -5 atc aac gcc tac ccc atc acc ggt gac acc gtc aac tgc cgc tcc ggt         96
Ile Asn Ala Tyr Pro Ile Thr Gly Asp Thr Val Asn Cys Arg Ser Gly
        -1   1               5                  10 cca gga aca tcc tac tca gta gtc aag tcc tac aaa aag ggc gca gat        144
Pro Gly Thr Ser Tyr Ser Val Val Lys Ser Tyr Lys Lys Gly Ala Asp
            15                  20                  25 gtt gca att acc tgc caa gca tcc ggc aca gac atc aaa ggc gat agc        192
Val Ala Ile Thr Cys Gln Ala Ser Gly Thr Asp Ile Lys Gly Asp Ser
30                  35                  40                  45 atc tgg gac aag acc gcc gat ggc tgc tat gtc gcg gac ttc tac gtg        240
Ile Trp Asp Lys Thr Ala Asp Gly Cys Tyr Val Ala Asp Phe Tyr Val
                50                  55                  60 aaa aca ggt agc tcc agc tac gtg acg aag aaa tgc aac agt ggc agc        288
Lys Thr Gly Ser Ser Ser Tyr Val Thr Lys Lys Cys Asn Ser Gly Ser
            65                  70                  75 ggt ggt ggt ggt ggc agc agc agc gga aat cta cct ggc ctt aca tcc        336
Gly Gly Gly Gly Gly Ser Ser Ser Gly Asn Leu Pro Gly Leu Thr Ser
        80                  85                  90 act cag tcc aag cat gcc aaa gct atc atc gga gaa gcg aag aag gag        384
Thr Gln Ser Lys His Ala Lys Ala Ile Ile Gly Glu Ala Lys Lys Glu
    95                  100                 105 gat cta ggt cgc cag ggc tgt ctt gct ggt att gca act gct ctt gtt        432
Asp Leu Gly Arg Gln Gly Cys Leu Ala Gly Ile Ala Thr Ala Leu Val
110                 115                 120                 125 gag gtgaggtcta gtctaattct gcagttcctt gaatcattct taacacattc tag         488
Glu tca aat att ctc atc tat gcc aac aaa aaa gtc ccc tct tca ctt aac        536
Ser Asn Ile Leu Ile Tyr Ala Asn Lys Lys Val Pro Ser Ser Leu Asn
            130                 135                 140
```

```
tac ccc cac gat gcc gtg ggc tcg gac tat gat agt gtt ggc atc ttc      584
Tyr Pro His Asp Ala Val Gly Ser Asp Tyr Asp Ser Val Gly Ile Phe
        145                 150                 155 cag cag cgc gcc aag tac tat ccc agt att gct gcc gat atg gat ccg      632
Gln Gln Arg Ala Lys Tyr Tyr Pro Ser Ile Ala Ala Asp Met Asp Pro
    160                 165                 170 gcc aaa tcg gct gcg cag ttc ttt aag ggt atg aag ggt gtc agt ggg      680
Ala Lys Ser Ala Ala Gln Phe Phe Lys Gly Met Lys Gly Val Ser Gly
175                 180                 185                 190 tgg aag act atg gag gtt ggg aag ctt tgc cag aag gtg cag ggt tcg      728
Trp Lys Thr Met Glu Val Gly Lys Leu Cys Gln Lys Val Gln Gly Ser
            195                 200                 205 gct tat ccc act cga tat gcg gga cgt gtc gat gag gct gag aag att      776
Ala Tyr Pro Thr Arg Tyr Ala Gly Arg Val Asp Glu Ala Glu Lys Ile
        210                 215                 220 tgt gct gct ggt ggt ttg tag                                          797
Cys Ala Ala Gly Gly Leu
        225

<210> SEQ ID NO 14
<211> LENGTH: 247
<212> TYPE: PRT
<213> ORGANISM: Penicillium antarcticum

<400> SEQUENCE: 14

Met His Phe Gln Leu Val Thr Leu Ser Val Ala Leu Leu Ser Pro Phe
                -15                 -10                  -5

Ile Asn Ala Tyr Pro Ile Thr Gly Asp Thr Val Asn Cys Arg Ser Gly
            -1   1               5                  10

Pro Gly Thr Ser Tyr Ser Val Val Lys Ser Tyr Lys Lys Gly Ala Asp
             15                  20                  25

Val Ala Ile Thr Cys Gln Ala Ser Gly Thr Asp Ile Lys Gly Asp Ser
 30                  35                  40                  45

Ile Trp Asp Lys Thr Ala Asp Gly Cys Tyr Val Ala Asp Phe Tyr Val
                 50                  55                  60

Lys Thr Gly Ser Ser Ser Tyr Val Thr Lys Lys Cys Asn Ser Gly Ser
                 65                  70                  75

Gly Gly Gly Gly Gly Ser Ser Ser Gly Asn Leu Pro Gly Leu Thr Ser
             80                  85                  90

Thr Gln Ser Lys His Ala Lys Ala Ile Ile Gly Glu Ala Lys Lys Glu
             95                 100                 105

Asp Leu Gly Arg Gln Gly Cys Leu Ala Gly Ile Ala Thr Ala Leu Val
110                 115                 120                 125

Glu Ser Asn Ile Leu Ile Tyr Ala Asn Lys Lys Val Pro Ser Ser Leu
                130                 135                 140

Asn Tyr Pro His Asp Ala Val Gly Ser Asp Tyr Asp Ser Val Gly Ile
            145                 150                 155

Phe Gln Gln Arg Ala Lys Tyr Tyr Pro Ser Ile Ala Ala Asp Met Asp
            160                 165                 170

Pro Ala Lys Ser Ala Ala Gln Phe Phe Lys Gly Met Lys Gly Val Ser
175                 180                 185

Gly Trp Lys Thr Met Glu Val Gly Lys Leu Cys Gln Lys Val Gln Gly
190                 195                 200                 205

Ser Ala Tyr Pro Thr Arg Tyr Ala Gly Arg Val Asp Glu Ala Glu Lys
                210                 215                 220

Ile Cys Ala Ala Gly Gly Leu
                225
```

```
<210> SEQ ID NO 15
<211> LENGTH: 228
<212> TYPE: PRT
<213> ORGANISM: Penicillium antarcticum
<220> FEATURE:
<221> NAME/KEY: mat_peptide
<222> LOCATION: (1)..(228)

<400> SEQUENCE: 15

Tyr Pro Ile Thr Gly Asp Thr Val Asn Cys Arg Ser Gly Pro Gly Thr
1               5                   10                  15

Ser Tyr Ser Val Val Lys Ser Tyr Lys Lys Gly Ala Asp Val Ala Ile
            20                  25                  30

Thr Cys Gln Ala Ser Gly Thr Asp Ile Lys Gly Asp Ser Ile Trp Asp
        35                  40                  45

Lys Thr Ala Asp Gly Cys Tyr Val Ala Asp Phe Tyr Val Lys Thr Gly
    50                  55                  60

Ser Ser Ser Tyr Val Thr Lys Lys Cys Asn Ser Gly Ser Gly Gly Gly
65                  70                  75                  80

Gly Gly Ser Ser Ser Gly Asn Leu Pro Gly Leu Thr Ser Thr Gln Ser
                85                  90                  95

Lys His Ala Lys Ala Ile Ile Gly Glu Ala Lys Lys Glu Asp Leu Gly
            100                 105                 110

Arg Gln Gly Cys Leu Ala Gly Ile Ala Thr Ala Leu Val Glu Ser Asn
        115                 120                 125

Ile Leu Ile Tyr Ala Asn Lys Lys Val Pro Ser Ser Leu Asn Tyr Pro
    130                 135                 140

His Asp Ala Val Gly Asp Tyr Asp Ser Val Gly Ile Phe Gln Gln
145                 150                 155                 160

Arg Ala Lys Tyr Tyr Pro Ser Ile Ala Ala Asp Met Asp Pro Ala Lys
            165                 170                 175

Ser Ala Ala Gln Phe Phe Lys Gly Met Lys Gly Val Ser Gly Trp Lys
        180                 185                 190

Thr Met Glu Val Gly Lys Leu Cys Gln Lys Val Gln Gly Ser Ala Tyr
    195                 200                 205

Pro Thr Arg Tyr Ala Gly Arg Val Asp Glu Ala Glu Lys Ile Cys Ala
210                 215                 220

Ala Gly Gly Leu
225

<210> SEQ ID NO 16
<211> LENGTH: 817
<212> TYPE: DNA
<213> ORGANISM: Ovatospora brasiliensis
<220> FEATURE:
<221> NAME/KEY: CDS
<222> LOCATION: (1)..(444)
<220> FEATURE:
<221> NAME/KEY: sig_peptide
<222> LOCATION: (1)..(60)
<220> FEATURE:
<221> NAME/KEY: mat_peptide
<222> LOCATION: (61)..(814)
<220> FEATURE:
<221> NAME/KEY: CDS
<222> LOCATION: (509)..(814)

<400> SEQUENCE: 16 atg caa atc tcc ctg atc gcc ctc acc ctc gcg gcc gcc gtc ctc cca      48
Met Gln Ile Ser Leu Ile Ala Leu Thr Leu Ala Ala Ala Val Leu Pro
-20                 -15                 -10                 -5
```

```
gcg gtc agc gcc tac ccc gtc aag gcc gac tcg ctc aac tgc cgc agc      96
Ala Val Ser Ala Tyr Pro Val Lys Ala Asp Ser Leu Asn Cys Arg Ser
        -1  1               5                  10 ggc ccg ggc acc agc tac aag gtc gtc aag acc tac aag aag ggc gcc     144
Gly Pro Gly Thr Ser Tyr Lys Val Val Lys Thr Tyr Lys Lys Gly Ala
            15                  20                  25 gac atc aag atc tcg tgc cag acc gaa ggc ccc agc gtc aac ggc gac     192
Asp Ile Lys Ile Ser Cys Gln Thr Glu Gly Pro Ser Val Asn Gly Asp
 30                  35                  40 aac ctc tgg atc aag acc cag gac ggg tgc tac gtc gcc gac tac tac     240
Asn Leu Trp Ile Lys Thr Gln Asp Gly Cys Tyr Val Ala Asp Tyr Tyr
 45                  50                  55                  60 gtc aag acg ggc acc aac ggc tat gtt gcc aag aag tgc tct tct ggt     288
Val Lys Thr Gly Thr Asn Gly Tyr Val Ala Lys Lys Cys Ser Ser Gly
                 65                  70                  75 gga agc act ggt ggc agc ggc ggc aag ggt aac ctg ccc ggt             336
Gly Ser Thr Gly Gly Ser Gly Gly Lys Gly Asn Leu Pro Gly
             80                  85                  90 ctg aat gcc aag cag tcg tct cat gct cgg gct atc gtc gcc cag gcg     384
Leu Asn Ala Lys Gln Ser Ser His Ala Arg Ala Ile Val Ala Gln Ala
             95                 100                 105 aag aag gac ggt gtc ggt ctc cac ggc tgc gag gcc ggt att gcg acc     432
Lys Lys Asp Gly Val Gly Leu His Gly Cys Glu Ala Gly Ile Ala Thr
110                 115                 120 gct ctt gtc gag gtaagcttct tccacggtat accatccaga ttcatattga         484
Ala Leu Val Glu
125 aacccatgac taaccctcca ccag tcc ggc atc aag gtc tac gcc aac aaa      535
                           Ser Gly Ile Lys Val Tyr Ala Asn Lys
                                       130                 135 aag gtg ccc gcc tcg ctc aag tac ccg cac gac gcc gtc ggc tcc gac     583
Lys Val Pro Ala Ser Leu Lys Tyr Pro His Asp Ala Val Gly Ser Asp
            140                 145                 150 cac gac agc atc ggc atc ttc cag cag cgc gcc gtc tac tac ccc aac     631
His Asp Ser Ile Gly Ile Phe Gln Gln Arg Ala Val Tyr Tyr Pro Asn
        155                 160                 165 atc gcc gcc gac atg gac ccc gcg cgc tcc gcc cac cag ttc ttt gcc     679
Ile Ala Ala Asp Met Asp Pro Ala Arg Ser Ala His Gln Phe Phe Ala
170                 175                 180                 185 aag atg aag ggc gtc tcg ggc tgg aag acc atg gct gtc ggc aag ctc     727
Lys Met Lys Gly Val Ser Gly Trp Lys Thr Met Ala Val Gly Lys Leu
                190                 195                 200 tgc cag aag gtc cag gtc tcg gct tac ccg gac cgc tat gcc aag cgg     775
Cys Gln Lys Val Gln Val Ser Ala Tyr Pro Asp Arg Tyr Ala Lys Arg
            205                 210                 215 gtg tcg gag gcc acc aag att tgc aag gct gct ggg atc tga             817
Val Ser Glu Ala Thr Lys Ile Cys Lys Ala Ala Gly Ile
        220                 225                 230

<210> SEQ ID NO 17
<211> LENGTH: 250
<212> TYPE: PRT
<213> ORGANISM: Ovatospora brasiliensis

<400> SEQUENCE: 17

Met Gln Ile Ser Leu Ile Ala Leu Thr Leu Ala Ala Ala Val Leu Pro
-20                 -15                 -10                  -5

Ala Val Ser Ala Tyr Pro Val Lys Ala Asp Ser Leu Asn Cys Arg Ser
        -1  1               5                  10
```

Gly Pro Gly Thr Ser Tyr Lys Val Lys Thr Tyr Lys Lys Gly Ala
            15                  20                  25

Asp Ile Lys Ile Ser Cys Gln Thr Glu Gly Pro Ser Val Asn Gly Asp
 30                  35                  40

Asn Leu Trp Ile Lys Thr Gln Asp Gly Cys Tyr Val Ala Asp Tyr Tyr
 45                  50                  55                  60

Val Lys Thr Gly Thr Asn Gly Tyr Val Ala Lys Lys Cys Ser Ser Gly
                 65                  70                  75

Gly Ser Thr Gly Gly Ser Gly Gly Lys Gly Asn Leu Pro Gly
                 80                  85                  90

Leu Asn Ala Lys Gln Ser Ser His Ala Arg Ala Ile Val Ala Gln Ala
             95                 100                 105

Lys Lys Asp Gly Val Gly Leu His Gly Cys Glu Ala Gly Ile Ala Thr
        110                 115                 120

Ala Leu Val Glu Ser Gly Ile Lys Val Tyr Ala Asn Lys Lys Val Pro
125                 130                 135                 140

Ala Ser Leu Lys Tyr Pro His Asp Ala Val Gly Ser Asp His Asp Ser
                145                 150                 155

Ile Gly Ile Phe Gln Gln Arg Ala Val Tyr Tyr Pro Asn Ile Ala Ala
                160                 165                 170

Asp Met Asp Pro Ala Arg Ser Ala His Gln Phe Phe Ala Lys Met Lys
        175                 180                 185

Gly Val Ser Gly Trp Lys Thr Met Ala Val Gly Lys Leu Cys Gln Lys
        190                 195                 200

Val Gln Val Ser Ala Tyr Pro Asp Arg Tyr Ala Lys Arg Val Ser Glu
205                 210                 215                 220

Ala Thr Lys Ile Cys Lys Ala Ala Gly Ile
                225                 230

<210> SEQ ID NO 18
<211> LENGTH: 230
<212> TYPE: PRT
<213> ORGANISM: Ovatospora brasiliensis
<220> FEATURE:
<221> NAME/KEY: mat_peptide
<222> LOCATION: (1)..(230)

<400> SEQUENCE: 18

Tyr Pro Val Lys Ala Asp Ser Leu Asn Cys Arg Ser Gly Pro Gly Thr
 1               5                  10                  15

Ser Tyr Lys Val Val Lys Thr Tyr Lys Lys Gly Ala Asp Ile Lys Ile
                 20                  25                  30

Ser Cys Gln Thr Glu Gly Pro Ser Val Asn Gly Asp Asn Leu Trp Ile
             35                  40                  45

Lys Thr Gln Asp Gly Cys Tyr Val Ala Asp Tyr Tyr Val Lys Thr Gly
 50                  55                  60

Thr Asn Gly Tyr Val Ala Lys Lys Cys Ser Ser Gly Ser Thr Gly
 65                  70                  75                  80

Gly Gly Ser Gly Gly Lys Gly Asn Leu Pro Gly Leu Asn Ala Lys
                 85                  90                  95

Gln Ser Ser His Ala Arg Ala Ile Val Ala Gln Ala Lys Lys Asp Gly
            100                 105                 110

Val Gly Leu His Gly Cys Glu Ala Gly Ile Ala Thr Ala Leu Val Glu
        115                 120                 125

Ser Gly Ile Lys Val Tyr Ala Asn Lys Lys Val Pro Ala Ser Leu Lys
130                 135                 140

```
Tyr Pro His Asp Ala Val Gly Ser Asp His Asp Ser Ile Gly Ile Phe
145                 150                 155                 160

Gln Gln Arg Ala Val Tyr Tyr Pro Asn Ile Ala Ala Asp Met Asp Pro
            165                 170                 175

Ala Arg Ser Ala His Gln Phe Phe Ala Lys Met Lys Gly Val Ser Gly
        180                 185                 190

Trp Lys Thr Met Ala Val Gly Lys Leu Cys Gln Lys Val Gln Val Ser
        195                 200                 205

Ala Tyr Pro Asp Arg Tyr Ala Lys Arg Val Ser Glu Ala Thr Lys Ile
        210                 215                 220

Cys Lys Ala Ala Gly Ile
225                 230

<210> SEQ ID NO 19
<211> LENGTH: 821
<212> TYPE: DNA
<213> ORGANISM: Penicillium wellingtonense
<220> FEATURE:
<221> NAME/KEY: CDS
<222> LOCATION: (1)..(447)
<220> FEATURE:
<221> NAME/KEY: sig_peptide
<222> LOCATION: (1)..(63)
<220> FEATURE:
<221> NAME/KEY: mat_peptide
<222> LOCATION: (64)..(818)
<220> FEATURE:
<221> NAME/KEY: CDS
<222> LOCATION: (513)..(818)

<400> SEQUENCE: 19 atg cct ttg aca aaa ttt ctc ccc gtc ctc gcc ctc tcc ctc cta aca      48
Met Pro Leu Thr Lys Phe Leu Pro Val Leu Ala Leu Ser Leu Leu Thr
    -20                 -15                 -10 ccc ttc gca acc gcc tac ccc ata act ggc gac gtg gta aac tgc cgc      96
Pro Phe Ala Thr Ala Tyr Pro Ile Thr Gly Asp Val Val Asn Cys Arg
-5              -1  1               5                   10 tcc ggc cca gga acc acc tac gac gtc gtc aaa tcc tac aaa cta aac     144
Ser Gly Pro Gly Thr Thr Tyr Asp Val Val Lys Ser Tyr Lys Leu Asn
                15                  20                  25 gcc gat gtc tcg att aca tgc caa gca ccc ggc acc gat gtc aag ggt     192
Ala Asp Val Ser Ile Thr Cys Gln Ala Pro Gly Thr Asp Val Lys Gly
            30                  35                  40 gat tcg gtc tgg gac aag acc gcc gac ggc tgc tat gtt gcg gat tac     240
Asp Ser Val Trp Asp Lys Thr Ala Asp Gly Cys Tyr Val Ala Asp Tyr
        45                  50                  55 tac gtg aaa acc ggt agc agc agc tac gtg aca acg aag tgt ggt ggt     288
Tyr Val Lys Thr Gly Ser Ser Ser Tyr Val Thr Thr Lys Cys Gly Gly
60                  65                  70                  75 gat gac gac ggc ggt gat aat gat ggt ggt agt tcc gga aat ctt ccc     336
Asp Asp Asp Gly Gly Asp Asn Asp Gly Gly Ser Ser Gly Asn Leu Pro
                80                  85                  90 ggt ctg aca tcg act cag tcc aag cat gcg aag gat atc att gcc gag     384
Gly Leu Thr Ser Thr Gln Ser Lys His Ala Lys Asp Ile Ile Ala Glu
            95                  100                 105 gcg aag agt gag gat ctt ggg cgg cag gga tgt ctg gct ggt att gct     432
Ala Lys Ser Glu Asp Leu Gly Arg Gln Gly Cys Leu Ala Gly Ile Ala
        110                 115                 120 act gct att gtt gag gtgagcagcc ccttcgcatt ttctttcttg tcctttcacc      487
Thr Ala Ile Val Glu
        125
```

```
ggatattcag ctctaacgca ttcag tca aat atc ctc ata tac gct aac agt       539
                            Ser Asn Ile Leu Ile Tyr Ala Asn Ser
                                130                 135 ggc gtc ccc gag tct ctg aaa tac ccg cat gac gca gtc ggt tct gat       587
Gly Val Pro Glu Ser Leu Lys Tyr Pro His Asp Ala Val Gly Ser Asp
        140                 145                 150 cac gat agt gtc ggg att ttc cag cag cgc gct atg ttt tat aag gat       635
His Asp Ser Val Gly Ile Phe Gln Gln Arg Ala Met Phe Tyr Lys Asp
        155                 160                 165 att gcg gct gat atg gat gcg ggt aaa tct gct ggg caa ttt ttt ggg       683
Ile Ala Ala Asp Met Asp Ala Gly Lys Ser Ala Gly Gln Phe Phe Gly
170                 175                 180                 185 aaa atg aag gct gtt agt ggg tgg aag agt atg gat gtg ggc act ttg       731
Lys Met Lys Ala Val Ser Gly Trp Lys Ser Met Asp Val Gly Thr Leu
                190                 195                 200 tgt cag aag gtg cag ggt tct gct tat cct tcg agg tat gcg gag cag       779
Cys Gln Lys Val Gln Gly Ser Ala Tyr Pro Ser Arg Tyr Ala Glu Gln
            205                 210                 215 gtg tcg aag gct gag aag att tgt aag gcg ggt ggg ctt tga               821
Val Ser Lys Ala Glu Lys Ile Cys Lys Ala Gly Gly Leu
        220                 225                 230

<210> SEQ ID NO 20
<211> LENGTH: 251
<212> TYPE: PRT
<213> ORGANISM: Penicillium wellingtonense

<400> SEQUENCE: 20

Met Pro Leu Thr Lys Phe Leu Pro Val Leu Ala Leu Ser Leu Leu Thr
        -20                 -15                 -10

Pro Phe Ala Thr Ala Tyr Pro Ile Thr Gly Asp Val Val Asn Cys Arg
 -5              -1  1               5                  10

Ser Gly Pro Gly Thr Thr Tyr Asp Val Val Lys Ser Tyr Lys Leu Asn
                15                  20                  25

Ala Asp Val Ser Ile Thr Cys Gln Ala Pro Gly Thr Asp Val Lys Gly
                30                  35                  40

Asp Ser Val Trp Asp Lys Thr Ala Asp Gly Cys Tyr Val Ala Asp Tyr
            45                  50                  55

Tyr Val Lys Thr Gly Ser Ser Ser Tyr Val Thr Thr Lys Cys Gly Gly
60                  65                  70                  75

Asp Asp Asp Gly Gly Asp Asn Asp Gly Gly Ser Gly Asn Leu Pro
                80                  85                  90

Gly Leu Thr Ser Thr Gln Ser Lys His Ala Lys Asp Ile Ile Ala Glu
            95                  100                 105

Ala Lys Ser Glu Asp Leu Gly Arg Gln Gly Cys Leu Ala Gly Ile Ala
        110                 115                 120

Thr Ala Ile Val Glu Ser Asn Ile Leu Ile Tyr Ala Asn Ser Gly Val
        125                 130                 135

Pro Glu Ser Leu Lys Tyr Pro His Asp Ala Val Gly Ser Asp His Asp
140                 145                 150                 155

Ser Val Gly Ile Phe Gln Gln Arg Ala Met Phe Tyr Lys Asp Ile Ala
                160                 165                 170

Ala Asp Met Asp Ala Gly Lys Ser Ala Gly Gln Phe Phe Gly Lys Met
            175                 180                 185

Lys Ala Val Ser Gly Trp Lys Ser Met Asp Val Gly Thr Leu Cys Gln
        190                 195                 200
```

Lys Val Gln Gly Ser Ala Tyr Pro Ser Arg Tyr Ala Glu Gln Val Ser
    205                 210                 215

Lys Ala Glu Lys Ile Cys Lys Ala Gly Gly Leu
220                 225                 230

<210> SEQ ID NO 21
<211> LENGTH: 230
<212> TYPE: PRT
<213> ORGANISM: Penicillium wellingtonense
<220> FEATURE:
<221> NAME/KEY: mat_peptide
<222> LOCATION: (1)..(230)

<400> SEQUENCE: 21

Tyr Pro Ile Thr Gly Asp Val Val Asn Cys Arg Ser Gly Pro Gly Thr
1               5                   10                  15

Thr Tyr Asp Val Val Lys Ser Tyr Lys Leu Asn Ala Asp Val Ser Ile
            20                  25                  30

Thr Cys Gln Ala Pro Gly Thr Asp Val Lys Gly Asp Ser Val Trp Asp
        35                  40                  45

Lys Thr Ala Asp Gly Cys Tyr Val Ala Asp Tyr Val Lys Thr Gly
    50                  55                  60

Ser Ser Ser Tyr Val Thr Thr Lys Cys Gly Gly Asp Asp Gly Gly
65                  70                  75                  80

Asp Asn Asp Gly Gly Ser Ser Gly Asn Leu Pro Gly Leu Thr Ser Thr
                85                  90                  95

Gln Ser Lys His Ala Lys Asp Ile Ile Ala Glu Ala Lys Ser Glu Asp
            100                 105                 110

Leu Gly Arg Gln Gly Cys Leu Ala Gly Ile Ala Thr Ala Ile Val Glu
        115                 120                 125

Ser Asn Ile Leu Ile Tyr Ala Asn Ser Gly Val Pro Glu Ser Leu Lys
    130                 135                 140

Tyr Pro His Asp Ala Val Gly Ser Asp His Asp Ser Val Gly Ile Phe
145                 150                 155                 160

Gln Gln Arg Ala Met Phe Tyr Lys Asp Ile Ala Ala Asp Met Asp Ala
                165                 170                 175

Gly Lys Ser Ala Gly Gln Phe Phe Gly Lys Met Lys Ala Val Ser Gly
            180                 185                 190

Trp Lys Ser Met Asp Val Gly Thr Leu Cys Gln Lys Val Gln Gly Ser
        195                 200                 205

Ala Tyr Pro Ser Arg Tyr Ala Glu Gln Val Ser Lys Ala Glu Lys Ile
    210                 215                 220

Cys Lys Ala Gly Gly Leu
225                 230

<210> SEQ ID NO 22
<211> LENGTH: 817
<212> TYPE: DNA
<213> ORGANISM: Penicillium roseopurpureum
<220> FEATURE:
<221> NAME/KEY: CDS
<222> LOCATION: (1)..(456)
<220> FEATURE:
<221> NAME/KEY: sig_peptide
<222> LOCATION: (1)..(66)
<220> FEATURE:
<221> NAME/KEY: mat_peptide
<222> LOCATION: (67)..(814)
<220> FEATURE:
<221> NAME/KEY: CDS
<222> LOCATION: (509)..(814)

```
<400> SEQUENCE: 22 atg cct tcc acc aag ttc ctg ccc ttc gtc gcc atc gct ctc atc gct      48
Met Pro Ser Thr Lys Phe Leu Pro Phe Val Ala Ile Ala Leu Ile Ala
        -20                 -15                 -10 gcg cct ctc tcc agc gca tac ccc atc acc ggc gat gtc gtg aac tgt      96
Ala Pro Leu Ser Ser Ala Tyr Pro Ile Thr Gly Asp Val Val Asn Cys
    -5                  -1   1               5                  10 cgc tcc ggg ccc ggt acc agc tac gat gta gtc aag tcc tac aag ctg     144
Arg Ser Gly Pro Gly Thr Ser Tyr Asp Val Val Lys Ser Tyr Lys Leu
                15                  20                  25 gac tcc gat gtc aca atc aag tgc caa gca tct gga acc gat gtc aag     192
Asp Ser Asp Val Thr Ile Lys Cys Gln Ala Ser Gly Thr Asp Val Lys
            30                  35                  40 ggc gac agt atc tgg gac aag acc tcc gac ggc tgc tat gtc gcg gac     240
Gly Asp Ser Ile Trp Asp Lys Thr Ser Asp Gly Cys Tyr Val Ala Asp
        45                  50                  55 tac tac gtg aag acc ggc agc agc agc tac gtt acg acc aag tgt gat     288
Tyr Tyr Val Lys Thr Gly Ser Ser Ser Tyr Val Thr Thr Lys Cys Asp
    60                  65                  70 gac aac gga ggc gat gat gat gat gat gaa ggt ggc agc tcg ggt gga     336
Asp Asn Gly Gly Asp Asp Asp Asp Asp Glu Gly Gly Ser Ser Gly Gly
75                  80                  85                  90 aac ttg ccc ggt cta acc tcc acc cag tcg aag cat gcg aag gaa atc     384
Asn Leu Pro Gly Leu Thr Ser Thr Gln Ser Lys His Ala Lys Glu Ile
                95                  100                 105 att gcc gaa gca aag agc gag aat cta gga cat cga gga tgc acc gct     432
Ile Ala Glu Ala Lys Ser Glu Asn Leu Gly His Arg Gly Cys Thr Ala
            110                 115                 120 ggt att gcg act gcg atc gtt gag gtaagacact cctcgtgaat aatattaaaa    486
Gly Ile Ala Thr Ala Ile Val Glu
            125                 130 aatcacctct gacattttct ag tca aat att cta atc tac gcc aat aac gcc    538
                        Ser Asn Ile Leu Ile Tyr Ala Asn Asn Ala
                                            135                 140 gtt ccc gag tct ctg aaa tac ccc cac gat aag gtg ggc tct gac cac     586
Val Pro Glu Ser Leu Lys Tyr Pro His Asp Lys Val Gly Ser Asp His
                145                 150                 155 gac agc gtc ggc atc ttc cag cag cgc gcc atg ttc tac aag gat att     634
Asp Ser Val Gly Ile Phe Gln Gln Arg Ala Met Phe Tyr Lys Asp Ile
            160                 165                 170 gcg gct gat atg gat gct ggc aag tct gct gct caa ttc ttt gag aag     682
Ala Ala Asp Met Asp Ala Gly Lys Ser Ala Ala Gln Phe Phe Glu Lys
        175                 180                 185 atg acg gct atc agc ggg tgg aag agt atg gat gtt ggt act ttg tgc     730
Met Thr Ala Ile Ser Gly Trp Lys Ser Met Asp Val Gly Thr Leu Cys
    190                 195                 200 cag aag gtg cag ggc tcc gct tat cct act cgg tat gct gag cag gtt     778
Gln Lys Val Gln Gly Ser Ala Tyr Pro Thr Arg Tyr Ala Glu Gln Val
205                 210                 215                 220 tca aag gcc gag aag att tgc tct gca ggt ggt ctt tga                 817
Ser Lys Ala Glu Lys Ile Cys Ser Ala Gly Gly Leu
                225                 230

<210> SEQ ID NO 23
<211> LENGTH: 254
<212> TYPE: PRT
<213> ORGANISM: Penicillium roseopurpureum
```

<400> SEQUENCE: 23

Met Pro Ser Thr Lys Phe Leu Pro Phe Val Ala Ile Ala Leu Ile Ala
    -20             -15                 -10

Ala Pro Leu Ser Ser Ala Tyr Pro Ile Thr Gly Asp Val Val Asn Cys
    -5              -1   1              5                    10

Arg Ser Gly Pro Gly Thr Ser Tyr Asp Val Lys Ser Tyr Lys Leu
            15                  20                  25

Asp Ser Asp Val Thr Ile Lys Cys Gln Ala Ser Gly Thr Asp Val Lys
            30                  35                  40

Gly Asp Ser Ile Trp Asp Lys Thr Ser Asp Gly Cys Tyr Val Ala Asp
            45                  50                  55

Tyr Tyr Val Lys Thr Gly Ser Ser Tyr Val Thr Thr Lys Cys Asp
            60                  65                  70

Asp Asn Gly Gly Asp Asp Asp Asp Glu Gly Gly Ser Ser Gly Gly
75                  80                  85                  90

Asn Leu Pro Gly Leu Thr Ser Thr Gln Ser Lys His Ala Lys Glu Ile
                95                  100                 105

Ile Ala Glu Ala Lys Ser Glu Asn Leu Gly His Arg Gly Cys Thr Ala
            110                 115                 120

Gly Ile Ala Thr Ala Ile Val Glu Ser Asn Ile Leu Ile Tyr Ala Asn
            125                 130                 135

Asn Ala Val Pro Glu Ser Leu Lys Tyr Pro His Asp Lys Val Gly Ser
140                 145                 150

Asp His Asp Ser Val Gly Ile Phe Gln Gln Arg Ala Met Phe Tyr Lys
155                 160                 165                 170

Asp Ile Ala Ala Asp Met Asp Ala Gly Lys Ser Ala Ala Gln Phe Phe
                175                 180                 185

Glu Lys Met Thr Ala Ile Ser Gly Trp Lys Ser Met Asp Val Gly Thr
            190                 195                 200

Leu Cys Gln Lys Val Gln Gly Ser Ala Tyr Pro Thr Arg Tyr Ala Glu
            205                 210                 215

Gln Val Ser Lys Ala Glu Lys Ile Cys Ser Ala Gly Gly Leu
    220                 225                 230

<210> SEQ ID NO 24
<211> LENGTH: 232
<212> TYPE: PRT
<213> ORGANISM: Penicillium roseopurpureum
<220> FEATURE:
<221> NAME/KEY: mat_peptide
<222> LOCATION: (1)..(232)

<400> SEQUENCE: 24

Tyr Pro Ile Thr Gly Asp Val Val Asn Cys Arg Ser Gly Pro Gly Thr
1               5                   10                  15

Ser Tyr Asp Val Val Lys Ser Tyr Lys Leu Asp Ser Asp Val Thr Ile
            20                  25                  30

Lys Cys Gln Ala Ser Gly Thr Asp Val Lys Gly Asp Ser Ile Trp Asp
            35                  40                  45

Lys Thr Ser Asp Gly Cys Tyr Val Ala Asp Tyr Tyr Val Lys Thr Gly
    50                  55                  60

Ser Ser Ser Tyr Val Thr Thr Lys Cys Asp Asp Asn Gly Gly Asp Asp
65                  70                  75                  80

Asp Asp Asp Glu Gly Gly Ser Ser Gly Gly Asn Leu Pro Gly Leu Thr
                85                  90                  95

```
Ser Thr Gln Ser Lys His Ala Lys Glu Ile Ile Ala Glu Ala Lys Ser
            100                 105                 110

Glu Asn Leu Gly His Arg Gly Cys Thr Ala Gly Ile Ala Thr Ala Ile
        115                 120                 125

Val Glu Ser Asn Ile Leu Ile Tyr Ala Asn Asn Ala Val Pro Glu Ser
    130                 135                 140

Leu Lys Tyr Pro His Asp Lys Val Gly Ser Asp His Asp Ser Val Gly
145                 150                 155                 160

Ile Phe Gln Gln Arg Ala Met Phe Tyr Lys Asp Ile Ala Ala Asp Met
                165                 170                 175

Asp Ala Gly Lys Ser Ala Ala Gln Phe Phe Glu Lys Met Thr Ala Ile
            180                 185                 190

Ser Gly Trp Lys Ser Met Asp Val Gly Thr Leu Cys Gln Lys Val Gln
        195                 200                 205

Gly Ser Ala Tyr Pro Thr Arg Tyr Ala Glu Gln Val Ser Lys Ala Glu
    210                 215                 220

Lys Ile Cys Ser Ala Gly Gly Leu
225                 230

<210> SEQ ID NO 25
<211> LENGTH: 810
<212> TYPE: DNA
<213> ORGANISM: Penicillium virgatum
<220> FEATURE:
<221> NAME/KEY: CDS
<222> LOCATION: (1)..(438)
<220> FEATURE:
<221> NAME/KEY: sig_peptide
<222> LOCATION: (1)..(60)
<220> FEATURE:
<221> NAME/KEY: mat_peptide
<222> LOCATION: (61)..(807)
<220> FEATURE:
<221> NAME/KEY: CDS
<222> LOCATION: (502)..(807)

<400> SEQUENCE: 25 atg atg ttc act cct ctt ttg gct ctt act ttt gcc gcc atc gcg ccg       48
Met Met Phe Thr Pro Leu Leu Ala Leu Thr Phe Ala Ala Ile Ala Pro
-20                 -15                 -10                 -5 att gtc aat gct tat cct atc acc ggc gac ggt gtc aat tgc cgc tct       96
Ile Val Asn Ala Tyr Pro Ile Thr Gly Asp Gly Val Asn Cys Arg Ser
        -1  1                 5                  10 ggt cct gga acc tcc tat tct gta gtc aag agc tac cag aag gga gcc      144
Gly Pro Gly Thr Ser Tyr Ser Val Val Lys Ser Tyr Gln Lys Gly Ala
            15                 20                  25 gat gtt gca att acg tgc caa gca cct ggc act gat gtc aaa ggt gac      192
Asp Val Ala Ile Thr Cys Gln Ala Pro Gly Thr Asp Val Lys Gly Asp
    30                  35                  40 aac atc tgg gac aag act gcc gac ggc tgc tat gtt gcc gac tac tat      240
Asn Ile Trp Asp Lys Thr Ala Asp Gly Cys Tyr Val Ala Asp Tyr Tyr
45                  50                  55                  60 atc aaa act gga agc agt agc tac gtt act gcg aaa tgc gat gac agc      288
Ile Lys Thr Gly Ser Ser Ser Tyr Val Thr Ala Lys Cys Asp Asp Ser
                65                  70                  75 ggg agc ggc agt gga ggc gac agc agt gga aac ctc cct ggt ttg acg      336
Gly Ser Gly Ser Gly Gly Asp Ser Ser Gly Asn Leu Pro Gly Leu Thr
            80                  85                  90 tcc act cag tcc aag cat gca aag gcc att atc ggt gaa gcg aag aaa      384
Ser Thr Gln Ser Lys His Ala Lys Ala Ile Ile Gly Glu Ala Lys Lys
        95                  100                 105
```

```
gaa gac ctg ggc cgc cag ggc tgt ctt gct ggt atc gca act gca ctt    432
Glu Asp Leu Gly Arg Gln Gly Cys Leu Ala Gly Ile Ala Thr Ala Leu
        110                 115                 120 gta gag gtaagcttca acgaagatac ttaatccagg tatgtttaat tagatactga     488
Val Glu
125 ctgacgatca cag tct aat atc tac atc tat gcc aac aaa aag gtg ccc    537
            Ser Asn Ile Tyr Ile Tyr Ala Asn Lys Lys Val Pro
                    130                 135 tcg tcc ctt aac tac ccg cac gac aag gtc ggc tcc gat tac gac agc   585
Ser Ser Leu Asn Tyr Pro His Asp Lys Val Gly Ser Asp Tyr Asp Ser
        140                 145                 150 gtg ggc atc ttc cag cag cgt gcc gtt tac tat ccc aac atc gct gcc   633
Val Gly Ile Phe Gln Gln Arg Ala Val Tyr Tyr Pro Asn Ile Ala Ala
155                 160                 165                 170 gat atg gat gcc gca aag tca gct gga cag ttc ttt gcc aag atg aag   681
Asp Met Asp Ala Ala Lys Ser Ala Gly Gln Phe Phe Ala Lys Met Lys
                175                 180                 185 ggt atc agt ggt tgg aag tcc atg gag gtt ggt aag ctt tgc cag aag   729
Gly Ile Ser Gly Trp Lys Ser Met Glu Val Gly Lys Leu Cys Gln Lys
            190                 195                 200 gtg caa ggc tcg gcg tac cct acc cga tat gcg gaa cgt ctt tct gag   777
Val Gln Gly Ser Ala Tyr Pro Thr Arg Tyr Ala Glu Arg Leu Ser Glu
        205                 210                 215 gcg aag aag att tgt gct gct ggt ggc ttg taa                       810
Ala Lys Lys Ile Cys Ala Ala Gly Gly Leu
220                 225

<210> SEQ ID NO 26
<211> LENGTH: 248
<212> TYPE: PRT
<213> ORGANISM: Penicillium virgatum

<400> SEQUENCE: 26

Met Met Phe Thr Pro Leu Leu Ala Leu Thr Phe Ala Ala Ile Ala Pro
-20                 -15                 -10                 -5

Ile Val Asn Ala Tyr Pro Ile Thr Gly Asp Gly Val Asn Cys Arg Ser
        -1  1               5                   10

Gly Pro Gly Thr Ser Tyr Ser Val Lys Ser Tyr Gln Lys Gly Ala
            15                  20                  25

Asp Val Ala Ile Thr Cys Gln Ala Pro Gly Thr Asp Val Lys Gly Asp
30                  35                  40

Asn Ile Trp Asp Lys Thr Ala Asp Gly Cys Tyr Val Ala Asp Tyr Tyr
45                  50                  55                  60

Ile Lys Thr Gly Ser Ser Ser Tyr Val Thr Ala Lys Cys Asp Asp Ser
            65                  70                  75

Gly Ser Gly Ser Gly Gly Asp Ser Ser Gly Asn Leu Pro Gly Leu Thr
            80                  85                  90

Ser Thr Gln Ser Lys His Ala Lys Ala Ile Gly Glu Ala Lys Lys
            95                  100                 105

Glu Asp Leu Gly Arg Gln Gly Cys Leu Ala Gly Ile Ala Thr Ala Leu
        110                 115                 120

Val Glu Ser Asn Ile Tyr Ile Tyr Ala Asn Lys Lys Val Pro Ser Ser
125                 130                 135                 140

Leu Asn Tyr Pro His Asp Lys Val Gly Ser Asp Tyr Asp Ser Val Gly
                145                 150                 155

Ile Phe Gln Gln Arg Ala Val Tyr Tyr Pro Asn Ile Ala Ala Asp Met
            160                 165                 170
```

```
Asp Ala Ala Lys Ser Ala Gly Gln Phe Phe Ala Lys Met Lys Gly Ile
            175                 180                 185

Ser Gly Trp Lys Ser Met Glu Val Gly Lys Leu Cys Gln Lys Val Gln
        190                 195                 200

Gly Ser Ala Tyr Pro Thr Arg Tyr Ala Glu Arg Leu Ser Glu Ala Lys
205                 210                 215                 220

Lys Ile Cys Ala Ala Gly Gly Leu
                225
```

<210> SEQ ID NO 27
<211> LENGTH: 228
<212> TYPE: PRT
<213> ORGANISM: Penicillium virgatum
<220> FEATURE:
<221> NAME/KEY: mat_peptide
<222> LOCATION: (1)..(228)

<400> SEQUENCE: 27

```
Tyr Pro Ile Thr Gly Asp Gly Val Asn Cys Arg Ser Gly Pro Gly Thr
1               5                   10                  15

Ser Tyr Ser Val Val Lys Ser Tyr Gln Lys Gly Ala Asp Val Ala Ile
            20                  25                  30

Thr Cys Gln Ala Pro Gly Thr Asp Val Lys Gly Asp Asn Ile Trp Asp
        35                  40                  45

Lys Thr Ala Asp Gly Cys Tyr Val Ala Asp Tyr Ile Lys Thr Gly
    50                  55                  60

Ser Ser Ser Tyr Val Thr Ala Lys Cys Asp Asp Ser Gly Ser Gly Ser
65                  70                  75                  80

Gly Gly Asp Ser Ser Gly Asn Leu Pro Gly Leu Thr Ser Thr Gln Ser
                85                  90                  95

Lys His Ala Lys Ala Ile Ile Gly Glu Ala Lys Lys Glu Asp Leu Gly
            100                 105                 110

Arg Gln Gly Cys Leu Ala Gly Ile Ala Thr Ala Leu Val Glu Ser Asn
        115                 120                 125

Ile Tyr Ile Tyr Ala Asn Lys Lys Val Pro Ser Ser Leu Asn Tyr Pro
    130                 135                 140

His Asp Lys Val Gly Ser Asp Tyr Asp Ser Val Gly Ile Phe Gln Gln
145                 150                 155                 160

Arg Ala Val Tyr Tyr Pro Asn Ile Ala Ala Asp Met Asp Ala Ala Lys
                165                 170                 175

Ser Ala Gly Gln Phe Phe Ala Lys Met Lys Gly Ile Ser Gly Trp Lys
            180                 185                 190

Ser Met Glu Val Gly Lys Leu Cys Gln Lys Val Gln Gly Ser Ala Tyr
        195                 200                 205

Pro Thr Arg Tyr Ala Glu Arg Leu Ser Glu Ala Lys Lys Ile Cys Ala
    210                 215                 220

Ala Gly Gly Leu
225
```

<210> SEQ ID NO 28
<211> LENGTH: 809
<212> TYPE: DNA
<213> ORGANISM: Aspergillus niveus
<220> FEATURE:
<221> NAME/KEY: CDS
<222> LOCATION: (1)..(438)
<220> FEATURE:
<221> NAME/KEY: sig_peptide
<222> LOCATION: (1)..(60)

<220> FEATURE:
<221> NAME/KEY: mat_peptide
<222> LOCATION: (61)..(806)
<220> FEATURE:
<221> NAME/KEY: CDS
<222> LOCATION: (501)..(806)

<400> SEQUENCE: 28

| atg | ctg | tat | ctt | ttt | ctc | act | gcc | ctt | tcg | ttt | gct | gcc | act | gct | ccc | 48 |
|---|---|---|---|---|---|---|---|---|---|---|---|---|---|---|---|---|
| Met | Leu | Tyr | Leu | Phe | Leu | Thr | Ala | Leu | Ser | Phe | Ala | Ala | Thr | Ala | Pro | |
| -20 | | | | -15 | | | | | -10 | | | | | -5 | | |

| ctg | gta | ggc | gca | tat | ccc | att | act | ggt | gat | gga | gta | aac | tgc | cgt | tct | 96 |
|---|---|---|---|---|---|---|---|---|---|---|---|---|---|---|---|---|
| Leu | Val | Gly | Ala | Tyr | Pro | Ile | Thr | Gly | Asp | Gly | Val | Asn | Cys | Arg | Ser | |
| | | | -1 | 1 | | | 5 | | | | | 10 | | | | |

| ggt | cct | ggt | aca | agc | cat | gcc | gtg | gtc | aag | tcc | tac | ccc | aag | ggc | cac | 144 |
|---|---|---|---|---|---|---|---|---|---|---|---|---|---|---|---|---|
| Gly | Pro | Gly | Thr | Ser | His | Ala | Val | Val | Lys | Ser | Tyr | Pro | Lys | Gly | His | |
| | | | 15 | | | | | 20 | | | | | 25 | | | |

| gag | ata | tcc | att | gtc | tgc | caa | gct | gcc | gga | acc | gac | gtc | aag | gga | gat | 192 |
|---|---|---|---|---|---|---|---|---|---|---|---|---|---|---|---|---|
| Glu | Ile | Ser | Ile | Val | Cys | Gln | Ala | Ala | Gly | Thr | Asp | Val | Lys | Gly | Asp | |
| | 30 | | | | | 35 | | | | | 40 | | | | | |

| gat | ctc | tgg | gat | aag | acg | tct | gac | ggc | tgc | tac | gtc | gcc | gat | tac | tac | 240 |
|---|---|---|---|---|---|---|---|---|---|---|---|---|---|---|---|---|
| Asp | Leu | Trp | Asp | Lys | Thr | Ser | Asp | Gly | Cys | Tyr | Val | Ala | Asp | Tyr | Tyr | |
| 45 | | | | | 50 | | | | | 55 | | | | | 60 | |

| gtg | aag | act | ggg | acg | acc | ggc | tat | gtc | acc | aag | cac | tgc | gat | ggc | ggc | 288 |
|---|---|---|---|---|---|---|---|---|---|---|---|---|---|---|---|---|
| Val | Lys | Thr | Gly | Thr | Thr | Gly | Tyr | Val | Thr | Lys | His | Cys | Asp | Gly | Gly | |
| | | | | 65 | | | | | 70 | | | | | 75 | | |

| agt | gat | ggt | ggc | agc | agt | ggc | ggc | agc | ggc | aat | ctt | cct | ggc | ctc | act | 336 |
|---|---|---|---|---|---|---|---|---|---|---|---|---|---|---|---|---|
| Ser | Asp | Gly | Gly | Ser | Ser | Gly | Gly | Ser | Gly | Asn | Leu | Pro | Gly | Leu | Thr | |
| | | | | 80 | | | | | 85 | | | | | 90 | | |

| gcc | act | cag | tcc | tct | cac | gcc | cat | aag | att | att | ggc | gaa | gca | aag | aag | 384 |
|---|---|---|---|---|---|---|---|---|---|---|---|---|---|---|---|---|
| Ala | Thr | Gln | Ser | Ser | His | Ala | His | Lys | Ile | Ile | Gly | Glu | Ala | Lys | Lys | |
| | | | 95 | | | | | 100 | | | | | 105 | | | |

| gaa | ggc | ctg | ggt | cgt | caa | ggt | tgt | ctg | gct | ggt | att | gca | act | gct | ttg | 432 |
|---|---|---|---|---|---|---|---|---|---|---|---|---|---|---|---|---|
| Glu | Gly | Leu | Gly | Arg | Gln | Gly | Cys | Leu | Ala | Gly | Ile | Ala | Thr | Ala | Leu | |
| | | | 110 | | | | | 115 | | | | | 120 | | | |

| gtc | gag | gtgagtcgct | ccgagctttt | ctccttccat | ttgggtactg | tactgacggt | | 488 |
|---|---|---|---|---|---|---|---|---|
| Val | Glu | | | | | | | |
| 125 | | | | | | | | |

| gaacgtgtat | ag | tcc | aac | atc | tta | gtt | tat | gcc | aac | agc | aag | gtc | ccg | gcg | 539 |
|---|---|---|---|---|---|---|---|---|---|---|---|---|---|---|---|
| | | Ser | Asn | Ile | Leu | Val | Tyr | Ala | Asn | Ser | Lys | Val | Pro | Ala | |
| | | | | 130 | | | | | 135 | | | | | | |

| tct | ctc | aac | tac | cct | cat | gac | gcc | gtc | ggc | cac | gac | tac | gac | agc | gtt | 587 |
|---|---|---|---|---|---|---|---|---|---|---|---|---|---|---|---|---|
| Ser | Leu | Asn | Tyr | Pro | His | Asp | Ala | Val | Gly | His | Asp | Tyr | Asp | Ser | Val | |
| 140 | | | | | 145 | | | | | 150 | | | | | 155 | |

| ggc | atc | ttc | cag | cag | cgt | gct | gtc | tac | tat | ccc | gac | atc | gcc | gcc | gat | 635 |
|---|---|---|---|---|---|---|---|---|---|---|---|---|---|---|---|---|
| Gly | Ile | Phe | Gln | Gln | Arg | Ala | Val | Tyr | Tyr | Pro | Asp | Ile | Ala | Ala | Asp | |
| | | | | 160 | | | | | 165 | | | | | 170 | | |

| atg | gac | ccc | gca | cgt | tct | gcc | gct | cag | ttc | ttt | gcc | aag | atg | aag | aat | 683 |
|---|---|---|---|---|---|---|---|---|---|---|---|---|---|---|---|---|
| Met | Asp | Pro | Ala | Arg | Ser | Ala | Ala | Gln | Phe | Phe | Ala | Lys | Met | Lys | Asn | |
| | | | 175 | | | | | 180 | | | | | 185 | | | |

| atc | agc | ggc | tgg | aag | acg | atg | gat | gtt | ggc | aag | ctt | tgc | cag | aag | gtg | 731 |
|---|---|---|---|---|---|---|---|---|---|---|---|---|---|---|---|---|
| Ile | Ser | Gly | Trp | Lys | Thr | Met | Asp | Val | Gly | Lys | Leu | Cys | Gln | Lys | Val | |
| | | 190 | | | | | 195 | | | | | 200 | | | | |

| cag | gtc | tct | gcc | tat | ccc | gat | cgg | tat | gca | gag | cgt | gtt | cct | gct | gcc | 779 |
|---|---|---|---|---|---|---|---|---|---|---|---|---|---|---|---|---|
| Gln | Val | Ser | Ala | Tyr | Pro | Asp | Arg | Tyr | Ala | Glu | Arg | Val | Pro | Ala | Ala | |
| | 205 | | | | | 210 | | | | | 215 | | | | | |

| gaa | aag | atc | tgc | tct | gct | ggg | ggg | cta | tag | | | | | | | 809 |
|---|---|---|---|---|---|---|---|---|---|---|---|---|---|---|---|---|
| Glu | Lys | Ile | Cys | Ser | Ala | Gly | Gly | Leu | | | | | | | | |
| 220 | | | | 225 | | | | | | | | | | | | |

```
<210> SEQ ID NO 29
<211> LENGTH: 248
<212> TYPE: PRT
<213> ORGANISM: Aspergillus niveus

<400> SEQUENCE: 29

Met Leu Tyr Leu Phe Leu Thr Ala Leu Ser Phe Ala Ala Thr Ala Pro
-20             -15                 -10                 -5

Leu Val Gly Ala Tyr Pro Ile Thr Gly Asp Gly Val Asn Cys Arg Ser
            -1  1               5                   10

Gly Pro Gly Thr Ser His Ala Val Val Lys Ser Tyr Pro Lys Gly His
            15                  20                  25

Glu Ile Ser Ile Val Cys Gln Ala Ala Gly Thr Asp Val Lys Gly Asp
    30                  35                  40

Asp Leu Trp Asp Lys Thr Ser Asp Gly Cys Tyr Val Ala Asp Tyr Tyr
45                  50                  55                  60

Val Lys Thr Gly Thr Thr Gly Tyr Val Thr Lys His Cys Asp Gly Gly
                65                  70                  75

Ser Asp Gly Gly Ser Ser Gly Gly Ser Gly Asn Leu Pro Gly Leu Thr
            80                  85                  90

Ala Thr Gln Ser Ser His Ala His Lys Ile Ile Gly Glu Ala Lys Lys
                95                  100                 105

Glu Gly Leu Gly Arg Gln Gly Cys Leu Ala Gly Ile Ala Thr Ala Leu
    110                 115                 120

Val Glu Ser Asn Ile Leu Val Tyr Ala Asn Ser Lys Val Pro Ala Ser
125                 130                 135                 140

Leu Asn Tyr Pro His Asp Ala Val Gly His Asp Tyr Asp Ser Val Gly
                145                 150                 155

Ile Phe Gln Gln Arg Ala Val Tyr Tyr Pro Asp Ile Ala Ala Asp Met
                160                 165                 170

Asp Pro Ala Arg Ser Ala Ala Gln Phe Phe Ala Lys Met Lys Asn Ile
            175                 180                 185

Ser Gly Trp Lys Thr Met Asp Val Gly Lys Leu Cys Gln Lys Val Gln
            190                 195                 200

Val Ser Ala Tyr Pro Asp Arg Tyr Ala Glu Arg Val Pro Ala Ala Glu
205                 210                 215                 220

Lys Ile Cys Ser Ala Gly Gly Leu
                225

<210> SEQ ID NO 30
<211> LENGTH: 228
<212> TYPE: PRT
<213> ORGANISM: Aspergillus niveus
<220> FEATURE:
<221> NAME/KEY: mat_peptide
<222> LOCATION: (1)..(228)

<400> SEQUENCE: 30

Tyr Pro Ile Thr Gly Asp Gly Val Asn Cys Arg Ser Gly Pro Gly Thr
1               5                   10                  15

Ser His Ala Val Val Lys Ser Tyr Pro Lys Gly His Glu Ile Ser Ile
            20                  25                  30

Val Cys Gln Ala Ala Gly Thr Asp Val Lys Gly Asp Asp Leu Trp Asp
        35                  40                  45

Lys Thr Ser Asp Gly Cys Tyr Val Ala Asp Tyr Tyr Val Lys Thr Gly
    50                  55                  60
```

-continued

```
Thr Thr Gly Tyr Val Thr Lys His Cys Asp Gly Gly Ser Asp Gly Gly
 65                  70                  75                  80

Ser Ser Gly Gly Ser Gly Asn Leu Pro Gly Leu Thr Ala Thr Gln Ser
                 85                  90                  95

Ser His Ala His Lys Ile Ile Gly Glu Ala Lys Lys Glu Gly Leu Gly
            100                 105                 110

Arg Gln Gly Cys Leu Ala Gly Ile Ala Thr Ala Leu Val Glu Ser Asn
        115                 120                 125

Ile Leu Val Tyr Ala Asn Ser Lys Val Pro Ala Ser Leu Asn Tyr Pro
    130                 135                 140

His Asp Ala Val Gly His Asp Tyr Asp Ser Val Gly Ile Phe Gln Gln
145                 150                 155                 160

Arg Ala Val Tyr Tyr Pro Asp Ile Ala Ala Asp Met Asp Pro Ala Arg
                165                 170                 175

Ser Ala Ala Gln Phe Phe Ala Lys Met Lys Asn Ile Ser Gly Trp Lys
            180                 185                 190

Thr Met Asp Val Gly Lys Leu Cys Gln Lys Val Gln Val Ser Ala Tyr
        195                 200                 205

Pro Asp Arg Tyr Ala Glu Arg Val Pro Ala Ala Glu Lys Ile Cys Ser
    210                 215                 220

Ala Gly Gly Leu
225

<210> SEQ ID NO 31
<211> LENGTH: 813
<212> TYPE: DNA
<213> ORGANISM: Chaetomium sp. ZY369
<220> FEATURE:
<221> NAME/KEY: CDS
<222> LOCATION: (1)..(429)
<220> FEATURE:
<221> NAME/KEY: sig_peptide
<222> LOCATION: (1)..(57)
<220> FEATURE:
<221> NAME/KEY: mat_peptide
<222> LOCATION: (58)..(810)
<220> FEATURE:
<221> NAME/KEY: CDS
<222> LOCATION: (505)..(810)

<400> SEQUENCE: 31 atg caa ctc tca ctc acg gct ctg gcc ctc gcg gcc gct ctc ccc atg      48
Met Gln Leu Ser Leu Thr Ala Leu Ala Leu Ala Ala Ala Leu Pro Met
                -15                 -10                  -5 gtc agc gcc tac ccc gtc aag gcg gac ttg ctc aac tgc cgc act ggc      96
Val Ser Ala Tyr Pro Val Lys Ala Asp Leu Leu Asn Cys Arg Thr Gly
     -1   1               5                  10 ccc gga acc agc tac gac ctt gtc acg caa tac aag aag ggc acc gac     144
Pro Gly Thr Ser Tyr Asp Leu Val Thr Gln Tyr Lys Lys Gly Thr Asp
         15                  20                  25 gtc aag atc acc tgc cag acc aca ggc acg gtc gtc gag ggt cat aac     192
Val Lys Ile Thr Cys Gln Thr Thr Gly Thr Val Val Glu Gly His Asn
 30                  35                  40                  45 ctc tgg gac aag acc tcg gac ggg tgc tac gtt gcc gac ttc tac atc     240
Leu Trp Asp Lys Thr Ser Asp Gly Cys Tyr Val Ala Asp Phe Tyr Ile
                 50                  55                  60 cag acg ggc act tcc ggc tat gtc gcg gac aaa tgc ggc gag acc ggc     288
Gln Thr Gly Thr Ser Gly Tyr Val Ala Asp Lys Cys Gly Glu Thr Gly
             65                  70                  75
```

```
ggt ggc ggt gac acc ggc ggc aac ctc ccc ggg ctc acc gcg gtg cag        336
Gly Gly Gly Asp Thr Gly Gly Asn Leu Pro Gly Leu Thr Ala Val Gln
         80                  85                  90 tcc agg aac gcc agg gct atc atc ggc gag gcg aag aag gaa ggg ctt        384
Ser Arg Asn Ala Arg Ala Ile Ile Gly Glu Ala Lys Lys Glu Gly Leu
     95                 100                 105 ggc cgc cag ggc tgt gag gcg ggc att gcg acc gcc att gtc gag            429
Gly Arg Gln Gly Cys Glu Ala Gly Ile Ala Thr Ala Ile Val Glu
110             115                 120 gtgagatcca atgacccacg ggactatgaa gcgcttgtgt cactacaagg tgaaccccgt       489
actaacacca cccag tcc aac atc cta att tac gcc aat aag aag gtc aag       540
                Ser Asn Ile Leu Ile Tyr Ala Asn Lys Lys Val Lys
                            125                 130                 135 gag tcg tac aac tac ccg cac gac gcc gtg ggc gag gac cac gac agc        588
Glu Ser Tyr Asn Tyr Pro His Asp Ala Val Gly Glu Asp His Asp Ser
                140                 145                 150 gtc ggc atc ttc cag cag cgc gtg acc ttc tac ccc gac atc gag gcc        636
Val Gly Ile Phe Gln Gln Arg Val Thr Phe Tyr Pro Asp Ile Glu Ala
            155                 160                 165 agc atg gac ccg gcc cgg tcc gcc gcc cag ttt ttc acc gag atg aag        684
Ser Met Asp Pro Ala Arg Ser Ala Ala Gln Phe Phe Thr Glu Met Lys
        170                 175                 180 cgg atc agc ggc tgg aag acc atg gac gtt ggg acg ctg tgc cag aag        732
Arg Ile Ser Gly Trp Lys Thr Met Asp Val Gly Thr Leu Cys Gln Lys
185                 190                 195                 200 gtg cag cgc tcc gcg tac cca gac cgc tat ggc aag cag gtc gac aag        780
Val Gln Arg Ser Ala Tyr Pro Asp Arg Tyr Gly Lys Gln Val Asp Lys
                205                 210                 215 gct ggg aag att tgt gct gct ggc ggt atg taa                            813
Ala Gly Lys Ile Cys Ala Ala Gly Gly Met
            220                 225

<210> SEQ ID NO 32
<211> LENGTH: 245
<212> TYPE: PRT
<213> ORGANISM: Chaetomium sp. ZY369

<400> SEQUENCE: 32

Met Gln Leu Ser Leu Thr Ala Leu Ala Leu Ala Ala Leu Pro Met
                -15                 -10                 -5

Val Ser Ala Tyr Pro Val Lys Ala Asp Leu Leu Asn Cys Arg Thr Gly
    -1   1               5                   10

Pro Gly Thr Ser Tyr Asp Leu Val Thr Gln Tyr Lys Lys Gly Thr Asp
        15                  20                  25

Val Lys Ile Thr Cys Gln Thr Gly Thr Val Val Glu Gly His Asn
 30              35                  40                  45

Leu Trp Asp Lys Thr Ser Asp Gly Cys Tyr Val Ala Asp Phe Tyr Ile
             50                  55                  60

Gln Thr Gly Thr Ser Gly Tyr Val Ala Asp Lys Cys Gly Glu Thr Gly
            65                  70                  75

Gly Gly Gly Asp Thr Gly Gly Asn Leu Pro Gly Leu Thr Ala Val Gln
        80                  85                  90

Ser Arg Asn Ala Arg Ala Ile Ile Gly Glu Ala Lys Lys Glu Gly Leu
    95                 100                 105

Gly Arg Gln Gly Cys Glu Ala Gly Ile Ala Thr Ala Ile Val Glu Ser
110             115                 120                 125

Asn Ile Leu Ile Tyr Ala Asn Lys Lys Val Lys Glu Ser Tyr Asn Tyr
                130                 135                 140
```

```
Pro His Asp Ala Val Gly Glu Asp His Asp Ser Val Gly Ile Phe Gln
            145                 150                 155

Gln Arg Val Thr Phe Tyr Pro Asp Ile Glu Ala Ser Met Asp Pro Ala
        160                 165                 170

Arg Ser Ala Ala Gln Phe Phe Thr Glu Met Lys Arg Ile Ser Gly Trp
    175                 180                 185

Lys Thr Met Asp Val Gly Thr Leu Cys Gln Lys Val Gln Arg Ser Ala
190                 195                 200                 205

Tyr Pro Asp Arg Tyr Gly Lys Gln Val Asp Lys Ala Gly Lys Ile Cys
            210                 215                 220

Ala Ala Gly Gly Met
            225

<210> SEQ ID NO 33
<211> LENGTH: 226
<212> TYPE: PRT
<213> ORGANISM: Chaetomium sp. ZY369
<220> FEATURE:
<221> NAME/KEY: mat_peptide
<222> LOCATION: (1)..(226)

<400> SEQUENCE: 33

Tyr Pro Val Lys Ala Asp Leu Leu Asn Cys Arg Thr Gly Pro Gly Thr
1               5                   10                  15

Ser Tyr Asp Leu Val Thr Gln Tyr Lys Lys Gly Thr Asp Val Lys Ile
            20                  25                  30

Thr Cys Gln Thr Thr Gly Thr Val Val Glu Gly His Asn Leu Trp Asp
        35                  40                  45

Lys Thr Ser Asp Gly Cys Tyr Val Ala Asp Phe Tyr Ile Gln Thr Gly
    50                  55                  60

Thr Ser Gly Tyr Val Ala Asp Lys Cys Gly Glu Thr Gly Gly Gly Gly
65                  70                  75                  80

Asp Thr Gly Gly Asn Leu Pro Gly Leu Thr Ala Val Gln Ser Arg Asn
                85                  90                  95

Ala Arg Ala Ile Ile Gly Glu Ala Lys Lys Glu Gly Leu Gly Arg Gln
            100                 105                 110

Gly Cys Glu Ala Gly Ile Ala Thr Ala Ile Val Glu Ser Asn Ile Leu
        115                 120                 125

Ile Tyr Ala Asn Lys Lys Val Lys Glu Ser Tyr Asn Tyr Pro His Asp
    130                 135                 140

Ala Val Gly Glu Asp His Asp Ser Val Gly Ile Phe Gln Gln Arg Val
145                 150                 155                 160

Thr Phe Tyr Pro Asp Ile Glu Ala Ser Met Asp Pro Ala Arg Ser Ala
                165                 170                 175

Ala Gln Phe Phe Thr Glu Met Lys Arg Ile Ser Gly Trp Lys Thr Met
            180                 185                 190

Asp Val Gly Thr Leu Cys Gln Lys Val Gln Arg Ser Ala Tyr Pro Asp
        195                 200                 205

Arg Tyr Gly Lys Gln Val Asp Lys Ala Gly Lys Ile Cys Ala Ala Gly
    210                 215                 220

Gly Met
225

<210> SEQ ID NO 34
<211> LENGTH: 804
<212> TYPE: DNA
<213> ORGANISM: Talaromyces atricola
```

-continued

```
<220> FEATURE:
<221> NAME/KEY: CDS
<222> LOCATION: (1)..(429)
<220> FEATURE:
<221> NAME/KEY: sig_peptide
<222> LOCATION: (1)..(60)
<220> FEATURE:
<221> NAME/KEY: mat_peptide
<222> LOCATION: (61)..(801)
<220> FEATURE:
<221> NAME/KEY: CDS
<222> LOCATION: (496)..(801)

<400> SEQUENCE: 34
```

| | | | | | | | | | | | | | | | | |
|---|---|---|---|---|---|---|---|---|---|---|---|---|---|---|---|---|
| atg | ttt | gcc | acc | tcg | ctc | att | gca | ctg | tcc | ctc | gcg | aca | att | ctc | ccc | 48 |
| Met | Phe | Ala | Thr | Ser | Leu | Ile | Ala | Leu | Ser | Leu | Ala | Thr | Ile | Leu | Pro | |
| -20 | | | | | -15 | | | | | -10 | | | | | -5 | |

| | | | | | | | | | | | | | | | | |
|---|---|---|---|---|---|---|---|---|---|---|---|---|---|---|---|---|
| atc | tcg | aac | gcg | tat | ccc | att | aag | act | gat | gga | ctt | cac | tgt | cgc | tcg | 96 |
| Ile | Ser | Asn | Ala | Tyr | Pro | Ile | Lys | Thr | Asp | Gly | Leu | His | Cys | Arg | Ser | |
| | | | -1 | 1 | | | | 5 | | | | | 10 | | | |

| | | | | | | | | | | | | | | | | |
|---|---|---|---|---|---|---|---|---|---|---|---|---|---|---|---|---|
| ggg | cct | gga | act | ggt | tat | tca | gtt | gtg | aag | acc | tat | aat | aag | ggt | gaa | 144 |
| Gly | Pro | Gly | Thr | Gly | Tyr | Ser | Val | Val | Lys | Thr | Tyr | Asn | Lys | Gly | Glu | |
| | | 15 | | | | | 20 | | | | | 25 | | | | |

| | | | | | | | | | | | | | | | | |
|---|---|---|---|---|---|---|---|---|---|---|---|---|---|---|---|---|
| gag | gtc | tca | atc | aaa | tgc | cag | gct | cct | gga | acc | aac | atc | aat | gga | gat | 192 |
| Glu | Val | Ser | Ile | Lys | Cys | Gln | Ala | Pro | Gly | Thr | Asn | Ile | Asn | Gly | Asp | |
| 30 | | | | | 35 | | | | | 40 | | | | | | |

| | | | | | | | | | | | | | | | | |
|---|---|---|---|---|---|---|---|---|---|---|---|---|---|---|---|---|
| att | ctc | tgg | gat | ctg | act | gag | aat | ggc | tgt | tat | gtc | gcg | gat | tac | tac | 240 |
| Ile | Leu | Trp | Asp | Leu | Thr | Glu | Asn | Gly | Cys | Tyr | Val | Ala | Asp | Tyr | Tyr | |
| 45 | | | | 50 | | | | | 55 | | | | | 60 | | |

| | | | | | | | | | | | | | | | | |
|---|---|---|---|---|---|---|---|---|---|---|---|---|---|---|---|---|
| gtt | agt | act | ggt | act | agt | ggc | tac | gtc | act | gat | aag | tgt | ggt | agc | agt | 288 |
| Val | Ser | Thr | Gly | Thr | Ser | Gly | Tyr | Val | Thr | Asp | Lys | Cys | Gly | Ser | Ser | |
| | | | | 65 | | | | | 70 | | | | | 75 | | |

| | | | | | | | | | | | | | | | | |
|---|---|---|---|---|---|---|---|---|---|---|---|---|---|---|---|---|
| ggt | ggc | ggt | ggc | agc | gat | gga | gat | ctt | ccg | ggt | ctc | aac | tct | gta | caa | 336 |
| Gly | Gly | Gly | Gly | Ser | Asp | Gly | Asp | Leu | Pro | Gly | Leu | Asn | Ser | Val | Gln | |
| | | 80 | | | | | 85 | | | | | 90 | | | | |

| | | | | | | | | | | | | | | | | |
|---|---|---|---|---|---|---|---|---|---|---|---|---|---|---|---|---|
| tcg | tcc | cac | gcc | cga | gcc | att | atc | gcg | gag | gcc | aag | cag | gag | agt | ctt | 384 |
| Ser | Ser | His | Ala | Arg | Ala | Ile | Ile | Ala | Glu | Ala | Lys | Gln | Glu | Ser | Leu | |
| | | 95 | | | | | 100 | | | | | 105 | | | | |

| | | | | | | | | | | | | |
|---|---|---|---|---|---|---|---|---|---|---|---|---|
| ggt | cac | cag | ggc | tgt | cta | gct | ggc | att | gca | act | gct | ctg | act | gag | | 429 |
| Gly | His | Gln | Gly | Cys | Leu | Ala | Gly | Ile | Ala | Thr | Ala | Leu | Thr | Glu | | |
| | 110 | | | | 115 | | | | | 120 | | | | | | |

| | | | |
|---|---|---|---|
| gtaggcttcg | atcccactcg | tctctaagtg | tctcattttc | agcaaccatt | actaattgag | 489 |

| | | | | | | | | | | | |
|---|---|---|---|---|---|---|---|---|---|---|---|
| ctgcag | tcg | agc | att | tta | gtt | tac | gca | aac | aag | gct | gtt | cca | gct | tcg | 537 |
| | Ser | Ser | Ile | Leu | Val | Tyr | Ala | Asn | Lys | Ala | Val | Pro | Ala | Ser | |
| | | | 125 | | | | | 130 | | | | | 135 | | |

| | | | | | | | | | | | | | | | | |
|---|---|---|---|---|---|---|---|---|---|---|---|---|---|---|---|---|
| atg | aac | tac | aaa | tac | gac | gcg | gtt | ggc | agc | gat | cac | gat | agc | att | ggc | 585 |
| Met | Asn | Tyr | Lys | Tyr | Asp | Ala | Val | Gly | Ser | Asp | His | Asp | Ser | Ile | Gly | |
| | | | 140 | | | | | 145 | | | | | 150 | | | |

| | | | | | | | | | | | | | | | | |
|---|---|---|---|---|---|---|---|---|---|---|---|---|---|---|---|---|
| atc | ttc | caa | caa | cgc | gct | atg | tac | tat | ccc | gat | atc | gct | gcc | gac | atg | 633 |
| Ile | Phe | Gln | Gln | Arg | Ala | Met | Tyr | Tyr | Pro | Asp | Ile | Ala | Ala | Asp | Met | |
| | 155 | | | | | 160 | | | | | 165 | | | | | |

| | | | | | | | | | | | | | | | | |
|---|---|---|---|---|---|---|---|---|---|---|---|---|---|---|---|---|
| gat | cct | gct | aag | tcc | gcc | gca | cag | ttc | ttc | gcc | aag | atg | aag | ggg | gtt | 681 |
| Asp | Pro | Ala | Lys | Ser | Ala | Ala | Gln | Phe | Phe | Ala | Lys | Met | Lys | Gly | Val | |
| 170 | | | | 175 | | | | | 180 | | | | | 185 | | |

| | | | | | | | | | | | | | | | | |
|---|---|---|---|---|---|---|---|---|---|---|---|---|---|---|---|---|
| agt | gga | tgg | caa | acc | atg | gat | gtt | ggt | gac | cta | tgc | cag | aag | gtt | caa | 729 |
| Ser | Gly | Trp | Gln | Thr | Met | Asp | Val | Gly | Asp | Leu | Cys | Gln | Lys | Val | Gln | |
| | | | 190 | | | | | 195 | | | | | 200 | | | |

| | | | | | | | | | | | | | | | |
|---|---|---|---|---|---|---|---|---|---|---|---|---|---|---|---|
| gga | tct | gct | tat | ccg | acc | cga | tat | gaa | cag | cat | ttg | tcc | gct | gct | aaa | 777
| Gly | Ser | Ala | Tyr | Pro | Thr | Arg | Tyr | Glu | Gln | His | Leu | Ser | Ala | Ala | Lys |
| | | | 205 | | | | | 210 | | | | | 215 | | |

| | | | | | | | |
|---|---|---|---|---|---|---|---|
| tcg | atc | tgc | tct | gct | gat | agt | gat | taa | 804
| Ser | Ile | Cys | Ser | Ala | Asp | Ser | Asp |
| 220 | | | | | | | 225 |

<210> SEQ ID NO 35
<211> LENGTH: 245
<212> TYPE: PRT
<213> ORGANISM: Talaromyces atricola

<400> SEQUENCE: 35

Met Phe Ala Thr Ser Leu Ile Ala Leu Ser Leu Ala Thr Ile Leu Pro
-20                 -15                 -10                 -5

Ile Ser Asn Ala Tyr Pro Ile Lys Thr Asp Gly Leu His Cys Arg Ser
            -1  1               5                   10

Gly Pro Gly Thr Gly Tyr Ser Val Val Lys Thr Tyr Asn Lys Gly Glu
                15                  20                  25

Glu Val Ser Ile Lys Cys Gln Ala Pro Gly Thr Asn Ile Asn Gly Asp
        30                  35                  40

Ile Leu Trp Asp Leu Thr Glu Asn Gly Cys Tyr Val Ala Asp Tyr Tyr
45                  50                  55                  60

Val Ser Thr Gly Thr Ser Gly Tyr Val Thr Asp Lys Cys Gly Ser Ser
                65                  70                  75

Gly Gly Gly Gly Ser Asp Gly Asp Leu Pro Gly Leu Asn Ser Val Gln
                80                  85                  90

Ser Ser His Ala Arg Ala Ile Ile Ala Glu Ala Lys Gln Glu Ser Leu
                95                  100                 105

Gly His Gln Gly Cys Leu Ala Gly Ile Ala Thr Ala Leu Thr Glu Ser
                110                 115                 120

Ser Ile Leu Val Tyr Ala Asn Lys Ala Val Pro Ala Ser Met Asn Tyr
125                 130                 135                 140

Lys Tyr Asp Ala Val Gly Ser Asp His Asp Ser Ile Gly Ile Phe Gln
                145                 150                 155

Gln Arg Ala Met Tyr Tyr Pro Asp Ile Ala Ala Asp Met Asp Pro Ala
                160                 165                 170

Lys Ser Ala Ala Gln Phe Phe Ala Lys Met Lys Gly Val Ser Gly Trp
                175                 180                 185

Gln Thr Met Asp Val Gly Asp Leu Cys Gln Lys Val Gln Gly Ser Ala
                190                 195                 200

Tyr Pro Thr Arg Tyr Glu Gln His Leu Ser Ala Ala Lys Ser Ile Cys
205                 210                 215                 220

Ser Ala Asp Ser Asp
                225

<210> SEQ ID NO 36
<211> LENGTH: 225
<212> TYPE: PRT
<213> ORGANISM: Talaromyces atricola
<220> FEATURE:
<221> NAME/KEY: mat_peptide
<222> LOCATION: (1)..(225)

<400> SEQUENCE: 36

```
Tyr Pro Ile Lys Thr Asp Gly Leu His Cys Arg Ser Gly Pro Gly Thr
1               5                   10                  15
Gly Tyr Ser Val Val Lys Thr Tyr Asn Lys Gly Glu Glu Val Ser Ile
            20                  25                  30
Lys Cys Gln Ala Pro Gly Thr Asn Ile Asn Gly Asp Ile Leu Trp Asp
        35                  40                  45
Leu Thr Glu Asn Gly Cys Tyr Val Ala Asp Tyr Val Ser Thr Gly
    50                  55                  60
Thr Ser Gly Tyr Val Thr Asp Lys Cys Gly Ser Ser Gly Gly Gly
65                  70                  75                  80
Ser Asp Gly Asp Leu Pro Gly Leu Asn Ser Val Gln Ser Ser His Ala
                85                  90                  95
Arg Ala Ile Ile Ala Glu Ala Lys Gln Glu Ser Leu Gly His Gln Gly
            100                 105                 110
Cys Leu Ala Gly Ile Ala Thr Ala Leu Thr Glu Ser Ser Ile Leu Val
        115                 120                 125
Tyr Ala Asn Lys Ala Val Pro Ala Ser Met Asn Tyr Lys Tyr Asp Ala
    130                 135                 140
Val Gly Ser Asp His Asp Ser Ile Gly Ile Phe Gln Gln Arg Ala Met
145                 150                 155                 160
Tyr Tyr Pro Asp Ile Ala Ala Asp Met Asp Pro Ala Lys Ser Ala Ala
                165                 170                 175
Gln Phe Phe Ala Lys Met Lys Gly Val Ser Gly Trp Gln Thr Met Asp
            180                 185                 190
Val Gly Asp Leu Cys Gln Lys Val Gln Gly Ser Ala Tyr Pro Thr Arg
        195                 200                 205
Tyr Glu Gln His Leu Ser Ala Ala Lys Ser Ile Cys Ser Ala Asp Ser
    210                 215                 220
Asp
225
```

<210> SEQ ID NO 37
<211> LENGTH: 794
<212> TYPE: DNA
<213> ORGANISM: Trichocladium asperum
<220> FEATURE:
<221> NAME/KEY: CDS
<222> LOCATION: (1)..(426)
<220> FEATURE:
<221> NAME/KEY: sig_peptide
<222> LOCATION: (1)..(57)
<220> FEATURE:
<221> NAME/KEY: mat_peptide
<222> LOCATION: (58)..(791)
<220> FEATURE:
<221> NAME/KEY: CDS
<222> LOCATION: (486)..(791)

<400> SEQUENCE: 37

```
atg cag ctc tcg ctc atc gcg ctc acc ctt gcg gcc gct gtc ccc ata    48
Met Gln Leu Ser Leu Ile Ala Leu Thr Leu Ala Ala Ala Val Pro Ile
            -15                 -10                 -5 gtc agc gcg tac cct gtc aag gaa aca ctc aac tgc cgc tct ggt ccc    96
Val Ser Ala Tyr Pro Val Lys Glu Thr Leu Asn Cys Arg Ser Gly Pro
        -1  1               5                   10 gga acc agc tac aaa gtt gtc aag aca tac aag cag ggt gcg gat gtc   144
Gly Thr Ser Tyr Lys Val Val Lys Thr Tyr Lys Gln Gly Ala Asp Val
    15                  20                  25
```

```
aag atc acc tgc cag acc acc ggt cca acc atc aag ggt tcc aat atc      192
Lys Ile Thr Cys Gln Thr Thr Gly Pro Thr Ile Lys Gly Ser Asn Ile
 30              35                  40                  45 tgg gac aag acc caa gat ggg tgc tac gtc gcc gac tat tac atc aag      240
Trp Asp Lys Thr Gln Asp Gly Cys Tyr Val Ala Asp Tyr Tyr Ile Lys
             50                  55                  60 aca ggg tct tcg ggc tat gtt gcc gcc aag tgt ggt gcc agt ggt ggt      288
Thr Gly Ser Ser Gly Tyr Val Ala Ala Lys Cys Gly Ala Ser Gly Gly
         65                  70                  75 gat ggc ggc ggc agt ggc acc ctc cct ggc cta aac gcg gtt cag tcc      336
Asp Gly Gly Gly Ser Gly Thr Leu Pro Gly Leu Asn Ala Val Gln Ser
     80                  85                  90 aag cac gcc aaa gcc atc gtt ggc caa gcg aag aaa gac ggt gtc ggc      384
Lys His Ala Lys Ala Ile Val Gly Gln Ala Lys Lys Asp Gly Val Gly
 95                 100                 105 cgc cac ggc tgt gag gcc ggt att gca act gcc ctt gtc gag                426
Arg His Gly Cys Glu Ala Gly Ile Ala Thr Ala Leu Val Glu
110             115                 120 gtaagacccc atcccatgac tgtccgggat aagaaccgcc atctaacgcc gcgatttag      485 tcg acc atg tat gtc tac gcc aac aac aag gtt ccc aaa tcg ctc aac      533
Ser Thr Met Tyr Val Tyr Ala Asn Asn Lys Val Pro Lys Ser Leu Asn
        125                 130                 135 tac ccg cat gac cgg gtc ggc tcg gat tac gac agc gtc ggc atc ttc      581
Tyr Pro His Asp Arg Val Gly Ser Asp Tyr Asp Ser Val Gly Ile Phe
140                 145                 150                 155 cag cag cgc gcc atc tac tat ccc aac atc gcc gcc gat atg gac cct      629
Gln Gln Arg Ala Ile Tyr Tyr Pro Asn Ile Ala Ala Asp Met Asp Pro
            160                 165                 170 gcc agg tct gca ggg cag ttc ttt gcc aag atg aag ggg gtc agc ggc      677
Ala Arg Ser Ala Gly Gln Phe Phe Ala Lys Met Lys Gly Val Ser Gly
        175                 180                 185 tgg aag acg atg gct gtt ggc aag ttg tgc cag aag gtg cag gtc tcg      725
Trp Lys Thr Met Ala Val Gly Lys Leu Cys Gln Lys Val Gln Val Ser
            190                 195                 200 gcc tac cct gac cgc tat gcg cag cag gtc tcc aaa gcc acc aag att      773
Ala Tyr Pro Asp Arg Tyr Ala Gln Gln Val Ser Lys Ala Thr Lys Ile
        205                 210                 215 tgt gct gct gct ggt ctc tag                                           794
Cys Ala Ala Ala Gly Leu
220             225

<210> SEQ ID NO 38
<211> LENGTH: 244
<212> TYPE: PRT
<213> ORGANISM: Trichocladium asperum

<400> SEQUENCE: 38

Met Gln Leu Ser Leu Ile Ala Leu Thr Leu Ala Ala Val Pro Ile
                -15                 -10                 -5

Val Ser Ala Tyr Pro Val Lys Glu Thr Leu Asn Cys Arg Ser Gly Pro
 -1  1               5                  10

Gly Thr Ser Tyr Lys Val Val Lys Thr Tyr Lys Gln Gly Ala Asp Val
         15                  20                  25

Lys Ile Thr Cys Gln Thr Thr Gly Pro Thr Ile Lys Gly Ser Asn Ile
 30              35                  40                  45

Trp Asp Lys Thr Gln Asp Gly Cys Tyr Val Ala Asp Tyr Tyr Ile Lys
             50                  55                  60

Thr Gly Ser Ser Gly Tyr Val Ala Ala Lys Cys Gly Ala Ser Gly Gly
         65                  70                  75
```

Asp Gly Gly Gly Ser Gly Thr Leu Pro Gly Leu Asn Ala Val Gln Ser
            80                  85                  90

Lys His Ala Lys Ala Ile Val Gly Gln Ala Lys Lys Asp Gly Val Gly
 95                 100                 105

Arg His Gly Cys Glu Ala Gly Ile Ala Thr Ala Leu Val Glu Ser Thr
110                 115                 120                 125

Met Tyr Val Tyr Ala Asn Asn Lys Val Pro Lys Ser Leu Asn Tyr Pro
                130                 135                 140

His Asp Arg Val Gly Ser Asp Tyr Asp Ser Val Gly Ile Phe Gln Gln
            145                 150                 155

Arg Ala Ile Tyr Tyr Pro Asn Ile Ala Ala Asp Met Asp Pro Ala Arg
        160                 165                 170

Ser Ala Gly Gln Phe Phe Ala Lys Met Lys Gly Val Ser Gly Trp Lys
175                 180                 185

Thr Met Ala Val Gly Lys Leu Cys Gln Lys Val Gln Val Ser Ala Tyr
190                 195                 200                 205

Pro Asp Arg Tyr Ala Gln Gln Val Ser Lys Ala Thr Lys Ile Cys Ala
            210                 215                 220

Ala Ala Gly Leu
            225

<210> SEQ ID NO 39
<211> LENGTH: 225
<212> TYPE: PRT
<213> ORGANISM: Trichocladium asperum
<220> FEATURE:
<221> NAME/KEY: mat_peptide
<222> LOCATION: (1)..(225)

<400> SEQUENCE: 39

Tyr Pro Val Lys Glu Thr Leu Asn Cys Arg Ser Gly Pro Gly Thr Ser
 1               5                  10                  15

Tyr Lys Val Val Lys Thr Tyr Lys Gln Gly Ala Asp Val Lys Ile Thr
                20                  25                  30

Cys Gln Thr Thr Gly Pro Thr Ile Lys Gly Ser Asn Ile Trp Asp Lys
            35                  40                  45

Thr Gln Asp Gly Cys Tyr Val Ala Asp Tyr Tyr Ile Lys Thr Gly Ser
 50                 55                  60

Ser Gly Tyr Val Ala Ala Lys Cys Gly Ala Ser Gly Gly Asp Gly Gly
 65                 70                  75                  80

Gly Ser Gly Thr Leu Pro Gly Leu Asn Ala Val Gln Ser Lys His Ala
                85                  90                  95

Lys Ala Ile Val Gly Gln Ala Lys Lys Asp Gly Val Gly Arg His Gly
            100                 105                 110

Cys Glu Ala Gly Ile Ala Thr Ala Leu Val Glu Ser Thr Met Tyr Val
        115                 120                 125

Tyr Ala Asn Asn Lys Val Pro Lys Ser Leu Asn Tyr Pro His Asp Arg
130                 135                 140

Val Gly Ser Asp Tyr Asp Ser Val Gly Ile Phe Gln Gln Arg Ala Ile
145                 150                 155                 160

Tyr Tyr Pro Asn Ile Ala Ala Asp Met Asp Pro Ala Arg Ser Ala Gly
                165                 170                 175

Gln Phe Phe Ala Lys Met Lys Gly Val Ser Gly Trp Lys Thr Met Ala
            180                 185                 190

Val Gly Lys Leu Cys Gln Lys Val Gln Val Ser Ala Tyr Pro Asp Arg
        195                 200                 205

```
                Tyr Ala Gln Gln Val Ser Lys Ala Thr Lys Ile Cys Ala Ala Ala Gly
                    210                 215                 220

Leu
                225

<210> SEQ ID NO 40
<211> LENGTH: 1063
<212> TYPE: DNA
<213> ORGANISM: Metarhizium carneum
<220> FEATURE:
<221> NAME/KEY: CDS
<222> LOCATION: (1)..(663)
<220> FEATURE:
<221> NAME/KEY: sig_peptide
<222> LOCATION: (1)..(57)
<220> FEATURE:
<221> NAME/KEY: mat_peptide
<222> LOCATION: (58)..(1060)
<220> FEATURE:
<221> NAME/KEY: CDS
<222> LOCATION: (755)..(1060)

<400> SEQUENCE: 40 atg cat ctc act tcc ctc tcc gta tac ttg gcc gtc ggc ggc tcc atg        48
Met His Leu Thr Ser Leu Ser Val Tyr Leu Ala Val Gly Gly Ser Met
                    -15                 -10                 -5 gtg gcg gca tac ccc atc aag gac aac aat gta aac tgc cgc tcc ggc        96
Val Ala Ala Tyr Pro Ile Lys Asp Asn Asn Val Asn Cys Arg Ser Gly
        -1   1                   5                  10 ccg gga acc agc ttc tcc gtc gtc aaa cag tac aag ctc gac caa gac       144
Pro Gly Thr Ser Phe Ser Val Val Lys Gln Tyr Lys Leu Asp Gln Asp
         15                  20                  25 gtc aca gtc agc tgc cag acc cac ggg gag agc att tcc ggc gac acg       192
Val Thr Val Ser Cys Gln Thr His Gly Glu Ser Ile Ser Gly Asp Thr
 30                  35                  40                  45 ctc tgg gac aag acg tcg gac ggg tgc tac gtg gcc gac tgg tac gtg       240
Leu Trp Asp Lys Thr Ser Asp Gly Cys Tyr Val Ala Asp Trp Tyr Val
                     50                  55                  60 agg acg ggc acg tcc aac atg gtc acc gga cag tgc ggc agc ggc tat       288
Arg Thr Gly Thr Ser Asn Met Val Thr Gly Gln Cys Gly Ser Gly Tyr
                 65                  70                  75 ccc atc aag gag gac aat gtc cac tgc cgc tca ggt ccc ggg acg acc       336
Pro Ile Lys Glu Asp Asn Val His Cys Arg Ser Gly Pro Gly Thr Thr
             80                  85                  90 ttt ggc gtc gtc aag acg tac ccc aag ggg caa aag gtc gag ctg tcc       384
Phe Gly Val Val Lys Thr Tyr Pro Lys Gly Gln Lys Val Glu Leu Ser
         95                 100                 105 tgc cag acc cag ggc gag acc gta tcg ggc aac agc ctc tgg gac aag       432
Cys Gln Thr Gln Gly Glu Thr Val Ser Gly Asn Ser Leu Trp Asp Lys
110                 115                 120                 125 acg acc gac ggc tgc tac gtg tcc gac tcg ctc gtc cag acg ggc aca       480
Thr Thr Asp Gly Cys Tyr Val Ser Asp Ser Leu Val Gln Thr Gly Thr
                130                 135                 140 tca aac atg gtc gct ggc cag tgt gcc ggc gcc ccc agc agt ccc ccc       528
Ser Asn Met Val Ala Gly Gln Cys Ala Gly Ala Pro Ser Ser Pro Pro
            145                 150                 155 tct gga gga tca gga aat ctc ccc ggc ctg agt gct act cag agc gcg       576
Ser Gly Gly Ser Gly Asn Leu Pro Gly Leu Ser Ala Thr Gln Ser Ala
        160                 165                 170 cac gcc cgc gcc atc atc gcc cag gtg aag aag gag gga ctt ggc aga       624
His Ala Arg Ala Ile Ile Ala Gln Val Lys Lys Glu Gly Leu Gly Arg
    175                 180                 185
```

```
cag ggc tgt gaa gcc ggc ctg gcc acc gga ctc act gag gtatgtctac      673
Gln Gly Cys Glu Ala Gly Leu Ala Thr Gly Leu Thr Glu
190             195                 200 catgaatgag caccagcgtg attatgattg tgcagacaga cagacgacga aacagtaaa    733 ggctaacatg aaccaaaaca g tcg agt ttg cgc atc ctg gcc aac aac gct     784
                       Ser Ser Leu Arg Ile Leu Ala Asn Asn Ala
                                205                 210 gtc ccg gcg tcc ttg aag tac gcg cac gac ggc atg ggc tct gac cac    832
Val Pro Ala Ser Leu Lys Tyr Ala His Asp Gly Met Gly Ser Asp His
    215                 220                 225 gac agc gtg ggc att ttc cag cag cgc gcc atg tat tac acc gat att    880
Asp Ser Val Gly Ile Phe Gln Gln Arg Ala Met Tyr Tyr Thr Asp Ile
230                 235                 240 gcc tgc gac atg gac gct gcc tgc tcc gcg agc agc ttc ttc aag ggc    928
Ala Cys Asp Met Asp Ala Ala Cys Ser Ala Ser Ser Phe Phe Lys Gly
245                 250                 255                 260 atg acg ggc ata tcc ggc tgg cgg acc atg gat gtt gcc aag ctc tgc    976
Met Thr Gly Ile Ser Gly Trp Arg Thr Met Asp Val Ala Lys Leu Cys
                265                 270                 275 cag gcc gtg cag cgg tcg gcc tat cct gat gcc tac cag aag tat gtt   1024
Gln Ala Val Gln Arg Ser Ala Tyr Pro Asp Ala Tyr Gln Lys Tyr Val
            280                 285                 290 ggt gcg gct gct gag atc tgc gct gct gga ggg tcg taa                1063
Gly Ala Ala Ala Glu Ile Cys Ala Ala Gly Gly Ser
295                 300
```

<210> SEQ ID NO 41
<211> LENGTH: 323
<212> TYPE: PRT
<213> ORGANISM: Metarhizium carneum

<400> SEQUENCE: 41

```
Met His Leu Thr Ser Leu Ser Val Tyr Leu Ala Val Gly Gly Ser Met
            -15                 -10                 -5

Val Ala Ala Tyr Pro Ile Lys Asp Asn Asn Val Asn Cys Arg Ser Gly
        -1  1               5                  10

Pro Gly Thr Ser Phe Ser Val Val Lys Gln Tyr Lys Leu Asp Gln Asp
        15                  20                  25

Val Thr Val Ser Cys Gln Thr His Gly Glu Ser Ile Ser Gly Asp Thr
30                  35                  40                  45

Leu Trp Asp Lys Thr

```
His Ala Arg Ala Ile Ile Ala Gln Val Lys Lys Glu Gly Leu Gly Arg
            175                 180                 185

Gln Gly Cys Glu Ala Gly Leu Ala Thr Gly Leu Thr Glu Ser Ser Leu
190                 195                 200                 205

Arg Ile Leu Ala Asn Asn Ala Val Pro Ala Ser Leu Lys Tyr Ala His
                    210                 215                 220

Asp Gly Met Gly Ser Asp His Asp Ser Val Gly Ile Phe Gln Gln Arg
                225                 230                 235

Ala Met Tyr Tyr Thr Asp Ile Ala Cys Asp Met Asp Ala Ala Cys Ser
            240                 245                 250

Ala Ser Ser Phe Phe Lys Gly Met Thr Gly Ile Ser Gly Trp Arg Thr
255                 260                 265

Met Asp Val Ala Lys Leu Cys Gln Ala Val Gln Arg Ser Ala Tyr Pro
270                 275                 280                 285

Asp Ala Tyr Gln Lys Tyr Val Gly Ala Ala Glu Ile Cys Ala Ala
                    290                 295                 300

Gly Gly Ser

<210> SEQ ID NO 42
<211> LENGTH: 304
<212> TYPE: PRT
<213> ORGANISM: Metarhizium carneum
<220> FEATURE:
<221> NAME/KEY: mat_peptide
<222> LOCATION: (1)..(304)

<400> SEQUENCE: 42

Tyr Pro Ile Lys Asp Asn Asn Val Asn Cys Arg Ser Gly Pro Gly Thr
1               5                   10                  15

Ser Phe Ser Val Val Lys Gln Tyr Lys Leu Asp Gln Asp Val Thr Val
                20                  25                  30

Ser Cys Gln Thr His Gly Glu Ser Ile Ser Gly Asp Thr Leu Trp Asp
            35                  40                  45

Lys Thr Ser Asp Gly Cys Tyr Val Ala Asp Trp Tyr Val Arg Thr Gly
    50                  55                  60

Thr Ser Asn Met Val Thr Gly Gln Cys Gly Ser Gly Tyr Pro Ile Lys
65                  70                  75                  80

Glu Asp Asn Val His Cys Arg Ser Gly Pro Gly Thr Thr Phe Gly Val
                85                  90                  95

Val Lys Thr Tyr Pro Lys Gly Gln Lys Val Glu Leu Ser Cys Gln Thr
                100                 105                 110

Gln Gly Glu Thr Val Ser Gly Asn Ser Leu Trp Asp Lys Thr Thr Asp
            115                 120                 125

Gly Cys Tyr Val Ser Asp Ser Leu Val Gln Thr Gly Thr Ser Asn Met
    130                 135                 140

Val Ala Gly Gln Cys Ala Gly Ala Pro Ser Ser Pro Ser Gly Gly
145                 150                 155                 160

Ser Gly Asn Leu Pro Gly Leu Ser Ala Thr Gln Ser Ala His Ala Arg
                165                 170                 175

Ala Ile Ile Ala Gln Val Lys Lys Glu Gly Leu Gly Arg Gln Gly Cys
            180                 185                 190

Glu Ala Gly Leu Ala Thr Gly Leu Thr Glu Ser Ser Leu Arg Ile Leu
        195                 200                 205

Ala Asn Asn Ala Val Pro Ala Ser Leu Lys Tyr Ala His Asp Gly Met
210                 215                 220
```

```
Gly Ser Asp His Asp Ser Val Gly Ile Phe Gln Gln Arg Ala Met Tyr
225                 230                 235                 240

Tyr Thr Asp Ile Ala Cys Asp Met Asp Ala Ala Cys Ser Ala Ser Ser
                245                 250                 255

Phe Phe Lys Gly Met Thr Gly Ile Ser Gly Trp Arg Thr Met Asp Val
            260                 265                 270

Ala Lys Leu Cys Gln Ala Val Gln Arg Ser Ala Tyr Pro Asp Ala Tyr
        275                 280                 285

Gln Lys Tyr Val Gly Ala Ala Ala Glu Ile Cys Ala Ala Gly Gly Ser
    290                 295                 300
```

<210> SEQ ID NO 43
<211> LENGTH: 838
<212> TYPE: DNA
<213> ORGANISM: Thielavia terrestris
<220> FEATURE:
<221> NAME/KEY: CDS
<222> LOCATION: (1)..(432)
<220> FEATURE:
<221> NAME/KEY: sig_peptide
<222> LOCATION: (1)..(57)
<220> FEATURE:
<221> NAME/KEY: mat_peptide
<222> LOCATION: (58)..(835)
<220> FEATURE:
<221> NAME/KEY: CDS
<222> LOCATION: (530)..(835)

<400> SEQUENCE: 43

```
atg cag ctc tcc ctc ctc gtc ctc tcc ctc gtg gcc gct gtg ccc atg     48
Met Gln Leu Ser Leu Leu Val Leu Ser Leu Val Ala Ala Val Pro Met
                -15                 -10                 -5 gcc agc gcg tac ccg gtc aag gcc gac act ctc aac tgc cgc tcc ggc     96
Ala Ser Ala Tyr Pro Val Lys Ala Asp Thr Leu Asn Cys Arg Ser Gly
        -1  1               5                  10 ccg ggc acc agt tac aag gtc atc aag acc tac aag aag ggc acc gat    144
Pro Gly Thr Ser Tyr Lys Val Ile Lys Thr Tyr Lys Lys Gly Thr Asp
    15                  20                  25 ctc aag atc acc tgc cag acg ccc ggc acc tcg gtc aac ggc gac aac    192
Leu Lys Ile Thr Cys Gln Thr Pro Gly Thr Ser Val Asn Gly Asp Asn
30                  35                  40                  45 ctg tgg gac aag acc tcg gac ggc tgc tac gtg gcc gat tac tac gtc    240
Leu Trp Asp Lys Thr Ser Asp Gly Cys Tyr Val Ala Asp Tyr Tyr Val
                50                  55                  60 aag acc ggc acc tcc ggc tac gtc acg gcc cat tgc gat gcc ggc agc    288
Lys Thr Gly Thr Ser Gly Tyr Val Thr Ala His Cys Asp Ala Gly Ser
            65                  70                  75 ggc agc ggc agc agc ggc ggc ggc aac ctg cca gga ctc aac tcg gtc    336
Gly Ser Gly Ser Ser Gly Gly Gly Asn Leu Pro Gly Leu Asn Ser Val
        80                  85                  90 cag tcc tcg cac gcc cgg gcc atc atc ggc gag gcg aag aag gag ggc    384
Gln Ser Ser His Ala Arg Ala Ile Ile Gly Glu Ala Lys Lys Glu Gly
    95                  100                 105 gtc ggc cgc cac ggc tgc gag gcc ggc atc gcg acc gcg ctt gtc gag    432
Val Gly Arg His Gly Cys Glu Ala Gly Ile Ala Thr Ala Leu Val Glu
110                 115                 120                 125 gtacgttgca tcctaacatc aaacttact tgccttgacc ccactgtcac cgccagaaaa   492
aaccaaaact aacacatcac ctcttcccct cacacag tcc aac atc ctg atc tac   547
                                        Ser Asn Ile Leu Ile Tyr
                                                        130
```

```
gcc aac aag gcg gtc ccg gcc tcg ctc aag tac ccg cac gac gcg gtg      595
Ala Asn Lys Ala Val Pro Ala Ser Leu Lys Tyr Pro His Asp Ala Val
            135                 140                 145 ggc tcg gac cac gac agc gtc ggc atc ttc cag cag cgc gcc aag tac      643
Gly Ser Asp His Asp Ser Val Gly Ile Phe Gln Gln Arg Ala Lys Tyr
        150                 155                 160 tac ccc aac atc gcg gcc gac atg gac ccg gcg cgc tcg gcc gcc cag      691
Tyr Pro Asn Ile Ala Ala Asp Met Asp Pro Ala Arg Ser Ala Ala Gln
165                 170                 175 ttc ttc gcc aag atg aag ggc atc aag ggc tgg cag agc atg gcc gtc      739
Phe Phe Ala Lys Met Lys Gly Ile Lys Gly Trp Gln Ser Met Ala Val
180                 185                 190                 195 ggc acg ctc tgc cag aag gtc cag ggc tcc gcg tac ccg gac cgc tat      787
Gly Thr Leu Cys Gln Lys Val Gln Gly Ser Ala Tyr Pro Asp Arg Tyr
                200                 205                 210 gcc aag cgg gtc tcg gag gcg acc aag att tgc cag gct ggt ggg ttg      835
Ala Lys Arg Val Ser Glu Ala Thr Lys Ile Cys Gln Ala Gly Gly Leu
            215                 220                 225 taa                                                                   838

<210> SEQ ID NO 44
<211> LENGTH: 246
<212> TYPE: PRT
<213> ORGANISM: Thielavia terrestris

<400> SEQUENCE: 44

Met Gln Leu Ser Leu Leu Val Leu Ser Leu Val Ala Ala Val Pro Met
                -15                 -10                  -5

Ala Ser Ala Tyr Pro Val Lys Ala Asp Thr Leu Asn Cys Arg Ser Gly
        -1  1               5                  10

Pro Gly Thr Ser Tyr Lys Val Ile Lys Thr Tyr Lys Lys Gly Thr Asp
            15                  20                  25

Leu Lys Ile Thr Cys Gln Thr Pro Gly Thr Ser Val Asn Gly Asp Asn
 30                  35                  40                  45

Leu Trp Asp Lys Thr Ser Asp Gly Cys Tyr Val Ala Tyr Tyr Val
                50                  55                  60

Lys Thr Gly Thr Ser Gly Tyr Val Thr Ala His Cys Asp Ala Gly Ser
                65                  70                  75

Gly Ser Gly Ser Ser Gly Gly Asn Leu Pro Gly Leu Asn Ser Val
            80                  85                  90

Gln Ser Ser His Ala Arg Ala Ile Ile Gly Glu Ala Lys Lys Glu Gly
 95                 100                 105

Val Gly Arg His Gly Cys Glu Ala Gly Ile Ala Thr Ala Leu Val Glu
110                 115                 120                 125

Ser Asn Ile Leu Ile Tyr Ala Asn Lys Ala Val Pro Ala Ser Leu Lys
                130                 135                 140

Tyr Pro His Asp Ala Val Gly Ser Asp His Asp Ser Val Gly Ile Phe
                145                 150                 155

Gln Gln Arg Ala Lys Tyr Tyr Pro Asn Ile Ala Ala Asp Met Asp Pro
            160                 165                 170

Ala Arg Ser Ala Ala Gln Phe Phe Ala Lys Met Lys Gly Ile Lys Gly
175                 180                 185

Trp Gln Ser Met Ala Val Gly Thr Leu Cys Gln Lys Val Gln Gly Ser
190                 195                 200                 205
```

Ala Tyr Pro Asp Arg Tyr Ala Lys Arg Val Ser Glu Ala Thr Lys Ile
            210                 215                 220

Cys Gln Ala Gly Gly Leu
            225

<210> SEQ ID NO 45
<211> LENGTH: 227
<212> TYPE: PRT
<213> ORGANISM: Thielavia terrestris
<220> FEATURE:
<221> NAME/KEY: mat_peptide
<222> LOCATION: (1)..(227)

<400> SEQUENCE: 45

Tyr Pro Val Lys Ala Asp Thr Leu Asn Cys Arg Ser Gly Pro Gly Thr
1               5                   10                  15

Ser Tyr Lys Val Ile Lys Thr Tyr Lys Lys Gly Thr Asp Leu Lys Ile
            20                  25                  30

Thr Cys Gln Thr Pro Gly Thr Ser Val Asn Gly Asp Asn Leu Trp Asp
        35                  40                  45

Lys Thr Ser Asp Gly Cys Tyr Val Ala Asp Tyr Tyr Val Lys Thr Gly
    50                  55                  60

Thr Ser Gly Tyr Val Thr Ala His Cys Asp Ala Gly Ser Gly Ser Gly
65                  70                  75                  80

Ser Ser Gly Gly Gly Asn Leu Pro Gly Leu Asn Ser Val Gln Ser Ser
                85                  90                  95

His Ala Arg Ala Ile Ile Gly Glu Ala Lys Lys Glu Gly Val Gly Arg
            100                 105                 110

His Gly Cys Glu Ala Gly Ile Ala Thr Ala Leu Val Glu Ser Asn Ile
        115                 120                 125

Leu Ile Tyr Ala Asn Lys Ala Val Pro Ala Ser Leu Lys Tyr Pro His
    130                 135                 140

Asp Ala Val Gly Ser Asp His Asp Ser Val Gly Ile Phe Gln Gln Arg
145                 150                 155                 160

Ala Lys Tyr Tyr Pro Asn Ile Ala Ala Asp Met Asp Pro Ala Arg Ser
                165                 170                 175

Ala Ala Gln Phe Phe Ala Lys Met Lys Gly Ile Lys Gly Trp Gln Ser
            180                 185                 190

Met Ala Val Gly Thr Leu Cys Gln Lys Val Gln Gly Ser Ala Tyr Pro
        195                 200                 205

Asp Arg Tyr Ala Lys Arg Val Ser Glu Ala Thr Lys Ile Cys Gln Ala
    210                 215                 220

Gly Gly Leu
225

<210> SEQ ID NO 46
<211> LENGTH: 144
<212> TYPE: PRT
<213> ORGANISM: Aspergillus clavatus

<400> SEQUENCE: 46

Ser Gly Asn Leu Pro Gly Leu Thr Ala Thr Gln Ser Ser His Ala Arg
1               5                   10                  15

Asp Ile Ile Gly Glu Ala Lys Lys Glu Asn Leu Gly Arg Gln Gly Cys
            20                  25                  30

Leu Ala Gly Ile Ala Thr Gly Leu Val Glu Ser Asn Leu Leu Ile Tyr
        35                  40                  45

```
Ala Asn Ser Lys Val Pro Ala Ser Leu Lys Tyr Lys His Asp Ala Val
     50                  55                  60

Gly His Asp Tyr Asp Ser Val Gly Ile Phe Gln Gln Arg Ala Ile Tyr
 65                  70                  75                  80

Tyr Pro Asp Ile Ala Ala Asp Met Asp Pro Ala Arg Ser Ala Ala Gln
                 85                  90                  95

Phe Phe Ala Lys Met Lys Asn Ile Ser Gly Trp Lys Thr Met Asn Val
            100                 105                 110

Gly Lys Leu Cys Gln Lys Val Gln Val Ser Ala Tyr Pro Asp Arg Tyr
        115                 120                 125

Ala Gln Arg Val Ser Ala Ala Glu Lys Ile Cys Ala Ala Gly Gly Leu
    130                 135                 140
```

<210> SEQ ID NO 47
<211> LENGTH: 137
<212> TYPE: PRT
<213> ORGANISM: Salinispora tropica

<400> SEQUENCE: 47

```
Gly Leu Thr Gln Thr Gln Met Asp Asn Ala Lys Thr Ile Val Asp Val
 1               5                  10                  15

Gly Thr Asp Met Asn Ile Pro His Arg Gly Leu Val Val Ala Ile Ala
                 20                  25                  30

Thr Ala Met Gln Glu Ser Thr Leu Leu Asn Tyr Ala Asn Ala Gly Val
             35                  40                  45

Pro Glu Ser Gln Asn Tyr Pro His Glu Ala Val Gly Trp Asp His Asp
     50                  55                  60

Ser Val Gly Leu Phe Gln Gln Arg Ser Ser Thr Gly Trp Gly Ser Ile
 65                  70                  75                  80

Ala Glu Leu Met Thr Pro Thr Tyr Ala Ala Glu Ala Phe Tyr Gln Ala
                 85                  90                  95

Leu Leu Gln Val Pro Gly Trp Gln Gly Met Ser Val Ala Trp Ala Ala
            100                 105                 110

Gln Ser Val Gln Val Ser Ala Phe Pro Asp Ala Tyr Ala Gln His Glu
        115                 120                 125

Thr Arg Ala Thr Thr Ile Val Ser Ala
    130                 135
```

<210> SEQ ID NO 48
<211> LENGTH: 137
<212> TYPE: PRT
<213> ORGANISM: Salinispora arenicola

<400> SEQUENCE: 48

```
Gly Leu Thr Gln Ala Gln Met Asp Asn Ala Lys Val Ile Val Asp Val
 1               5                  10                  15

Gly Thr Arg Met Asp Ile Pro His Arg Gly Leu Ile Val Ala Ile Ala
                 20                  25                  30

Thr Ala Met Gln Glu Ser Thr Leu Leu Asn Tyr Ala Asn Gly Gly Val
             35                  40                  45

Pro Glu Ser Arg Asn Tyr Pro His Gln Ala Val Gly Trp Asp His Asp
     50                  55                  60

Ser Val Gly Leu Phe Gln Gln Arg Pro Ser Ser Gly Trp Gly Ser Val
 65                  70                  75                  80

Ala Gln Leu Met Arg Pro Thr Tyr Ala Ala Glu Ala Phe Tyr Gln Ala
                 85                  90                  95
```

Leu Leu Thr Ile Pro Gly Trp Gln Glu Met Ser Val Ala Trp Ala Ala
            100                 105                 110

Gln Ser Val Gln Val Ser Ala Phe Pro Asp Ala Tyr Ala Gln His Val
        115                 120                 125

Thr Arg Ala Thr Thr Val Val Thr Ala
        130                 135

<210> SEQ ID NO 49
<211> LENGTH: 135
<212> TYPE: PRT
<213> ORGANISM: Rhodococcus erythropolis

<400> SEQUENCE: 49

Gly Leu Asn Ala Ser Gln Thr Ala Leu Ala Lys Gln Ala Val Ala Ile
1               5                   10                  15

Gly Glu Ser Met Gly Val Pro Asp Gln Gly Ile Val Val Ala Leu Ala
            20                  25                  30

Thr Met Ser Gln Glu Ser Thr Tyr Arg Met Leu Ala Ser Ser Asn Val
        35                  40                  45

Pro Glu Ser Leu Gln Tyr Pro His Asp Gly Val Gly Ser Asp His Leu
    50                  55                  60

Ser Val Asn Gln Tyr Gln Gln Val Gly Ile Trp Gly Thr Ala Glu
65                  70                  75                  80

Asp Leu Met Asn Pro Val Thr Ala Asn Val Lys Phe Phe Asp Ala Leu
                85                  90                  95

Leu Lys Val Ser Gly Trp Gln Ser Met Pro Val Thr Val Ala Ala Gln
            100                 105                 110

Thr Val Gln Gly Ser Ala His Pro Glu Ala Tyr Ala Asp Asp Glu Thr
        115                 120                 125

Leu Ala Arg Gln Leu Ala Ser
        130                 135

<210> SEQ ID NO 50
<211> LENGTH: 135
<212> TYPE: PRT
<213> ORGANISM: Mycobacterium phage Pacc40

<400> SEQUENCE: 50

Met Thr His Thr Asn Asp Thr Tyr Ala Arg Glu Ile Leu Arg Ala Gly
1               5                   10                  15

Asn Asp Leu Gly Ile Thr Pro Arg Gly Ile Val Ile Ala Phe Ala Thr
            20                  25                  30

Val Phe Val Glu Ser Asp Trp Tyr Met Trp Ala Asn Ala Lys Val Pro
        35                  40                  45

Glu Ser Leu Arg Leu Pro His Glu Arg Val Gly Asn Asp Gly Arg Ser
    50                  55                  60

Val Gly Leu Phe Gln Gln Gln Val Val Trp Gly Asn Gly Ala Trp Trp
65                  70                  75                  80

Trp Gly Asp Ala Ala Thr Cys Met Asp Pro Tyr Lys Ser Ala Arg Leu
                85                  90                  95

Phe Phe Glu Arg Leu Lys Thr Arg Asp Tyr Ser Thr Gly Asp Pro Gly
            100                 105                 110

Ala His Ala Gln Ala Ile Gln Arg Ser Ala Tyr Pro Asp Arg Tyr Gly
        115                 120                 125

Gln Arg Met Ser Glu Ala Gln
        130                 135

```
<210> SEQ ID NO 51
<211> LENGTH: 144
<212> TYPE: PRT
<213> ORGANISM: Penicillium rubens

<400> SEQUENCE: 51
```

| | | | | | | | | | | | | | | |
|---|---|---|---|---|---|---|---|---|---|---|---|---|---|---|
| Ser | Gly | Asn | Leu | Pro | Gly | Leu | Thr | Ser | Thr | Gln | Ser | Lys | His | Ala | Lys |
| 1 | | | | 5 | | | | | 10 | | | | | 15 |

| Asp | Ile | Ile | Gly | Glu | Ala | Lys | Lys | Glu | Asp | Leu | Gly | Arg | Gln | Gly | Cys |
|---|---|---|---|---|---|---|---|---|---|---|---|---|---|---|---|
| | | | | 20 | | | | | 25 | | | | | 30 | |

| Leu | Ala | Gly | Ile | Ala | Thr | Gly | Leu | Val | Glu | Ser | Asn | Met | Leu | Met | Tyr |
|---|---|---|---|---|---|---|---|---|---|---|---|---|---|---|---|
| | | | 35 | | | | | 40 | | | | | 45 | | |

| Ala | Asn | Lys | Lys | Val | Pro | Glu | Ser | Leu | Lys | Tyr | Pro | His | Asp | Ala | Val |
|---|---|---|---|---|---|---|---|---|---|---|---|---|---|---|---|
| | 50 | | | | | 55 | | | | | 60 | | | | |

| Gly | Ser | Asp | Tyr | Asp | Ser | Val | Gly | Ile | Phe | Gln | Gln | Arg | Ala | Val | Tyr |
|---|---|---|---|---|---|---|---|---|---|---|---|---|---|---|---|
| 65 | | | | | 70 | | | | | 75 | | | | | 80 |

| Tyr | Pro | Asp | Ile | Ala | Ala | Asp | Met | Asp | Ala | Ala | Lys | Ser | Ala | Ala | Gln |
|---|---|---|---|---|---|---|---|---|---|---|---|---|---|---|---|
| | | | | 85 | | | | | 90 | | | | | 95 | |

| Phe | Phe | Lys | Gly | Met | Lys | Ala | Ile | Ser | Gly | Trp | Lys | Thr | Met | Glu | Val |
|---|---|---|---|---|---|---|---|---|---|---|---|---|---|---|---|
| | | | 100 | | | | | 105 | | | | | 110 | | |

| Gly | Lys | Leu | Cys | Gln | Lys | Val | Gln | Arg | Ser | Ala | Tyr | Pro | Ser | Arg | Tyr |
|---|---|---|---|---|---|---|---|---|---|---|---|---|---|---|---|
| | 115 | | | | | 120 | | | | | 125 | | | | |

| Ser | Glu | Arg | Val | Ala | Glu | Ala | Lys | Lys | Ile | Cys | Ala | Ala | Gly | Gly | Leu |
|---|---|---|---|---|---|---|---|---|---|---|---|---|---|---|---|
| 130 | | | | | 135 | | | | | 140 | | | | | |

```
<210> SEQ ID NO 52
<211> LENGTH: 136
<212> TYPE: PRT
<213> ORGANISM: Micromonospora aurantiaca

<400> SEQUENCE: 52
```

| Gly | Leu | Asp | Arg | Thr | Gln | Met | Asn | Asn | Ala | Lys | Lys | Ile | Val | Gln | Ala |
|---|---|---|---|---|---|---|---|---|---|---|---|---|---|---|---|
| 1 | | | | 5 | | | | | 10 | | | | | 15 | |

| Gly | Lys | Glu | Met | Gly | Met | Pro | Arg | Arg | Ala | Leu | Val | Ile | Ala | Val | Ala |
|---|---|---|---|---|---|---|---|---|---|---|---|---|---|---|---|
| | | | 20 | | | | | 25 | | | | | 30 | | |

| Thr | Ala | Met | Gln | Glu | Ser | Thr | Leu | Leu | Asn | Tyr | Ala | Ser | Gly | Val | Leu |
|---|---|---|---|---|---|---|---|---|---|---|---|---|---|---|---|
| | | | 35 | | | | | 40 | | | | | 45 | | |

| Pro | Glu | Ser | Gln | Ser | Tyr | Pro | His | Gln | Ala | Ile | Gly | Trp | Asp | His | Asp |
|---|---|---|---|---|---|---|---|---|---|---|---|---|---|---|---|
| | 50 | | | | | 55 | | | | | 60 | | | | |

| Ser | Val | Gly | Leu | Phe | Gln | Gln | Arg | Pro | Ser | Ser | Gly | Trp | Gly | Thr | Val |
|---|---|---|---|---|---|---|---|---|---|---|---|---|---|---|---|
| 65 | | | | | 70 | | | | | 75 | | | | | 80 |

| Glu | Gln | Leu | Met | Asp | Pro | Glu | Tyr | Ala | Thr | Lys | Ala | Phe | Leu | Ser | Ala |
|---|---|---|---|---|---|---|---|---|---|---|---|---|---|---|---|
| | | | | 85 | | | | | 90 | | | | | 95 | |

| Leu | Ala | Glu | Ile | Pro | Gly | Trp | Gln | Ser | Leu | Pro | Leu | Ser | Val | Ala | Ala |
|---|---|---|---|---|---|---|---|---|---|---|---|---|---|---|---|
| | | | 100 | | | | | 105 | | | | | 110 | | |

| Gln | Ala | Val | Gln | Ile | Ser | Ala | Phe | Pro | Asp | Ala | Tyr | Ala | Gln | His | Glu |
|---|---|---|---|---|---|---|---|---|---|---|---|---|---|---|---|
| | | 115 | | | | | 120 | | | | | 125 | | | |

| Trp | Arg | Ala | Gly | Glu | Val | Val | Ala |
|---|---|---|---|---|---|---|---|
| | 130 | | | | | 135 | |

```
<210> SEQ ID NO 53
<211> LENGTH: 147
<212> TYPE: PRT
<213> ORGANISM: Micromonospora aurantiaca
```

-continued

<400> SEQUENCE: 53

```
Thr Gly Asp Met Pro Arg Phe Ala Glu Tyr Gly Glu Arg Gln Leu Arg
1               5                   10                  15

Asn Ala Ala Val Ile Ile Lys Val Gly Gln Asp Met Lys Leu Pro Ala
            20                  25                  30

Arg Gly Trp Val Ile Ala Leu Ala Thr Ala Met Gln Glu Ser Ala Leu
        35                  40                  45

Arg Asn Leu Ala Asn Ser Thr Val Pro Ala Ser Leu Ala Leu Pro His
    50                  55                  60

Glu Gly Val Gly Ala Asp His Asp Ser Leu Gly Leu Phe Gln Gln Arg
65                  70                  75                  80

Pro Gly Trp Gly Ser Val Glu Gln Arg Met Thr Pro Ser Tyr Ala Ala
                85                  90                  95

Arg Lys Phe Tyr Gln Lys Met Glu Lys Val Pro Asp Trp Gln Gln Arg
            100                 105                 110

Pro Leu Thr Val Val Ala Gln Lys Val Gln Val Ser Ala Tyr Pro Asp
        115                 120                 125

Ala Tyr Ala Lys His Glu Glu Leu Ala Gly Ala Ile Val Asp Ala Leu
    130                 135                 140

Ala Gly Gly
145
```

<210> SEQ ID NO 54
<211> LENGTH: 137
<212> TYPE: PRT
<213> ORGANISM: Micromonospora aurantiaca

<400> SEQUENCE: 54

```
Gly Leu Asp Gln Arg Gln Met Asp Asn Ala Lys Ala Ile Val Asp Val
1               5                   10                  15

Gly Arg Glu Met Lys Met Pro Arg Arg Ala Leu Val Val Ala Val Ala
            20                  25                  30

Thr Ala Met Gln Glu Ser Asn Leu Tyr Asn Leu Ala Ser Asp Val Leu
        35                  40                  45

Pro Gln Ser Phe Asp His Pro His Gln Gly Ser Gly Ser Asp His Asp
    50                  55                  60

Ser Val Gly Leu Phe Gln Gln Arg Pro Ser Ser Gly Trp Gly Thr Val
65                  70                  75                  80

Ala Gln Leu Met Arg Pro Ala Tyr Ala Ala Arg Ala Phe Tyr Ala Ala
                85                  90                  95

Leu Arg Glu Val Pro Gly Trp Glu Asp Met Ser Val Thr Ala Ala Ala
            100                 105                 110

Gln Ala Val Gln Val Ser Ala Tyr Pro Asp Ala Tyr Ala Arg His Glu
        115                 120                 125

Lys Arg Ala Thr Thr Val Val Ser Ala
    130                 135
```

<210> SEQ ID NO 55
<211> LENGTH: 143
<212> TYPE: PRT
<213> ORGANISM: Tuber melanosporum

<400> SEQUENCE: 55

Gly Asn Leu Pro Gly Leu Asp Ala Thr Gln Ser Arg His Ala Arg Thr
1               5                   10                  15

Ile Ile Ala Val Ala Arg Glu Tyr Gly Val Gly Asn Arg Gly Cys Gln
            20                  25                  30

Val Ser Ile Val Thr Ala Met Gln Glu Ser Arg Ile Arg Val Leu Ala
        35                  40                  45

Asn Pro Ser Val Pro Asp Ser Asn Lys Tyr Pro His Asp Gly Thr Gly
    50                  55                  60

Ser Asp His Asp Ser Val Gly Ile Phe Gln Gln Arg Pro Gln Phe Trp
65                  70                  75                  80

Gly Thr Val Lys Asp Cys Met Asp Pro Lys Thr Ser Ala Gly Lys Phe
                85                  90                  95

Phe Thr Ala Leu Lys Lys Val Asn Gly Trp Glu Arg Met Glu Ile Gly
            100                 105                 110

Arg Ala Ala Gln Ser Val Gln Arg Ser Ala Phe Pro Asp Ala Tyr Thr
        115                 120                 125

Lys His Thr Pro Leu Ala Lys Gly Val Cys Glu Ala Gly Gly Ile
    130                 135                 140

<210> SEQ ID NO 56
<211> LENGTH: 142
<212> TYPE: PRT
<213> ORGANISM: Hypocrea atroviridis

<400> SEQUENCE: 56

Asn Leu Pro Gly Leu Asn Ala Val Gln Thr Lys Tyr Ala Asn Ala Ile
1               5                   10                  15

Ile Ala Lys Ala Lys Ala Asp Asp Val Gly Ser His Gly Cys Gln Ala
            20                  25                  30

Ala Ile Ala Thr Ala Met Val Glu Ser Ser Ile Ile Met Tyr Ala Asn
        35                  40                  45

Lys Ala Val Pro Gly Ser Leu Lys Tyr Pro His Asp Arg Ile Gly Ser
    50                  55                  60

Asp His Asp Arg Val Gly Leu Phe Gln Gln Arg Ala Ser Ile Tyr Lys
65                  70                  75                  80

Asn Val Lys Cys Asp Met Asp Ala Ala Cys Ser Ala Gly Gln Phe Phe
                85                  90                  95

Ala Glu Met Lys Lys Val Ser Gly Trp Gln Thr Met Ala Val Gly Thr
            100                 105                 110

Leu Cys Gln Lys Ile Gln Arg Ser Ala Tyr Pro Asp Arg Tyr Ala Lys
        115                 120                 125

Gln Val Gly Leu Ala Thr Asn Val Cys Lys Ala Gly Gly Leu
    130                 135                 140

<210> SEQ ID NO 57
<211> LENGTH: 137
<212> TYPE: PRT
<213> ORGANISM: Metarhizium acridum

<400> SEQUENCE: 57

Leu Thr Glu Leu Gln Ala Lys Tyr Ala Arg Gly Ile Ile Ala Gln Ala
1 5 10 15

Lys Lys Glu Arg Leu Gly Ala Gln Gly Cys Arg Ala Gly Ile Ala Thr
20 25 30

```
Ala Leu Val Glu Ser Thr Leu Ile Met His Ala Asn Tyr Ala Val Pro
            35                  40                  45

Asp Ser Leu Val Tyr Asp Tyr Asp Arg Leu Gly Tyr Asp Arg Asp Ser
 50                  55                  60

Val Gly Leu Phe Gln Gln Arg Ala Ser Ile Tyr Thr Asp Ile Lys Cys
 65                  70                  75                  80

Ser Met Asn Ala Ala Cys Ser Ala His Gln Phe Thr Glu Met Lys
                85                  90                  95

Gly Val Pro Glu Trp Arg Tyr Met Asp Val Gly Thr Leu Cys Gln Glu
                100                 105                 110

Val Gln Arg Ser Glu Asn Pro Glu Gln Tyr His Glu Phe Ile Asp Gln
            115                 120                 125

Ala Val Asp Ile Cys Lys Glu Gly Gly
        130                 135

<210> SEQ ID NO 58
<211> LENGTH: 142
<212> TYPE: PRT
<213> ORGANISM: Metarhizium robertsii

<400> SEQUENCE: 58

Asn Leu Pro Ser Leu Asn Ala Ala Gln Ser Gly Tyr Ala Lys Ser Ile
 1               5                  10                  15

Ile Ala Lys Ala Lys Ala Ala Gly Val Gln Arg His Gly Cys Gln Ala
                20                  25                  30

Ala Ile Ala Thr Gly Leu Val Glu Ser Lys Leu Leu Met Tyr Ala Asn
            35                  40                  45

Asn Ala Val Pro Ala Ser Leu Thr Tyr Arg His Gly Gly Ile Ser Ser
 50                  55                  60

Asp Asn Asp Ser Ile Gly Ile Phe Gln Gln Arg Ala Ser Val Tyr Lys
 65                  70                  75                  80

Asn Ile Ala Cys Ser Met Asp Ala Gly Cys Ser Ala Gly Gln Phe Phe
                85                  90                  95

Ser Gln Met Lys Arg Ile Gly Gly Trp Gln Thr Leu Ser Val Gly Ala
                100                 105                 110

Leu Cys Gln Lys Ile Gln Gln Ser Ser Phe Pro Asp Arg Tyr Glu Lys
            115                 120                 125

Gln Val Ala Ala Ala Ser Ile Cys Ala Ala Gly Gly Leu
        130                 135                 140

<210> SEQ ID NO 59
<211> LENGTH: 137
<212> TYPE: PRT
<213> ORGANISM: Verrucosispora maris

<400> SEQUENCE: 59

Gly Leu Thr Gln Ala Gln Met Asp Asn Ala Lys Val Ile Val Asp Val
 1               5                  10                  15

Gly Val Asp Met Lys Ile Pro Arg Lys Gly Leu Val Val Ala Val Ala
                20                  25                  30

Thr Ala Met Gln Glu Ser Thr Leu Leu Asn Tyr Ala Ser Gly Val Leu
            35                  40                  45

Pro Glu Ser Gln Asn Tyr Pro His Gln Ala Ile Gly Trp Asp His Asp
 50                  55                  60

Ser Val Gly Leu Phe Gln Gln Arg Pro Ser Ser Gly Trp Gly Thr Val
 65                  70                  75                  80
```

Arg Asp Leu Met Arg Pro Ala Tyr Ser Ala Arg Ala Phe Tyr Glu Ala
            85                  90                  95

Leu Leu Glu Val Pro Gly Trp Glu Gln Met Ser Leu Thr Leu Ala Ala
            100                 105                 110

Gln Ala Val Gln Ile Ser Ala Phe Pro Tyr Ala Tyr Ala Gln His Glu
        115                 120                 125

Glu Arg Ala Asn Thr Ile Val Ala Ala
    130                 135

<210> SEQ ID NO 60
<211> LENGTH: 133
<212> TYPE: PRT
<213> ORGANISM: Verrucosispora maris

<400> SEQUENCE: 60

Ser Gly Ala Gln Val Ala Asn Ala Val Val Ile Val Thr Ala Gly Arg
1               5                   10                  15

Gln Arg Gln Val Pro Ala Arg Gly Tyr Val Ile Ala Leu Ala Thr Ala
            20                  25                  30

Met Gln Glu Ser Thr Leu Arg Asn Leu Ala Asn Ala Asn Val Pro Glu
        35                  40                  45

Ser Leu Ala Leu Pro His Glu Gly Val Gly Arg Asp His Asp Ser Val
    50                  55                  60

Gly Leu Phe Gln Gln Arg Pro Gly Trp Gly Thr Val Arg Glu Arg Met
65                  70                  75                  80

Thr Pro Ser Tyr Ala Ala Asp Arg Phe Tyr Glu Ala Leu Ala Arg Val
            85                  90                  95

Asp Gly Trp Glu Arg Met Arg Leu Thr Asp Ala Ala Gln Ala Val Gln
            100                 105                 110

Arg Ser Ala Tyr Pro Glu Glu Tyr Gln Lys Trp Glu Asp Asp Ala Glu
        115                 120                 125

Leu Leu Ala Ala Ala
    130

<210> SEQ ID NO 61
<211> LENGTH: 142
<212> TYPE: PRT
<213> ORGANISM: Beauveria bassiana

<400> SEQUENCE: 61

Asn Leu Pro Gly Leu Asn Ala Leu Gln Thr Lys Tyr Ala Asn Ala Ile
1               5                   10                  15

Ile Ala Gln Ala Lys Lys Asp Gly Val Gly Ala His Gly Cys Gln Ala
            20                  25                  30

Gly Ile Ala Thr Ala Met Val Glu Ser Thr Leu Val Met Tyr Ala Asn
        35                  40                  45

Lys Ala Val Pro Ala Ser Leu Lys Tyr Pro His Asp Arg Val Gly Ser
    50                  55                  60

Asp His Asp Ser Val Gly Leu Phe Gln Gln Arg Ala Ser Ile Tyr Lys
65                  70                  75                  80

Asn Val Lys Cys Asp Met Asp Ala Ala Cys Ser Ala Gly Gln Phe Phe
            85                  90                  95

Ala Glu Met Lys Arg Ile Asn Gly Trp Gln Lys Ile Ala Val Gly Thr
            100                 105                 110

```
Leu Cys Gln Lys Val Gln Arg Ser Ala Tyr Pro Asp Arg Tyr Ala Lys
            115                 120                 125

Gln Val Gly Leu Ala Thr Asn Val Cys Lys Ala Gly Gly Leu
    130                 135                 140

<210> SEQ ID NO 62
<211> LENGTH: 143
<212> TYPE: PRT
<213> ORGANISM: Thielavia terrestris

<400> SEQUENCE: 62

Gly Asn Leu Pro Gly Leu Asn Ser Val Gln Ser Ser His Ala Arg Ala
1               5                   10                  15

Ile Ile Gly Glu Ala Lys Lys Glu Gly Val Gly Arg His Gly Cys Glu
            20                  25                  30

Ala Gly Ile Ala Thr Ala Leu Val Glu Ser Asn Ile Leu Ile Tyr Ala
        35                  40                  45

Asn Lys Ala Val Pro Ala Ser Leu Lys Tyr Pro His Asp Ala Val Gly
    50                  55                  60

Ser Asp His Asp Ser Val Gly Ile Phe Gln Gln Arg Ala Lys Tyr Tyr
65                  70                  75                  80

Pro Asn Ile Ala Ala Asp Met Asp Pro Ala Arg Ser Ala Ala Gln Phe
                85                  90                  95

Phe Ala Lys Met Lys Gly Ile Lys Gly Trp Gln Ser Met Ala Val Gly
            100                 105                 110

Thr Leu Cys Gln Lys Val Gln Gly Ser Ala Tyr Pro Asp Arg Tyr Ala
        115                 120                 125

Lys Arg Val Ser Glu Ala Thr Lys Ile Cys Gln Ala Gly Gly Leu
    130                 135                 140

<210> SEQ ID NO 63
<211> LENGTH: 137
<212> TYPE: PRT
<213> ORGANISM: Micromonospora peucetia

<400> SEQUENCE: 63

Gly Leu Thr Gln Ala Gln Met Asp Asn Ala Lys Val Ile Val Asp Val
1               5                   10                  15

Gly Val Glu Leu Lys Met Pro Arg Arg Ala Leu Val Val Ala Val Ala
            20                  25                  30

Thr Ser Met Gln Glu Ser Arg Leu Tyr Asn Leu Ala Ser Asp Val Leu
        35                  40                  45

Pro Glu Ser Thr Arg Tyr Pro His Gln Gly Ser Gly Ser Asp His Asp
    50                  55                  60

Ser Val Gly Leu Phe Gln Gln Arg Pro Ser Ser Gly Trp Gly Thr Val
65                  70                  75                  80

Arg Glu Leu Met Arg Pro Ser Tyr Ala Ala Arg Ala Phe Tyr Glu Ala
                85                  90                  95

Leu Arg Asp Val Pro Gly Trp Gln Gln Met Ser Val Ala Gly Ala Ala
            100                 105                 110

Gln Ala Val Gln Val Ser Ala Phe Pro Asp Ala Tyr Ala Gln His Glu
        115                 120                 125

Gly Leu Ala Thr Thr Val Val Ala Ala
    130                 135
```

```
<210> SEQ ID NO 64
<211> LENGTH: 153
<212> TYPE: PRT
<213> ORGANISM: Microbacterium laevaniformans

<400> SEQUENCE: 64
```

| | | | | | | | | | | | | | | | |
|---|---|---|---|---|---|---|---|---|---|---|---|---|---|---|---|
| Gly | Ser | Thr | Arg | Thr | Leu | Gly | Ala | Thr | Glu | Leu | Gly | His | Ala | Ala | Thr |
| 1 | | | | 5 | | | | | 10 | | | | | 15 | |
| Ile | Leu | Ser | Val | Ala | Arg | Ser | Leu | Gly | Val | Ser | Ala | Arg | Gly | Gln | Gln |
| | | | 20 | | | | | 25 | | | | | 30 | | |
| Ile | Ala | Ile | Met | Thr | Ala | Leu | Gln | Glu | Ser | Gly | Leu | Lys | Met | Tyr | Ala |
| | | | 35 | | | | | 40 | | | | | 45 | | |
| Asn | Ser | Ser | Val | Pro | Glu | Ser | Leu | Asp | Tyr | Pro | His | Asp | Ala | Val | Gly |
| | | | 50 | | | | | 55 | | | | | 60 | | |
| Ser | Asp | His | Asp | Ser | Val | Asn | Tyr | Phe | Gln | Gln | Arg | Val | Ser | Gly | Trp |
| 65 | | | | | 70 | | | | | 75 | | | | | 80 |
| Gly | Thr | Val | Glu | Glu | Leu | Met | Asp | Pro | Leu | Tyr | Ala | Ala | Lys | Ala | Phe |
| | | | | 85 | | | | | 90 | | | | | 95 | |
| Phe | Gly | Gly | Glu | Glu | Gly | Pro | Asn | Gly | Gly | Ser | Pro | Arg | Gly | Leu | Leu |
| | | | | 100 | | | | | 105 | | | | | 110 | |
| Asp | Ile | Pro | Gly | Trp | Glu | Asp | Met | Gly | Leu | Gly | Glu | Ala | Ala | Gln | Thr |
| | | | | 115 | | | | | 120 | | | | | 125 | |
| Val | Gln | Val | Ser | Ala | Tyr | Pro | Thr | Ala | Tyr | Asp | Lys | Trp | Glu | Pro | Ala |
| | | | 130 | | | | | 135 | | | | | 140 | | |
| Ala | Gln | Gln | Ile | Ile | Thr | Ala | Val | Gly | | | | | | | |
| 145 | | | | | 150 | | | | | | | | | | |

```
<210> SEQ ID NO 65
<211> LENGTH: 134
<212> TYPE: PRT
<213> ORGANISM: Mycobacterium abscessus

<400> SEQUENCE: 65
```

| | | | | | | | | | | | | | | | |
|---|---|---|---|---|---|---|---|---|---|---|---|---|---|---|---|
| Ala | Ser | Arg | Asp | Asp | Tyr | Ala | Arg | Ala | Ile | Ile | Ala | Glu | Gly | Lys | Arg |
| 1 | | | | 5 | | | | | 10 | | | | | 15 | |
| Arg | Gly | Ile | Thr | Ala | Arg | Gly | Ile | Gln | Ile | Gly | Leu | Ala | Thr | Ala | Ile |
| | | | 20 | | | | | 25 | | | | | 30 | | |
| Val | Glu | Ser | Ala | Leu | Lys | Met | Trp | Ala | Asn | Glu | Lys | Val | Pro | Glu | Ser |
| | | | 35 | | | | | 40 | | | | | 45 | | |
| Phe | Asn | Tyr | Pro | His | Asp | Ala | Val | Gly | Asp | Gly | Tyr | Ser | Val | Gly | |
| | | | 50 | | | | | 55 | | | | | 60 | | |
| Leu | Phe | Gln | Gln | Gln | Ile | Val | Lys | Gly | Pro | Asn | Gly | Trp | Trp | Trp | Ala |
| 65 | | | | | 70 | | | | | 75 | | | | | 80 |
| Asp | Cys | Ala | Thr | Cys | Met | Asn | Pro | Ala | Arg | Ser | Ala | Gly | Leu | Phe | Phe |
| | | | | 85 | | | | | 90 | | | | | 95 | |
| Asp | Arg | Leu | Ala | Lys | Leu | Pro | Tyr | Asn | Asp | Ala | Leu | Arg | Leu | Pro | Gly |
| | | | | 100 | | | | | 105 | | | | | 110 | |
| Ser | Phe | Ala | Gln | Gln | Val | Gln | Gln | Ser | Asp | Phe | Pro | Glu | Arg | Tyr | Asp |
| | | | | 115 | | | | | 120 | | | | | 125 | |
| Gln | Arg | Phe | Ala | Glu | Ala | | | | | | | | | | |
| | | | 130 | | | | | | | | | | | | |

```
<210> SEQ ID NO 66
<211> LENGTH: 137
<212> TYPE: PRT
<213> ORGANISM: Micromonospora lupini str. Lupac
```

<400> SEQUENCE: 66

Gly Leu Asp Asp Gln Met Glu Asn Ala Glu Ala Ile Val Arg Ala
1               5                   10                  15

Gly Arg Lys Met Gly Val Pro Arg Arg Gly Leu Val Ile Ala Val Ala
            20                  25                  30

Thr Ala Met Gln Glu Ser Asn Leu Tyr Asn Val Ala Ser Gly Val Leu
        35                  40                  45

Pro Glu Ser Gln Asp Tyr Pro His Gln Gly Val Gly Trp Asp His Asp
    50                  55                  60

Ser Val Gly Leu Phe Gln Gln Arg Ser Ser Gly Trp Gly Pro Val
65                  70                  75                  80

Gly Arg Leu Met Asp Pro Glu Phe Ala Thr Arg Gln Phe Leu Thr Ala
                85                  90                  95

Leu Glu Gln Val Pro Gly Trp Gln Gln Met Arg Leu Thr Asp Ala Ala
            100                 105                 110

Gln Ala Val Gln Val Ser Ala Tyr Pro Glu His Tyr Gln Gln His Glu
        115                 120                 125

Trp Arg Ala Thr Arg Val Val Asp Ala
    130                 135

<210> SEQ ID NO 67
<211> LENGTH: 137
<212> TYPE: PRT
<213> ORGANISM: Micromonospora lupini str. Lupac

<400> SEQUENCE: 67

Gly Leu Asp Gln Val Gln Met Asp Asn Ala Lys Ile Ile Val Asp Val
1               5                   10                  15

Gly Arg Glu Leu Lys Met Pro Arg Arg Ala Leu Val Val Ala Leu Ala
            20                  25                  30

Thr Ala Met Gln Glu Ser Asn Leu Tyr Asn Leu Ala Ser Asp Val Leu
        35                  40                  45

Pro Glu Ser Thr Gln Tyr Pro His Gln Gly Ser Gly Ala Asp His Asp
    50                  55                  60

Ser Val Gly Leu Phe Gln Gln Arg Pro Ser Ser Gly Trp Gly Thr Val
65                  70                  75                  80

Ala Glu Leu Met Arg Pro Ser Tyr Ala Ala Arg Ala Phe Tyr Thr Ala
                85                  90                  95

Leu Ala Glu Ile Pro Gly Trp Glu Asp Met Ser Val Thr Ala Ala Ala
            100                 105                 110

Gln Ala Val Gln Ile Ser Ala Phe Pro Asp Ala Tyr Ala Gln His Glu
        115                 120                 125

Glu Arg Ala Ser Thr Val Ala Ala Ala
    130                 135

<210> SEQ ID NO 68
<211> LENGTH: 144
<212> TYPE: PRT
<213> ORGANISM: Metarhizium album

<400> SEQUENCE: 68

Ala Gly Gly Leu Pro Gly Leu Asp Ala Val Gln Ser Gly Tyr Ala Arg
1               5                   10                  15

Ser Ile Ile Ala Lys Ala Lys Thr Ala Gly Val Gly Arg Arg Gly Cys
            20                  25                  30

```
Ala Ala Ala Ile Ala Thr Gly Leu Val Glu Ser Thr Leu Met Met Tyr
             35                  40                  45

Ala Asn Ser Ala Val Pro Glu Ser Leu Arg His His His Asp Arg Val
 50                  55                  60

Gly Ser Asp His Asp Ser Ile Gly Leu Phe Gln Gln Arg Ala Ser Val
65                  70                  75                  80

Tyr Arg Asn Ile Ala Cys Asp Met Asp Ala Gly Cys Ser Ala Gly Gln
                 85                  90                  95

Phe Phe Ala Arg Ile Lys Gly Val Ser Gly Trp His Thr Met Ala Thr
            100                 105                 110

Gly Thr Leu Ser Gln Thr Val Gln Gln Ser Ser Tyr Pro Gly Arg Tyr
            115                 120                 125

Gly Ala Gln Ala Arg Ala Ala Ala Ile Cys Ala Ala Gly Gly Leu
130                 135                 140
```

<210> SEQ ID NO 69
<211> LENGTH: 142
<212> TYPE: PRT
<213> ORGANISM: Aschersonia aleyrodis

<400> SEQUENCE: 69

```
Asn Leu Pro Gly Leu Asn Ala Val Gln Ser Arg Tyr Ala Arg Ala Ile
1               5                   10                  15

Ile Ala Glu Ala Ser Asn Asp Gly Val Gly Arg Gln Gly Cys Glu Ala
             20                  25                  30

Ala Ile Ala Thr Gly Leu Val Glu Ser Ser Ile Ile Met Tyr Ala Asn
             35                  40                  45

Ser Lys Val Pro Ala Ser Leu Asn Tyr His His Asp Arg Val Gly Ser
50                  55                  60

Asp His Asp Ser Val Gly Ile Phe Gln Gln Arg Ala Ser Ile Tyr Lys
65                  70                  75                  80

Asp Ile Ala Cys Asp Met Asp Ala Ala Cys Ser Ala Gly Gln Phe Phe
                 85                  90                  95

Gln Glu Met Arg Arg Ile Lys Gly Trp Gln Thr Met Ala Val Gly Thr
            100                 105                 110

Leu Cys Gln Lys Val Gln Arg Ser Ala Tyr Pro Asp Arg Tyr Asn Lys
            115                 120                 125

Arg Val Ala Glu Ala Arg Ser Ile Cys Ser Ala Gly Gly Leu
130                 135                 140
```

<210> SEQ ID NO 70
<211> LENGTH: 139
<212> TYPE: PRT
<213> ORGANISM: Metarhizium album

<400> SEQUENCE: 70

```
Gly Leu Thr Glu Leu Gln Ser Lys Tyr Ala Arg Arg Ile Thr Ala Gln
1               5                   10                  15

Ala Arg Lys Glu Glu Leu Gly Ala Gln Gly Cys Gln Ala Ala Ile Ala
             20                  25                  30

Thr Ala Leu Met Glu Ser Thr Leu Ile Met His Ala Asn Ser Ala Val
             35                  40                  45

Pro Gly Ser Leu Ala Phe His His Asp Arg Leu Gly Tyr Asp Gly Asp
50                  55                  60

Ser Val Gly Leu Phe Gln Gln Arg Ala Ser Ile Tyr Thr Asp Leu Gly
65                  70                  75                  80
```

```
Cys Ser Met Asn Ala Ala Cys Ser Ala His Gln Phe Phe Val Glu Met
                85                  90                  95

Arg Asp Val Pro Asp Trp Glu Ser Met Asp Val Gly Thr Leu Cys Gln
            100                 105                 110

Ala Val Gln Arg Ser Gln Asn Pro Glu Arg Tyr Tyr Glu Phe Ile Asp
        115                 120                 125

Leu Ala Ala Ser Val Cys Ala Glu Ala Gly Leu
    130                 135

<210> SEQ ID NO 71
<211> LENGTH: 139
<212> TYPE: PRT
<213> ORGANISM: Cordyceps brongniartii

<400> SEQUENCE: 71

Pro Gly Leu Asn His Ala Gln Ser Arg Asn Ala Lys Ala Ala Ile Asp
1               5                   10                  15

Gln Val Arg Ala Glu Gly Leu Asn Arg Gln Ala Cys Leu Ala Val Ile
            20                  25                  30

Ser Thr Ala Leu Gln Glu Ser Glu Leu Gln Ile Tyr Ala Asn Pro Ile
        35                  40                  45

Val Pro Ala Ser Met Asn Tyr Pro His Asp Lys Val Gly Gly Asp Gln
    50                  55                  60

Asp Ser Ile Gly Met Phe Gln Gln Arg Ala Lys Phe Tyr Ser Asp Ile
65                  70                  75                  80

Ala Thr Asp Met Ser Ala Gly Ser Thr Arg Leu Phe Leu Ala Asp
                85                  90                  95

Met Lys Gly Ile Ala Gly Trp Gln Thr Met Glu Val Ser Ala Leu Cys
            100                 105                 110

Gln Thr Val Gln Lys Ala Glu Ala Gly Asn Leu Tyr Gly Gln Arg Ile
        115                 120                 125

Ser Leu Ala Glu Gln Val Cys Ser Ala Ala Gly
    130                 135

<210> SEQ ID NO 72
<211> LENGTH: 139
<212> TYPE: PRT
<213> ORGANISM: Metarhizium rileyi

<400> SEQUENCE: 72

Gly Leu Asp Glu Val Gln Ser Lys Tyr Ala Gly Arg Ile Ile Ala Gln
1               5                   10                  15

Val Lys Met Glu Asn Leu Gly Pro Lys Ala Cys Gln Thr Ala Ile Thr
            20                  25                  30

Thr Ser Leu Met Glu Ser Thr Leu Ile Met His Ala Asn Glu Arg Val
        35                  40                  45

Pro Glu Ser Leu Thr Tyr Glu His Glu Arg Leu Gly Tyr Asp Gly Asp
    50                  55                  60

Ser Val Gly Leu Phe Gln Gln Arg Ala Leu Phe Tyr Thr Asp Ile Lys
65                  70                  75                  80

Cys Asn Met Asp Ala Val Cys Ser Ala His Gln Phe Leu Ala Arg Met
                85                  90                  95

Lys Glu Ile Pro Glu Trp Glu Thr Ile Asp Val Gly Thr Leu Ala Gln
            100                 105                 110
```

```
Lys Val Gln Arg Ser Glu Gln Pro Glu Arg Tyr His Gln Phe Val Asp
        115                 120                 125

Gln Ser Val Ser Ile Cys Asn Leu Gly Gly Leu
        130                 135

<210> SEQ ID NO 73
<211> LENGTH: 139
<212> TYPE: PRT
<213> ORGANISM: Cordyceps confragosa

<400> SEQUENCE: 73

Pro Gly Ile Asn Glu Glu Gln Ser Arg Asn Ala Gly Ala Ala Ile Trp
1               5                   10                  15

Gln Val Arg Asn Tyr Arg Leu Gly Arg Gln Ala Cys Leu Ala Val Ile
            20                  25                  30

Ser Thr Ala Leu Gln Glu Ser Glu Leu Glu Val Tyr Ala Asn Pro Arg
        35                  40                  45

Val Pro Glu Ser Tyr Lys Tyr Pro His Asn Arg Glu Gly Gly Asp Gln
    50                  55                  60

Asp Ser Val Gly Met Phe Gln Gln Arg Lys Ala Tyr Tyr Pro Asp Ile
65                  70                  75                  80

Ala Ala Asp Met Asp Pro Ala Arg Ser Thr Gly Gln Phe Leu Asp Ala
                85                  90                  95

Met Leu Arg Val Pro Gly Trp Gln Asn Met Glu Ile Ser Gln Leu Asp
            100                 105                 110

Gln Ala Val Gln His Ala Glu Ala Gly Asn Leu Tyr Gly Gln Arg Ile
        115                 120                 125

Pro Leu Ala Thr Arg Ile Cys Asn Ala Ala Gly
    130                 135

<210> SEQ ID NO 74
<211> LENGTH: 139
<212> TYPE: PRT
<213> ORGANISM: Cordyceps confragosa

<400> SEQUENCE: 74

Pro Gly Leu Asn Asn Val Gln Ser Arg Asn Ala Lys Ala Ala Ile Gly
1               5                   10                  15

Glu Val Arg Ala Glu Gly Leu Asn Arg Gln Ala Cys Leu Ala Val Ile
            20                  25                  30

Ser Thr Ala Leu Gln Glu Ser Glu Leu Gln Ile Tyr Ala Asn Pro Arg
        35                  40                  45

Val Pro Ala Ser Met Asn Tyr Pro His Asp Lys Val Gly Gly Asp Gln
    50                  55                  60

Asp Ser Val Gly Met Phe Gln Gln Arg Ala Gln Phe Tyr Pro Asn Ile
65                  70                  75                  80

Ala Thr Asp Met Ser Ala Ala Gly Ser Thr Arg Gln Phe Leu Ser Val
                85                  90                  95

Met Lys Gly Ile Lys Gly Trp Gln Thr Met Glu Ile Ser Ala Leu Asp
            100                 105                 110

Gln Ala Val Gln Arg Ala Gln Ala Gly Asn Leu Tyr Ala Lys Arg Ile
        115                 120                 125

Pro Leu Ala Lys Gln Val Cys Ser Ala Ala Gly
    130                 135
```

-continued

<210> SEQ ID NO 75
<211> LENGTH: 142
<212> TYPE: PRT
<213> ORGANISM: Cordyceps confragosa

<400> SEQUENCE: 75

Gly Ser Tyr Pro Gly Leu Asp Ala Val Gln Ser Arg Asn Ala Ala
1               5                   10                  15

Ala Ile Gly Glu Val Arg Ala Glu Gly Leu Asn Arg Gln Ala Cys Leu
            20                  25                  30

Ala Val Ile Ser Thr Ala Leu Gln Glu Ser Thr Leu His Ile Tyr Ala
        35                  40                  45

Asn Pro Arg Val Pro Ala Ser Tyr Asn Tyr Pro His Asp Leu Glu Gly
    50                  55                  60

Gly Asp Gln Asp Ser Val Gly Met Phe Gln Gln Arg Ala Gln Phe Tyr
65                  70                  75                  80

Pro Asp Ile Gly Ala Asp Met Ser Ala Ala Gly Ser Thr Arg Gln Phe
                85                  90                  95

Leu Ala Val Met Lys Gly Ile Pro Gly Trp Gln Thr Met Glu Val Ser
            100                 105                 110

Ala Leu Asp Gln Ala Val Gln Arg Ala Glu Ala Gly Asn Leu Tyr Ala
        115                 120                 125

Gln Arg Leu Pro Leu Ala Asn Gln Val Cys Ser Ala Ala Gly
    130                 135                 140

<210> SEQ ID NO 76
<211> LENGTH: 142
<212> TYPE: PRT
<213> ORGANISM: Isaria fumosorosea

<400> SEQUENCE: 76

Gly Ser Tyr Pro Gly Leu Asp Ala Thr Gln Ser Arg Asn Ala Ala Ala
1               5                   10                  15

Ala Ile Gly Glu Val Arg Ala Glu Gly Leu Gly Arg Gln Ala Cys Leu
            20                  25                  30

Ala Val Ile Ser Thr Ala Leu Gln Glu Ser Thr Leu His Ile Tyr Ala
        35                  40                  45

Asn Pro Val Val Pro Ala Ser Met Asn Tyr Pro His Asp Leu Val Gly
    50                  55                  60

Gly Asp Gln Asp Ser Val Gly Met Phe Gln Gln Arg Pro Glu Trp Tyr
65                  70                  75                  80

Pro Asp Ile Ala Ala Asp Met Ser Ala Ala Gly Ser Thr Arg Gln Phe
                85                  90                  95

Leu Ala Ala Met Lys Gln Val Ala Gly Trp Glu Thr Met Glu Val Ser
            100                 105                 110

Ala Leu Asp Gln Ala Val Gln Lys Ala Glu Ala Gly Asn Leu Tyr Ala
        115                 120                 125

Gln Arg Leu Pro Leu Ala Asn Gln Val Cys Ser Ala Ala Gly
    130                 135                 140

<210> SEQ ID NO 77
<211> LENGTH: 144
<212> TYPE: PRT
<213> ORGANISM: Isaria fumosorosea

<400> SEQUENCE: 77

Ala Ala Asn Leu Pro Gly Leu Asn Ala Val Gln Thr Lys Tyr Ala Arg
1               5                   10                  15

Ala Ile Ile Ala Gln Ala Lys Lys Asp Gly Val Gly Ala His Gly Cys
            20                  25                  30

Gln Ala Gly Ile Ala Thr Ala Met Val Glu Ser Ser Ile Ile Met Tyr
        35                  40                  45

Ala Asn Asn Ala Val Pro Glu Ser Leu Lys Tyr Pro His Asp Arg Val
50                  55                  60

Gly Ser Asp His Asp Ser Val Gly Leu Phe Gln Gln Arg Ala Ser Ile
65                  70                  75                  80

Tyr Lys Asn Val Lys Cys Asp Met Asn Ala Ala Cys Ser Ala Gly Gln
                85                  90                  95

Phe Tyr Ala Glu Met Lys Arg Val Ser Gly Trp Lys Thr Met Ala Val
            100                 105                 110

Gly Thr Leu Cys Gln Lys Val Gln Arg Ser Ala Tyr Pro Asp Arg Tyr
        115                 120                 125

Ala Lys Gln Val Gly Leu Ala Thr Asn Ile Cys Lys Ala Gly Gly Leu
130                 135                 140

<210> SEQ ID NO 78
<211> LENGTH: 141
<212> TYPE: PRT
<213> ORGANISM: Isaria fumosorosea

<400> SEQUENCE: 78

Ile Ala Gly Leu Asp Glu Thr Gln Ser Arg His Ala Gln Ala Ile Ile
1               5                   10                  15

Asp Val Val Lys Thr Glu Gly Val Gly Ala Leu Gly Cys Gln Ala Ala
            20                  25                  30

Ile Ala Thr Ala Leu Thr Glu Ser Glu Leu Tyr Met His Ala Asn His
        35                  40                  45

Ala Val Pro Gly Ser Leu Asp Lys Pro His Arg Val Gly Ala Asp
50                  55                  60

Gln Asp Ser Val Gly Leu Phe Gln Gln Arg Ala Val Phe Tyr Thr Asp
65                  70                  75                  80

Val Gly Cys Thr Met Asp Ala Ala Cys Ser Ala Gly Leu Phe Val Lys
            85                  90                  95

Asp Leu Arg Ala Val Ala Gly Trp Gln Gly Met Glu Thr Ala Ala Leu
        100                 105                 110

Cys Gln Ala Ile Gln Arg Ser Gln Ile Pro Asp Ala Tyr Ile Lys Asn
        115                 120                 125

Val Ala Lys Ala Val Glu Val Cys Gly Gly Ser Gly Leu
130                 135                 140

<210> SEQ ID NO 79
<211> LENGTH: 143
<212> TYPE: PRT
<213> ORGANISM: Purpureocillium lilacinum

<400> SEQUENCE: 79

Gly Asn Leu Pro Thr Leu Asn Ala Val Gln Ser Lys Asn Ala Arg Ala
1               5                   10                  15

Ile Ile Ala Gln Thr Lys Lys Gln Gly Leu Gly Arg Gln Gly Cys Met
            20                  25                  30

```
Ala Ala Leu Ala Thr Gly Leu Thr Glu Ser Gln Ile Lys Ile Leu Ala
            35                  40                  45

Asn Asn Lys Val Pro Ala Ser Leu Lys Tyr His Tyr Asp Gly Lys Gly
 50                  55                  60

Ser Asp His Asp Ser Val Gly Ile Phe Gln Gln Arg Ala Met Tyr Tyr
 65                  70                  75                  80

Lys Asp Ile Lys Cys Asp Met Asp Ala Ala Cys Ser Ala Ser Leu Phe
                 85                  90                  95

Phe Lys Gly Met Thr Ala Ile Lys Gly Trp Lys Thr Met Asp Val Ala
            100                 105                 110

Lys Leu Cys Gln Ala Val Gln Arg Ser Ala Val Pro Thr Ala Tyr Arg
            115                 120                 125

Lys Tyr Thr Ser Gln Ala Lys Thr Ile Cys Ala Ala Gly Gly Leu
            130                 135                 140
```

<210> SEQ ID NO 80
<211> LENGTH: 143
<212> TYPE: PRT
<213> ORGANISM: Pochonia chlamydosporia

<400> SEQUENCE: 80

```
Gly Asn Leu Pro Thr Leu Asn Ala Leu Gln Thr Lys His Ala Arg Ala
 1               5                  10                  15

Ile Ile Ala Gln Thr Lys Lys Gln Gly Leu Gly Arg Gln Gly Cys Glu
            20                  25                  30

Ala Ala Ile Ala Thr Gly Leu Thr Glu Ser Ser Leu Arg Ile Leu Ala
            35                  40                  45

Asn Arg Ser Val Pro Lys Ser Leu Asn Tyr Lys Tyr Asp Gly Ile Gly
 50                  55                  60

Ser Asp His Asp Ser Val Gly Ile Phe Gln Gln Arg Ala Met Tyr Tyr
 65                  70                  75                  80

Lys Asp Ile Lys Cys Asp Met Asp Ala Ala Cys Ser Ala Ser Leu Phe
                 85                  90                  95

Phe Lys Gly Met Val Ala Val Lys Gly Trp Lys Thr Met Asp Val Ala
            100                 105                 110

Lys Leu Cys Gln Ala Val Gln Arg Ser Ala Val Pro Thr Ala Tyr Arg
            115                 120                 125

Lys Tyr Thr Ser Ala Ala Lys Ser Ile Cys Ser Ala Gly Gly Ile
            130                 135                 140
```

<210> SEQ ID NO 81
<211> LENGTH: 144
<212> TYPE: PRT
<213> ORGANISM: Pochonia chlamydosporia

<400> SEQUENCE: 81

```
Ala Ala Asn Leu Pro Gly Leu Asn Ser Leu Gln Ser Gly Tyr Ala Arg
 1               5                  10                  15

Ala Ile Ile Ala Lys Ala Lys Ala Asp Gly Val Gly Arg His Gly Cys
            20                  25                  30

Glu Ala Ala Ile Ala Thr Gly Leu Val Glu Ser Ser Leu Ile Met Tyr
            35                  40                  45

Ala Asn Asn Ala Val Pro Ala Ser Leu Lys Tyr His His Asp Arg Val
 50                  55                  60

Gly Ser Asp His Asp Ser Ile Gly Ile Phe Gln Gln Arg Ala Ser Ile
 65                  70                  75                  80
```

```
Tyr Lys Asn Ile Ala Cys Asp Met Glu Ala Gly Cys Ser Ala Gly Gln
                85                  90                  95

Phe Ile Ala Glu Met Lys Arg Ile Ser Gly Trp Gln Thr Met Ala Val
            100                 105                 110

Gly Thr Leu Cys Gln Lys Val Gln Arg Ser Ala Tyr Pro Asp Arg Tyr
        115                 120                 125

Ala Lys Gln Val Pro Thr Ala Thr Lys Val Cys Ala Ala Gly Gly Leu
    130                 135                 140
```

<210> SEQ ID NO 82
<211> LENGTH: 143
<212> TYPE: PRT
<213> ORGANISM: Pochonia chlamydosporia

<400> SEQUENCE: 82

```
Ser Gly Asn Leu Pro Gly Leu Asn Ser Val Gln Thr Gly His Ala Arg
1               5                   10                  15

Ala Ile Ile Ala Gln Thr Lys Lys Gln Gly Leu Gly Arg Gln Gly Cys
            20                  25                  30

Glu Ala Ala Ile Ala Thr Gly Leu Thr Glu Ser Gly Leu Arg Ile Leu
        35                  40                  45

Ala Asn Asn Val Val Pro Ala Ser Leu Lys Tyr Pro His Asp Gly Met
    50                  55                  60

Gly Ser Asp His Asp Ser Val Gly Ile Phe Gln Gln Arg Ala Met Tyr
65                  70                  75                  80

Tyr Thr Asp Ile Gly Cys Asp Met Asp Ala Ala Cys Ser Ala Ser Ser
                85                  90                  95

Phe Phe Lys Gly Met Thr Ala Ile Lys Gly Trp Gln Thr Met Asp Val
            100                 105                 110

Ala Lys Leu Cys Gln Ala Val Gln Arg Ser Ala Val Pro Asp Ala Tyr
        115                 120                 125

Lys Lys Tyr Val Gly Ala Ala Ser Ile Cys Ala Ala Gly Gly
    130                 135                 140
```

<210> SEQ ID NO 83
<211> LENGTH: 143
<212> TYPE: PRT
<213> ORGANISM: Penicillium oxalicum

<400> SEQUENCE: 83

```
Gly Asn Leu Pro Gly Leu Ser Ala Thr Gln Ser Gln His Ala Arg Asp
1               5                   10                  15

Ile Ile Ala Glu Ala Lys Arg Glu Gly Leu Gly Leu Gln Gly Cys Ser
            20                  25                  30

Ala Gly Ile Ala Thr Ala Leu Val Glu Ser Ser Ile Leu Ile Tyr Ala
        35                  40                  45

Asn Asn Ala Val Pro Ala Ser Leu Asn Tyr Pro His Asp Ala Val Gly
    50                  55                  60

Ser Asp His Asp Ser Ile Gly Ile Phe Gln Gln Arg Ala Met Tyr Tyr
65                  70                  75                  80

Pro Asn Ile Ala Ala Asp Met Asp Ala Ala Lys Ser Ala Ala Gln Phe
                85                  90                  95

Phe Gln Lys Met Lys Ser Ile Ser Gly Trp Gln Thr Met Ala Ile Gly
            100                 105                 110
```

```
Thr Leu Cys Gln Lys Val Gln Val Ser Ala Tyr Pro Asp Arg Tyr Ala
            115                 120                 125

Ala Arg Ala Ala Asp Ala Gln Asn Ile Cys Lys Ala Gly Gly Ile
130                 135                 140

<210> SEQ ID NO 84
<211> LENGTH: 148
<212> TYPE: PRT
<213> ORGANISM: Metarhizium anisopliae

<400> SEQUENCE: 84

Thr Gly Asp Leu Pro Arg Thr Tyr Ser Asn Leu Ser Gly Leu Gln
1               5                   10                  15

Ser Lys Tyr Ala Arg Gly Ile Met Ala Gln Ala Lys Arg Glu His Leu
            20                  25                  30

Gly Ser Gln Gly Cys Arg Ala Gly Ile Ala Thr Ala Leu Val Glu Ser
        35                  40                  45

Thr Leu Ile Met His Ala Asn Met Ala Val Pro Ala Ser Leu Ala Tyr
    50                  55                  60

Asp Phe Asp Arg Leu Gly Lys Asp Ala Asp Ser Ile Gly Leu Phe Gln
65                  70                  75                  80

Gln Arg Ala Ser Ile Tyr Thr Asn Ile Lys Cys Ser Met Asp Val Ala
                85                  90                  95

Cys Ser Ala His Gln Phe Phe Lys Glu Met Lys Thr Val Pro Gln Trp
            100                 105                 110

Lys Tyr Met Pro Ile Gly Gln Leu Cys Gln Glu Val Gln His Ser Glu
        115                 120                 125

Asn Pro Glu Arg Tyr His Asp Phe Ile Asp Gln Ala Thr Glu Ile Cys
    130                 135                 140

Gln Ala Ala Gly
145

<210> SEQ ID NO 85
<211> LENGTH: 143
<212> TYPE: PRT
<213> ORGANISM: Metarhizium anisopliae

<400> SEQUENCE: 85

Gly Asn Leu Pro Asp Leu Asn Ala Leu Gln Ser Lys Tyr Ala Arg Gly
1               5                   10                  15

Ile Ile Ala Gln Ala Lys Lys Asp Gly Val Gly Ala His Gly Cys Gln
            20                  25                  30

Ala Gly Ile Ala Thr Ala Leu Thr Glu Ser Ser Leu Val Met Tyr Ala
        35                  40                  45

Asn Asn Ala Val Pro Ala Ser Leu Lys Tyr Pro His Asp Arg Val Gly
    50                  55                  60

Ser Asp His Asp Ser Val Gly Leu Phe Gln Gln Arg Ala Ser Ile Tyr
65                  70                  75                  80

Lys Asp Val Lys Cys Asp Met Asp Ala Ala Cys Ser Ala Gly Leu Phe
                85                  90                  95

Phe Thr Glu Met Lys Arg Val Lys Gly Trp Gln Thr Met Ala Val Gly
            100                 105                 110

Thr Leu Cys Gln Arg Val Gln Arg Ser Ala Tyr Pro Asp Arg Tyr Asn
        115                 120                 125

Lys Phe Val Pro Thr Ala Thr Lys Val Cys Lys Ala Gly Gly Leu
    130                 135                 140
```

```
<210> SEQ ID NO 86
<211> LENGTH: 144
<212> TYPE: PRT
<213> ORGANISM: Penicillium roqueforti

<400> SEQUENCE: 86
```

Ser Ser Asn Leu Pro Gly Leu Ser Ala Thr Gln Thr Lys His Ala Lys
1               5                   10                  15

Ala Ile Ile Ala Glu Ala Lys Lys Glu Gly Leu Gly Arg Gln Gly Cys
            20                  25                  30

Leu Ala Gly Ile Ser Thr Ala Leu Val Glu Ser Asn Ile Leu Ile Tyr
        35                  40                  45

Ala Asn Lys Lys Val Pro Ala Ser Leu Lys Tyr His His Asp Ala Val
50                  55                  60

Ala Glu Asp Tyr Asp Ser Val Gly Ile Phe Gln Gln Arg Ala Val Tyr
65                  70                  75                  80

Tyr Pro Asn Ile Ala Ala Asp Met Asp Ala Ala Lys Ser Ala Ala Gln
                85                  90                  95

Phe Phe Lys Ile Met Lys Lys Val Ser Gly Trp Lys Lys Met Asn Thr
            100                 105                 110

Gly Lys Leu Cys Gln Lys Val Gln Gly Ser Ala Tyr Pro Ser Arg Tyr
        115                 120                 125

Gln Glu Arg Val Pro Glu Ser Lys Lys Ile Cys Ser Ala Gly Gly Leu
    130                 135                 140

```
<210> SEQ ID NO 87
<211> LENGTH: 140
<212> TYPE: PRT
<213> ORGANISM: Talaromyces islandicus

<400> SEQUENCE: 87
```

Gly Asn Leu Pro Gly Leu Asp Ser Thr Gln Ser Ser His Ala Arg Ala
1               5                   10                  15

Ile Ile Ala Glu Ala Lys Arg Glu Lys Leu Gly His Gln Gly Cys Leu
            20                  25                  30

Ala Gly Ile Ala Thr Ala Leu Thr Glu Ser Ser Ile Leu Ile Tyr Ala
        35                  40                  45

Asn Ser Ala Val Pro Ala Ser Leu Asn Tyr Pro His Asp Ala Val Gly
    50                  55                  60

Ser Asp His Asp Ser Val Gly Ile Phe Gln Gln Arg Ala Val Tyr Tyr
65                  70                  75                  80

Pro Asn Ile Ala Ala Asp Met Asp Pro Ala Lys Ser Ala Ala Gln Phe
                85                  90                  95

Phe Ala Lys Met Lys Gly Val Ser Gly Trp Gln Thr Met Asn Val Gly
            100                 105                 110

Glu Leu Cys Gln Lys Val Gln Gly Ser Ala Tyr Pro Thr Arg Tyr Gln
        115                 120                 125

Glu His Leu Ser Ala Ala Glu Ser Ile Cys Ser Ala
    130                 135                 140

```
<210> SEQ ID NO 88
<211> LENGTH: 144
<212> TYPE: PRT
<213> ORGANISM: Penicillium expansum
```

<400> SEQUENCE: 88

```
Ser Gly Asn Leu Pro Gly Leu Thr Ser Thr Gln Ser Lys His Ala Lys
1               5                   10                  15
Ala Ile Ile Ala Glu Ala Lys Lys Glu Asn Leu Gly Arg Gln Gly Cys
            20                  25                  30
Leu Ala Gly Ile Ala Thr Gly Leu Val Glu Ser Asn Ile Leu Val Tyr
        35                  40                  45
Ala Asn Lys Lys Val Pro Asp Ser Leu Lys Tyr Pro His Asp Ala Val
    50                  55                  60
Gly Ser Asp Asn Asp Ser Val Gly Ile Phe Gln Gln Arg Ala Ile Tyr
65                  70                  75                  80
Tyr Pro Asp Ile Ala Ala Asp Met Asp Ala Ala Lys Ser Ala Ala Gln
                85                  90                  95
Phe Phe Lys Gly Ile Lys Asn Val Asn Gly Trp Lys Thr Met Glu Val
            100                 105                 110
Gly Lys Leu Cys Gln Lys Val Gln Gly Ser Ala Tyr Pro Ser Arg Tyr
        115                 120                 125
Ala Glu Arg Leu Asp Asp Ala Lys Lys Ile Cys Val Ala Gly Gly Leu
    130                 135                 140
```

<210> SEQ ID NO 89
<211> LENGTH: 142
<212> TYPE: PRT
<213> ORGANISM: Acremonium chrysogenum

<400> SEQUENCE: 89

```
Asn Leu Pro Gly Leu Asp Ser Thr Gln Thr Ala Asn Ala Gln Gly Ile
1               5                   10                  15
Leu Glu Gln Val Gly Thr Asp Asp Val Gly Leu Gln Gly Cys Leu Ala
            20                  25                  30
Gly Phe Ala Thr Ala Leu Val Glu Ser Asn Ile Tyr Ile Tyr Ala Asn
        35                  40                  45
Glu Ala Val Pro Glu Ser Leu Asn Tyr Pro Tyr Asp Lys Met Gly Ser
    50                  55                  60
Asp His Asp Ser Val Gly Ile Phe Gln Gln Arg Ala Met Phe Tyr Pro
65                  70                  75                  80
Asp Ile Ala Ala Asn Met Asp Pro Ala Arg Ser Ala Gly Gln Phe Phe
                85                  90                  95
Asp Lys Met Val Ser Ile Ser Gly Trp Glu Thr Met Asp Val Gly Glu
            100                 105                 110
Leu Cys Gln Ala Val Gln Val Ser Ala Tyr Pro Asp Arg Tyr Ala Glu
        115                 120                 125
Arg Val Glu Glu Ala Arg Ala Ile Cys Asn Ala Gly Gly Ile
    130                 135                 140
```

<210> SEQ ID NO 90
<211> LENGTH: 139
<212> TYPE: PRT
<213> ORGANISM: Mycobacterium chelonae

<400> SEQUENCE: 90

```
Ser Thr Lys Asp Arg His Ala Leu Ala Thr Ile Asn Glu Gly Lys Arg
1               5                   10                  15
Leu Gly Ile Thr Pro Lys Gly Ile Cys Ile Ala Ile Ala Val Glu Leu
            20                  25                  30
```

Val Glu Thr Asn Leu Thr Met Tyr Ala Asn Ser Asn Val Pro Ala Ser
            35                  40                  45

Leu Gly Tyr Pro His Glu Lys Val Gly Ser Asp His Asp Ser Thr Gly
 50                  55                  60

Leu Phe Gln Gln Arg Gln Ala Trp Gly Pro Leu Ser Glu Thr Met Asp
65                  70                  75                  80

Pro Thr Leu Ser Ala Arg Leu Phe Phe Leu Gly Gly His Ser Gly Gln
                85                  90                  95

Arg Gly Leu Thr Asp Phe Asp Tyr Asn Ser Asn Ser Arg Thr Pro Gly
                100                 105                 110

Gly Trp Ala Gln Ala Val Gln Val Ser Ala Phe Pro Tyr Arg Tyr Asp
            115                 120                 125

Glu Arg Tyr Thr Glu Ala Gln Gln Ile Tyr Ala
    130                 135

<210> SEQ ID NO 91
<211> LENGTH: 121
<212> TYPE: PRT
<213> ORGANISM: Mycobacterium sp. TKK

<400> SEQUENCE: 91

Asn Gly Lys Ala Val Ile Ala Ala Gly Leu Gln Met Lys Val Pro Glu
1               5                   10                  15

Lys Gly Ile Ile Ile Gly Leu Ala Val Gly Met Glu Glu Ser Gly Leu
            20                  25                  30

Arg Asn Leu Ala Asn Ser Asn Val Pro Glu Ser Leu Gly Ile Pro His
                35                  40                  45

Glu Gly Val Gly His Asp His Lys Ser Val Gly Ile Met Gln Gln Gln
 50                  55                  60

Pro Trp Trp Gly Ser Leu Arg Asp Leu Met Thr Pro Gly Val Ala Ala
65                  70                  75                  80

Gln Lys Phe Phe Ala Lys Leu Leu Lys Val Gly Gly Trp Gln Asn Met
                85                  90                  95

Ala Pro Thr Val Ala Ala Gln Thr Val Gln Gly Ser Ala Tyr Pro Asp
                100                 105                 110

Ala Tyr Ala Ala Phe Val Thr Gln Ala
            115                 120

<210> SEQ ID NO 92
<211> LENGTH: 142
<212> TYPE: PRT
<213> ORGANISM: Torrubiella hemipterigena

<400> SEQUENCE: 92

Gly Asn Leu Pro Thr Leu Asn Ser Val Gln Ser Arg Asn Ala Asn Gly
1               5                   10                  15

Ile Ile Ala Glu Val Lys Arg Arg Asn Leu Gly Arg Gln Gly Cys Leu
            20                  25                  30

Ala Ala Ile Thr Thr Gly Leu Thr Glu Ser Ser Ile Arg Ile Leu Ala
                35                  40                  45

Asn Asn Ala Val Pro Ser Ser Leu Asn Tyr Ala His Asp Gly Leu Gly
 50                  55                  60

Ser Asp His Asp Ser Val Gly Ile Phe Gln Gln Arg Ala Lys Tyr Tyr
65                  70                  75                  80

Thr Asn Ile Gln Cys Asp Met Thr Ala Asp Cys Ser Ala Gly Leu Phe
                85                  90                  95

```
Leu Ala Lys Met Ala Gly Ile Ser Gly Trp Gln Thr Met Asp Val Ala
                100                 105                 110

Thr Leu Cys Gln Lys Val Gln Val Ser Ala Val Pro Asp Ala Tyr Lys
            115                 120                 125

Lys Tyr Thr Ser Gln Ala Gly Thr Ile Cys Ser Ala Ala Gly
        130                 135                 140

<210> SEQ ID NO 93
<211> LENGTH: 142
<212> TYPE: PRT
<213> ORGANISM: Torrubiella hemipterigena

<400> SEQUENCE: 93

Asn Leu Pro Gly Leu Asn Ala Val Gln Thr Lys Tyr Ala Asn Ala Ile
1               5                   10                  15

Ile Ala Glu Ala Lys Lys Val Gly Val Gly Ala His Gly Cys Gln Ala
                20                  25                  30

Ala Ile Ala Thr Gly Leu Val Glu Ser Ser Ile Ile Met Tyr Ala Asn
            35                  40                  45

Lys Gly Val Pro Ala Ser Leu Asn Tyr Pro His Asp Arg Val Gly Ser
50                  55                  60

Asp His Asp Ser Ile Gly Ile Phe Gln Gln Arg Ala Ser Ile Tyr Lys
65                  70                  75                  80

Asn Ile Lys Cys Asp Met Asp Ala Ala Cys Ser Ala Gly Gln Phe Phe
                85                  90                  95

Thr Glu Met Lys Lys Val Lys Gly Trp Gln Thr Met Ala Val Gly Thr
                100                 105                 110

Leu Cys Gln Lys Val Gln Arg Ser Ala Tyr Pro Asp Arg Tyr Ala Lys
            115                 120                 125

Gln Val Gly Leu Ala Thr Lys Val Cys Lys Ala Gly Gly Leu
        130                 135                 140

<210> SEQ ID NO 94
<211> LENGTH: 147
<212> TYPE: PRT
<213> ORGANISM: Arthrobacter sp. PAMC

<400> SEQUENCE: 94

Leu Thr Ala Ala Gln Val Lys Val Ala Arg Ala Phe Ile Gly Val Gly
1               5                   10                  15

Lys Gln Leu Ser Ile Ser Asp Ile Gly Leu Gln Ile Ala Ile Met Val
                20                  25                  30

Gly Leu Gln Glu Ser Gly Leu Arg Val Leu Ala Asn Ser Ser Val Leu
            35                  40                  45

Ala Ser Met Thr Phe Ala His Asp Gly Val Gly Ser Asp His Asp Ser
50                  55                  60

Val Gly Ser Ala Gln Gln Arg Pro Ser Ala Gly Trp Gly Ser Val Ala
65                  70                  75                  80

Asp Leu Met Ser Pro Val Tyr Asp Ala Gln Ala Phe Phe Gly Gly Thr
                85                  90                  95

Ser Gly Pro Asn His Gly Ser Pro Arg Gly Leu Leu Asp Ile Pro Gly
            100                 105                 110

Trp Lys Ser Met Pro Lys Gly Glu Ala Ala Gln Ala Val Gln Val Ser
            115                 120                 125
```

```
Ala Phe Pro Glu Leu Tyr Ala Gln Trp Glu Gly Lys Ala Ser Ser Ile
            130                 135                 140

Val Ala Ala
145

<210> SEQ ID NO 95
<211> LENGTH: 137
<212> TYPE: PRT
<213> ORGANISM: Actinoplanes utahensis

<400> SEQUENCE: 95

Gly Leu Asn Gln Ala Gln Met Ser Asn Ala Thr Ile Val Arg Leu
1               5                   10                  15

Ala Gln Glu Arg Asp Leu Pro Arg Arg Ala Met Leu Ile Ala Val Met
            20                  25                  30

Thr Ala Phe Gln Glu Ser Ser Leu Arg Asn Leu Ala Asn Ser Ser Val
        35                  40                  45

Pro Ala Ser Leu Asp Arg Pro His Gln Gly Val Gly Asp Asp Phe Asp
    50                  55                  60

Ser Val Gly Leu Phe Gln Gln Arg Pro Ser Gln Gly Trp Gly Thr Val
65                  70                  75                  80

Ala Gln Leu Met Asp Pro Arg Tyr Ala Ala Asp Ala Phe Tyr Asp Arg
                85                  90                  95

Leu Val Glu Ile Pro Asp Trp Glu Ser Leu Ser Leu Gly Asp Ala Ala
            100                 105                 110

Gln Ala Val Gln Arg Ser Ala Val Pro Asp Ala Tyr Ala Asp His Glu
        115                 120                 125

Asp Arg Ala Ile Arg Ile Val Asp Ala
    130                 135

<210> SEQ ID NO 96
<211> LENGTH: 137
<212> TYPE: PRT
<213> ORGANISM: Metarhizium majus

<400> SEQUENCE: 96

Leu Thr Glu Leu Gln Ser Lys Tyr Ala Arg Gly Ile Ile Arg Gln Ala
1               5                   10                  15

Lys Lys Glu His Leu Gly Ser Gln Gly Cys Met Ala Gly Ile Ala Thr
            20                  25                  30

Ala Leu Val Glu Ser Thr Leu Leu Met His Ala Asn Tyr Ala Val Pro
        35                  40                  45

Asp Ser Leu Val Tyr Glu Tyr Asp Arg Leu Gly His Asp Ala Asp Ser
    50                  55                  60

Ile Gly Leu Phe Gln Gln Arg Ala Ser Ile Tyr Pro Asn Ile Lys Cys
65                  70                  75                  80

Ser Met Asp Val Ala Cys Ser Ala Arg Gln Phe Phe Glu Gly Met Lys
                85                  90                  95

Arg Val Pro Asp Trp Arg Tyr Met Asp Val Gly Lys Leu Cys Gln Glu
            100                 105                 110

Val Gln Arg Ser Glu Asn Pro Glu Arg Tyr His Glu Phe Ile Asn Gln
        115                 120                 125

Ala Lys Gly Ile Cys Gln Gln Gly Gly
    130                 135
```

<210> SEQ ID NO 97
<211> LENGTH: 137
<212> TYPE: PRT
<213> ORGANISM: Micromonospora carbonacea

<400> SEQUENCE: 97

Gly Leu Ser Gln Leu Gln Met Asp Asn Ala Lys Thr Ile Val Asp Val
1               5                   10                  15

Gly Arg Asp Met Lys Leu Pro Arg Arg Gly Leu Val Val Ala Val Ala
                20                  25                  30

Thr Ala Met Gln Glu Ser Asp Leu His Asn Leu Ala Ser Asp Val Leu
            35                  40                  45

Pro Glu Ser Ala Asn Tyr Pro His Gln Gly Ser Gly Ser Asp His Asp
        50                  55                  60

Ser Val Gly Leu Phe Gln Gln Arg Pro Ser Ser Gly Trp Gly Thr Val
65                  70                  75                  80

Arg Asp Leu Met Arg Pro Ala Tyr Ala Ala Arg Val Phe Tyr Glu Ala
                85                  90                  95

Leu Leu Glu Val Pro Gly Trp Glu Glu Met Ser Leu Thr Ala Ala Ala
                100                 105                 110

Gln Ala Val Gln Ile Ser Ala Phe Pro Asp Ala Tyr Ala Gln His Glu
            115                 120                 125

Glu Arg Ala Thr Thr Val Val Ala Ala
    130                 135

<210> SEQ ID NO 98
<211> LENGTH: 131
<212> TYPE: PRT
<213> ORGANISM: Mycobacterium immunogenum

<400> SEQUENCE: 98

Leu Asp Ala Gly Gln Met Glu Val Ala Arg Lys Ile Ile Glu Glu Gly
1               5                   10                  15

Leu Arg Arg Gly Leu Ser Pro Glu Ala Ile Gln Ile Ala Leu Ala Thr
                20                  25                  30

Ala Leu Thr Glu Ser Gly Leu Arg Ser Leu Ala Asn Ser Ser Val Pro
            35                  40                  45

Asp Ser Met Met Leu Ala Asn Asp Gly Val Gly His Asp His Asp Ser
        50                  55                  60

Val Gly Pro Phe Gln Gln Arg Gln Ser Trp Gly Ala Thr Ala Asp Leu
65                  70                  75                  80

Met Asp Pro Ser Arg Ser Ala Gly Lys Phe Tyr Asp Gln Leu Val Lys
                85                  90                  95

Val Ser Gly Trp Gln Asp Met Ser Val Ala Gln Ala Ala Gln Ala Val
                100                 105                 110

Gln Arg Ser Ala Phe Pro Asp Ala Tyr Ala Lys Tyr Glu Ala Gln Ala
            115                 120                 125

Ser Gln Ile
    130

<210> SEQ ID NO 99
<211> LENGTH: 139
<212> TYPE: PRT
<213> ORGANISM: Hirsutella minnesotensis

<400> SEQUENCE: 99

Ala Ser Lys Val Ser Gly Leu Asp Pro Val Gln Ser Arg Asn Ala Asp
1               5                   10                  15

Ala Ile Ile Ala Gln Ala Lys Lys Asp Arg Val Gly Glu His Gly Cys
            20                  25                  30

Thr Ala Ala Leu Thr Thr Ala Leu Ser Gln Thr Gly Ile Lys Ile Leu
        35                  40                  45

Ala Asn Lys Lys Val Pro Asp Ser Val Lys Tyr Lys His Asp Asp Leu
    50                  55                  60

Gly Thr Gln Gly Asp Ser Val Gly Ile Phe Gln Gln Ser Val Gln Lys
65                  70                  75                  80

Tyr Lys Asp Ile Ala Cys Val Met Lys Ala Asp Cys Ser Ala Ala Leu
                85                  90                  95

Phe Phe Arg Asp Ile Lys Ala Val Lys Gly Trp Glu Lys Met Asp Val
            100                 105                 110

Thr Lys Leu Leu Glu Ser Thr Asn Lys Ala Gly Thr Pro Ala Ala Phe
        115                 120                 125

Lys Lys Phe Glu Gly Gln Ala Ala Lys Ile Cys
    130                 135

<210> SEQ ID NO 100
<211> LENGTH: 141
<212> TYPE: PRT
<213> ORGANISM: Hirsutella minnesotensis

<400> SEQUENCE: 100

Asp Leu Pro Gly Leu Asn Pro Thr Gln Glu Ala His Ala Arg Ala Ile
1               5                   10                  15

Ile Gly Ala Asn Asn Gln Gly Asn Tyr Gly Arg Gln Gly Cys Leu Ala
            20                  25                  30

Ala Ile Thr Thr Gly Leu Thr Glu Ser Lys Leu Arg Ile Leu Ala Asn
        35                  40                  45

Pro Lys Val Pro Ala Ser Leu Lys Tyr Lys His Asp Ala Thr Gly Thr
    50                  55                  60

Asp His Asp Ser Ile Gly Ile Phe Gln Gln Arg Ala Ser Ile Tyr Lys
65                  70                  75                  80

Asn Ile Ala Cys Asp Met Asp Ala Ala Cys Ser Ala Gly Gln Phe Phe
                85                  90                  95

Lys Glu Met Lys Ala Ile Ser Gly Trp Gln Thr Met Asp Val Pro Thr
            100                 105                 110

Leu Cys Gln Lys Val Gln Arg Ser Ala Phe Pro Ala Arg Tyr Arg Glu
        115                 120                 125

Tyr Leu Ala Ser Ala Thr Ala Ile Cys Gln Ala Ala Gly
    130                 135                 140

<210> SEQ ID NO 101
<211> LENGTH: 143
<212> TYPE: PRT
<213> ORGANISM: Penicillium brasilianum

<400> SEQUENCE: 101

Gly Asn Leu Pro Gly Leu Ser Ala Thr Gln Ser Lys His Ala Arg Asp
1               5                   10                  15

Ile Ile Ala Glu Ala Lys Arg Glu Asp Leu Gly Leu His Gly Cys Ser
            20                  25                  30

```
Ala Gly Ile Ala Thr Ala Leu Val Glu Ser Asn Ile Leu Ile Tyr Ala
            35                  40                  45

Asn Lys Asp Val Pro Lys Ser Leu Asn Tyr Pro His Asp Ala Val Gly
 50                  55                  60

Ser Asp His Asp Ser Val Gly Ile Phe Gln Gln Arg Ala Met Tyr Tyr
 65                  70                  75                  80

Pro Asp Ile Ala Ala Asp Met Asp Ala Ala Lys Ser Ala Ala Gln Phe
                85                  90                  95

Phe Lys Lys Met Lys Asn Ile Ser Gly Trp Lys Ser Met Ala Val Gly
                100                 105                 110

Thr Leu Cys Gln Lys Val Gln Gly Ser Ala Tyr Pro Thr Arg Tyr Ala
            115                 120                 125

Glu Arg Val Ser Glu Ala Glu Lys Ile Cys Asn Ala Gly Gly Ile
130                 135                 140

<210> SEQ ID NO 102
<211> LENGTH: 143
<212> TYPE: PRT
<213> ORGANISM: Tolypocladium ophioglossoides

<400> SEQUENCE: 102

Asn Leu Pro Asp Leu Asn Ala Val Gln Ser Ala His Ala Arg Ser Ile
 1               5                  10                  15

Ile Asp Glu Val Lys Lys Val Gly Val Gly Met His Gly Cys Glu Ala
                20                  25                  30

Ala Ile Thr Thr Gly Leu Thr Glu Ser Gln Ser Ser Leu Arg Ile
            35                  40                  45

Leu Ala Asn Lys Asn Val Pro Ala Ser Leu Asn Tyr Ala His Asp Gly
 50                  55                  60

Leu Gly Ser Asp His Asp Ser Ile Gly Ile Phe Gln Gln Arg Ala Met
 65                  70                  75                  80

Tyr Tyr Lys Asp Ile Ala Cys Asp Met Lys Ala Asp Cys Ser Ala Gly
                85                  90                  95

Leu Phe Phe Asn Gly Met Lys Asp Ile Lys Gly Trp Gln Thr Met Asp
                100                 105                 110

Ile Ala Thr Leu Cys Gln Lys Val Gln Arg Ser Ala Tyr Pro Thr Ala
            115                 120                 125

Tyr Gln Lys Tyr Thr Gly Thr Ala Ala Lys Val Cys Lys Ala Gly
130                 135                 140

<210> SEQ ID NO 103
<211> LENGTH: 143
<212> TYPE: PRT
<213> ORGANISM: Madurella mycetomatis

<400> SEQUENCE: 103

Gly Asn Leu Pro Gly Leu Asn Ser Val Gln Ser Lys His Ala Arg Ala
 1               5                  10                  15

Ile Ile Ala Gln Ala Lys Lys Asp Lys Val Gly Arg His Gly Cys Gln
                20                  25                  30

Ala Gly Ile Ala Thr Ala Ile Val Glu Ser Asn Ile Leu Val Tyr Ala
            35                  40                  45

Asn Arg Lys Val Pro Ala Ser Met Lys Tyr Pro His Asp Ala Val Gly
 50                  55                  60

Ser Asp His Asp Ser Val Gly Ile Phe Gln Gln Arg Ala Arg Tyr Tyr
 65                  70                  75                  80
```

Pro Asn Ile Ala Ala Asn Met Asp Pro Ala Arg Ser Ala Gly Gln Phe
            85                  90                  95

Phe Ala Lys Met Lys Lys Val Lys Gly Trp Lys Thr Met Ala Val Gly
        100                 105                 110

Lys Leu Cys Gln Lys Val Gln Val Ser Ala Tyr Pro Asp Arg Tyr Ala
    115                 120                 125

Lys Gln Val Ser Lys Ala Ala Lys Ile Cys Ala Ala Gly Gly Leu
130                 135                 140

<210> SEQ ID NO 104
<211> LENGTH: 144
<212> TYPE: PRT
<213> ORGANISM: Aspergillus udagawae

<400> SEQUENCE: 104

Ser Gly Ser Leu Pro Gly Leu Asn Ala Lys Gln Ser Ala His Ala His
1               5                   10                  15

Lys Val Ile Asp Glu Ala Lys Lys Glu Gly Leu Gly Arg Gln Gly Cys
            20                  25                  30

Leu Ala Gly Ile Ala Thr Ala Leu Val Glu Ser Asn Leu Leu Met Tyr
        35                  40                  45

Ala Asn Ser Lys Val Pro Ala Ser Leu Asn Tyr Pro His Asp Ala Val
    50                  55                  60

Gly His Asp Tyr Asp Ser Val Gly Ile Phe Gln Gln Arg Ala Val Tyr
65                  70                  75                  80

Tyr Pro Asn Ile Ala Ala Asp Met Asp Ala Ala Arg Ser Ala Ala Gln
                85                  90                  95

Phe Phe Ala Lys Met Lys Asn Ile Ser Gly Trp Lys Thr Met Glu Val
            100                 105                 110

Gly Lys Leu Cys Gln Lys Val Gln Val Ser Ala Tyr Pro Asp Arg Tyr
        115                 120                 125

Ala Gln Arg Val Pro Ala Ala Glu Lys Ile Cys Ala Ala Gly Gly Leu
    130                 135                 140

<210> SEQ ID NO 105
<211> LENGTH: 138
<212> TYPE: PRT
<213> ORGANISM: Nocardia farcinica

<400> SEQUENCE: 105

Ser Lys Lys Asp Glu Tyr Ala Leu Ala Ile Leu Ala Glu Gly Arg Arg
1               5                   10                  15

Arg Gly Ile Thr Pro Arg Gly Ile Val Ile Ala Phe Ala Thr Val Tyr
            20                  25                  30

Val Glu Cys Asp Phe Ile Met Tyr Ala Asn Glu Lys Val Pro Glu Ser
        35                  40                  45

Leu Arg Leu Pro His Glu Arg Val Gly Arg Asp Gly Phe Ser Val Gly
    50                  55                  60

Leu Phe Gln Gln Gln Ile Val Arg Gly Ala Gly Gly Ala Tyr Trp Trp
65                  70                  75                  80

Ala Asp Cys Ala Thr Cys Met Asp Pro Thr Leu Ser Ala Gly Leu Phe
                85                  90                  95

Phe Glu Arg Leu Ala Arg Leu Asp Tyr Asn Ser Asn Glu His Ser Pro
            100                 105                 110

```
Gly Trp Tyr Ala Gln Ala Val Gln Arg Ser Ala Tyr Pro His Arg Tyr
            115                 120                 125

Asp Glu Arg Met Lys Asp Ala Gln Ala Leu
    130                 135

<210> SEQ ID NO 106
<211> LENGTH: 137
<212> TYPE: PRT
<213> ORGANISM: Micromonospora sp. HK10

<400> SEQUENCE: 106

Gly Leu Asp Gln Arg Gln Met Asp Asn Ala Lys Val Ile Val Asp Val
1               5                   10                  15

Gly Arg Ala Met Lys Met Pro Arg Arg Ala Leu Val Ile Ala Val Ala
            20                  25                  30

Thr Ala Met Gln Glu Ser Asn Leu Tyr Asn Leu Ala Ser Asp Val Leu
        35                  40                  45

Pro Glu Ser Tyr Asp Tyr Pro His Gln Gly Ser Gly Ser Asp His Asp
    50                  55                  60

Ser Val Gly Leu Phe Gln Gln Arg Pro Ser Ser Gly Trp Gly Thr Val
65                  70                  75                  80

Ala Gln Leu Met Arg Pro Ser Tyr Ala Ala Gln Ala Phe Tyr Thr Ala
                85                  90                  95

Leu Lys Glu Val Pro Gly Trp Thr Glu Leu Ser Leu Thr Ala Ala Ala
            100                 105                 110

Gln Ala Val Gln Val Ser Ala Tyr Pro Asp Ala Tyr Ala Pro His Glu
        115                 120                 125

Glu Arg Ala Thr Thr Val Val Ala Ala
    130                 135

<210> SEQ ID NO 107
<211> LENGTH: 137
<212> TYPE: PRT
<213> ORGANISM: Micromonospora sp. HK10

<400> SEQUENCE: 107

Gly Leu Asp Gln Ala Gln Met Asp Asn Ala Lys Lys Ile Val Gln Ala
1               5                   10                  15

Gly Arg Glu Met Gly Val Pro Arg Arg Gly Leu Val Ile Ala Val Ala
            20                  25                  30

Thr Ala Met Gln Glu Ser Thr Leu Leu Asn Tyr Ala Ser Gly Val Leu
        35                  40                  45

Pro Glu Ser Gln Ser Tyr Pro His Gln Ala Ile Gly Trp Asp His Asp
    50                  55                  60

Ser Val Gly Leu Phe Gln Gln Arg Pro Ser Ser Gly Trp Gly Thr Val
65                  70                  75                  80

Arg Glu Leu Met Asp Pro Glu Tyr Ala Thr Lys Ala Phe Leu Ser Ala
                85                  90                  95

Leu Glu Glu Ile Pro Gly Trp Gln Asp Leu Pro Leu Thr Val Ala Ala
            100                 105                 110

Gln Ala Val Gln Val Ser Ala Phe Pro Asp Ala Tyr Ala Gln His Glu
        115                 120                 125

Trp Arg Ala Ala Gln Val Val Gly Ala
    130                 135
```

```
<210> SEQ ID NO 108
<211> LENGTH: 144
<212> TYPE: PRT
<213> ORGANISM: Penicillium murcianum

<400> SEQUENCE: 108

Ser Gly Asn Leu Pro Gly Leu Ser Ser Thr Gln Ser Lys His Ala Lys
1               5                   10                  15

Ala Ile Ile Gly Glu Ala Lys Lys Glu Asp Leu Gly Arg Gln Gly Cys
            20                  25                  30

Leu Ala Gly Ile Ala Thr Ala Leu Val Glu Ser Asn Ile Leu Ile Tyr
        35                  40                  45

Ala Asn Lys Asp Val Pro Ser Ser Leu Asn Tyr Pro His Asp Ala Val
    50                  55                  60

Gly Ser Asp Tyr Asp Ser Val Gly Ile Phe Gln Gln Arg Ala Lys Tyr
65                  70                  75                  80

Tyr Pro Asp Ile Ala Ala Asp Met Asp Ala Ala Lys Ser Ala Ala Gln
                85                  90                  95

Phe Phe Lys Gly Met Lys Gly Val Ser Gly Trp Lys Thr Met Glu Val
            100                 105                 110

Gly Lys Leu Cys Gln Lys Val Gln Gly Ser Ala Tyr Pro Thr Arg Tyr
        115                 120                 125

Ala Glu Arg Val Asp Glu Ala Lys Lys Ile Cys Ala Ala Gly Gly Leu
    130                 135                 140

<210> SEQ ID NO 109
<211> LENGTH: 147
<212> TYPE: PRT
<213> ORGANISM: Micromonospora sp.

<400> SEQUENCE: 109

Thr Gly Glu Leu Pro Arg Phe Ala Glu Tyr Gly Asp Thr Gln Ile Arg
1               5                   10                  15

Asn Ala Ala Ile Ile Ile Lys Val Gly Gln Asp Met Gly Val Pro Ser
            20                  25                  30

Arg Gly Trp Val Ile Ala Leu Ala Thr Ala Met Gln Glu Ser Ala Leu
        35                  40                  45

Arg Asn Leu Ala Asn Ser Gly Val Pro Glu Ser Leu Ala Leu Pro His
    50                  55                  60

Glu Gly Val Gly Ala Asp His Asp Ser Leu Gly Leu Phe Gln Gln Arg
65                  70                  75                  80

Pro Gly Trp Gly Thr Val Ala Glu Arg Met Asn Pro Ala Tyr Thr Ala
                85                  90                  95

Arg Lys Phe Tyr Glu Lys Leu Val Lys Val Arg Ser Trp Gln Arg Arg
            100                 105                 110

Pro Leu Thr Val Val Ala Gln Gln Val Gln Ile Ser Ala Tyr Pro Asp
        115                 120                 125

Ala Tyr Ala Lys His Glu Glu Leu Ala Ser Thr Ile Val Asp Ala Leu
    130                 135                 140

Ala Gly Gly
145

<210> SEQ ID NO 110
<211> LENGTH: 142
<212> TYPE: PRT
<213> ORGANISM: Trichoderma gamsii
```

```
<400> SEQUENCE: 110

Asn Leu Pro Gly Leu Asn Ala Val Gln Thr Lys Tyr Ala Asn Ala Ile
1               5                   10                  15

Ile Ala Lys Ala Lys Ala Glu Gly Val Gly Ala His Gly Cys Gln Ala
            20                  25                  30

Ala Ile Ala Thr Ala Met Val Glu Ser Ser Ile Ile Met Tyr Ala Asn
        35                  40                  45

Asn Gly Val Pro Glu Ser Leu Lys Tyr Pro His Asp Arg Val Gly Ser
    50                  55                  60

Asp His Asp Arg Ile Gly Leu Phe Gln Gln Pro Ala Ser Ile Tyr Lys
65                  70                  75                  80

Asn Ile Lys Cys Asp Met Asp Ala Ala Cys Ser Ala Gly Gln Phe Tyr
                85                  90                  95

Thr Glu Met Lys Lys Ile Ser Gly Trp Lys Asn Met Ala Ile Gly Thr
            100                 105                 110

Leu Ala Gln Lys Val Gln Arg Ser Ala Tyr Pro Asp Arg Tyr Ala Lys
        115                 120                 125

Gln Val Gly Leu Ala Thr Asn Val Cys Lys Ala Gly Gly Leu
    130                 135                 140

<210> SEQ ID NO 111
<211> LENGTH: 151
<212> TYPE: PRT
<213> ORGANISM: Arthrobacter sp. Soil761

<400> SEQUENCE: 111

Leu Thr Pro Arg Gln Glu Ser Val Ala Arg Thr Tyr Ile Ala Val Gly
1               5                   10                  15

Gln Gln Leu Gly Ile Pro Arg Ser Gly Gln Ile Ile Ala Ile Met Met
            20                  25                  30

Ala Leu Gln Glu Ser Ser Leu Arg Met Leu Ala Asn Pro Ser Val Pro
        35                  40                  45

Ala Ser Val Gln Phe Pro Asn Asp Gly Val Gly Arg Asp His Asp Ser
    50                  55                  60

Ile Gly Ser Ala Gln Gln Arg Pro Ala Ala Gly Trp Gly Thr Val Glu
65                  70                  75                  80

Gln Leu Met Asp Ala Ser Tyr Asn Ala Arg Ala Phe Tyr Gly Gly Pro
                85                  90                  95

Ser Gly Pro Asn Arg Gly Ser Pro Arg Gly Leu Leu Asp Ile Pro Gly
            100                 105                 110

Trp Gln Gly Met Asp Lys Gly Leu Ala Ala Gln Ala Val Gln Val Ser
        115                 120                 125

Ala Phe Pro Glu Leu Tyr Ala Arg Trp Glu Arg Ala Ala Thr Ala Ile
    130                 135                 140

Val Ala Ala Leu Glu Gly Gly
145                 150

<210> SEQ ID NO 112
<211> LENGTH: 144
<212> TYPE: PRT
<213> ORGANISM: Arthrobacter sp. Soil736
```

<400> SEQUENCE: 112

Leu Thr Ser Asp Gln Ile Ala Val Ala Lys Gly Tyr Ile Ser Val Gly
1               5                   10                  15

Lys Gln Leu Gly Val Pro Gln Glu Ala Leu Ile Ile Ala Ile Met Met
            20                  25                  30

Ala Leu Gln Glu Ser Ser Leu Arg Val Leu Ala Asn Ser Asn Val Pro
        35                  40                  45

Ala Ser Phe Gln Phe Ser His Asp Gly Val Gly Ser Asp His Asp Ser
    50                  55                  60

Leu Gly Thr Ala Gln Gln Arg Pro Ala Ala Gly Trp Gly Ser Val Glu
65                  70                  75                  80

Glu Leu Met Asp Pro Asp Tyr Asn Ala Arg Ala Phe Tyr Gly Gly Pro
                85                  90                  95

Ser Gly Pro Asn Arg Gly Ser Pro Arg Gly Leu Leu Asp Val Ser Gly
            100                 105                 110

Trp Gln Ser Met Asp Lys Gly Gln Ala Ala Gln Ala Val Gln Val Ser
        115                 120                 125

Ala Phe Pro Glu Leu Tyr Ala Arg Trp Glu Ser Gln Ala Thr Ala Ile
    130                 135                 140

<210> SEQ ID NO 113
<211> LENGTH: 153
<212> TYPE: PRT
<213> ORGANISM: Microbacterium sp. No. 7

<400> SEQUENCE: 113

Gly Ser Thr Arg Thr Leu Thr Ala Thr Glu Leu Gly His Ala Ala Thr
1               5                   10                  15

Ile Leu Ala Val Ala Arg Ser Leu Gly Val Ser Glu Arg Gly Gln Gln
            20                  25                  30

Ile Ala Met Met Thr Ala Leu Gln Glu Ser Gly Leu Lys Met Tyr Ala
        35                  40                  45

Asn Ser Ser Val Pro Ala Ser Leu Asp Tyr Pro His Asp Ala Val Gly
    50                  55                  60

Ser Asp His Asp Ser Val Asn Phe Phe Gln Gln Arg Val Ser Gly Trp
65                  70                  75                  80

Gly Ser Val Lys Asp Leu Met Asp Pro Thr Tyr Ala Ala Arg Ala Phe
                85                  90                  95

Phe Gly Gly Pro Asp Gly Pro Asn Glu Gly Ser Pro Arg Gly Leu Leu
            100                 105                 110

Asp Ile Pro Gly Trp Glu Ser Met Ser Leu Gly Glu Ala Ala Gln Thr
        115                 120                 125

Val Gln Val Ser Ala Phe Pro Asp Ala Tyr Asp Lys Trp Glu Gly Ala
    130                 135                 140

Ala Gln Gln Ile Ile Ser Ser Val Gly
145                 150

<210> SEQ ID NO 114
<211> LENGTH: 144
<212> TYPE: PRT
<213> ORGANISM: Arthrobacter sp. Soil762

<400> SEQUENCE: 114

```
Leu Thr Ala Arg Gln Ile Ala Val Ala Ser Asp Tyr Ile Ser Val Gly
1               5                   10                  15

Lys Gln Leu Gly Val Pro Arg Asp Gly Gln Ile Ile Ala Ile Met Met
            20                  25                  30

Ser Leu Gln Glu Ser Gly Leu Arg Val Leu Ala Asn Ala Asn Val Pro
        35                  40                  45

Glu Ser Leu Asn Tyr Pro His Asp Gly Val Gly Ser Asp His Asp Ser
    50                  55                  60

Leu Gly Ser Ala Gln Gln Arg Pro Ala Ala Gly Trp Gly Ser Ile Ala
65                  70                  75                  80

Gln Leu Met Asp Ser Met Tyr Asn Val Gln Ala Phe Tyr Gly Gly Pro
                85                  90                  95

Ala Gly Pro Asn Arg Gly Ser Pro Pro Gly Leu Leu Asp Ile Arg Gly
            100                 105                 110

Trp Gln Ser Met Ser Lys Gly Gln Ala Ala Gln Ala Val Gln Val Ser
        115                 120                 125

Ala Phe Pro Glu Leu Tyr Ala His Trp Glu Pro Gln Ala Thr Ala Ile
    130                 135                 140
```

<210> SEQ ID NO 115
<211> LENGTH: 141
<212> TYPE: PRT
<213> ORGANISM: Micromonospora halophytica

<400> SEQUENCE: 115

```
Leu Pro Gly Tyr Gly Asp Asn Gln Leu Arg Asn Ala Ala Val Ile Ile
1               5                   10                  15

Thr Val Gly Gln Glu Met Lys Val Pro Pro Arg Gly Trp Val Val Ala
            20                  25                  30

Val Ala Thr Ala Met Gln Glu Ser Arg Leu Leu Asn Leu Ala Asn Arg
        35                  40                  45

Thr Val Ala Gln Ser Arg Arg Ile Pro Asn Gln Gly Val Gly Ala Asp
    50                  55                  60

His Asp Ser Val Gly Leu Phe Gln Gln Arg Ala Ser Trp Gly Thr Val
65                  70                  75                  80

Glu Gln Arg Met Thr Pro Glu Tyr Ala Ala Arg Lys Phe Tyr Glu Lys
                85                  90                  95

Leu Val Gln Val Pro Gly Trp Gln Thr Met Pro Leu Thr Arg Ala Ala
            100                 105                 110

Gln Arg Val Gln Ile Ser Ala Phe Pro Asp Ala Tyr Ala Lys His Glu
        115                 120                 125

Asp Leu Ala Ala Arg Ile Val Asp Ala Leu Ala Gly Gly
    130                 135                 140
```

<210> SEQ ID NO 116
<211> LENGTH: 137
<212> TYPE: PRT
<213> ORGANISM: Micromonospora nigra

<400> SEQUENCE: 116

```
Gly Leu Thr Arg Ala Gln Met Asp Asn Ala Glu Ala Ile Val Arg Ala
1               5                   10                  15

Gly Arg Glu Met Gly Val Pro Arg Ala Leu Val Ile Ala Val Ala
            20                  25                  30
```

Thr Ala Met Gln Glu Ser Thr Leu Tyr Asn Val Ala Ser Gly Val Leu
            35                  40                  45

Pro Glu Ser Gln Arg His Pro His Gln Gly Val Gly Trp Asp His Asp
 50                  55                  60

Ser Val Gly Leu Phe Gln Gln Arg Ser Ser Gly Trp Gly Pro Val
 65                  70                  75                  80

Gly Arg Leu Met Asp Pro Glu Phe Ala Thr Arg Gln Phe Leu Thr Ala
                 85                  90                  95

Leu Leu Arg Val Pro Gly Trp Gln Arg Met Arg Leu Thr Asp Ala Ala
            100                 105                 110

Gln Ala Val Gln Val Ser Ala Tyr Pro Gly His Tyr Ala Arg His Glu
            115                 120                 125

Gly Leu Ala Thr Glu Val Val Asp Ala
    130                 135

<210> SEQ ID NO 117
<211> LENGTH: 143
<212> TYPE: PRT
<213> ORGANISM: Penicillium patulum

<400> SEQUENCE: 117

Gly Lys Leu Pro Gly Leu Ser Ser Thr Gln Ser Lys His Ala Lys Asp
 1               5                  10                  15

Ile Ile Gly Glu Ala Lys Lys Glu Gly Leu Gly Arg Gln Gly Cys Leu
             20                  25                  30

Ala Gly Ile Ala Thr Gly Leu Val Glu Ser Asn Leu Leu Ile Tyr Ala
             35                  40                  45

Asn Lys Lys Val Pro Ala Ser Leu Lys Tyr Pro His Asp Ala Val Gly
 50                  55                  60

Ser Asp His Asp Ser Val Gly Ile Phe Gln Gln Arg Ala Met Tyr Tyr
 65                  70                  75                  80

Pro Asp Ile Ala Ala Asp Met Asp Ala Ala Lys Ser Ala Ala Gln Phe
                 85                  90                  95

Phe Lys Glu Met Lys Arg Val Ser Gly Trp Lys Ser Met Asp Val Gly
            100                 105                 110

Lys Leu Cys Gln Lys Val Gln Arg Ser Ala Tyr Pro Ser Arg Tyr Ala
            115                 120                 125

Asp Arg Val Gly Asp Ala Lys Lys Ile Cys Ala Ala Gly Gly Leu
    130                 135                 140

<210> SEQ ID NO 118
<211> LENGTH: 152
<212> TYPE: PRT
<213> ORGANISM: Arthrobacter sp. Leaf69

<400> SEQUENCE: 118

Val Thr Ala Arg Gln Met Ala Val Ala Gly Asp Tyr Val Ser Ile Gly
 1               5                  10                  15

Gln Gln Leu Gly Ile Pro Arg Asp Gly Gln Ile Ile Ala Ile Met Met
             20                  25                  30

Ala Leu Gln Glu Ser Ser Leu Arg Val Leu Ala Asn Val Asn Val Pro
             35                  40                  45

Ala Ser Leu Gln Tyr Pro His Asp Gly Leu Gly Ser Asp His Asp Ser
 50                  55                  60

Leu Gly Thr Ala Gln Gln Arg Pro Ala Ala Gly Trp Gly Thr Val Glu
 65                  70                  75                  80

```
Gln Leu Met Asp Pro Lys Tyr Asn Val Arg Ala Phe Tyr Gly Gly Pro
                85                  90                  95

Ser Gly Pro Asn Arg Gly Ser Pro Pro Gly Leu Leu Asp Ile Arg Gly
            100                 105                 110

Trp Gln Ser Met Asn Lys Gly Gln Ala Ala Gln Ala Val Gln Val Ser
        115                 120                 125

Ala Phe Pro Glu Leu Tyr Ala Arg Trp Glu Glu Ala Thr Ala Ile
    130                 135                 140

Val Glu Ala Leu Asp Gly Gly Met
145                 150
```

<210> SEQ ID NO 119
<211> LENGTH: 144
<212> TYPE: PRT
<213> ORGANISM: Mycobacterium abscessus

<400> SEQUENCE: 119

```
Asn Ala Gln Val Val Ala Val Gly Glu Lys Met His Ile Pro Pro
1               5                   10                  15

Gln Gly Ile Ile Val Ala Leu Ala Thr Ala Leu Gln Glu Ser Gly Leu
            20                  25                  30

Lys Asn Tyr Ala Asn Asp Gly Thr Gly Gln Leu Arg Gly Asp Gln Gln
        35                  40                  45

Gly Ile Ala Ser Ser Leu Gln Leu Pro His Asp Ala Val Gly Arg Asp
    50                  55                  60

His Gly Ser Leu Gly Ile Met Gln Gln Gln Tyr Pro Trp Trp Gly Thr
65                  70                  75                  80

Ile Gln Glu Leu Met Thr Pro Ala Ile Ala Ala Arg Lys Phe Tyr Glu
                85                  90                  95

Ala Leu Leu Lys Val Asn Asn Trp Gln Asn Leu Pro Val Thr Val Ala
            100                 105                 110

Ala Gln Thr Val Gln Gly Ser Ala Phe Pro Asp Ala Tyr Ala Ala Gln
        115                 120                 125

Glu Pro Lys Ala Arg Ala Leu Tyr Ala Thr Tyr Arg Gly Ala Gly Gly
    130                 135                 140
```

<210> SEQ ID NO 120
<211> LENGTH: 137
<212> TYPE: PRT
<213> ORGANISM: Mycobacterium canariasense

<400> SEQUENCE: 120

```
Thr Lys Asp Gln Val Ala Ser Glu Phe Ile Ala Glu Gly Lys Arg Arg
1               5                   10                  15

Gly Ile Thr Glu Arg Gly Ile Val Ile Cys Ile Ala Thr Gly Leu Val
            20                  25                  30

Glu Ser Asn Leu Thr Val Tyr Ala Asn Ser Lys Val Pro Glu Ser Leu
        35                  40                  45

Ser Leu Pro His Asp Ala Val Gly Ser Asp Gly Lys Ser Val Gly Pro
    50                  55                  60

Leu Gln Gln Gln Val Val Trp Gly Asn Gly Gly Trp Trp Trp Gly Asp
65                  70                  75                  80

Ala Ala Thr Cys Met Asp Pro Thr Arg Ser Ala Gly Leu Phe Tyr Asp
                85                  90                  95

Arg Leu Val Lys Lys Pro Tyr Gln Ser Ala Thr Ser Asp Val Ala Ala
            100                 105                 110
```

```
Gly Ala Ile Ala Gln Ser Ile Gln Gly Ser Ala Phe Pro Asp Arg Tyr
            115                 120                 125

Ala Thr Arg Met Ala Glu Ala Arg Gln
            130                 135

<210> SEQ ID NO 121
<211> LENGTH: 147
<212> TYPE: PRT
<213> ORGANISM: Micromonospora rifamycinica

<400> SEQUENCE: 121

Ser Gly Asn Ile Pro Arg Leu Gly Ser Tyr Gly Gln Thr Gln Met Arg
1               5                   10                  15

Asn Ala Ala Val Ile Ile Lys Val Gly Gln Asp Met Arg Val Pro Pro
            20                  25                  30

Arg Gly Trp Val Ile Ala Val Ala Thr Ala Met Gln Glu Ser Ala Leu
        35                  40                  45

Arg Asn Leu Ser Asn Ser Thr Val Ala Gly Ser Arg Gly Ile Pro Asn
    50                  55                  60

Glu Gly Val Gly Ser Asp His Asp Ser Val Gly Leu Phe Gln Gln Arg
65                  70                  75                  80

Ala Gly Trp Gly Ser Val Ala Gln Arg Met Ser Pro Asp Tyr Ala Ala
                85                  90                  95

Arg Lys Phe Tyr Glu Lys Leu Leu Lys Val Asp Gly Trp Glu Arg Met
            100                 105                 110

Pro Leu Thr Arg Ala Ala Gln Lys Val Gln Ile Ser Ala Tyr Pro Asp
        115                 120                 125

Ala Tyr Ala Lys His Glu Asp Ile Ala Ser Gln Ile Val Asn Ala Leu
    130                 135                 140

Ala Gly Gly
145

<210> SEQ ID NO 122
<211> LENGTH: 137
<212> TYPE: PRT
<213> ORGANISM: Micromonospora rifamycinica

<400> SEQUENCE: 122

Gly Leu Asp Arg Ala Gln Met Asn Asn Ala Gln Lys Ile Val Lys Ala
1               5                   10                  15

Gly Arg Ala Met Gly Val Pro Arg Ala Leu Val Ile Ala Val Ala
            20                  25                  30

Thr Ala Met Gln Glu Ser Asn Leu Tyr Asn Tyr Ala Ser Gly Val Leu
            35                  40                  45

Pro Glu Ser Gln Asn Tyr Pro His Glu Ala Ile Gly Trp Asp His Asp
        50                  55                  60

Ser Val Gly Leu Phe Gln Gln Arg Pro Ser Ser Gly Trp Gly Glu Val
65                  70                  75                  80

Gly Gln Leu Met Asp Pro Ala Phe Ala Thr Arg Ala Phe Leu Thr Ala
                85                  90                  95

Leu Leu Ala Ile Pro Gly Trp Glu Asp Leu Pro Leu Thr Val Ala Ala
            100                 105                 110

Gln Ala Val Gln Ile Ser Ala Tyr Pro Asp Leu Tyr Ala Gln His Glu
        115                 120                 125

Trp Arg Ala Thr Glu Val Val Ala Ala
    130                 135
```

<210> SEQ ID NO 123
<211> LENGTH: 144
<212> TYPE: PRT
<213> ORGANISM: Arthrobacter alpinus

<400> SEQUENCE: 123

Leu Ser Glu Ser Gln Thr Lys Val Ala Lys Thr Tyr Ile Ala Val Gly
1               5                   10                  15

Arg Ala Arg Gly Val Pro Asn Gly Gly Ile Val Ile Ala Leu Met Met
            20                  25                  30

Gly Phe Gln Glu Ser Gly Met Gln Met Leu Ala Asn Ala Ser Val Pro
        35                  40                  45

Glu Ser Leu Asn Phe Pro His Asp Gly Val Gly Ser Asp His Asp Ser
50                  55                  60

Val Gly Ser Ala Gln Gln Arg Pro Ser Ala Gly Trp Gly Ser Val Glu
65                  70                  75                  80

Glu Leu Met Gln Pro Ala Tyr Asn Ala Glu Ala Phe Tyr Gly Gly Pro
                85                  90                  95

Gln Gly Pro Asn Arg Gly Ser Pro Arg Gly Leu Leu Asp Ile Pro Gly
            100                 105                 110

Trp Gln Gly Leu Asp Lys Gly Ala Ala Ala Gln Ala Val Gln Gly Ser
        115                 120                 125

Ala Phe Pro Glu Arg Tyr Ala Lys Trp Gln Pro Glu Ala Glu Ala Ile
130                 135                 140

<210> SEQ ID NO 124
<211> LENGTH: 148
<212> TYPE: PRT
<213> ORGANISM: Microbacterium hominis

<400> SEQUENCE: 124

Leu Gly His Thr Gln Leu Thr His Ala Ala Thr Ile Ile Thr Thr Gly
1               5                   10                  15

Ser Gly Ile Glu Gly Val Gly Arg Gln Gly Val Leu Ile Ala Leu Met
            20                  25                  30

Ala Ala Leu Thr Glu Ser Thr Leu Arg Met Leu Ala Asn Ala Ala His
        35                  40                  45

Pro Ala Ser Leu Asp Leu Pro His Asp Gly Val Gly Gly Asp His Asp
50                  55                  60

Ser Leu Gly Leu Phe Gln Met Arg Pro Thr Ser Gly Trp Gly Ser Val
65                  70                  75                  80

Asp Gln Leu Met Asp Pro Lys Tyr Gln Ala Arg Ala Phe Phe Gly Gly
                85                  90                  95

Glu Thr Gly Pro Asn Phe Pro Ser Pro Ala Gly Leu Leu Asp Ile Ala
            100                 105                 110

Gly Trp Gln Ser Ala Asp Pro Gly Ala Ala Gln Ala Val Glu Arg
        115                 120                 125

Ser Ala Phe Pro Asp Arg Tyr Gln Arg Tyr Gln Pro Val Ala Glu Ala
130                 135                 140

Ile Ile Ser Ala
145

<210> SEQ ID NO 125
<211> LENGTH: 130
<212> TYPE: PRT
<213> ORGANISM: Gordonia phage Obliviate

<400> SEQUENCE: 125

Ala Ile Thr Glu Gln Ala Lys Lys Met Gly Val Ser Lys Arg Gly Ala
1               5                   10                  15

Ile Ile Gly Val Ala Thr Gly Leu Val Glu Ser Gly Asp Pro Met Lys
            20                  25                  30

Met Trp Ala Asn Asn Ala Val Pro Glu Ser Leu Lys Phe Pro His Asp
        35                  40                  45

Glu Val Gly Ser Asp His Asp Ser Ile Gly Leu Phe Gln Gln Arg Gln
50                  55                  60

Ala Gly Trp Gly Thr Val Ala Asp Arg Met Asp Pro His Arg Ser Ala
65                  70                  75                  80

Ala Met Phe Phe Asp Ala Leu Met Lys Val Pro Gly Trp Glu Thr Met
                85                  90                  95

Asp Met Gly Ala Ala Gln Ala Val Gln Arg Ser Ala Phe Pro Gly
            100                 105                 110

Lys Tyr Ala Glu Arg Met Pro Arg Ala Thr Glu Leu Val Asp Lys Phe
            115                 120                 125

Gly Ile
    130

<210> SEQ ID NO 126
<211> LENGTH: 147
<212> TYPE: PRT
<213> ORGANISM: Micromonospora rosaria

<400> SEQUENCE: 126

Thr Gly Ser Met Pro Arg Thr Phe Gly Tyr Gly Glu Arg Gln Met Arg
1               5                   10                  15

Asn Ala Ala Ile Ile Ile Lys Val Gly Gln Asp Met Lys Val Pro Ala
            20                  25                  30

Arg Gly Trp Val Ile Ala Ile Ala Thr Ala Ile Gln Glu Ser Gly Leu
        35                  40                  45

Lys Asn Tyr Ala Asn Ser Thr Val Pro Glu Ser Leu Ala Ile Pro His
50                  55                  60

Glu Ala Val Gly Ser Asp His Asp Ser Val Gly Leu Phe Gln Gln Arg
65                  70                  75                  80

Pro Gly Trp Gly Thr Val Ala Gln Arg Met Asn Pro Ser Tyr Ser Ala
                85                  90                  95

Arg Lys Phe Tyr Glu Lys Leu Val Lys Val Pro Asp Trp Glu Lys Arg
            100                 105                 110

Ser Leu Thr Asn Ala Ala Gln Met Val Gln Ile Ser Ala Phe Pro Asp
            115                 120                 125

Ala Tyr Ala Lys His Glu Glu Thr Ala Ser Arg Ile Val Asp Leu Leu
130                 135                 140

Ala Gly Gly
145

<210> SEQ ID NO 127
<211> LENGTH: 131
<212> TYPE: PRT
<213> ORGANISM: Tsukamurella pseudospumae

<400> SEQUENCE: 127

Thr Pro Asp Gln Val Ala Ala Phe Ile Val Glu Gly Leu Arg Ser
1               5                   10                  15

Gly Val Ser Glu Arg Gly Ile Val Ile Cys Leu Ala Thr Gly Leu Val
            20                  25                  30

Glu Ser Asn Leu Thr Val Tyr Ala Asn Pro Ala Asp Pro Glu Ser Leu
        35                  40                  45

Ala Glu Pro His Asp Ala Val Gly Ser Asp Ala Asn Ser Val Gly Pro
    50                  55                  60

Leu Gln Gln Arg Ala Pro Trp Trp Gly Ser Ser Ala Arg Glu Arg Met
65                  70                  75                  80

Asn Pro Thr Leu Ser Ser Arg Leu Phe Tyr Arg Ala Leu Arg Ala Leu
                85                  90                  95

Pro Tyr Asp Ser Pro Ala His Ser Pro Gly Trp Tyr Ala Gln Gln Val
            100                 105                 110

Gln Arg Ser Ala Phe Pro Asp Arg Tyr Asp Arg Ile Thr Glu Ala
        115                 120                 125

Gln Ala Ile
    130

<210> SEQ ID NO 128
<211> LENGTH: 137
<212> TYPE: PRT
<213> ORGANISM: Micromonospora rosaria

<400> SEQUENCE: 128

Gly Leu Thr Gln Val Gln Met Asp Asn Ala Lys Val Ile Val Asp Val
1               5                   10                  15

Gly Ala Asp Leu Lys Met Pro Arg Arg Ala Leu Val Val Ala Val Ala
            20                  25                  30

Thr Ala Met Gln Glu Ser Asn Leu Tyr Asn Leu Ala Ser Asp Val Leu
        35                  40                  45

Pro Glu Ser His Gln Tyr Thr Asp Gln Gly Ser Gly Ser Asp His Asp
    50                  55                  60

Ser Val Gly Leu Phe Gln Gln Arg Pro Ser Ser Gly Trp Gly Thr Val
65                  70                  75                  80

Arg Asp Leu Met Arg Pro Ala His Ala Ala Gln Leu Phe Tyr Glu Ala
                85                  90                  95

Leu Arg Gln Ile Pro Gly Trp Gln Ser Leu Ser Ile Ala Ala Ala Ala
            100                 105                 110

Gln Ala Val Gln Ile Ser Ala Phe Pro Asp Ala Tyr Ala Gln His Glu
        115                 120                 125

Gln Arg Ala Ser Thr Val Val Thr Ala
    130                 135

<210> SEQ ID NO 129
<211> LENGTH: 142
<212> TYPE: PRT
<213> ORGANISM: Tilletia walkeri

<400> SEQUENCE: 129

Gly Leu Ile Ser Gly Leu Asn Ala Ile Gln Thr Ala His Ala Tyr Gln
1               5                   10                  15

Ile Ala Lys Ala Val Arg Ala Lys Gly Leu Pro Arg Gln Ala Cys Leu
            20                  25                  30

```
Ala Ala Ile Thr Thr Gly Ile Thr Glu Ala Asn Leu Leu Asn Tyr Ala
         35                  40                  45

Asn Ser Asp Val Ser Ala Ser Phe Asn Tyr Gln Tyr Asp Ala Val Ser
 50                  55                  60

Ser Asp Tyr Asp Ser Val Gly Val Phe Gln Gln Arg Val Thr Tyr Tyr
65                   70                  75                  80

Pro Asp Val Gly Ala Asp Met Asp Pro Gln Gln Ala Ala Ser Gln Phe
             85                  90                  95

Leu Asp Lys Met Val Asn Ile Asn Gly Trp Glu Asn Thr Asp Val Gly
            100                 105                 110

Thr Leu Cys Gln Asp Val Gln Gly Ser Ala Tyr Pro Asp Arg Tyr Asn
        115                 120                 125

Glu Asn Val Gly Gln Ala Gln Asp Ile Cys Thr Ala Met Gly
130                 135                 140

<210> SEQ ID NO 130
<211> LENGTH: 142
<212> TYPE: PRT
<213> ORGANISM: Tilletia controversa

<400> SEQUENCE: 130

Gly Leu Leu Ser Gly Trp Asn Ala Leu Gln Thr Ala His Ala Tyr Gln
1               5                   10                  15

Ile Ala Lys Ala Val Arg Ala Lys Gly Leu Pro Arg Gln Ala Cys Leu
            20                  25                  30

Ala Ala Ile Cys Thr Gly Ile Thr Glu Ala Asn Leu Leu Asn Tyr Ala
         35                  40                  45

Asn Ser Asp Val Ala Glu Ser Phe Asn Tyr Gln Tyr Asp Ala Val Ser
 50                  55                  60

Ser Asp Tyr Asp Ser Val Gly Val Phe Gln Gln Arg Val Thr Tyr Tyr
65                   70                  75                  80

Pro Asn Val Ala Ala Asp Met Asp Pro Gln Ser Ala Ala Ala Gln Phe
             85                  90                  95

Leu Asp Lys Met Val Asn Ile Asn Gly Trp Glu Thr Thr Asp Val Gly
            100                 105                 110

Ser Leu Cys Gln Ala Val Gln Gly Ser Ala Tyr Pro Asp Arg Tyr Asn
        115                 120                 125

Glu His Val Gly Gln Ala Gln Asp Ile Cys Ser Ala Met Gly
130                 135                 140

<210> SEQ ID NO 131
<211> LENGTH: 145
<212> TYPE: PRT
<213> ORGANISM: Pochonia chlamydosporia 170

<400> SEQUENCE: 131

Asn Leu Pro Gly Leu Asn Ala Leu Gln Ser Lys Tyr Ala Asn Ala Ile
1               5                   10                  15

Ile Ala Gln Ala Lys Lys Asp Gly Val Gly Pro His Gly Leu Thr Asn
            20                  25                  30

Tyr Pro Leu Tyr Ala Thr Leu Thr Leu Val Gln Thr Ser Ile Ile Met
         35                  40                  45

Tyr Ala Asn Lys Gly Val Pro Gln Ser Leu Asn Tyr Pro His Asp Arg
 50                  55                  60

Val Gly Ser Asp His Asp Asn Ile Gly Leu Phe Gln Leu Arg Ala Ser
65                   70                  75                  80
```

```
Val Tyr Lys Asn Ile Ala Cys Asp Met Asp Ala Gly Cys Ser Ala Gly
                85                  90                  95

Leu Phe Leu Asp Ala Met Arg Lys Ile Lys Gly Trp Glu Arg Met Ala
            100                 105                 110

Ile Gly Thr Leu Cys Gln Lys Val Gln Arg Thr Ala Tyr Pro Asp Arg
            115                 120                 125

Tyr Ala Lys Gln Val Gly Leu Ala Thr Asn Val Cys Lys Ala Gly Gly
        130                 135                 140

Leu
145

<210> SEQ ID NO 132
<211> LENGTH: 138
<212> TYPE: PRT
<213> ORGANISM: Pochonia chlamydosporia 170

<400> SEQUENCE: 132

Leu Leu Glu Val Gln Gln Lys Tyr Ala Lys Leu Ile Ile Ala Gln Ala
1               5                   10                  15

Lys Lys Glu Asn Val Gly Arg His Gly Cys Gln Thr Gly Ile Ala Thr
            20                  25                  30

Ala Leu Thr Glu Ser Thr Leu Ile Met His Ala Asn Pro Val Val Pro
        35                  40                  45

Glu Ser Leu Gly Tyr Pro His Glu Arg Leu Gly Tyr Asp Gly Asp Ser
    50                  55                  60

Val Gly Leu Phe Gln Gln Arg Ala Ile Tyr Tyr Thr Asp Ile Lys Cys
65                  70                  75                  80

Ser Met Asn Ala Lys Cys Ser Ala His Gln Phe Tyr Glu Ile Met Lys
                85                  90                  95

Lys Ile Pro Asp Trp Gln Asn Ile Pro Val Gly Val Leu Cys Gln Lys
            100                 105                 110

Val Gln Ile Ser Ala Ile Pro Glu Ala Tyr Asn Lys Phe Val Glu Gln
            115                 120                 125

Ala Gly Ser Ile Cys Ala Ala Ala Gly Met
        130                 135

<210> SEQ ID NO 133
<211> LENGTH: 142
<212> TYPE: PRT
<213> ORGANISM: Pochonia chlamydosporia 170

<400> SEQUENCE: 133

Asn Leu Pro Gly Leu Asn Asp Val Gln Ser Ala Asn Ala Arg Ala Val
1               5                   10                  15

Ile Asp Glu Asn Asn Lys Glu Lys Leu Gly Lys Gln Gly Cys Ile Ala
            20                  25                  30

Ala Leu Thr Thr Gly Leu Thr Glu Ser Ser Leu Arg Ile Leu Ala Asn
        35                  40                  45

Asn Gly Val Pro Ala Ser Leu Asn Tyr Lys His Asp Gly Leu Gly Ser
    50                  55                  60

Asp His Asp Ser Ile Gly Ile Phe Gln Gln Arg Ala Ser Ile Tyr Thr
65                  70                  75                  80

Asn Ile Glu Cys Asp Met Gly Ala Ala Cys Ser Ala Ser Gln Phe Phe
                85                  90                  95

Lys Gly Met Thr Ala Val Ser Gly Trp Glu Thr Met Asp Val Ala Thr
            100                 105                 110
```

```
Leu Cys Gln Lys Val Gln Arg Ser Ala Phe Pro Asp Ala Tyr Lys Lys
            115                 120                 125

Trp Val Gly Thr Ala Thr Asp Ala Cys Ala Ala Gly Val
    130                 135                 140

<210> SEQ ID NO 134
<211> LENGTH: 141
<212> TYPE: PRT
<213> ORGANISM: Purpureocillium lilacinum

<400> SEQUENCE: 134

Asn Leu Pro Gly Leu Asn Ala Lys Gln Ser His Ala Arg Ala Ile
1               5                   10                  15

Ile Ala Glu Thr Lys Lys Glu Lys Leu Gly His Gln Gly Cys Leu Ala
                20                  25                  30

Ala Ile Thr Thr Gly Leu Thr Glu Ser Ser Leu Arg Val Leu Ala Asn
            35                  40                  45

Lys Lys Val Pro Gln Ser Leu Lys Tyr Lys Asn Asp Gly Leu Gly Ser
        50                  55                  60

Asp His Asp Ser Ile Gly Ile Phe Gln Gln Arg Ala Met Tyr Tyr Lys
65                  70                  75                  80

Asp Ile Lys Cys Asp Met Asp Ala Ala Cys Ser Ala Ser Leu Phe Phe
                85                  90                  95

Lys Gly Met Lys Ala Val Lys Gly Trp Gln Lys Met Asp Val Ala Thr
            100                 105                 110

Leu Cys Gln Lys Val Gln Arg Ser Ala Val Pro Ser Ala Tyr Lys Lys
        115                 120                 125

His Val Asp Ala Ala Gly Lys Ile Cys Lys Ala Gly Gly
    130                 135                 140

<210> SEQ ID NO 135
<211> LENGTH: 144
<212> TYPE: PRT
<213> ORGANISM: Paraphaeosphaeria sporulosa

<400> SEQUENCE: 135

Ser Gly Thr Leu Pro Gly Leu Asn Ser Val Gln Thr Arg Asn Ala Arg
1               5                   10                  15

Ala Ile Ile Ala Arg Thr Lys Lys Asp Phe Ala Ala Ser Gln Gln Lys
                20                  25                  30

Arg Ala Cys Tyr Val Ala Ile Thr Thr Ala Phe Gln Glu Ser Gly Ile
            35                  40                  45

Arg Ile Leu Ala Asn Ser Lys Tyr Pro Ala Ser Leu Asn Tyr Pro His
        50                  55                  60

Asp Gly Val Gly Ser Asp His Asp Ser Val Gly Ile Phe Gln Gln Arg
65                  70                  75                  80

Pro Ser Trp Gly Ser Thr Lys Asp Arg Met Asn Ala Asp Leu Ser Ala
            85                  90                  95

His Phe Phe Phe Asn Ala Leu Lys Arg Val Arg Gly Trp Gln Ser Leu
        100                 105                 110

Ala Ile Gly Val Ala Ala Gln Lys Val Gln Val Ser Ala Phe Pro Asp
    115                 120                 125

Ala Tyr Asn Lys Trp Val Ala Lys Ala Glu Lys Val Cys Asn Ala Gly
        130                 135                 140
```

<210> SEQ ID NO 136
<211> LENGTH: 139
<212> TYPE: PRT
<213> ORGANISM: Cordyceps brongniartii RCEF 3172

<400> SEQUENCE: 136

Pro Gly Leu Asp Ala Val Gln Ser Arg Asn Ala Ala Ala Ile Gly
1               5                   10                  15

Gln Val Arg Ala Glu Gly Leu Asn Arg Gln Ala Cys Leu Ala Val Ile
            20                  25                  30

Ser Thr Thr Leu Gln Glu Ser Thr Leu His Val Tyr Ala Asn Pro Val
        35                  40                  45

Val Pro Ala Ser Ile Asn Tyr Pro His Asp Leu Val Gly Gly Asp Gln
    50                  55                  60

Asp Ser Thr Gly Met Phe Gln Gln Arg Pro Glu Tyr Tyr Pro Asp Ile
65                  70                  75                  80

Ala Ala Asp Met Ser Ala Ala Gly Ser Thr Arg Gln Phe Leu Ala Ala
                85                  90                  95

Met Lys Gln Val Ser Asn Trp Gln Thr Met Glu Val Ser Ala Leu Asp
            100                 105                 110

Gln Ala Val Gln Arg Ala Glu Ala Gly Asn Leu Tyr Ala Gln Arg Leu
        115                 120                 125

Pro Leu Ala Ser Arg Val Cys Ser Ala Ala Gly
    130                 135

<210> SEQ ID NO 137
<211> LENGTH: 134
<212> TYPE: PRT
<213> ORGANISM: Gordonia phage Utz

<400> SEQUENCE: 137

Lys Tyr Pro Phe Ala Ile Thr Glu Gln Ala Lys Lys Met Gly Leu Ser
1               5                   10                  15

Lys Arg Ala Ala Ile Ile Gly Asn Ala Thr Ala Leu Val Glu Val Gly
            20                  25                  30

Asp Pro Met Lys Met Tyr Ala Asn Thr Ala Val Pro Glu Ser Leu Lys
        35                  40                  45

Phe Pro His Asp Ala Val Gly Ser Asp His Asp Ser Ile Gly Leu Phe
    50                  55                  60

Gln Gln Arg Gln Ala Gly Trp Gly Thr Val Ala Asp Arg Met Asp Pro
65                  70                  75                  80

His Arg Ser Ala Lys Met Phe Tyr Asp Ala Leu Val Lys Val Pro Gly
                85                  90                  95

Trp Glu Thr Met Asp Met Gly Ala Ala Ala Gln Ala Val Gln Arg Ser
            100                 105                 110

Ala Phe Pro Gly Lys Tyr Ala Gly Arg Met Ala Arg Ala Thr Glu Leu
        115                 120                 125

Val Asp Lys Phe Gly Ile
    130

<210> SEQ ID NO 138
<211> LENGTH: 155
<212> TYPE: PRT
<213> ORGANISM: Arthrobacter nicotinovorans

<400> SEQUENCE: 138

Ser Gly Ser Met Pro Asp Gly Gln Ala Val Gly Leu Ser Ala Gly Gln
1               5                   10                  15

Ile Ala Val Ala Gln Gly Tyr Ile Ser Val Gly Lys Gln Leu Gly Val
            20                  25                  30

Pro Arg Glu Ala Met Val Ile Ala Ile Met Met Ser Leu Gln Glu Thr
        35                  40                  45

Thr Leu Arg Met Leu Ala Asn Ala Asn Val Pro Ala Ser Phe Gln Phe
    50                  55                  60

Pro His Asp Gly Val Gly Ser Asp His Asp Ser Val Gly Ser Ala Gln
65                  70                  75                  80

Gln Arg Pro Ala Ala Gly Trp Gly Thr Val Ala Glu Leu Met Asp Leu
                85                  90                  95

Thr Tyr Asn Ala Arg Ala Phe Tyr Gly Gly Pro Ser Gly Pro Asn Lys
            100                 105                 110

Gly Ser Pro Arg Gly Leu Leu Asp Val Pro Gly Trp Ser Ala Met Ser
        115                 120                 125

Lys Gly Gln Ala Ala Gln Ala Val Gln Val Ser Ala Phe Pro Glu Leu
130                 135                 140

Tyr Ala Arg Trp Glu Gln Gln Ala Thr Ala Ile
145                 150                 155

<210> SEQ ID NO 139
<211> LENGTH: 132
<212> TYPE: PRT
<213> ORGANISM: Mycobacterium conceptionense

<400> SEQUENCE: 139

Thr Asn Asp Ala Tyr Ala Arg Glu Ile Ile Arg Ala Gly Arg Asp Leu
1               5                   10                  15

Gly Ile Thr Pro Arg Gly Ile Val Ile Ala Phe Ala Thr Val Tyr Val
            20                  25                  30

Glu Ser Asn Trp Ile Met Trp Ala Asn Ala Ala Val Pro Glu Ser Leu
        35                  40                  45

Ala Ile Pro His Glu Arg Val Gly Ser Asp Gly Lys Ser Val Gly Leu
    50                  55                  60

Phe Gln Gln Gln Val Val Trp Gly Asn Gly Ala Trp Trp Trp Gly Ser
65                  70                  75                  80

Ala Ala Asp Cys Met Asp Pro Tyr Lys Ser Ala Arg Leu Phe Phe Gln
                85                  90                  95

Arg Leu Ala Lys Arg Asp Tyr Asn Asn Gly Asp Pro Gly Ala His Ala
            100                 105                 110

Gln Ala Ile Gln Gln Ser Ala Tyr Pro Asp Arg Tyr Gly Gln Arg Met
        115                 120                 125

Ser Glu Ala Gln
    130

<210> SEQ ID NO 140
<211> LENGTH: 137
<212> TYPE: PRT
<213> ORGANISM: Micromonospora narathiwatensis

```
<400> SEQUENCE: 140

Gly Leu Asp Gln Arg Gln Met Asp Asn Ala Lys Val Ile Val Asp Ala
1               5                   10                  15

Gly Arg Ala Met Asn Leu Pro Arg Arg Ala Leu Val Val Ala Val Ala
            20                  25                  30

Thr Ala Met Gln Glu Ser Asn Leu Tyr Asn Leu Ala Ser Asp Val Leu
        35                  40                  45

Pro Glu Ser Tyr Asn Tyr Pro His Gln Gly Ser Gly Ser Asp His Asp
    50                  55                  60

Ser Val Gly Leu Phe Gln Gln Arg Pro Ser Ser Gly Trp Gly Thr Val
65                  70                  75                  80

Ala Glu Leu Met Gln Pro Ala Tyr Ala Ala Arg Ala Phe Phe Ala Ala
                85                  90                  95

Leu Ala Glu Val Pro Gly Trp Ala Asp Leu Ser Leu Thr Glu Ala Ala
            100                 105                 110

Gln Ala Val Gln Val Ser Ala Tyr Pro Asp Ala Tyr Ala Gln His Glu
        115                 120                 125

Glu Arg Ala Thr Thr Val Val Ala Ala
    130                 135

<210> SEQ ID NO 141
<211> LENGTH: 137
<212> TYPE: PRT
<213> ORGANISM: Micromonospora narathiwatensis

<400> SEQUENCE: 141

Gly Leu Asp Gly Asp Gln Met Ala Asn Ala Val Ser Ile Val Arg Ala
1               5                   10                  15

Gly Gln Glu Met Gly Val Pro Gln Arg Gly Leu Val Ile Ala Val Ala
            20                  25                  30

Thr Ala Met Gln Glu Ser Asn Leu Tyr Asn Tyr Ala Ser Gly Val Leu
        35                  40                  45

Pro Glu Ser Gln Asn Tyr Pro His Gln Ala Ile Gly Trp Asp His Asp
    50                  55                  60

Ser Val Gly Leu Phe Gln Gln Arg Pro Ser Ser Gly Trp Gly Ala Val
65                  70                  75                  80

Arg Asp Leu Met Gln Pro Ala Tyr Ala Thr Lys Gln Phe Leu Ser Ala
                85                  90                  95

Leu Leu Gln Ile Pro Gly Trp Gln Asn Met Ala Leu Thr Asp Ala Ala
            100                 105                 110

Gln Ala Val Gln Val Ser Ala Phe Pro Trp Ala Tyr Ala Gln His Glu
        115                 120                 125

Trp Arg Ala Thr Glu Val Val Asp Ala
    130                 135

<210> SEQ ID NO 142
<211> LENGTH: 137
<212> TYPE: PRT
<213> ORGANISM: Micromonospora auratinigra

<400> SEQUENCE: 142

Gly Leu Asp Gln Arg Gln Met Asp Asn Ala Lys Ala Ile Val Asp Val
1               5                   10                  15

Ala Arg Ala Met Lys Leu Pro Arg Arg Ala Met Val Ile Ala Val Ala
            20                  25                  30
```

```
Thr Ala Met Gln Glu Ser Asp Leu Tyr Asn Leu Ala Ser Asp Val Leu
            35                  40                  45

Pro Glu Ser Phe Asp Tyr Pro His Gln Gly Ser Gly Ser Asp His Asp
 50                      55                  60

Ser Ile Gly Leu Phe Gln Gln Arg Pro Ser Ser Gly Trp Gly Thr Val
 65                  70                  75                  80

Ala Gln Ile Met Arg Pro Ala Tyr Ala Arg Ala Phe Leu Thr Ala
                85                  90                  95

Leu Cys Glu Val Pro Gly Trp Thr Gly Leu Ser Leu Thr Asp Ala Ala
                100                 105                 110

Gln Ala Val Gln Val Ser Ala Phe Pro Asp Ala Tyr Ala Gln His Glu
            115                 120                 125

Lys Arg Ala Ser Thr Val Val Ala Ala
        130                 135

<210> SEQ ID NO 143
<211> LENGTH: 136
<212> TYPE: PRT
<213> ORGANISM: Mycobacterium sp. E1747

<400> SEQUENCE: 143

Thr Ala Asp Gln Tyr Ala Pro Ala Val Leu Gln Ala Gly Arg Asp Leu
 1               5                  10                  15

Gly Ile Thr Pro Lys Gly Val Val Ile Gly Phe Ala Thr Val Tyr Val
                20                  25                  30

Glu Ser Asn Trp Thr Met Tyr Ala Asn Ala Lys Val Pro Glu Ser Met
            35                  40                  45

Asn Ile Pro His Asp Ala Val Gly Ser Asp Gly Leu Ser Val Gly Leu
 50                      55                  60

Phe Gln Gln Gln Val Arg Asp Asp Gly Asn Gly Trp Trp Trp Gly Asp
 65                  70                  75                  80

Ala Ala Thr Cys Met Asp Pro Tyr Lys Ser Ala Gln Leu Phe Phe Ser
                85                  90                  95

Arg Leu Lys Arg Leu Asp Tyr Asn Ser Glu Ala Gln Ser Pro Gly Ser
                100                 105                 110

Tyr Ala Gln Ala Ile Gln Gln Ser Ala Phe Pro Asp Arg Tyr Asp Gln
            115                 120                 125

Arg Met Gly Asp Ala Gln Ser Leu
        130                 135

<210> SEQ ID NO 144
<211> LENGTH: 137
<212> TYPE: PRT
<213> ORGANISM: Micromonospora sediminicola

<400> SEQUENCE: 144

Gly Leu Asp Gln Arg Gln Met Asp Asn Ala Lys Ala Ile Val Asp Val
 1               5                  10                  15

Gly Arg Glu Met Arg Leu Pro Arg Arg Ala Leu Val Val Ala Val Ala
                20                  25                  30

Thr Ala Met Gln Glu Ser Asp Leu Tyr Asn Leu Ala Ser Asp Val Leu
            35                  40                  45

Pro Glu Ser Phe Asp Tyr Pro His Gln Gly Ser Gly Ser Asp His Asp
 50                      55                  60

Ser Ile Gly Leu Phe Gln Gln Arg Pro Ser Ser Gly Trp Gly Thr Val
 65                  70                  75                  80
```

```
Ala Glu Ile Met Arg Pro Ala Tyr Ala Ala Arg Ala Phe Phe Thr Ala
            85                  90                  95

Leu Ala Glu Val Pro Gly Trp Glu Glu Met Ser Val Thr Ala Ala Ala
        100                 105                 110

Gln Ala Val Gln Val Ser Ala Phe Pro Asp Ala Tyr Ala Lys His Glu
    115                 120                 125

Gln Arg Ala Ala Thr Val Val Ala Ala
130                 135

<210> SEQ ID NO 145
<211> LENGTH: 153
<212> TYPE: PRT
<213> ORGANISM: Microbacterium sp. H83

<400> SEQUENCE: 145

Gly Ser Lys Arg Thr Leu Gly Pro Thr Glu Leu Asn His Ala Ala Thr
1               5                  10                  15

Ile Leu Ser Ile Ala Arg Ser Leu Gly Val Ser Val Lys Gly Gln Gln
            20                  25                  30

Ile Ala Ile Met Thr Ala Leu Gln Glu Ser Gly Leu Lys Met Tyr Ala
        35                  40                  45

Asn Ser Ser Val Pro Ala Ser Leu Asp Tyr Pro His Asp Ala Val Gly
    50                  55                  60

Ser Asp His Asp Ser Val Asn Phe Phe Gln Gln Arg Val Ser Gly Trp
65                  70                  75                  80

Gly Thr Val Ala Glu Leu Met Asp Pro Thr Tyr Ala Thr Lys Ala Phe
                85                  90                  95

Phe Gly Gly Pro Glu Gly Pro Asn Gln Gly Ser Pro Arg Gly Leu Leu
            100                 105                 110

Asp Val Pro Gly Trp Glu Ser Met Pro Leu Gly Lys Ala Ala Gln Thr
        115                 120                 125

Val Gln Val Ser Ala Tyr Pro Asp Ala Tyr Asp Lys Trp Glu Thr Ala
    130                 135                 140

Ala Gln Gln Ile Ile Thr Ala Val Gly
145                 150

<210> SEQ ID NO 146
<211> LENGTH: 137
<212> TYPE: PRT
<213> ORGANISM: Micromonospora coriariae

<400> SEQUENCE: 146

Gly Leu Asp Gln Ala Gln Met Asp Asn Ala Thr Ala Ile Val Arg Ala
1               5                  10                  15

Gly Gln Lys Met Asp Val Pro Arg Arg Ala Leu Val Ile Ala Val Ala
            20                  25                  30

Thr Ala Met Gln Glu Ser Asn Leu Tyr Asn Tyr Ala Ser Gly Val Leu
        35                  40                  45

Pro Glu Ser Gln Asn Tyr Pro His Gln Ala Ile Gly Trp Asp His Asp
    50                  55                  60

Ser Val Gly Leu Phe Gln Gln Arg Pro Ser Thr Gly Trp Gly Ala Val
65                  70                  75                  80

Pro Asp Leu Met Lys Pro Glu Tyr Ala Thr Gln Gln Phe Leu Thr Ala
                85                  90                  95

Leu Leu Glu Val Pro Gly Trp Gln Asp Leu Pro Leu Thr Val Ala Ala
            100                 105                 110
```

```
Gln Thr Val Gln Val Ser Ala Phe Gly Trp Leu Tyr Ala Gln His Glu
        115                 120                 125

Trp Arg Ala Thr Glu Val Val Asp Ala
        130                 135

<210> SEQ ID NO 147
<211> LENGTH: 137
<212> TYPE: PRT
<213> ORGANISM: Micromonospora citrea

<400> SEQUENCE: 147

Gly Leu Asp Asn Ala Gln Met Glu Asn Ala Glu Val Ile Val Arg Thr
1               5                   10                  15

Gly Arg Lys Met Gly Met Pro Arg Arg Ala Leu Val Ile Ala Val Ala
            20                  25                  30

Thr Ala Met Gln Glu Ser Asn Leu Tyr Asn Val Ala Ser Gly Val Leu
        35                  40                  45

Pro Glu Ser Gln Asn Tyr Pro His Gln Gly Ile Gly Trp Asp His Asp
    50                  55                  60

Ser Val Gly Leu Phe Gln Gln Arg Ser Ser Ser Gly Trp Gly Glu Val
65                  70                  75                  80

Gly Gln Leu Met Asp Pro Ala Phe Ala Thr Arg Gln Phe Leu Ser Ala
                85                  90                  95

Leu Ala Glu Val Pro Gly Trp Gln Gln Met Arg Leu Thr Asp Ala Ala
            100                 105                 110

Gln Ala Val Gln Ile Ser Ala Tyr Pro Glu His Tyr Ala Lys His Glu
        115                 120                 125

Trp Arg Ala Thr Glu Val Val Glu Ala
        130                 135

<210> SEQ ID NO 148
<211> LENGTH: 137
<212> TYPE: PRT
<213> ORGANISM: Micromonospora peucetia

<400> SEQUENCE: 148

Ile Pro Gln Tyr Gly Glu Arg Gln Leu Arg Asn Ala Ala Arg Ile Ile
1               5                   10                  15

Lys Val Gly Gln Glu Met Lys Val Ser Pro Arg Gly Trp Val Ile Ala
            20                  25                  30

Val Ala Thr Ala Leu Gln Glu Ser Arg Leu Leu Asn Leu Ala Asn Arg
        35                  40                  45

Thr Val Ser Glu Ser Glu Thr Ile Pro Asn Glu Gly Ile Gly Ala Asp
    50                  55                  60

His Asp Ser Val Gly Leu Phe Gln Gln Arg Ala Ser Trp Gly Ser Val
65                  70                  75                  80

Thr Gln Arg Met Thr Pro Glu Tyr Ala Ala Arg Lys Phe Tyr Glu Lys
                85                  90                  95

Leu Val Arg Val Pro Gly Trp Glu Thr Met Pro Leu Ser Arg Ala Ala
            100                 105                 110

Gln Ala Val Gln Ile Ser Ala Phe Pro Asp Ala Tyr Ala Lys His Glu
        115                 120                 125

Asp Val Ala Ala Arg Ile Val Ser Ala
        130                 135
```

```
<210> SEQ ID NO 149
<211> LENGTH: 147
<212> TYPE: PRT
<213> ORGANISM: Micromonospora yangpuensis

<400> SEQUENCE: 149
```

Thr Gly Arg Met Pro Arg Ser Ala Gly Tyr Gly Glu Arg Gln Leu Arg
1               5                   10                  15

Asn Ala Ala Ile Ile Ile Lys Val Gly Gln Asp Met Lys Val Pro Ala
            20                  25                  30

Arg Gly Trp Val Ile Ala Ile Ala Thr Ala Ile Gln Glu Ser Gly Leu
        35                  40                  45

Lys Asn Tyr Ala Asn Ser Thr Val Pro Glu Ser Leu Ala Leu Pro His
    50                  55                  60

Glu Ala Val Gly Arg Asp His Asp Ser Val Gly Leu Phe Gln Gln Arg
65                  70                  75                  80

Pro Gly Trp Gly Ser Val Lys Gln Arg Met Thr Pro Ser Tyr Ser Ala
                85                  90                  95

Arg Lys Phe Tyr Glu Lys Leu Ile Gln Val Pro Asn Trp Glu Lys Arg
            100                 105                 110

Ser Leu Thr Asp Ala Ala Gln Arg Val Gln Ile Ser Ala Phe Pro Asp
        115                 120                 125

Ala Tyr Ala Lys His Glu Glu Thr Ala Ser Arg Ile Val Asp Ala Leu
    130                 135                 140

Ala Gly Gly
145

```
<210> SEQ ID NO 150
<211> LENGTH: 137
<212> TYPE: PRT
<213> ORGANISM: Micromonospora rhizosphaerae

<400> SEQUENCE: 150
```

Gly Leu Asp Lys Ala Gln Met Asp Asn Ala Glu Ala Ile Val Lys Ala
1               5                   10                  15

Gly Gln Glu Met Gly Val Pro Arg Arg Ala Leu Val Ile Ala Val Ala
            20                  25                  30

Thr Ala Met Gln Glu Ser Asn Leu Tyr Asn Tyr Ala Ser Gly Val Leu
        35                  40                  45

Pro Glu Ser Gln Asn Tyr Pro His Gln Ala Ile Gly Trp Asp His Asp
    50                  55                  60

Ser Val Gly Leu Phe Gln Gln Arg Pro Ser Ser Gly Trp Gly Ser Val
65                  70                  75                  80

Pro Asp Leu Met Lys Pro Glu Phe Ala Thr Arg Gln Phe Leu Thr Ala
                85                  90                  95

Leu Val Ala Val Pro Gly Trp Gln Asp Met Pro Leu Thr Leu Ala Ala
            100                 105                 110

Gln Thr Val Gln Val Ser Ala Phe Pro Trp Ala Tyr Ala Gln His Glu
        115                 120                 125

Trp Arg Ala Asn Glu Val Val Asn Ala
    130                 135

```
<210> SEQ ID NO 151
<211> LENGTH: 147
<212> TYPE: PRT
<213> ORGANISM: Micromonospora echinaurantiaca
```

-continued

<400> SEQUENCE: 151

Thr Gly Lys Met Pro Arg Met Ser Glu Tyr Gly Glu Ser Gln Leu Arg
1               5                   10                  15

Asn Ala Ala Arg Ile Val Lys Val Gly Gln Glu Met Lys Val Pro Pro
            20                  25                  30

Arg Gly Trp Val Ile Ala Val Ala Thr Ala Met Gln Glu Ser Gly Leu
        35                  40                  45

Arg Asn Leu Ala Asn Arg Thr Val Ala Gln Ser Arg Asp Leu Pro Asn
    50                  55                  60

Glu Gly Val Gly Ala Asp His Asp Ser Val Gly Leu Phe Gln Gln Arg
65                  70                  75                  80

Ala Asn Trp Gly Ser Val Ala Gln Arg Met Thr Pro Glu Tyr Ala Ala
                85                  90                  95

Arg Lys Phe Tyr Glu Lys Leu Leu Lys Val Pro Gly Trp Gln Arg Met
            100                 105                 110

Pro Leu Thr Thr Ala Ala Gln Lys Val Gln Ile Ser Ala Phe Pro Asp
        115                 120                 125

Ala Tyr Ala Lys His Glu Ala Leu Ala Ala Arg Ile Val Asp Ala Leu
    130                 135                 140

Ala Gly Gly
145

<210> SEQ ID NO 152
<211> LENGTH: 137
<212> TYPE: PRT
<213> ORGANISM: Micromonospora inositola

<400> SEQUENCE: 152

Gly Leu Asp Glu Asp Gln Met Asp Asn Ala Lys Ala Ile Val Arg Ala
1               5                   10                  15

Gly Arg Asp Met Gly Val Pro Arg Arg Gly Leu Val Ile Ala Val Ala
            20                  25                  30

Thr Ala Met Gln Glu Ser Asn Leu Tyr Asn Tyr Ala Ser Ala Val Leu
        35                  40                  45

Pro Glu Ser Gln Asn Tyr Pro His Gln Ala Ile Gly Trp Asp His Asp
    50                  55                  60

Ser Val Gly Leu Phe Gln Gln Arg Pro Ser Ser Gly Trp Gly Thr Val
65                  70                  75                  80

Gly Asp Leu Met Arg Pro Glu Tyr Ala Thr Lys Gln Phe Leu Thr Ala
                85                  90                  95

Leu Glu Gln Ile Pro Gly Trp Gln Asp Met Ala Leu Thr Asp Ala Ala
            100                 105                 110

Gln Ala Val Gln Val Ser Ala Phe Pro Trp Ala Tyr Ala Gln His Glu
        115                 120                 125

Trp Arg Ala Asp Glu Val Val Asp Ala
    130                 135

<210> SEQ ID NO 153
<211> LENGTH: 137
<212> TYPE: PRT
<213> ORGANISM: Micromonospora inositola

```
<400> SEQUENCE: 153

Gly Leu Asp Gln Arg Gln Met Asp Asn Ala Lys Val Ile Val Asp Val
1               5                   10                  15

Gly Arg Asp Met Lys Leu Pro Arg Arg Ala Leu Ile Val Ala Ile Ala
                20                  25                  30

Thr Ala Met Gln Glu Ser Asn Leu Tyr Asn Leu Ala Ser Asp Val Leu
            35                  40                  45

Pro Glu Ser Tyr Asp Tyr Pro His Gln Gly Ser Gly Ala Asp His Asp
        50                  55                  60

Ser Val Gly Leu Phe Gln Gln Arg Pro Ser Ser Gly Trp Gly Thr Val
65                  70                  75                  80

Ala Glu Leu Met Arg Pro Ala Tyr Ala Ala Arg Ala Phe Tyr Ala Ala
                85                  90                  95

Leu Ala Glu Val Pro Gly Trp Ala Asp Leu Ser Ile Thr Gln Ala Ala
                100                 105                 110

Gln Ala Val Gln Val Ser Ala Phe Pro Asp Ala Tyr Ala Gln His Glu
            115                 120                 125

Gln Arg Ala Thr Thr Val Val Asp Ala
        130                 135

<210> SEQ ID NO 154
<211> LENGTH: 137
<212> TYPE: PRT
<213> ORGANISM: Micromonospora coxensis

<400> SEQUENCE: 154

Gly Leu Thr Gln Ala Gln Met Asp Asn Ala Lys Val Ile Val Asp Val
1               5                   10                  15

Gly Val Gly Met Gly Val Pro Arg Arg Gly Leu Val Val Ala Ile Ala
                20                  25                  30

Thr Ala Met Gln Glu Ser Asn Leu His Asn Leu Ala Ser Asp Val Leu
            35                  40                  45

Pro Glu Ser Phe Asp His Pro His Gln Gly Ser Gly Ser Asp His Asp
        50                  55                  60

Ser Val Gly Leu Phe Gln Gln Arg Pro Ser Ser Gly Trp Gly Thr Val
65                  70                  75                  80

Ala Gln Leu Met Arg Pro Ala Tyr Ala Ala Arg Ala Phe Tyr Thr Ala
                85                  90                  95

Leu Leu Glu Val Pro Gly Trp Gln Asp Met Ser Val Thr Ala Ala Ala
                100                 105                 110

Gln Ala Val Gln Ile Ser Ala Phe Pro Asp Ala Tyr Ala Lys His Glu
            115                 120                 125

Gln Arg Ala Gly Thr Val Val Ala Ala
        130                 135

<210> SEQ ID NO 155
<211> LENGTH: 126
<212> TYPE: PRT
<213> ORGANISM: Micromonospora mirobrigensis

<400> SEQUENCE: 155

Gly Leu Asp Glu Thr Gln Met Asp Asn Ala Lys Ala Ile Val Arg Ser
1               5                   10                  15

Ala Lys Lys Met Gly Val Pro Arg Gln Ala Met Val Ile Ala Val Ala
                20                  25                  30
```

```
Thr Ala Met Gln Glu Ser Thr Leu Leu Asn Tyr Ala Ser Gly Val Leu
            35                  40                  45

Pro Glu Ser Gln Asp Tyr Pro His Gln Ala Ile Gly Trp Asp His Asp
 50                  55                  60

Ser Val Gly Leu Phe Gln Gln Arg Pro Ser Ser Gly Trp Gly Thr Val
 65                  70                  75                  80

Glu Gln Leu Met Asp Pro Glu Phe Ala Thr Gln Ala Phe Leu Ser Val
                    85                  90                  95

Leu Leu Gln Val Pro Gly Trp Gln Asp Met Pro Leu Thr Leu Ala Ala
                100                 105                 110

Gln Ile Val Gln Val Ser Ala Phe Pro Asp Ala Tyr Ala Gln
            115                 120                 125
```

<210> SEQ ID NO 156
<211> LENGTH: 137
<212> TYPE: PRT
<213> ORGANISM: Micromonospora viridifaciens

<400> SEQUENCE: 156

```
Gly Leu Asp Arg Ala Gln Met Asp Asn Ala Thr Thr Ile Val Arg Thr
 1               5                  10                  15

Gly Arg Asp Met Gly Val Pro Arg Arg Gly Leu Ile Ile Ala Val Ala
                20                  25                  30

Thr Ala Met Gln Glu Ser Asn Leu Tyr Asn Tyr Ala Ser Gly Val Leu
            35                  40                  45

Pro Glu Ser Gln Asn Tyr Pro His Gln Ala Ile Gly Trp Asp His Asp
 50                  55                  60

Ser Val Gly Leu Phe Gln Gln Arg Pro Ser Ser Gly Trp Gly Thr Val
 65                  70                  75                  80

Ala Asp Leu Met Lys Pro Ala Tyr Ala Thr Arg Gln Phe Leu Ala Ala
                    85                  90                  95

Leu Glu Gln Ile Pro Gly Trp Gln Asn Met Ala Leu Thr Asp Ala Ala
                100                 105                 110

Gln Ala Val Gln Ile Ser Ala Phe Pro Trp Ala Tyr Ala Gln His Glu
            115                 120                 125

Trp Arg Ala Thr Glu Val Val Asp Ala
130                 135
```

<210> SEQ ID NO 157
<211> LENGTH: 139
<212> TYPE: PRT
<213> ORGANISM: Micromonospora haikouensis

<400> SEQUENCE: 157

```
Val Pro Gly Val Gly Glu Trp Thr Ser Ala Gln Thr Thr His Ala Thr
 1               5                  10                  15

Val Ile Val Ser Val Gly Arg Gln Arg Arg Val Ala Pro Arg Gly Tyr
                20                  25                  30

Val Ile Ala Leu Ala Val Ala Met Gln Glu Ser Thr Leu Arg Asn Leu
            35                  40                  45

Ala Asn Ser Thr Val Pro Glu Ser Leu Asn Ile Pro His Asp Ala Val
 50                  55                  60

Gly Ser Asp His Asp Ser Val Gly Leu Phe Gln Gln Arg Pro Gly Trp
 65                  70                  75                  80

Gly Ser Val Arg Glu Arg Met Thr Pro Ser Tyr Ala Ala Arg Lys Phe
                    85                  90                  95
```

Tyr Glu Ala Leu Val Asp Val Asp Gly Trp Gln Arg Met Arg Leu Thr
            100                 105                 110

Asp Ala Ala Gln Ala Val Gln Arg Ser Gly Thr Pro Glu Ala Tyr Gln
        115                 120                 125

Lys Trp Glu Asp Asp Ala Glu Ala Leu Ala Ala
    130                 135

<210> SEQ ID NO 158
<211> LENGTH: 137
<212> TYPE: PRT
<213> ORGANISM: Micromonospora peucetia

<400> SEQUENCE: 158

Gly Leu Asp Lys Ala Gln Met Lys Asn Ala Gln Ala Ile Val Arg Thr
1               5                   10                  15

Gly Arg Glu Met Glu Met Pro Arg Arg Ala Leu Val Ile Ala Val Ala
            20                  25                  30

Thr Ala Met Gln Glu Ser Asn Leu Tyr Asn Val Ala Ser Gly Val Leu
        35                  40                  45

Pro Glu Ser Arg Asn His Pro His Gln Gly Ile Gly Trp Asp His Asp
    50                  55                  60

Ser Val Gly Leu Phe Gln Gln Arg Ser Ser Gly Trp Gly Glu Val
65                  70                  75                  80

Gly Gln Leu Met Asp Pro Glu Phe Ala Thr Arg Gln Phe Leu Ala Ala
            85                  90                  95

Leu Ala Gln Val Pro Gly Trp Gln Gln Met Arg Leu Thr Asp Ala Ala
            100                 105                 110

Gln Ala Val Gln Ile Ser Ala Tyr Pro Glu His Tyr Ala Lys His Glu
        115                 120                 125

Gly Arg Ala Thr Thr Val Val Gly Ala
    130                 135

<210> SEQ ID NO 159
<211> LENGTH: 137
<212> TYPE: PRT
<213> ORGANISM: Micromonospora citrea

<400> SEQUENCE: 159

Gly Leu Thr Gln Ala Gln Met Asp Asn Ala Lys Val Ile Val Asp Val
1               5                   10                  15

Gly Ala Asp Leu Lys Met Pro Arg Arg Ala Met Val Val Ala Val Ala
            20                  25                  30

Thr Ala Met Gln Glu Ser Asn Leu Tyr Asn Leu Ala Ser Asp Val Leu
        35                  40                  45

Pro Glu Ser Arg Gln Tyr Pro His Gln Gly Ser Gly Ser Asp His Asp
    50                  55                  60

Ser Val Gly Leu Phe Gln Gln Arg Pro Ser Ser Gly Trp Gly Thr Val
65                  70                  75                  80

Arg Glu Leu Met Arg Pro Ala Tyr Ala Ala Arg Ala Phe Tyr Glu Ala
            85                  90                  95

Leu Arg Glu Val Pro Gly Trp Gln Glu Met Ser Val Ala Ala Ala
            100                 105                 110

Gln Ala Val Gln Val Ser Ala Phe Pro Asp Ala Tyr Ala Arg His Glu
        115                 120                 125

Glu Arg Ala Thr Thr Ile Val Ala Ala
    130                 135

<210> SEQ ID NO 160
<211> LENGTH: 137
<212> TYPE: PRT
<213> ORGANISM: Micromonospora saelicesensis

<400> SEQUENCE: 160

Gly Leu Asp Gln Ala Gln Met Asp Asn Ala Lys Ile Ile Val Asp Val
1               5                   10                  15

Gly Leu Glu Met Lys Met Pro Arg Arg Ala Leu Val Val Ala Leu Ser
            20                  25                  30

Thr Ala Met Gln Glu Ser Asn Leu Tyr Asn Leu Ala Ser Asp Val Leu
        35                  40                  45

Pro Glu Ser Ala Glu Tyr Pro Asn Gln Gly Ser Gly Ser Asp His Asp
    50                  55                  60

Ser Val Gly Leu Phe Gln Gln Arg Pro Ser Ser Gly Trp Gly Thr Val
65                  70                  75                  80

Ala Gln Leu Met Arg Pro Ser Tyr Ala Ala Arg Ala Phe Tyr Thr Ala
                85                  90                  95

Leu Asn Glu Ile Pro Gly Trp Gln Asp Met Ser Val Thr Ala Ala Ala
            100                 105                 110

Gln Ala Val Gln Ile Ser Ala Tyr Pro Asp Ala Tyr Ala Gln His Glu
        115                 120                 125

Asp Arg Ala Thr Thr Val Ala Ala Ala
    130                 135

<210> SEQ ID NO 161
<211> LENGTH: 137
<212> TYPE: PRT
<213> ORGANISM: Micromonospora echinospora

<400> SEQUENCE: 161

Gly Leu Thr Gln Arg Gln Met Asp Asn Ala Lys Ala Ile Val Asp Val
1               5                   10                  15

Gly Val Glu Leu Arg Met Pro Arg Arg Ala Leu Val Val Ala Ile Ala
            20                  25                  30

Thr Ala Met Gln Glu Ser Asp Leu His Asn Leu Ala Asn Asp Arg Ile
        35                  40                  45

Ala Glu Ser Ala Arg Tyr Pro His Gln Gly Ser Gly Thr Asp His Asp
    50                  55                  60

Ser Val Gly Leu Phe Gln Gln Arg Pro Ser Ser Gly Trp Gly Ser Val
65                  70                  75                  80

Arg Glu Leu Met Gln Pro Ala Tyr Ala Ala Arg Val Phe Tyr Arg Ala
                85                  90                  95

Leu Arg Glu Val Ser Gly Trp Glu Asp Met Ser Val Thr Ala Ala Ala
            100                 105                 110

Gln Ala Val Gln Arg Ser Ala Tyr Pro Gly Ala Tyr Ala Lys His Glu
        115                 120                 125

Arg Arg Ala Thr Thr Val Val Asp Ala
    130                 135

<210> SEQ ID NO 162
<211> LENGTH: 137
<212> TYPE: PRT
<213> ORGANISM: Micromonospora purpureochromogenes

<400> SEQUENCE: 162

Gly Leu Asp Gln Ala Gln Met Asp Asn Ala Lys Ala Ile Val Lys Ala
1               5                   10                  15

Gly Arg Lys Met Gly Val Pro Arg Gln Ala Leu Ile Ile Ala Val Ala
                20                  25                  30

Thr Ala Met Gln Glu Ser Asn Leu Tyr Asn Tyr Ala Ser Gly Val Leu
            35                  40                  45

Pro Glu Ser Gln Asn Tyr Pro Tyr Gln Ala Ile Gly Trp Asp His Asp
        50                  55                  60

Ser Val Gly Leu Phe Gln Gln Arg Pro Ser Ser Gly Trp Gly Glu Val
65                  70                  75                  80

Arg Asp Leu Met Asp Pro Glu Tyr Ala Thr Gln Ala Phe Leu Ser Ala
                85                  90                  95

Leu Leu Glu Ile Pro Gly Trp Gln Asp Leu Ala Leu Thr Asp Ala Ala
            100                 105                 110

Gln Ala Val Gln Val Ser Ala Phe Pro Trp Ala Tyr Ala Gln His Glu
        115                 120                 125

Trp Arg Ala Thr Glu Val Val Glu Ala
    130                 135

<210> SEQ ID NO 163
<211> LENGTH: 143
<212> TYPE: PRT
<213> ORGANISM: Micromonospora echinofusca

<400> SEQUENCE: 163

Ser Ala Asn Pro Pro Gly Ser Ala Ala Asp Ala Ser Trp Lys Pro Ala
1               5                   10                  15

Gln Val Gly His Ala Ala Thr Ile Val Arg Val Gly Ala Glu Lys Asp
                20                  25                  30

Val Pro Ser Lys Gly Trp Thr Val Ala Val Ala Thr Ala Met Gln Glu
            35                  40                  45

Ser Thr Leu Arg Asn Leu Ala Asn Ser Met Val Pro Glu Ser Leu Gly
        50                  55                  60

Ile Pro His Glu Gly Val Gly Arg Asp His Asp Ser Val Gly Leu Phe
65                  70                  75                  80

Gln Gln Arg Pro Gly Trp Gly Thr Val Val Gln Arg Met Thr Pro Asp
                85                  90                  95

Tyr Ala Ala Gly Lys Phe Tyr Asp Ala Leu Val Lys Val Asn Gly Trp
            100                 105                 110

Glu Ala Met Ser Leu Ala Glu Ala Ala Gln Ala Val Gln Val Ser Arg
        115                 120                 125

Tyr Pro Asp Ala Tyr Ala Lys Trp Gln Ser Glu Ala Gln Arg Leu
    130                 135                 140

<210> SEQ ID NO 164
<211> LENGTH: 137
<212> TYPE: PRT
<213> ORGANISM: Micromonospora echinaurantiaca

<400> SEQUENCE: 164

Gly Leu Thr Gln Ala Gln Met Asp Asn Ala Lys Ile Ile Val Asp Val
1               5                   10                  15

Gly Val Asp Met Lys Ile Pro Arg Arg Gly Leu Val Val Ala Ile Ala
                20                  25                  30

```
Thr Ala Met Gln Glu Ser Asn Leu Tyr Asn Tyr Ala Ser Gly Val Leu
            35                  40                  45

Pro Glu Ser Gln Asn Tyr Pro His Gln Ala Ile Gly Trp Asp His Asp
 50                  55                  60

Ser Val Gly Leu Phe Gln Gln Arg Pro Ser Ser Gly Trp Gly Thr Val
 65                  70                  75                  80

Lys Asp Leu Met Arg Pro Ala Tyr Ala Ala Arg Ala Phe Tyr Glu Ala
                 85                  90                  95

Leu Arg Glu Ile Pro Gly Trp Gln Glu Met Ser Val Thr Ala Ala Ala
                100                 105                 110

Gln Ala Val Gln Ile Ser Ala Phe Pro Asp Ala Tyr Ala Gln His Glu
                115                 120                 125

Gly Arg Ala Thr Thr Val Val Ala Ala
            130                 135

<210> SEQ ID NO 165
<211> LENGTH: 131
<212> TYPE: PRT
<213> ORGANISM: Micromonospora citrea

<400> SEQUENCE: 165

Ser Ala Gln Ser Thr Asn Ala Ala Thr Ile Val Ala Val Gly Arg Gln
 1               5                  10                  15

Arg Gln Val Pro Pro Arg Gly Phe Val Ile Ala Leu Ala Thr Ala Met
                20                  25                  30

Gln Glu Ser Thr Leu Arg Asn Leu Ala Asn Ser Thr Val Pro Glu Ser
            35                  40                  45

Leu Ser Leu Pro His Glu Gly Val Gly Arg Asp His Asp Ser Val Gly
 50                  55                  60

Leu Phe Gln Gln Arg Pro Gly Trp Gly Ser Val Arg Glu Arg Met Thr
 65                  70                  75                  80

Pro Ser Tyr Ala Ala Lys Phe Tyr Glu Ala Leu Val Arg Val Asp
                 85                  90                  95

Gly Trp Gln Arg Met Arg Leu Thr Asp Ala Gln Ala Val Gln Arg
                100                 105                 110

Ser Gly Leu Pro Glu Ala Tyr Gln Lys Trp Glu Ala Asp Ala Glu Gln
                115                 120                 125

Leu Ala Ala
    130

<210> SEQ ID NO 166
<211> LENGTH: 137
<212> TYPE: PRT
<213> ORGANISM: Micromonospora echinaurantiaca

<400> SEQUENCE: 166

Gly Leu Thr Glu Ala Gln Met Glu Asn Ala Glu Ala Ile Val Arg Thr
 1               5                  10                  15

Gly Arg Glu Met Gly Val Pro Arg Arg Ala Leu Val Ile Ala Val Ala
                20                  25                  30

Thr Ala Met Gln Glu Ser Asn Leu Tyr Asn Tyr Ala Ser Gly Val Leu
            35                  40                  45

Pro Glu Ser Gln Asn Tyr Pro His Gln Ala Val Gly Trp Asp His Asp
 50                  55                  60

Ser Val Gly Leu Phe Gln Gln Arg Pro Ser Ser Gly Trp Gly Pro Val
 65                  70                  75                  80
```

Arg Arg Leu Met Glu Pro Glu Phe Ala Thr Arg Gln Phe Leu Ser Ala
                85                  90                  95

Leu Glu Gln Val Pro Gly Trp Gln Arg Met Arg Leu Thr Asp Ala Ala
            100                 105                 110

Gln Ala Val Gln Ile Ser Ala Tyr Pro Glu His Tyr Ala Lys His Glu
        115                 120                 125

Trp Arg Ala Thr Lys Val Val Glu Ala
    130                 135

<210> SEQ ID NO 167
<211> LENGTH: 133
<212> TYPE: PRT
<213> ORGANISM: Micromonospora pallida

<400> SEQUENCE: 167

Gly Leu Ser Gln Arg Gln Met Asp Asn Ala Lys Thr Ile Val Asp Val
1               5                   10                  15

Gly Val Arg Ser Arg Met Pro Arg Arg Ala Leu Val Val Ala Val Ala
            20                  25                  30

Thr Ala Met Gln Glu Ser Asn Leu His Asn Val Ala Asn Asp Gln Ile
        35                  40                  45

Ala Glu Ser Leu Arg Tyr Pro His Gln Gly Thr Gly Thr Asp His Asp
    50                  55                  60

Ser Val Gly Leu Phe Gln Gln Arg Pro Ser Ser Gly Trp Gly Ser Val
65                  70                  75                  80

Arg Glu Leu Met Gln Pro Thr Tyr Ala Ala Ser Ala Phe Tyr Arg Ala
                85                  90                  95

Leu Arg Glu Val Pro Gly Trp Gln Lys Leu Ser Val Thr Ala Ala Ala
            100                 105                 110

Gln Ala Val Gln Gln Ser Ala Tyr Pro Gly Ala Tyr Ala Lys His Glu
        115                 120                 125

Arg Arg Ala Thr Ala
    130

<210> SEQ ID NO 168
<211> LENGTH: 137
<212> TYPE: PRT
<213> ORGANISM: Micromonospora rhizosphaerae

<400> SEQUENCE: 168

Gly Leu Asp Gln Arg Gln Met Asp Asn Ala Lys Val Ile Val Asp Val
1               5                   10                  15

Gly Arg Glu Met Lys Met Pro Arg Arg Gly Leu Ile Ile Ala Val Ala
            20                  25                  30

Thr Ala Met Gln Glu Ser Asn Leu Tyr Asn Tyr Ala Ser Gly Val Leu
        35                  40                  45

Pro Glu Ser Gln Asn Tyr Pro Tyr Gln Ala Ile Gly Trp Asp His Asp
    50                  55                  60

Ser Val Gly Leu Phe Gln Gln Arg Pro Ser Ser Gly Trp Gly Thr Val
65                  70                  75                  80

Ala Glu Leu Met Arg Pro Ala Tyr Ala Ala Arg Ala Phe Tyr Ser Ala
                85                  90                  95

Leu Asn Glu Val Pro Gly Trp Gln Asp Leu Ser Leu Thr Gln Ala Ala
            100                 105                 110

```
Gln Ala Val Gln Val Ser Ala Phe Pro Asp Ala Tyr Ala Arg His Glu
        115                 120                 125

Glu Arg Ala Thr Thr Val Val Asp Ala
    130                 135

<210> SEQ ID NO 169
<211> LENGTH: 141
<212> TYPE: PRT
<213> ORGANISM: Micromonospora pallida

<400> SEQUENCE: 169

Gly Pro Val Ala Gly Leu Thr Val Ala Gln Met Asn Asn Ala Lys Lys
1               5                   10                  15

Ile Val Arg Ala Gly Arg Ala Met Gly Val Pro Arg Arg Ala Leu Val
            20                  25                  30

Ile Ala Val Ala Thr Ala Met Gln Glu Ser Asn Leu Tyr Asn Leu Ala
        35                  40                  45

Ser Gly Val Val Pro Glu Ser Gln Asn His Pro Asn Gln Gly Val Gly
    50                  55                  60

Trp Asp His Asp Ser Ile Gly Leu Phe Gln Gln Arg Ala Ser Met Gly
65                  70                  75                  80

Trp Gly Thr Val Ala Gln Ile Met Asp Pro Ala Tyr Ala Thr Arg Gln
                85                  90                  95

Phe Leu Thr Val Leu Leu Thr Val Pro Gly Trp Gln Met Arg Leu
            100                 105                 110

Thr Asp Ala Ala Gln Ala Val Gln Val Ser Gly Phe Pro Glu Ala Tyr
        115                 120                 125

Ala Gln His Glu Ser Arg Ala Thr Val Ile Val Asn Ala
    130                 135                 140

<210> SEQ ID NO 170
<211> LENGTH: 137
<212> TYPE: PRT
<213> ORGANISM: Micromonospora krabiensis

<400> SEQUENCE: 170

Gly Leu Thr Arg Ala Gln Met Lys Asn Ala Gly Ala Ile Val Arg Thr
1               5                   10                  15

Gly Arg Glu Met Lys Val Pro Arg Arg Ala Leu Val Ile Ala Val Ala
            20                  25                  30

Thr Ala Met Gln Glu Ser Asn Leu Tyr Asn Tyr Ala Ser Gly Val Leu
        35                  40                  45

Pro Glu Ser Gln Asn Tyr Pro His Gln Ala Ile Gly Trp Asp His Asp
    50                  55                  60

Ser Val Gly Leu Phe Gln Gln Arg Pro Ser Ser Gly Trp Gly Ser Val
65                  70                  75                  80

Gly Asp Leu Met Arg Pro Glu Tyr Ala Thr Arg Gln Phe Leu Thr Ala
                85                  90                  95

Leu Glu Glu Val Pro Gly Trp Gln Gln Met Pro Leu Thr Asp Ala Ala
            100                 105                 110

Gln Ala Val Gln Val Ser Ala Phe Gly Trp Leu Tyr Ala Gln His Glu
        115                 120                 125

Trp Ala Ala Thr Glu Val Val Asp Ala
    130                 135
```

<210> SEQ ID NO 171
<211> LENGTH: 137
<212> TYPE: PRT
<213> ORGANISM: Micromonospora krabiensis

<400> SEQUENCE: 171

Gly Leu Thr Gln Ala Gln Met Asp Asn Ala Lys Val Ile Val Asp Val
1               5                   10                  15

Gly Arg Asp Leu Asp Val Pro Lys Phe Gly Met Ile Ile Ala Val Ala
                20                  25                  30

Thr Ala Met Gln Glu Ser Thr Leu Leu Asn Tyr Ala Ser Gly Val Leu
            35                  40                  45

Pro Glu Ser Gln Asp Tyr Pro His Gln Ala Ile Gly Trp Asp His Asp
50                  55                  60

Ser Val Gly Leu Phe Gln Gln Arg Pro Ser Ser Gly Trp Gly Thr Val
65                  70                  75                  80

Ala Glu Leu Met Arg Pro Ala Phe Ala Ala Arg Ala Phe Tyr Leu Ala
                85                  90                  95

Leu Leu Glu Val Pro Gly Trp Gln Asp Met Ser Leu Thr Val Ala Ala
            100                 105                 110

Gln Thr Val Gln Val Ser Ala Phe Pro Asp Ala Tyr Ala Gln His Glu
        115                 120                 125

Asp Arg Ala Thr Glu Val Val Glu Ala
    130                 135

<210> SEQ ID NO 172
<211> LENGTH: 143
<212> TYPE: PRT
<213> ORGANISM: Mycobacterium phage Tonenili

<400> SEQUENCE: 172

Glu Gly Arg Arg Ala Arg Ser Gly Gln Gly Gln Leu Asp His Pro Val
1               5                   10                  15

Ile Ser Glu Lys Gly Ile Val Ile Ala Leu Ala Thr Gly Leu Val Glu
                20                  25                  30

Ser Asn Leu Thr Met Tyr Ala Asn Arg Ala Asp Pro Asp Ser Leu Lys
            35                  40                  45

Tyr Pro His Asp Ala Val Gly Ser Asp Ala Asn Ser Val Gly Val Phe
50                  55                  60

Gln Gln Arg Ala Pro Trp Trp Gly Thr Leu Ala Asp Arg Met Asp Val
65                  70                  75                  80

Ala Arg Ser Ala Ala Met Phe Tyr Gly Ser Leu Ala Arg Gln Arg Ile
                85                  90                  95

Val Asp Asn Ala Gly Thr Pro Asn Glu Lys Arg Phe Asp Tyr Asn Thr
            100                 105                 110

Asp Arg Val Ser Pro Gly Thr Trp Ala Gln Met Val Gln Lys Ser Ala
        115                 120                 125

Phe Pro Asp Arg Tyr Asp Gln Arg Met Ala Glu Ala Arg Lys Ile
    130                 135                 140

<210> SEQ ID NO 173
<211> LENGTH: 102
<212> TYPE: PRT
<213> ORGANISM: Mycobacterium phage Tonenili -continued

```
<400> SEQUENCE: 173

Thr Ile Met Val Glu Ser Asn Trp Ile Met Tyr Ala Asn Asn Ala Val
1               5                   10                  15

Pro Glu Ser Leu Asn Phe Pro His Asp Ala Ile Gly Ser Asp His Asp
            20                  25                  30

Ser Ile Gly Leu Phe Gln Gln Arg Pro Ser Trp Gly Thr Val Ala Gln
        35                  40                  45

Arg Met Asn Pro Arg Glu Ser Ala Gly Met Phe Leu Lys Glu Leu Ala
    50                  55                  60

Lys Leu Asp Trp Arg Asn Met Asp Arg Gly Ala Ala Cys Gln Ala Val
65                  70                  75                  80

Gln Arg Ser Ala Phe Pro Gly Arg Tyr Ala Ala Gln Glu Gln Ala Ala
                85                  90                  95

Val Glu Met Val Arg Ala
            100

<210> SEQ ID NO 174
<211> LENGTH: 142
<212> TYPE: PRT
<213> ORGANISM: Pseudonocardia sp. SCN 72 86

<400> SEQUENCE: 174

Leu Asp Glu Lys Gln Leu Ala Asn Ala Ala Thr Ile Ile Thr Val Gly
1               5                   10                  15

Thr Gln Ala Gly Val Pro Ala Ala Gly Leu Lys Val Ala Leu Met Thr
            20                  25                  30

Ala Leu Gln Glu Ser Lys Leu Arg Met Leu Ala Asn Ser Thr Val Pro
        35                  40                  45

Ala Ser Leu Asp Tyr Pro His Glu Gly Val Gly Ser Asp His Asp Ser
    50                  55                  60

Val Asn Met Phe Gln Gln Arg Pro His Trp Gly Lys Leu Ala Asp Leu
65                  70                  75                  80

Met Asp Ala Arg Tyr Ala Val Arg Ala Phe Phe Gly Gly Pro Asn Gly
                85                  90                  95

Pro Asn Gly Gly Ser Pro Arg Gly Leu Leu Asp Ile Lys Gly Trp Asp
            100                 105                 110

Thr Met Pro Pro Gly Gln Ala Ala Gln Arg Val Gln Val Ser Ala Phe
        115                 120                 125

Pro Asp Ala Tyr Asp Gln Trp Glu Gly Ala Ala Glu Thr Ile
    130                 135                 140

<210> SEQ ID NO 175
<211> LENGTH: 148
<212> TYPE: PRT
<213> ORGANISM: Microbacterium pygmaeum

<400> SEQUENCE: 175

Leu Arg Arg Ala Gln Leu Thr His Ala Ala Thr Ile Ile Thr Val Gly
1               5                   10                  15

Ser Gly Ile Asp Gly Val Gly Arg Gln Gly Val Leu Ile Ala Leu Met
            20                  25                  30

Ala Ala Leu Thr Glu Ser Thr Leu Arg Met Leu Ala Asn Ala Ala His
        35                  40                  45

Pro Ala Ser Leu Asp Met Pro Asn Asp Gly Val Gly Ser Asp His Asp
    50                  55                  60
```

Ser Leu Gly Leu Phe Gln Met Arg Pro Thr Ser Gly Trp Gly Thr Val
65                  70                  75                  80

Ala Glu Leu Met Asp Ala Arg Tyr Gln Val Arg Ala Phe Phe Gly Gly
                85                  90                  95

Pro Asp Gly Pro Asn Tyr Pro Ser Pro Ala Gly Leu Leu Asp Ile Ala
            100                 105                 110

Gly Trp Gln Thr Ala Asp Pro Gly Thr Ala Gln Ala Val Glu Arg
        115                 120                 125

Ser Ala Tyr Pro Asp Arg Tyr Gln Asn Tyr Gln Pro Val Ala Glu Ser
    130                 135                 140

Ile Ile Ala Ala
145

<210> SEQ ID NO 176
<211> LENGTH: 123
<212> TYPE: PRT
<213> ORGANISM: Pseudonocardia sp. SCN 73 27

<400> SEQUENCE: 176

Gly Phe Ala Gly Pro Gln Leu Ala Asn Ala Ala Ala Ile Val Ser Val
1               5                   10                  15

Gly Val Glu Met Gly Val Ser Gln Arg Gly Gln Val Ile Ala Val Ala
                20                  25                  30

Thr Ala Ile Gln Glu Ser Lys Leu Leu Met Tyr Ala Asn Ser Thr Val
            35                  40                  45

Pro Ala Ser Leu Asp Leu Pro His Asp Arg Val Gly Ser Asp His Asp
        50                  55                  60

Ser Val Gly Leu Phe Gln Gln Arg Ala Pro Trp Gly Pro Leu Gln Val
65                  70                  75                  80

Arg Met Asp Ala Arg Gly Ser Ala Lys Leu Phe Tyr Ala Arg Leu Leu
                85                  90                  95

Thr Val Pro Gly Trp Gln Ser Met Pro Leu Ala Gln Ala Ala Gln Ala
            100                 105                 110

Val Gln Ile Ser Ala Phe Pro Asp Ala Tyr Ala
        115                 120

<210> SEQ ID NO 177
<211> LENGTH: 145
<212> TYPE: PRT
<213> ORGANISM: Mycobacterium phage Lukilu

<400> SEQUENCE: 177

Thr Gln Asp Gly Ile Ala Ile Gly Ile Ile Ala Glu Gly Arg Arg Ser
1               5                   10                  15

Arg Ser Gly Glu Gly Gln Leu Asp His Pro Val Met Ser Ala Lys Gly
                20                  25                  30

Ile Val Ile Ala Leu Ala Val Ala Leu Val Glu Thr Asn Leu Lys Met
            35                  40                  45

Tyr Ala Asn Arg Ser Asp Pro Glu Ser Leu Asn Phe Pro His Asp Ala
        50                  55                  60

Val Gly Ser Asp Ala Asn Ser Val Gly Val Phe Gln Gln Arg Ala Pro
65                  70                  75                  80

Trp Trp Gly Thr Val Ala Asp Arg Met Asp Val Ala Arg Ser Ala Ala
                85                  90                  95

Met Phe Tyr Asn Ser Leu Tyr Arg Gln Arg Val Gly Gly Ala Asp Tyr
            100                 105                 110

Asn Thr Asp Arg Val Ser Pro Gly Thr Trp Gly Gln Met Val Gln Gln
            115                 120                 125

Ser Ala Phe Pro Asp Arg Tyr Asp Lys Arg Met Ala Glu Ala Arg Gln
        130                 135                 140

Ile
145

<210> SEQ ID NO 178
<211> LENGTH: 147
<212> TYPE: PRT
<213> ORGANISM: Micromonospora avicenniae

<400> SEQUENCE: 178

Ser Gly Lys Met Pro Arg Leu Ala Asp Tyr Gly Asp Ser Gln Leu Arg
1               5                   10                  15

Asn Ala Ala Arg Ile Ile Gly Thr Gly Gln Lys Met Lys Val Pro Pro
            20                  25                  30

Arg Gly Trp Val Ile Ala Val Ala Thr Ala Met Gln Glu Ser Arg Leu
        35                  40                  45

Arg Asn Leu Ala Asn Arg Thr Val Gly Glu Ser Gln Gly Leu Pro Asn
    50                  55                  60

Glu Gly Val Gly Ala Asp His Asp Ser Val Gly Leu Phe Gln Gln Arg
65                  70                  75                  80

Ala Ser Trp Gly Thr Val Arg Gln Arg Met Thr Pro Glu Tyr Ala Ala
                85                  90                  95

Lys Lys Phe Tyr Glu Gly Leu Leu Asp Ile Pro Asp Trp Glu Gln Leu
            100                 105                 110

Pro Leu Thr Glu Ala Ala Gln Arg Val Gln Arg Ser Ala Phe Pro Asp
        115                 120                 125

Ala Tyr Ala Lys His Glu Ala Val Ala Ala Gln Ile Val Asp Ala Leu
    130                 135                 140

Ala Gly Gly
145

<210> SEQ ID NO 179
<211> LENGTH: 127
<212> TYPE: PRT
<213> ORGANISM: Mycobacterium abscessus subsp. abscessus

<400> SEQUENCE: 179

Ser Lys Asp Asp Tyr Ala Arg Ala Ile Ile Ala Glu Gly Lys Arg Arg
1               5                   10                  15

Gly Ile Ser Pro Leu Gly Ile Gln Ile Gly Leu Ala Thr Val Tyr Val
            20                  25                  30

Glu Ser Asp Phe Ile Met Tyr Ala Asn Glu Asp Pro Glu Ser Leu
        35                  40                  45

Asn Tyr Pro His Glu Ala Leu Ser Glu Asp Ala Asn Ser Thr Gly Leu
    50                  55                  60

Phe Gln Gln Arg Ala Pro Trp Trp Gly Thr Val Ala Asp Arg Met Asp
65                  70                  75                  80

Ala Thr Arg Ser Ala Gly Leu Phe Phe Ala Ala Leu Ala Lys Leu Asp
                85                  90                  95

Tyr Asn Asn Pro Ala Arg Ser Pro Gly Ser Tyr Ala Gln Ala Val Gln
            100                 105                 110

Lys Ser Ala Phe Pro Asp Arg Tyr Asp Lys Arg Phe Asn Asp Ala
        115                 120                 125

-continued

```
<210> SEQ ID NO 180
<211> LENGTH: 140
<212> TYPE: PRT
<213> ORGANISM: Mycobacterium abscessus subsp. abscessus

<400> SEQUENCE: 180

Ala Gly Thr Val Gly Asp Leu Asp Gly Arg Gln Thr Gln Val Ala Lys
1               5                   10                  15

Asp Ile Val Ala Glu Gly Leu Arg Arg Gly Ile Pro Phe Lys Gly Leu
            20                  25                  30

Val Ile Gly Val Ala Thr Ala Leu Gln Glu Ser Ser Leu Arg Glu Leu
        35                  40                  45

Ala Asn Pro Ser Val Pro Glu Ser Met Gln Ile Pro His Asp Gly Val
    50                  55                  60

Gly Lys Asp His Asp Ser Val Gly Pro Phe Gln Gln Arg Gln Ser Trp
65                  70                  75                  80

Gly Ala Thr Ala Asp Leu Met Asn Ser Arg Thr Ser Ala Gly Lys Phe
                85                  90                  95

Phe Ala Ala Leu Gln Lys Val Ala Gly Trp Gln Asn Met Ser His Thr
            100                 105                 110

Glu Ala Ala Gln Ala Val Gln Arg Ser Ala Phe Pro Ser Ala Tyr Ala
        115                 120                 125

Lys His Val Ala His Ala Asp Arg Ile Val Arg Ala
    130                 135                 140

<210> SEQ ID NO 181
<211> LENGTH: 121
<212> TYPE: PRT
<213> ORGANISM: Mycobacterium abscessus subsp. abscessus

<400> SEQUENCE: 181

Asn Gly Lys Ala Val Ile Ala Thr Gly Leu Gln Met Lys Ile Pro Glu
1               5                   10                  15

Lys Gly Ile Ile Val Ala Leu Ala Thr Ala Met Gln Glu Ser Gly Leu
            20                  25                  30

Lys Asn Tyr Ala Asn Pro Asn Val Pro Glu Ser Met Gln Ile Pro His
        35                  40                  45

Glu Ala Val Gly His Asp His Ala Ser Val Gly Ile Phe Gln Gln Gln
    50                  55                  60

Pro Trp Trp Gly Ser Ile Lys Asp Leu Met Thr Pro Gly Val Ala Ala
65                  70                  75                  80

Gln Lys Phe Tyr Ala Ala Leu Leu Lys Val Gly Gly Trp Glu Ser Met
                85                  90                  95

Ala Pro Thr Gln Ala Gln Ala Val Gln Arg Ser Ala Tyr Pro Asp
            100                 105                 110

Ala Tyr Ala Asp Asp Val Pro Ala Ala
        115                 120

<210> SEQ ID NO 182
<211> LENGTH: 137
<212> TYPE: PRT
<213> ORGANISM: Micromonospora avicenniae

<400> SEQUENCE: 182

Gly Leu Thr Arg Thr Gln Met Lys Asn Ala Glu Ile Ile Val Arg Thr
1               5                   10                  15

Gly Arg Gly Met Gly Val Pro Arg Arg Gly Met Val Ile Ala Val Ala
            20                  25                  30
```

```
Thr Ala Met Gln Glu Ser Asn Leu Tyr Asn Leu Ala Ser Gly Val Ile
         35                  40                  45

Pro Glu Ser Gln Arg His Pro His Gln Gly Leu Gly Trp Asp His Asp
 50                  55                  60

Ser Val Gly Leu Phe Gln Gln Arg Ser Ser Gly Trp Gly Pro Val
 65                  70                  75                  80

Asp Arg Leu Met Asp Pro Glu Phe Ala Thr Arg Gln Phe Leu Gly Ala
                 85                  90                  95

Leu Glu Arg Val Pro Gly Trp Gln Gln Met Arg Leu Thr Asp Ala Ala
             100                 105                 110

Gln Ala Val Gln Val Ser Ala Tyr Pro Asp Tyr Tyr Ala Lys His Glu
         115                 120                 125

Trp Arg Ala Asn Glu Val Val Asp Ala
130                 135

<210> SEQ ID NO 183
<211> LENGTH: 134
<212> TYPE: PRT
<213> ORGANISM: Mycobacterium abscessus subsp. abscessus

<400> SEQUENCE: 183

Leu Asn Glu Arg Gln Met Glu Ile Ala Arg Thr Ile Val Ala Glu Ala
 1               5                  10                  15

Gln Arg Arg Gly Leu Ser Pro Phe Ala Ala Lys Ile Ala Leu Ala Thr
             20                  25                  30

Gly Leu Thr Glu Ser Gly Leu Arg Asn Leu Ala Asn Ser Asn Val Pro
         35                  40                  45

Ala Ser Leu Asn Ile Leu Asn Asp Gly Val Gly Lys Asp His Asp Ser
 50                  55                  60

Thr Gly Val Phe Gln Gln Arg Gln Ser Trp Gly Ala Thr Arg Glu Leu
 65                  70                  75                  80

Met Thr Pro Met Leu Ala Ala Gly Lys Phe Tyr Asp Ala Leu Val Lys
                 85                  90                  95

Val Pro Gly Trp Glu His Met Ser Leu Ala Ala Ala Gln Ser Val
             100                 105                 110

Gln Arg Ser Ala Phe Pro Ser Ala Tyr Ala Lys Tyr Glu Gln Gln Ala
         115                 120                 125

Asn Gln Val Tyr Gln Ala
130

<210> SEQ ID NO 184
<211> LENGTH: 127
<212> TYPE: PRT
<213> ORGANISM: Mycobacterium abscessus subsp. abscessus

<400> SEQUENCE: 184

Ser Lys Asp Asp Tyr Ala Arg Ala Ile Ile Ala Glu Gly Arg Arg Lys
 1               5                  10                  15

Gly Ile Thr Pro Arg Gly Ile Gln Ile Gly Leu Ala Thr Val Tyr Val
             20                  25                  30

Glu Ser Asp Phe Ile Met Tyr Ala Asn Glu Ala Asp Pro Asp Ser Leu
         35                  40                  45

Asn Tyr Pro His Glu Asp Leu Ser Glu Asp Glu Asn Ser Thr Gly Leu
 50                  55                  60

Phe Gln Gln Arg Ala Pro Trp Trp Gly Thr Val Ala Asp Arg Met Asp
 65                  70                  75                  80
```

Ala Ala Arg Ser Ala Gly Leu Phe Phe Ala Ala Leu Ala Lys Leu Asp
85 90 95

Tyr Asn Asn Pro Ser Arg Ser Pro Gly Ser Tyr Ala Gln Ser Val Gln
100 105 110

Gln Ser Ala Phe Pro Asp Arg Tyr Asp Gln Arg Phe Asn Asp Ala
115 120 125

<210> SEQ ID NO 185
<211> LENGTH: 130
<212> TYPE: PRT
<213> ORGANISM: Mycobacterium abscessus subsp. abscessus

<400> SEQUENCE: 185

Gln Met Gln Val Ala Lys Ser Ile Val Ala Glu Gly Val Arg Arg His
1 5 10 15

Leu Pro Pro Lys Ala Met Gln Ile Ala Ile Ala Thr Ala Leu Gln Glu
20 25 30

Ser Gly Met Arg Ser Leu Ala Asn Pro Asn Val Pro Ala Ser Met Gln
35 40 45

Ile Pro His Gln Gly Val Gly Arg Asp His Asp Ser Val Gly Pro Phe
50 55 60

Gln Gln Arg Gln Ser Trp Gly Ala Thr Ala Asp Leu Met Asn Pro Ala
65 70 75 80

Thr Ser Ala Gly Lys Phe Tyr Asp Lys Leu Val Arg Ile Pro Gly Trp
85 90 95

Gln Glu Met Pro Leu Thr Gln Ala Ala Gln Arg Val Gln Val Ser Ala
100 105 110

Tyr Pro Asn Ala Tyr Ala Lys His Thr Gly Pro Ala Gly Gln Ile Val
115 120 125

Ala Ala
130

<210> SEQ ID NO 186
<211> LENGTH: 135
<212> TYPE: PRT
<213> ORGANISM: Mycobacterium abscessus subsp. abscessus

<400> SEQUENCE: 186

Ser Lys Glu Asp Gly Tyr Ala Arg Ala Ile Ile Ala Glu Gly Lys Arg
1 5 10 15

Arg Gly Ile Ser Pro Arg Gly Ile Gln Ile Gly Leu Ala Thr Val Phe
20 25 30

Val Glu Ala Ala Leu Lys Met Trp Ala Asn Glu Lys Val Pro Glu Ser
35 40 45

Leu Glu Phe Pro His Asp Asp Val Gly Tyr Asp Gly Tyr Ser Val Gly
50 55 60

Leu Phe Gln Gln Gln Val Val Met Gly Leu Asn Gly Gln Trp Trp Trp
65 70 75 80

Ala Asp Cys Ala Thr Cys Met Asn Pro Thr Leu Ser Ala Gly Leu Phe
85 90 95

Phe Asp Arg Leu Ala Lys Leu Pro Tyr Asn Asp Thr Ser Arg Ser Pro
100 105 110

Gly Ser Phe Ala Gln Asp Val Gln Gln Ser Ala Tyr Pro Asp Arg Tyr
115 120 125

Asp Lys Arg Phe Ala Glu Ala
130 135

```
<210> SEQ ID NO 187
<211> LENGTH: 127
<212> TYPE: PRT
<213> ORGANISM: Pseudonocardia sp. Ae717_Ps2

<400> SEQUENCE: 187

Ile Glu Gly Leu Gly Pro Glu Gln Val Ser Asn Ala Gly Leu Ile Val
1               5                   10                  15

Ala Thr Gly Val Glu Met Asp Val Pro Arg His Gly Arg Val Ile Ala
            20                  25                  30

Leu Ala Thr Ala Met Gln Glu Ser Leu Lys Asn Leu Ala Asn Ser
        35                  40                  45

Asn Val Pro Gln Ser Leu Glu Leu Pro Asn Gln Gly Val Gly Ser Asp
50                  55                  60

His Asp Ser Val Gly Leu Phe Gln Gln Arg Glu Ala Gly Trp Gly Asp
65                  70                  75                  80

Val Ala Thr Arg Met Asp Pro Arg Gln Ser Ala Arg Leu Phe Tyr Asn
                85                  90                  95

Ala Leu Leu Gln Val Pro Gly Trp Glu Ser Leu Pro Val Thr Arg Ala
            100                 105                 110

Ala Gln Leu Val Gln Ile Ser Ala Phe Pro Asp Ala Tyr Ala Lys
        115                 120                 125

<210> SEQ ID NO 188
<211> LENGTH: 74
<212> TYPE: PRT
<213> ORGANISM: Podospora anserina

<400> SEQUENCE: 188

Tyr Pro Ile Thr Gly Asp Val Val Asn Cys Arg Ser Gly Pro Gly Thr
1               5                   10                  15

Ser Tyr Ser Val Val Lys Gln Tyr Thr Gln Gly Gln Asp Val Thr Ile
            20                  25                  30

Thr Cys Gln Thr Glu Gly Thr Asn Val Asn Gly Val Thr Ile Trp Asp
        35                  40                  45

Lys Thr Ala Asp Gly Asn Cys Tyr Val Ser Asp Tyr Tyr Val Gln Thr
50                  55                  60

Gly Val Asn Gly Tyr Val Thr Glu Arg Cys
65                  70

<210> SEQ ID NO 189
<211> LENGTH: 73
<212> TYPE: PRT
<213> ORGANISM: Penicillium chrysogenum

<400> SEQUENCE: 189

Tyr Pro Ile Thr Gly Asp Gly Val Asn Cys Arg Ser Gly Pro Gly Thr
1               5                   10                  15

Ser Tyr Ser Val Val Lys Ser Tyr Lys Gln Gly Ala Asp Val Ala Ile
            20                  25                  30

Thr Cys Gln Thr Ala Gly Thr Ser Val Asn Gly Asn Glu Ile Trp Asp
        35                  40                  45

Lys Thr Glu Asp Gly Cys Tyr Ile Thr Asp Tyr Tyr Ile Arg Thr Gly
50                  55                  60

Ser Ser Ser Tyr Val Thr Lys Lys Cys
65                  70
```

```
<210> SEQ ID NO 190
<211> LENGTH: 73
<212> TYPE: PRT
<213> ORGANISM: Nectria haematococca

<400> SEQUENCE: 190

Tyr Pro Val Thr Ser Asp Asn Leu Asn Cys Arg Ser Gly Pro Gly Thr
1               5                   10                  15

Ala Phe Ala Ile Lys Lys Ser Tyr Lys Asn Gly Gln Asp Val Thr Ile
                20                  25                  30

Thr Cys Gln Thr Glu Gly Asp Asn Ile Glu Gly Asn Ser Ile Trp Asp
            35                  40                  45

Lys Thr Ser Asp Gly Cys Tyr Val Ala Asp Lys Tyr Val Lys Thr Gly
        50                  55                  60

Lys Asp Gly Tyr Val Lys Gly Lys Cys
65                  70

<210> SEQ ID NO 191
<211> LENGTH: 61
<212> TYPE: PRT
<213> ORGANISM: Metarhizium acridum

<400> SEQUENCE: 191

Tyr Pro Ile Thr Gly Thr Thr Val Asn Cys Arg Ala Gly Pro Ala Thr
1               5                   10                  15

Asp Pro Ala Ile Val Arg Ala Tyr Lys Asp Asp Lys Val Ser Ile
                20                  25                  30

Ala Arg Gln Thr Gln Gly Pro Asp Ile Asn Gly Gly Thr Ile Trp Asp
            35                  40                  45

Lys Thr Ala Asp Gly Cys Tyr Val Ser Asp Tyr Phe Val
        50                  55                  60

<210> SEQ ID NO 192
<211> LENGTH: 73
<212> TYPE: PRT
<213> ORGANISM: Metarhizium robertsii

<400> SEQUENCE: 192

Phe Pro Val Thr Ala Asp Ser Leu Asn Cys Arg Ala Glu Pro Asn Thr
1               5                   10                  15

Ser Ser Ala Val Lys Lys Thr Tyr Lys Lys Thr Asp Asp Val Lys Ile
                20                  25                  30

Ser Cys Gln Thr Glu Gly Pro Ser Ile Asn Gly Asn Ser Ile Trp Asp
            35                  40                  45

Lys Thr Gln Asp Gly Cys Tyr Val Ala Asp Tyr Ile Lys Thr Gly
        50                  55                  60

Ser Ser Gly Tyr Val Thr Gly Lys Cys
65                  70

<210> SEQ ID NO 193
<211> LENGTH: 73
<212> TYPE: PRT
<213> ORGANISM: Metarhizium robertsii

<400> SEQUENCE: 193

Tyr Ala Ile Glu Ala Asp Gly Val Asn Cys Arg Ser Gly Pro Ser Thr
1               5                   10                  15

Ser Asp Lys Val Val Arg Thr Tyr Asn Lys Gly Asn Asp Val Lys Leu
                20                  25                  30
```

Glu Cys Gln Thr Ala Gly Gln Ala Ile His Gly Asp Ser Leu Trp Asp
        35                  40                  45

Lys Thr Thr Asp Gly Cys Tyr Val Ala Asp Tyr Tyr Val Lys Thr Gly
 50                  55                  60

Thr Thr Asn Met Val Thr Gly Gln Cys
 65                  70

<210> SEQ ID NO 194
<211> LENGTH: 73
<212> TYPE: PRT
<213> ORGANISM: Fusarium oxysporum

<400> SEQUENCE: 194

Tyr Pro Val Thr Ser Asp Asn Leu Asn Cys Arg Ser Gly Pro Gly Thr
 1               5                   10                  15

Ala Phe Ala Ile Lys Lys Ser Tyr Lys Lys Gly Gln Asp Val Thr Ile
                20                  25                  30

Thr Cys Gln Thr Gln Gly Asp Asn Val Glu Gly Asn Ser Ile Trp Asp
        35                  40                  45

Lys Thr Ser Asp Gly Cys Tyr Val Ala Asp Lys Tyr Val Lys Thr Gly
 50                  55                  60

Lys Asp Gly Tyr Val Lys Gly Lys Cys
 65                  70

<210> SEQ ID NO 195
<211> LENGTH: 69
<212> TYPE: PRT
<213> ORGANISM: Fusarium oxysporum

<400> SEQUENCE: 195

Asp Glu Gly Val Arg Cys Arg Ser Gly Pro Thr Thr Ser His Ala Ile
 1               5                   10                  15

Gln Arg Gln Phe Thr Lys Gly Thr Asp Val Thr Ile Thr Cys Gln Ile
                20                  25                  30

Glu Gly Thr Asn Ile Glu Gly Asn Ala Leu Trp Asp Lys Thr Thr Phe
        35                  40                  45

Gly Cys Tyr Val Ser Asp Tyr Tyr Val Ala Thr Gly Ser Ser Gly Tyr
 50                  55                  60

Val Thr Ser Lys Cys
 65

<210> SEQ ID NO 196
<211> LENGTH: 73
<212> TYPE: PRT
<213> ORGANISM: Thielavia terrestris

<400> SEQUENCE: 196

Tyr Pro Val Lys Ala Asp Thr Leu Asn Cys Arg Ser Gly Pro Gly Thr
 1               5                   10                  15

Ser Tyr Lys Val Ile Lys Thr Tyr Lys Lys Gly Thr Asp Leu Lys Ile
                20                  25                  30

Thr Cys Gln Thr Pro Gly Thr Ser Val Asn Gly Asp Asn Leu Trp Asp
        35                  40                  45

Lys Thr Ser Asp Gly Cys Tyr Val Ala Asp Tyr Tyr Val Lys Thr Gly
 50                  55                  60

Thr Ser Gly Tyr Val Thr Ala His Cys
 65                  70

<210> SEQ ID NO 197
<211> LENGTH: 73
<212> TYPE: PRT
<213> ORGANISM: Thielavia terrestris

<400> SEQUENCE: 197

Tyr Pro Ile Lys Gly Asp Gly Val Asn Cys Arg Thr Gly Pro Gly Thr
1               5                   10                  15

Ser Tyr Lys Val Val Lys Ser Tyr Ala Lys Gly Val Asp Val Lys Ile
            20                  25                  30

Thr Cys Gln Thr His Gly Glu Ser Ile Asn Gly Asp Thr Leu Trp Asp
        35                  40                  45

Lys Thr Ser Asp Gly Cys Tyr Val Ala Asp Tyr Tyr Val Lys Thr Gly
    50                  55                  60

Thr Thr Asn Met Val Thr Gly Gln Cys
65                  70

<210> SEQ ID NO 198
<211> LENGTH: 73
<212> TYPE: PRT
<213> ORGANISM: Trichosporon asahii

<400> SEQUENCE: 198

Tyr Pro Ile Lys Thr Asp Gly Val Arg Cys Arg Ser Gly Pro Gly Thr
1               5                   10                  15

Ser Tyr Asp Ile Lys Lys Thr Tyr Ser Ala Gly Asp Lys Val Thr Leu
            20                  25                  30

Ser Cys Tyr Lys Thr Gly Thr Ser Val Glu Gly Asn Thr Tyr Trp Asp
        35                  40                  45

Lys Thr Gly Asp Gly Cys Tyr Val Ser Asp Tyr Tyr Val Lys Thr Gly
    50                  55                  60

Ser Thr Thr Pro Val Val Ser Lys Cys
65                  70

<210> SEQ ID NO 199
<211> LENGTH: 72
<212> TYPE: PRT
<213> ORGANISM: Trichosporon asahii

<400> SEQUENCE: 199

Tyr Pro Val Lys Glu Thr Leu His Cys Arg Ser Ser Pro Ser Thr Ser
1               5                   10                  15

Gly Lys Ile Val Lys Asp Tyr Pro Lys Gly Thr Lys Ile Lys Leu Ser
            20                  25                  30

Cys Tyr Ser Arg Gly Gln Ser Ile Gly Gly Asn Thr Ile Trp Asp Lys
        35                  40                  45

Thr Thr Asp Gly Cys Phe Val Ala Asp Tyr Tyr Val Thr Thr Gly Thr
    50                  55                  60

Thr Asn Pro Val Val Ala Ala Cys
65                  70

<210> SEQ ID NO 200
<211> LENGTH: 73
<212> TYPE: PRT
<213> ORGANISM: Fusarium oxysporum

```
<400> SEQUENCE: 200

Tyr Pro Ile Thr Gly Asn Asn Val Asn Cys Arg Glu Gly Pro Ser Thr
1               5                   10                  15

Gly Tyr Glu Val Val Lys Thr Tyr His Lys Gly Asp Asp Val Lys Leu
            20                  25                  30

Thr Cys Gln Thr Ser Gly Glu Gly Val Leu Gly Asn Ser Leu Trp Asp
        35                  40                  45

Lys Thr Ser Asp Gly Cys Tyr Val Ala Asp Tyr Tyr Val Lys Thr Gly
    50                  55                  60

Thr Ser Gly Met Val Thr Lys Asp Cys
65                  70

<210> SEQ ID NO 201
<211> LENGTH: 73
<212> TYPE: PRT
<213> ORGANISM: Fusarium oxysporum

<400> SEQUENCE: 201

Tyr Pro Val Thr Ser Asp Asn Leu Asn Cys Arg Ser Gly Pro Gly Thr
1               5                   10                  15

Ala Phe Ala Ile Lys Lys Ser Tyr Lys Lys Gly Gln Asp Val Thr Ile
            20                  25                  30

Thr Cys Gln Thr Gln Gly Asp Lys Val Glu Gly Asn Ser Ile Trp Asp
        35                  40                  45

Lys Thr Ser Asp Gly Cys Tyr Val Ala Asp Lys Tyr Val Lys Thr Gly
    50                  55                  60

Lys Asp Gly Tyr Val Lys Gly Lys Cys
65                  70

<210> SEQ ID NO 202
<211> LENGTH: 72
<212> TYPE: PRT
<213> ORGANISM: Trichosporon asahii

<400> SEQUENCE: 202

Tyr Pro Val Lys Glu Gly Leu Asn Cys Arg Ser Glu Pro Asn Thr Gly
1               5                   10                  15

Gly Gly Ile Val Thr Ser Tyr Ala Ala Gly Thr Gln Val Thr Ile Thr
            20                  25                  30

Cys Ala Thr His Gly Glu Ala Val Asn Gly His Asp Val Trp Asp Lys
        35                  40                  45

Thr Thr Asp Gly Cys Phe Val Ser Asp Trp Tyr Val Ser Thr Gly Thr
    50                  55                  60

Ala Glu Phe Val Ala Ser Glu Cys
65                  70

<210> SEQ ID NO 203
<211> LENGTH: 73
<212> TYPE: PRT
<213> ORGANISM: Trichosporon asahii

<400> SEQUENCE: 203

Tyr Pro Ile Lys Thr Asp Gly Val Arg Cys Arg Ser Gly Pro Gly Thr
1               5                   10                  15

Ser Tyr Asp Ile Lys Lys Thr Tyr Ser Ala Gly Asp Lys Val Thr Leu
            20                  25                  30

Ser Cys Tyr Lys Thr Gly Thr Ser Val Glu Gly Asn Thr Tyr Trp Asp
        35                  40                  45
```

```
Lys Thr Gly Asp Gly Cys Tyr Val Ser Asp Tyr Tyr Val Lys Thr Gly
            50                  55                  60

Ser Thr Thr Pro Val Val Ser Lys Cys
 65                  70

<210> SEQ ID NO 204
<211> LENGTH: 73
<212> TYPE: PRT
<213> ORGANISM: Fusarium oxysporum

<400> SEQUENCE: 204

Tyr Pro Val Thr Ser Asp Asn Leu Asn Cys Arg Ser Gly Pro Gly Thr
  1               5                  10                  15

Ala Phe Ala Ile Lys Lys Ser Tyr Lys Lys Gly Gln Asp Val Thr Ile
             20                  25                  30

Asn Cys Gln Thr Gln Gly Asp Asn Val Glu Gly Asn Ser Ile Trp Asp
         35                  40                  45

Lys Thr Ser Asp Gly Cys Tyr Val Ala Asp Lys Tyr Val Lys Thr Gly
     50                  55                  60

Lys Asp Gly Tyr Val Lys Gly Lys Cys
 65                  70

<210> SEQ ID NO 205
<211> LENGTH: 69
<212> TYPE: PRT
<213> ORGANISM: Fusarium oxysporum

<400> SEQUENCE: 205

Asp Glu Gly Val Arg Cys Arg Ser Gly Pro Thr Thr Ser Asn Ala Ile
  1               5                  10                  15

Gln Arg Gln Phe Ala Lys Gly Thr Asp Val Ala Ile Thr Cys Gln Thr
             20                  25                  30

Glu Gly Thr His Ile Lys Gly Asn Ala Leu Trp Asp Lys Thr Thr Phe
         35                  40                  45

Gly Cys Tyr Val Ser Asp Cys Tyr Val Ala Thr Gly Ser Ser Gly Tyr
     50                  55                  60

Val Thr Ser Lys Cys
 65

<210> SEQ ID NO 206
<211> LENGTH: 73
<212> TYPE: PRT
<213> ORGANISM: Fusarium oxysporum

<400> SEQUENCE: 206

Tyr Pro Val Thr Ser Asp Asn Leu Asn Cys Arg Ser Gly Pro Gly Thr
  1               5                  10                  15

Ala Phe Ala Ile Lys Lys Ser Tyr Lys Lys Gly Gln Asp Val Thr Ile
             20                  25                  30

Thr Cys Gln Thr Gln Gly Asp Asn Val Glu Gly Asn Ser Ile Trp Asp
         35                  40                  45

Lys Thr Ser Asp Gly Cys Tyr Val Ala Asp Lys Tyr Val Lys Thr Gly
     50                  55                  60

Lys Asp Gly Tyr Val Lys Gly Lys Cys
 65                  70
```

<210> SEQ ID NO 207
<211> LENGTH: 69
<212> TYPE: PRT
<213> ORGANISM: Fusarium oxysporum

<400> SEQUENCE: 207

Asp Glu Gly Val Arg Cys Arg Ser Gly Pro Thr Thr Ser His Ala Ile
1               5                   10                  15

Gln Arg Gln Phe Thr Lys Gly Thr Asp Val Thr Ile Thr Cys Gln Ile
            20                  25                  30

Glu Gly Thr Asn Ile Glu Gly Asn Ala Leu Trp Asp Lys Thr Thr Phe
        35                  40                  45

Gly Cys Tyr Val Ser Asp Tyr Val Ala Thr Gly Ser Ser Gly Tyr
    50                  55                  60

Val Thr Ser Lys Cys
65

<210> SEQ ID NO 208
<211> LENGTH: 73
<212> TYPE: PRT
<213> ORGANISM: Fusarium oxysporum

<400> SEQUENCE: 208

Tyr Pro Val Thr Ser Asp Asn Leu Asn Cys Arg Ser Gly Pro Gly Thr
1               5                   10                  15

Ala Phe Ala Ile Lys Lys Ser Tyr Lys Lys Gly Gln Asp Val Thr Ile
            20                  25                  30

Thr Cys Gln Thr Gln Gly Asp Asn Val Glu Gly Asn Ser Ile Trp Asp
        35                  40                  45

Lys Thr Ser Asp Gly Cys Tyr Val Ala Asp Lys Tyr Val Lys Thr Gly
    50                  55                  60

Lys Asp Gly Tyr Val Lys Gly Lys Cys
65                  70

<210> SEQ ID NO 209
<211> LENGTH: 73
<212> TYPE: PRT
<213> ORGANISM: Fusarium oxysporum

<400> SEQUENCE: 209

Tyr Pro Val Thr Ser Asp Asn Leu Asn Cys Arg Ser Gly Pro Gly Thr
1               5                   10                  15

Ala Phe Ala Ile Lys Lys Ser Tyr Lys Lys Gly Gln Asp Val Thr Ile
            20                  25                  30

Thr Cys Gln Thr Gln Gly Asp Lys Val Glu Gly Asn Ser Ile Trp Asp
        35                  40                  45

Lys Thr Ser Asp Gly Cys Tyr Val Ala Asp Lys Tyr Val Lys Thr Gly
    50                  55                  60

Lys Asp Gly Tyr Val Lys Gly Lys Cys
65                  70

<210> SEQ ID NO 210
<211> LENGTH: 69
<212> TYPE: PRT
<213> ORGANISM: Fusarium oxysporum

```
<400> SEQUENCE: 210

Asp Glu Gly Val Arg Cys Arg Ser Gly Pro Thr Thr Ser Asn Ala Ile
1               5                   10                  15

Gln Arg Gln Phe Ala Lys Gly Thr Asp Val Ala Ile Thr Cys Gln Thr
            20                  25                  30

Glu Gly Thr His Ile Lys Gly Asn Val Pro Trp Asp Lys Thr Thr Phe
        35                  40                  45

Gly Cys Tyr Val Ser Asp Tyr Tyr Val Ala Thr Gly Ser Ser Gly Tyr
    50                  55                  60

Val Thr Ser Lys Cys
65

<210> SEQ ID NO 211
<211> LENGTH: 69
<212> TYPE: PRT
<213> ORGANISM: Gibberella moniliformis

<400> SEQUENCE: 211

Asp Glu Gly Val Arg Cys Arg Ser Gly Pro Thr Thr Ser His Ala Ile
1               5                   10                  15

Gln Arg Gln Phe Thr Lys Gly Thr Asp Gly Thr Ile Thr Tyr Gln Thr
            20                  25                  30

Glu Gly Thr Asn Ile Glu Gly Asn Thr Leu Trp Asp Lys Thr Thr Phe
        35                  40                  45

Gly Cys Phe Val Ser Asp Tyr Tyr Val Ala Thr Gly Ser Ser Gly Tyr
    50                  55                  60

Val Thr Ser Lys Cys
65

<210> SEQ ID NO 212
<211> LENGTH: 73
<212> TYPE: PRT
<213> ORGANISM: Fusarium oxysporum

<400> SEQUENCE: 212

Tyr Pro Val Thr Ser Asp Asn Leu Asn Cys Arg Ser Gly Pro Gly Thr
1               5                   10                  15

Ala Phe Ala Ile Lys Lys Ser Tyr Lys Lys Gly Gln Asp Val Thr Ile
            20                  25                  30

Thr Cys Gln Thr Gln Gly Asp Asn Val Glu Gly Asn Ser Ile Trp Asp
        35                  40                  45

Lys Thr Ser Asp Gly Cys Tyr Val Ala Asp Lys Tyr Val Lys Thr Gly
    50                  55                  60

Lys Asp Gly Tyr Val Lys Asp Lys Cys
65                  70

<210> SEQ ID NO 213
<211> LENGTH: 69
<212> TYPE: PRT
<213> ORGANISM: Fusarium oxysporum

<400> SEQUENCE: 213

Asp Glu Gly Val Arg Cys Arg Ser Gly Pro Thr Thr Ser His Ala Ile
1               5                   10                  15

Gln Arg Gln Phe Thr Lys Gly Thr Asp Val Thr Ile Thr Cys Gln Ile
            20                  25                  30

Glu Gly Thr Asn Ile Glu Gly Asn Ala Leu Trp Asp Lys Thr Thr Phe
        35                  40                  45
```

```
Gly Cys Tyr Val Ser Asp Tyr Tyr Val Ala Thr Gly Ser Ser Gly Tyr
        50                  55                  60

Val Thr Ser Lys Cys
 65

<210> SEQ ID NO 214
<211> LENGTH: 73
<212> TYPE: PRT
<213> ORGANISM: Fusarium oxysporum

<400> SEQUENCE: 214

Tyr Pro Val Thr Ser Asp Asn Leu Asn Cys Arg Ser Gly Pro Gly Thr
 1               5                  10                  15

Ala Phe Ala Ile Lys Lys Ser Tyr Lys Lys Gly Gln Asp Val Thr Ile
                20                  25                  30

Thr Cys Gln Thr Gln Gly Asp Asn Val Glu Gly Asn Ser Ile Trp Asp
            35                  40                  45

Lys Thr Ser Asp Gly Cys Tyr Val Ala Asp Lys Tyr Val Lys Thr Gly
        50                  55                  60

Lys Asp Gly Tyr Val Lys Gly Lys Cys
 65                  70

<210> SEQ ID NO 215
<211> LENGTH: 69
<212> TYPE: PRT
<213> ORGANISM: Fusarium oxysporum

<400> SEQUENCE: 215

Asp Glu Gly Val Arg Cys Arg Ser Gly Pro Thr Thr Ser His Ala Ile
 1               5                  10                  15

Gln Arg Gln Phe Thr Lys Gly Thr Asp Val Thr Ile Thr Cys Gln Ile
                20                  25                  30

Glu Gly Thr Asn Ile Glu Gly Asn Ala Leu Trp Asp Lys Thr Thr Phe
            35                  40                  45

Gly Cys Tyr Val Ser Asp Tyr Tyr Val Ala Thr Gly Ser Ser Gly Tyr
        50                  55                  60

Val Thr Ser Lys Cys
 65

<210> SEQ ID NO 216
<211> LENGTH: 73
<212> TYPE: PRT
<213> ORGANISM: Penicillium oxalicum

<400> SEQUENCE: 216

Tyr Pro Val Lys Thr Asp Gly Leu His Cys Arg Ser Gly Pro Gly Thr
 1               5                  10                  15

Ser Tyr Ser Ile Val Lys Thr Tyr Asn Thr Gly Thr Asp Leu Thr Ile
                20                  25                  30

Thr Cys Gln Thr Pro Gly Pro Val Ile Asn Gly Asp Glu Leu Trp Asp
            35                  40                  45

Lys Thr Ser Asp Gly Cys Tyr Val Ser Asp Tyr Tyr Val Lys Thr Gly
        50                  55                  60

Thr Ser Gly Tyr Val Ala Pro His Cys
 65                  70
```

<210> SEQ ID NO 217
<211> LENGTH: 73
<212> TYPE: PRT
<213> ORGANISM: Penicillium oxalicum

<400> SEQUENCE: 217

Tyr Pro Val Lys Thr Asp Asp Leu His Cys Arg Ser Gly Pro Gly Thr
1               5                   10                  15

Asn Tyr Ala Val Val Lys Ser Tyr Lys Ile Gly Thr Asp Leu Thr Ile
            20                  25                  30

Thr Cys Gln Ala Pro Gly Thr Val Val Ser Gly Asp Glu Leu Trp Asp
        35                  40                  45

Lys Thr Ser Asp Gly Cys Tyr Val Ser Asp Tyr Tyr Val Lys Thr Gly
    50                  55                  60

Thr Ser Gly Tyr Val Thr Lys Gln Cys
65                  70

<210> SEQ ID NO 218
<211> LENGTH: 69
<212> TYPE: PRT
<213> ORGANISM: Fusarium oxysporum

<400> SEQUENCE: 218

Asp Glu Gly Val Arg Cys Arg Ser Gly Pro Thr Thr Ser Asn Ala Ile
1               5                   10                  15

Gln Arg Gln Phe Ala Lys Gly Thr Asp Val Ala Ile Thr Cys Gln Thr
            20                  25                  30

Glu Gly Thr His Ile Lys Gly Asn Val Pro Trp Asp Lys Thr Thr Phe
        35                  40                  45

Gly Cys Tyr Ile Ser Asp Tyr Tyr Val Ala Lys Gly Ser Ser Gly Tyr
    50                  55                  60

Val Thr Ser Lys Cys
65

<210> SEQ ID NO 219
<211> LENGTH: 69
<212> TYPE: PRT
<213> ORGANISM: Fusarium oxysporum

<400> SEQUENCE: 219

Asp Glu Gly Val Arg Cys Arg Ser Gly Pro Thr Thr Ser His Ala Ile
1               5                   10                  15

Gln Arg Gln Phe Thr Lys Gly Thr Asp Val Thr Ile Thr Cys Gln Ile
            20                  25                  30

Glu Gly Thr Asn Ile Glu Gly Asn Ala Leu Trp Asp Lys Thr Thr Phe
        35                  40                  45

Gly Cys Tyr Leu Ser Asp Tyr Tyr Val Ala Thr Gly Ser Ser Gly Tyr
    50                  55                  60

Val Thr Ser Lys Cys
65

<210> SEQ ID NO 220
<211> LENGTH: 73
<212> TYPE: PRT
<213> ORGANISM: Fusarium oxysporum

```
<400> SEQUENCE: 220

Tyr Pro Val Thr Ser Asp Asn Leu Asn Cys Arg Ser Gly Pro Gly Thr
1               5                   10                  15

Gly Phe Ala Ile Lys Lys Ser Tyr Lys Lys Gly Gln Asp Ile Thr Ile
            20                  25                  30

Thr Cys Gln Thr Gln Gly Asp Asn Val Glu Gly Asn Ser Ile Trp Asp
        35                  40                  45

Lys Thr Ser Asn Gly Cys Tyr Val Ala Asp Lys Tyr Val Lys Thr Gly
    50                  55                  60

Lys Asp Gly Tyr Val Lys Gly Lys Cys
65                  70

<210> SEQ ID NO 221
<211> LENGTH: 69
<212> TYPE: PRT
<213> ORGANISM: Gibberella fujikuroi

<400> SEQUENCE: 221

Asp Glu Gly Val Arg Cys Arg Ser Gly Pro Thr Thr Ser His Ala Ile
1               5                   10                  15

Gln Thr His Phe Val Lys Gly Thr Asp Val Thr Ile Thr Cys Gln Thr
            20                  25                  30

Glu Gly Thr Tyr Ile Gly Gly Ser Thr Leu Trp Asp Lys Thr Thr Phe
        35                  40                  45

Gly Cys Tyr Val Ser Asp Tyr Tyr Val Ala Thr Gly Ser Ser Gly Tyr
    50                  55                  60

Val Thr Ser Lys Cys
65

<210> SEQ ID NO 222
<211> LENGTH: 59
<212> TYPE: PRT
<213> ORGANISM: Penicillium roqueforti

<400> SEQUENCE: 222

Tyr Pro Val Thr Gly Ser Val Ile Asp Cys His Ser Gly Pro Gly Ala
1               5                   10                  15

Ser His Ser Val Val Lys Thr Tyr Glu Glu Arg Ala Asp Ile Glu Ile
            20                  25                  30

Val Cys Gln Ala Thr Gly Thr Thr Val Asp Gly Ser Asp Ile Trp His
        35                  40                  45

Gln Thr Val Asp Asp Cys Tyr Val Ser Asp Phe
    50                  55

<210> SEQ ID NO 223
<211> LENGTH: 74
<212> TYPE: PRT
<213> ORGANISM: Pyronema omphalodes

<400> SEQUENCE: 223

Tyr Pro Leu Val His Thr Asp Thr Leu Asn Cys Arg Ser Ser Pro Ser
1               5                   10                  15

Thr Ser Ser Ser Ile Thr Lys Thr Tyr Lys Lys Ser Asp Asp Ile Lys
            20                  25                  30

Ile Thr Cys Gln Thr Tyr Gly Asp Thr Ile Lys Gly Asn Asn Ile Trp
        35                  40                  45
```

```
Asp Lys Thr Pro Asp Gly Cys Tyr Val Ser Asp Tyr Tyr Val Lys Thr
 50                  55                  60

Gly Lys Ser Gly Phe Val Val Gly Lys Cys
 65                  70

<210> SEQ ID NO 224
<211> LENGTH: 72
<212> TYPE: PRT
<213> ORGANISM: Pyronema omphalodes

<400> SEQUENCE: 224

Tyr Pro Ala Lys Glu Thr Leu Arg Cys Arg Thr Ser Pro Ser Thr Ser
 1               5                  10                  15

Ala Ser Ile His Lys Thr Tyr Pro Ala Gly Ala Asp Ile Lys Ile Thr
                 20                  25                  30

Cys Gln Thr Thr Gly Thr Lys Val Leu Thr Ser Asn Val Trp Asp Lys
             35                  40                  45

Thr Ser Asp Gly Cys Tyr Val Ser Asp Tyr Tyr Val Ser Thr Gly His
         50                  55                  60

Ser Gly Ile Phe Leu Ser Lys Cys
 65                  70

<210> SEQ ID NO 225
<211> LENGTH: 73
<212> TYPE: PRT
<213> ORGANISM: Pseudogymnoascus pannorum

<400> SEQUENCE: 225

Phe Pro Ile Thr Gly Asn Thr Val Asn Cys Arg Ser Gly Pro Gly Thr
 1               5                  10                  15

Asp Phe Ser Ile Lys Gln Thr Tyr Ala Lys Gly Glu Ala Val Ala Ile
                 20                  25                  30

Thr Cys Gln Thr Ser Gly Thr Lys Ile Asn Gly Asn Asp Ile Trp Asp
             35                  40                  45

Leu Thr Thr Asp Gly Cys Tyr Val Thr Asp Phe Tyr Val Lys Thr Gly
         50                  55                  60

Ser Ile Ser Tyr Val Leu Pro Lys Cys
 65                  70

<210> SEQ ID NO 226
<211> LENGTH: 68
<212> TYPE: PRT
<213> ORGANISM: Fusarium oxysporum

<400> SEQUENCE: 226

Asp Lys Gly Val Arg Cys Arg Ser Gly Pro Thr Thr Ser His Ala Ile
 1               5                  10                  15

Gln Arg Gln Phe Thr Lys Gly Thr Asp Val Thr Ile Thr Cys Gln Ile
                 20                  25                  30

Glu Gly Thr Asn Ile Glu Gly Asn Ala Leu Trp Asp Lys Thr Thr Phe
             35                  40                  45

Gly Cys Tyr Val Ser Asp Tyr Tyr Val Ala Thr Gly Ser Ser Gly Tyr
         50                  55                  60

Val Thr Leu Lys
 65
```

-continued

<210> SEQ ID NO 227
<211> LENGTH: 68
<212> TYPE: PRT
<213> ORGANISM: Fusarium oxysporum

<400> SEQUENCE: 227

Asp Lys Gly Val Arg Cys Arg Ser Gly Pro Thr Thr Ser His Ala Ile
1               5                   10                  15

Gln Arg Gln Phe Thr Lys Gly Thr Asp Val Thr Ile Thr Cys Gln Ile
                20                  25                  30

Glu Gly Thr Asn Ile Glu Gly Asn Ala Leu Trp Asp Lys Thr Thr Phe
            35                  40                  45

Gly Cys Tyr Val Ser Asp Tyr Tyr Val Ala Thr Gly Ser Ser Gly Tyr
        50                  55                  60

Val Thr Leu Lys
65

<210> SEQ ID NO 228
<211> LENGTH: 73
<212> TYPE: PRT
<213> ORGANISM: Acremonium chrysogenum

<400> SEQUENCE: 228

Tyr Pro Ile Thr Gly Asn Glu Val Asn Cys Arg Ser Gly Pro Ser Thr
1               5                   10                  15

Ser Ser Asp Ile Val Thr Ser Tyr Lys Lys Gly Asp Glu Val Gln Val
                20                  25                  30

Thr Cys Gln Ile Asp Gly Glu Asp Ile Phe Gly Asn Thr Ile Trp Asp
            35                  40                  45

Gln Thr Glu Asp Gly Cys Tyr Val Ala Asp Phe Tyr Val Lys Thr Gly
        50                  55                  60

Ser Asn Ala Phe Val Thr Glu Ala Cys
65                  70

<210> SEQ ID NO 229
<211> LENGTH: 73
<212> TYPE: PRT
<213> ORGANISM: Acremonium chrysogenum

<400> SEQUENCE: 229

Tyr Pro Ile Thr Ala Asp Asp Val Lys Cys Arg Ala Gly Pro Ser Thr
1               5                   10                  15

Ser His Asp Ile Val Thr Ala Phe Ala Glu Gly His Glu Val Glu Leu
                20                  25                  30

Glu Cys Gln Ile Val Gly Glu Asn Ile Phe Gly Asn Ser Ile Trp Asp
            35                  40                  45

Lys Thr Thr Asp Gly Cys Tyr Val Ser Asp Tyr Tyr Val Arg Thr Gly
        50                  55                  60

Ser Asp Gly Met Val Val Asp Asn Cys
65                  70

<210> SEQ ID NO 230
<211> LENGTH: 73
<212> TYPE: PRT
<213> ORGANISM: Acremonium chrysogenum

```
<400> SEQUENCE: 230

Tyr Pro Val Thr Ala Asp Ser Leu Asn Cys Arg Glu Gly Ala Gly Thr
1               5                   10                  15

Asp Thr Ala Val Val Thr Thr Tyr Thr Ala Gly Thr Asp Val Glu Val
            20                  25                  30

Val Cys Gln Ala Glu Gly Glu Val Ile Glu Gly Ser Ser Ile Trp Asp
        35                  40                  45

Gln Thr Gln Asp Gly Cys Tyr Val Ser Asp Val Tyr Val Asp Thr Gly
    50                  55                  60

Ser Asp Gly Tyr Val Ala Asp Lys Cys
65                  70

<210> SEQ ID NO 231
<211> LENGTH: 73
<212> TYPE: PRT
<213> ORGANISM: Metarhizium anisopliae

<400> SEQUENCE: 231

Tyr Ala Ile Glu Ala Asp Gly Val Asn Cys Arg Ser Gly Pro Ser Thr
1               5                   10                  15

Ser Asp Lys Val Val Arg Thr Tyr Asn Lys Gly Asn Asp Val Lys Leu
            20                  25                  30

Glu Cys Gln Thr Ala Gly Gln Ala Ile His Gly Asp Ser Leu Trp Asp
        35                  40                  45

Lys Thr Thr Asp Gly Cys Tyr Val Ala Asp Tyr Tyr Val Lys Thr Gly
    50                  55                  60

Thr Thr Asn Met Val Thr Gly Gln Cys
65                  70

<210> SEQ ID NO 232
<211> LENGTH: 73
<212> TYPE: PRT
<213> ORGANISM: Metarhizium anisopliae

<400> SEQUENCE: 232

Phe Pro Val Thr Ala Asp Ser Leu Asn Cys Arg Ala Glu Pro Asn Thr
1               5                   10                  15

Ser Ser Ala Val Lys Lys Thr Tyr Lys Lys Thr Asp Asp Val Lys Ile
            20                  25                  30

Ser Cys Gln Thr Glu Gly Pro Ser Ile Asn Gly Asn Ser Ile Trp Asp
        35                  40                  45

Lys Thr Gln Asp Gly Cys Tyr Val Ala Asp Tyr Tyr Ile Lys Thr Gly
    50                  55                  60

Ser Ser Gly Tyr Val Thr Gly Lys Cys
65                  70

<210> SEQ ID NO 233
<211> LENGTH: 73
<212> TYPE: PRT
<213> ORGANISM: Pseudogymnoascus pannorum

<400> SEQUENCE: 233

Tyr Pro Ile Thr Gly Thr Tyr Val Asn Cys Arg Thr Gly Pro Ser Thr
1               5                   10                  15

Ser Phe Asp Ile Val Arg Ser Tyr Glu Leu Gly Asp Glu Val Asp Leu
            20                  25                  30

Thr Cys Gln Ile Ala Gly Glu Thr Val Thr Gly Asp Asn Leu Trp Asp
        35                  40                  45
```

```
Phe Thr Thr Asp Gly Cys Tyr Val Ala Asp Tyr Phe Val Lys Thr Gly
    50                  55                  60

Thr Phe Gly Met Val Val Asp Glu Cys
65                  70

<210> SEQ ID NO 234
<211> LENGTH: 73
<212> TYPE: PRT
<213> ORGANISM: Pseudogymnoascus pannorum

<400> SEQUENCE: 234

Tyr Pro Ile Thr Gly Thr Tyr Val Asn Cys Arg Ser Gly Pro Ser Thr
1               5                   10                  15

Ser Phe Asp Ile Val Arg Ser Tyr Glu Leu Gly Asp Glu Val Ser Leu
                20                  25                  30

Thr Cys Gln Ile Ala Gly Glu Thr Val Glu Gly Asp Tyr Leu Trp Asp
            35                  40                  45

Leu Thr Thr Asp Gly Cys Tyr Val Ala Asp Tyr Phe Val Lys Thr Gly
        50                  55                  60

Thr Val Gly Met Val Ala Glu Glu Cys
65                  70

<210> SEQ ID NO 235
<211> LENGTH: 74
<212> TYPE: PRT
<213> ORGANISM: Pseudogymnoascus pannorum

<400> SEQUENCE: 235

Tyr Pro Ile Ser Gly Asp Ser Val Asn Cys Arg Ser Gly Pro Ala Thr
1               5                   10                  15

Ser Tyr Lys Val Ile Lys Thr Tyr Ala Lys Gly His Asp Val Lys Val
                20                  25                  30

Thr Cys Gln Thr Val Gly Glu Thr Val Lys Gly Asp Asn Leu Trp Asp
            35                  40                  45

Lys Thr Ala Asp Gly Cys Tyr Val Ala Asp Tyr Tyr Val Lys Thr Gly
        50                  55                  60

Thr Thr Gly Arg Val Val Lys Thr Glu Cys
65                  70

<210> SEQ ID NO 236
<211> LENGTH: 73
<212> TYPE: PRT
<213> ORGANISM: Pseudogymnoascus pannorum

<400> SEQUENCE: 236

Val Thr Ser Pro Thr Thr Val Lys Cys Arg Ser Gly Pro Gly Thr Gln
1               5                   10                  15

Tyr Lys Ile Val Lys Thr Tyr Pro Ala Ser Gly Arg Glu Cys Tyr Ser
                20                  25                  30

Cys Tyr Glu Ser Gly Thr Cys Ile Asn Gly Asn Cys Ser Trp Asp Tyr
            35                  40                  45

Asn Tyr Met Asp Asn Cys Tyr Ile Ser Gly Tyr Tyr Thr Gly Ser Ala
        50                  55                  60

Cys Thr Thr Ala Ala Leu Gly Lys Cys
65                  70
```

```
<210> SEQ ID NO 237
<211> LENGTH: 74
<212> TYPE: PRT
<213> ORGANISM: Pseudogymnoascus pannorum

<400> SEQUENCE: 237
```

Tyr Pro Ile Ser Gly Thr Ser Val Asn Cys Arg Ser Gly Pro Ala Thr
1               5                   10                  15

Ser Tyr Lys Val Ile Lys Thr Tyr Lys Lys Gly Gln Asp Val Lys Ile
            20                  25                  30

Thr Cys Gln Thr Val Gly Glu Thr Val Ser Gly Asp Asn Leu Trp Asp
        35                  40                  45

Lys Thr Ser Asp Gly Cys Tyr Val Ala Asp Tyr Tyr Val Lys Thr Gly
    50                  55                  60

Thr Thr Gly Arg Val Val Lys Thr Glu Cys
65                  70

```
<210> SEQ ID NO 238
<211> LENGTH: 73
<212> TYPE: PRT
<213> ORGANISM: Pseudogymnoascus pannorum

<400> SEQUENCE: 238
```

Tyr Pro Ile Lys Gly Ser Val Val Asn Cys Arg Ala Gly Pro Gly Thr
1               5                   10                  15

Asn Phe Pro Ile Val Lys Thr Phe Lys Lys Gly Asp Thr Val Asp Ile
            20                  25                  30

Thr Cys Gln Thr Pro Gly Thr Ser Ile Ser Gly Asn Ser Ile Trp Asp
        35                  40                  45

Leu Ile Pro Asp Asn Cys Phe Ile Thr Asp Tyr Tyr Val Lys Thr Gly
    50                  55                  60

Thr Gly Lys Tyr Ile Lys Pro Arg Cys
65                  70

```
Cys Tyr Glu Ser Gly Thr Cys Ile Asn Gly Asn Cys Ser Trp Asp Tyr
            35                  40                  45

Asn Tyr Met Asp Asn Cys Tyr Ile Ser Gly Tyr Tyr Thr Gly Ser Ala
 50                  55                  60

Cys Thr Thr Ala Ala Leu Gly Lys Cys
 65                  70
```

<210> SEQ ID NO 241
<211> LENGTH: 73
<212> TYPE: PRT
<213> ORGANISM: Pseudogymnoascus pannorum

<400> SEQUENCE: 241

```
Tyr Pro Ile Thr Gly Asn Thr Val Asn Cys Arg Ser Gly Pro Gly Thr
 1               5                  10                  15

Asp Phe Pro Ile Lys Lys Thr Phe Ala Lys Gly Ser Ile Val Ser Ile
            20                  25                  30

Thr Cys Gln Thr Pro Gly Thr Lys Ile Asn Gly Asn Glu Ile Trp Asp
            35                  40                  45

Leu Thr Ser Asp Gly Cys Phe Val Ser Asp Phe Tyr Val Lys Thr Gly
 50                  55                  60

Ser Ile Thr Tyr Val Lys Pro Lys Cys
 65                  70
```

<210> SEQ ID NO 242
<211> LENGTH: 73
<212> TYPE: PRT
<213> ORGANISM: Pseudogymnoascus pannorum

<400> SEQUENCE: 242

```
Tyr Pro Ile Thr Gly Thr Ser Val Asn Cys Arg Ser Gly Pro Ser Thr
 1               5                  10                  15

Lys Phe Asp Val Val Arg Ser Tyr Val Leu Gly Asp Glu Val Thr Leu
            20                  25                  30

Thr Cys Gln Ile Ala Gly Glu Thr Val Thr Gly Asp Tyr Leu Trp Asp
            35                  40                  45

Leu Thr Thr Asp Gly Cys Tyr Val Ala Asp Tyr Phe Val Lys Thr Gly
 50                  55                  60

Thr Val Gly Met Val Thr Glu Ala Cys
 65                  70
```

<210> SEQ ID NO 243
<211> LENGTH: 73
<212> TYPE: PRT
<213> ORGANISM: Pseudogymnoascus pannorum

<400> SEQUENCE: 243

```
Tyr Pro Ile Thr Gly Thr Tyr Val Asn Cys Arg Ser Gly Pro Ser Thr
 1               5                  10                  15

Ser Tyr Asp Ile Ile Arg Ser Tyr Glu Leu Gly Asp Glu Val Asp Leu
            20                  25                  30

Thr Cys Gln Ile Ala Gly Glu Thr Val Thr Gly Asp Asn Leu Trp Asp
            35                  40                  45

Phe Thr Thr Asp Gly Cys Tyr Val Ala Asp Tyr Phe Val Lys Thr Gly
 50                  55                  60

Thr Phe Gly Met Val Val Asp Glu Cys
 65                  70
```

<210> SEQ ID NO 244
<211> LENGTH: 74
<212> TYPE: PRT
<213> ORGANISM: Pseudogymnoascus pannorum

<400> SEQUENCE: 244

Tyr Pro Ile Ser Gly Asp Ser Val Asn Cys Arg Ser Gly Pro Ala Thr
1               5                   10                  15

Ser Tyr Lys Val Ile Lys Thr Tyr Ala Lys Gly His Asp Val Lys Val
            20                  25                  30

Thr Cys Gln Thr Val Gly Glu Thr Val Lys Gly Asp Asn Leu Trp Asp
        35                  40                  45

Lys Thr Ala Asp Gly Cys Tyr Val Ala Asp Tyr Tyr Val Lys Thr Gly
    50                  55                  60

Thr Thr Gly Arg Val Val Lys Thr Glu Cys
65                  70

<210> SEQ ID NO 245
<211> LENGTH: 73
<212> TYPE: PRT
<213> ORGANISM: Pseudogymnoascus pannorum

<400> SEQUENCE: 245

Tyr Pro Ile Thr Gly Thr Tyr Val Asn Cys Arg Thr Gly Pro Ser Thr
1               5                   10                  15

Ser Phe Asp Ile Val Arg Ser Tyr Glu Leu Gly Asp Glu Val Asp Leu
            20                  25                  30

Thr Cys Gln Ile Ala Gly Glu Thr Val Thr Gly Asp Asn Leu Trp Asp
        35                  40                  45

Phe Thr Thr Asp Gly Cys Tyr Val Ala Asp Tyr Phe Val Lys Thr Gly
    50                  55                  60

Thr Phe Gly Met Val Val Asp Glu Cys
65                  70

<210> SEQ ID NO 246
<211> LENGTH: 73
<212> TYPE: PRT
<213> ORGANISM: Pseudogymnoascus pannorum

<400> SEQUENCE: 246

Tyr Pro Ile Thr Gly Thr Tyr Val Asn Cys Arg Ser Gly Pro Ser Thr
1               5                   10                  15

Ser Phe Asp Ile Val Arg Ser Tyr Glu Leu Gly Asp Glu Val Ser Leu
            20                  25                  30

Thr Cys Gln Ile Ala Gly Glu Thr Val Glu Gly Asp Tyr Leu Trp Asp
        35                  40                  45

Leu Thr Thr Asp Gly Cys Tyr Val Ala Asp Tyr Phe Val Lys Thr Gly
    50                  55                  60

Thr Val Gly Met Val Ala Glu Glu Cys
65 70

<210> SEQ ID NO 247
<211> LENGTH: 72
<212> TYPE: PRT
<213> ORGANISM: Pseudogymnoascus pannorum

<400> SEQUENCE: 247

Tyr Pro Ile Ser Gly Asp Ser Val Asn Cys Arg Ser Gly Pro Ala Thr
1               5                   10                  15

Ser Tyr Lys Val Ile Lys Thr Tyr Leu Lys Gly His Asp Val Asp Leu
            20                  25                  30

Thr Cys Gln Thr Val Gly Glu Thr Val Lys Gly Asp Ser Leu Trp Asp
        35                  40                  45

Lys Thr Thr Asp Gly Cys Tyr Val Ala Asp Tyr Tyr Val Lys Thr Gly
    50                  55                  60

Thr Thr Gly Arg Val Val Lys Lys
65                  70

<210> SEQ ID NO 248
<211> LENGTH: 73
<212> TYPE: PRT
<213> ORGANISM: Pseudogymnoascus pannorum

<400> SEQUENCE: 248

Tyr Pro Ile Lys Gly Ser Val Val Asn Cys Arg Ser Gly Pro Gly Thr
1               5                   10                  15

Asn Phe Ala Ile Val Lys Thr Phe Lys Lys Gly Asp Thr Val Asp Ile
            20                  25                  30

Thr Cys Gln Thr Pro Gly Thr Ser Ile Ser Gly Asn Ser Ile Trp Asp
        35                  40                  45

Leu Thr Pro Asp Asn Cys Phe Ile Thr Asp Tyr Tyr Val Lys Thr Gly
    50                  55                  60

Thr Gly Lys Tyr Ile Lys Pro Arg Cys
65                  70

<210> SEQ ID NO 249
<211> LENGTH: 67
<212> TYPE: PRT
<213> ORGANISM: Pseudogymnoascus pannorum

<400> SEQUENCE: 249

Cys Arg Ser Gly Pro Gly Thr Gly Tyr Ser Val Ile Ala Thr Val Lys
1               5                   10                  15

Lys Gly Ser Tyr Tyr Ser Phe Gly Cys Tyr Lys Thr Gly Thr Cys Val
            20                  25                  30

Ser Gly Asn Cys Thr Trp Asp Arg Ile Phe Trp Asp Gly Lys Ser Cys
        35                  40                  45

Tyr Val Ser Gly Tyr Tyr Thr Asp Ser Ala Cys Ser Ala Ser Ala Leu
    50                  55                  60

Gly Lys Cys
65

<210> SEQ ID NO 250
<211> LENGTH: 73
<212> TYPE: PRT
<213> ORGANISM: Pseudogymnoascus pannorum

<400> SEQUENCE: 250

Tyr Pro Ile Thr Gly Thr Phe Val Asn Cys Arg Ser Gly Pro Ser Thr
1               5                   10                  15

Lys Phe Asp Val Val Arg Ser Tyr Val Leu Gly Asp Glu Val Thr Leu
            20                  25                  30

Thr Cys Gln Ile Ala Gly Glu Thr Val Thr Gly Asp Tyr Leu Trp Asp
        35                  40                  45

```
Leu Thr Thr Asp Gly Cys Tyr Val Ala Asp Tyr Phe Val Lys Thr Gly
    50                  55                  60

Thr Val Gly Met Val Thr Glu Ala Cys
65                  70

<210> SEQ ID NO 251
<211> LENGTH: 67
<212> TYPE: PRT
<213> ORGANISM: Pseudogymnoascus pannorum

<400> SEQUENCE: 251

Cys Arg Ser Gly Pro Gly Thr Gly Tyr Ser Val Ile Ala Thr Val Lys
1               5                   10                  15

Lys Gly Ser Tyr Tyr Ser Phe Gly Cys Tyr Lys Thr Gly Thr Cys Val
            20                  25                  30

Ser Gly Asn Cys Thr Trp Asp Arg Ile Phe Trp Asp Gly Lys Ser Cys
        35                  40                  45

Tyr Val Ser Gly Tyr Tyr Thr Asp Ser Ala Cys Ser Ala Ser Ala Leu
    50                  55                  60

Gly Lys Cys
65

<210> SEQ ID NO 252
<211> LENGTH: 73
<212> TYPE: PRT
<213> ORGANISM: Pseudogymnoascus pannorum

<400> SEQUENCE: 252

Tyr Pro Ile Thr Gly Thr Lys Val Asn Cys Arg Thr Gly Pro Ser Thr
1               5                   10                  15

Ser Phe Glu Ile Ile Arg Ser Tyr Lys Leu Gly Asp Glu Val Ser Leu
            20                  25                  30

Thr Cys Gln Ile Ala Gly Glu Thr Val Gln Gly Asn Tyr Leu Trp Asp
        35                  40                  45

Leu Thr Thr Asp Gly Cys Tyr Val Ala Asp Tyr Phe Val Lys Thr Gly
    50                  55                  60

Ser Asp Gly Met Val Thr Glu Gly Cys
65                  70

<210> SEQ ID NO 253
<211> LENGTH: 73
<212> TYPE: PRT
<213> ORGANISM: Aspergillus clavatus

<400> SEQUENCE: 253

Tyr Pro Ile Thr Gly Asp Gly Val Asn Cys Arg Ser Gly Pro Gly Thr
1               5                   10                  15

Ser Tyr Lys Val Val Lys Ser Tyr Pro Lys Gly His Gln Val Ser Ile
            20                  25                  30

Val Cys Gln Ala Thr Gly Thr Asp Val Lys Gly Asp Ser Leu Trp Asp
        35                  40                  45

Lys Thr Ser Asp Gly Cys Tyr Val Ala Asp Tyr Tyr Val Lys Thr Gly
    50                  55                  60

Thr Thr Gly Tyr Val Thr Lys His Cys
65                  70
```

<210> SEQ ID NO 254
<211> LENGTH: 73
<212> TYPE: PRT
<213> ORGANISM: Aspergillus clavatus

<400> SEQUENCE: 254

Tyr Pro Ile Thr Gly Asp Thr Val Asn Cys Arg Ser Gly Pro Gly Thr
1               5                   10                  15

Ser His Ala Val Val Lys Ser Tyr Lys Lys Gly Glu Asp Val Lys Ile
            20                  25                  30

Val Cys Gln Ala Pro Gly Thr Asp Val Lys Gly Glu Ser Ile Trp Asp
        35                  40                  45

Lys Thr Ser Asp Gly Cys Tyr Val Ala Asp Tyr Tyr Val Lys Thr Gly
    50                  55                  60

Thr Thr Gly Tyr Val Thr Lys Lys Cys
65                  70

<210> SEQ ID NO 255
<211> LENGTH: 73
<212> TYPE: PRT
<213> ORGANISM: Neosartorya fischeri

<400> SEQUENCE: 255

Tyr Pro Ile Thr Gly Asn Glu Val Asn Cys Arg Ala Gly Pro Ser Thr
1               5                   10                  15

Asn Asp Lys Val Val Lys Ser Tyr His Lys Gly Asp Asp Val Lys Leu
            20                  25                  30

Ser Cys Gln Thr Tyr Gly Glu Asn Val Gln Gly Asn Ser Ile Trp Asp
        35                  40                  45

Lys Thr Thr Asp Gly Cys Tyr Val Ser Asp Phe Tyr Val Lys Thr Gly
    50                  55                  60

Ser Asn Ser Met Val Thr Lys Glu Cys
65                  70

<210> SEQ ID NO 256
<211> LENGTH: 73
<212> TYPE: PRT
<213> ORGANISM: Neosartorya fischeri

<400> SEQUENCE: 256

Tyr Pro Ile Thr Gly Asp Gly Val Asn Cys Arg Ser Gly Pro Gly Thr
1               5                   10                  15

Asn His Pro Val Val Lys Ser Tyr Pro Lys Gly His Asp Val Ser Ile
            20                  25                  30

Val Cys Gln Ala Pro Gly Thr Asp Val Lys Gly Asp Lys Leu Trp Asp
        35                  40                  45

Lys Thr Ser Asp Gly Cys Tyr Val Ala Asp Tyr Tyr Val Lys Thr Gly
    50                  55                  60

Ser Thr Asp Tyr Val Thr Lys His Cys
65                  70

<210> SEQ ID NO 257
<211> LENGTH: 73
<212> TYPE: PRT
<213> ORGANISM: Neosartorya fischeri

<400> SEQUENCE: 257

Tyr Pro Ile Thr Gly Asp Gly Val Asn Cys Arg Ser Gly Pro Gly Thr
1               5                   10                  15

Asn His Pro Val Val Lys Ser Tyr Pro Lys Gly His Asp Val Ser Ile
            20                  25                  30

Val Cys Gln Ala Pro Gly Thr Asp Val Lys Gly Asp Lys Leu Trp Asp
        35                  40                  45

Lys Thr Ser Asp Gly Cys Tyr Val Ala Asp Tyr Tyr Val Lys Thr Gly
    50                  55                  60

Ser Ser Asp Tyr Val Thr Lys His Cys
65                  70

<210> SEQ ID NO 258
<211> LENGTH: 73
<212> TYPE: PRT
<213> ORGANISM: Aspergillus terreus

<400> SEQUENCE: 258

Tyr Pro Ile Thr Gly Asp Gly Val Asn Cys Arg Ser Gly Pro Gly Thr
1               5                   10                  15

Ser His Ala Val Val Lys Ser Tyr Pro Lys Gly His Glu Ile Ser Ile
            20                  25                  30

Val Cys Gln Ala Ala Gly Thr Asp Val Lys Gly Asp Asn Leu Trp Asp
        35                  40                  45

Lys Thr Ser Asp Gly Cys Tyr Val Ala Asp Tyr Tyr Val Lys Thr Gly
    50                  55                  60

Ser Thr Gly Tyr Val Thr Lys His Cys
65                  70

<210> SEQ ID NO 259
<211> LENGTH: 64
<212> TYPE: PRT
<213> ORGANISM: Aspergillus terreus

<400> SEQUENCE: 259

Cys Arg Thr Gly Pro Ser Thr Asn Asp Gly Ile Thr Lys Thr Tyr Lys
1               5                   10                  15

Lys Gly Asp Asp Val Lys Leu Ser Cys Gln Thr Tyr Gly Glu Ser Ile
            20                  25                  30

Gln Gly Ser Thr Ile Trp Asp Lys Thr Thr Asp Gly Cys Tyr Val Ala
        35                  40                  45

Asp Tyr Tyr Val Lys Thr Gly Thr Ser Gly Met Val Thr Gly Glu Cys
    50                  55                  60

<210> SEQ ID NO 260
<211> LENGTH: 73
<212> TYPE: PRT
<213> ORGANISM: Aspergillus terreus

<400> SEQUENCE: 260

Tyr Thr Ile Thr Ala Asp Gly Val Asn Cys Arg Ser Gly Pro Gly Thr
1               5                   10                  15

Ser Asn Lys Ser Val Lys Thr Tyr Ala Lys Gly Thr Asp Val Lys Ile
            20                  25                  30

Ser Cys Gln Gln Ala Gly Glu Ser Ile Phe Gly Asn Ser Leu Trp Asp
        35                  40                  45

```
Lys Thr Ser Asp Gly Cys Tyr Val Ser Asp Tyr Tyr Val Lys Thr Gly
    50                  55                  60

Ser Thr Gly Tyr Val Thr Asp Lys Cys
65                  70

<210> SEQ ID NO 261
<211> LENGTH: 73
<212> TYPE: PRT
<213> ORGANISM: Chaetomium globosum

<400> SEQUENCE: 261

Tyr Pro Ile Thr Gly Ser Val Val Asn Cys Arg Ser Gly Pro Gly Thr
1               5                   10                  15

Ser Tyr Ala Val Lys Lys Ser Tyr Ala Lys Gly Ala Asp Val Lys Ile
                20                  25                  30

Ser Cys Gln Thr Ser Gly Thr Ser Val Asn Gly Asn Asn Ile Trp Asp
            35                  40                  45

Lys Thr Gln Asp Gly Cys Tyr Val Ala Asp Tyr Tyr Val Lys Thr Gly
    50                  55                  60

Thr Asn Gly Tyr Val Thr Lys Lys Cys
65                  70

<210> SEQ ID NO 262
<211> LENGTH: 73
<212> TYPE: PRT
<213> ORGANISM: Chaetomium globosum

<400> SEQUENCE: 262

Tyr Pro Ile Thr Gly Ser Val Val Asn Cys Arg Ser Gly Pro Gly Thr
1               5                   10                  15

Ser Tyr Ala Val Lys Lys Ser Tyr Asn Lys Gly Ala Asp Val Thr Ile
                20                  25                  30

Ser Cys Gln Thr Thr Gly Thr Ser Val Asn Gly Asn Ser Ile Trp Asp
            35                  40                  45

Lys Thr Gln Asp Gly Cys Tyr Val Ala Asp Tyr Tyr Val Lys Thr Gly
    50                  55                  60

Thr Asn Gly Tyr Val Thr Lys Lys Cys
65                  70

<210> SEQ ID NO 263
<211> LENGTH: 73
<212> TYPE: PRT
<213> ORGANISM: Chaetomium globosum

<400> SEQUENCE: 263

Tyr Pro Ile Thr Gly Asn Asp Val Asn Cys Arg Ser Gly Pro Asp Thr
1               5                   10                  15

Ser Tyr Lys Ser Val Lys Thr Tyr Lys Lys Gly Ala Asp Val Lys Leu
                20                  25                  30

Thr Cys Gln Thr Tyr Gly Glu Ser Ile Asn Gly Asn Ala Ile Trp Asp
            35                  40                  45

Lys Thr Ser Asp Gly Cys Tyr Val Ser Asp Tyr Tyr Val Lys Thr Gly
    50                  55                  60

Ser Asn Ser Met Val Thr Lys Glu Cys
65                  70
```

-continued

```
<210> SEQ ID NO 264
<211> LENGTH: 73
<212> TYPE: PRT
<213> ORGANISM: Neosartorya fumigata

<400> SEQUENCE: 264

Tyr Pro Ile Thr Gly Asn Gly Val Asn Cys Arg Ala Gly Pro Ser Thr
1               5                   10                  15

Asn Asp Lys Val Ile Lys Ser Tyr Ala Lys Gly Thr Asp Val Lys Leu
            20                  25                  30

Ser Cys Gln Thr Tyr Gly Glu Asn Ile Asn Gly Asn Ser Ile Trp Asp
        35                  40                  45

Lys Thr Thr Asp Gly Cys Tyr Val Ala Asp Tyr Tyr Val Lys Thr Gly
    50                  55                  60

Ser Asn Ser Met Val Thr Lys Glu Cys
65                  70

<210> SEQ ID NO 265
<211> LENGTH: 73
<212> TYPE: PRT
<213> ORGANISM: Neosartorya fumigata

<400> SEQUENCE: 265

Tyr Pro Ile Thr Gly Asn Gly Val Asn Cys Arg Ser Gly Pro Gly Thr
1               5                   10                  15

Asn Tyr Pro Val Val Lys Ser Tyr Pro Lys Gly His Glu Val Ser Ile
            20                  25                  30

Val Cys Gln Ala Pro Gly Thr Asp Ile Lys Gly Asp Lys Leu Trp Asp
        35                  40                  45

Lys Thr Ser Asp Gly Cys Tyr Val Ala Asp Tyr Tyr Val Lys Thr Gly
    50                  55                  60

Thr Thr Gly Tyr Val Thr Lys His Cys
65                  70

<210> SEQ ID NO 266
<211> LENGTH: 73
<212> TYPE: PRT
<213> ORGANISM: Neosartorya fumigata

<400> SEQUENCE: 266

Tyr Pro Ile Thr Gly Asp Gly Val Asn Cys Arg Ser Gly Pro Gly Thr
1               5                   10                  15

Asn Tyr Pro Val Val Lys Ser Tyr Pro Lys Gly His Glu Val Ser Ile
            20                  25                  30

Val Cys Gln Ala Pro Gly Thr Asp Ile Lys Gly Asp Lys Leu Trp Asp
        35                  40                  45

Lys Thr Ser Asp Gly Cys Tyr Val Ala Asp Tyr Tyr Val Lys Thr Gly
    50                  55                  60

Thr Thr Asn Tyr Val Ala Lys His Cys
65                  70

<210> SEQ ID NO 267
<211> LENGTH: 73
<212> TYPE: PRT
<213> ORGANISM: Penicillium chrysogenum
```

-continued

<400> SEQUENCE: 267

Tyr Pro Ile Thr Gly Asp Ser Val Asn Cys Arg Ser Gly Pro Gly Thr
1               5                   10                  15

Thr His Ala Val Val Lys Ser Tyr Lys Lys Ala Gln Asp Val Thr Val
            20                  25                  30

Thr Cys Gln Thr Ala Gly Glu Ser Ile Phe Gly Asp Asn Leu Trp Asp
        35                  40                  45

Lys Thr Ser Asp Gly Cys Tyr Val Ala Asp Tyr Tyr Val Gln Thr Gly
    50                  55                  60

Thr Ser Asn Tyr Val Thr Thr Lys Cys
65                  70

<210> SEQ ID NO 268
<211> LENGTH: 73
<212> TYPE: PRT
<213> ORGANISM: Penicillium chrysogenum

<400> SEQUENCE: 268

Tyr Pro Ile Thr Ser Asp Gln Leu Asn Cys Arg Ser Gly Pro Ser Thr
1               5                   10                  15

Ser Asp Ser Val Val Lys Thr Tyr Lys Ser Gly Ala Asp Val Lys Val
            20                  25                  30

Ser Cys Gln Thr Tyr Gly Glu Ser Ile Asn Gly Asn Thr Ile Trp Asp
        35                  40                  45

Lys Thr Ser Asp Asn Cys Tyr Val Ala Asp Tyr Tyr Val Lys Thr Gly
    50                  55                  60

Ser Asp Ser Met Val Thr Glu Ser Cys
65                  70

<210> SEQ ID NO 269
<211> LENGTH: 73
<212> TYPE: PRT
<213> ORGANISM: Nectria haematococca

<400> SEQUENCE: 269

Tyr Pro Ile Thr Gly Asp Val Arg Cys Arg Ser Gly Pro Gly Thr
1               5                   10                  15

Ser Tyr Ala Ile Lys Lys Thr Phe Lys Lys Gly Thr Asn Val Lys Ile
            20                  25                  30

Thr Cys Gln Thr Thr Gly Thr Asn Ile Lys Gly Asn Asn Ile Trp Asp
        35                  40                  45

Lys Val Ser Glu Gly Cys Tyr Val Ser Asp Tyr Tyr Val Lys Thr Gly
    50                  55                  60

Ser Ser Gly Phe Val Thr Lys Lys Cys
65                  70

<210> SEQ ID NO 270
<211> LENGTH: 73
<212> TYPE: PRT
<213> ORGANISM: Nectria haematococca

<400> SEQUENCE: 270

Tyr Pro Ile Thr Gly Asp Asp Val Lys Cys Arg Ser Gly Pro Gly Thr
1               5                   10                  15

Ser Tyr Ala Val Lys Lys Val Leu Lys Lys Gly Thr Asp Val Thr Ile
            20                  25                  30

```
Thr Cys Gln Thr Glu Gly Thr Asn Ile Ser Gly Asn Thr Ile Trp Asp
            35                  40                  45

Lys Ile Ser Asp Gly Cys Tyr Val Ser Asp Tyr Val Lys Thr Gly
 50                  55                  60

Ser Asn Gly Tyr Val Lys Pro Lys Cys
 65                  70
```

<210> SEQ ID NO 271
<211> LENGTH: 73
<212> TYPE: PRT
<213> ORGANISM: Hypocrea jecorina

<400> SEQUENCE: 271

```
Tyr Pro Ile Thr Gly Asp Val Val Asn Cys Arg Thr Gly Pro Gly Thr
 1               5                  10                  15

Ser Tyr Ala Ile Lys Thr Ser Tyr Lys Lys Ser His Asp Ile Ser Ile
            20                  25                  30

Ser Cys Gln Thr Thr Gly Thr Ser Val Asn Gly Asn Asn Ile Trp Asp
            35                  40                  45

Lys Thr Ala Asp Gly Cys Tyr Val Ala Asp Tyr Val Lys Thr Gly
 50                  55                  60

Ser Ser Gly Phe Val Thr Lys Lys Cys
 65                  70
```

<210> SEQ ID NO 272
<211> LENGTH: 73
<212> TYPE: PRT
<213> ORGANISM: Thielavia terrestris

<400> SEQUENCE: 272

```
Tyr Ala Ile Thr Gly Asp Thr Val Asn Cys Arg Ser Gly Pro Gly Thr
 1               5                  10                  15

Asn Tyr Ala Val Lys Lys Thr Tyr Ala Lys Gly His Asp Val Thr Leu
            20                  25                  30

Ser Cys Gln Thr Ser Gly Thr Thr Val Asn Gly Asn Ser Ile Trp Asp
            35                  40                  45

Lys Thr Ser Asp Gly Cys Tyr Val Ser Asp Tyr Val Lys Thr Gly
 50                  55                  60

Ser Asn Ser Tyr Val Thr Lys Lys Cys
 65                  70
```

<210> SEQ ID NO 273
<211> LENGTH: 74
<212> TYPE: PRT
<213> ORGANISM: Thielavia heterothallica

<400> SEQUENCE: 273

```
Tyr Pro Val Thr Ala Asn Gly Gly Leu Ser Cys Arg Ser Gly Pro Gly
 1               5                  10                  15

Thr Ser Tyr Pro Val Lys Lys Thr Tyr Lys Lys Gly Phe Asp Ile Lys
            20                  25                  30

Ile Ser Cys Gln Thr Thr Gly Thr Ser Val Asn Gly Tyr Asn Ile Trp
            35                  40                  45

Asp Lys Thr Gln Asp Gly Cys Tyr Val Ser Asp Tyr Tyr Val Lys Thr
 50                  55                  60

Gly Lys Ser Gly Phe Val Thr Thr Lys Cys
 65                  70
```

<210> SEQ ID NO 274
<211> LENGTH: 73
<212> TYPE: PRT
<213> ORGANISM: Hypocrea jecorina

<400> SEQUENCE: 274

Tyr Pro Ile Thr Gly Asp Thr Val Asn Cys Arg Ser Gly Pro Gly Thr
1               5                   10                  15

Ser Phe Ala Ile Lys Lys Thr Tyr Lys Lys Ser Gln Asp Val Ser Val
            20                  25                  30

Thr Cys Gln Thr Ser Gly Thr Ser Val Asn Gly Asn Ser Ile Trp Asp
        35                  40                  45

Lys Thr Ser Asp Gly Cys Tyr Val Ala Asp Tyr Tyr Val Lys Thr Gly
    50                  55                  60

Ser Ser Ser Tyr Val Thr Lys Lys Cys
65                  70

<210> SEQ ID NO 275
<211> LENGTH: 73
<212> TYPE: PRT
<213> ORGANISM: Chaetomium thermophilum

<400> SEQUENCE: 275

Tyr Pro Ile Thr Gly Glu Gly Val Asn Cys Arg Ser Gly Pro Gly Thr
1               5                   10                  15

Ser Tyr Lys Val Ile Lys Ser Tyr Lys Lys Gly Thr Asp Val Lys Ile
            20                  25                  30

Ser Cys Gln Ile Lys Gly Glu Ser Ile Asn Gly Asn Asn Leu Trp Asp
        35                  40                  45

Lys Thr Gln Asp Gly Cys Tyr Val Ser Asp Tyr Tyr Val Lys Thr Gly
    50                  55                  60

Ser Asn Ser Met Val Thr Lys Gln Cys
65                  70

<210> SEQ ID NO 276
<211> LENGTH: 73
<212> TYPE: PRT
<213> ORGANISM: Chaetomium thermophilum

<400> SEQUENCE: 276

Tyr Lys Ile Thr Gly Asn Asn Val Asn Cys Arg Ser Gly Pro Gly Thr
1               5                   10                  15

Ser Tyr Ser Val Lys Lys Thr Tyr Ala Lys Gly Thr Asp Val Lys Ile
            20                  25                  30

Thr Cys Gln Thr Thr Gly Thr Asn Ile Asn Gly Asn Asn Ile Trp Asp
        35                  40                  45

Lys Thr Ser Asp Gly Cys Tyr Val Ser Asp Tyr Tyr Val Lys Thr Gly
    50                  55                  60

Thr Asn Gly Tyr Val Thr Thr Lys Cys
65                  70

<210> SEQ ID NO 277
<211> LENGTH: 73
<212> TYPE: PRT
<213> ORGANISM: Fusarium oxysporum

```
<400> SEQUENCE: 277

Tyr Pro Ile Thr Gly Asn Asp Val Lys Cys Arg Ser Gly Pro Gly Thr
1               5                   10                  15

Ser Tyr Ala Val Lys Lys Val Leu Lys Lys Gly Thr Asp Val Lys Ile
            20                  25                  30

Thr Cys Gln Thr Glu Gly Thr Asn Ile Ser Gly Asn Thr Ile Trp Asp
        35                  40                  45

Lys Ile Ser Asp Gly Cys Tyr Val Ser Asp Tyr Val Lys Thr Gly
    50                  55                  60

Ser Ser Gly Tyr Ile Lys Pro Lys Cys
65                  70

<210> SEQ ID NO 278
<211> LENGTH: 73
<212> TYPE: PRT
<213> ORGANISM: Thielavia heterothallica

<400> SEQUENCE: 278

Tyr Pro Ile Thr Gly Asp Asp Val Asn Cys Arg Thr Gly Pro Gly Thr
1               5                   10                  15

Ser Phe Lys Ser Val Lys Thr Tyr Pro Lys Gly Thr Asp Val Lys Leu
            20                  25                  30

Ser Cys Gln Thr Tyr Gly Glu Val Ile Phe Gly Asn Ser Ile Trp Asp
        35                  40                  45

Lys Thr Gln Asp Gly Cys Tyr Val Ser Asp Tyr Val Lys Thr Gly
    50                  55                  60

Ser Asn Asn Met Val Thr Gly Glu Cys
65                  70

<210> SEQ ID NO 279
<211> LENGTH: 74
<212> TYPE: PRT
<213> ORGANISM: Thielavia heterothallica

<400> SEQUENCE: 279

Tyr Pro Val Thr Ala Asn Gly Gly Leu Ser Cys Arg Ser Gly Pro Gly
1               5                   10                  15

Thr Ser Tyr Ala Val Lys Lys Thr Tyr Lys Lys Gly Phe Asp Val Lys
            20                  25                  30

Ile Ser Cys Gln Thr Thr Gly Thr Ser Val Asn Gly Asn Asn Ile Trp
        35                  40                  45

Asp Lys Thr Gln Asp Gly Cys Tyr Val Ala Asp Tyr Tyr Val Lys Thr
    50                  55                  60

Gly Lys Asn Gly Phe Val Thr Ser Lys Cys
65                  70

<210> SEQ ID NO 280
<211> LENGTH: 73
<212> TYPE: PRT
<213> ORGANISM: Hypocrea virens

<400> SEQUENCE: 280

Tyr Pro Ile Thr Gly Glu Ala Val Asn Cys Arg Thr Gly Pro Gly Thr
1               5                   10                  15

Ser Phe Ala Ile Lys Lys Thr Tyr Lys Lys Ser Gln Asp Val Ser Val
            20                  25                  30
```

```
Thr Cys Gln Thr Ser Gly Ser Val Asn Gly Asn Ser Ile Trp Asp
            35                  40                  45

Lys Thr Ser Asp Gly Cys Tyr Val Ala Asp Tyr Tyr Val Lys Thr Gly
 50                      55                  60

Ser Ser Ser Tyr Val Thr Lys Lys Cys
 65                  70
```

<210> SEQ ID NO 281
<211> LENGTH: 73
<212> TYPE: PRT
<213> ORGANISM: Metarhizium robertsii

<400> SEQUENCE: 281

```
Tyr Pro Ile Thr Gly Thr Thr Val Asn Cys Arg Ser Gly Pro Ser Thr
 1               5                  10                  15

His Asp Lys Val Ile Lys Thr Tyr Asn Lys Gly Asn Asp Ile Lys Ile
                20                  25                  30

Ser Cys Gln Val Ala Gly Glu Thr Val Ser Gly Asn Asn Leu Trp Asp
            35                  40                  45

Lys Thr Gln Asp Gly Cys Phe Val Ser Asp Tyr Tyr Val Lys Thr Gly
 50                      55                  60

Ser Asn Gly Met Val Thr Gly Gln Cys
 65                  70
```

<210> SEQ ID NO 282
<211> LENGTH: 73
<212> TYPE: PRT
<213> ORGANISM: Fusarium oxysporum

<400> SEQUENCE: 282

```
Tyr Pro Ile Thr Gly Asn Asp Val Lys Cys Arg Ser Gly Pro Gly Thr
 1               5                  10                  15

Ser Tyr Ala Val Lys Lys Val Leu Lys Lys Gly Thr Asp Val Lys Ile
                20                  25                  30

Thr Cys Gln Thr Glu Gly Thr Asn Ile Ser Gly Asn Thr Ile Trp Asp
            35                  40                  45

Lys Ile Ser Asp Gly Cys Tyr Val Ser Asp Tyr Tyr Val Lys Thr Gly
 50                      55                  60

Ser Ser Gly Tyr Ile Lys Pro Lys Cys
 65                  70
```

<210> SEQ ID NO 283
<211> LENGTH: 73
<212> TYPE: PRT
<213> ORGANISM: Chaetomium thermophilum

<400> SEQUENCE: 283

```
Tyr Ala Ile Thr Gly Asp Asn Val Asn Cys Arg Ser Gly Pro Gly Thr
 1               5                  10                  15

Ser Tyr Ala Val Lys Lys Val Tyr Lys Gly Thr Asp Val Lys Ile
                20                  25                  30

Ser Cys Gln Thr Thr Gly Thr Asn Ile Asn Gly Asn Asn Leu Trp Asp
            35                  40                  45

Lys Thr Ser Asp Gly Cys Tyr Val Ser Asp Tyr Tyr Val Lys Thr Gly
 50                      55                  60

Ser Asn Gly Tyr Val Thr Ser Lys Cys
 65                  70
```

```
<210> SEQ ID NO 284
<211> LENGTH: 73
<212> TYPE: PRT
<213> ORGANISM: Thielavia terrestris

<400> SEQUENCE: 284

Tyr Pro Ile Thr Gly Asn Gly Val Asn Cys Arg Ser Gly Pro Gly Thr
1               5                   10                  15

Ser His Ala Val Lys Lys Val Tyr Ala Lys Gly Thr Asp Ile Lys Val
                20                  25                  30

Thr Cys Gln Thr Glu Gly Thr Ser Ile Asn Gly Asn Ser Ile Trp Asp
            35                  40                  45

Lys Thr Ser Asp Gly Cys Tyr Val Ala Asp Tyr Val Lys Thr Gly
        50                  55                  60

Ser Asn Ser Tyr Val Thr Lys Lys Cys
65                  70

<210> SEQ ID NO 285
<211> LENGTH: 73
<212> TYPE: PRT
<213> ORGANISM: Fusarium oxysporum

<400> SEQUENCE: 285

Tyr Pro Ile Thr Gly Asn Asp Val Lys Cys Arg Ser Gly Pro Gly Thr
1               5                   10                  15

Ser Tyr Ala Val Lys Lys Val Leu Lys Lys Gly Thr Asp Val Lys Ile
                20                  25                  30

Thr Cys Gln Thr Glu Gly Thr Asn Ile Ser Gly Asn Thr Ile Trp Asp
            35                  40                  45

Lys Thr Ser Asp Gly Cys Tyr Val Ser Asp Tyr Val Lys Thr Gly
        50                  55                  60

Ser Ser Gly Tyr Ile Lys Pro Lys Cys
65                  70

<210> SEQ ID NO 286
<211> LENGTH: 73
<212> TYPE: PRT
<213> ORGANISM: Fusarium oxysporum

<400> SEQUENCE: 286

Tyr Pro Ile Thr Gly Asn Asp Val Lys Cys Arg Ser Gly Pro Gly Thr
1               5                   10                  15

Ser Tyr Ala Val Lys Glu Val Leu Lys Lys Gly Thr Asp Val Lys Ile
                20                  25                  30

Thr Cys Gln Thr Glu Gly Thr Asn Ile Ser Gly Asn Thr Ile Trp Asp
            35                  40                  45

Lys Ile Ser Asp Gly Cys Tyr Val Ser Asp Tyr Val Lys Thr Gly
        50                  55                  60

Ser Ser Gly Tyr Ile Lys Pro Lys Cys
65                  70

<210> SEQ ID NO 287
<211> LENGTH: 73
<212> TYPE: PRT
<213> ORGANISM: Fusarium oxysporum
```

<400> SEQUENCE: 287

Phe Pro Ile Thr Gly Asn Thr Val Asn Cys Arg Ser Gly Pro Gly Thr
1               5                   10                  15

Ser Tyr Ser Val Lys Arg Thr Tyr Lys Lys Gly Gln Asp Val Ser Ile
            20                  25                  30

Thr Cys Gln Thr Tyr Gly Thr Asn Val Asn Gly Asn Ser Ile Trp Asp
        35                  40                  45

Lys Thr Ser Asp Gly Cys Tyr Val Ala Asp Tyr Tyr Val Lys Thr Gly
    50                  55                  60

Ser Asp Glu Phe Val Thr Lys Lys Cys
65                  70

<210> SEQ ID NO 288
<211> LENGTH: 73
<212> TYPE: PRT
<213> ORGANISM: Fusarium oxysporum

<400> SEQUENCE: 288

Tyr Pro Ile Thr Gly Asn Asp Val Lys Cys Arg Ser Gly Pro Gly Thr
1               5                   10                  15

Ser Tyr Ala Val Lys Lys Val Leu Lys Gly Thr Asp Val Lys Ile
            20                  25                  30

Thr Cys Gln Thr Glu Gly Thr Asn Ile Ser Gly Asn Thr Ile Trp Asp
        35                  40                  45

Lys Ile Ser Asp Gly Cys Tyr Val Ser Asp Tyr Tyr Val Lys Thr Gly
    50                  55                  60

Ser Asn Gly Tyr Ile Lys Pro Lys Cys
65                  70

<210> SEQ ID NO 289
<211> LENGTH: 73
<212> TYPE: PRT
<213> ORGANISM: Fusarium oxysporum

<400> SEQUENCE: 289

Tyr Pro Ile Thr G

Thr Cys Gln Thr Glu Gly Thr Asn Ile Ser Gly Asn Thr Ile Trp Asp
            35                  40                  45

Lys Ile Ser Asp Gly Cys Tyr Val Ser Asp Tyr Val Lys Thr Gly
 50                  55                  60

Ser Ser Gly Tyr Ile Lys Pro Lys Cys
 65                  70

<210> SEQ ID NO 291
<211> LENGTH: 73
<212> TYPE: PRT
<213> ORGANISM: Fusarium oxysporum

<400> SEQUENCE: 291

Tyr Pro Ile Thr Gly Asn Asp Val Lys Cys Arg Ser Gly Pro Gly Thr
 1               5                  10                  15

Ser Tyr Ala Val Lys Lys Val Leu Lys Lys Gly Thr Asp Val Lys Ile
            20                  25                  30

Thr Cys Gln Thr Glu Gly Thr Asn Ile Ser Gly Asn Thr Ile Trp Asp
            35                  40                  45

Lys Ile Ser Asp Gly Cys Tyr Val Ser Asp Tyr Val Lys Thr Gly
 50                  55                  60

Ser Ser Gly Tyr Ile Lys Pro Lys Cys
 65                  70

<210> SEQ ID NO 292
<211> LENGTH: 73
<212> TYPE: PRT
<213> ORGANISM: Penicillium roqueforti

<400> SEQUENCE: 292

Tyr Pro Ile Thr Gly Asp Thr Val Asn Cys Arg Ser Gly Pro Gly Thr
 1               5                  10                  15

Ser His Thr Val Val Lys Thr Tyr Lys Lys Ala His Asp Val Lys Ile
            20                  25                  30

Thr Cys Gln Thr Thr Gly Asp Ser Ile Ser Gly Asn Asn Ile Trp Asp
            35                  40                  45

Lys Thr Ser Asp Gly Cys Tyr Val Ala Asp Tyr Tyr Lys Val Lys Thr Gly
 50                  55                  60

Ser Asn Ser Tyr Val Thr Ala Lys Cys
 65                  70

<210> SEQ ID NO 293
<211> LENGTH: 73
<212> TYPE: PRT
<213> ORGANISM: Penicillium roqueforti

<400> SEQUENCE: 293

Tyr Ala Ile Thr Ala Ser Val Ala Asn Cys Arg Thr Gly Pro Ser Thr
 1               5                  10                  15

Ser Asn Ala Val Val Thr Thr Tyr Lys Lys Gly Ala Asp Val Lys Ile
            20                  25                  30

Thr Cys Gln Thr Tyr Gly Glu Asn Ile Gln Gly Asn Ser Ile Trp Asp
            35                  40                  45

Lys Thr Ser Asp Gly Cys Tyr Val Ala Asp Tyr Tyr Val Lys Thr Gly
 50                  55                  60

Ser Asn Ser Met Val Thr Lys Asp Cys
 65                  70

<210> SEQ ID NO 294
<211> LENGTH: 73
<212> TYPE: PRT
<213> ORGANISM: Trichoderma reesei

<400> SEQUENCE: 294

Tyr Pro Ile Thr Gly Asp Thr Val Asn Cys Arg Ser Gly Pro Gly Thr
1               5                   10                  15

Ser Phe Ala Ile Lys Lys Thr Tyr Lys Lys Ser Gln Asp Val Ser Val
            20                  25                  30

Thr Cys Gln Thr Ser Gly Thr Ser Val Asn Gly Asn Ser Ile Trp Asp
        35                  40                  45

Lys Thr Ser Asp Gly Cys Tyr Val Ala Asp Tyr Tyr Val Lys Thr Gly
    50                  55                  60

Ser Ser Ser Tyr Val Thr Lys Lys Cys
65                  70

<210> SEQ ID NO 295
<211> LENGTH: 73
<212> TYPE: PRT
<213> ORGANISM: Metarhizium anisopliae

<400> SEQUENCE: 295

Tyr Pro Ile Thr Gly Thr Thr Val Asn Cys Arg Ser Gly Pro Ser Thr
1               5                   10                  15

His Asp Lys Val Ile Lys Thr Tyr Asn Lys Gly Asn Asp Ile Lys Ile
            20                  25                  30

Ser Cys Gln Val Ala Gly Glu Asn Val Ser Gly Asn Asn Leu Trp Asp
        35                  40                  45

Lys Thr Arg Asp Gly Cys Tyr Val Ser Asp Tyr Tyr Val Lys Thr Gly
    50                  55                  60

Ser Asn Gly Met Val Thr Gly Gln Cys
65                  70

<210> SEQ ID NO 296
<211> LENGTH: 73
<212> TYPE: PRT
<213> ORGANISM: Pseudogymnoascus pannorum

<400> SEQUENCE: 296

Tyr Pro Ile Thr Gly Ser Thr Val Asn Cys Arg Ser Gly Pro Gly Thr
1               5                   10                  15

Ser Tyr Ala Val Lys Lys Thr Tyr Lys Lys Gly Asp Ala Val Thr Ile
            20                  25                  30

Thr Cys Gln Lys Glu Gly Pro Val Val Ser Gly Asn Ser Ile Trp Asp
        35                  40                  45

Lys Thr Ser Asp Gly Cys Tyr Val Ala Asp Tyr Tyr Val Lys Thr Gly
    50                  55                  60

Ser Asn Gly Tyr Val Lys Pro Lys Cys
65                  70

<210> SEQ ID NO 297
<211> LENGTH: 72
<212> TYPE: PRT
<213> ORGANISM: Pseudogymnoascus pannorum -continued

<400> SEQUENCE: 297

Tyr Pro Ile Ser Gly Asp Ser Val Asn Cys Arg Ser Gly Pro Ala Thr
1               5                   10                  15

Ser Tyr Lys Val Ile Lys Thr Tyr Lys Lys Gly His Asp Val Lys Ile
            20                  25                  30

Thr Cys Gln Thr Val Gly Glu Thr Ile Lys Gly Gly Asn Leu Trp Asp
        35                  40                  45

Lys Thr Ser Asp Gly Cys Tyr Val Thr Asp Tyr Tyr Val Lys Thr Gly
    50                  55                  60

Thr Thr Gly Arg Val Val Lys Lys
65                  70

<210> SEQ ID NO 298
<211> LENGTH: 72
<212> TYPE: PRT
<213> ORGANISM: Pseudogymnoascus pannorum

<400> SEQUENCE: 298

Phe Pro Val Thr Ala Thr Val Asn Cys Arg Ser Gly Pro Gly Thr Gly
1               5                   10                  15

Phe Ala Val Lys Lys Ser Tyr Thr Lys Gly His Ala Val Thr Ile Ser
            20                  25                  30

Cys Gln Thr Gly Gly Thr Ser Val Gln Gly Asn Ser Ile Trp Asp Lys
        35                  40                  45

Thr Ser Asp Gly Cys Tyr Val Ala Asp Tyr Tyr Val Lys Thr Gly Ser
    50                  55                  60

Ser Gly Tyr Val Lys Pro Lys Cys
65                  70

<210> SEQ ID NO 299
<211> LENGTH: 73
<212> TYPE: PRT
<213> ORGANISM: Pseudogymnoascus pannorum

<400> SEQUENCE: 299

Phe Pro Ile Thr Gly Asp Thr Val Asn Cys Arg Ser Gly Pro Gly Thr
1               5                   10                  15

Ser Tyr Ala Val Lys Lys Ser Tyr Asn Lys Gly His Ser Val Thr Ile
            20                  25                  30

Thr Cys Gln Thr Gly Gly Thr Ser Val Lys Gly Asn Ser Ile Trp Asp
        35                  40                  45

Lys Thr Ser Asp Gly Cys Tyr Val Ala Asp Tyr Tyr Val Lys Thr Gly
    50                  55                  60

Ser Ser Gly Tyr Val Lys Pro Lys Cys
65                  70

<210> SEQ ID NO 300
<211> LENGTH: 73
<212> TYPE: PRT
<213> ORGANISM: Pseudogymnoascus pannorum

<400> SEQUENCE: 300

Phe Pro Ile Thr Gly Asp Ser Val Asn Cys Arg Ser Gly Pro Gly Thr
1               5                   10                  15

Ser Tyr Ala Val Lys Lys Ser Tyr Ala Lys Gly His Ser Val Thr Ile
            20                  25                  30

```
Thr Cys Gln Thr Gly Gly Thr Ser Val Asn Gly Asn Ser Ile Trp Asp
            35                  40                  45

Lys Thr Ser Asp Gly Cys Tyr Val Ala Asp Tyr Tyr Val Lys Thr Gly
 50                      55                  60

Ser Ser Gly Tyr Val Lys Pro Lys Cys
 65                  70
```

<210> SEQ ID NO 301
<211> LENGTH: 73
<212> TYPE: PRT
<213> ORGANISM: Pseudogymnoascus pannorum

<400> SEQUENCE: 301

```
Tyr Pro Ile Asn Ala Ala Gly Val Asn Cys Arg Ser Gly Pro Gly Thr
 1               5                  10                  15

Ser Tyr Ala Val Lys Lys Ser Tyr Ala Lys Asp His Ala Val Thr Val
            20                  25                  30

Thr Cys Gln Thr Ala Gly Thr Ser Val Asn Gly Asn Ser Ile Trp Asp
            35                  40                  45

Lys Thr Ser Asp Gly Cys Tyr Val Ala Asp Tyr Tyr Val Asn Thr Gly
 50                      55                  60

Ser Ser Gly Tyr Val Lys Pro Lys Cys
 65                  70
```

<210> SEQ ID NO 302
<211> LENGTH: 73
<212> TYPE: PRT
<213> ORGANISM: Pseudogymnoascus pannorum

<400> SEQUENCE: 302

```
Tyr Pro Ile Asn Ala Ala Gly Val Asn Cys Arg Ser Gly Pro Gly Thr
 1               5                  10                  15

Gly Tyr Ala Val Lys Lys Ser Tyr Ala Lys Asp His Ala Val Thr Val
            20                  25                  30

Thr Cys Gln Thr Ala Gly Thr Thr Val Asn Gly Asn Ser Ile Trp Asp
            35                  40                  45

Lys Thr Ser Asp Gly Cys Tyr Val Ala Asp Tyr Tyr Val Asn Thr Gly
 50                      55                  60

Ser Ser Gly Tyr Val Lys

<210> SEQ ID NO 304
<211> LENGTH: 73
<212> TYPE: PRT
<213> ORGANISM: Pseudogymnoascus pannorum

<400> SEQUENCE: 304

Tyr Pro Ile Thr Gly Lys Thr Val Asn Cys Arg Ala Gly Pro Gly Thr
1               5                   10                  15

Ser Tyr Pro Val Lys Lys Thr Tyr Ser Lys Gly Asp Thr Val Thr Ile
                20                  25                  30

Thr Cys Gln Thr Ser Gly Thr Lys Val Asn Gly Asn Ala Ile Trp Asp
            35                  40                  45

Leu Thr Ser Asp Gly Cys Tyr Leu Thr Asp Tyr Tyr Val Lys Thr Gly
    50                  55                  60

Thr Ser Lys Tyr Ile Lys Pro Gln Cys
65                  70

<210> SEQ ID NO 305
<211> LENGTH: 69
<212> TYPE: PRT
<213> ORGANISM: Pseudogymnoascus pannorum

<400> SEQUENCE: 305

Tyr Pro Ile Ser Gly Thr Asp Val Asn Cys Arg Ser Gly Pro Ala Thr
1               5                   10                  15

Ser Tyr Lys Val Val Lys Thr Tyr Lys Lys Gly His Asp Val Lys Val
                20                  25                  30

Thr Cys Gln Thr Val Gly Glu Thr Ile Lys Gly Asp Asn Leu Trp Asp
            35                  40                  45

Lys Thr Ser Asp Gly Cys Tyr Val Ala Asp Tyr Tyr Val Lys Thr Gly
    50                  55                  60

Thr Thr Gly Arg Val
65

<210> SEQ ID NO 306
<211> LENGTH: 73
<212> TYPE: PRT
<213> ORGANISM: Pseudogymnoascus pannorum

<400> SEQUENCE: 306

Tyr Pro Ile Asn Thr Ala Gly Val Asn Cys Arg Ser Gly Pro Gly Thr
1               5                   10                  15

Ser Tyr Ala Val Lys Lys Ser Tyr Ala Lys Asp His Ala Val Thr Val
                20                  25                  30

Thr Cys Gln Thr Ala Gly Thr Ser Val Asn Gly Asn Ala Ile Trp Asp
            35                  40                  45

Lys Thr Ser Asp Gly Cys Tyr Val Ala Asp Tyr Tyr Val Asn Thr Gly
    50                  55                  60

Ser Asn Gly Tyr Val Lys Pro Lys Cys
65                  70

<210> SEQ ID NO 307
<211> LENGTH: 73
<212> TYPE: PRT
<213> ORGANISM: Pseudogymnoascus pannorum

```
<400> SEQUENCE: 307

Tyr Pro Ile Asn Ala Ala Gly Val Asn Cys Arg Ser Gly Pro Gly Thr
1               5                   10                  15

Gly Tyr Ala Val Lys Lys Ser Tyr Ala Lys Asp His Ala Val Thr Val
            20                  25                  30

Thr Cys Gln Thr Ala Gly Thr Ser Val Asn Gly Asn Ser Ile Trp Asp
        35                  40                  45

Lys Thr Ser Asp Gly Cys Tyr Val Ala Asp Tyr Val Asn Thr Gly
50                  55                  60

Ser Ser Gly Tyr Val Lys Pro Lys Cys
65                  70

<210> SEQ ID NO 308
<211> LENGTH: 74
<212> TYPE: PRT
<213> ORGANISM: Pseudogymnoascus pannorum

<400> SEQUENCE: 308

Tyr Pro Ile Ser Gly Thr Ser Val Asn Cys Arg Ser Gly Pro Ala Thr
1               5                   10                  15

Ser Tyr Lys Val Ile Lys Ala Tyr Lys Lys Gly Gln Asp Val Lys Ile
            20                  25                  30

Thr Cys Gln Thr Val Gly Glu Thr Val Ser Gly Asp Asn Leu Trp Asp
        35                  40                  45

Lys Thr Thr Asp Gly Cys Tyr Val Ala Asp Tyr Tyr Val Lys Thr Gly
50                  55                  60

Thr Thr Gly Arg Val Val Asn Ala Glu Cys
65                  70

<210> SEQ ID NO 309
<211> LENGTH: 73
<212> TYPE: PRT
<213> ORGANISM: Pseudogymnoascus pannorum

<400> SEQUENCE: 309

Phe Pro Ile Thr Gly Asp Ser Val Asn Cys Arg Ser Gly Pro Gly Thr
1               5                   10                  15

Ser Tyr Ala Val Lys Lys Ser Tyr Ala Lys Gly His Ser Val Thr Ile
            20                  25                  30

Thr Cys Gln Thr Gly Gly Thr Ser Val Asn Gly Asn Ser Ile Trp Asp
        35                  40                  45

Lys Thr Ser Asp Gly Cys Tyr Val Ala Asp Tyr Val Lys Thr Gly
50                  55                  60

Ser Ser Gly Tyr Val Lys Pro Lys Cys
65                  70

<210> SEQ ID NO 310
<211> LENGTH: 73
<212> TYPE: PRT
<213> ORGANISM: Pseudogymnoascus pannorum

<400> SEQUENCE: 310

Phe Pro Ile Thr Gly Asp Thr Val Asn Cys Arg Ser Gly Pro Gly Thr
1               5                   10                  15

Ser Tyr Ala Val Lys Lys Ser Tyr Ala Lys Gly His Asp Val Thr Ile
            20                  25                  30
```

```
Thr Cys Gln Thr Gly Gly Ser Val Ser Gly Asn Ser Ile Trp Asp
        35                  40                  45

Lys Thr Ser Asp Gly Cys Tyr Val Ala Asp Tyr Tyr Val Lys Thr Gly
 50                  55                  60

Ser Ser Gly Tyr Val Lys Pro Lys Cys
 65                  70

<210> SEQ ID NO 311
<211> LENGTH: 64
<212> TYPE: PRT
<213> ORGANISM: Pseudogymnoascus pannorum

<400> SEQUENCE: 311

Tyr Pro Ile Thr Gly Lys Thr Val Asn Cys Arg Ala Gly Pro Gly Thr
 1               5                  10                  15

Ser Tyr Pro Val Lys Lys Thr Tyr Ser Lys Gly Asp Thr Val Thr Ile
                20                  25                  30

Thr Cys Gln Thr Ser Gly Thr Lys Val Asn Gly Asn Ala Ile Trp Asp
        35                  40                  45

Leu Thr Ser Asp Gly Cys Tyr Leu Thr Asp Tyr Tyr Val Lys Thr Gly
 50                  55                  60

<210> SEQ ID NO 312
<211> LENGTH: 73
<212> TYPE: PRT
<213> ORGANISM: Pseudogymnoascus pannorum

<400> SEQUENCE: 312

Phe Pro Ile Thr Gly Asp Ser Val Asn Cys Arg Ser Gly Pro Gly Thr
 1               5                  10                  15

Ser Tyr Ala Val Lys Lys Ser Tyr Ala Lys Gly His Asp Val Thr Ile
                20                  25                  30

Thr Cys Gln Thr Gly Gly Thr Ser Val Ser Gly Asn Ser Ile Trp Asp
        35                  40                  45

Lys Thr Ser Asp Gly Cys Tyr Val Ala Asp Tyr Tyr Val Lys Thr Gly
 50                  55                  60

Ser Ser Gly Tyr Val Lys Pro Lys Cys
 65                  70

<210> SEQ ID NO 313
<211> LENGTH: 72
<212> TYPE: PRT
<213> ORGANISM: Pseudogymnoascus pannorum

<400> SEQUENCE: 313

Phe Pro Val Thr Glu Thr Val Asn Cys Arg Ser Gly Pro Gly Thr Ser
 1               5                  10                  15

Tyr Gly Val Lys Lys Ser Tyr Thr Lys Gly His Ala Val Thr Ile Ser
                20                  25                  30

Cys Gln Thr Gly Gly Thr Ser Val Lys Gly Asn Ser Ile Trp Asp Lys
        35                  40                  45

Thr Ser Asp Gly Cys Tyr Val Ala Asp Tyr Tyr Val Lys Thr Gly Ser
 50                  55                  60

Asn Gly Tyr Val Lys Pro Lys Cys
 65                  70
```

```
<210> SEQ ID NO 314
<211> LENGTH: 72
<212> TYPE: PRT
<213> ORGANISM: Pseudogymnoascus pannorum

<400> SEQUENCE: 314
```

Phe Pro Val Thr Ala Thr Val Asn Cys Arg Ser Gly Pro Gly Thr Gly
1               5                   10                  15

Tyr Ala Val Lys Lys Ser Tyr Thr Lys Gly Asn Ala Val Thr Ile Ser
            20                  25                  30

Cys Gln Thr Gly Gly Thr Ser Val Asn Gly Asn Ser Ile Trp Asp Lys
        35                  40                  45

Thr Ser Asp Gly Cys Tyr Val Ala Asp Tyr Tyr Val Lys Thr Gly Ser
    50                  55                  60

Ser Gly Tyr Val Lys Pro Lys Cys
65                  70

```
<210> SEQ ID NO 315
<211> LENGTH: 73
<212> TYPE: PRT
<213> ORGANISM: Pseudogymnoascus pannorum

<400> SEQUENCE: 315
```

Tyr Pro Ile Asn Ala Ala Gly Val Asn Cys Arg Ser Gly Pro Gly Thr
1               5                   10                  15

Ser Tyr Ala Val Lys Lys Ser Tyr Ala Lys Asp His Ala Val Thr Val
            20                  25                  30

Thr Cys Gln Thr Ala Gly Thr Ser Val Asn Gly Asn Ala Ile Trp Asp
        35                  40                  45

Lys Thr Ser Asp Gly Cys Tyr Val Ala Asp Tyr Tyr Val Asn Thr Gly
    50                  55                  60

Ser Asn Gly Tyr Val Lys Pro Lys Cys
65                  70

```
<210> SEQ ID NO 316
<211> LENGTH: 73
<212> TYPE: PRT
<213> ORGANISM: Pseudogymnoascus pannorum

<400> SEQUENCE: 316
```

Phe Pro Ile Thr Gly Ala Thr Val Asn Cys Arg Ser Gly Pro Gly Thr
1               5                   10                  15

Ser Tyr Ala Val Lys Lys Ser Tyr Ala Lys Gly His Asp Val Thr Ile
            20                  25                  30

Thr Cys Gln Thr Gly Gly Thr Ser Val Asn Gly Asn Ser Ile Trp Asp
        35                  40                  45

Lys Thr Ser Asp Gly Cys Tyr Val Ala Asp Tyr Tyr Val Lys Thr Gly
    50                  55                  60

Ser Ser Gly Tyr Val Lys Pro Lys Cys
65                  70

```
<210> SEQ ID NO 317
<211> LENGTH: 10
<212> TYPE: PRT
<213> ORGANISM: Artificial Sequence
<220> FEATURE:
<223> OTHER INFORMATION: SEQ ID NO: 317 is conserved motif I
```

```
<220> FEATURE:
<221> NAME/KEY: MISC_FEATURE
<222> LOCATION: (3)..(3)
<223> OTHER INFORMATION: The amino acid in position 3 of the conserved
      motif is either isoleucine (I) or leucine (L).
<220> FEATURE:
<221> NAME/KEY: MISC_FEATURE
<222> LOCATION: (6)..(6)
<223> OTHER INFORMATION: The amino acid in position 6 of the conserved
      motif is either alanine (A) or glycine (G).
<220> FEATURE:
<221> NAME/KEY: MISC_FEATURE
<222> LOCATION: (7)..(7)
<223> OTHER INFORMATION: The amino acid in position 7 of the conserved
      motif is either isoleucine (I) or leucine (L).
<220> FEATURE:
<221> NAME/KEY: MISC_FEATURE
<222> LOCATION: (8)..(8)
<223> OTHER INFORMATION: The amino acid in position 8 of the conserved
      motif is either threonine (T) or valine (V).

<400> SEQUENCE: 317

Ala Gly Xaa Ala Thr Xaa Xaa Xaa Glu Ser
1               5                   10

<210> SEQ ID NO 318
<211> LENGTH: 14
<212> TYPE: PRT
<213> ORGANISM: Artificial Sequence
<220> FEATURE:
<223> OTHER INFORMATION: SEQ ID NO: 318 is conserved motif II
<220> FEATURE:
<221> NAME/KEY: MISC_FEATURE
<222> LOCATION: (2)..(2)
<223> OTHER INFORMATION: The amino acid in position 2 of the conserved
      motif is either alanine (A) or glycine (G).
<220> FEATURE:
<221> NAME/KEY: MISC_FEATURE
<222> LOCATION: (3)..(3)
<223> OTHER INFORMATION: The amino acid in position 3 of the conserved
      motif is any amino acid.
<220> FEATURE:
<221> NAME/KEY: MISC_FEATURE
<222> LOCATION: (7)..(7)
<223> OTHER INFORMATION: The amino acid in position 7 of the conserved
      motif is any amino acid.
<220> FEATURE:
<221> NAME/KEY: MISC_FEATURE
<222> LOCATION: (10)..(10)
<223> OTHER INFORMATION: The amino acid in position 10 of the conserved
      motif is any amino acid.

<400> SEQUENCE: 318

Val Xaa Xaa Leu Cys Gln Xaa Val Gln Xaa Ser Ala Tyr Pro
1               5                   10

<210> SEQ ID NO 319
<211> LENGTH: 11
<212> TYPE: PRT
<213> ORGANISM: Artificial Sequence
<220> FEATURE:
<223> OTHER INFORMATION: SEQ ID NO: 254 is conserved motif III
      [CGY][YF][VIL][ASTP][DG]X[YF][VIT]X[TS][GAN].
<220> FEATURE:
<221> NAME/KEY: MISC_FEATURE
<222> LOCATION: (1)..(1)
<223> OTHER INFORMATION: The amino acid in position 1 of the conserved
      motif is cysteine, glycine or tyrosine.
<220> FEATURE:
<221> NAME/KEY: MISC_FEATURE
<222> LOCATION: (2)..(2)
<223> OTHER INFORMATION: The amino acid in position 2 of the conserved
      motif is phenylalanine or tyrosine.
```

```
<220> FEATURE:
<221> NAME/KEY: MISC_FEATURE
<222> LOCATION: (3)..(3)
<223> OTHER INFORMATION: The amino acid in position 3 of the conserved
      motif is valine, isoleucine or leucine.
<220> FEATURE:
<221> NAME/KEY: MISC_FEATURE
<222> LOCATION: (4)..(4)
<223> OTHER INFORMATION: The amino acid in position 4 of the conserved
      motif is alanine, proline, serine or threonine.
<220> FEATURE:
<221> NAME/KEY: MISC_FEATURE
<222> LOCATION: (5)..(5)
<223> OTHER INFORMATION: The amino acid in position 5 of the conserved
      motif is aspartic acid or glycine.
<220> FEATURE:
<221> NAME/KEY: MISC_FEATURE
<222> LOCATION: (6)..(6)
<223> OTHER INFORMATION: The amino acid in position 6 of the conserved
      motif is any amino acid.
<220> FEATURE:
<221> NAME/KEY: MISC_FEATURE
<222> LOCATION: (7)..(7)
<223> OTHER INFORMATION: The amino acid in position 7 of the conserved
      motif is phenylalanine or tyrosine.
<220> FEATURE:
<221> NAME/KEY: MISC_FEATURE
<222> LOCATION: (8)..(8)
<223> OTHER INFORMATION: The amino acid in position 8 of the conserved
      motif is isoleucine, threonine or valine..
<220> FEATURE:
<221> NAME/KEY: MISC_FEATURE
<222> LOCATION: (9)..(9)
<223> OTHER INFORMATION: The amino acid in position 9 of the conserved
      motif is any amino acid.
<220> FEATURE:
<221> NAME/KEY: MISC_FEATURE
<222> LOCATION: (10)..(10)
<223> OTHER INFORMATION: The amino acid in position 10 of the conserved
      motif is serine or threonine.
<220> FEATURE:
<221> NAME/KEY: MISC_FEATURE
<222> LOCATION: (11)..(11)
<223> OTHER INFORMATION: The amino acid in position 11 of the conserved
      motif is alanine, glycine or asparagine.

<400> SEQUENCE: 319

Xaa Xaa Xaa Xaa Xaa Xaa Xaa Xaa Xaa Xaa Xaa
1               5                   10

<210> SEQ ID NO 320
<211> LENGTH: 10767
<212> TYPE: DNA
<213> ORGANISM: Artificial Sequence
<220> FEATURE:
<223> OTHER INFORMATION: Synthetic DNA construct of plasmid pDAu770.

<400> SEQUENCE: 320
taggcgtatc acgaggccct tcgtctcgc  gcgtttcggt gatgacggtg aaaacctctg    60
acacatgcag ctcccggaga cggtcacagc ttgtctgtaa gcggatgccg ggagcagaca   120
agcccgtcag ggcgcgtcag cgggtgttgg cgggtgtcgg ggctggctta actatgcggc   180
atcagagcag attgtactga gagtgcacca tatgcggtgt gaaataccgc acagatgcgt   240
aaggagaaaa taccgcatca ggcgccattc gccattcagg ctgcgcaact gttgggaagg   300
gcgatcggtg cgggcctctt cgctattacg ccagctggcg aaagggggat gtgctgcaag   360
gcgattaagt tgggtaacgc caggttttc  ccagtcacga cgttgtaaaa cgacggccag   420
tgaattggcc tccatggccg cggccgcgct ttgctaaaac tttggttgat ggaaggtatc   480
tggcgataaa ctccgacgac gtctagaagc aacaatctta tgcaaacgct cattggttct   540
```

```
tttcgaccgc aacatccatc atgaaactgg tattttgtct gtgtcagcag tctagaaccc    600
cttgccgggt attttagcat ttcattttc  tataaaaagg taccagcatg tatggatcgt    660
atcttccgta ccgtggttat taaatcccag cagaggccga taggcttaag aagtgaacat    720
ggcatggtta aggaagaagc cattactgag tatatatggc tagaataatc gctgggaaag    780
atttatgctt ccaagaggcg taggacggta taccatacag tacggtattt atgaacaatt    840
cgataatacc actccccaaa gcgggagata ggacacccgc ctcaggcacc aaccaccccc    900
tttttcaact gtcagtggtg cacgtttcca tcgagcataa gcttggtacc ctaaggatag    960
gccctaatct tatctacatg tgactgcatc gatgtgtttg gtcaaaatga ggcatgtggc   1020
tcaccccaca ggcggagaaa cgtgtggcta gtgcatgaca gtcccctcca tagattcaat   1080
ttaattttc  gcggcaattg tcgtgcagtt tgtatctaca tttcattcca tatatcaaga   1140
gttagtagtt ggacatcctg attattttgt ctaattactg aaaactcgaa gtactaacct   1200
actaataagc cagtttcaac cactaagtgc tcatttatac aatatttgca gaaccccgcg   1260
ctacccctcc atcgccaaca tgtcttccaa gtcgcaattg acctacagcg cacgcgctag   1320
caagcacccc aatgcgctcg taaagaagct cttcgaggtt gccgaggcca agaaaaccaa   1380
tgtcaccgtt tccgccgacg tgacaaccac caaagagctg ctggatttgg ctgaccgtat   1440
gcgcaccggg gttgaagttc ctattccgag ttcctattct tcaaatagta taggaacttc   1500
attagtttaa acgtacgatt ttgacatttg ctccattgtc gaggatggat ggaacgagcg   1560
gcgtgcgcca cgaaagtgag gctattgcct atcagctctt tgctacattc cggaaacaaa   1620
catcccttt  tgtgaattat ctacgcaact tagatggcgt gaacgcatct tcaaagtctt   1680
tcggcaggtc cggcacgact tttgcatcca gagaagcgcc tacatgtgta ttcgaccacc   1740
tcctagcgcg cttggatatg aggaaatatt actgagagtc gaaaacaagc tccaccgcac   1800
cagctcttct tggagtttta tattaaagaa tattcccagc tcgttgtatt attctttttc   1860
taccgtgcta atgtatcaag gactttggta cctattaacg ttattattcg tgtgctattc   1920
ccaaacataa ccctgtatat gtttcgaacg ccgttatgac ccatgtctta catactcatt   1980
aagtcattcc cttggataat ctcgactcag atgcggcgt  tgatgtagga ggagaggtaa   2040
tcgaggacct cctgggagat gatgccgttc caggcgggt  agcggatgga gccctcggcg   2100
gagcccttga gctgctcgat atgctgccac tcctcgatgg ggttggtctc atccttgagg   2160
gcgatcatct ccttggagat gggatcgtag gcgtagtagc gggagactag tgcgaagtaa   2220
tgatcgggga tggcggtgat ctgatgggtg taggtggtgc gggcgacggc ggaggcgcgc   2280
ttatcggacc agttgccgac gacgttggtg agctcggtga ggcccttcat ggagaggaag   2340
gaggtcatga gatggcggcc gatatgggac ttggggccgt tcttgatggc gaagatggag   2400
taggggcgt  tcttcttgag ggccttgttg taggagcgga cgaggttatc cttgaggagc   2460
tggtactcct gcttgttgga ggaggagttg ccgtgcggt  tgacgcgctt gaggacgggc   2520
tcggagttgc ggaggaactc atcgaggtag acgagggat  cgatgcggcc gcgggcggag   2580
aagaagtaga tatggcggga gacggaggtc ttggtctcgg tgacgaggca ctggatgatg   2640
acgccgaggt acttgttctg gacgagcttg aaggacttgg gatcgacgtt cttgatatcg   2700
gagaagcggc cgcagttgat gaaggtggcg aggaagagga actggtagag ggtcttggtc   2760
ttggtgaagc gggaggtgta ctcgaaggag ttgaggatct tctcggtgat ctcccagatg   2820
gactcgccct cggagaggag ggccttgagc atcttcttgg aatgggagtt gcccttatcg   2880
gcctcctcgg aggactcgaa ctggagctgg agggaggaga cgatatcggt gatatcggac   2940
```

```
tgatgcttct ggccgtagta ggggatgatg gtgaactccc aggcggggat gagcttcttg      3000
agggaggcct ccaggatggt ggccttctgg gtcttgtact tgaactggag ggacttgttg      3060
acgatatcga aggagaggga gttggagatg atggtgttgt aggacatgaa ggtggcgcgc      3120
ttgatggcgg tgccgttatg ggtgatcatc cagcagaggt aggtgagctc ggcggcgcag      3180
agggcgatct tctcgccgga ggggcgctcg aagcgctcga cgaactggcg gacgaggacc      3240 ttggggggg tcttgcagag gatatcgaac tggggcatgg tgctcagata ctacggctga       3300
tcgcgtagag gtactgagca aaacagatgt cagtaaggag aagagttgaa tgaatggaag      3360
aagagtagga aaggaggtat gggggaaaga tatacgtact gatgcggacg aagagagaaa      3420
gaaggaaaaa agttgtggga ggggaaggag ggggaatcct tatatggagg ggcaagcgag      3480
aaggcgaatt agtgggcggg cttaagccct cgaccgccgc ccttatcatt ggacatggag      3540
gggtaatgcc cccaccacgc atgtgcggga ccgacgcaga atctgcacgg cggagtctct      3600
tccagactgt tgacttttgg gcgatgactc ttgttgctgc ggccttttgg gtacaccaac      3660
ctcgttgatc ttgtttcctt ggttctcttt cgctcggaga cccgaccatg accccaccat      3720
cagtcactat cctgcctcgt cgataaaaat tttttcttcc ctctgattgt tacatagtat      3780
gtttccacct ttccggtgga tttcggacag tcaaactggg catcaacgca gtggtgggct      3840
gcttcgtttg ctgcgtgttg tacttgtttg catttgaacc ccgcggtcgt tcgagtcctt      3900
aattggtccg ctcccggtca cacccaagc agctgtggcc cggccgagtg cgcctgtct      3960 ggtccacagt taattaaagg agagagttga acctggacgc cgcgcaaaaa gcaaagacgc      4020
gcctcgtggg cggtggatca atgatcggat ttagtggcag atggcatcac aggcggccaa      4080
tgaccaccgg gccaactggc cccgacattc cagcaatact gcctaattga ctccaccatg      4140
catctcggct attattgaac tgggtttgat ggatggggac cctcttggaa ttgtcaaaga      4200
ttttgaagcg aagacgatct attggacggt agagatatac tcttgattta gtcgttggga      4260
ggcccctggg gaaagcaatg atggggaatg ttgctgctcc actgtggacc tcggctatgg      4320
aattacgtgc ttggatctaa gatgagctca tggctatgca ttgaatgaca gtgatatcag      4380
cagagcaagc agagaaggat ggaatgctaa ttttctagtg cttttgtgcaa gggtaaatca      4440 gggactgtct gtctggtctt ctacacgaag gaaagaccat ggctttcacg gtgtctgtat      4500
ttccggatat cctcaattcc gtcggtcgat tacaatcaca tgacttggct tccatttcac      4560
tactattatg cacacccact acatacatga tcatataacc aattgccctc atccccatcc      4620
tttaactata gcgaaatgga ttgattgtct accgccaggt gtcagtcacc ctctagatct      4680
cgagctcgct agagtcgacc tatggagtca ccacatttcc cagcaacttc cccacttcct      4740
ctgcaatcgc caacgtcctc tcttcactga gtctccgtcc gataacctgc actgcaaccg      4800
gtgccccatg gtacgcctcc ggatcatact cttcctgcac gagggcatca agctcactaa      4860
ccgccttgaa actctcattc ttcttatcga tgttcttatc cgcaaaggta accggaacaa      4920
ccacgctcgt gaaatccagc aggttgatca cagaggcata cccatagtac cggaactggt      4980
catgccgtac cgcagcggta ggcgtaatcg gcgcgatgat ggcgtccagt tccttcccgg      5040
ccttttcttc agcctcccgc catttctcaa ggtactccat ctggtaattc cacttctgga      5100
gatgcgtgtc ccagagctcg ttcatgttaa cagctttgat gttcgggttc agtaggtctt      5160
tgatatttgg aatcgccggc tcgccggatg cactgatatc gcgcattacg tcggcgctgc      5220
cgtcagccgc gtagatatgg gagatgagat cgtggccgaa atcgtgcttg tatgcgtcc       5280 acggggtcac ggtgtgaccg gctttggcga gtgcggcgac ggtggtttcc acgccgcgca      5340
```

```
ggataggagg gtgtggaagg acattgccgt cgaagttgta gtagccgata ttgagcccgc   5400
cgttcttgat cttggaggca ataatgtccg actcggactg cgccagggc atggggatga    5460 ccttggagtc gtatttccat ggctcctgac cgaggacgga tttggtgaag aggcggaggt   5520
ctaacatact tcatcagtga ctgccggtct cgtatatagt ataaaaagca agaaaggagg   5580
acagtggagg cctggtatag agcaggaaaa gaaggaagag gcgaaggact caccctcaac   5640
agagtgcgta atcggcccga caacgctgtg caccgtctcc tgaccctcca tgctgttcgc   5700
catctttgca tacggcagcc gcccatgact cggccttaga ccgtacagga agttgaacgc   5760
ggccggcact cgaatcgagc caccgatatc cgttcctaca ccgatgacgc caccacgaat   5820
cccaacgatc gcaccctcac caccagaact gccgccgcac gaccagttct tgttgcgtgg   5880
gttgacggtg cgcccgatga tgttgttgac tgtctcgcag accatcaggg tctgcgggac   5940
agaggtcttg acgtagaaga cggcaccggc tttgcggagc atggttgtca gaaccgagtc   6000
cccttcgtcg tacttgttta gccatgagat gtagcccatt gatgtttcgt agccctggtg   6060
gcatatgtta gctgacaaaa agggacatct aacgactag gggcaacggt gtaccttgac    6120
tcgaagctgg tctttgagag agatggggag gccatggagt ggaccaacgg gtctcttgtg   6180 cttttgcgtag tattcatcga gttcccttgc ctgcgcgaga gcggcgtcag ggaagaactc   6240
gtgggcgcag tttgtctgca cagaagccag cgtcagcttg atagtcccat aaggtggcgt   6300
tgttacatct ccctgagagg tagaggggac cctactaact gctgggcgat gctgcccgt    6360 ttacagaatg ctagcgtaac ttccaccgag gtcaactctc cggccgccag cttggacaca   6420
agatctgcag cggaggcctc tgtgatcttc agttcggcct ctgaaaggat caccgatttc   6480
tttgggaaat caataacgct gtcttccgca ggcagcgtct ggactttcca ttcatcaggg   6540 atggttttg cgaggcgggc gcgcttatca gcggccagtt cttcccagga ttgaggcatg    6600
tgcatgcaat gtgtgtttat gtggaagtaa gatacgacga gtttgattga gaaaagacag   6660
ggtgattgtc aagttcagta tggaagaaag agtagaagaa gatcagacga cagggaagag   6720
cgatgacata aaaggtggaa gacggaagaa aaacgaacca aatcaatccc actctatggc   6780
gggggttgga ctgcctgagg ccggcactgg tggggcttat cgataagttc tcgtcaccgg   6840
atgcaatgcg ctgtcaactg ctgacttggc cctgaacatc ctgtcctcta cagatccata   6900
ctatacaatg atcccagtta tagtgcggta aggtgcatat catatctcat tctcatgact   6960
cattcgactt ttttttagag aaagtacata cgtggaacat acactaaacg caacaggtcg   7020
cgacaacact ggtatacaaa acggtccccg gtgaatgacg ttattagtgt ctatccccca   7080
ctcacacccg aaaagaataa tagaaactaa cagaaaaagc ggcccgagga taagaggaac   7140
attcaaacag aaggggaatc ataaaaaccg aaaaatgcaa ggaaaagaga actcaaatca   7200
ataattttca taatactgtc gagagtaata cggaccagcg tctctcaggg acatgcgtcg   7260
gcgcaaggca tcatccaatc tctcatctaa cacatccagc attcgtgttc gatagtctaa   7320
ctgcttctct cggcgctcaa gtcttgcttc ccgatcatcg agttaattaa gaagttccta   7380
tactttctag agaataggaa ctcggaatag gaacttcaag gtaccgagct ctatcctcaa   7440
tacccatttt tccacgattc cattgtcata tccaattccg tttcttttc ttgttttccc     7500 ctcatccaat cccgtccatc atttactcct ttttcttgtg aatgcaagtg gcactaagaa   7560
atccaacccc cagacaaatt ttcctactca ggaacacaaa aacctcgttt ctgctccctt   7620
ctcgtacttc attcctatcg tctcggaatt tcctcaacaa cccttccga ctttgcgaca     7680 gcgtcgcgat tccagactta tgtgttctcg ttcctactgt cgttaccagt ctatttattc   7740
```

```
cgaaacctct gatcgctgaa tttcacacac aacacccccc cgttgatgct ggtggagaat    7800
ccgtagcgtc aagagttgaa ttcactccat gttgtaacga agtccacgaa ttgagacgat    7860
tgatgattac aaccccgcga tcgcctatcg acgattcgac gagatgccat tctcatcctc    7920
ctcatcctcc tccaccccg aggtgtctac caccccgctc gcagattact tctggatcgc    7980
aggtgtcgat ggcgcggaaa tcttagagac tttccaaaga ctcggcgacg aatacagggc    8040
aaacagtgcc accgctcctg gccccgctct tgcggacacg atcgaggaag atgcggacgc    8100
ggaggaggca cacgaccccc gtctggactc cctctctcga cccaattcca tggctggggg    8160
ccgcaattcc ttccagcggt tctcaatgcg ctcaggagac tccagtgagt ccagtgggaa    8220
tggtaccagc agcaaccgga gcagtctgac catcaagggt aatcagtcgc ccagagggtc    8280
gtcgtttcta aagatttcg actttgacaa ggccctgttc aagtttgcaa acgagcggga    8340
gtcgttcctg tcggatctga gtctcagtgc cggagcaatc actcccacct cccgtcctag    8400
gtccaggtta cgtacacaga agattgtctc cgaggaaagt ccctcccagc catccagctt    8460
gcttcgatca ggcattggta gtgtgcggcg tcatatggca ttcagagaca tgaatagtat    8520
gaaacggcag ccgtcagttg ctcgtcgcgg ccgcagcttg gcgtaatcat ggtcatagct    8580
gtttcctgtg tgaaattgtt atccgctcac aattccacac aacatacgag ccggaagcat    8640
aaagtgtaaa gcctggggtg cctaatgagt gagctaactc acattaattg cgttgcgctc    8700
actgcccgct ttccagtcgg gaaacctgtc gtgccagctg cattaatgaa tcggccaacg    8760
cgcggggaga ggcggtttgc gtattgggcg ctcttccgct tcctcgctca ctgactcgct    8820
gcgctcggtc gttcggctgc ggcgagcggt atcagctcac tcaaaggcgg taatacggtt    8880
atccacagaa tcaggggata acgcaggaaa gaacatgtga gcaaaaggcc agcaaaaggc    8940
caggaaccgt aaaaaggccg cgttgctggc gttttccat aggctccgcc ccctgacga    9000 gcatcacaaa aatcgacgct caagtcagag gtggcgaaac ccgacaggac tataaagata    9060
ccaggcgttt cccctggaa gctccctcgt gcgctctcct gttccgaccc tgccgcttac    9120
cggatacctg tccgcctttt tcccttcggg aagcgtggcg ctttctcata gctcacgctg    9180
taggtatctc agttcggtgt aggtcgttcg ctccaagctg gctgtgtgc acgaaccccc    9240 cgttcagccc gaccgctgcg ccttatccgg taactatcgt cttgagtcca acccggtaag    9300
acacgactta tcgccactgg cagcagccac tggtaacagg attagcagag cgaggtatgt    9360
aggcggtgct acagagttct tgaagtggtg gcctaactac ggctacacta agaacagt    9420 atttggtatc tgcgctctgc tgaagccagt taccttcgga aaaagagttg gtagctcttg    9480
atccggcaaa caaaccaccg ctggtagcgg tggtttttt gtttgcaagc agcagattac    9540
gcgcagaaaa aaggatctc aagaagatcc tttgatcttt tctacggggt ctgacgctca    9600
gtggaacgaa aactcacgtt aagggatttt ggtcatgaga ttatcaaaaa ggatcttcac    9660
ctagatcctt ttaaattaaa aatgaagttt taaatcaatc taaagtatat atgagtaaac    9720
ttggtctgac agttaccaat gcttaatcag tgaggcacct atctcagcga tctgtctatt    9780
tcgttcatcc atagttgcct gactccccgt cgtgtagata actacgatac gggagggctt    9840
accatctggc cccagtgctg caatgatacc gcgagaccca cgctcaccgg ctccagattt    9900
atcagcaata aaccagccag ccggaagggc cgagcgcaga agtggtcctg caactttatc    9960
cgcctccatc cagtctatta attgttgccg ggaagctaga gtaagtagtt cgccagttaa    10020 tagtttcgc aacgttgttg ccattgctac aggcatcgtg gtgtcacgct cgtcgtttgg    10080
tatggcttca ttcagctccg gttcccaacg atcaaggcga gttacatgat cccccatgtt    10140
```

-continued

```
gtgcaaaaaa gcggttagct ccttcggtcc tccgatcgtt gtcagaagta agttggccgc    10200
agtgttatca ctcatggtta tggcagcact gcataattct cttactgtca tgccatccgt    10260
aagatgcttt tctgtgactg gtgagtactc aaccaagtca ttctgagaat agtgtatgcg    10320
gcgaccgagt tgctcttgcc cggcgtcaat acgggataat accgcgccac atagcagaac    10380
tttaaaagtg ctcatcattg gaaaacgttc ttcggggcga aaactctcaa ggatcttacc    10440
gctgttgaga tccagttcga tgtaacccac tcgtgcaccc aactgatctt cagcatcttt    10500
tactttcacc agcgtttctg ggtgagcaaa acaggaagg  caaaatgccg caaaaagggg    10560
aataagggcg acacggaaat gttgaatact catactcttc cttttcaat  attattgaag    10620 catttatcag ggttattgtc tcatgagcgg atacatattt gaatgtattt agaaaaataa    10680
acaaataggg gttccgcgca catttccccg aaaagtgcca cctgacgtct aagaaaccat    10740
tattatcatg acattaacct ataaaaa                                        10767
```

<210> SEQ ID NO 321
<211> LENGTH: 45
<212> TYPE: DNA
<213> ORGANISM: Artificial Sequence
<220> FEATURE:
<223> OTHER INFORMATION: SEQ ID NO: 321 is the forward primer KKSC0972-F.

<400> SEQUENCE: 321
ctatatacac aactggggat ccaccatgca gctctccctc ctcgt                    45

<210> SEQ ID NO 322
<211> LENGTH: 46
<212> TYPE: DNA
<213> ORGANISM: Artificial Sequence
<220> FEATURE:
<223> OTHER INFORMATION: SEQ ID NO: 322 is the reverse primer KKSC0972-R.

<400> SEQUENCE: 322
tagagtcgac ccagccgcgc cggccattac aacccaccag cctggc                   46

<210> SEQ ID NO 323
<211> LENGTH: 27
<212> TYPE: DNA
<213> ORGANISM: Artificial Sequence
<220> FEATURE:
<223> OTHER INFORMATION: SEQ ID NO: 323 is forward primer F1.

<400> SEQUENCE: 323
gaattcgagc tcggtacctt gaagttc                                        27

<210> SEQ ID NO 324
<211> LENGTH: 31
<212> TYPE: DNA
<213> ORGANISM: Artificial Sequence
<220> FEATURE:
<223> OTHER INFORMATION: SEQ ID NO: 324 is reverse primer F1.

<400> SEQUENCE: 324
ggtggatccc cagttgtgta tatagaggat t                                   31

<210> SEQ ID NO 325
<211> LENGTH: 26
<212> TYPE: DNA
<213> ORGANISM: Artificial Sequence
<220> FEATURE:
<223> OTHER INFORMATION: SEQ ID NO: 325 is forward primer F3.

<400> SEQUENCE: 325
tgcgcggcgc ggctgggtcg actcta        26

<210> SEQ ID NO 326
<211> LENGTH: 27
<212> TYPE: DNA
<213> ORGANISM: Artificial Sequence
<220> FEATURE:
<223> OTHER INFORMATION: SEQ ID NO: 326 is reverse primer F3.

<400> SEQUENCE: 326
ttcacacagg aaacagctat gaccatg        27

<210> SEQ ID NO 327
<211> LENGTH: 25
<212> TYPE: DNA
<213> ORGANISM: Artificial Sequence
<220> FEATURE:
<223> OTHER INFORMATION: SEQ ID NO: 327 Primer bind forward.

<400> SEQUENCE: 327
ctatatacac aactgggat ccacc        25

<210> SEQ ID NO 328
<211> LENGTH: 26
<212> TYPE: DNA
<213> ORGANISM: Artificial Sequence
<220> FEATURE:
<223> OTHER INFORMATION: SEQ ID NO: 328 Primer bind reverse.

<400> SEQUENCE: 328
tagagtcgac ccagccgcgc cggcca        26

<210> SEQ ID NO 329
<211> LENGTH: 146
<212> TYPE: PRT
<213> ORGANISM: Ovatospora brasiliensis

<400> SEQUENCE: 329

Gly Gly Lys Gly Asn Leu Pro Gly Leu Asn Ala Lys Gln Ser Ser His
1               5                   10                  15

Ala Arg Ala Ile Val Ala Gln Ala Lys Lys Asp Gly Val Gly Leu His
            20                  25                  30

Gly Cys Glu Ala Gly Ile Ala Thr Ala Leu Val Glu Ser Gly Ile Lys
        35                  40                  45

Val Tyr Ala Asn Lys Lys Val Pro Ala Ser Leu Lys Tyr Pro His Asp
    50                  55                  60

Ala Val Gly Ser Asp His Asp Ser Ile Gly Ile Phe Gln Gln Arg Ala
65                  70                  75                  80

Val Tyr Tyr Pro Asn Ile Ala Ala Asp Met Asp Pro Ala Arg Ser Ala
                85                  90                  95

His Gln Phe Phe Ala Lys Met Lys Gly Val Ser Gly Trp Lys Thr Met
            100                 105                 110

Ala Val Gly Lys Leu Cys Gln Lys Val Gln Val Ser Ala Tyr Pro Asp
        115                 120                 125

Arg Tyr Ala Lys Arg Val Ser Glu Ala Thr Lys Ile Cys Lys Ala Ala
    130                 135                 140

Gly Ile
145